US009949971B2

(12) United States Patent
Hamdy et al.

(10) Patent No.: US 9,949,971 B2
(45) Date of Patent: Apr. 24, 2018

(54) THERAPEUTIC COMBINATIONS OF A BTK INHIBITOR, A PI3K INHIBITOR AND/OR A JAK-2 INHIBITOR

(71) Applicant: Acerta Pharma B.V., Oss (NL)

(72) Inventors: Ahmed Hamdy, Santa Cruz, CA (US); Wayne Rothbaum, Delray Beach, FL (US); Raquel Izumi, San Carlos, CA (US); Brian Lannutti, Solana Beach, CA (US); Todd Covey, San Carlos, CA (US); Roger Ulrich, Sammamish, WA (US); Dave Johnson, Aptos, CA (US); Tjeerd Barf, Ravenstein (NL); Allard Kaptein, Zaltbommel (NL)

(73) Assignee: Acerta Pharma B.V., Oss (NL)

( * ) Notice: Subject to any disclaimer, the term of this patent is extended or adjusted under 35 U.S.C. 154(b) by 0 days.

(21) Appl. No.: 15/319,740

(22) PCT Filed: Jun. 17, 2015

(86) PCT No.: PCT/IB2015/001811
§ 371 (c)(1),
(2) Date: Dec. 16, 2016

(87) PCT Pub. No.: WO2015/193740
PCT Pub. Date: Dec. 23, 2015

(65) Prior Publication Data
US 2017/0136014 A1 May 18, 2017

Related U.S. Application Data

(60) Provisional application No. 62/013,506, filed on Jun. 17, 2014, provisional application No. 62/035,785, filed on Aug. 11, 2014, provisional application No. 62/087,975, filed on Dec. 5, 2014, provisional application No. 62/115,493, filed on Feb. 12, 2015.

(51) Int. Cl.
| | | |
|---|---|---|
| *A61K 31/4985* | (2006.01) | |
| *A61K 31/519* | (2006.01) | |
| *A61K 31/52* | (2006.01) | |
| *A61K 31/529* | (2006.01) | |
| *A61K 39/395* | (2006.01) | |
| *C07K 16/28* | (2006.01) | |

(52) U.S. Cl.
CPC ........ *A61K 31/4985* (2013.01); *A61K 31/519* (2013.01); *A61K 31/52* (2013.01); *A61K 31/529* (2013.01); *A61K 39/39558* (2013.01); *C07K 16/2887* (2013.01); *C07K 2317/732* (2013.01)

(58) Field of Classification Search
CPC .. C07D 401/12; C07D 403/04; C07D 487/04; C07D 401/06; A61K 31/519
USPC ........ 514/183, 252.06, 255.05, 259.1, 262.1, 514/326
See application file for complete search history.

(56) References Cited

U.S. PATENT DOCUMENTS

| | | |
|---|---|---|
| 7,459,554 B2 | 12/2008 | Dong et al. |
| 7,825,118 B2 | 11/2010 | Honigberg et al. |
| 7,960,396 B2 | 6/2011 | Honigberg et al. |
| 8,377,946 B1 | 2/2013 | Chen et al. |
| 8,658,794 B2 | 2/2014 | deMan et al. |
| 9,290,504 B2 | 3/2016 | Barf et al. |
| 2006/0084654 A1 | 4/2006 | Beck et al. |
| 2008/0076921 A1 | 3/2008 | Honigberg et al. |
| 2009/0312319 A1 | 12/2009 | Ren et al. |
| 2011/0257203 A1 | 10/2011 | Honigberg et al. |
| 2012/0053189 A1 | 3/2012 | Loury |
| 2012/0095026 A1 | 4/2012 | Honigberg et al. |
| 2012/0129821 A1 | 5/2012 | Honigberg et al. |
| 2012/0135944 A1 | 5/2012 | Honigberg et al. |
| 2012/0165328 A1 | 6/2012 | Honigberg et al. |
| 2013/0018032 A1 | 1/2013 | Chen et al. |
| 2013/0079327 A1 | 3/2013 | Yamamoto et al. |
| 2014/0073593 A1 | 3/2014 | Conklin et al. |
| 2014/0206681 A1 | 7/2014 | Kim et al. |
| 2014/0212425 A1 | 7/2014 | Chang et al. |

FOREIGN PATENT DOCUMENTS

| | | |
|---|---|---|
| EP | 2548877 | 1/2013 |
| WO | 2001019828 | 3/2001 |
| WO | 2007064993 | 6/2001 |
| WO | 2002080926 | 10/2002 |
| WO | 2003065995 | 8/2003 |
| WO | 2005037836 | 4/2005 |

(Continued)

OTHER PUBLICATIONS

Bogani et al., "mTOR Inhibitors Alone and in Combination with JAK2 Inhibitors Effectively Inhibit Cells of Myeloproliferative Neoplasms", PLoS One. 2013;8(1):e54826.
Lim et al., "Discovery of 1-Amino-5H-pyridol[4,3-b]indol-4-carboxamide Inhibitors of Janus Kinase 2 (JAK2) for the Treatment of Myeloproliferative Disorders", J.Med.Chem., vol. 54, pp. 7334-7349 (2011).
William et al., "Discovery of the Macrocycle 11-(2-Pyrrolidin-1-yl-ethoxy)-14,19-dioxa-5,7,26-triaza-tetracyclo[19.3.1.1(2,6). 1(8,12)]heptacosa-1(25),2(26),3,5,8,10,12(27),16,21,23-decaene (SB1518), a Potent Janus Kinase 2/Fms-Like Tyrosine Kinase-3 (JAK2/FLT3) Inhibitor for the Treatment of Myelofibrosis and Lymphoma", J.Med.Chem., vol. 54, pp. 4638-4658 (2011).
International Search Report for PCT/IB2015/001811 dated Jun. 13, 2016.

(Continued)

*Primary Examiner* — Raymond J Henley, III
(74) *Attorney, Agent, or Firm* — Morgan, Lewis & Bockius LLP

(57) ABSTRACT

Therapeutic combinations of a Janus kinase-2 (JAK-2) inhibitor, a Bruton's tyrosine kinase (BTK) inhibitor, and/or a phosphoinositide 3-kinase (PI3K) inhibitor, including PI3K inhibitors selective for the γ- and δ-isoforms and selective for both γ- and δ-isoforms, are described. In some embodiments, the invention provides pharmaceutical compositions comprising combinations of (1) a PI3K-δ inhibitor and a BTK inhibitor, (2) a JAK-2 inhibitor and a BTK inhibitor, or (3) a JAK-2 inhibitor, PI3K-δ inhibitor, and BTK inhibitor, and methods of using the pharmaceutical compositions for treating a disease, in particular a cancer.

26 Claims, 125 Drawing Sheets

(56) References Cited

FOREIGN PATENT DOCUMENTS

| WO | 2005097800 | | 10/2005 |
|---|---|---|---|
| WO | 2007061737 | | 5/2007 |
| WO | 2007064883 | | 6/2007 |
| WO | 2007106503 | | 9/2007 |
| WO | 2008121742 | | 10/2008 |
| WO | 2009076170 | | 6/2009 |
| WO | 2010126960 | | 11/2010 |
| WO | 2011095556 | | 8/2011 |
| WO | 2011119663 | | 9/2011 |
| WO | 2011152351 | | 12/2011 |
| WO | 2011153514 | | 12/2011 |
| WO | 2012158843 | | 11/2012 |
| WO | 2013003629 | | 1/2013 |
| WO | 2013010380 | | 1/2013 |
| WO | 2013010868 | | 1/2013 |
| WO | 2013010868 | A1 | 1/2013 |
| WO | 2013010869 | | 1/2013 |
| WO | 2013059738 | | 4/2013 |
| WO | 2014143807 | | 9/2014 |
| WO | 2014159745 | | 10/2014 |
| WO | 2014168975 | | 10/2014 |
| WO | 2014168975 | A1 | 10/2014 |
| WO | 2015018522 | | 2/2015 |
| WO | 2015127234 | A1 | 8/2015 |

OTHER PUBLICATIONS

Berge et al. "Pharmaceutical salts" 66(1) J. Pharm. Sci. 1-19 (1977).
Bingham et al., "Over one hundred solvates of sulfathlazole" Chem. Commun. 603-04 (2001).
Caira et al., "Preparation and Crystal Characterization of a Polymorph, a Monohydrate, and an Ethyl Acetate Solvate of the Antifungal Fluconazole," 93(3) J. Pharma. Sci. 601-11 (2004).
Davis et al., "Chronic active B-cell-receptor signaling in diffuse large B-cell lymphoma," 463 Nature 88-92 (2010).
Dhar et al., "Synthesis and SAR of p38a MAP kinase inhibitors based on heterobicyclic scaffolds," 17 Bioorg. & Med. Chem. Lett. 5019-24 (2007).
Gaudet et al., "A Homogeneous Fluorescence Polarization Assay Adaptable for a Range of Protein Serine/Threonine and Tyrosine Kinases," 8(2) J. Biomol. Screening 164-75 (2003).
Gilfillan et al., "The tyrosine kinase network regulating mast cell activation," 288 Immun. Rev. 149-69 (2009).
Gould "Salt selection for basic drugs" 33 Int'l J. Pharmaceutics 201-217 (1986).
Harder et al., "Gain- and Loss-of-Function Lyn Mutant Mice Define a Critical Inhibitory Role for Lyn in the Myeloid Lineage" 15 immunity 603-15 (2001).
Hartz et al., "Synthesis and Evaluation of imidazo[1,5-a]pyrazines as Corticotrophin Releasing Hormone Receptor Ligands," 12 Bioorg. & Met Chem. Lett. 291-94 (2002).
Ji et al., "A novel, potent, and selective insulin-like growth factor-I receptor kinase inhibitor blocks insulin-like growth factor-I receptor signaling in vitro and inhibits insulin-like growth factor-Ireceptor-dependent tumor growth in vivo," 6(8) Mol. Cancer Ther. 2158-67 (2007).
King et al., "Nucleofugality effects in the pyridine promoted formation of esters from 2-substituted ethanesulfonyl chlorides," 66 Can. J. Chem. 1109-16 (1988).
Klinghoffer et al., "Src family kinases are required for integrin but not PDGFR signal transduction," 18(9) EMBO J. 2459-71 (1999).
Lim et al., "Anti-CD20 monoclonal antibodies: historical and future perspectives," 95(1) Haematologica 135-43 (2010).
Lowell et al., "Deficiency of the Hck and Src Tyrosine Kinases Results in Extreme Levels of Extramedullary Hematopoiesis," 87(5) Blood 1780-92 (1996).
Mitchell et al., "Synthesis of C-nucleoside isosteres of 9-(2-hydroxyethoxymethyl)guanine (acyclovir)," 21 (3) J. Heterocyclic Chem. 697-99 (1984).
Mukaiyama et al., "Synthesis and c-Src inhibitory activity of imidazo[1,5-a]pyrazine derivatives as an agent for treatment of acute ischemic stroke," 15 Bioorg. & Med. Chem. 868-85 (2007).
Mulvihill et al., "1,3-Disubstituted-imidazo[1,5-a]pyrazines as insulin-like growth-factor-I receptor (IGF-IR) inhibitors", 17 Bioorg. & Med. Chem. Lett. 1091-97 (2007).
Mulvihill et al., "Novel 2-phenylquinolin-7-yl-derived imidazo[1,5-a]pyrazines as potent insulin-growth factor-I receptor (IGF-IR) inhibitors", 16 Bioorg. & Med. Chem. 1359-75 (2008).
Odom et al., "Negative Regulation of immunoglobulin E-dependent Allergic Responses by Lyn Kinase," 199(11) J. Exp. Med. 1491-1502 (2004).
Pan et al., "Discovery of Selective Irreversible Inhibitors for Burton's Tyrosine Kinase," 2 ChemMedChem 58-61 (2007).
Roby et al., "Alterations in Reproductive Function In Src Tyrosine Kinase Knockout Mice", 26 Endocrine 169-76 (2005).
Shinohara et al., "Tyrosine Kinases Btk and Tec Regulate Osteoclast Differentiation by Linking RANK and ITAM Signals" 132 Cell 794-806 (2008).
Van Tonder et al., "Preparation and Physicochemical Characterization of 5 Niclosamide Solvates and 1 Hemisolvate", 5(1) AAPS PharmSciTech Article 12 (2004).
Written Opinion dated Aug. 10, 2016 relating to PCT/IB2016/053988.
International Search Report dated Aug. 10, 2016 relating to PCT/IB2016/053988.

THERAPEUTIC COMBINATIONS OF A BTK INHIBITOR, A PI3K INHIBITOR AND/OR A JAK-2 INHIBITOR

CROSS-REFERENCE TO RELATED APPLICATIONS

This application claims the benefit of U.S. Provisional Application No. 62/013,506 filed on Jun. 17, 2014; U.S. Provisional Application No. 62/035,785 filed on Aug. 11, 2014; U.S. Provisional Application No. 62/087,975 filed on Dec. 5, 2014; and U.S. Provisional Application No. 62/115,493 filed on Feb. 12, 2015, all of which are herein incorporated by reference in their entireties.

SEQUENCE LISTING

Sequence Listing Submission via EFS-Web. A computer readable text file, entitled "SequenceListing.txt," created on or about 16 Dec. 2016 with a file size of about 14 kb contains the sequence listing for this application and is hereby incorporated by reference in its entirety.

FIELD OF THE INVENTION

Therapeutic combinations of a phosphoinositide 3-kinase (PI3K) inhibitor, a Janus kinase-2 (JAK-2) inhibitor, and a Bruton's tyrosine kinase (BTK) inhibitor and uses of the therapeutic combinations are disclosed herein. In particular, a combination of a BTK inhibitor and a JAK-2 inhibitor and uses thereof are disclosed.

BACKGROUND OF THE INVENTION

PI3K kinases are members of a unique and conserved family of intracellular lipid kinases that phosphorylate the 3'-OH group on phosphatidylinositols or phosphoinositides. PI3K kinases are key signaling enzymes that relay signals from cell surface receptors to downstream effectors. The PI3K family comprises 15 kinases with distinct substrate specificities, expression patterns, and modes of regulation. The class I PI3K kinases (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases.

The PI3K signaling pathway is known to be one of the most highly mutated in human cancers. PI3K signaling is also a key factor in disease states including hematologic malignancies, non-Hodgkin lymphoma (such as diffuse large B-cell lymphoma), allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome. The role of PI3K in cancer has been discussed, for example, in J. A. Engleman, Nat. Rev. Cancer 2009, 9, 550-562. The PI3K-δ and PI3K-γ isoforms are preferentially expressed in normal and malignant leukocytes.

The delta (δ) isoform of class I PI3K (PI3K-δ) is involved in mammalian immune system functions such as T-cell function, B-cell activation, mast cell activation, dendritic cell function, and neutrophil activity. Due to its role in immune system function, PI3K-δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. The gamma (γ) isoform of class I PI3K (PI3K-γ) is also involved in immune system functions and plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). One important function of Akt is to augment the activity of mTOR, through phosphorylation of TSC2 and other mechanisms. mTOR is a serine-threonine kinase related to the lipid kinases of the PI3K family and has been implicated in a wide range of biological processes including cell growth, cell proliferation, cell motility and survival. Disregulation of the mTOR pathway has been reported in various types of cancer.

In view of the above, PI3K inhibitors are prime targets for drug development, as described in J. E. Kurt and I. Ray-Coquard, Anticancer Res. 2012, 32, 2463-70. Several PI3K inhibitors are known, including those that are PI3K-δ or PI3K-γ inhibitors and those that are PI3K-δ,γ inhibitors.

Bruton's Tyrosine Kinase (BTK) is a Tec family non-receptor protein kinase expressed in B cells and myeloid cells. The function of BTK in signaling pathways activated by the engagement of the B cell receptor (BCR) and FCER1 on mast cells is well established. Functional mutations in BTK in humans result in a primary immunodeficiency disease characterized by a defect in B cell development with a block between pro- and pre-B cell stages. The result is an almost complete absence of B lymphocytes, causing a pronounced reduction of serum immunoglobulin of all classes. These findings support a key role for BTK in the regulation of the production of auto-antibodies in autoimmune diseases.

Other diseases with an important role for dysfunctional B cells are B cell malignancies. The reported role for BTK in the regulation of proliferation and apoptosis of B cells indicates the potential for BTK inhibitors in the treatment of B cell lymphomas. BTK inhibitors have thus been developed as potential therapies, as described in O. J. D'Cruz and F. M. Uckun, OncoTargets and Therapy 2013, 6, 161-176.

Janus kinase-2 (JAK-2) is an enzyme that is a member of the Janus kinase family of four cytoplasmic tyrosine kinases that also includes JAK-1, JAK-3, and Tyk2 (tyrosine kinase 2). The Janus kinase family transduces cytokine-mediated signals as part of the JAK-STAT signalling pathway (where STAT is an acronym for "signal transducer and activator of transcription"), as described in K. Ghoreschi, A. Laurence, J. J. O'Shea, Janus kinases in immune cell signaling. Immunol. Rev. 2009, 228, 273-287. The JAK-STAT pathway mediates signalling by cytokines that affects proliferation, differentiation, and survival in many cell types, and is commonly expressed in leukocytes. The Janus kinase family of enzymes is required for signaling by cytokine and growth factor receptors that lack intrinsic kinase activity. JAK-2 is implicated in signaling processes by members of the type II cytokine receptor family (such as interferon receptors), the GM-CSF receptor family (IL-3R, IL-5R and GM-CSF-R), the gp130 receptor family (e.g. IL-6R), and the single chain receptors (e.g. Epo-R, Tpo-R, GH-R, PRL-R), as described in U.S. Patent Application Publication No. 2012/0157500, the disclosure of which is incorporated herein by reference. JAK-2 signaling is activated downstream from the prolactin receptor. JAK-2 inhibitors were developed after discovery of an activating tyrosine kinase mutation (the V617F mutation) in myeloproliferative cancers and disorders. JAK-2 inhibitors have been developed as potential therapies for myeloproliferative neoplasms, polycythemia vera, essential thrombocythemia, and primary myelofibrosis, as discussed in S. Verstovsek, Therapeutic potential of JAK2 inhibitors, *Hematology (American Society of Hematology Education Book)*, 2009, 636-642. JAK-2 inhibitorsmay reverse hyperphosphorylation of JAK-2 and effectively treat myeloproliferative cancers and disorders.

In many solid tumors, the supportive microenvironment (which may make up the majority of the tumor mass) is a dynamic force that enables tumor survival. The tumor microenvironment is generally defined as a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.*, 2012, 72, 2473. Although tumors express antigens that should be recognized by T cells, tumor clearance by the immune system is rare because of immune suppression by the microenvironment. Addressing the tumor cells themselves with e.g. chemotherapy has also proven to be insufficient to overcome the protective effects of the microenvironment. New approaches are thus urgently needed for more effective treatment of solid tumors that take into account the role of the microenvironment.

The CD20 antigen, also called human B-lymphocyte-restricted differentiation antigen Bp35, or B1), is found on the surface of normal "pre-B" and mature B lymphocytes, including malignant B lymphocytes. Nadler, et al., *J. Clin. Invest.* 1981, 67, 134-40; Stashenko, et al., *J. Immunol.* 1980, 139, 3260-85. The CD20 antigen is a glycosylated integral membrane protein with a molecular weight of approximately 35 kD. Tedder, et al., *Proc. Natl. Acad. Sci. USA,* 1988, 85, 208-12. CD20 is also expressed on most B cell non-Hodgkin's lymphoma cells, but is not found on hematopoietic stem cells, pro-B cells, normal plasma cells, or other normal tissues. Anti-CD20 antibodies are currently used as therapies for many B cell hematological malignancies, including indolent non-Hodgkin's lymphoma (NHL), aggressive NHL, and chronic lymphocytic leukemia (CLL)/small lymphocytic leukemia (SLL). Lim, et. al., *Haematologica* 2010, 95, 135-43; Beers, et. al., *Sem. Hematol.* 2010, 47, 107-14; Klein, et al., *mAbs* 2013, 5, 22-33. However, there is an urgent need to provide for more efficacious therapies in many B cell hematological malignancies.

The present invention provides the unexpected finding that the combination of a JAK-2 inhibitor and a BTK inhibitor is synergistically effective in the treatment of any of several types of cancers such as leukemia, lymphoma, and solid tumor cancers. The present invention also provides the unexpected finding that a combination of a PI3K inhibitor, a JAK-2 inhibitor, and a BTK inhibitor is synergistically effective in the treatment of any of several types of cancers such as leukemia, lymphoma, and solid tumor cancers. The present invention further provides the unexpected finding that the combination of a JAK-2 inhibitor and a PI3K inhibitor is synergistically effective in the treatment of any of several types of cancers such as leukemia, lymphoma, and solid tumor cancers. The present invention further provides the unexpected finding that the combination of a PI3K inhibitor and a BTK inhibitor is synergistically effective in the treatment of any of several types of cancers such as leukemia, lymphoma, and solid tumor cancers. The present invention further provides the unexpected finding that the combination of an anti-CD20 antibody with a BTK inhibitor, a PI3K inhibitor, and/or a JAK-2 inhibitor, is synergistically effective in the treatment of any of several types of cancers such as leukemia, lymphoma, and solid tumor cancers.

SUMMARY OF THE INVENTION

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof. In an embodiment, the JAK-2 inhibitor is administered to the mammal before administration of the BTK inhibitor. In an embodiment, the JAK-2 inhibitor is administered to the mammal simultaneously with the administration of the BTK inhibitor. In an embodiment, the JAK-2 inhibitor is administered to the mammal after administration of the BTK inhibitor.

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, wherein the BTK inhibitor is selected from the group consisting of:

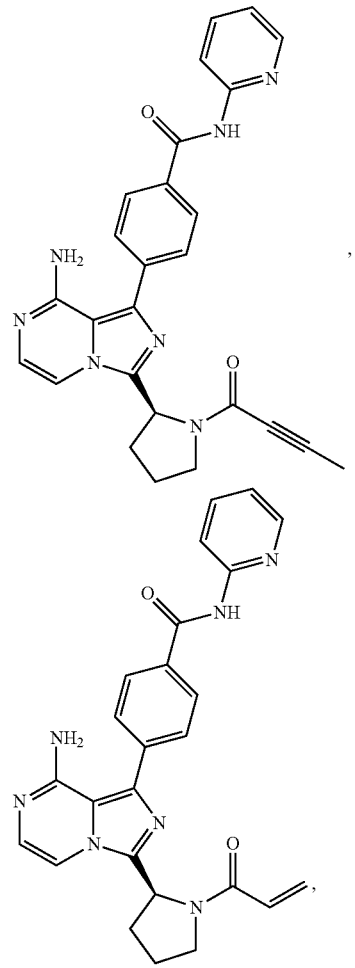

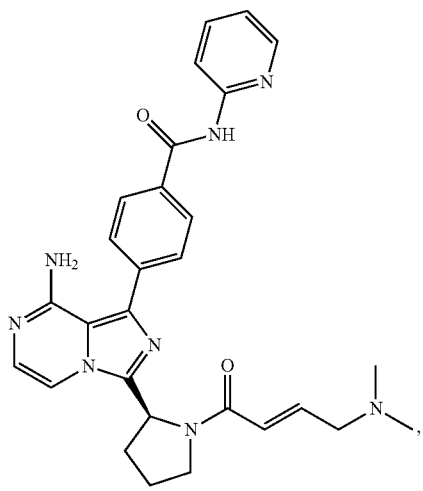

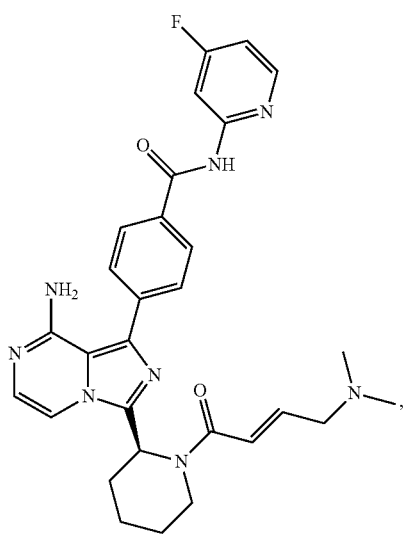

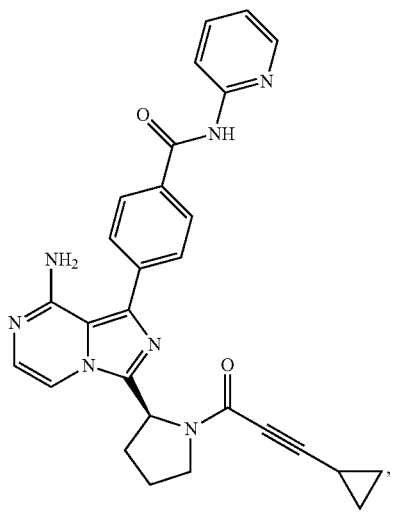

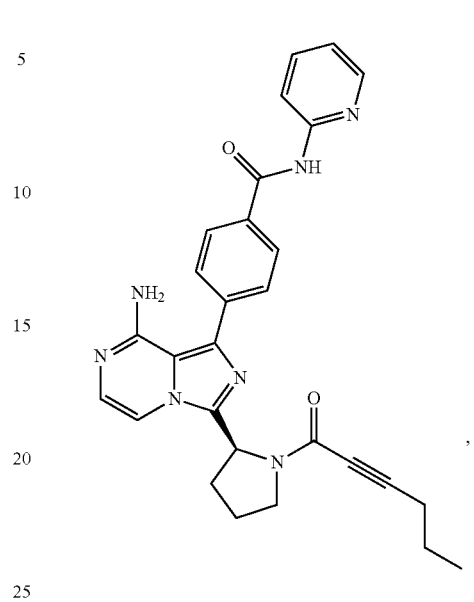

and pharmaceutically-acceptable salts, cocrystals, hydrates, solvates, and prodrugs thereof.

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, wherein the BTK inhibitor is selected from the group consisting of:

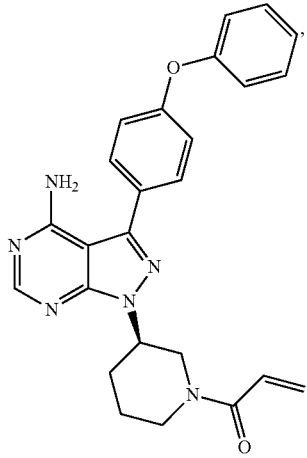

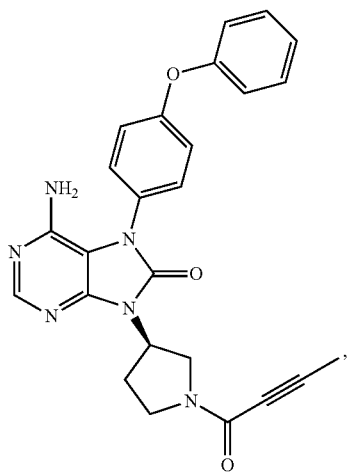

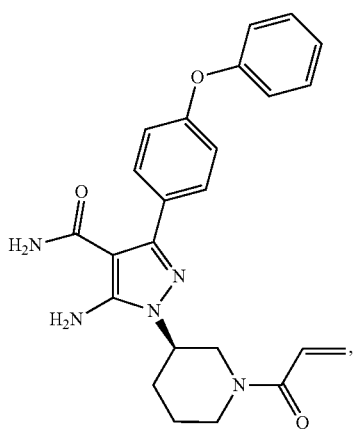

and pharmaceutically-acceptable salts, cocrystals, hydrates, solvates, and prodrugs thereof.

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, wherein the JAK-2 inhibitor is selected from the group consisting of:

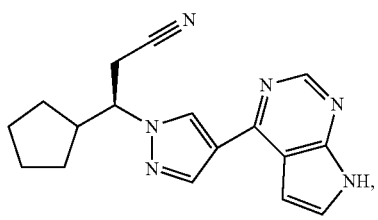

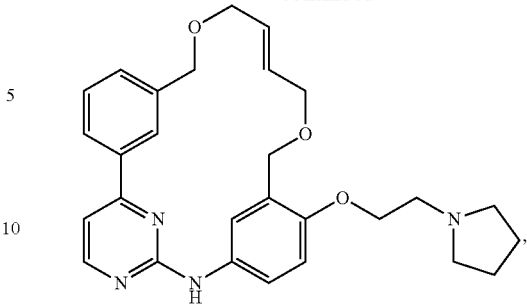

and pharmaceutically-acceptable salts, cocrystals, hydrates, solvates, or prodrugs thereof.

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, further comprising the step of administering a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, biosimilars thereof, and combinations thereof.

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, further comprising the step of administering a phosphoinositide 3-kinase (PI3K) inhibitor or a pharmaceutically acceptable salt, solvate, hydrate, cocrystal, or prodrug thereof. In an embodiment, the PI3K inhibitor is a PI3K-δ inhibitor. In an embodiment, the PI3K inhibitor is administered to the mammal before administration of the BTK inhibitor. In an embodiment, wherein the PI3K inhibitor is administered to the mammal concurrently with the administration of the BTK inhibitor. In an embodiment, the PI3K inhibitor is administered to the mammal after administration of the BTK inhibitor. In an embodiment, the PI3K inhibitor is selected from the group consisting of:

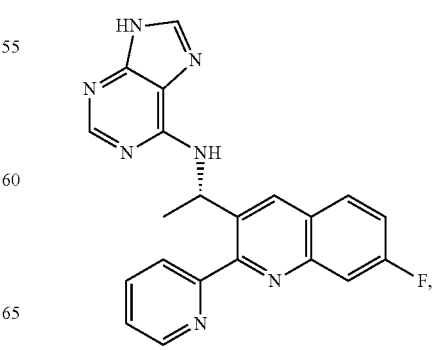

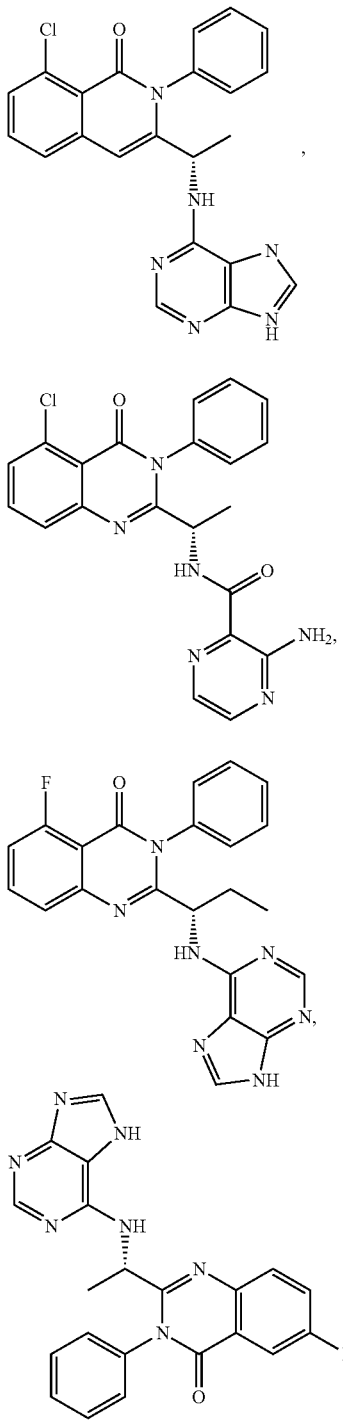

and pharmaceutically acceptable salts, solvates, hydrates, cocrystals, and prodrugs thereof.

In an embodiment, the invention provides a method of treating a hyperproliferative disease, wherein the hyperproliferative disease is a cancer, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, wherein the cancer is a B cell hematological malignancy, and wherein the B cell hematological malignancy is selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, and myelofibrosis. In an embodiment, the cancer is a solid tumor cancer, wherein the solid tumor cancer is selected from the group consisting of bladder cancer, non-small cell lung cancer, cervical cancer, anal cancer, pancreatic cancer, squamous cell carcinoma including head and neck cancer, renal cell carcinoma, melanoma, ovarian cancer, small cell lung cancer, glioblastoma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, and brain cancer.

In an embodiment, the invention provides a method of treating a hyperproliferative disease, comprising co-administering, to a mammal in need thereof, therapeutically effective amounts of (1) a Janus kinase-2 (JAK-2) inhibitor or a pharmaceutically acceptable salt, solvate, hydrate, cocrystal, or prodrug thereof, and (2) a Bruton's tyrosine kinase (BTK) inhibitor or a pharmaceutically acceptable salt, solvate, hydrate, cocrystal, or prodrug thereof, further comprising the step of administering a therapeutically effective amount of gemcitabine or albumin-bound paclitaxel.

In an embodiment, the invention provides a method of treating a cancer in a human comprising the step of co-administering (1) a therapeutically effective amount of a Janus kinase-2 (JAK-2) inhibitor or a pharmaceutically acceptable salt, solvate, hydrate, cocrystal, or prodrug thereof, and (2) a therapeutically effective amount of a Bruton's tyrosine kinase (BTK) inhibitor or a pharmaceutically acceptable salt, solvate, hydrate, cocrystal, or prodrug thereof, wherein the therapeutically effective amount is effective to inhibit signaling between the tumor cells of the cancer and at least one tumor microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In an embodiment, the cancer is a solid tumor cancer selected from the group consisting of bladder cancer, non-small cell lung cancer, cervical cancer, anal cancer, pancreatic cancer, squamous cell carcinoma including head and neck cancer, renal cell carcinoma, melanoma, ovarian cancer, small cell lung cancer, glioblastoma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, and brain cancer. In an embodiment, the BTK inhibitor is selected from the group consisting of:

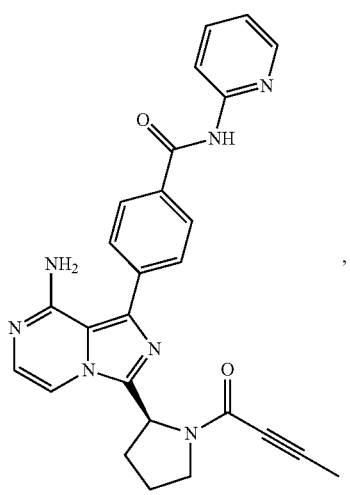
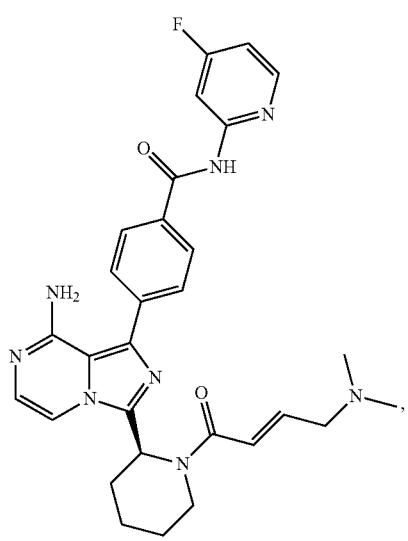
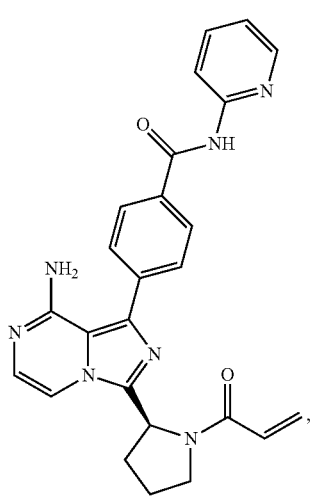
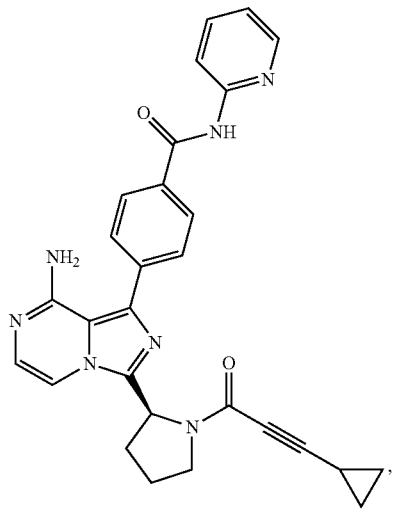
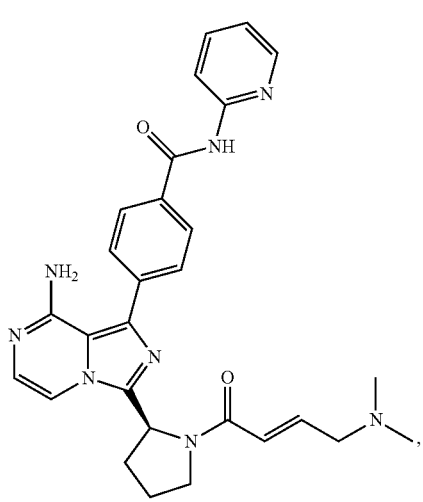
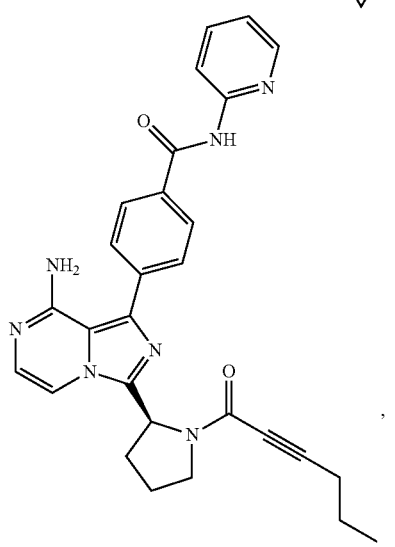
and pharmaceutically-acceptable salts, cocrystals, hydrates, solvates, or prodrugs thereof. In an embodiment, the JAK-2 inhibitor is selected from the group consisting of:

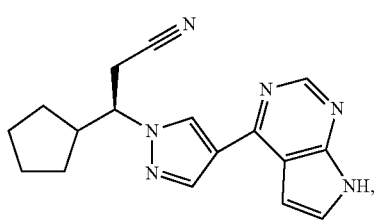

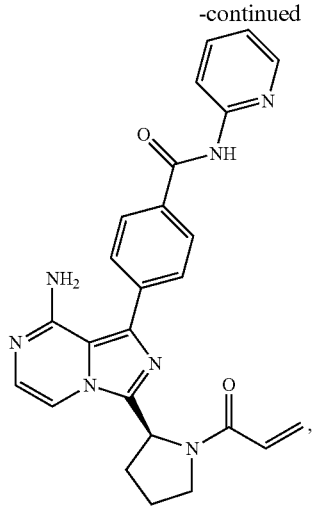

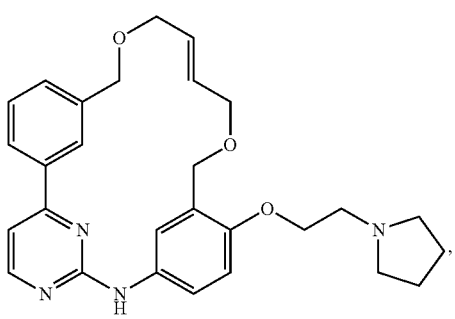

and pharmaceutically-acceptable salts, cocrystals, hydrates, solvates, and prodrugs thereof.

In an embodiment, the invention provides a method of treating a cancer in a human intolerant to a bleeding event comprising the step of administering (1) a therapeutically effective amount of a Janus kinase-2 (JAK-2) inhibitor or a pharmaceutically acceptable salt, solvate, hydrate, cocrystal, or prodrug thereof, and (2) a therapeutically effective amount of a Bruton's tyrosine kinase (BTK) inhibitor or a pharmaceutically acceptable salt, solvate, hydrate, cocrystal, or prodrug thereof, wherein the BTK inhibitor is selected from the group consisting of:

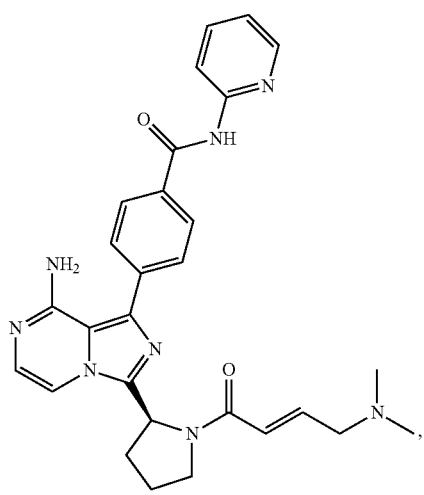

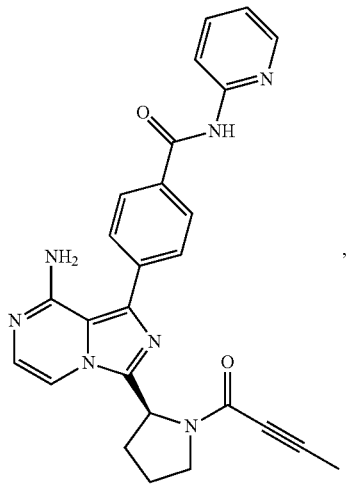

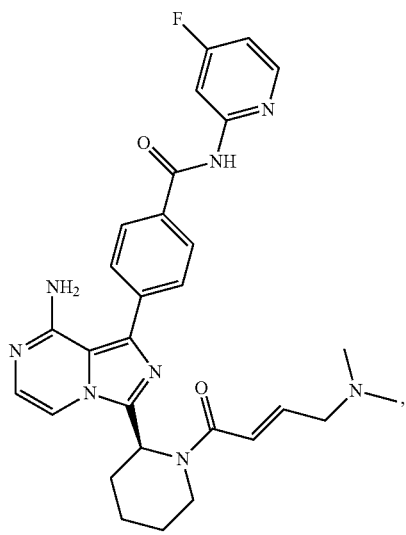

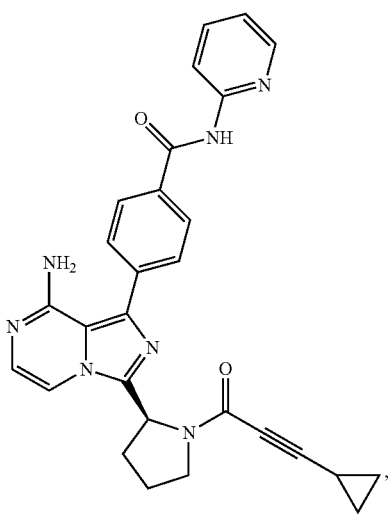

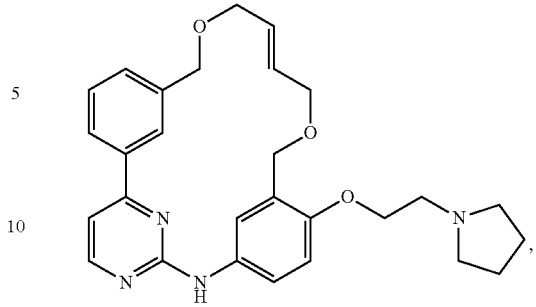

and pharmaceutically-acceptable salts, cocrystals, hydrates, solvates, or prodrugs thereof. In an embodiment, the bleeding event is selected from the group consisting of subdural hematoma, gastrointestinal bleeding, hematuria, post-procedural hemorrhage, bruising, petechiae, and combinations thereof. In an embodiment, the JAK-2 inhibitor is selected from the group consisting of:

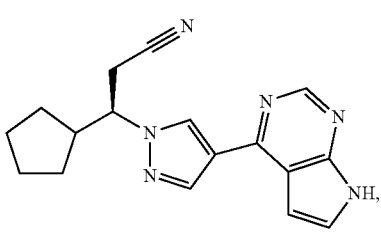

and pharmaceutically-acceptable salts, cocrystals, hydrates, solvates, and prodrugs thereof.

In an embodiment, the invention provides a method of treating a cancer in a human intolerant to a bleeding event comprising the step of administering (1) a therapeutically effective amount of a Janus kinase-2 (JAK-2) inhibitor or a pharmaceutically acceptable salt, solvate, hydrate, cocrystal, or prodrug thereof, and (2) a therapeutically effective amount of a Bruton's tyrosine kinase (BTK) inhibitor or a pharmaceutically acceptable salt, solvate, hydrate, cocrystal, or prodrug thereof, further comprising the step of administering a therapeutically effective amount of an anticoagulant or antiplatelet active pharmaceutical ingredient. In an embodiment, the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof. In an embodiment, the cancer is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, esophageal cancer, testicular cancer, gynecological cancer, thyroid cancer, aquired immune deficiency syndrome (AIDS)-related cancers (e.g., lymphoma and Kaposi's sarcoma), viral-induced cancer, glioblastoma, esophageal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hogkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, Burkitt's lymphoma, and myelofibrosis.

In some embodiments, the invention provides a composition comprising therapeutically effective amounts of (1) a JAK-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof, for use in the treatment of cancer. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-γ inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-γ,δ inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof, for use in the treatment of cancer; and (3) a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; and (4) a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a method of treating leukemia, lymphoma or a solid tumor cancer in a subject, comprising co-administering to a mammal in need thereof any of the foregoing compositions.

In some embodiments, the invention provides a method of treating leukemia, lymphoma or a solid tumor cancer in a subject, comprising co-administering to a mammal in need thereof a therapeutically effective amount of a PI3K inhibitor and a BTK inhibitor.

In some embodiments, the invention provides a method of treating leukemia, lymphoma or a solid tumor cancer in a subject, comprising co-administering to a mammal in need thereof a therapeutically effective amount of a PI3K-γ inhibitor and a BTK inhibitor.

In some embodiments, the invention provides a method of treating leukemia, lymphoma or a solid tumor cancer in a subject, comprising co-administering to a mammal in need thereof a therapeutically effective amount of a PI3K-δ inhibitor and a BTK inhibitor.

In some embodiments, the invention provides a method of treating leukemia, lymphoma or a solid tumor cancer in a subject, comprising co-administering to a mammal in need thereof a therapeutically effective amount of a PI3K-γ,δ inhibitor and a BTK inhibitor.

In some embodiments, the invention provides a method of treating leukemia, lymphoma or a solid tumor cancer in a subject, comprising co-administering to a mammal in need thereof a therapeutically effective amount of a JAK-2 inhibitor and a BTK inhibitor.

In some embodiments, the invention provides a method of treating leukemia, lymphoma or a solid tumor cancer in a subject, comprising co-administering to a mammal in need thereof a therapeutically effective amount of a PI3K inhibitor, a JAK-2 inhibitor, and a BTK inhibitor.

In some embodiments, the invention provides a method of treating leukemia, lymphoma or a solid tumor cancer in a subject, comprising co-administering to a mammal in need thereof a therapeutically effective amount of a PI3K-γ inhibitor, a JAK-2 inhibitor, and a BTK inhibitor.

In some embodiments, the invention provides a method of treating leukemia, lymphoma or a solid tumor cancer in a subject, comprising co-administering to a mammal in need thereof a therapeutically effective amount of a PI3K-δ inhibitor, a JAK-2 inhibitor, and a BTK inhibitor.

In some embodiments, the invention provides a method of treating leukemia, lymphoma or a solid tumor cancer in a subject, comprising co-administering to a mammal in need thereof a therapeutically effective amount of a PI3K-γ,δ inhibitor, a JAK-2 inhibitor, and a BTK inhibitor.

BRIEF DESCRIPTION OF THE DRAWINGS

The foregoing summary, as well as the following detailed description of the invention, will be better understood when read in conjunction with the appended drawings.

("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 18:
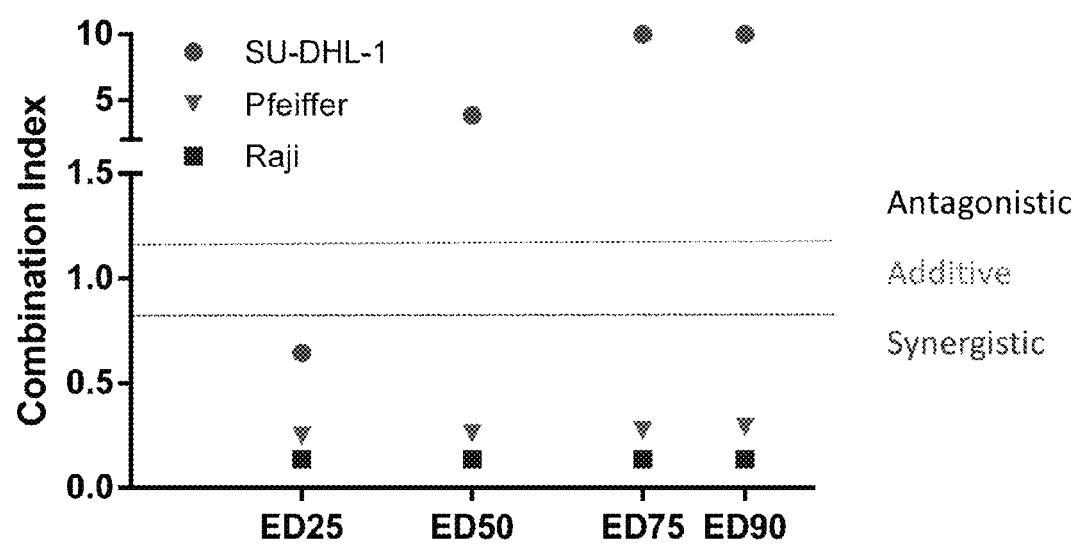

FIG. 18 illustrates the synergy observed in certain cell lines when the BTK inhibitor of Formula (XVIII) and the PI3K-δ inhibitor of Formula (IX) are combined. The tested cell lines include Raji (B lymphocyte, Burkitt's lymphoma), SU-DHL-1 (DLBCL-ABC), and Pfeiffer (follicular lymphoma). The dose-effect curves for these cell lines are given in FIG. 19, FIG. 20, and FIG. 21.

Figure 19:
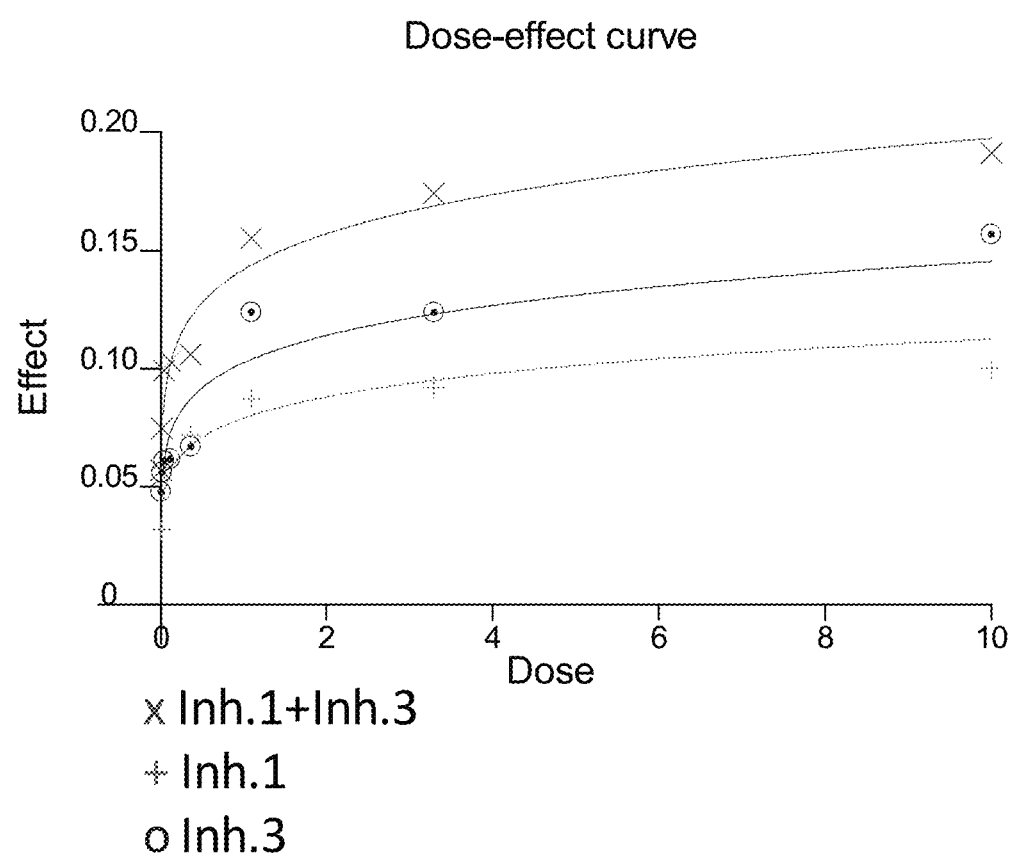

FIG. 19 illustrates the dose-effect curves obtained for the tested Raji cell line (B lymphocyte, Burkitt's lymphoma) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 20:
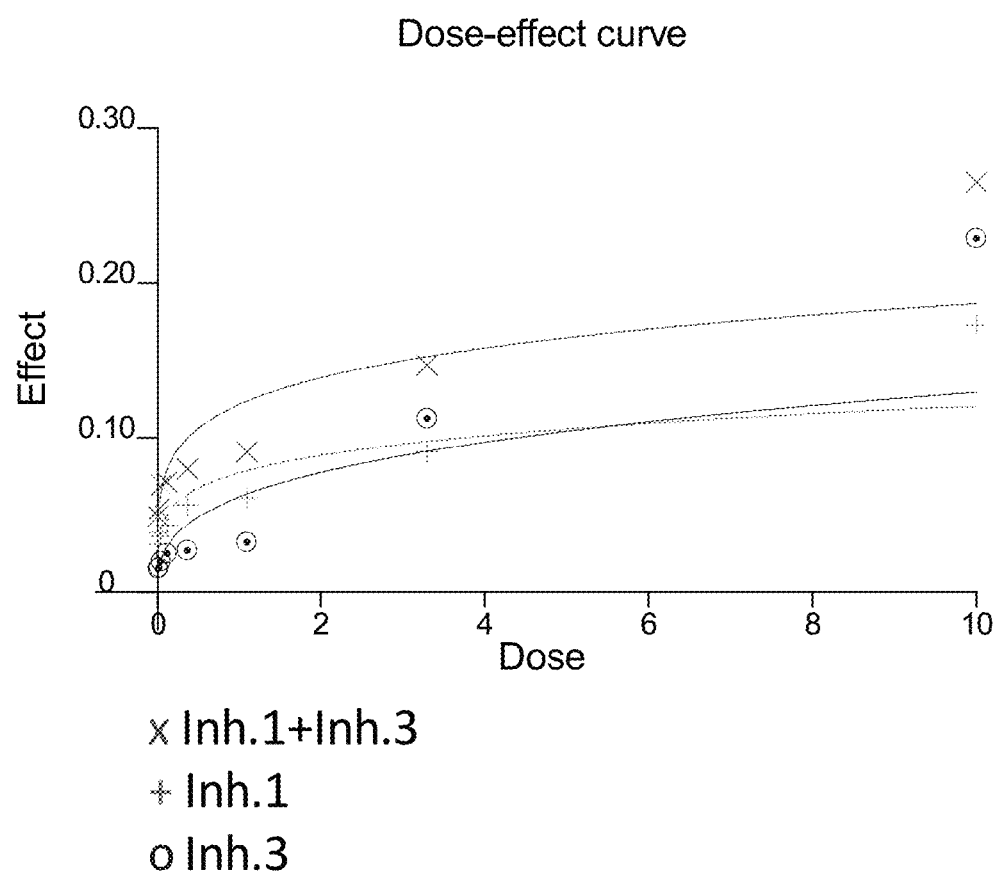

FIG. 20 illustrates the dose-effect curves obtained for the tested SU-DHL-1 cell line (DLBCL-ABC) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 21:
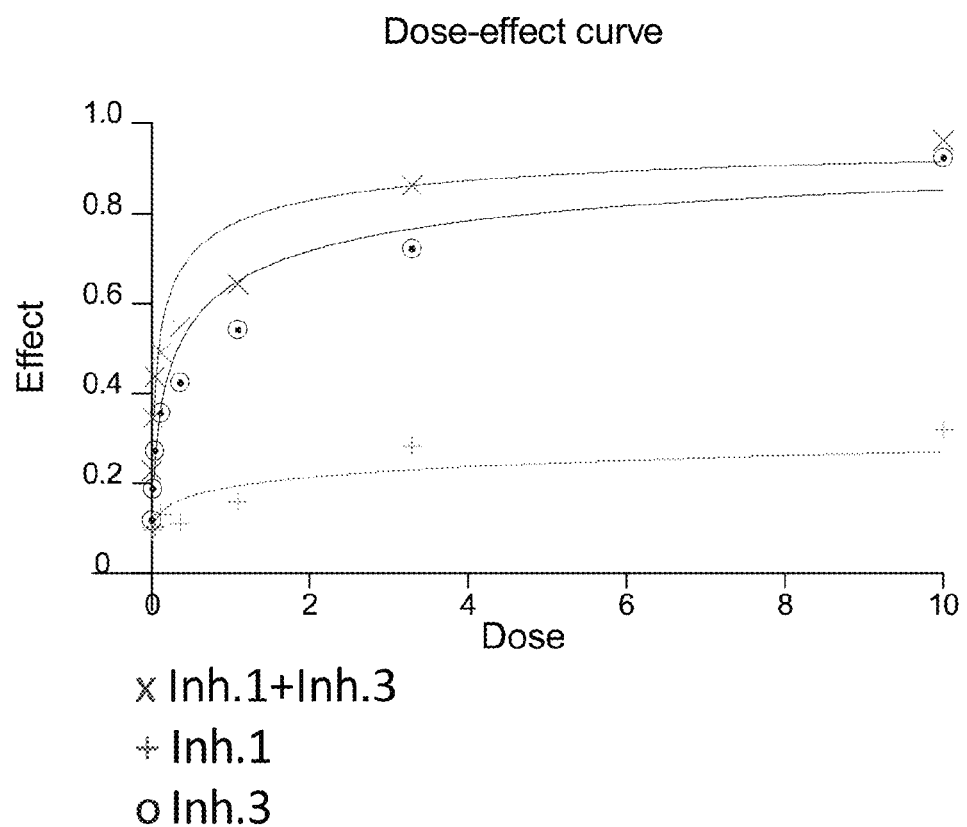

FIG. 21 illustrates the dose-effect curves obtained for the tested Pfeiffer cell line (follicular lymphoma) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 22:
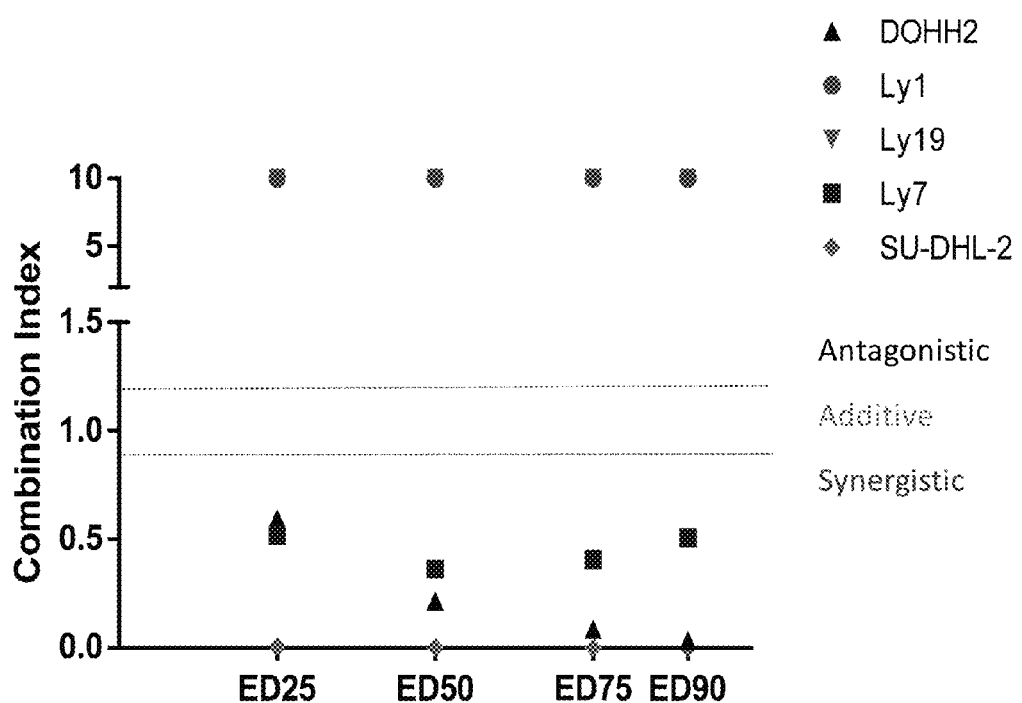

FIG. 22 illustrates the synergy observed in certain cell lines when the BTK inhibitor of Formula (XVIII) and the PI3K-δ inhibitor of Formula (IX) are combined. The tested cell lines include Ly1 (Germinal center B-cell like diffuse large B-cell lymphoma, DLBCL-GCB), Ly7 (DLBCL-GCB), Ly19 (DLBCL-GCB), SU-DHL-2 (Activated B-cell like diffuse large B-cell lymphoma, DLBCL-ABC), and DOHH2 (follicular lymphoma, FL). The dose-effect curves for these cell lines are given in FIG. 23, FIG. 24, FIG. 25, and FIG. 26, except for the Ly19 cell line, which is not graphed because of a negative slope.

Figure 23:
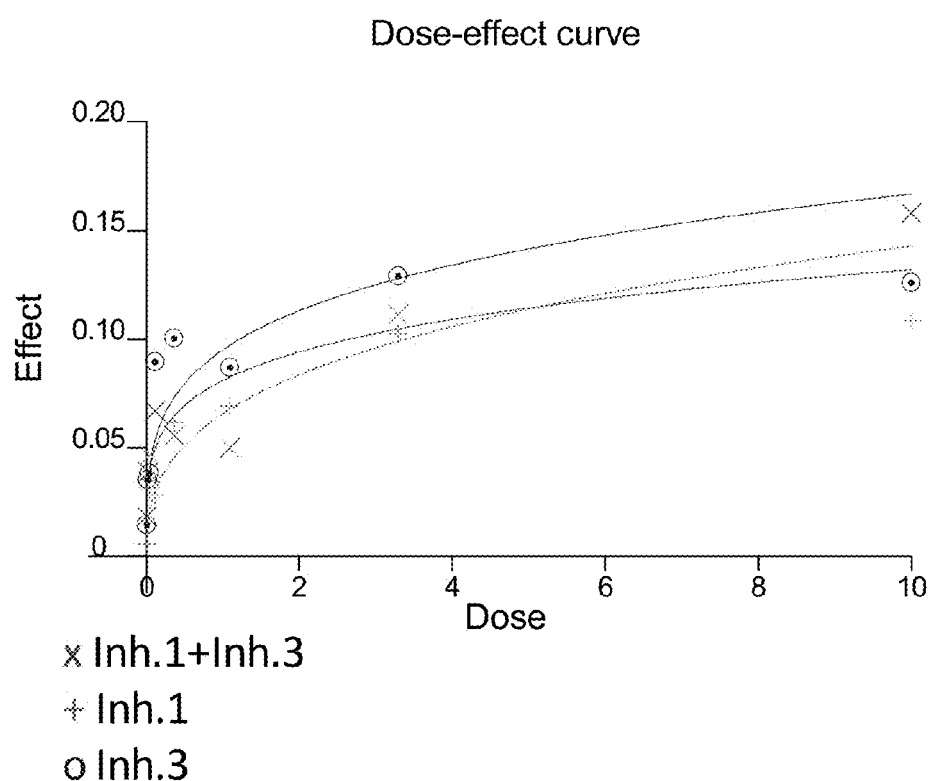

FIG. 23 illustrates the dose-effect curves obtained for the tested Ly1 cell line (DLBCL-GCB) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 24:
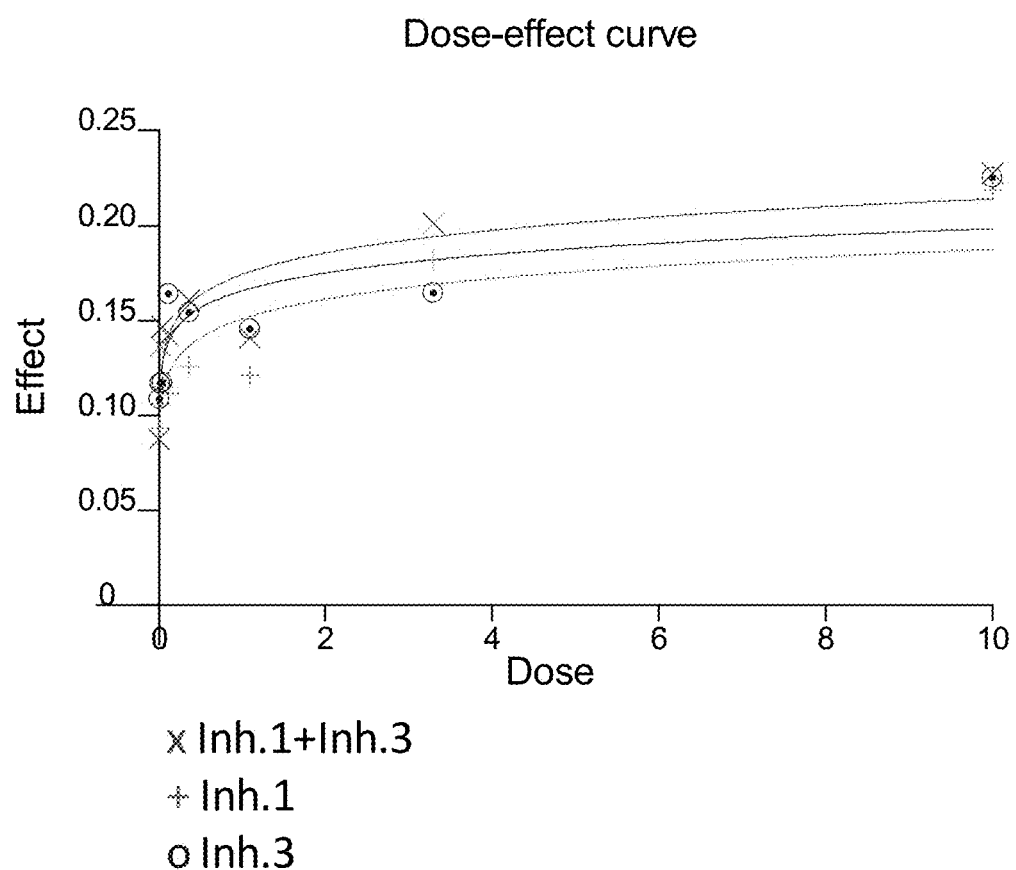

FIG. 24 illustrates the dose-effect curves obtained for the tested Ly7 cell line (DLBCL-GCB) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 25:
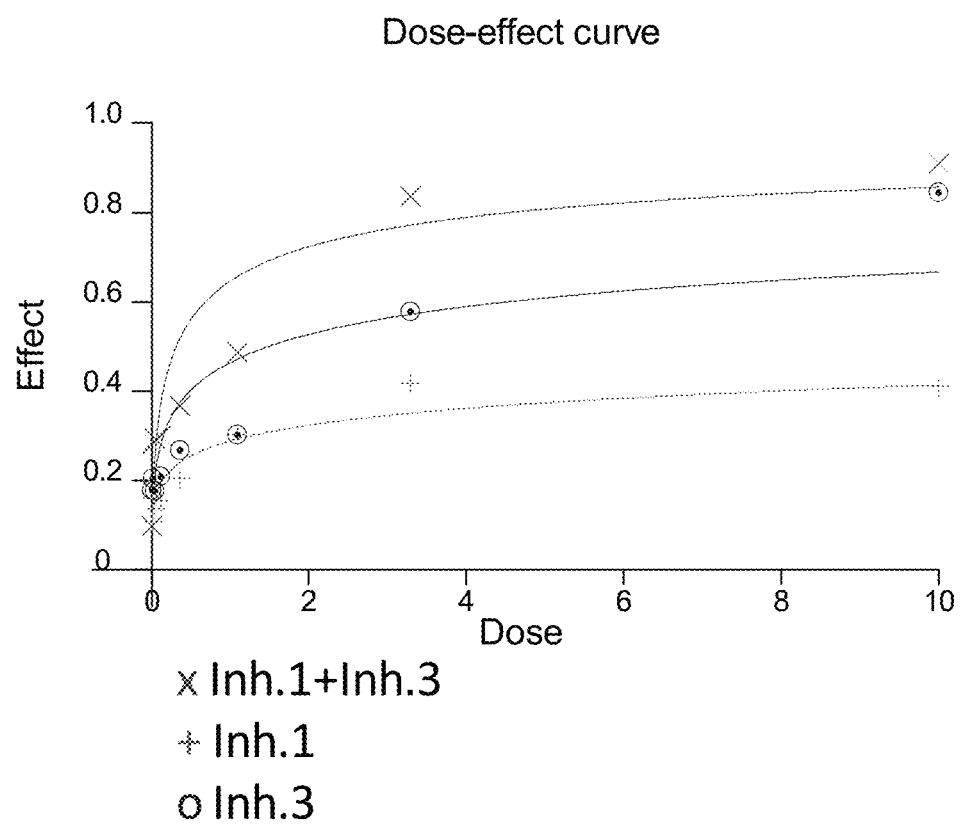

FIG. 25 illustrates the dose-effect curves obtained for the tested DOHH2 cell line (FL) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 26:
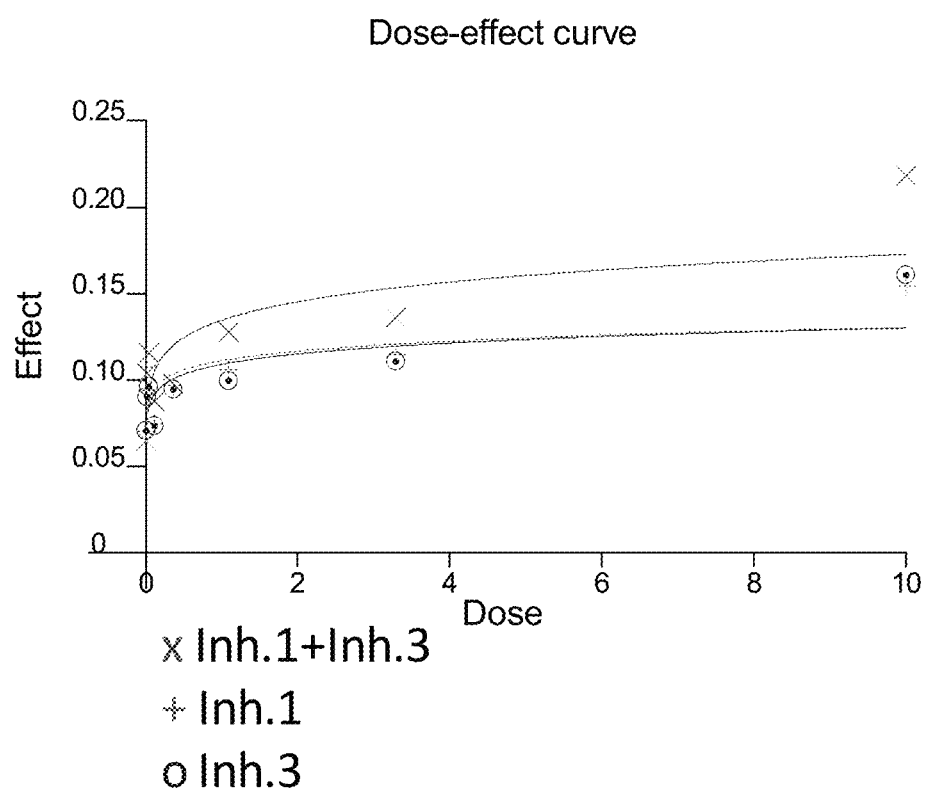

FIG. 26 illustrates the dose-effect curves obtained for the tested SU-DHL-2 cell line (DLBCL-ABC) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 27:
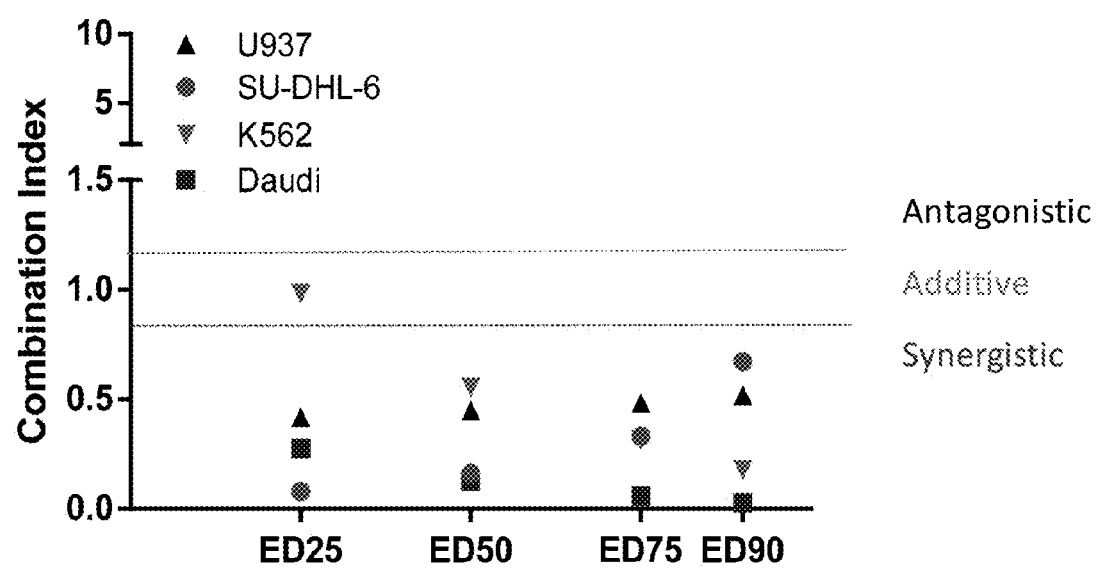

FIG. 27 illustrates the synergy observed in certain cell lines when Formula (XVIII) and Formula (IX) are combined. The tested cell lines include U937 (histiocytic lymphoma and/or myeloid), K562 (leukemia, myeloid, and/or chronic myelogenous leukemia), Daudi (human Burkitt's lymphoma), and SU-DHL-6 (DLBCL-GCB and/or peripheral T-cell lymphoma, PTCL). The dose-effect curves for these cell lines are given in FIG. 28, FIG. 29, FIG. 30, and FIG. 31.

Figure 28:
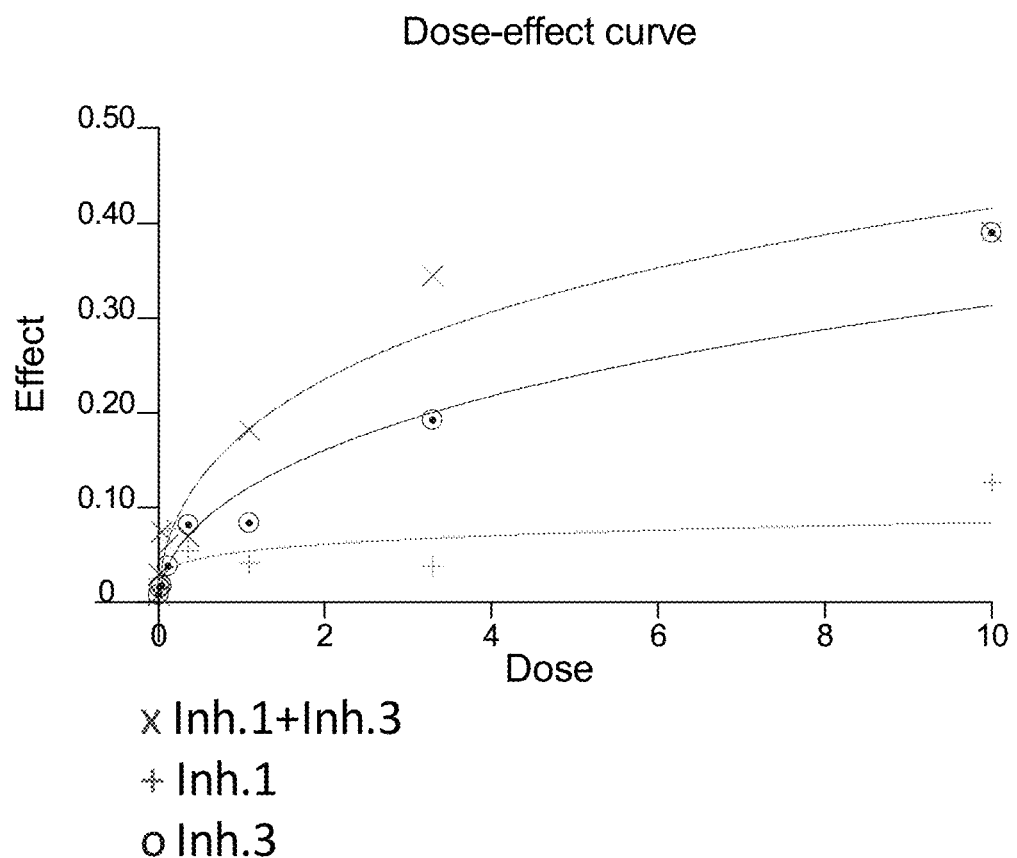

FIG. 28 illustrates the dose-effect curves obtained for the tested U937 cell line (histiocytic lymphoma and/or myeloid) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 29:
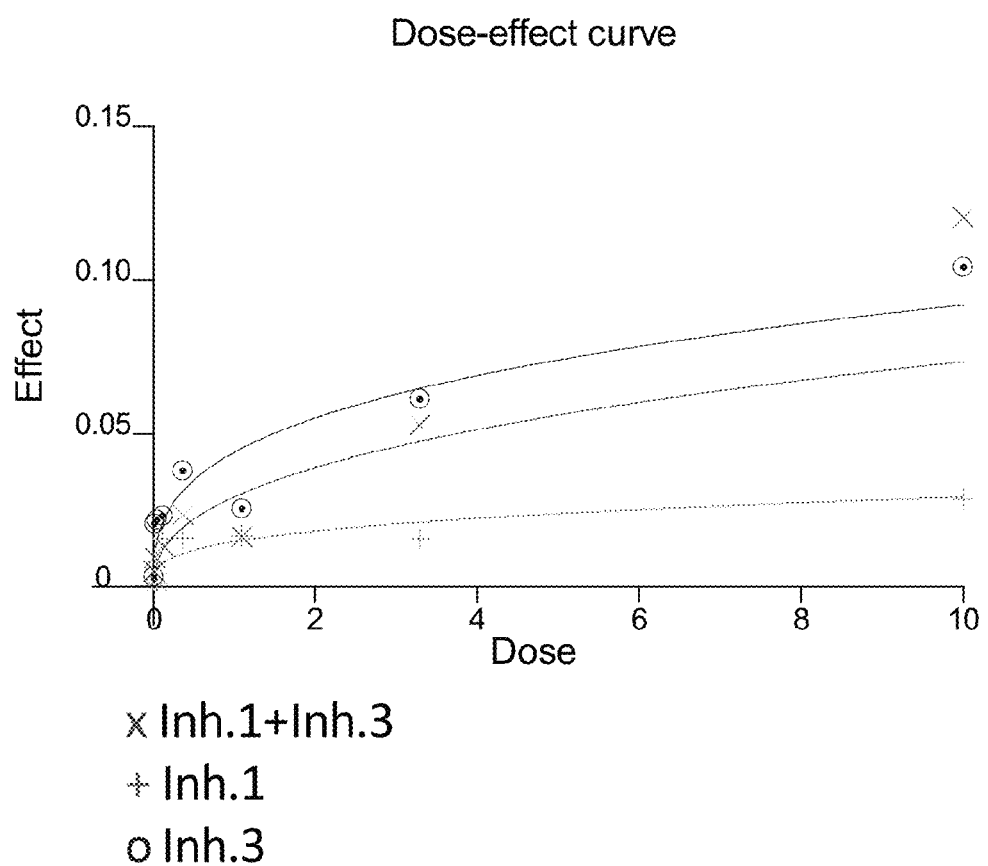

FIG. 29 illustrates the dose-effect curves obtained for the tested K562 cell line (leukemia, myeloid, and/or chronic myelogenous leukemia) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 30:
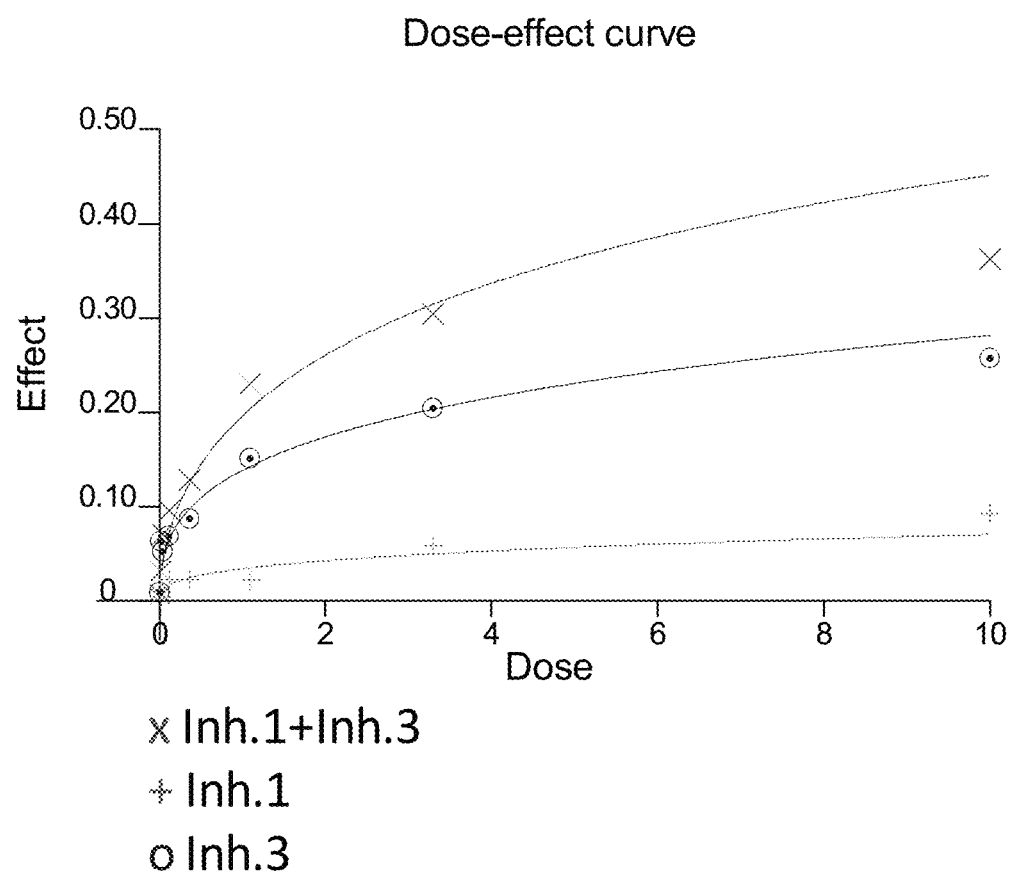

FIG. 30 illustrates the dose-effect curves obtained for the tested Daudi cell line (human Burkitt's lymphoma) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 31:
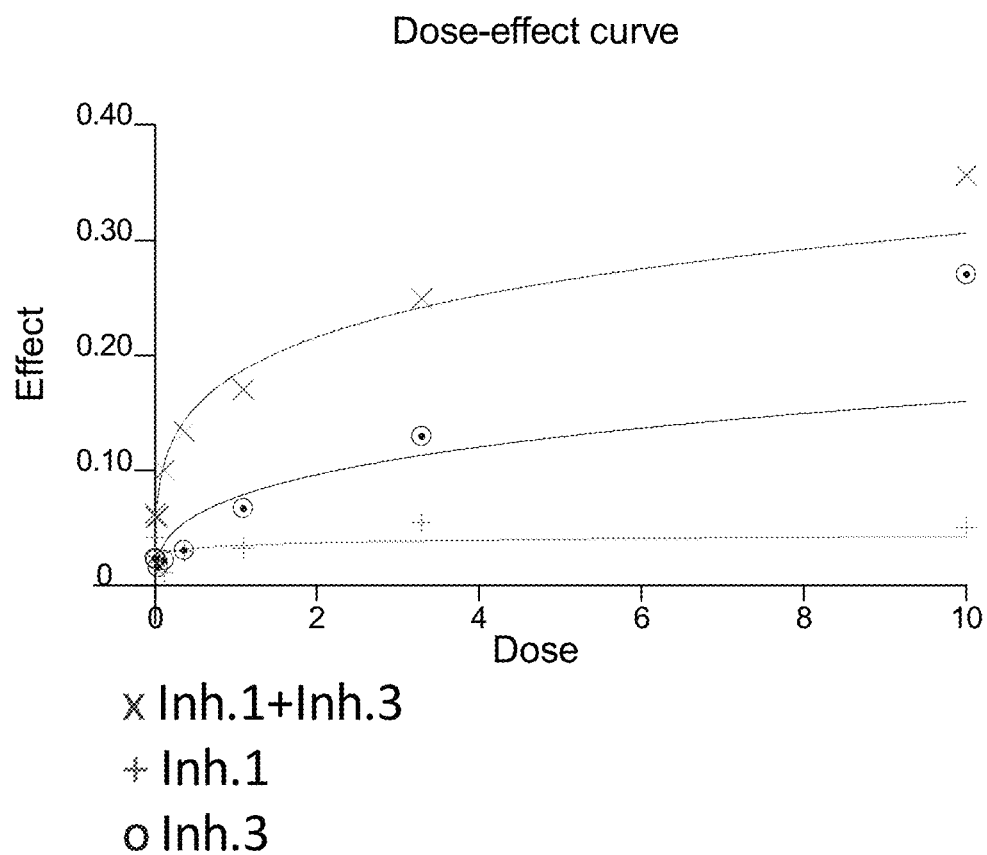

FIG. 31 illustrates the dose-effect curves obtained for the tested SU-DHL-6 cell line (DLBCL-GCB and/or PTCL) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 32:
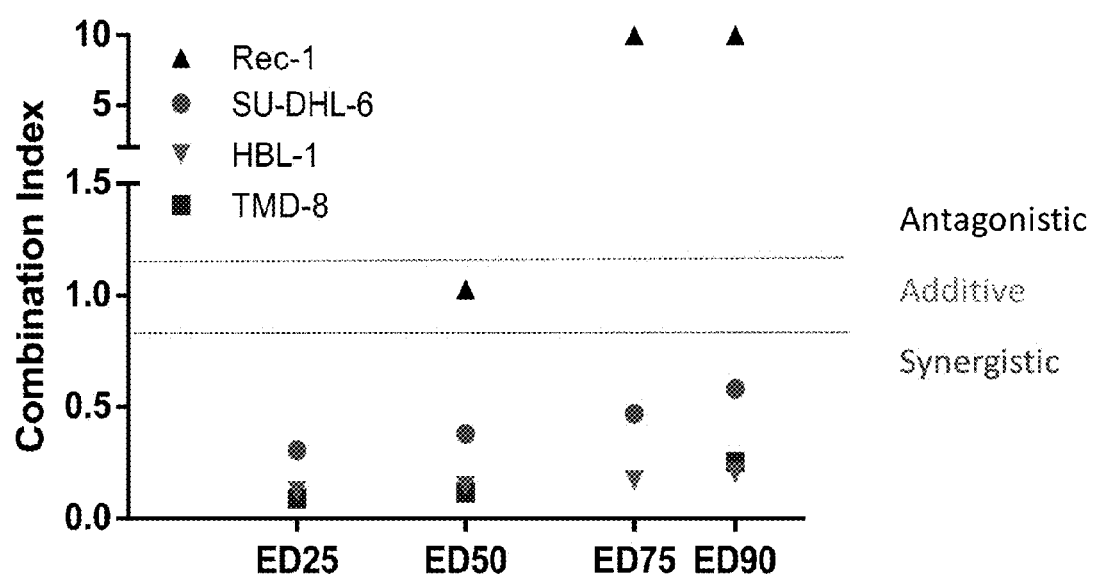

FIG. 32 illustrates the synergy observed in certain cell lines when the BTK inhibitor of Formula (XVIII) and the PI3K-δ inhibitor of Formula (IX) are combined. The tested cell lines include SU-DHL-6 (DLBCL-GCB or PTCL), TMD-8 (DLBCL-ABC), HBL-1 (DLBCL-ABC), and Rec-1 (follicular lymphoma). The dose-effect curves for these cell lines are given in FIG. 34, FIG. 35, FIG. 36, and FIG. 37.

Figure 33:
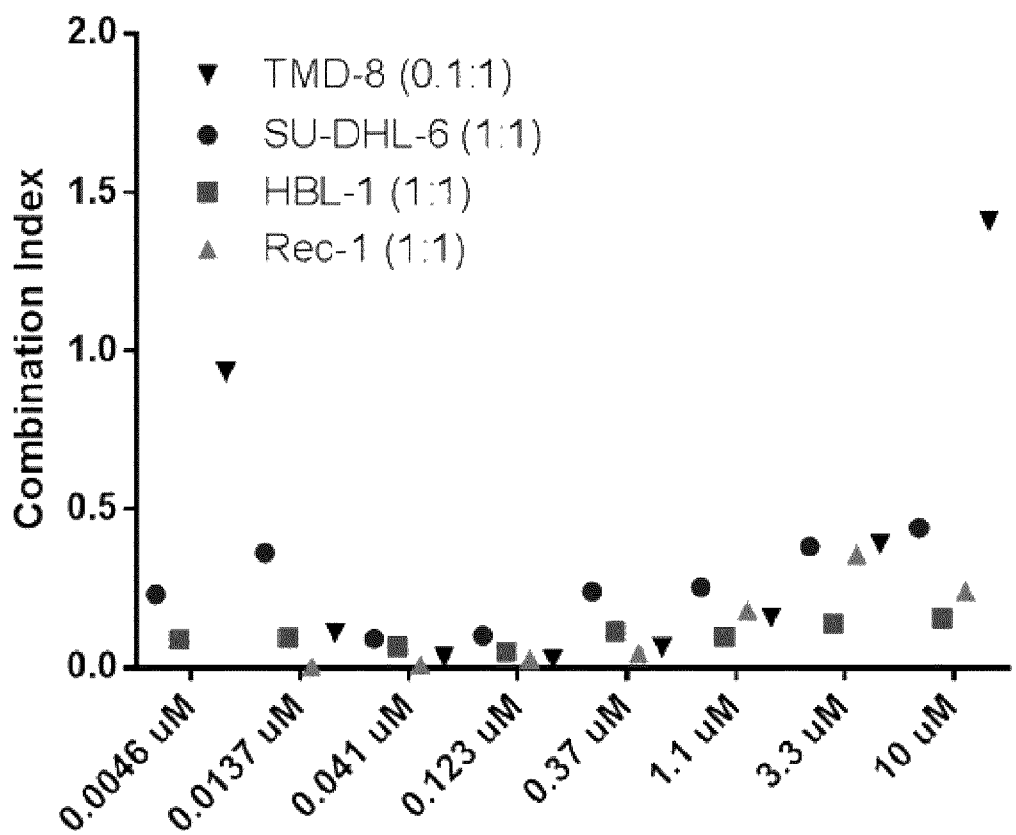

FIG. 33 illustrates the synergy observed in certain cell lines when the BTK inhibitor of Formula (XVIII) and the PI3K-δ inhibitor of Formula (IX) are combined. The tested cell lines include SU-DHL-6 (DLBCL-GCB or PTCL), TMD-8 (DLBCL-ABC), HBL-1 (DLBCL-ABC), and Rec-1 (follicular lymphoma). All corresponding CIs are shown for each of the combinations tested as listed on the x axis.

Figure 34:
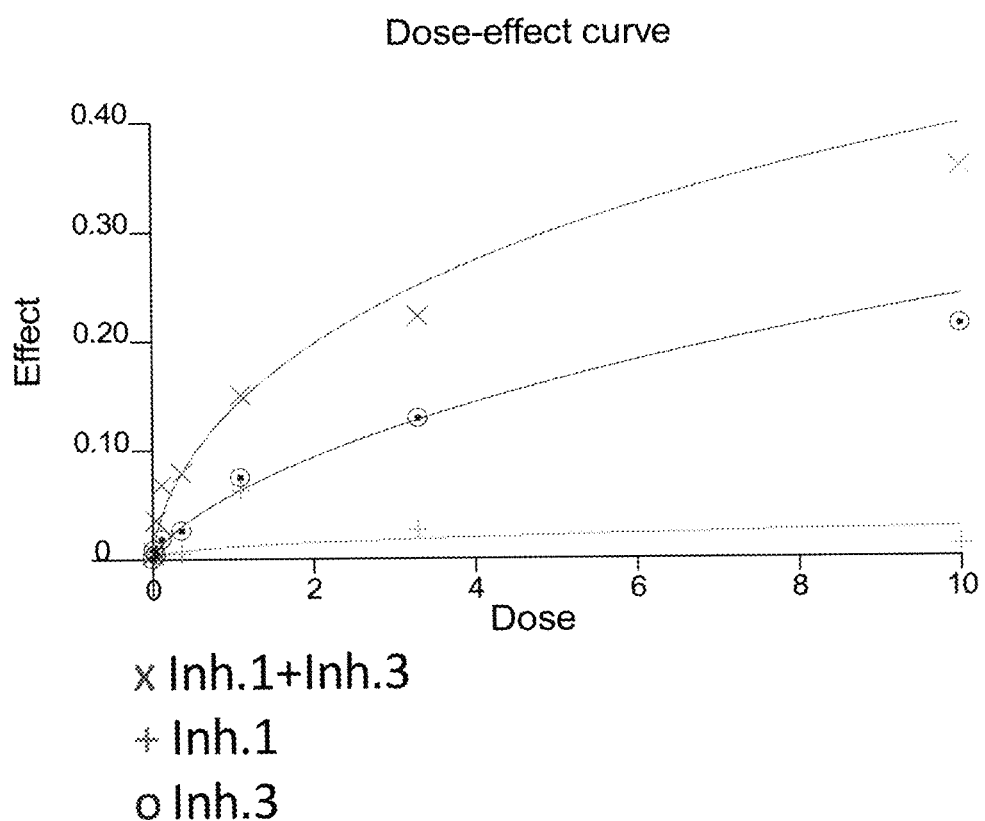

FIG. 34 illustrates the dose-effect curves obtained for the tested SU-DHL-6 cell line (DLBCL-GCB or PTCL) cell line using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 35:
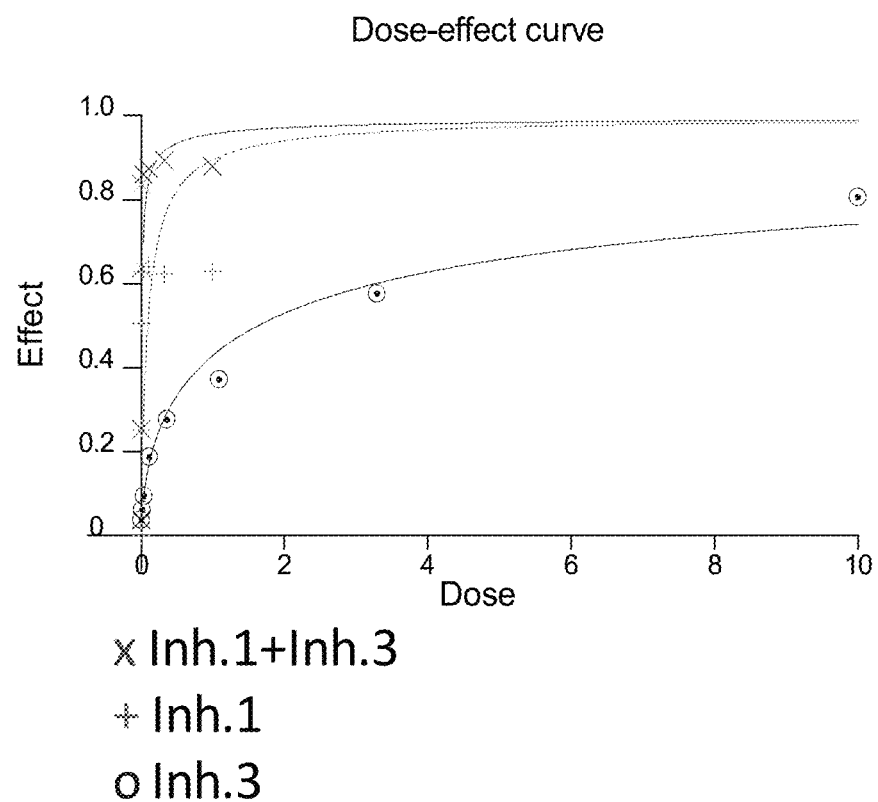

FIG. 35 illustrates the dose-effect curves obtained for the tested TMD-8 cell line (DLBCL-ABC) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 36:
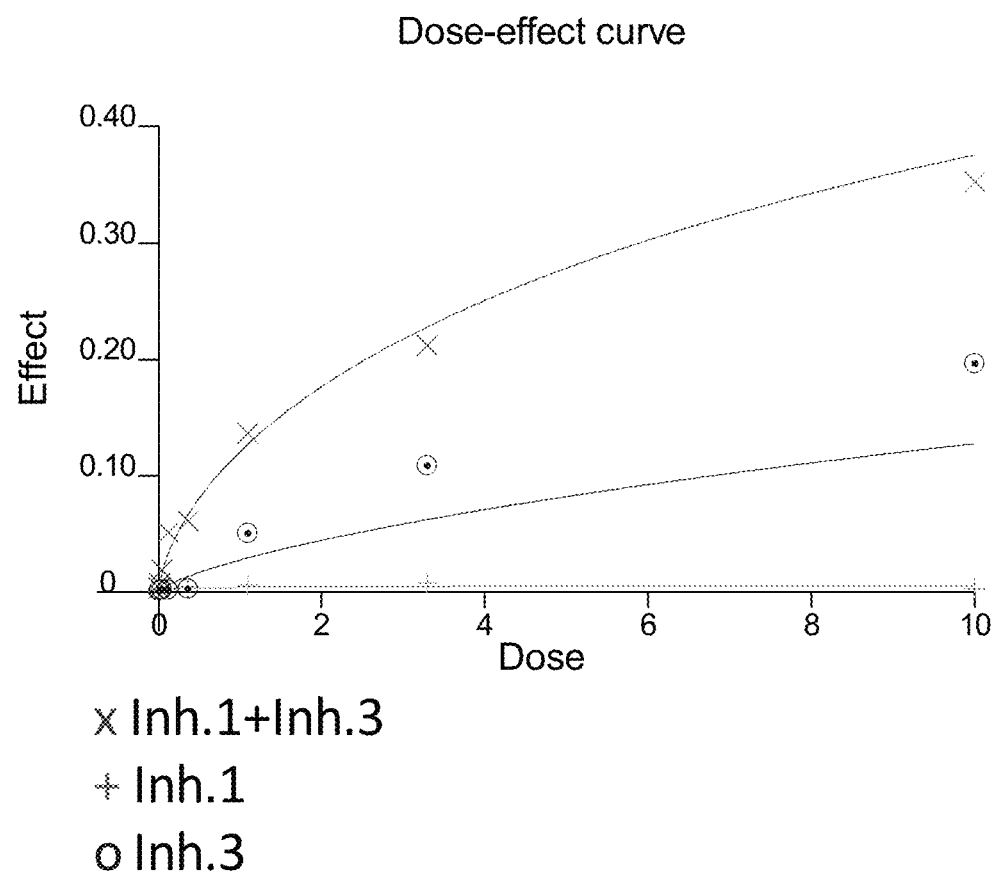

FIG. 36 illustrates the dose-effect curves obtained for the tested HBL-1 cell line (DLBCL-ABC) using combined dosing of the BTK inhibitor of Formula (XVIII) ("Inh.") and the PI3K-δ inhibitor of Formula (IX) ("Inh.3"). The y-axis ("Effect") is given in units of Fa (fraction affected) and the x-axis ("Dose") is given in linear units of μM.

Figure 37:
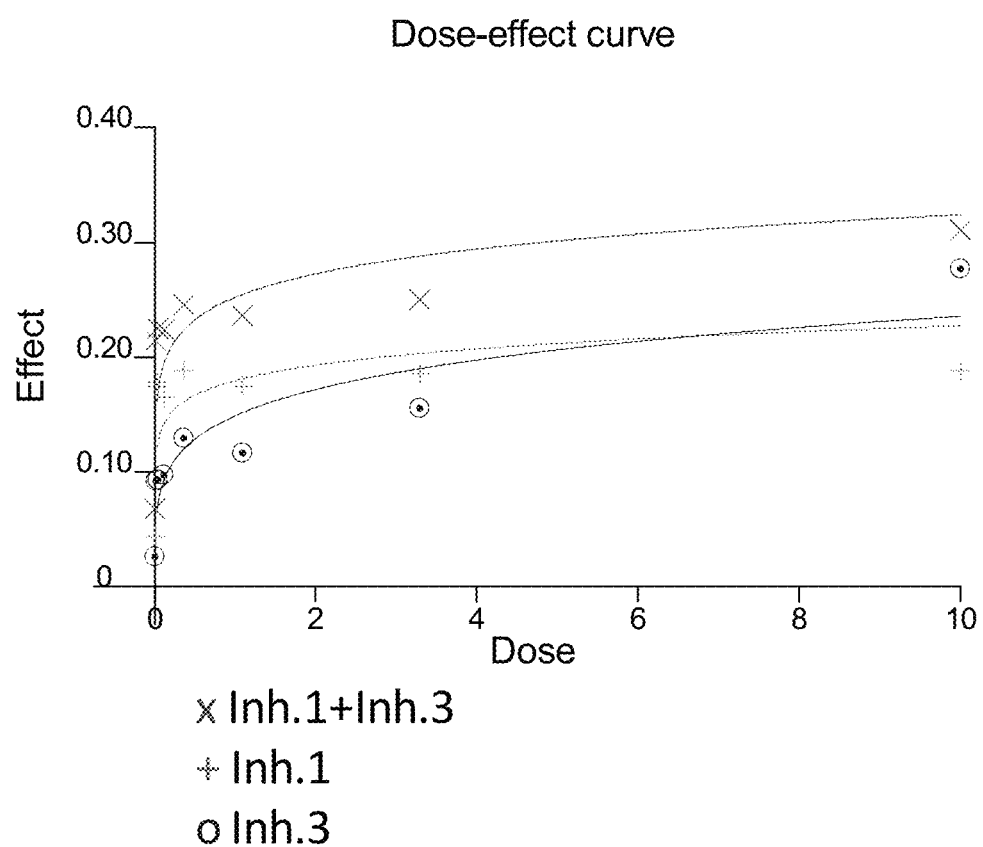

FIG. 37 illustrates the dose-effect curves obtained for the tested Rec-1 cell line (follicular lymphoma) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of μM.

Figure 38:
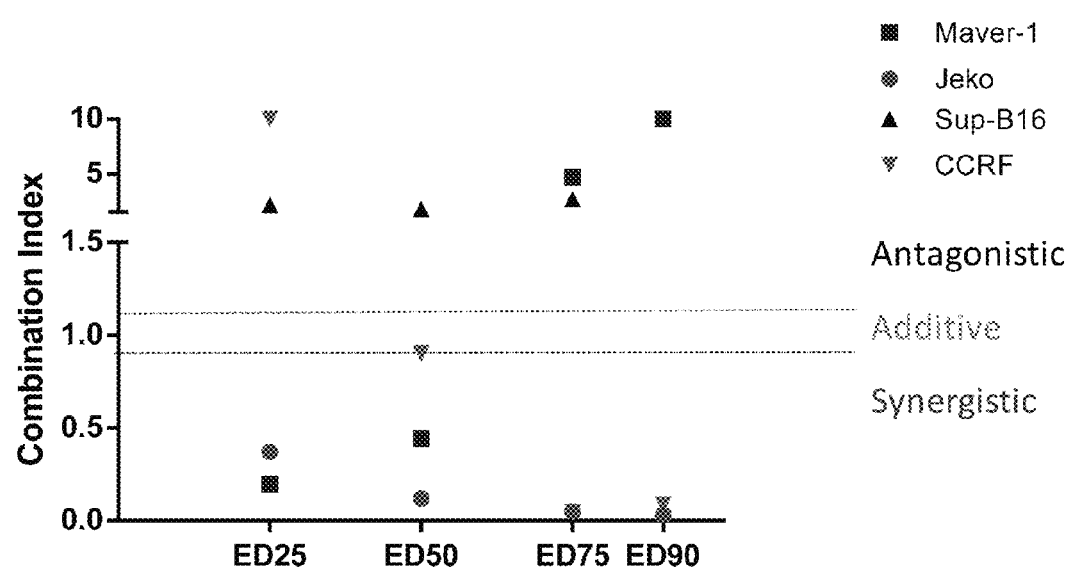

FIG. 38 illustrates the synergy observed in certain cell lines when the BTK inhibitor of Formula (XVIII) and the JAK-2 inhibitor of Formula XXX (ruxolitinib) are combined. The tested cell lines included Maver-1 (B cell lymphoma, mantle), Jeko (B cell lymphoma, mantle), SUP-B15 (B lymphoblast, acute lymphoblastic leukemia), and CCRF (B lymphoblast, acute lymphoblastic leukemia). The dose-effect curves for these cell lines are given in FIG. 39, FIG. 40, FIG. 41, and FIG. 42.

Figure 39:
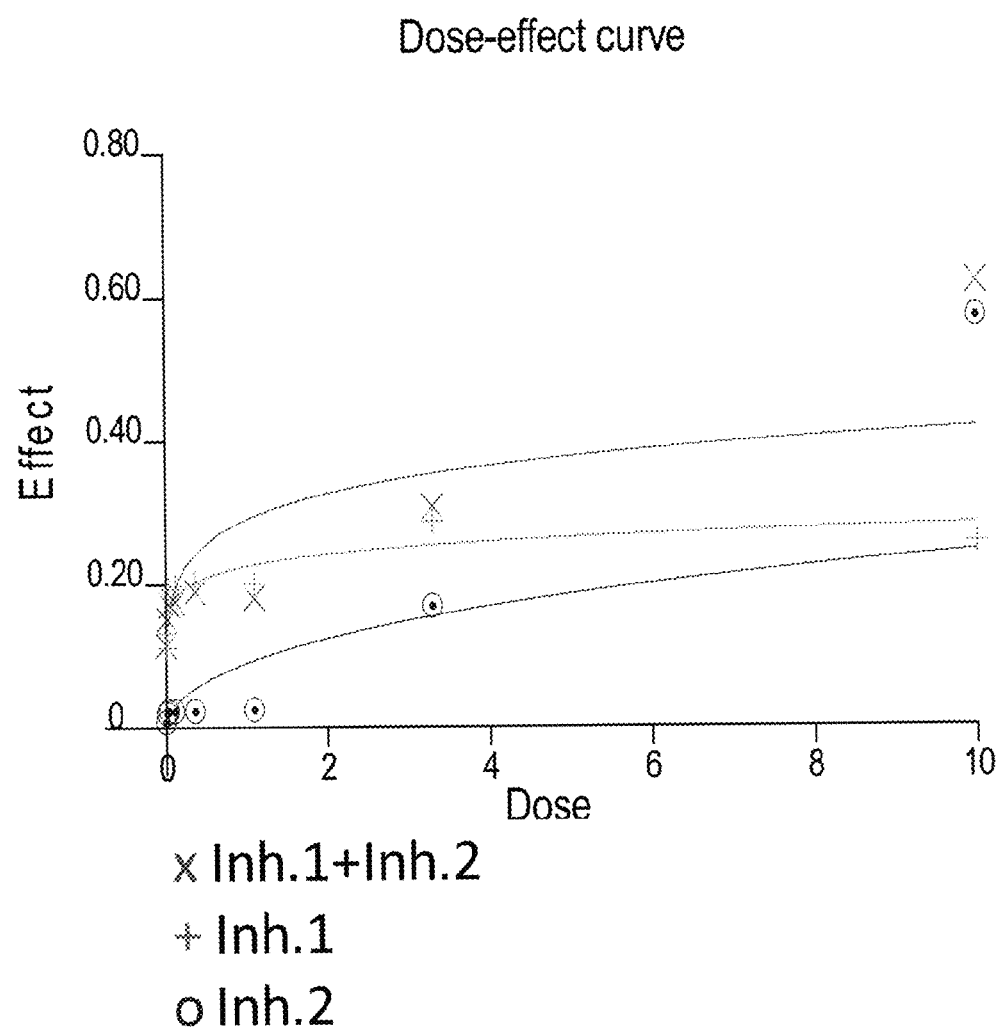

FIG. 39 illustrates the dose-effect curves obtained for the tested Maver-1 cell line (B cell lymphoma, mantle) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 40:
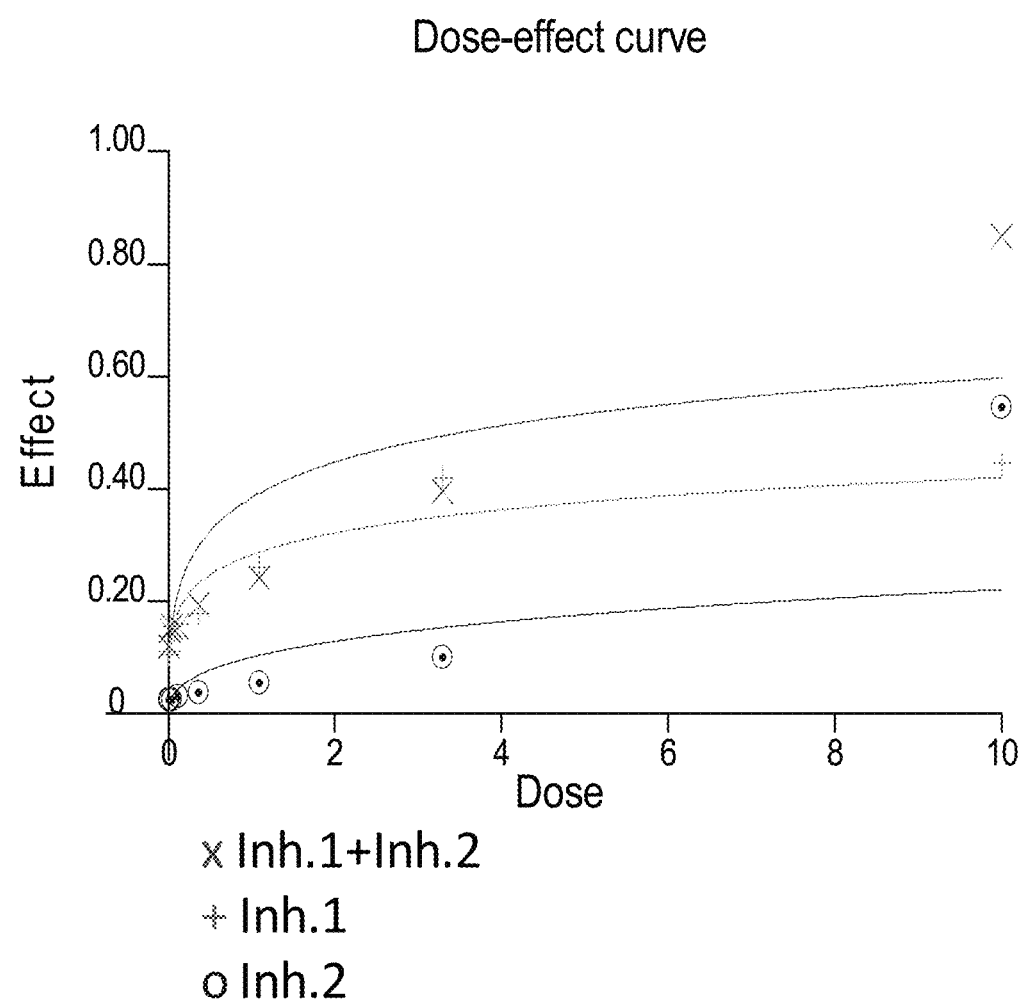

FIG. 40 illustrates the dose-effect curves obtained for the tested Jeko cell line (B cell lymphoma, mantle) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 41:
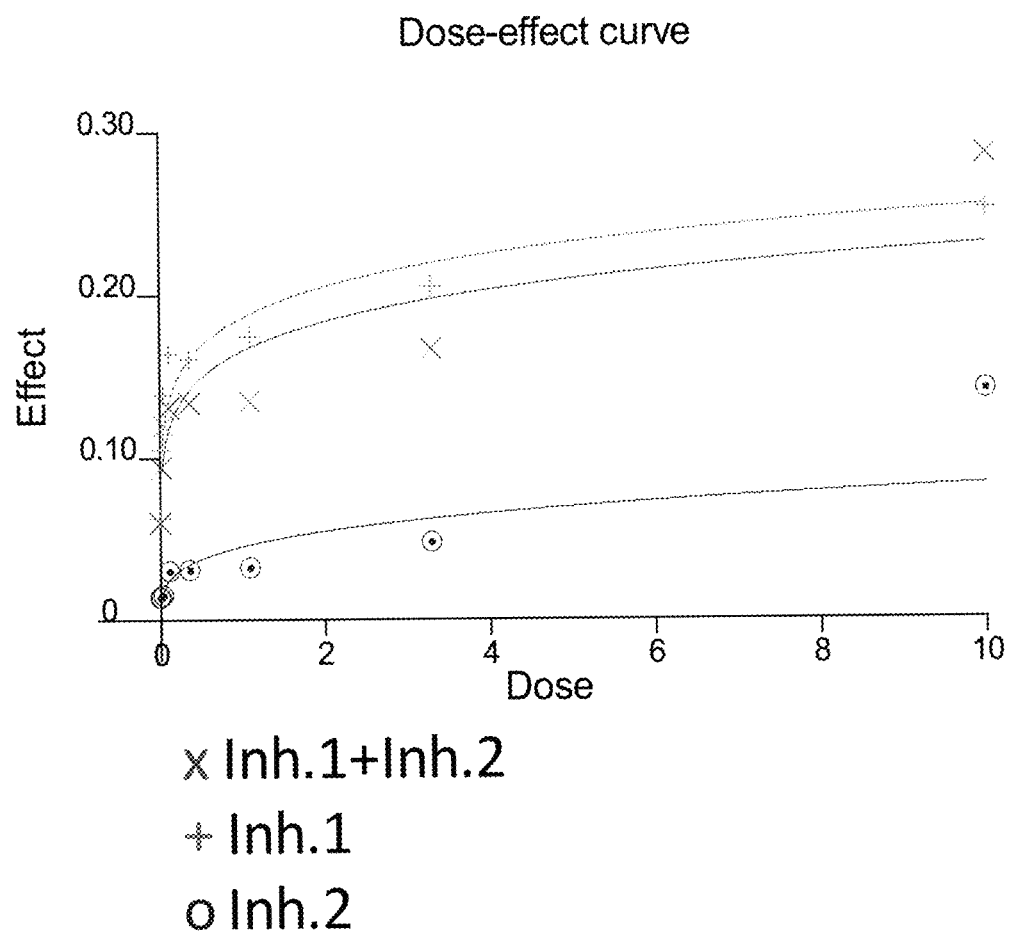

FIG. 41 illustrates the dose-effect curves obtained for the tested SUP-B15 cell line (B lymphoblast, acute lymphoblastic leukemia) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 42:
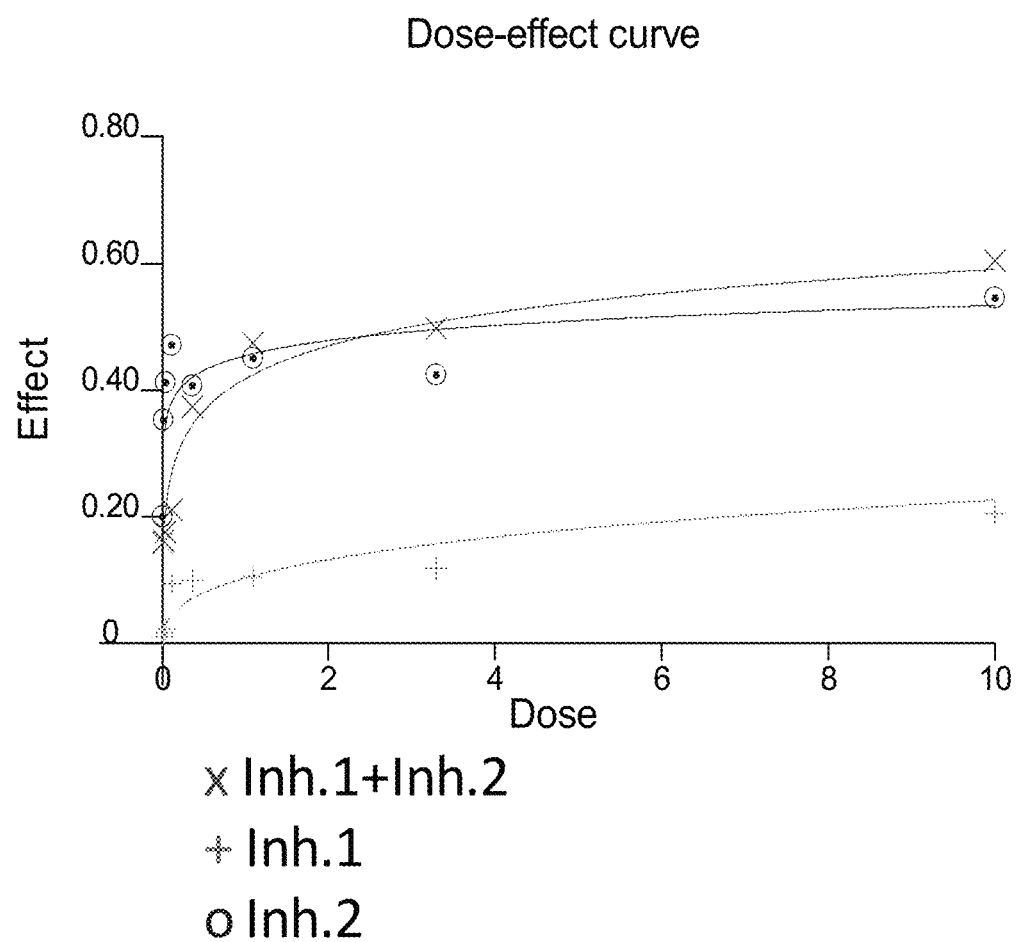

FIG. 42 illustrates the dose-effect curves obtained for the tested CCRF cell line (B lymphoblast, acute lymphoblastic leukemia) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 43:
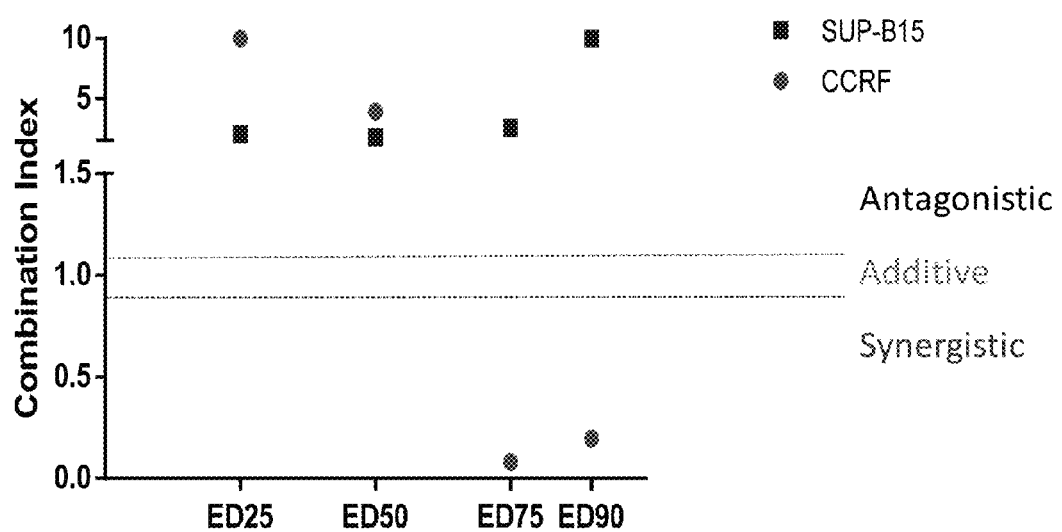

FIG. 43 illustrates the synergy observed in certain cell lines when the BTK inhibitor of Formula (XVIII) and the JAK-2 inhibitor of Formula XXX (ruxolitinib) are combined. Repeat experiments for two of the cell lines previously shown in FIG. 38 are shown, including SUP-B15 (B lymphoblast, acute lymphoblastic leukemia) and CCRF (B lymphoblast, acute lymphoblastic leukemia).

Figure 44:
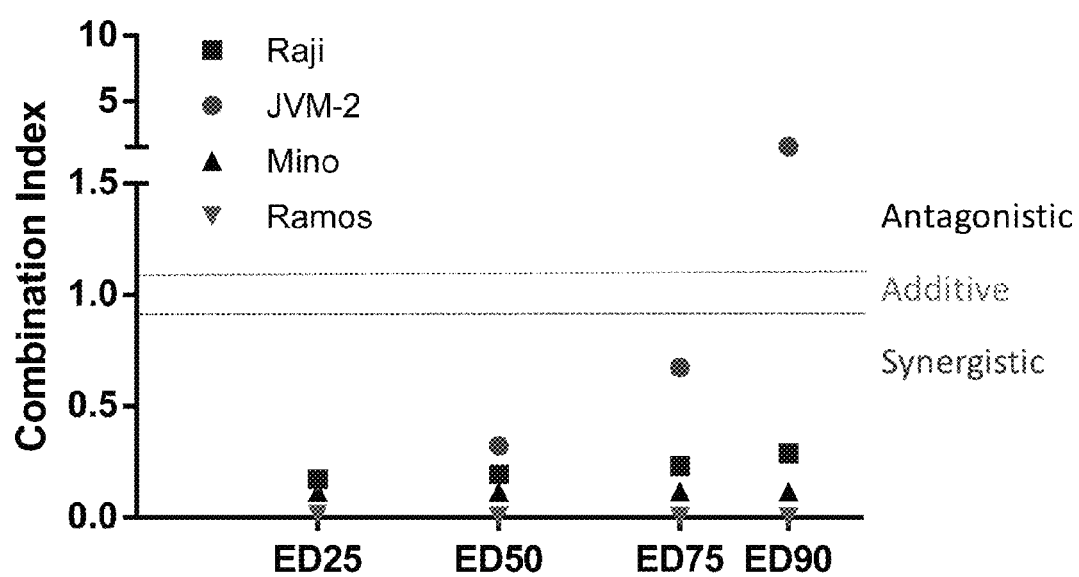

FIG. 44 illustrates the synergy observed in certain cell lines when the BTK inhibitor of Formula (XVIII) and the JAK-2 inhibitor of Formula XXX (ruxolitinib) are combined. The tested cell lines included JVM-2 (prolymphocytic leukemia), Raji (B lymphocyte, Burkitt's lymphoma), Ramos (B lymphocyte, Burkitt's lymphoma), and Mino (mantle cell lymphoma). The dose-effect curves for these cell lines are given in FIG. 45, FIG. 46, FIG. 47, and FIG. 48.

Figure 45:
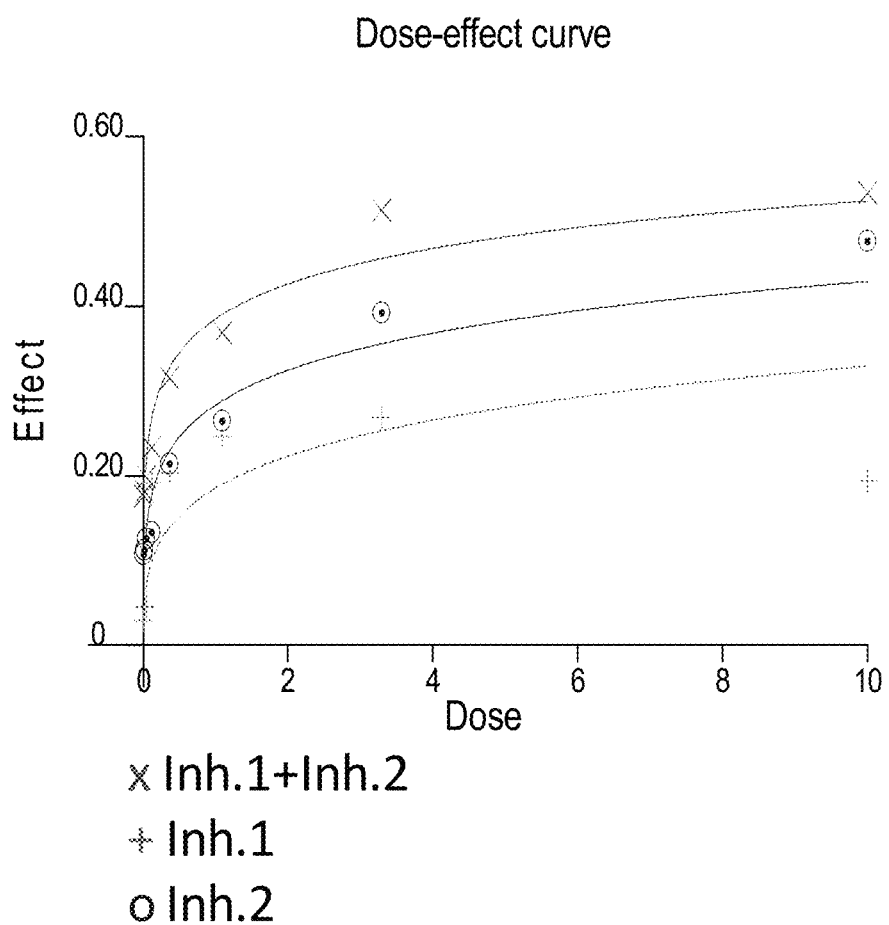

FIG. 45 illustrates the dose-effect curves obtained for the tested JVM-2 cell line (prolymphocytic leukemia) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 46:
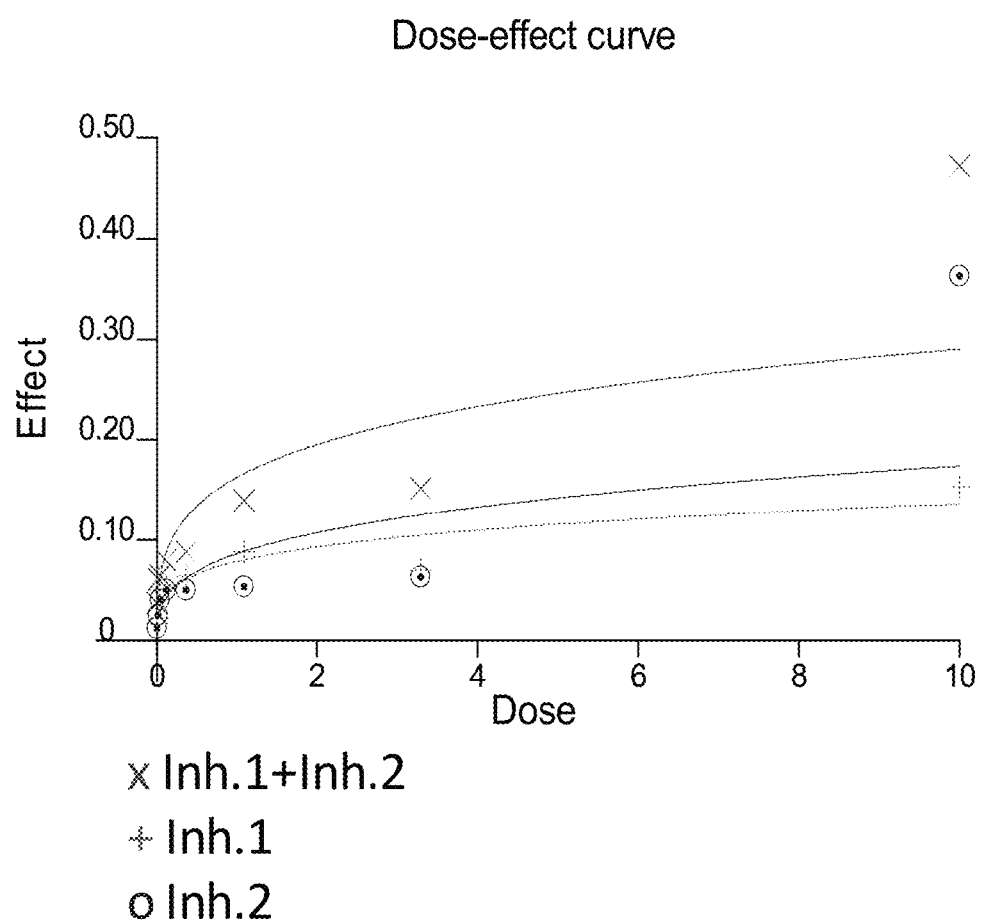

FIG. 46 illustrates the dose-effect curves obtained for the tested Raji cell line (B lymphocyte, Burkitt's lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 47:
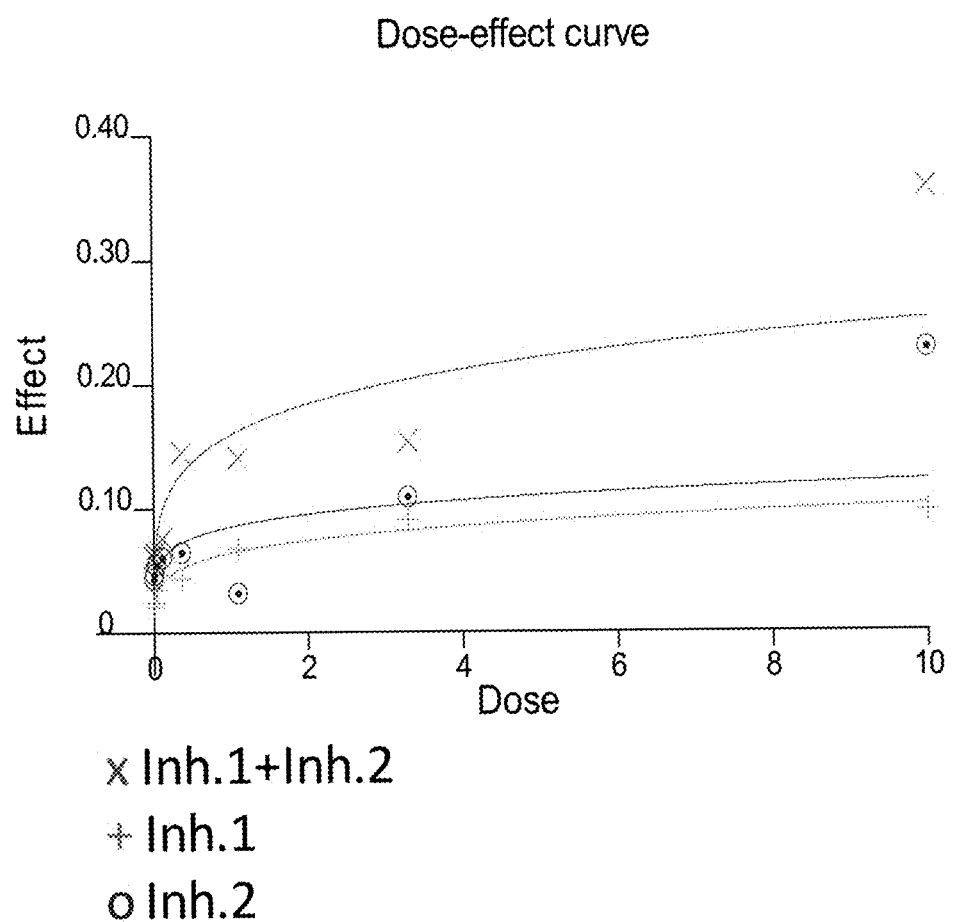

FIG. 47 illustrates the dose-effect curves obtained for the tested Ramos cell line (B lymphocyte, Burkitt's lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 48:
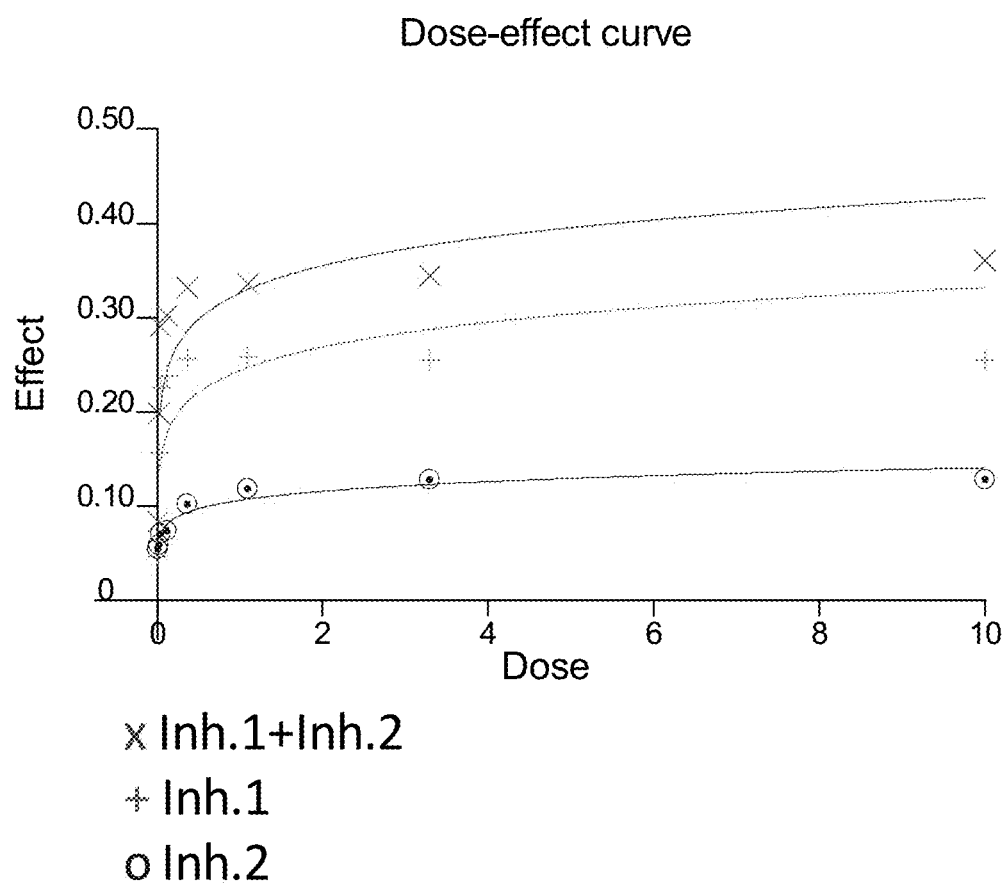

FIG. 48 illustrates the dose-effect curves obtained for the tested Mino cell line (mantle cell lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 49:
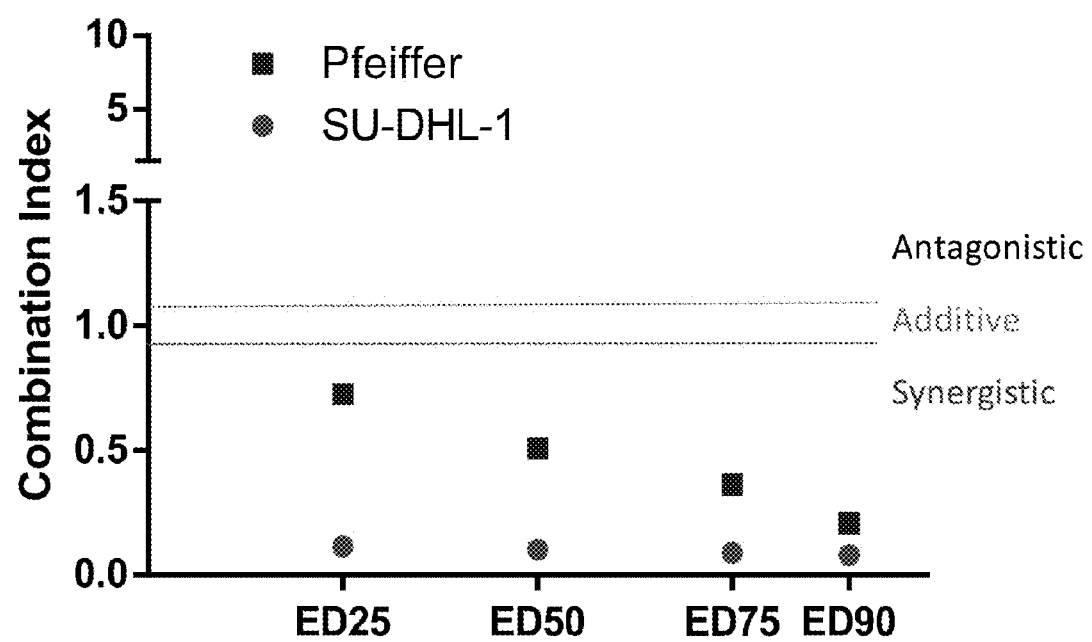

FIG. 49 illustrates the synergy observed in certain cell lines when the BTK inhibitor of Formula (XVIII) and the JAK-2 inhibitor of Formula XXX (ruxolitinib) are combined. The tested cell lines included Pfeiffer (follicular lymphoma) and SU-DHL-1 (DLBCL-ABC). The dose-effect curves for these cell lines are given in FIG. 50 and FIG. 51.

Figure 50:
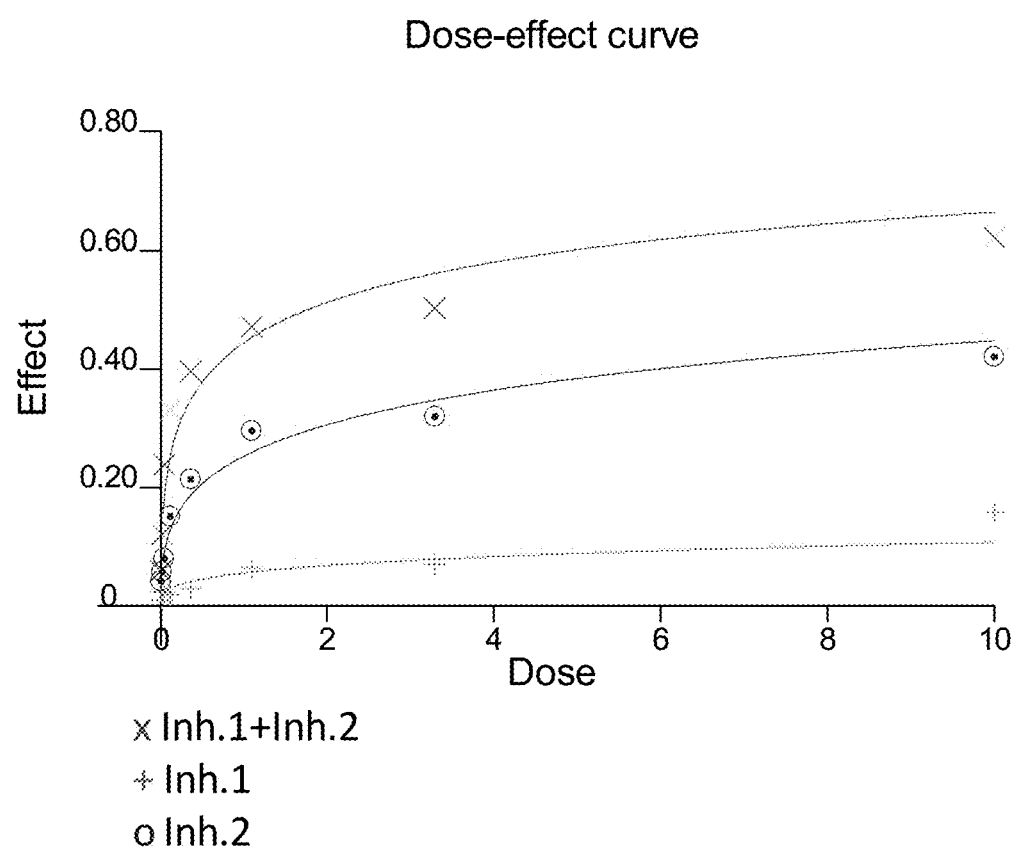

FIG. 50 illustrates the dose-effect curves obtained for the tested Pfeiffer cell line (follicular lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 51:
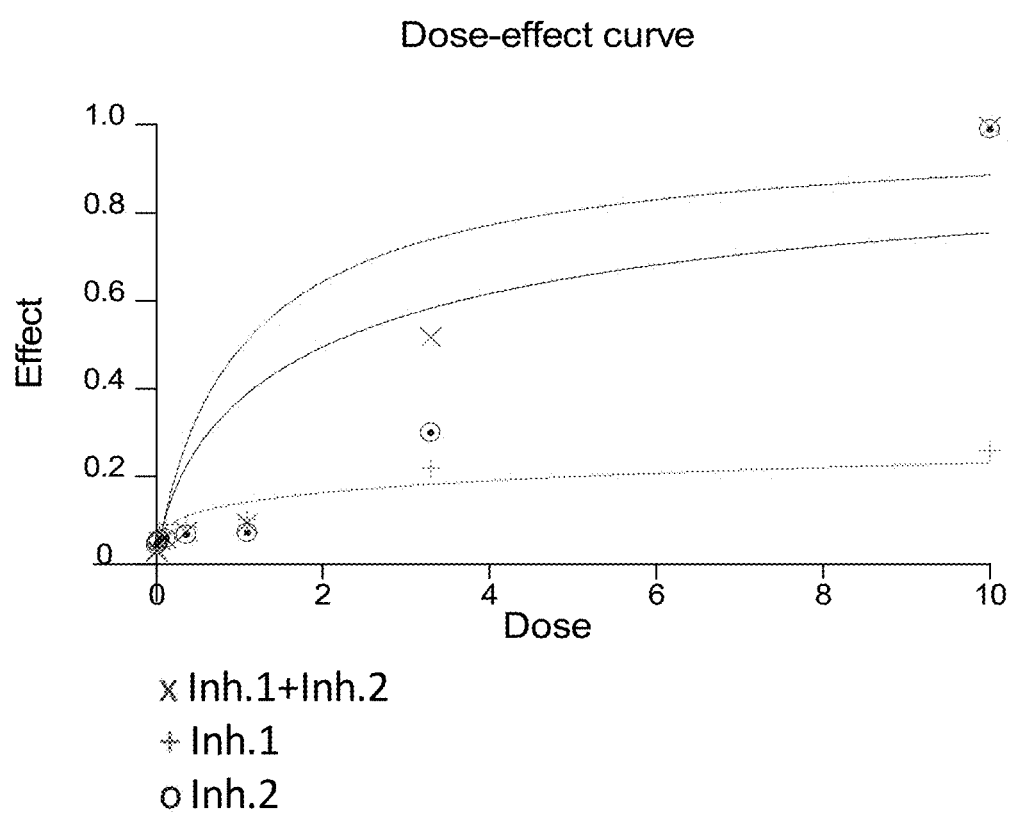

FIG. 51 illustrates the dose-effect curves obtained for the tested SU-DHL-1 cell line (follicular lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 52:
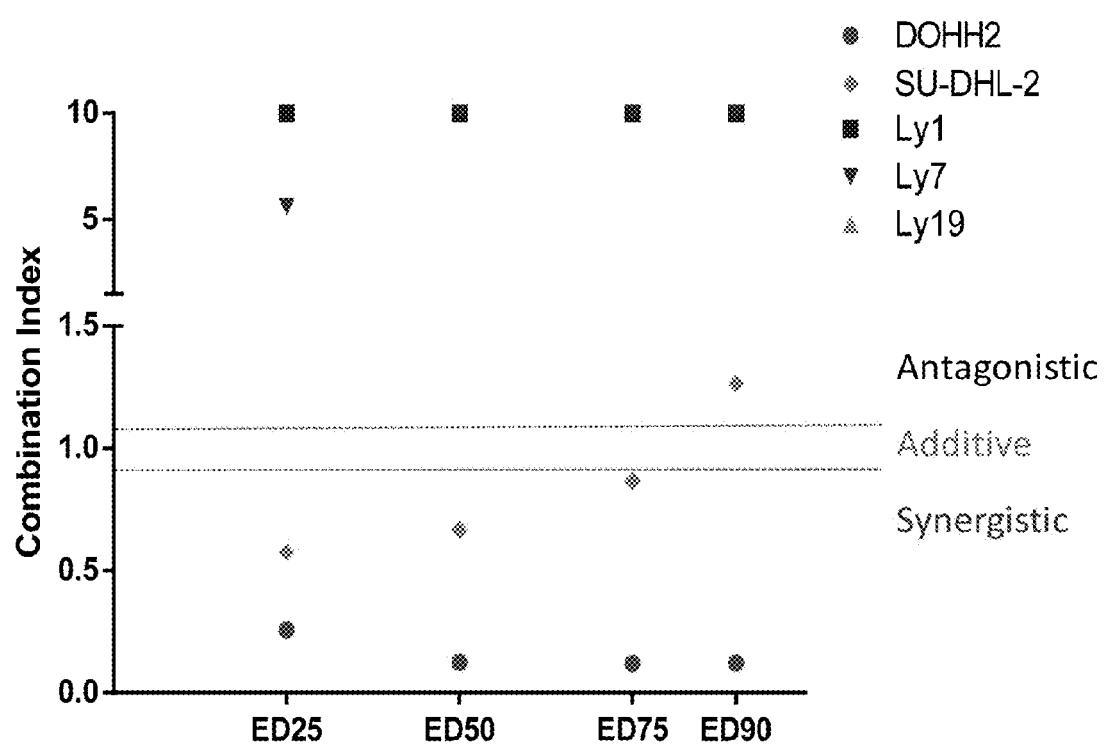

FIG. 52 illustrates the synergy observed in certain cell lines when the BTK inhibitor of Formula (XVIII) and the JAK-2 inhibitor of Formula XXX (ruxolitinib) are combined. The tested cell lines included DOHH2 (follicular lymphoma), SU-DHL-1 (DLBCL-ABC), Ly1 (DLBCL-GCB), Ly7 (DLBCL-GCB), and Ly19 (DLBCL-GCB). The dose-effect curves for these cell lines are given in FIG. 53, FIG. 54, FIG. 55, and FIG. 56, except for the Ly19 cell line, which is not graphed because of a negative slope.

Figure 53:
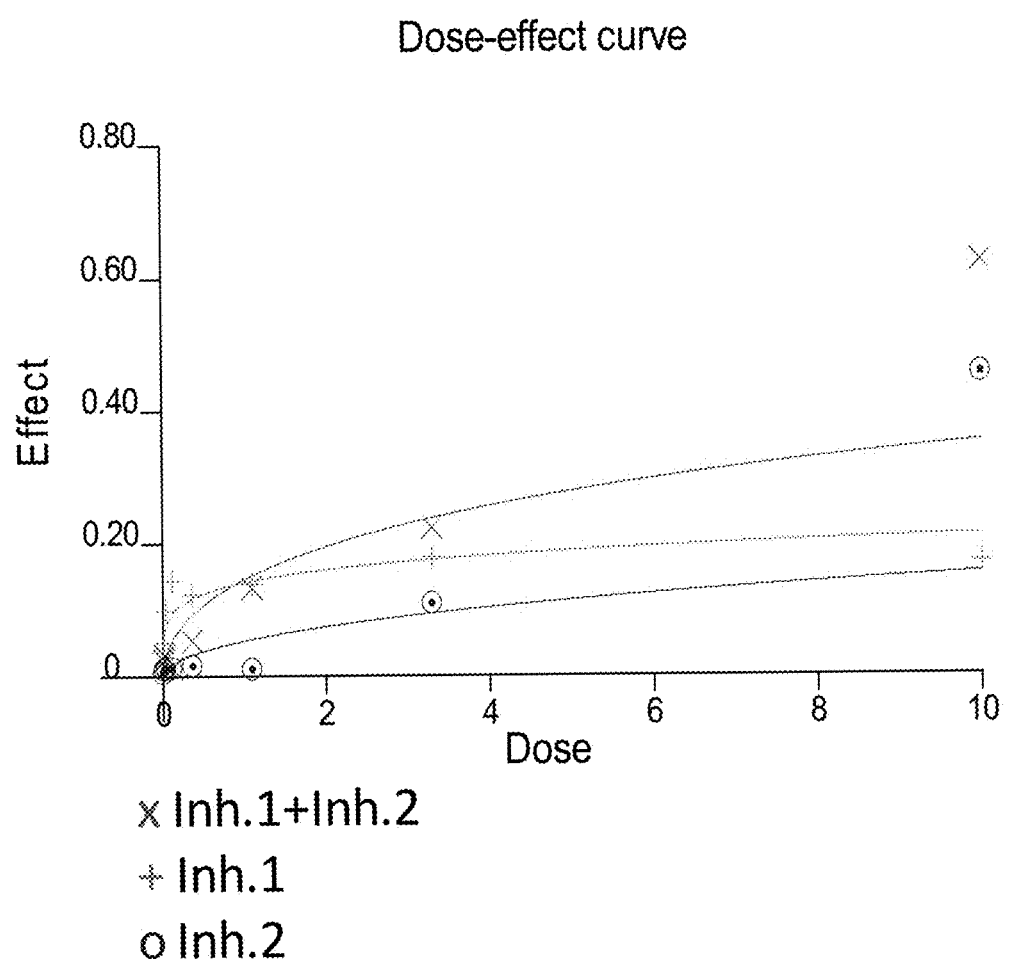

FIG. 53 illustrates the dose-effect curves obtained for the tested DOHH2 cell line (follicular lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 54:
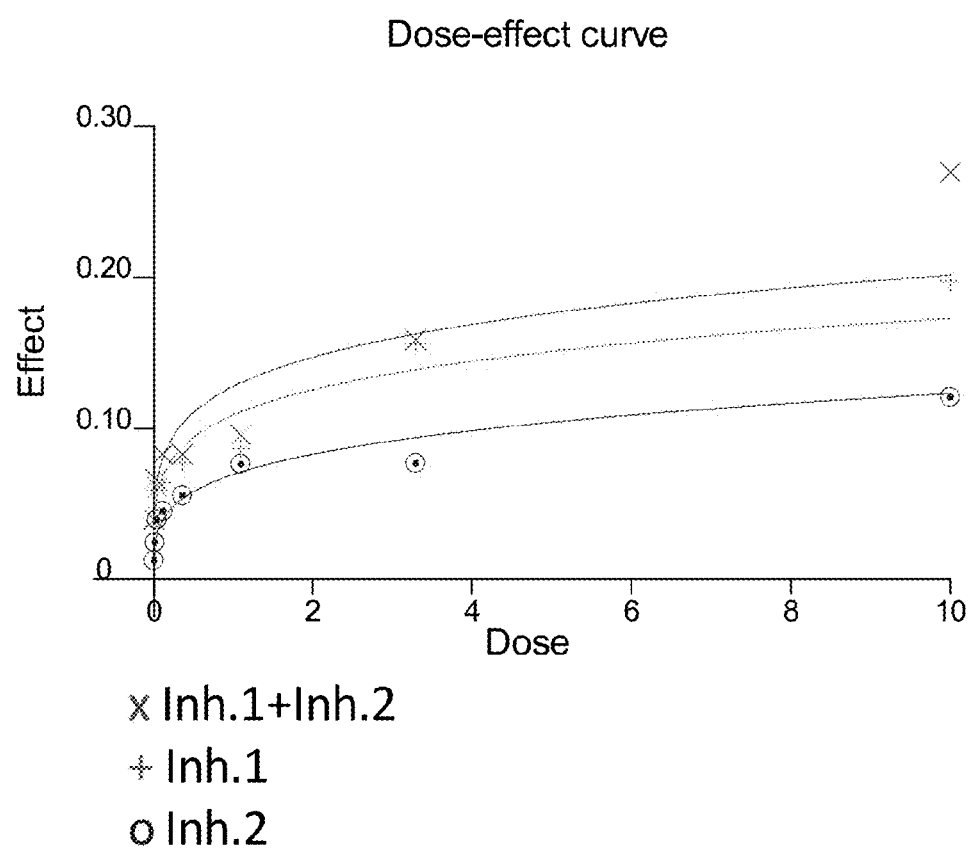

FIG. 54 illustrates the dose-effect curves obtained for the tested SU-DHL-1 cell line (DLBCL-ABC) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 55:
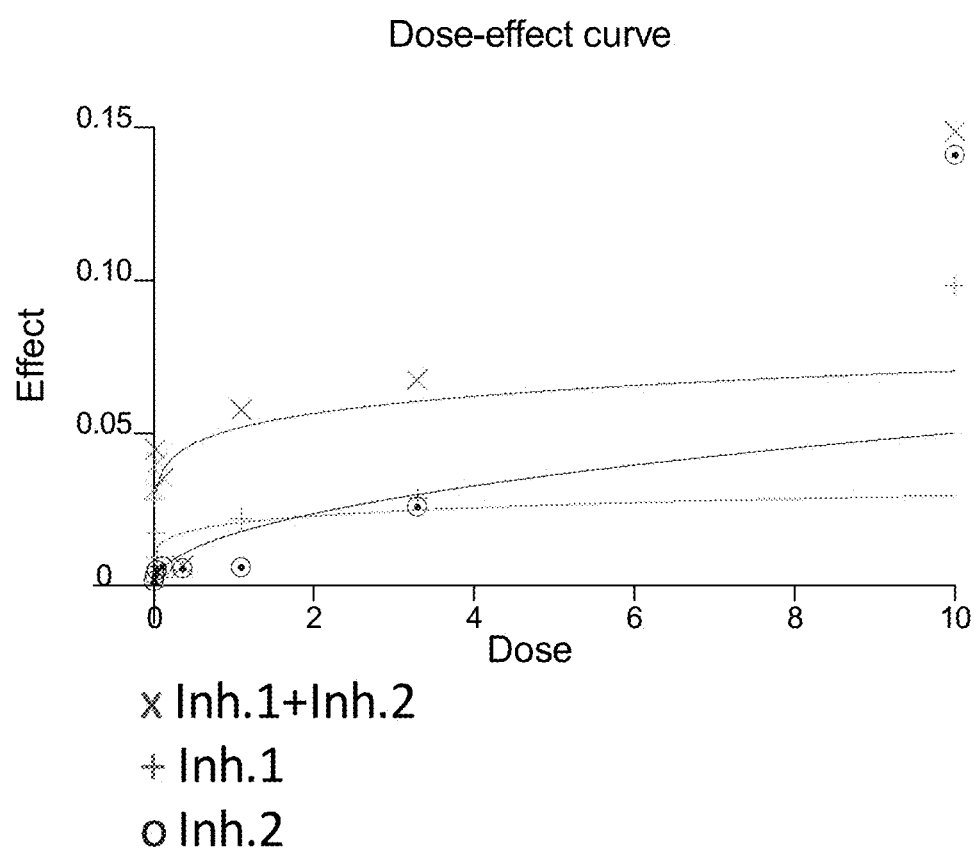

FIG. 55 illustrates the dose-effect curves obtained for the tested Ly1 cell line (DLBCL-GCB) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 56:
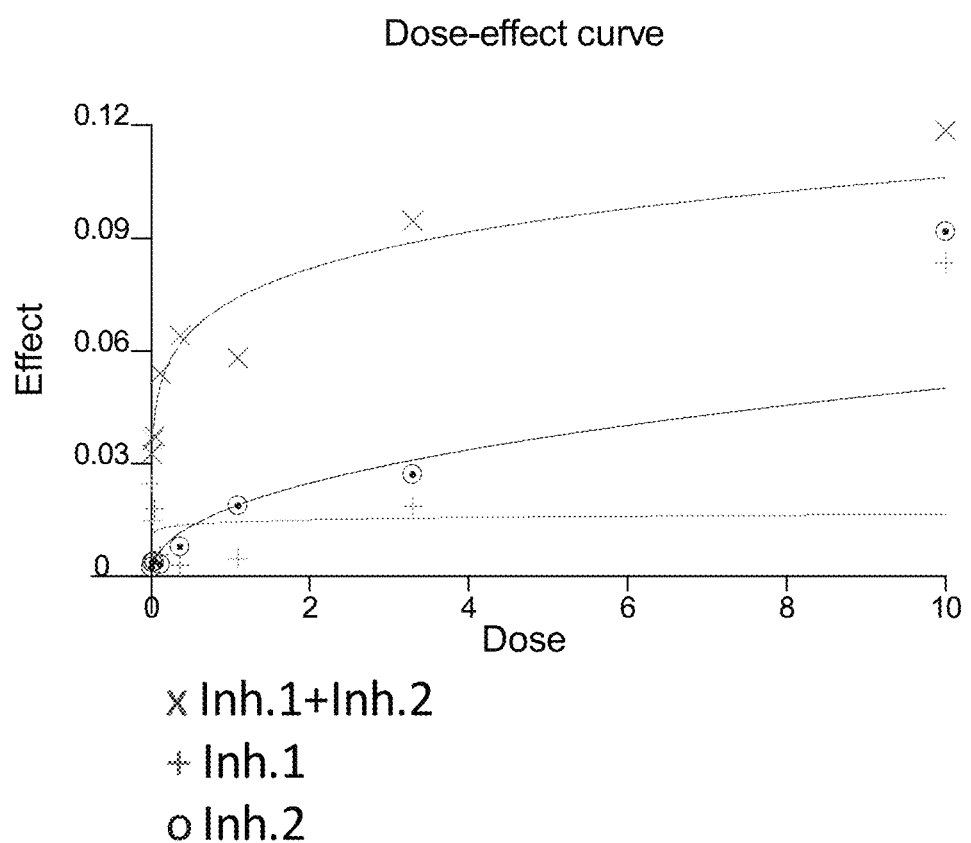

FIG. 56 illustrates the dose-effect curves obtained for the tested Ly7 cell line (DLBCL-GCB) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 57:
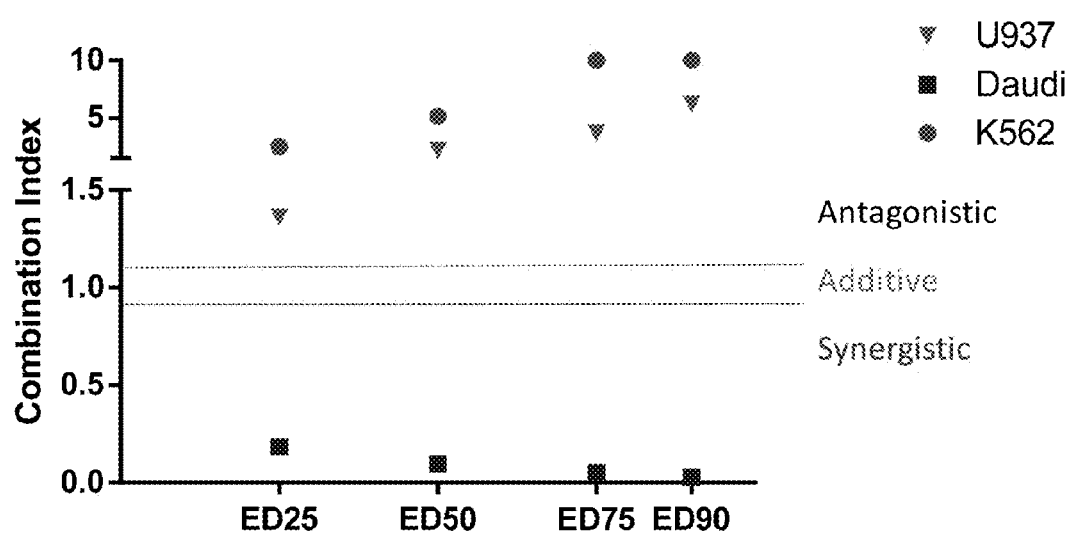

FIG. 57 illustrates the synergy observed in certain cell lines when the BTK inhibitor of Formula (XVIII) and the JAK-2 inhibitor of Formula XXX (ruxolitinib) are combined. The tested cell lines included U937 (histiocytic lymphoma), Daudi (human Burkitt's lymphoma), and K562 (leukemia, myeloid, and/or chronic myelogenous leukemia). The dose-effect curves for these cell lines are given in FIG. 58, FIG. 59, and FIG. 60.

Figure 58:
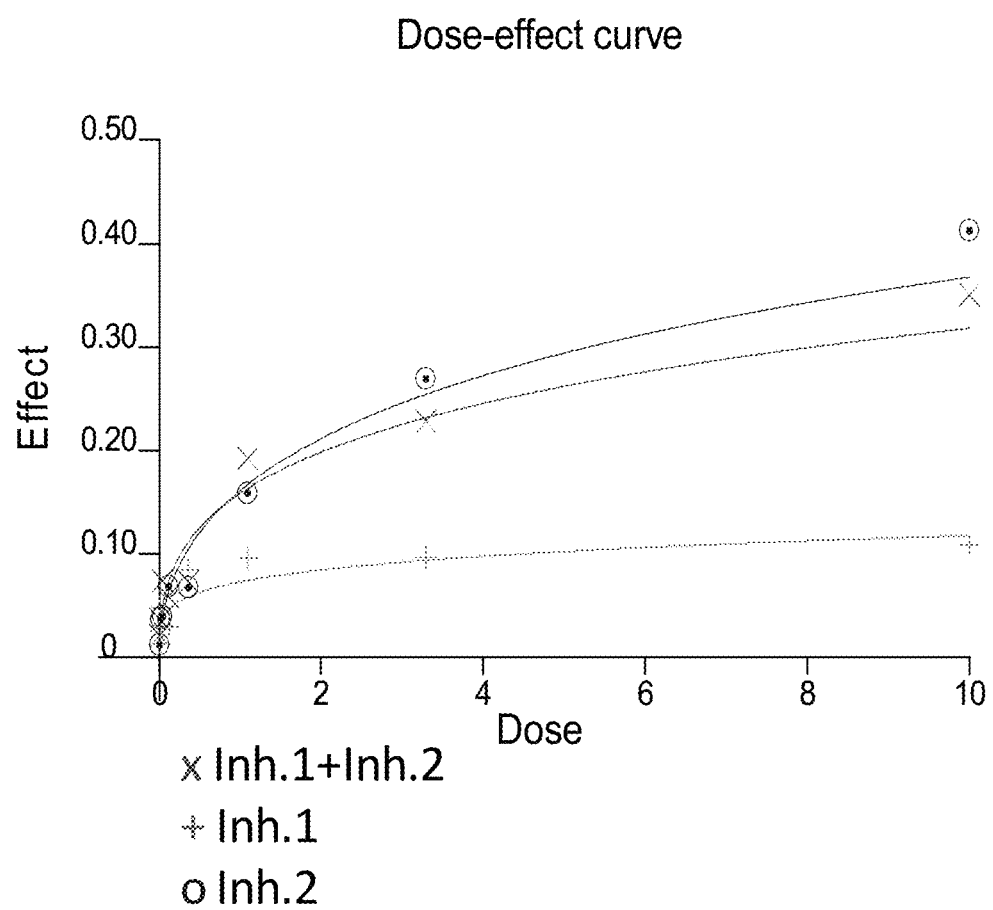

FIG. 58 illustrates the dose-effect curves obtained for the tested U937 cell line (histiocytic lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 59:
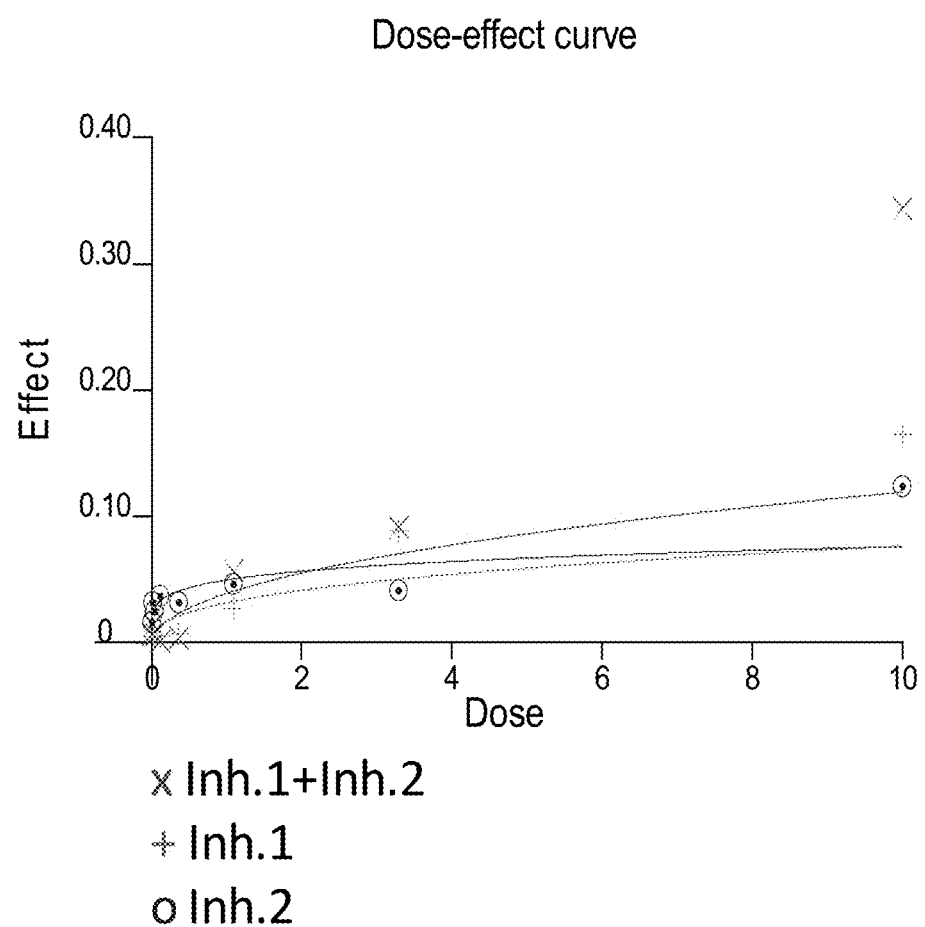

FIG. 59 illustrates the dose-effect curves obtained for the tested Daudi cell line (human Burkitt's lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 60:
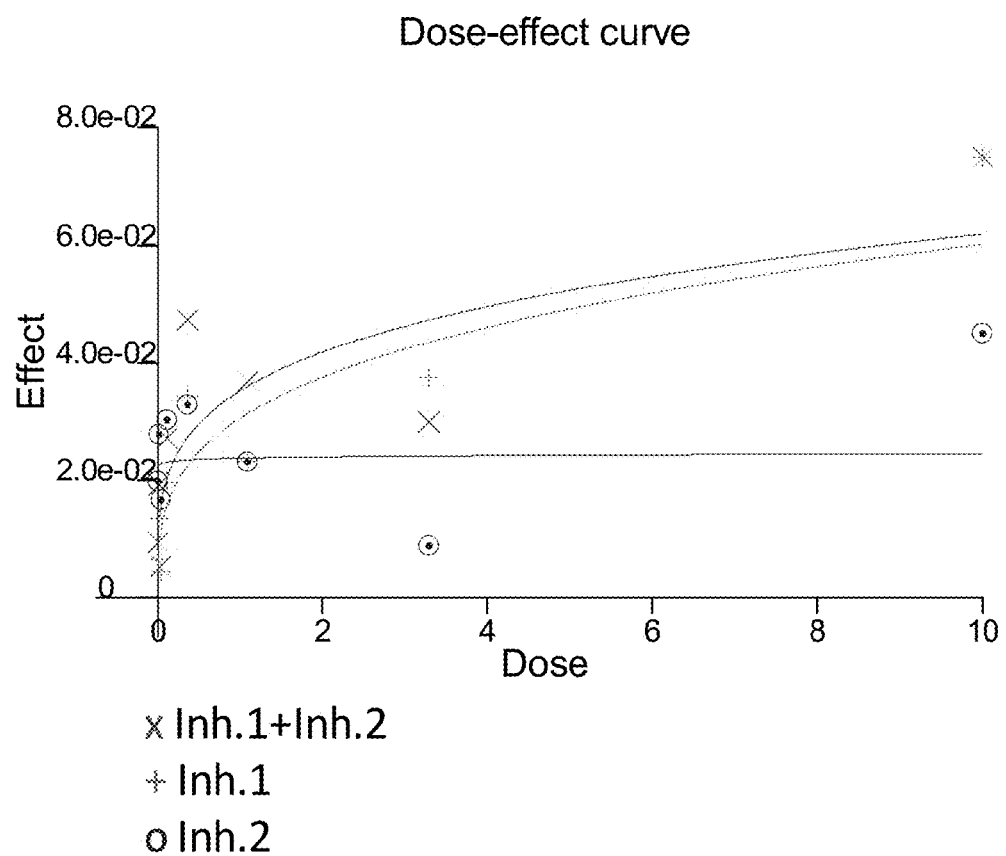

FIG. 60 illustrates the dose-effect curves obtained for the tested K562 cell line (leukemia, myeloid, and/or chronic myelogenous leukemia) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 61:
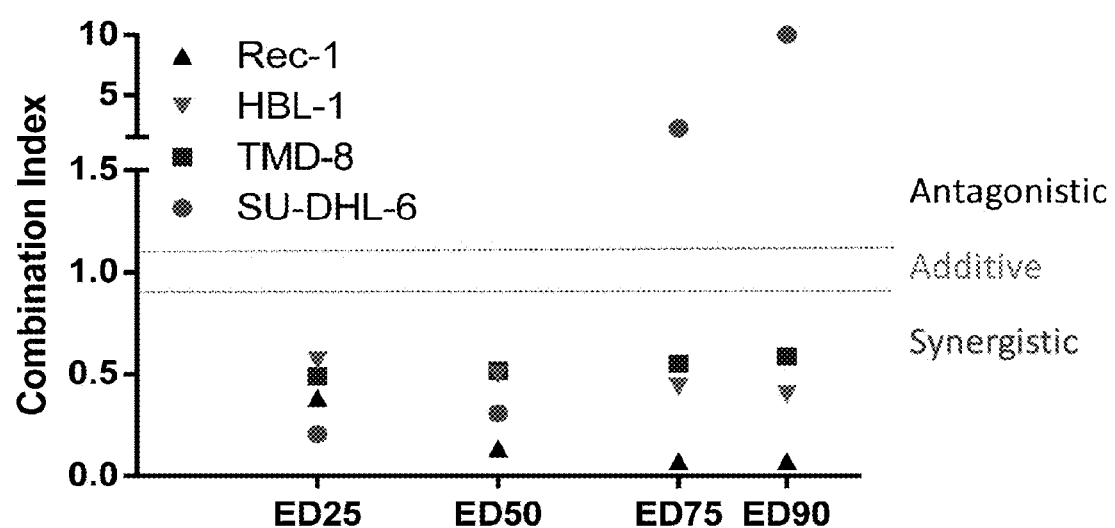

FIG. 61 illustrates the synergy observed in certain cell lines when the BTK inhibitor of Formula (XVIII) and the JAK-2 inhibitor of Formula XXX (ruxolitinib) are combined. The tested cell lines include SU-DHL-6 (DLBCL-GCB or PTCL), TMD-8 (DLBCL-ABC), HBL-1 (DLBCL-ABC), and Rec-1 (follicular lymphoma). The dose-effect curves for these cell lines are given in FIG. 62, FIG. 63, FIG. 64, and FIG. 65.

Figure 62:
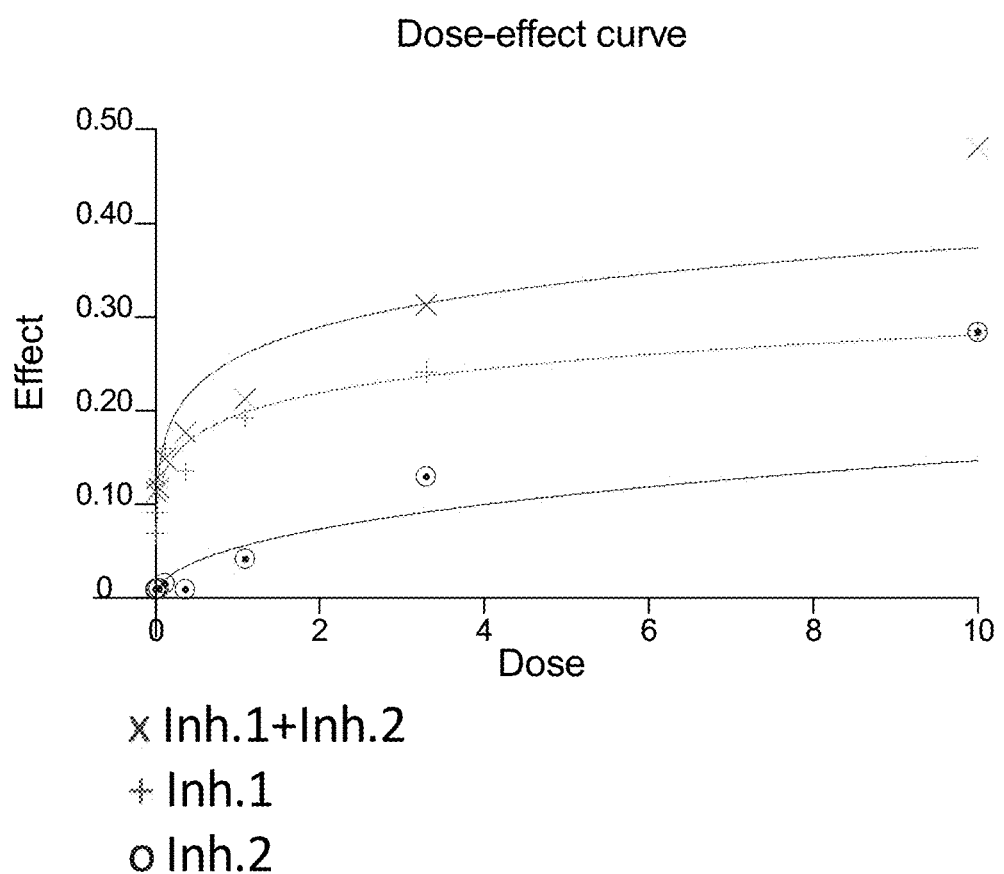

FIG. 62 illustrates the dose-effect curves obtained for the tested SU-DHL-6 cell line (DLBCL-GCB or PTCL) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 63:
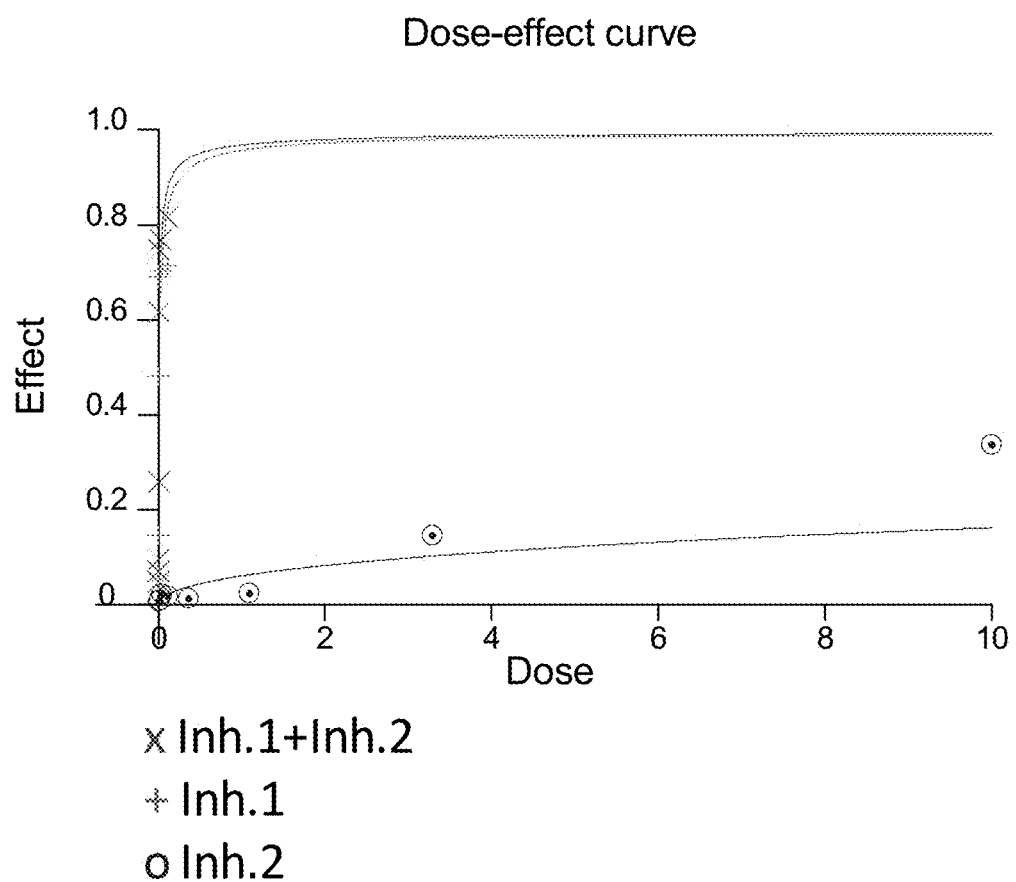

FIG. 63 illustrates the dose-effect curves obtained for the tested TMD-8 cell line (DLBCL-ABC) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of PIM.

Figure 64:
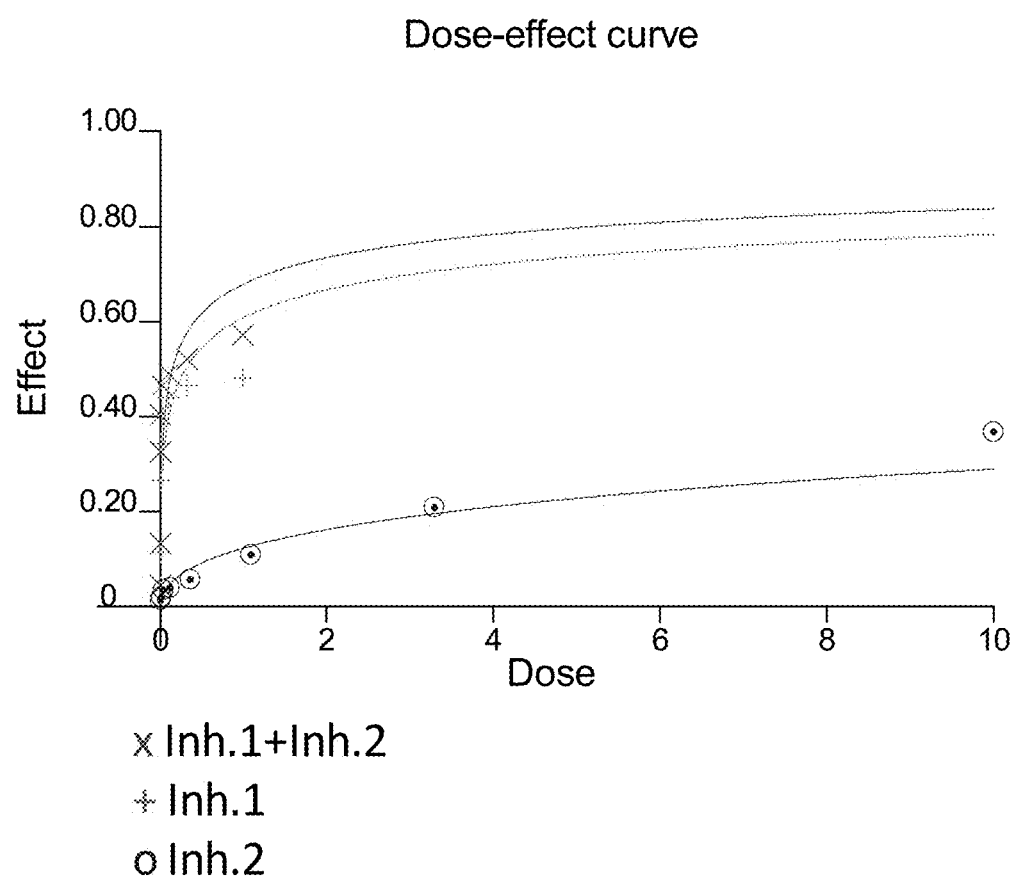

FIG. 64 illustrates the dose-effect curves obtained for the tested HBL-1 cell line (DLBCL-ABC) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 65:
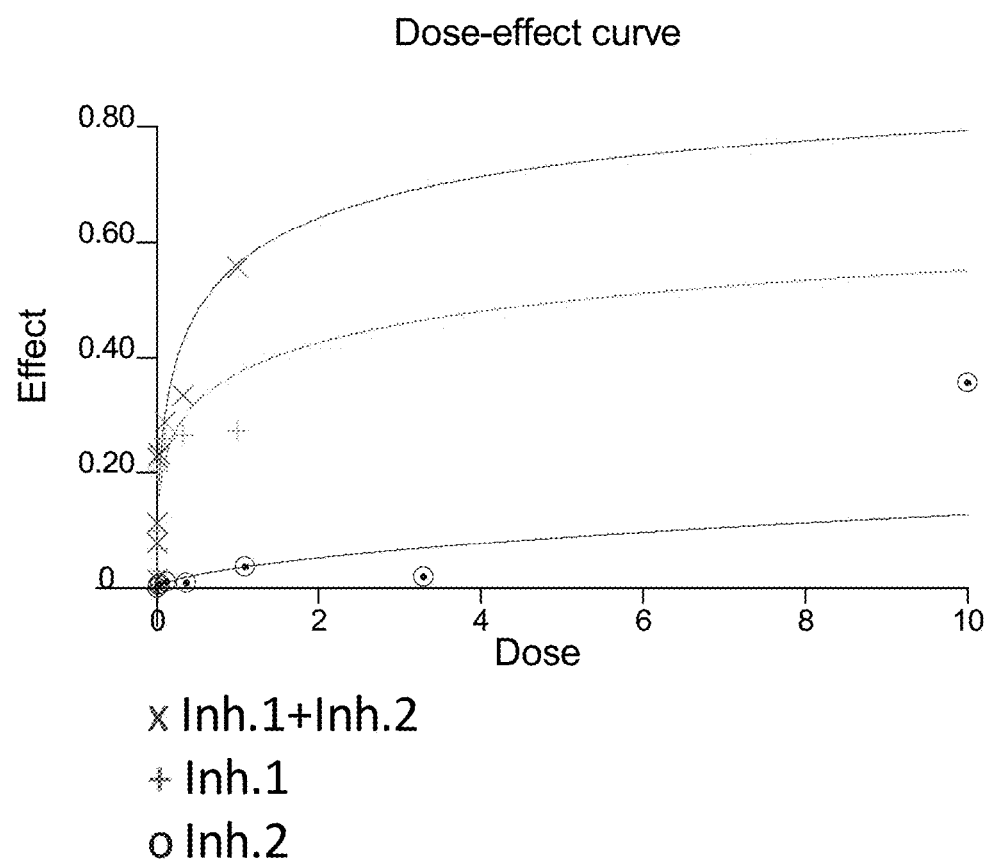

FIG. 65 illustrates the dose-effect curves obtained for the tested Rec-1 cell line (follicular lymphoma) using combined dosing of the BTK inhibitor of Formula (XVIII) ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of μM.

Figure 66:
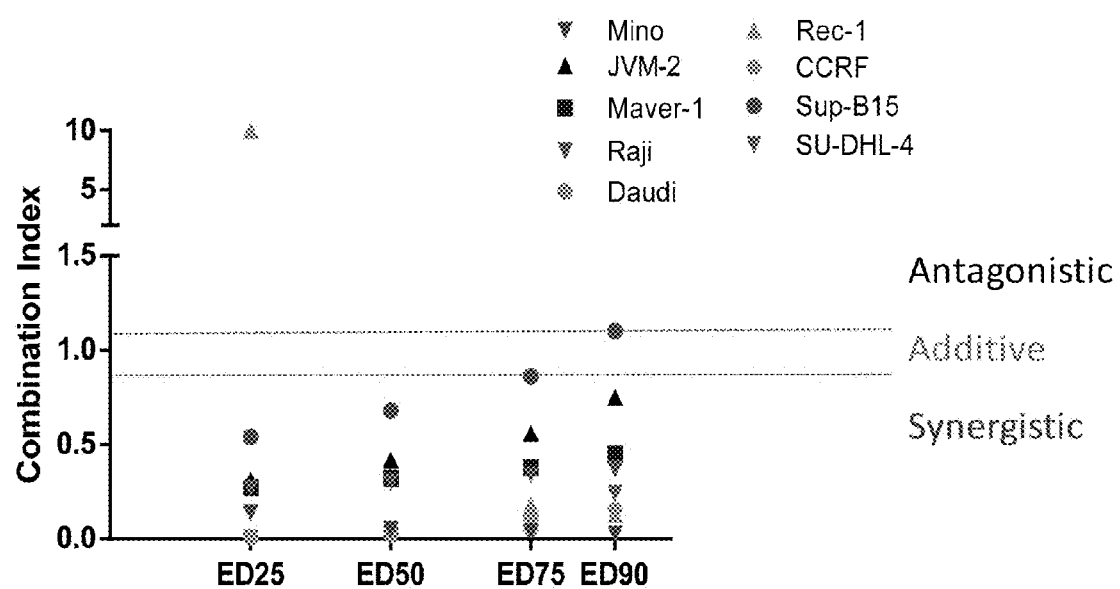

FIG. 66 illustrates the synergy observed in certain cell lines when the BTK inhibitor of Formula (XVIII) and the JAK-2 inhibitor of Formula LIV (pacritinib) are combined. The tested cell lines include Mino (mantle cell lymphoma), Maver-1 (B cell lymphoma, mantle cell lymophoma), Raji (B lymphocyte, Burkitt's lymphoma), JVM-2 (prolymphocytic leukemia), Daudi (Human Burkitt's lymphoma), Rec-1 (follicular lymphoma), SUP-B15 (B lymphoblast, acute lymphoblastic leukemia), CCRF (B lymphoblast, acute lymphoblastic leukemia), and SU-DHL-4 (DLBCL-ABC). The dose-effect curves for these cell lines are given in FIG. 67, FIG. 68, FIG. 69, FIG. 70, FIG. 71, FIG. 72, FIG. 73, FIG. 74, and FIG. 75.

Figure 67:
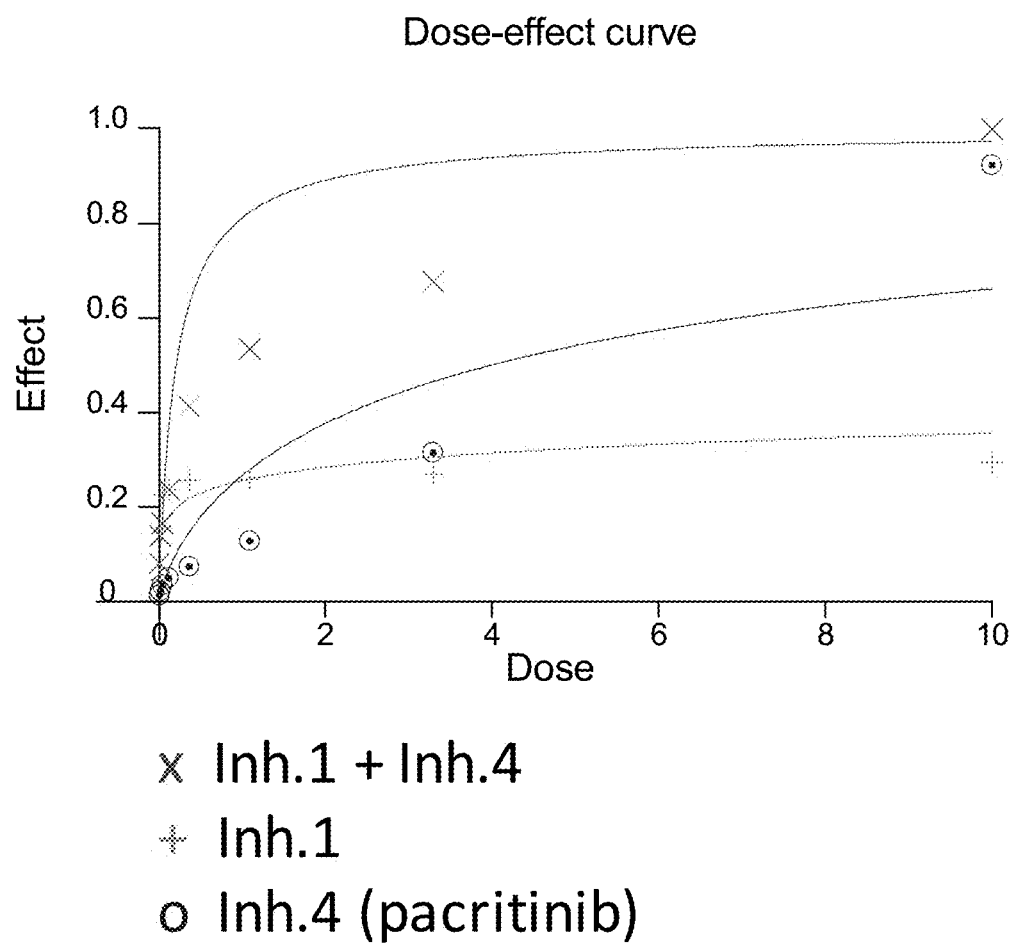

FIG. 67 illustrates the dose-effect curves obtained for the tested Mino cell line (mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 68:
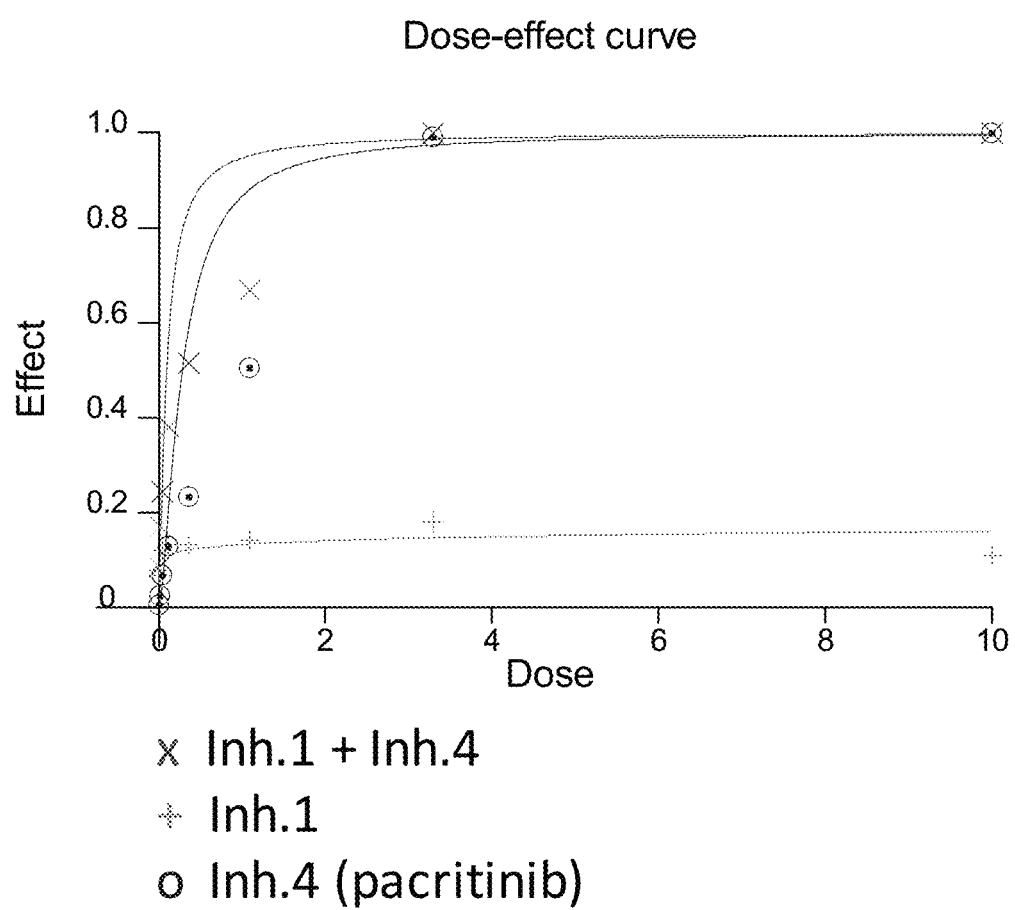

FIG. 68 illustrates the dose-effect curves obtained for the tested Maver-1 cell line (B cell lymphoma, mantle cell lymophoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 69:
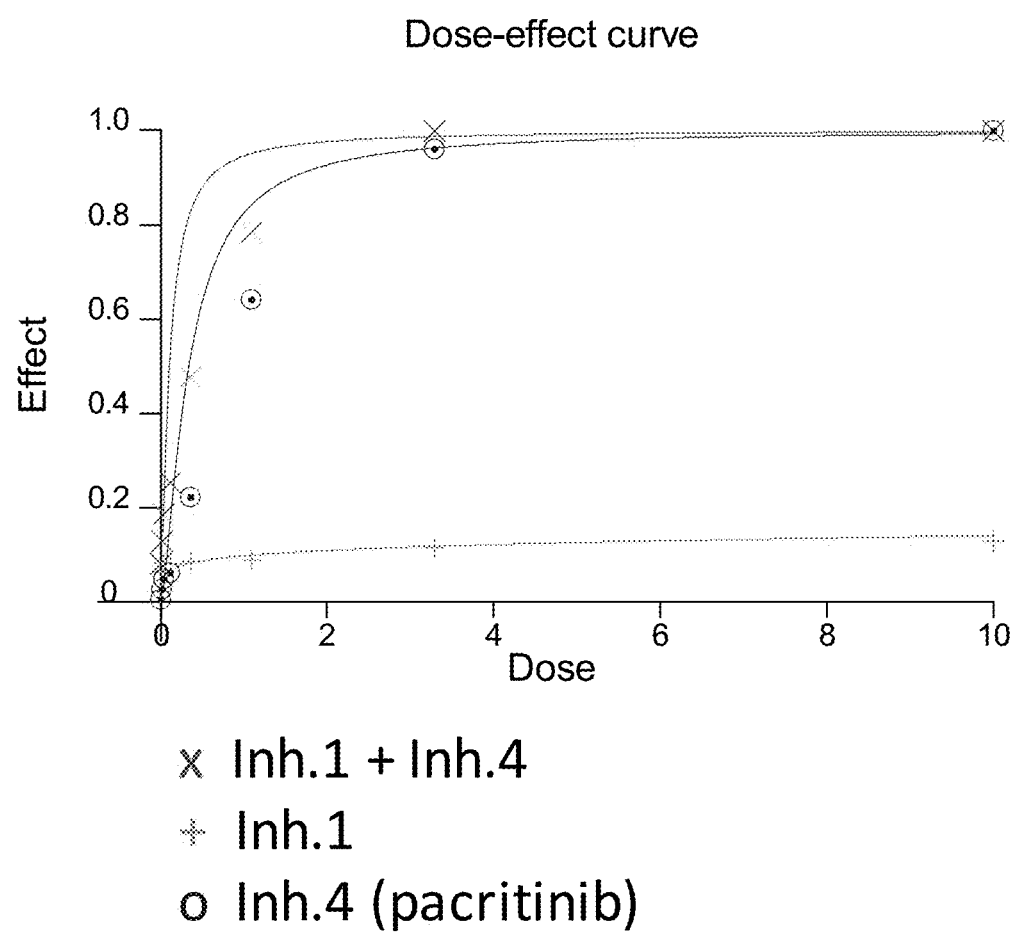

FIG. 69 illustrates the dose-effect curves obtained for the tested Raji cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 70:
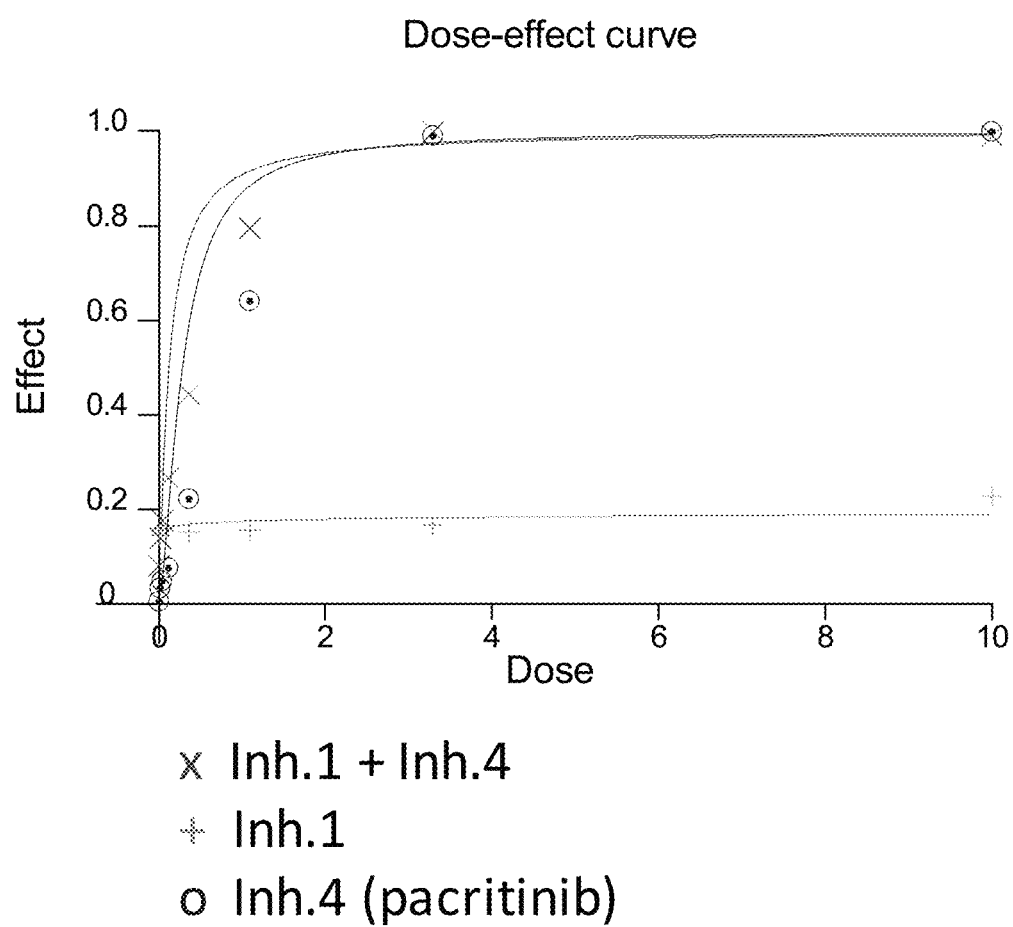

FIG. 70 illustrates the dose-effect curves obtained for the tested JVM-2 cell line (prolymphocytic leukemia) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 71:
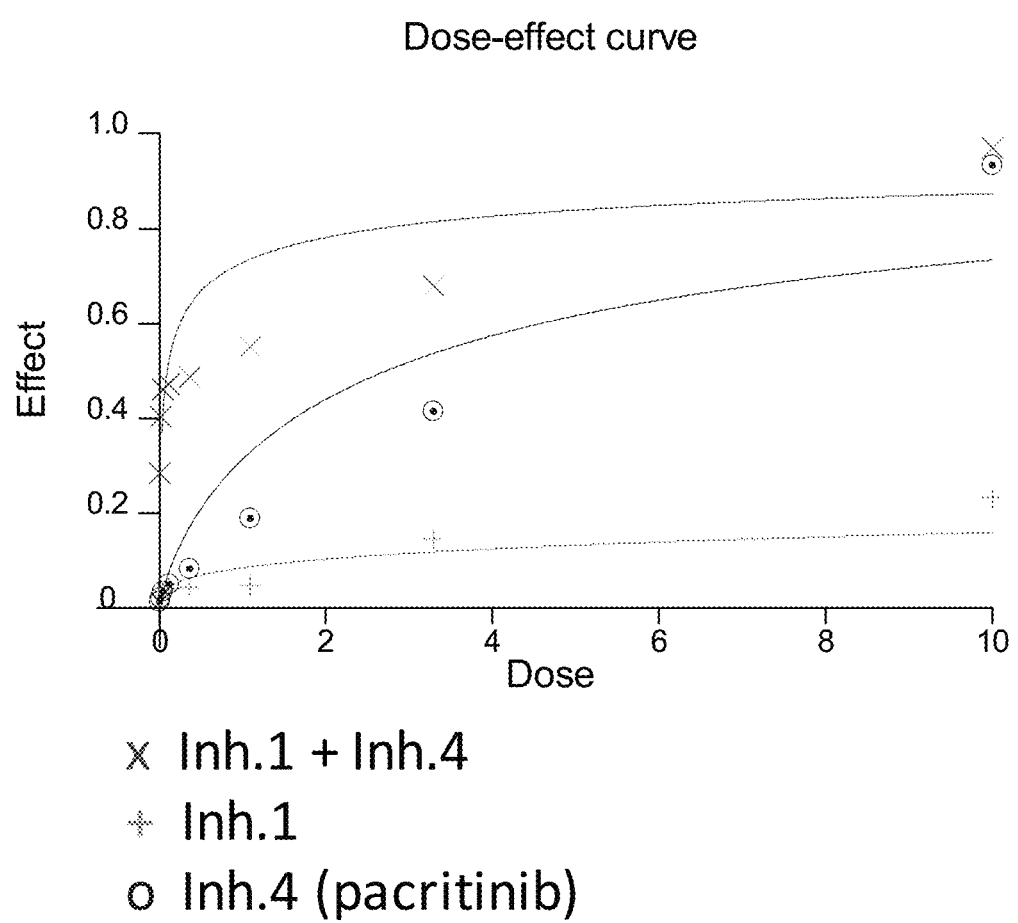

FIG. 71 illustrates the dose-effect curves obtained for the tested Daudi cell line (Human Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 72:
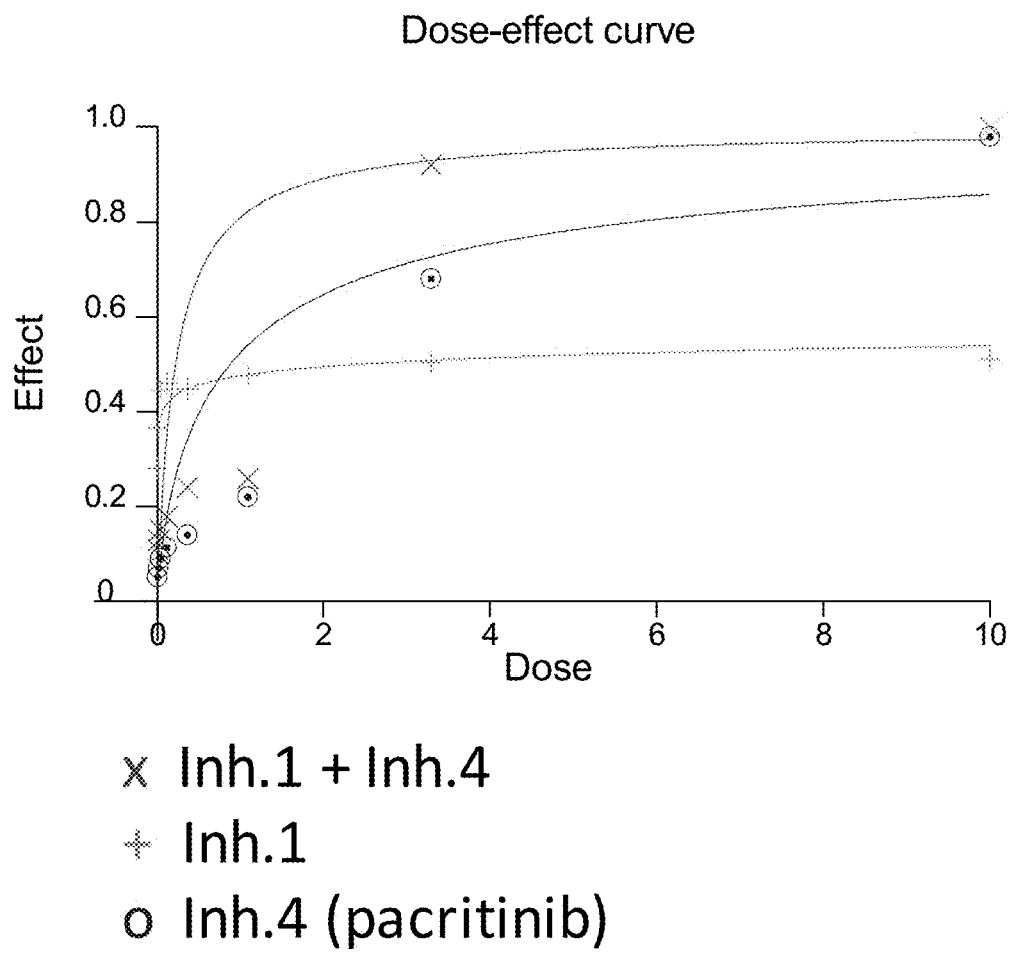

FIG. 72 illustrates the dose-effect curves obtained for the tested Rec-1 cell line (follicular lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 73:
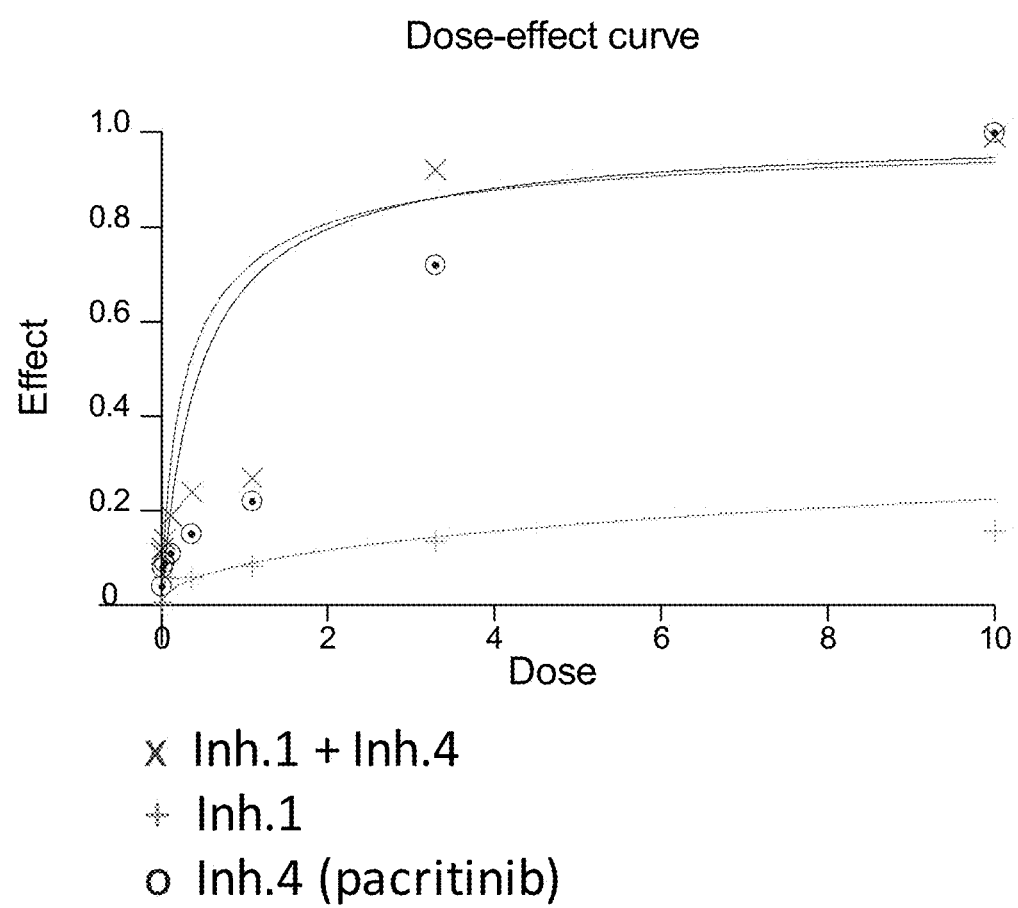

FIG. 73 illustrates the dose-effect curves obtained for the tested SUP-B15 cell line (B lymphoblast, acute lymphoblastic leukemia) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 74:
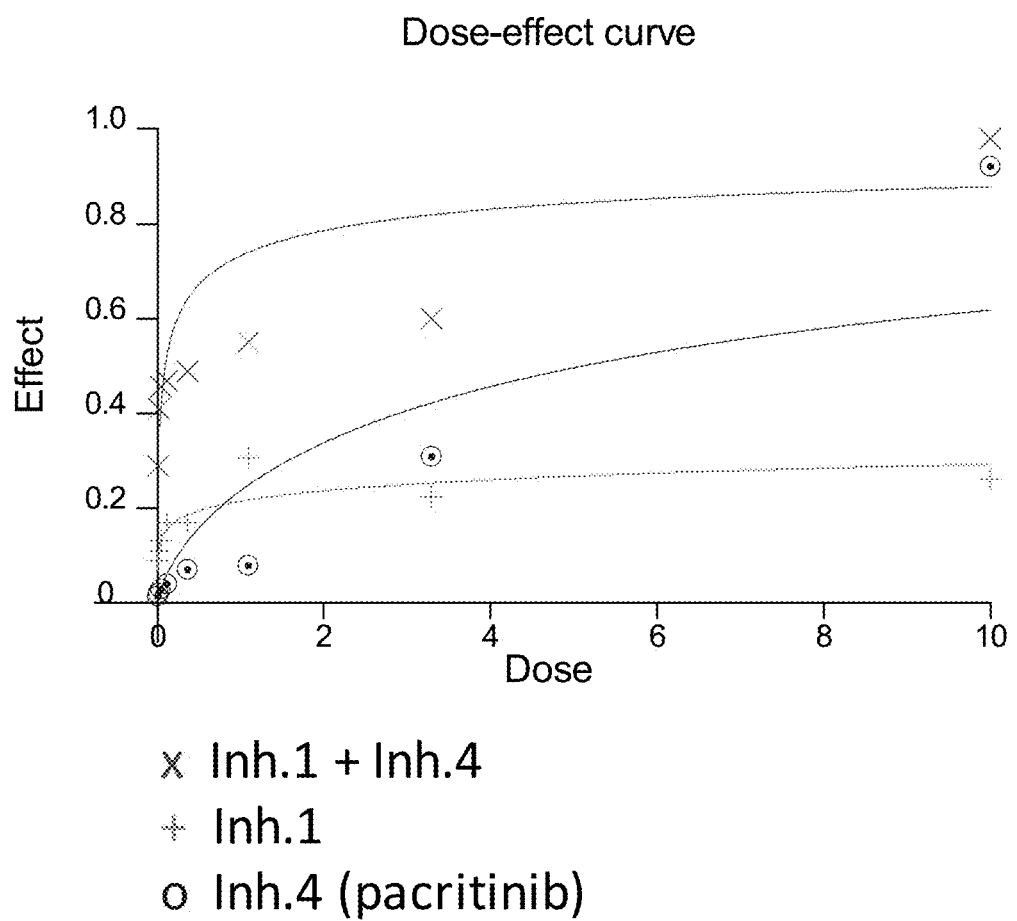

FIG. 74 illustrates the dose-effect curves obtained for the tested CCRF cell line (B lymphoblast, acute lymphoblastic leukemia) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 75:
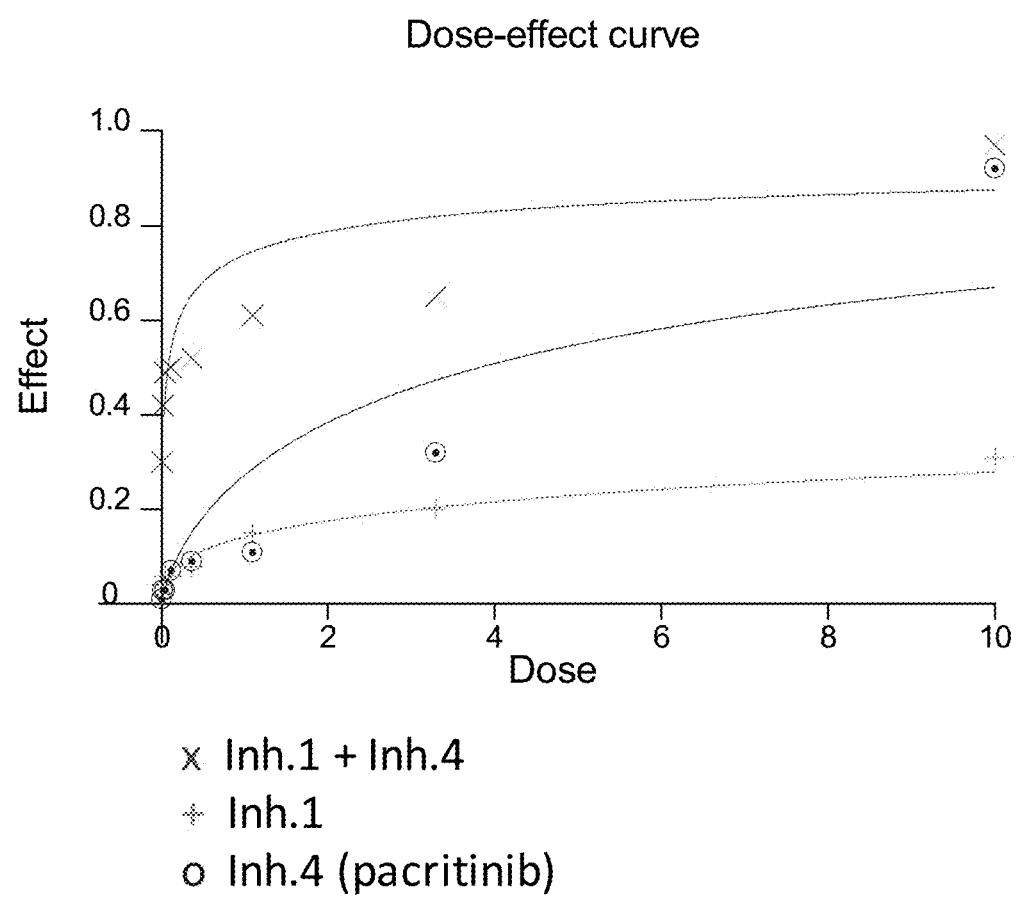

FIG. 75 illustrates the dose-effect curves obtained for the tested SU-DHL-4 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 76:
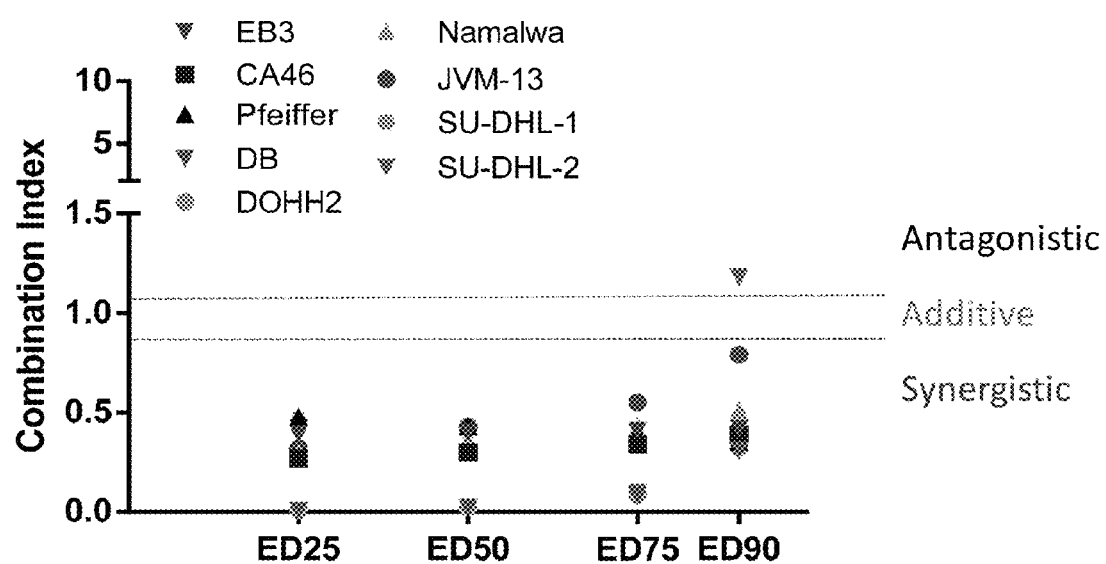

FIG. 76 illustrates the synergy observed in certain cell lines when the BTK inhibitor of Formula (XVIII) and the JAK-2 inhibitor of Formula LIV (pacritinib) are combined. The tested cell lines include EB3 (B lymphocyte, Burkitt's lymphoma), CA46 (B lymphocyte, Burkitt's lymphoma), DB (B cell lymphoma, mantle cell lymphoma), Pfeiffer (follicular lymphoma), DOHH2 (follicular lymphoma), Namalwa (B lymphocyte, Burkitt's lymphoma), JVM-13 (B cell lymphoma, mantle cell lymphoma), SU-DHL-1 (DLBCL-ABC), and SU-DHL-2 (DLBCL-ABC). The dose-effect curves for these cell lines are given in FIG. 77, FIG. 78, FIG. 79, FIG. 80, FIG. 81, FIG. 82, FIG. 83, FIG. 84, and FIG. 85.

Figure 77:
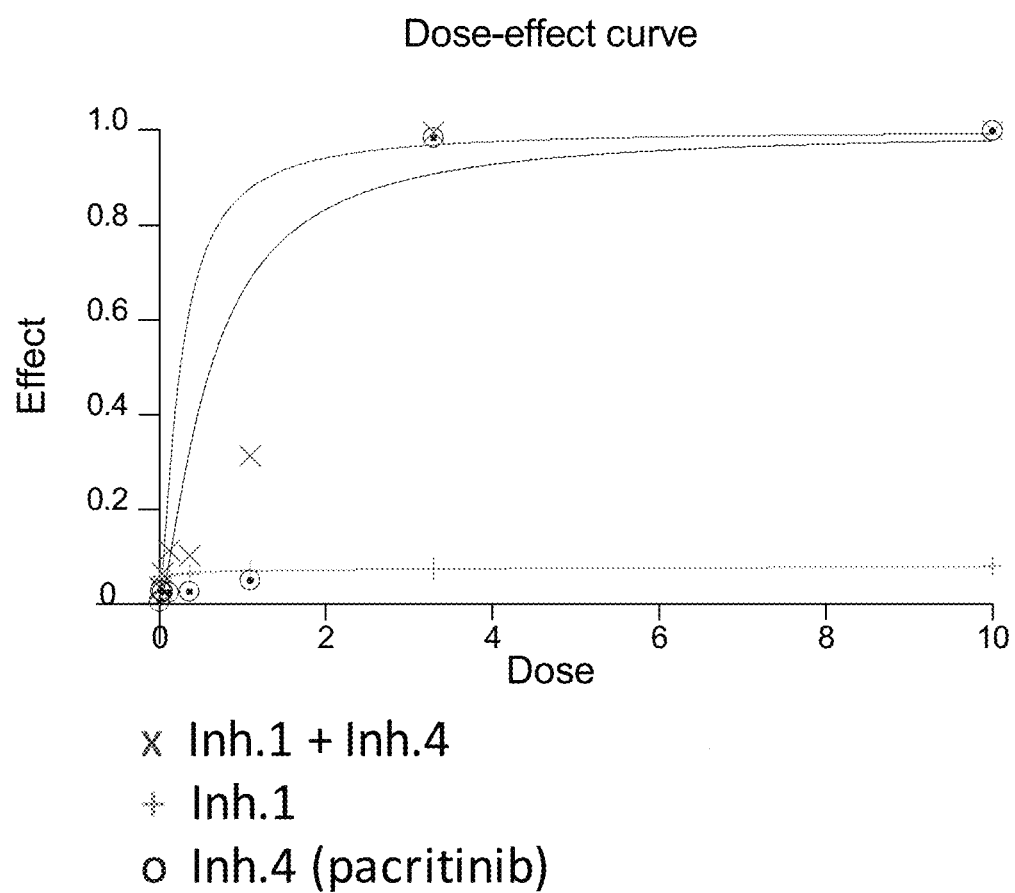

FIG. 77 illustrates the dose-effect curves obtained for the tested EB3 cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 78:
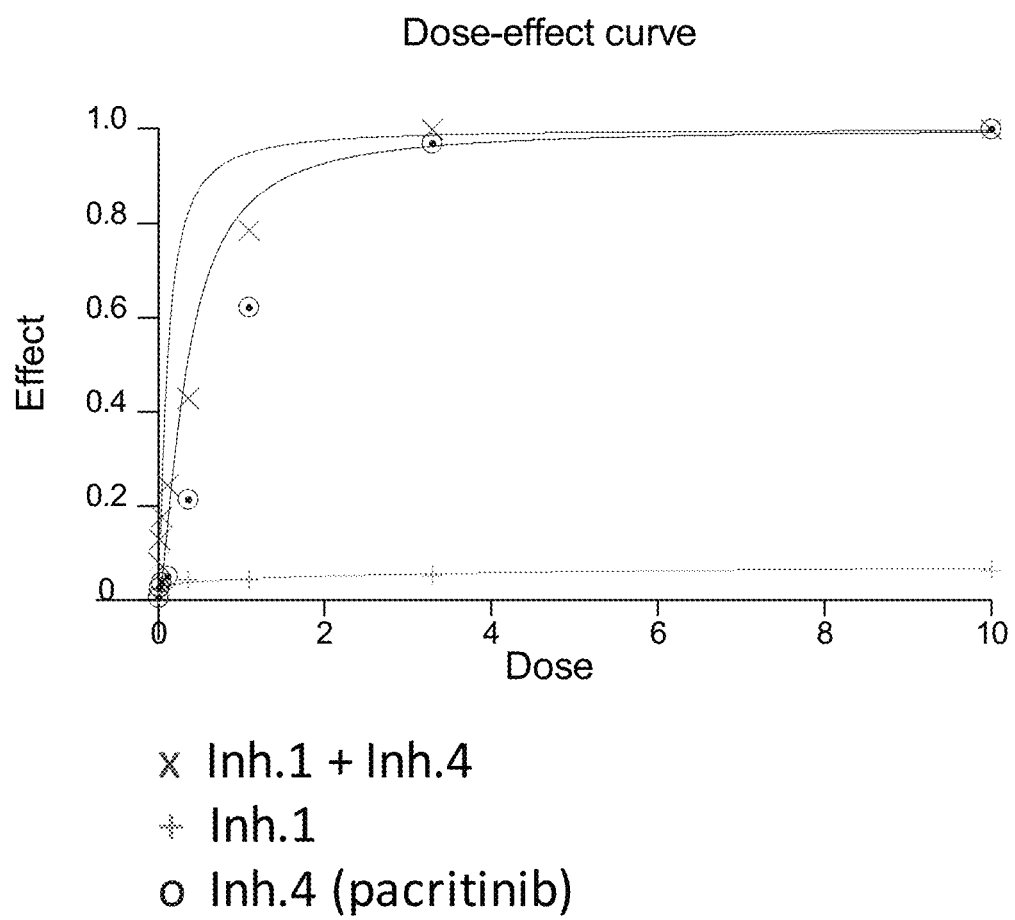

FIG. 78 illustrates the dose-effect curves obtained for the tested CA46 cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 79:
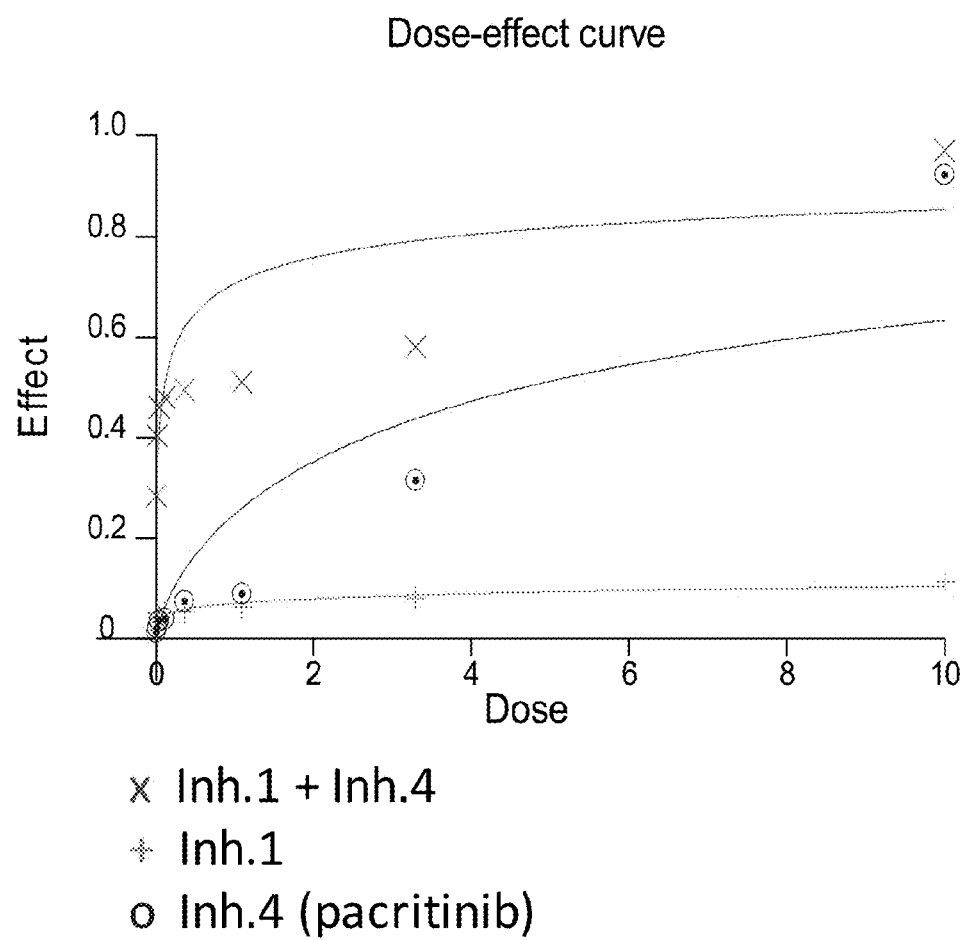

FIG. 79 illustrates the dose-effect curves obtained for the tested DB cell line (B cell lymphoma, mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 80:
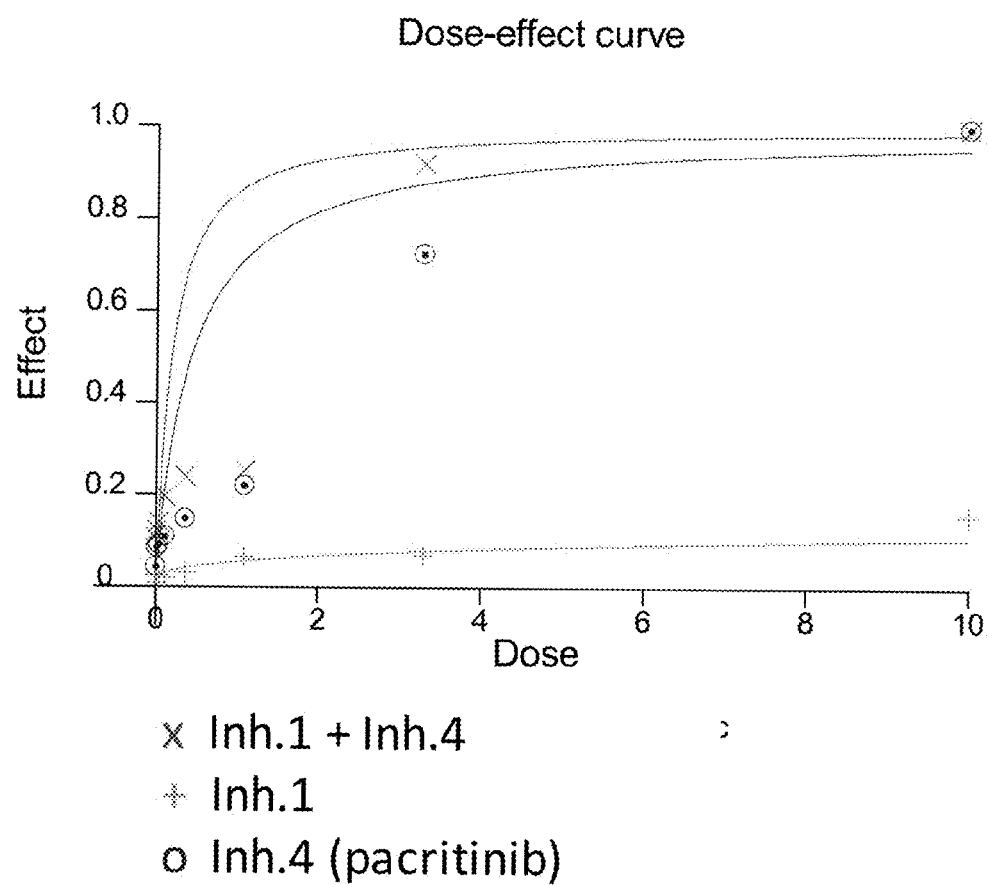

FIG. 80 illustrates the dose-effect curves obtained for the tested Pfeiffer cell line (follicular lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 81:
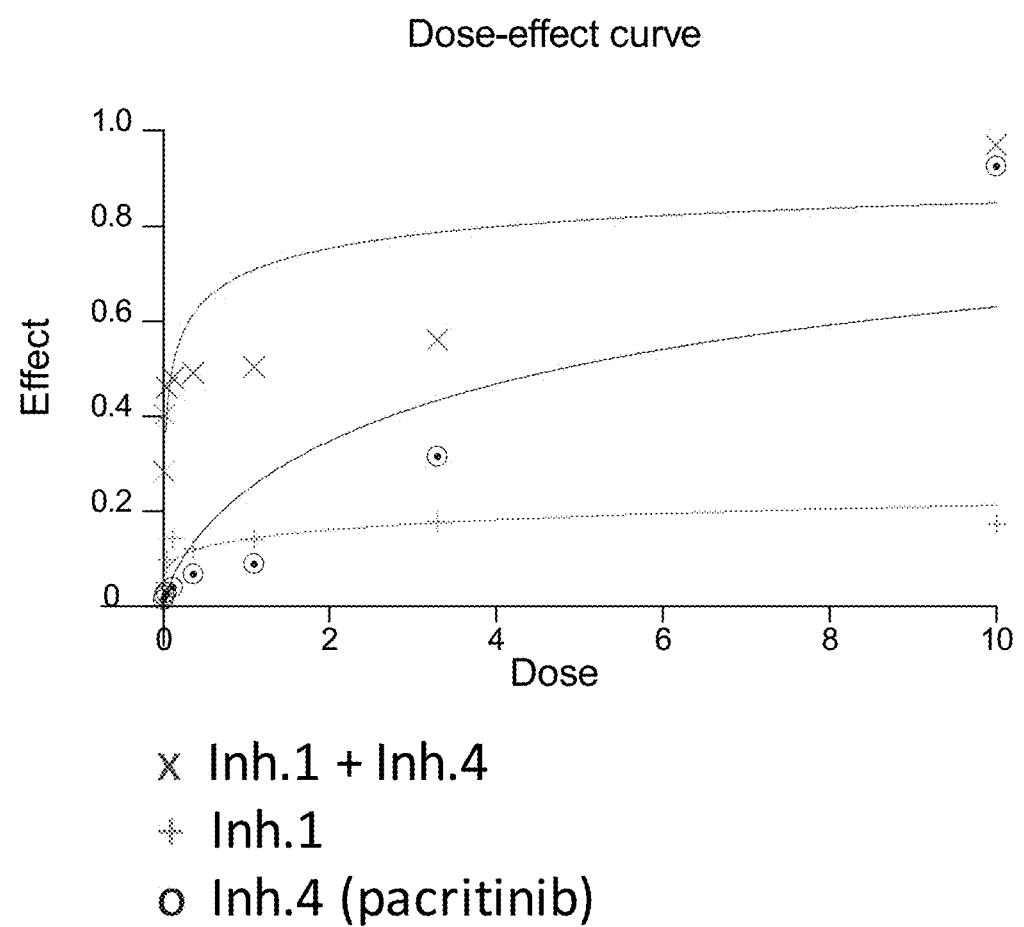

FIG. 81 illustrates the dose-effect curves obtained for the tested DOHH2 cell line (follicular lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 82:
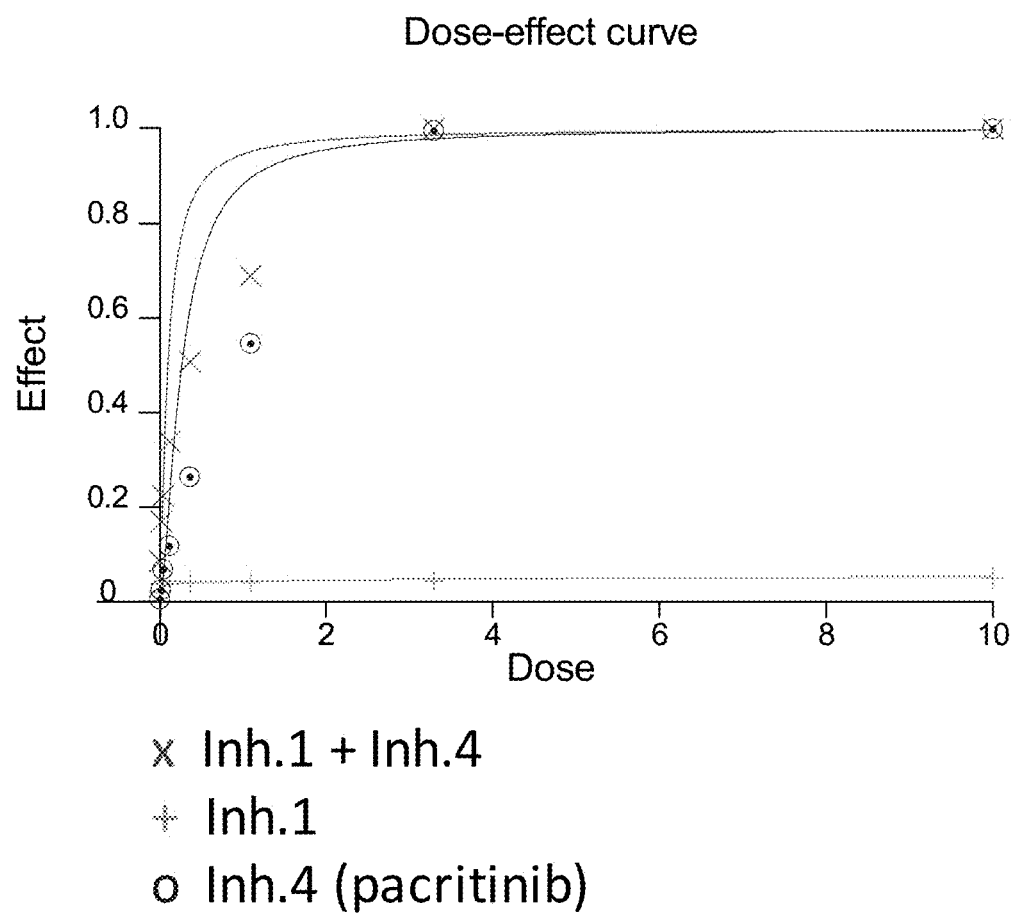

FIG. 82 illustrates the dose-effect curves obtained for the tested Namalwa cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 83:
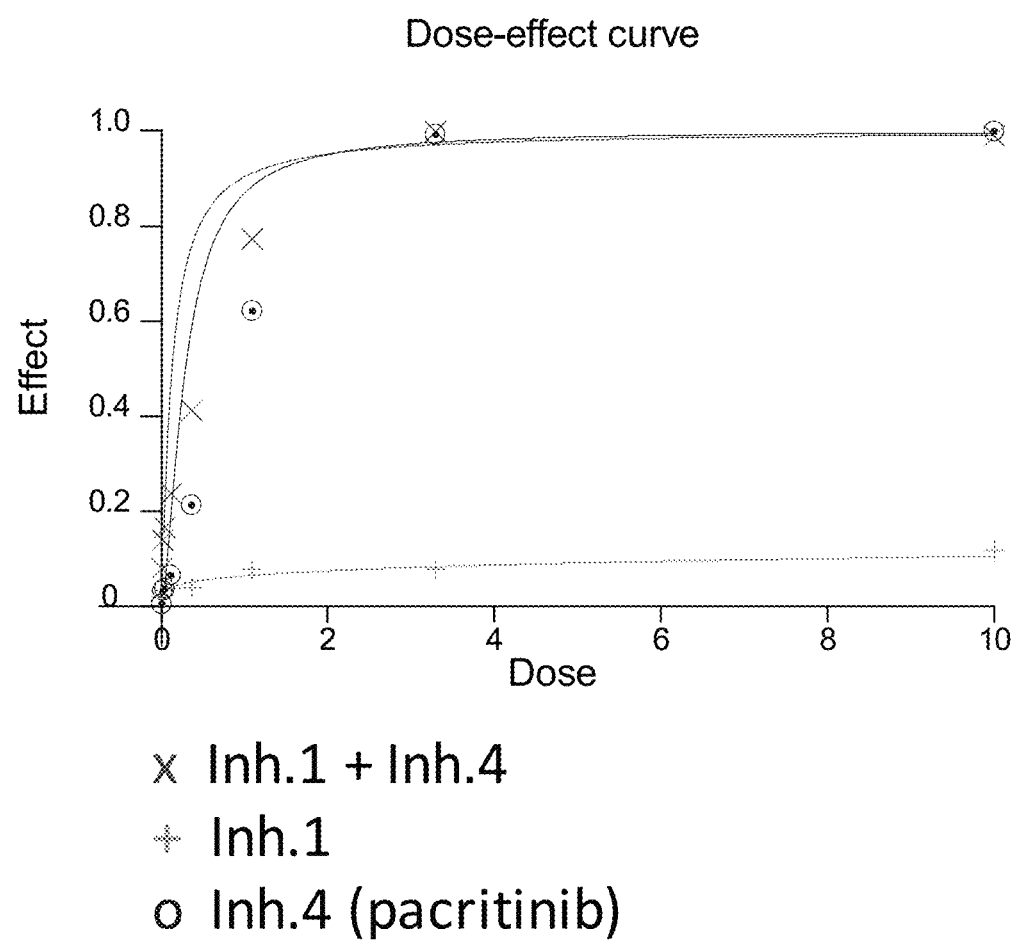

FIG. 83 illustrates the dose-effect curves obtained for the tested JVM-13 cell line (B cell lymphoma, mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 84:
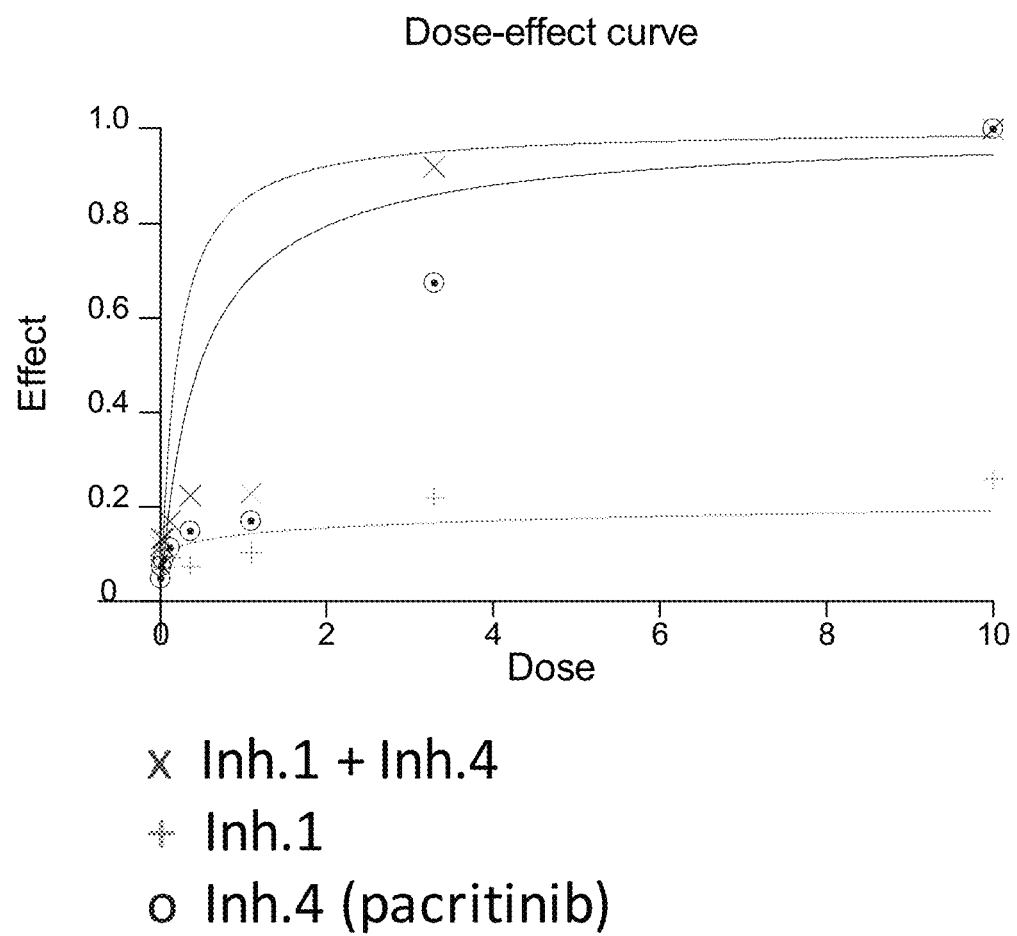

FIG. 84 illustrates the dose-effect curves obtained for the tested SU-DHL-1 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 85:
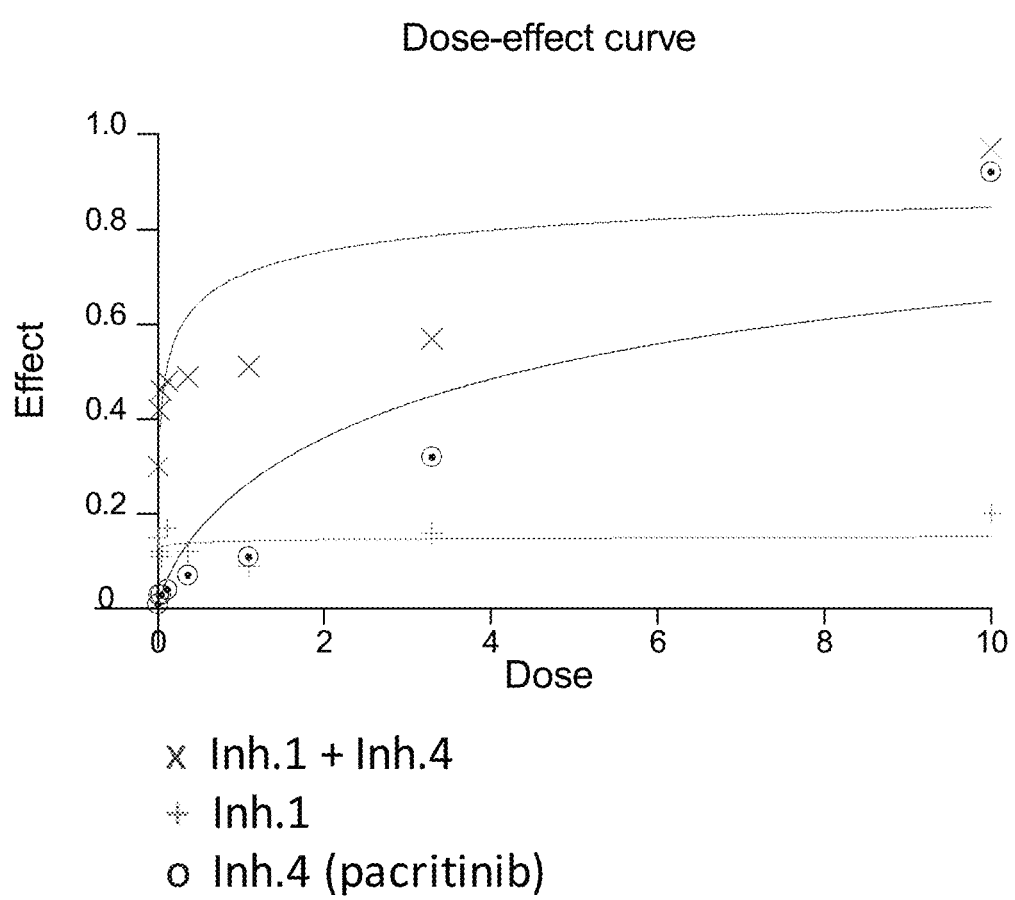

FIG. 85 illustrates the dose-effect curves obtained for the tested SU-DHL-2 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 86:
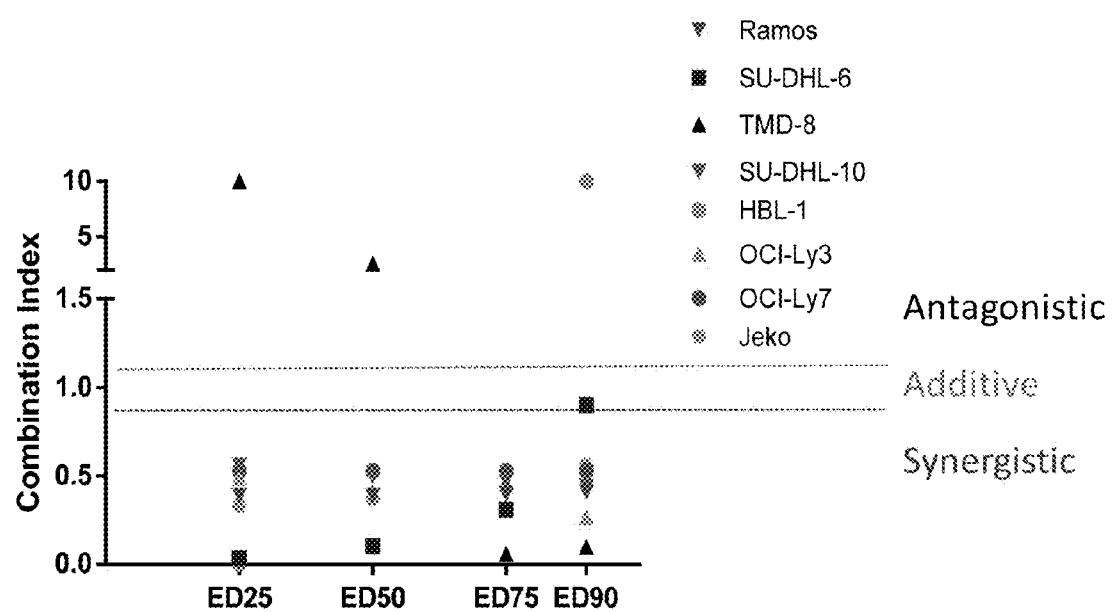

FIG. 86 illustrates the synergy observed in certain cell lines when the BTK inhibitor of Formula (XVIII) and the JAK-2 inhibitor of Formula LIV (pacritinib) are combined. The tested cell lines include Jeko (B cell lymphoma, mantle cell lymphoma), TMD-8 (DLBCL-ABC), SU-DHL6 (DLBCL-GCB), Ramos (human Burkitt's lymphoma), HBL-1 (DLBCL-ABC), SU-DHL-10 (DLBCL-GCB), OCI-Ly7 (DLBCL-ABC), and OCI-Ly3 (DLBCL-ABC). The dose-effect curves for these cell lines are given in FIG. 87, FIG. 88, FIG. 89, FIG. 90, FIG. 91, FIG. 92, FIG. 93, and FIG. 94.

Figure 87:
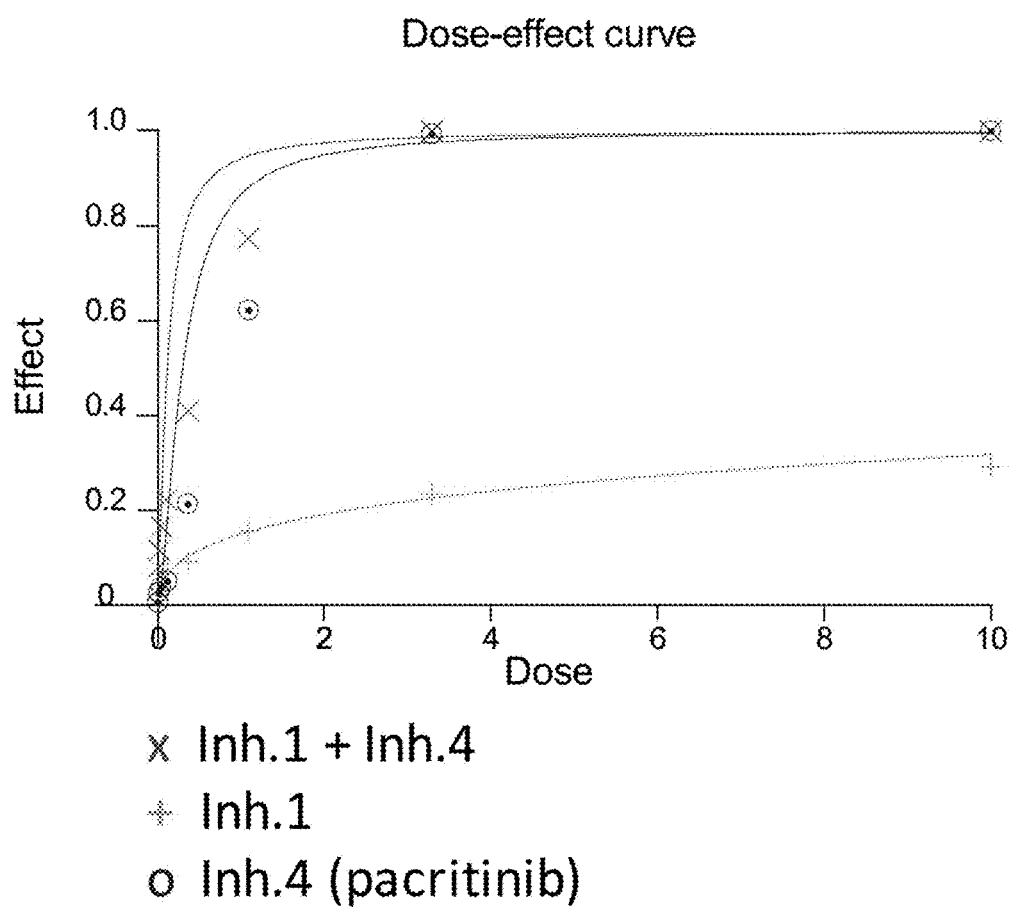

FIG. 87 illustrates the dose-effect curves obtained for the tested Jeko cell line (B cell lymphoma, mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 88:
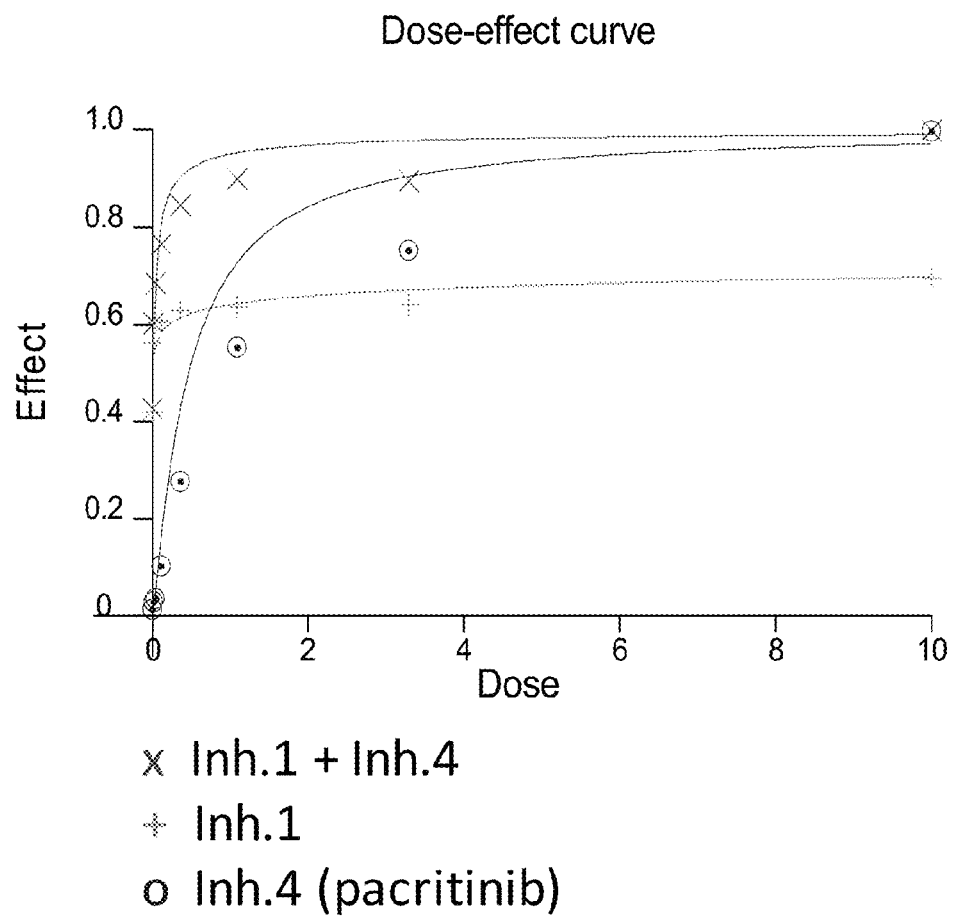

FIG. 88 illustrates the dose-effect curves obtained for the tested TMD-8 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 89:
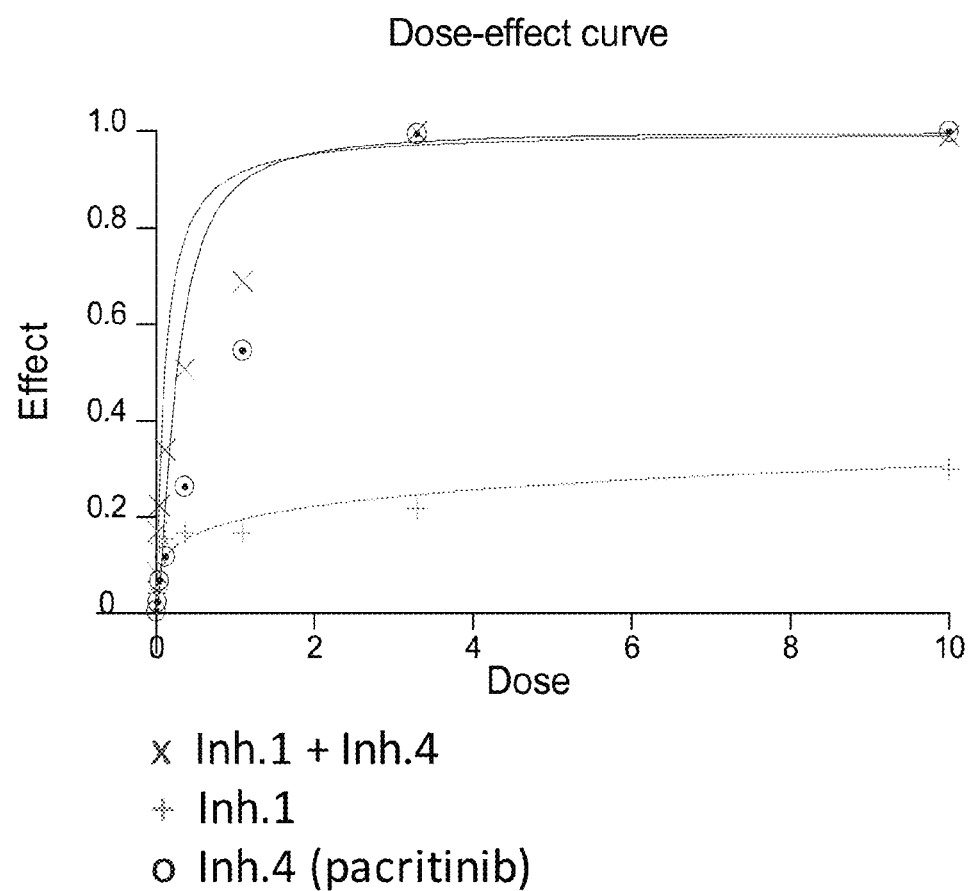

FIG. 89 illustrates the dose-effect curves obtained for the tested SU-DHL6 cell line (DLBCL-GCB) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 90:
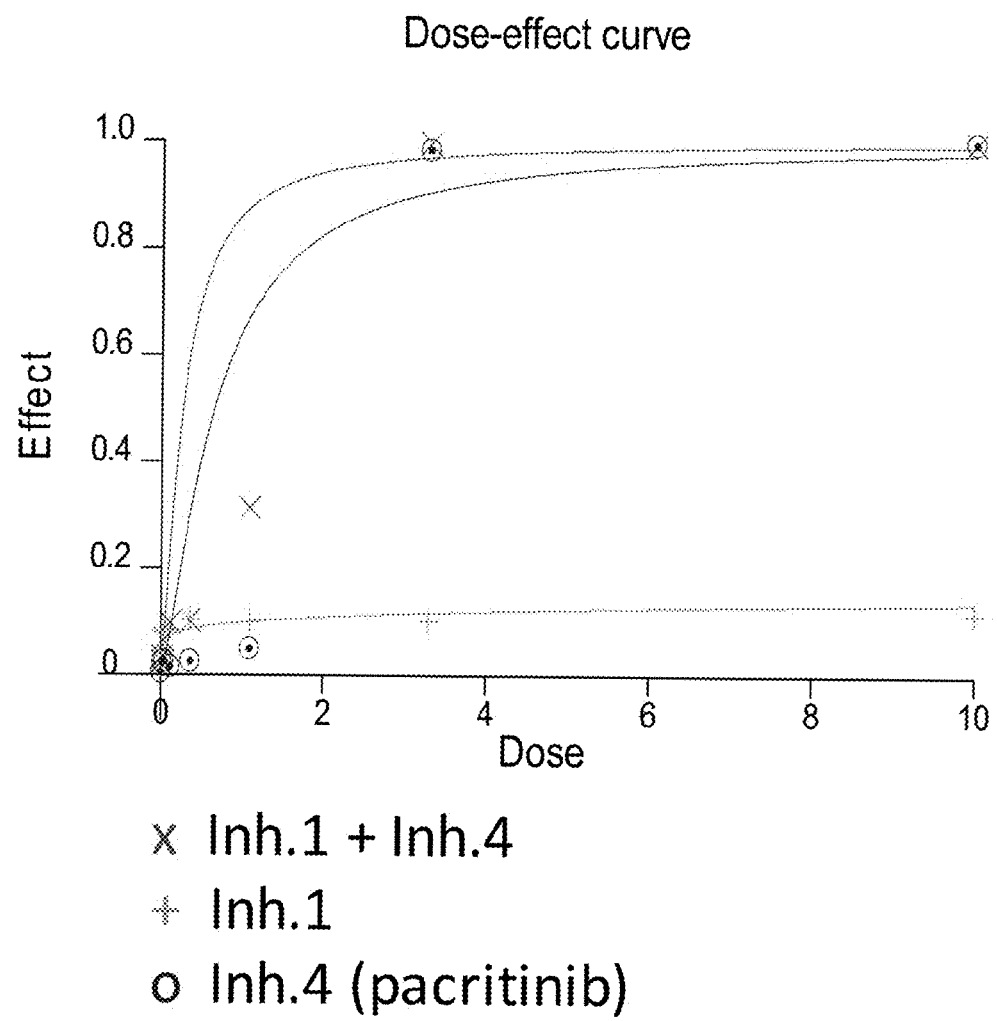

FIG. 90 illustrates the dose-effect curves obtained for the tested Ramos cell line (human Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 91:
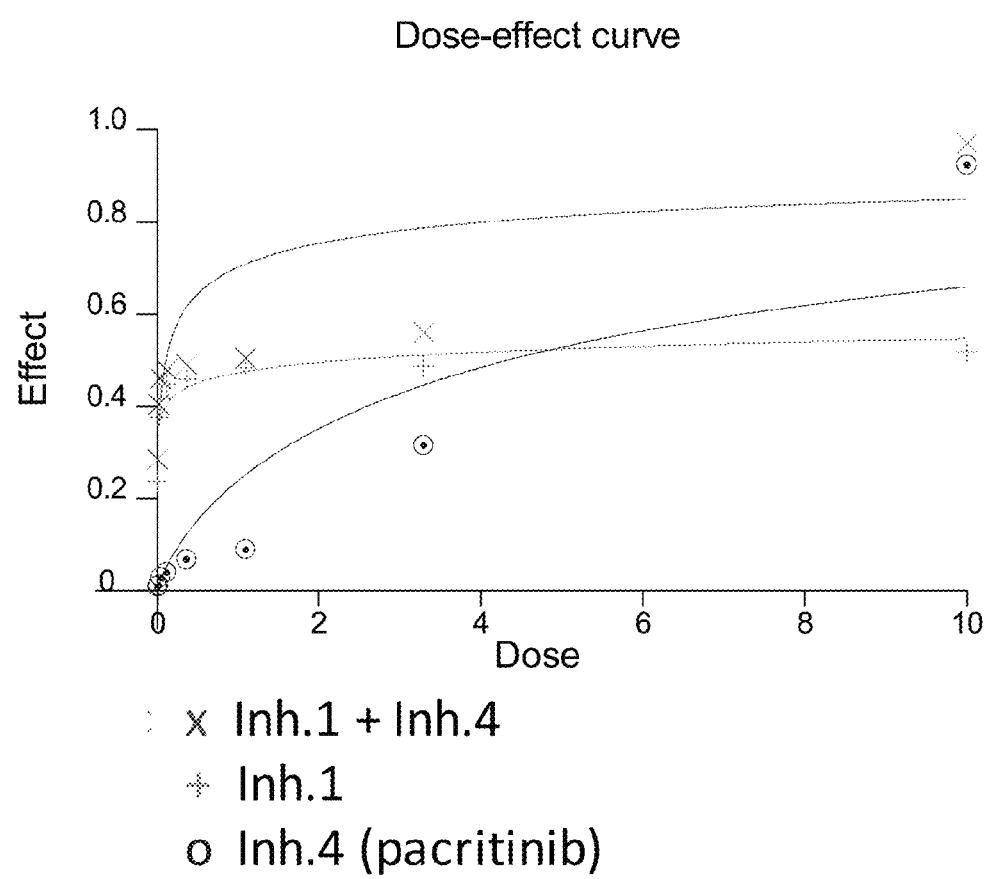

FIG. 91 illustrates the dose-effect curves obtained for the tested HBL-1 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 92:
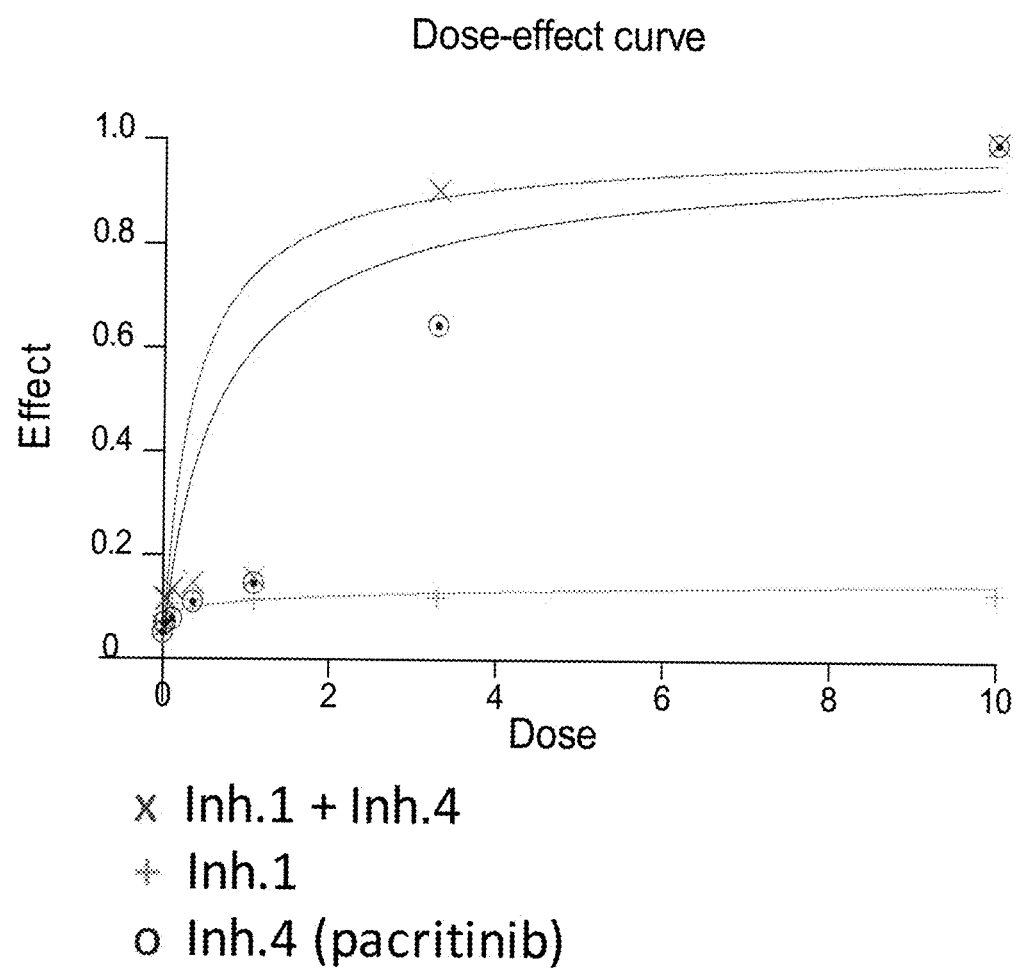

FIG. 92 illustrates the dose-effect curves obtained for the tested SU-DHL-10 cell line (DLBCL-GCB) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 93:
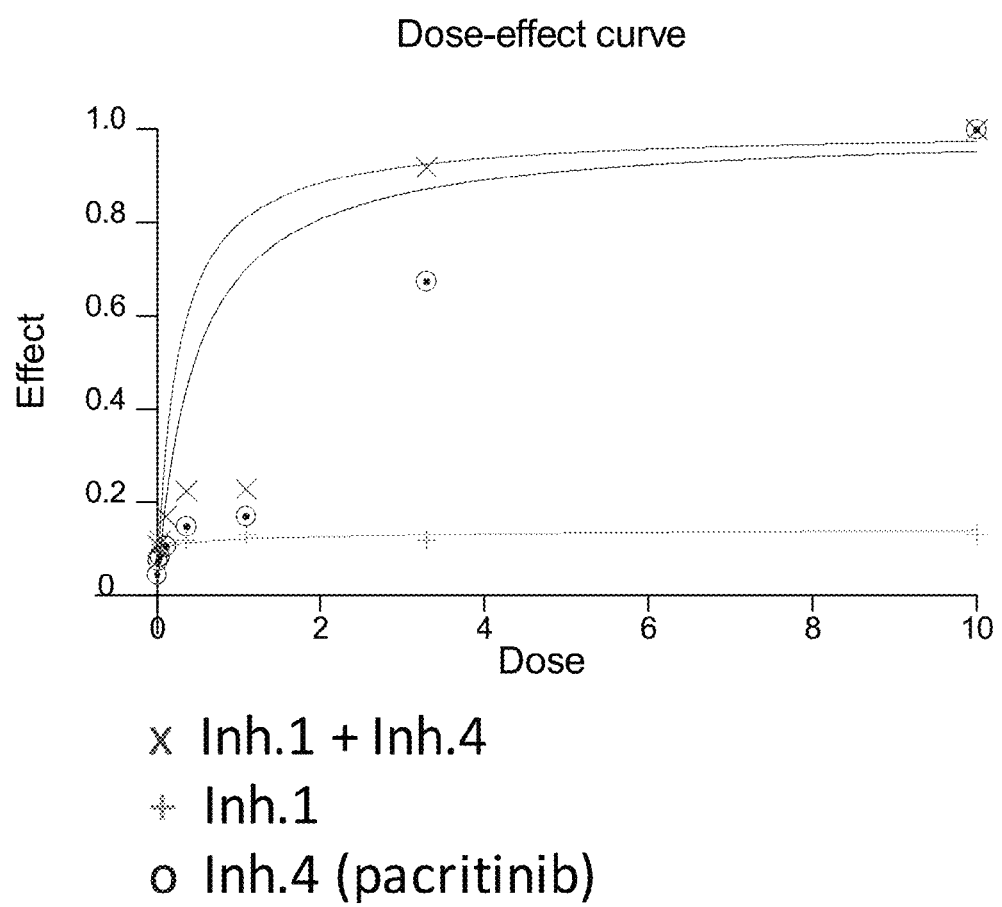

FIG. 93 illustrates the dose-effect curves obtained for the tested OCI-Ly7 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 94:
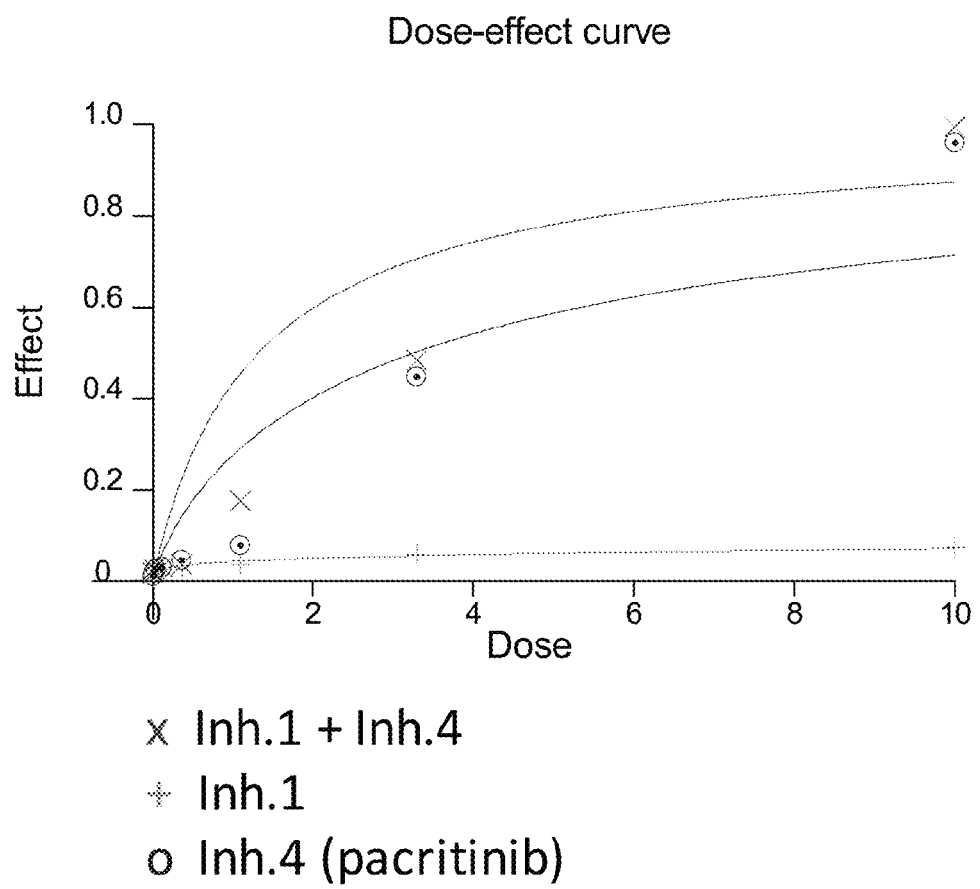

FIG. 94 illustrates the dose-effect curves obtained for the tested OCI-Ly3 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 95:
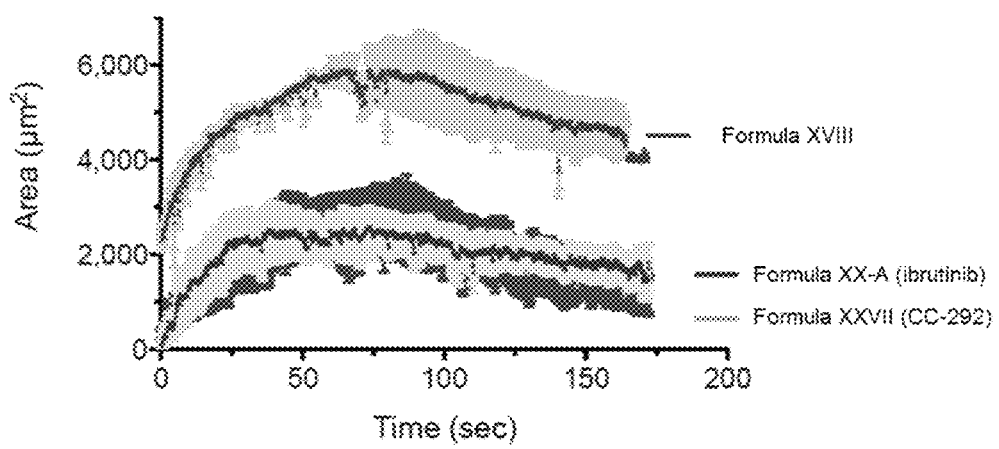

FIG. 95 illustrates a quantitative comparison obtained by in vivo analysis of early thrombus dynamics in a humanized mouse laser injury model using three BTK inhibitors at a concentration 1 µM.

Figure 96:
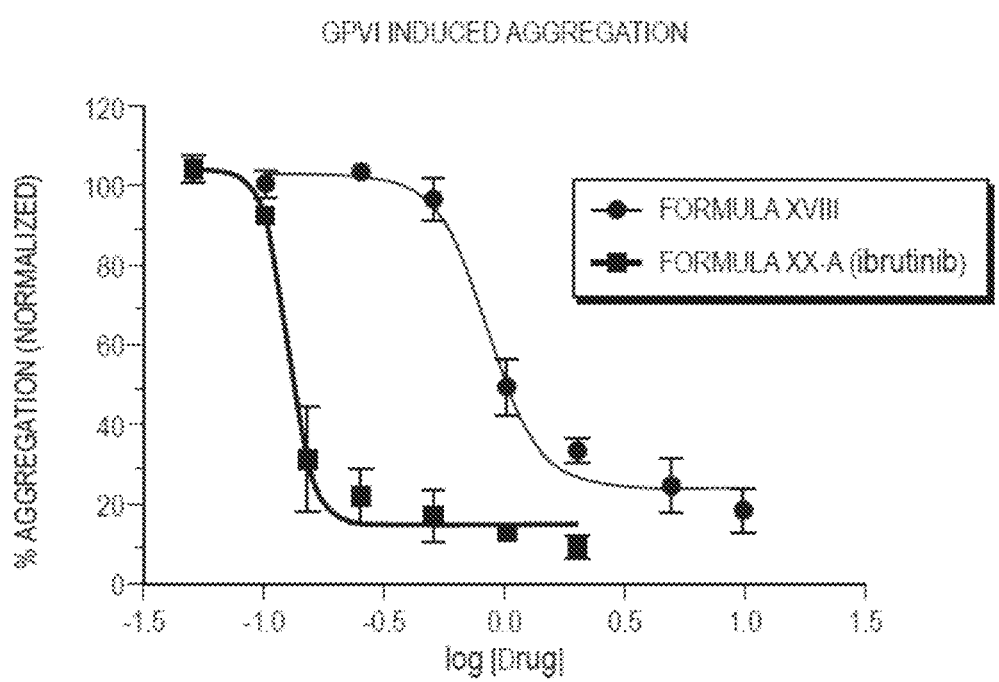

FIG. 96 illustrates the results of GPVI platelet aggregation studies of Formula XVIII (IC50=1.15 µM) and Formula XX-A (ibrutinib, IC50=0.13 µM).

Figure 97:
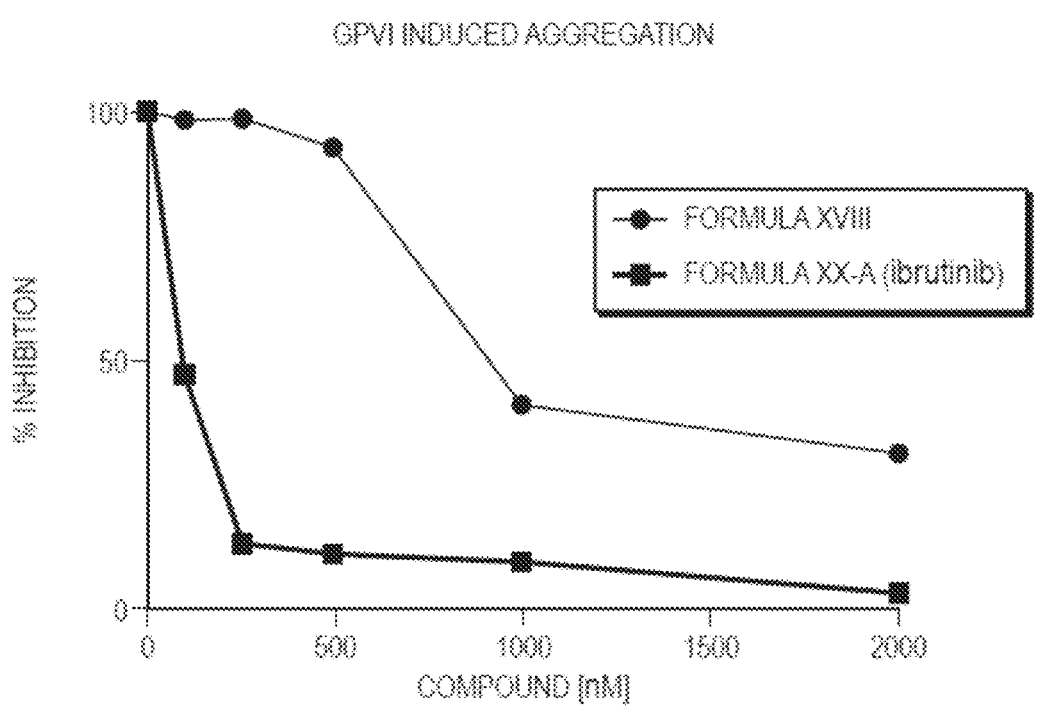

FIG. 97 illustrates the results of GPVI platelet aggregation studies of Formula XVIII and Formula XX-A (ibrutinib).

Figure 98:
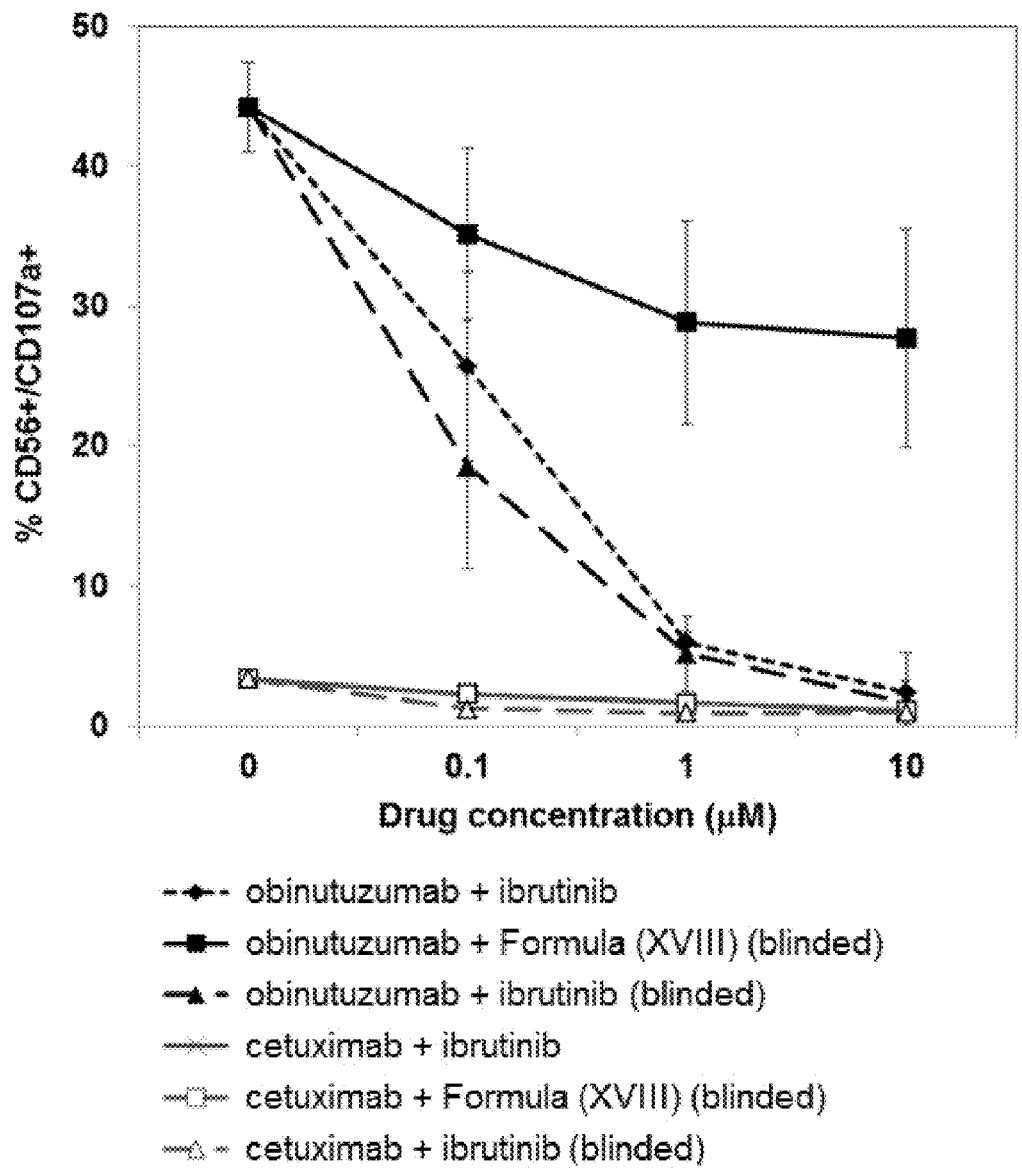

FIG. 98 shows NK cell degranulation results. The percentage of $CD56^+/CD107a^+$ NK cells observed in whole blood after pretreatment for 1 hour with the BTK inhibitors and stimulatation with MEC-1 cells opsonised with obinutuzumab at 1 µg/mL for 4 hours (n=3) is shown.

Figure 99:
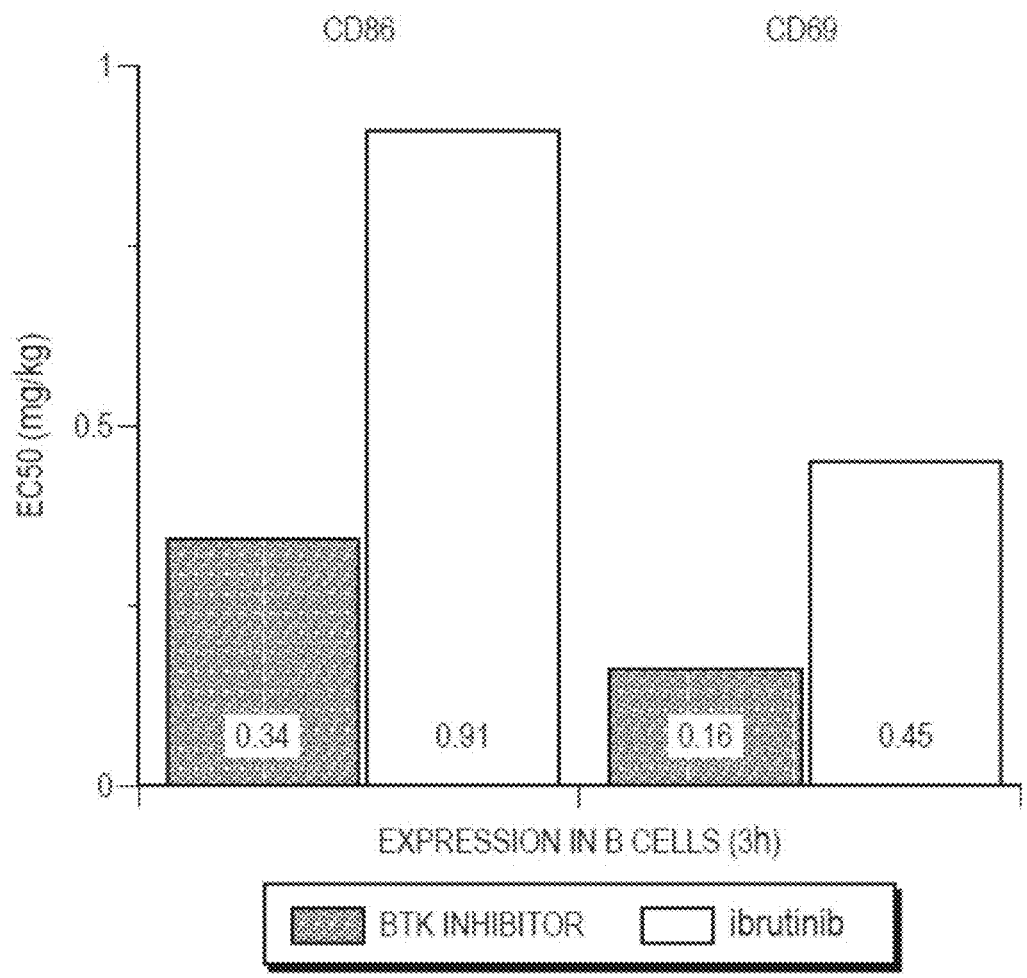

FIG. 99 illustrates in vivo potency of Formula (XVIII) (labeled "BTK inhibitor") and ibrutinib. Mice were gavaged at increasing drug concentration and sacrificed at one time point (3 hours post-dose). BCR is stimulated with IgM and the expression of activation markers CD69 and CD86 are monitored by flow cytometry to determine $EC_{50}$ values. The results show that Formula (XVIII) is more potent at inhibiting expression of activation makers than ibrutinib.

Figure 100:
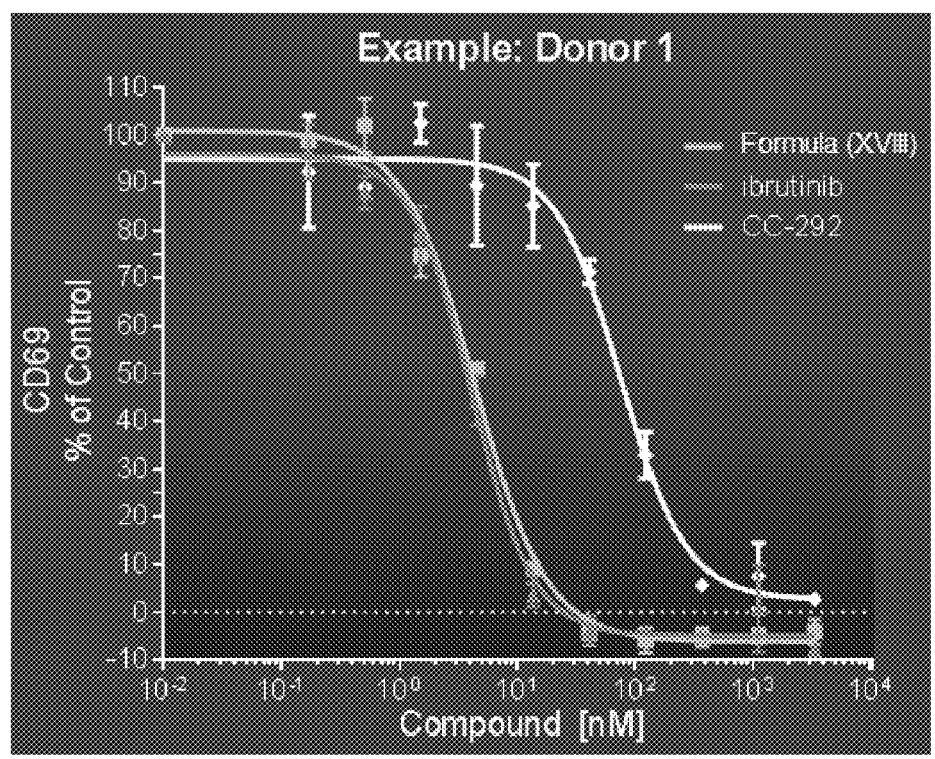

FIG. 100 illustrates in vitro potency in whole blood of Formula (XVIII), ibrutinib and CC-292 in inhibition of signals through the B cell receptor.

Figure 101:
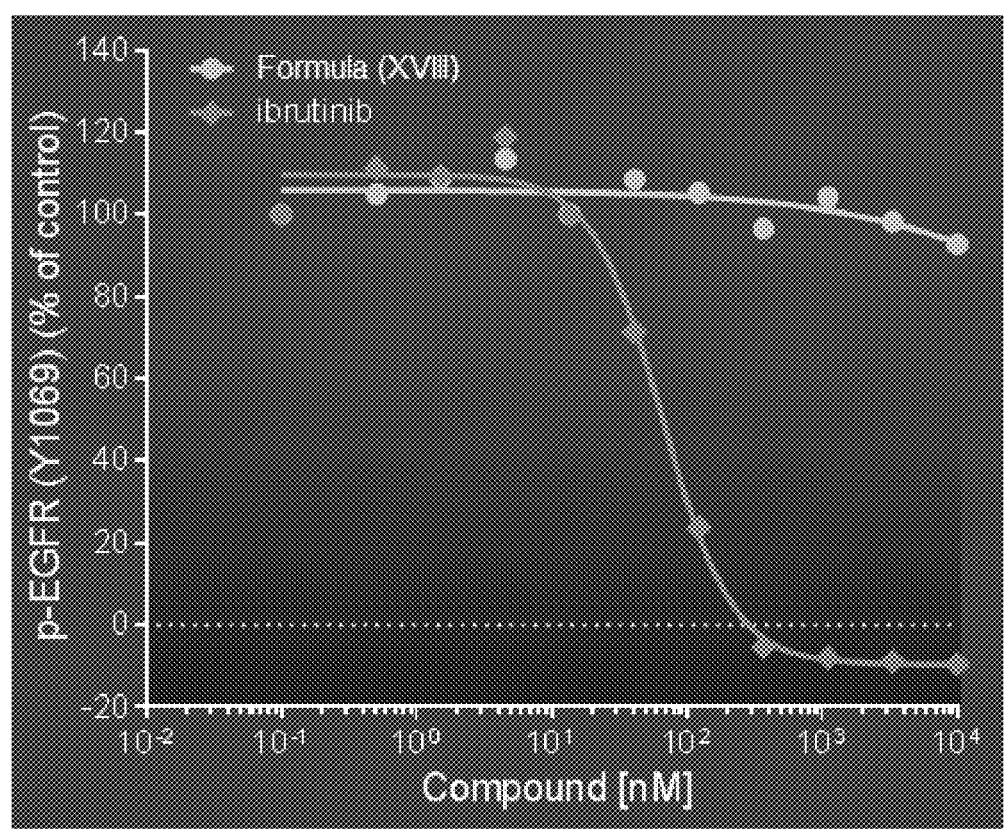

FIG. 101 illustrates EGF receptor phosphorylation in vitro for Formula (XVIII) and ibrutinib.

Figure 1:
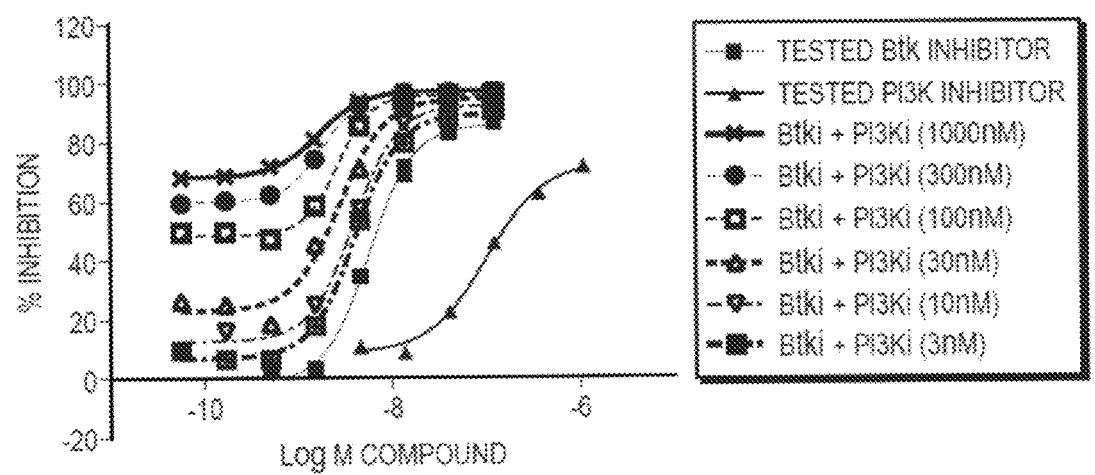
FIG. 1 illustrates the sensitivity of the TMD8 diffuse large B cell lymphoma (DLBCL) cell line to individual treatment with the BTK inhibitor of Formula (XVIII) ("Tested Btk Inhibitor") and the PI3K inhibitor of Formula (IX) ("Tested PI3K Inhibitor") and combined treatment with Formula (XVIII) and Formula (IX) ("Btki+PI3Ki") at different concentrations. The concentration of the first active pharmaceutical ingredient in the combination (the BTK inhibitor) and the concentration of the individual active pharmaceutical ingredients is given on the x-axis, and the concentration of the added PI3K inhibitor in combination with the BTK inhibitor is given in the legend.
Figure 2:
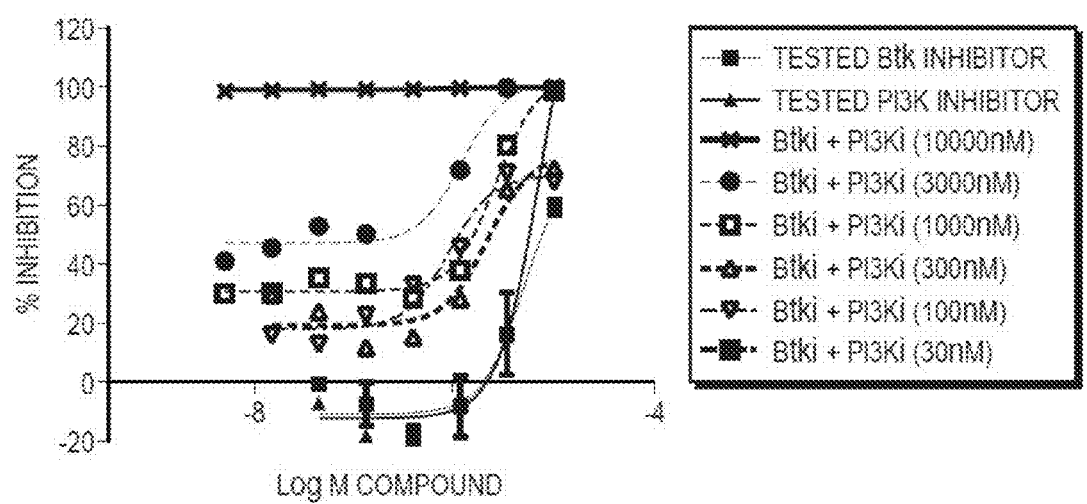
FIG. 2 illustrates the sensitivity of the MINO mantle cell lymphoma cell to individual treatment with the BTK inhibitor of Formula (XVIII) ("Tested Btk Inhibitor") and the PI3K inhibitor of Formula (IX) ("Tested PI3K Inhibitor") and combined treatment with Formula (XVIII) and Formula (IX) ("Btki+PI3Ki") at different concentrations. The concentration of the first active pharmaceutical ingredient in the combination (the BTK inhibitor) and the concentration of the individual active pharmaceutical ingredients is given on the x-axis, and the concentration of the added PI3K inhibitor in combination with the BTK inhibitor is given in the legend.
Figure 3:
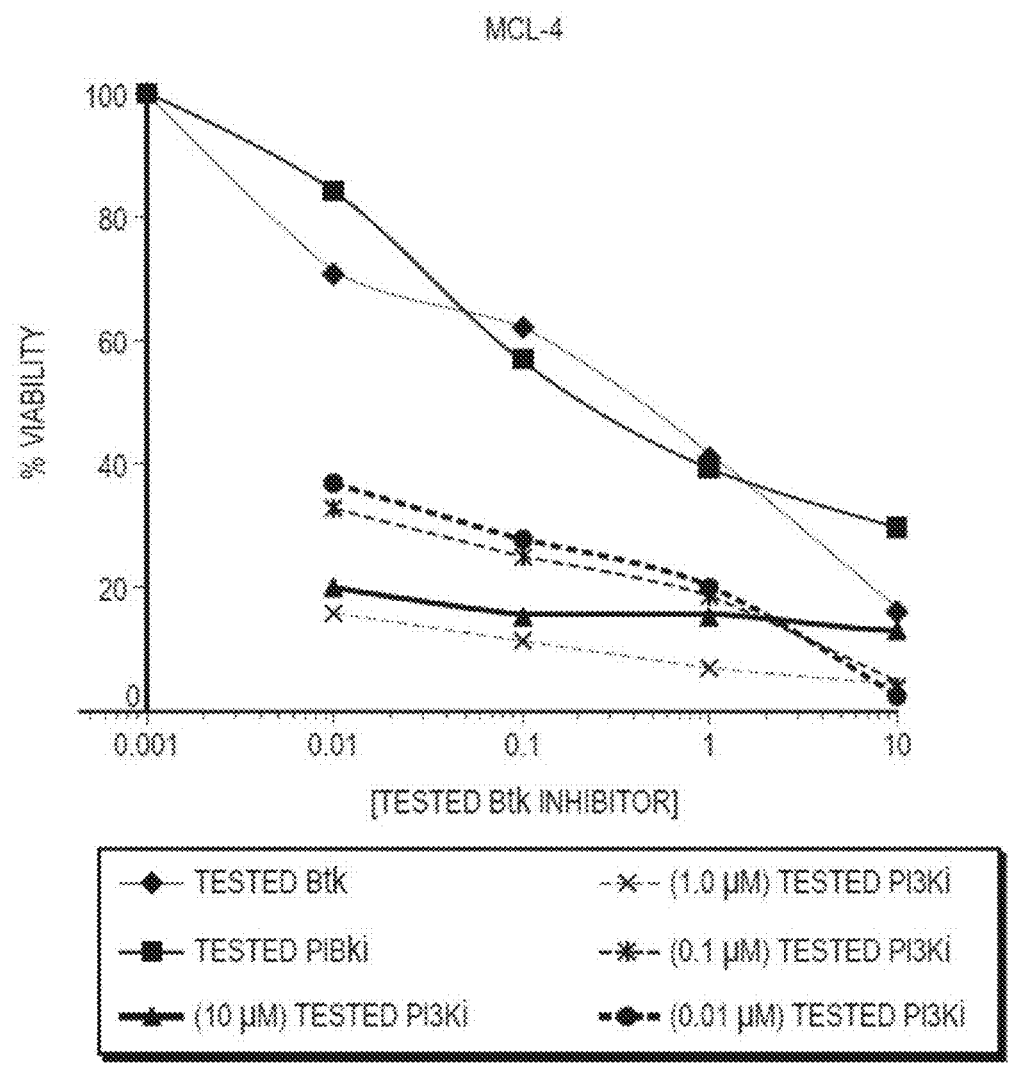
FIG. 3 illustrates the activity in primary mantle cell lymphoma cells of Formula (XVIII) ("Tested Btki") and Formula (IX) ("Tested PI3Ki"). The percentage viability of cells ("% viability", y-axis) is plotted versus the concentration of the active pharmaceutical ingredient(s). Treatment with single BTK ("Tested Btki") or PI3K inhibitors ("Tested PI3Ki") is compared to four combinations of Formula (XVIII) and Formula (IX) ("(10 µM) Tested PI3Ki", "(1.0 µM) Tested PI3Ki," "(0.1 µM) Tested PI3Ki," "(0.01 µM) Tested PI3Ki").
Figure 4:
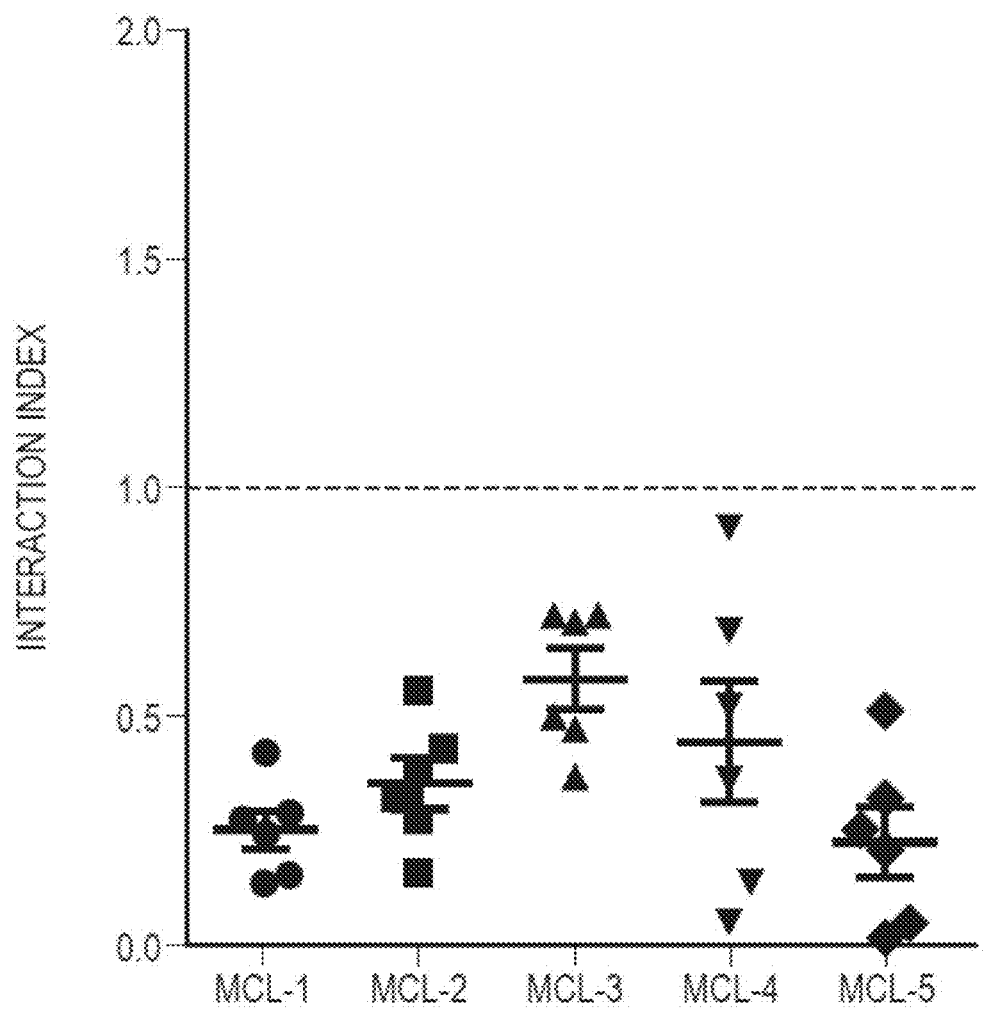
FIG. 4 illustrates the interaction index of the combination of the BTK inhibitor of Formula (XVIII) and the PI3K inhibitor of Formula (IX) in primary mantle cell lymphoma cells from different patients (MCL-1 to MCL-5). Each symbol represents a concentration from 10 µM to 0.1 nM.
Figure 5:
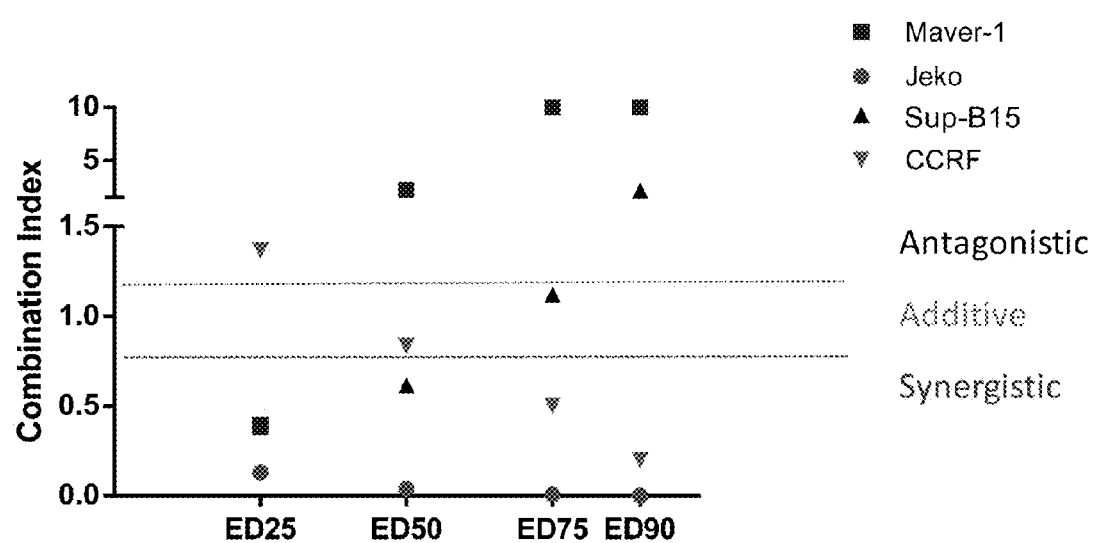
FIG. 5 illustrates the synergy observed in certain cell lines when the BTK inhibitor of Formula (XVIII) and the PI3K-δ inhibitor of Formula (IX) are combined. The tested cell lines include Maver-1 (B cell lymphoma, mantle), Jeko (B cell lymphoma, mantle), CCRF (B lymphoblast, acute lymphoblastic leukemia), and SUP-B15 (B lymphoblast, acute lymphoblastic leukemia). The dose-effect curves for these cell lines are given in FIG. 6, FIG. 7, FIG. 8, and FIG. 9. ED25, ED50, ED75, and ED90 refer to the effective doses causing 25%, 50%, 75%, and 90% of the maximum biological effect (proliferation).
Figure 6:
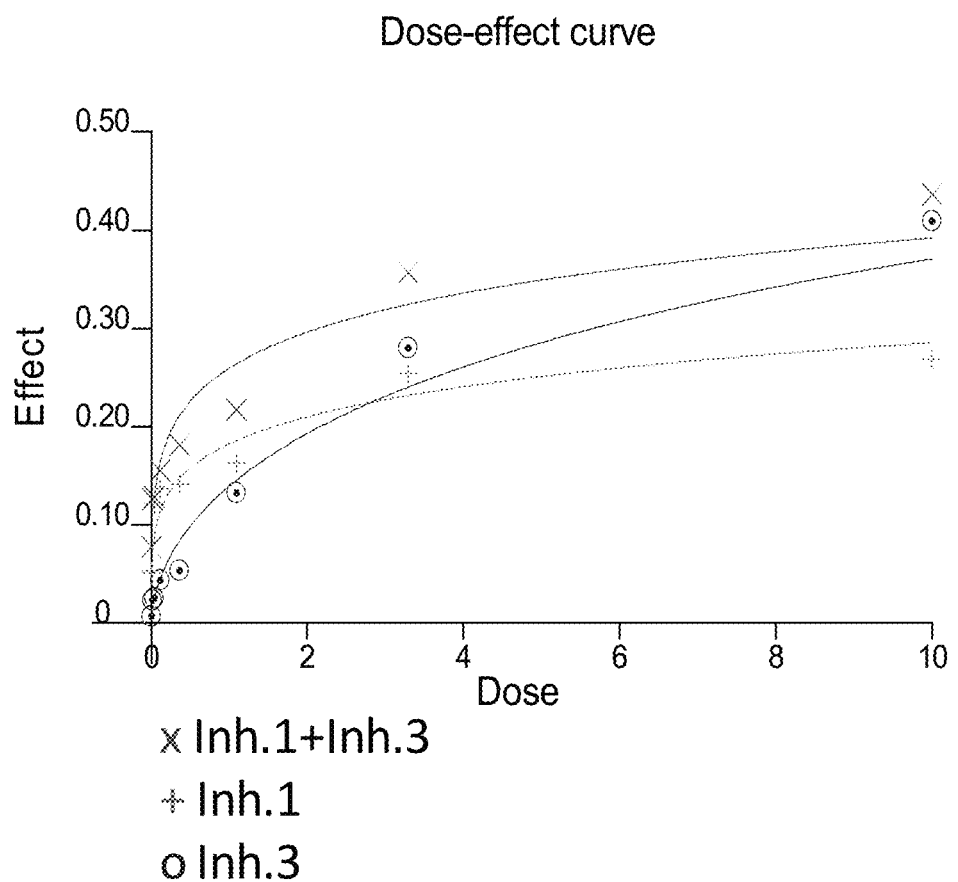
FIG. 6 illustrates the dose-effect curves obtained for the tested Maver-1 cell line (B cell lymphoma, mantle) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 7:
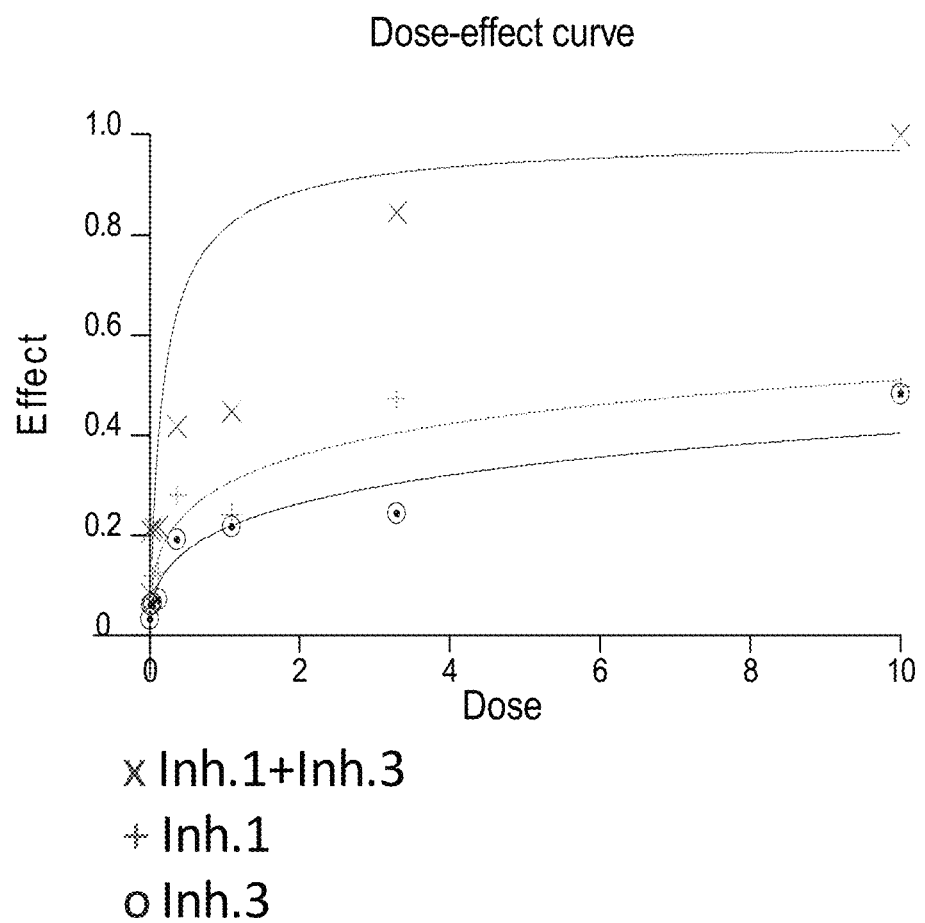
FIG. 7 illustrates the dose-effect curves obtained for the tested Jeko cell line (B cell lymphoma, mantle) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 8:
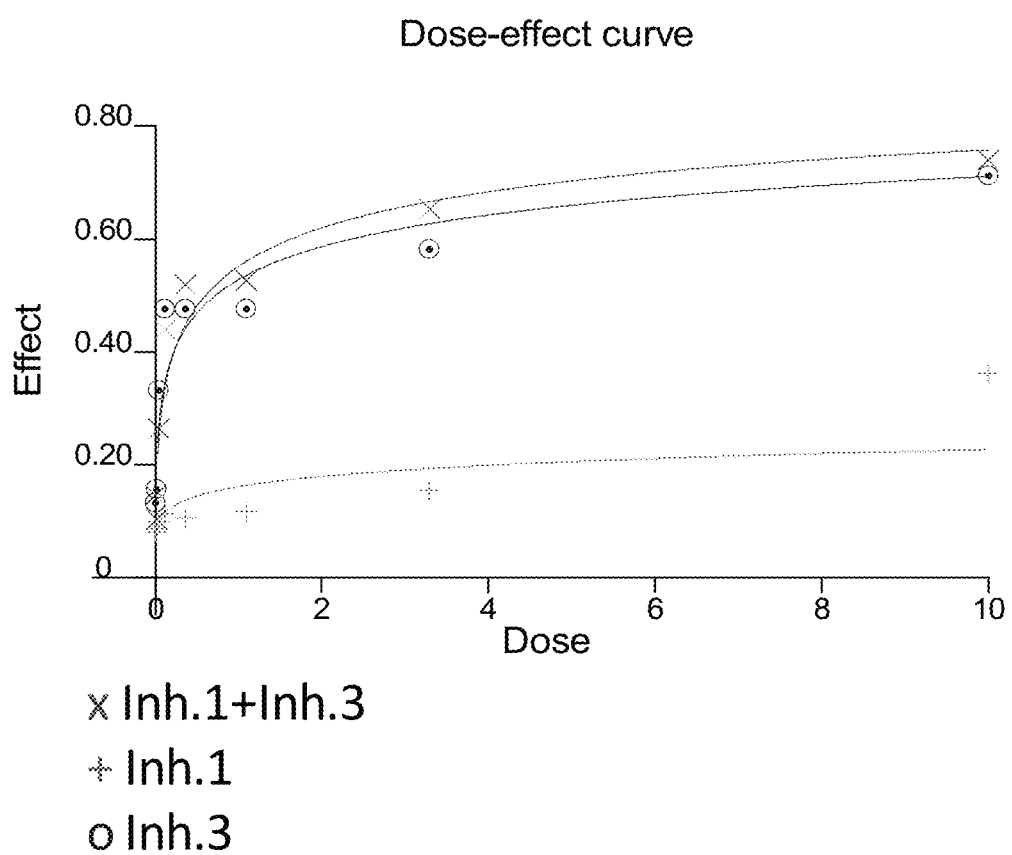
FIG. 8 illustrates the dose-effect curves obtained for the tested CCRF cell line (B lymphoblast, acute lymphoblastic leukemia) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 9:
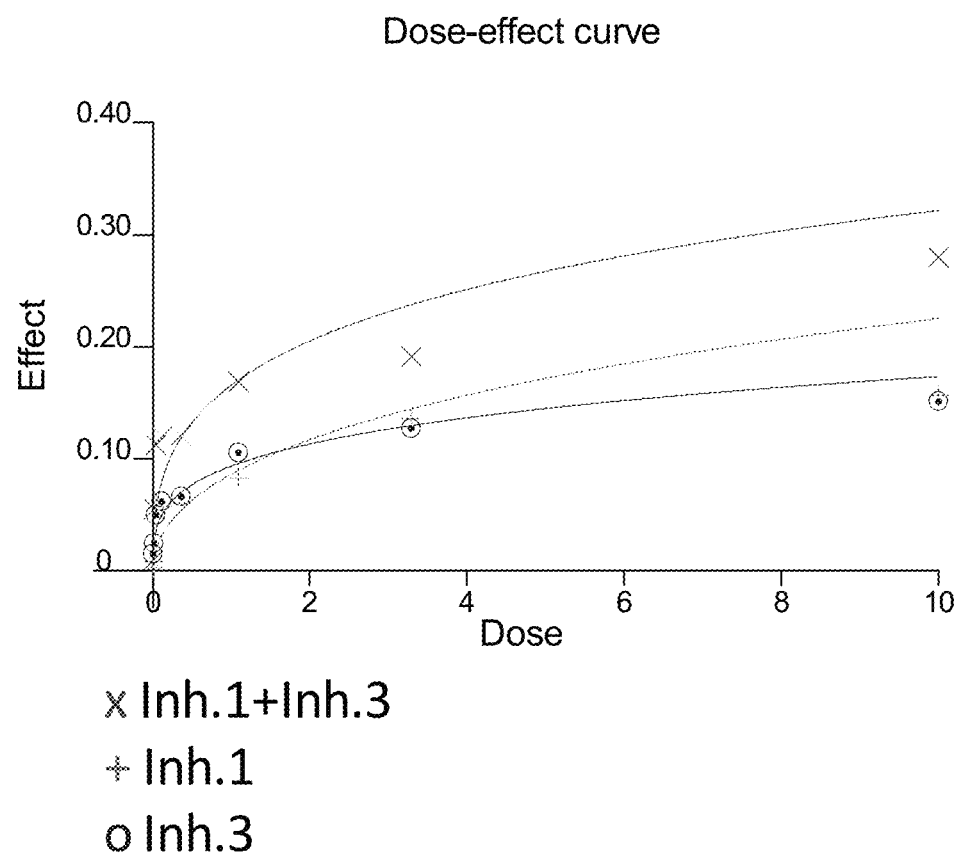
FIG. 9 illustrates the dose-effect curves obtained for the tested SUP-B15 cell line (B lymphoblast, acute lymphoblastic leukemia) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 10:
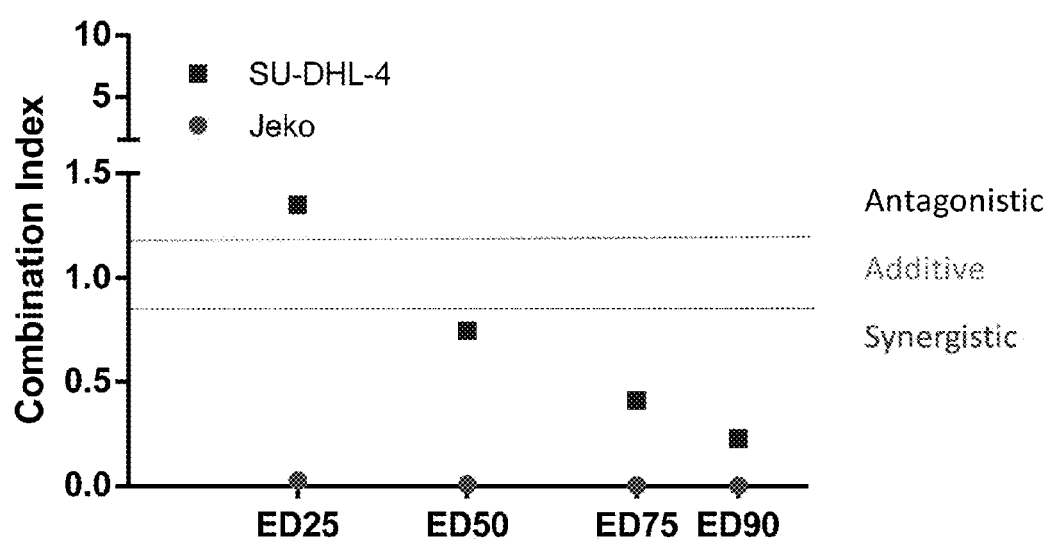
FIG. 10 illustrates the synergy observed in certain cell lines when the BTK inhibitor of Formula (XVIII) and the PI3K-δ inhibitor of Formula (IX) are combined. The tested cell lines include Jeko (B cell lymphoma, mantle cell lymphoma) and SU-DHL-4 (activated B cell like (ABC) diffuse large B cell lymphoma). The dose-effect curves for these cell lines are given in FIG. 11 and FIG. 12.
Figure 11:
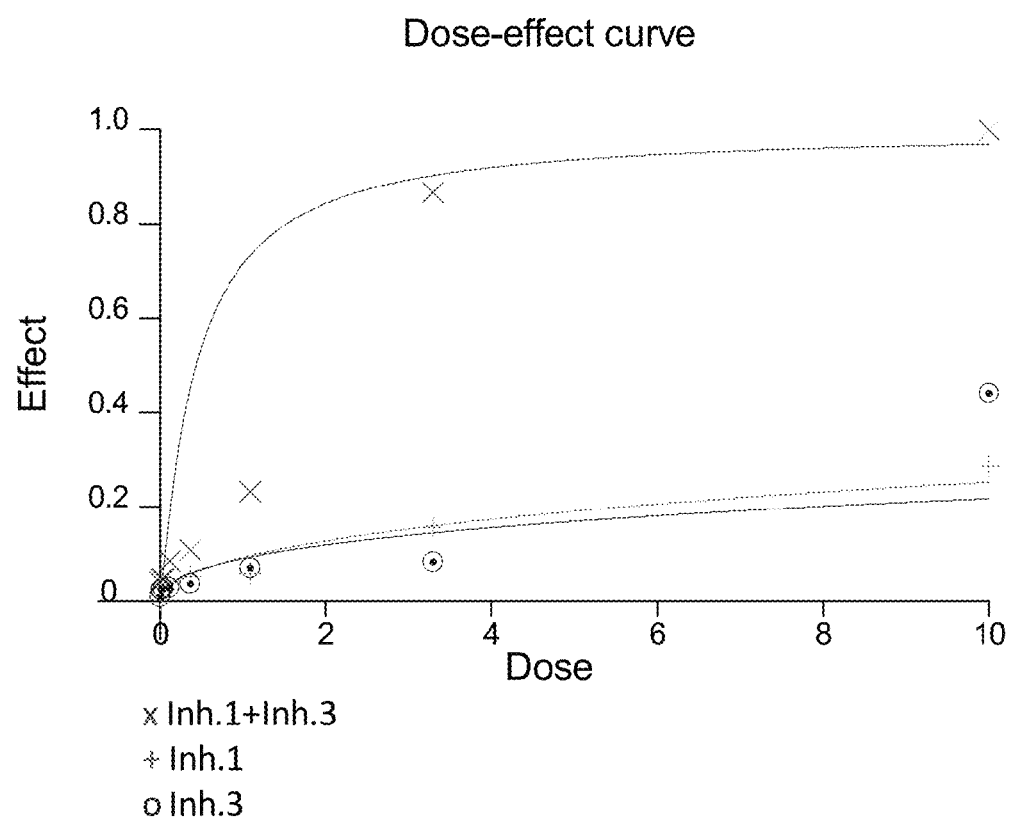
FIG. 11 illustrates the dose-effect curves obtained for the tested Jeko cell line (B cell lymphoma, mantle) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 12:
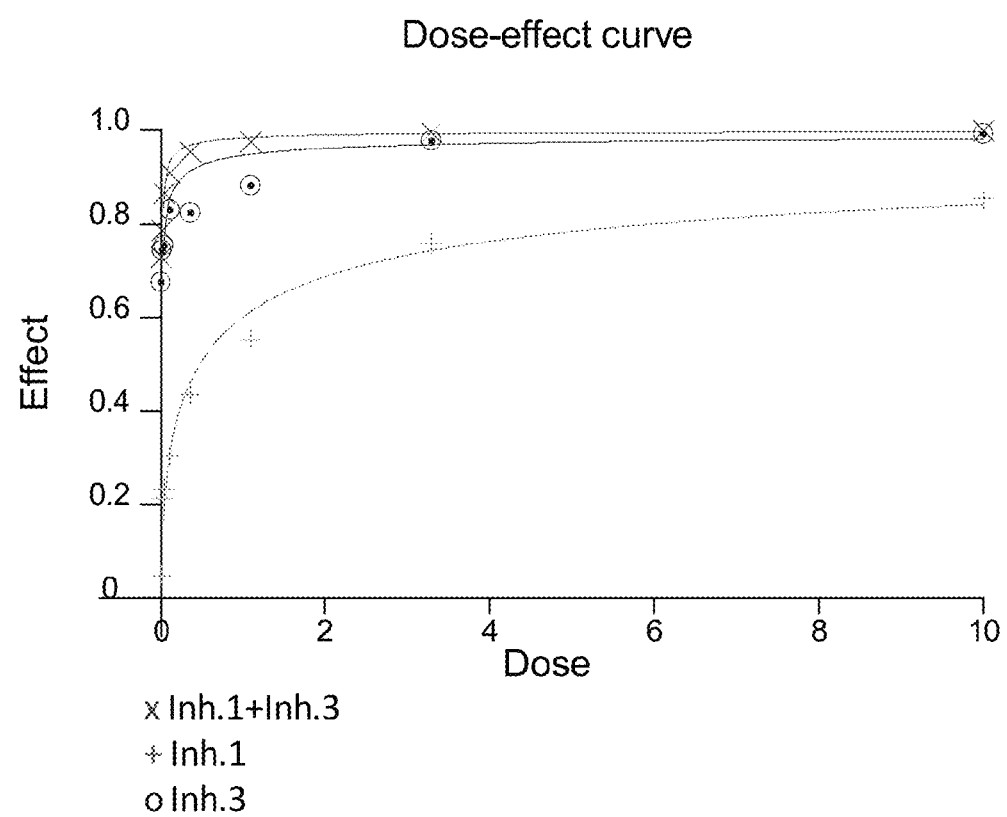
FIG. 12 illustrates the dose-effect curves obtained for the tested SU-DHL-4 cell line (diffuse large B cell lymphoma, ABC) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 13:
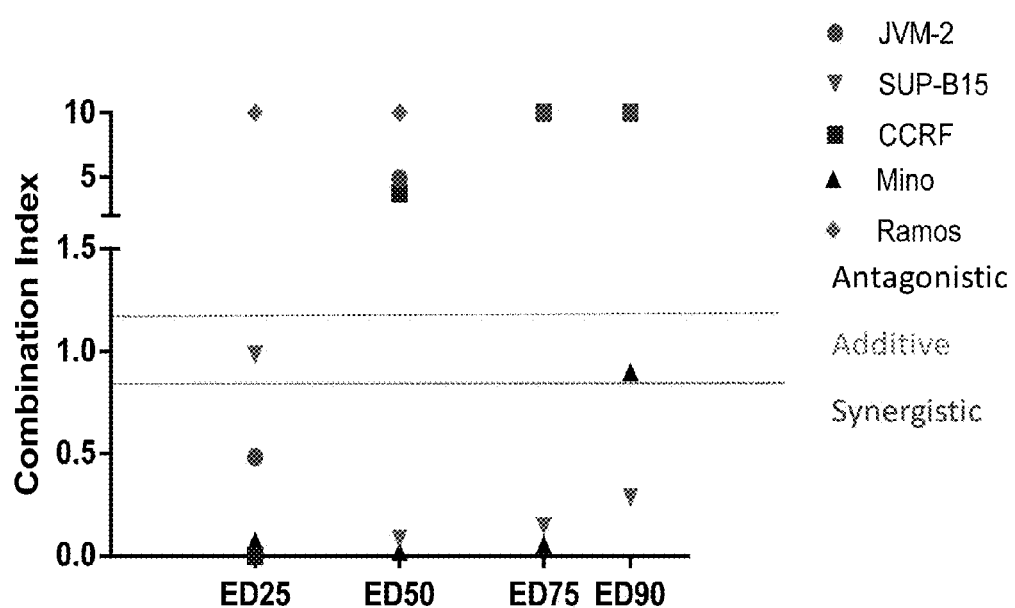
FIG. 13 illustrates the synergy observed in certain cell lines when the BTK inhibitor of Formula (XVIII) and the PI3K-δ inhibitor of Formula (IX) are combined. The tested cell lines include CCRF (B lymphoblast, acute lymphoblastic leukemia), SUP-B15 (B lymphoblast, acute lymphoblastic leukemia), JVM-2 (prolymphocytic leukemia), Ramos (Burkitt's lymphoma), and Mino (mantle cell lymphoma). The dose-effect curves for these cell lines are given in FIG. 14, FIG. 15, FIG. 16, and FIG. 17. No dose-effect curve is given for Ramos (Burkitt's lymphoma) because of negative slope.
Figure 14:
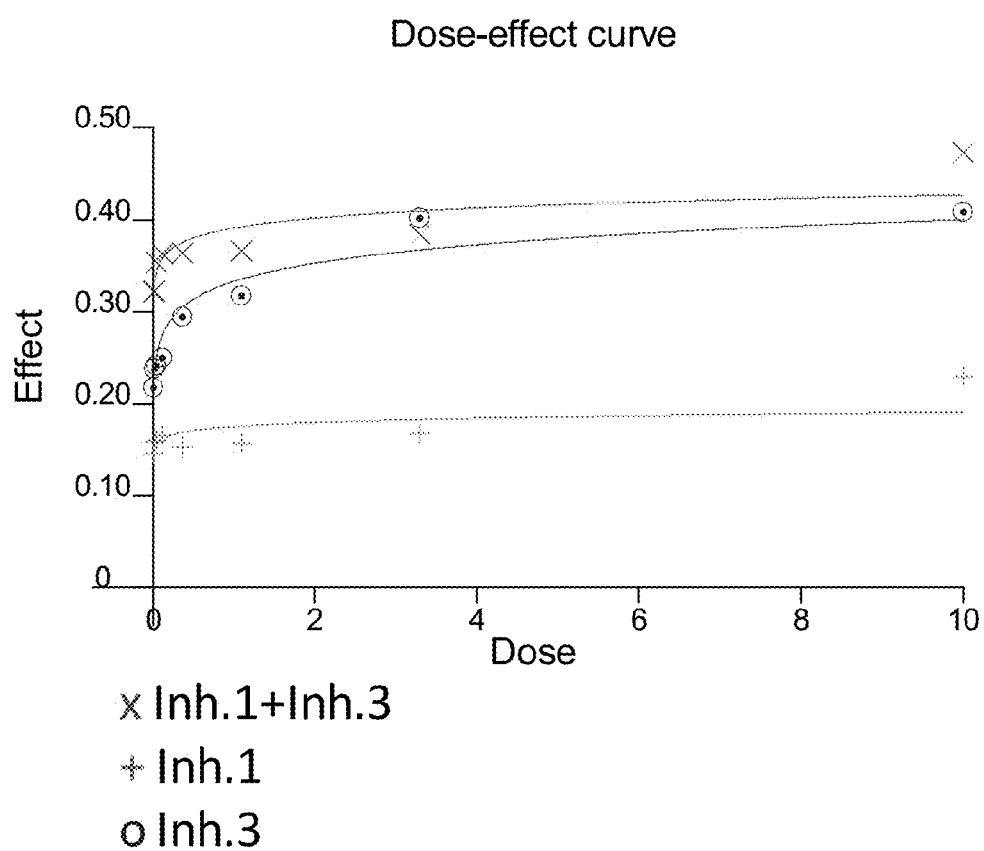
FIG. 14 illustrates the dose-effect curves obtained for the tested CCRF cell line (B lymphoblast, acute lymphoblastic leukemia) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 15:
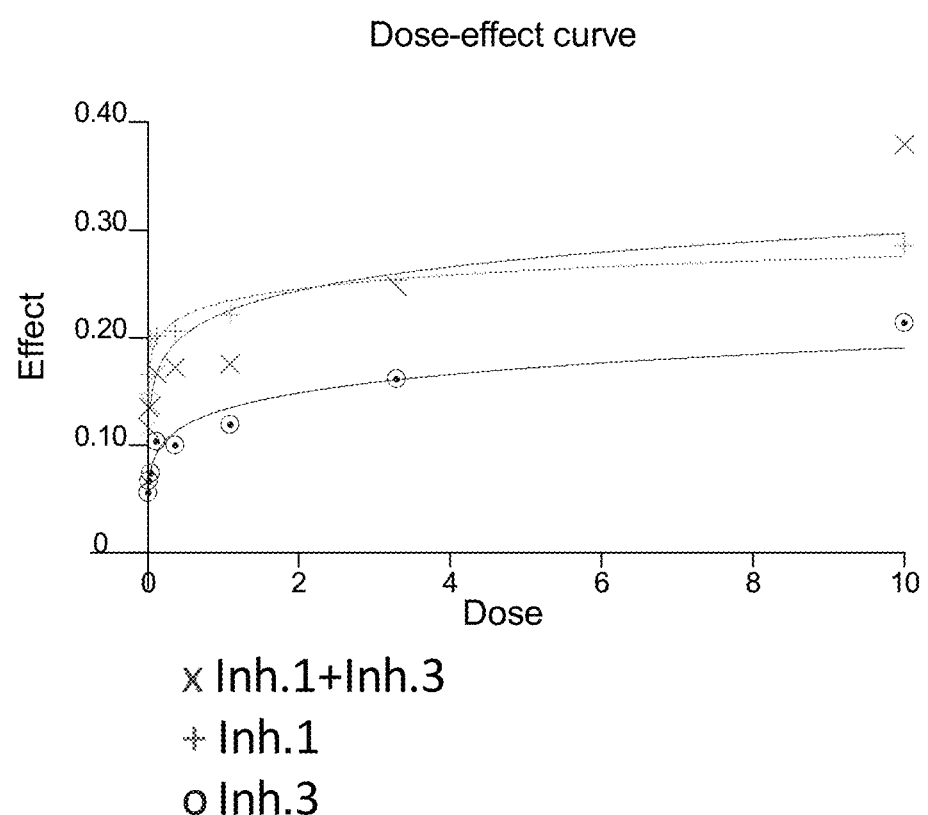
FIG. 15 illustrates the dose-effect curves obtained for the tested SUP-B15 cell line (B lymphoblast, acute lymphoblastic leukemia) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 16:
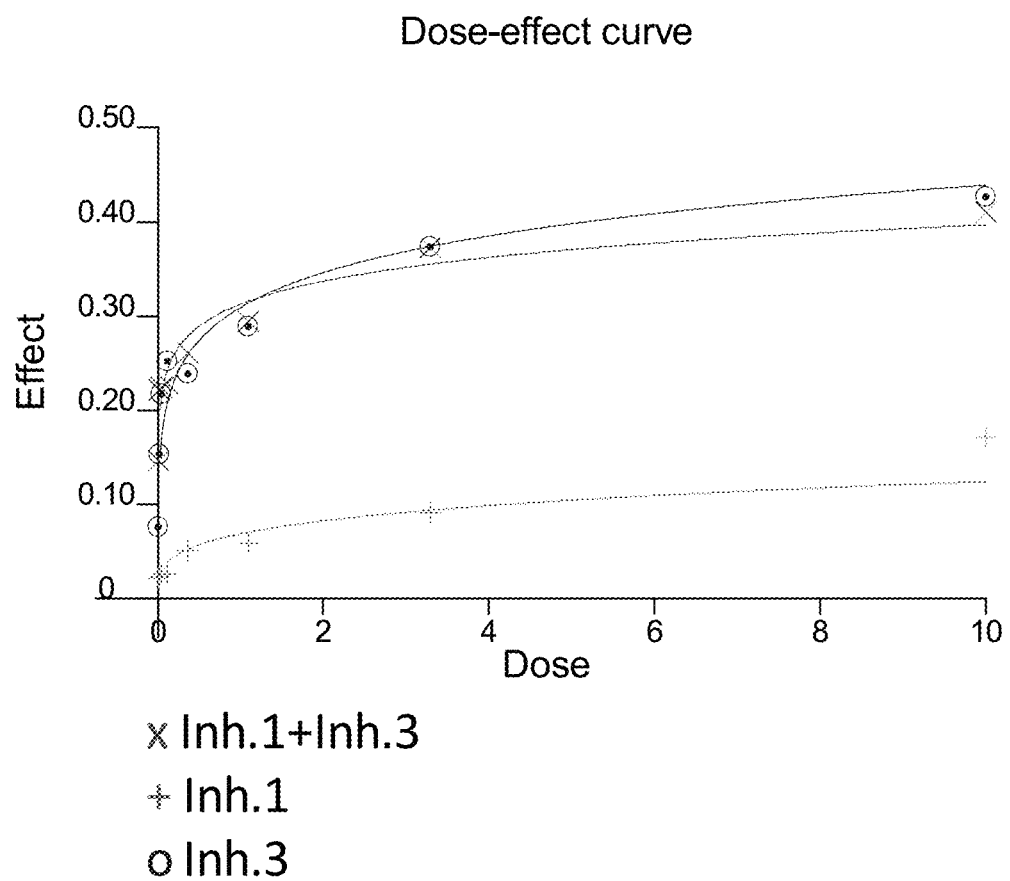
FIG. 16 illustrates the dose-effect curves obtained for the tested JVM-2 cell line (prolymphocytic leukemia) using combined dosing of the BTK inhibitor of Formula (XVIII) ("Inh.1") and the PI3K-δ inhibitor of Formula (IX) ("Inh.3"). The y-axis ("Effect") is given in units of Fa (fraction affected) and the x-axis ("Dose") is given in linear units of µM.
Figure 17:
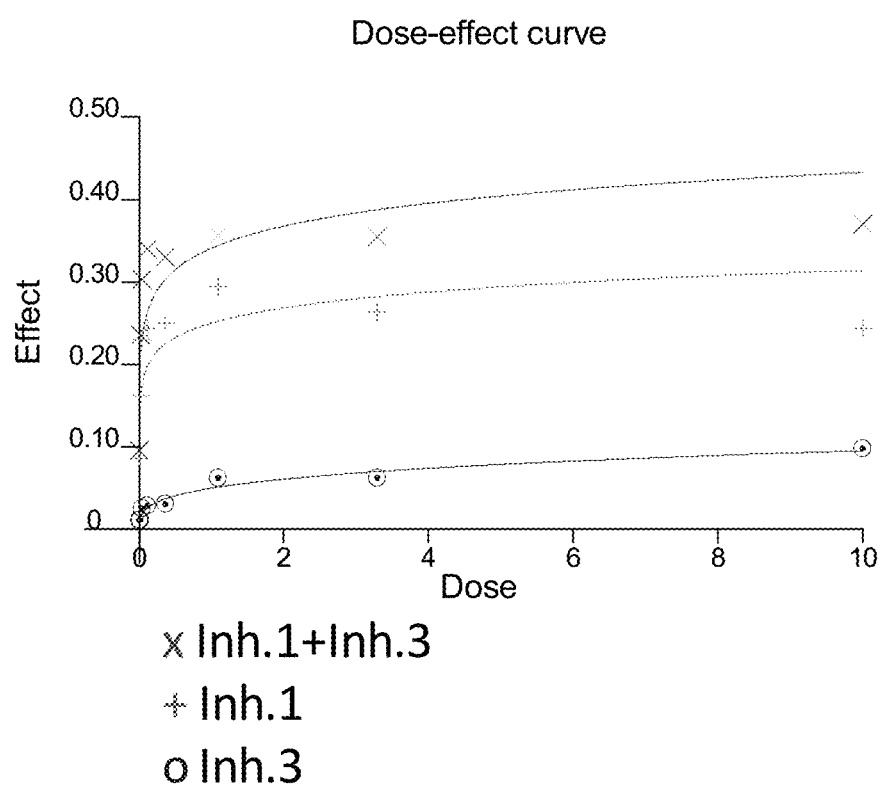
FIG. 17 illustrates the dose-effect curves obtained for the tested Mino cell line (mantle cell lymphoma) using combined dosing of the BTK inhibitor of Formula (XVIII)
Figure 102:
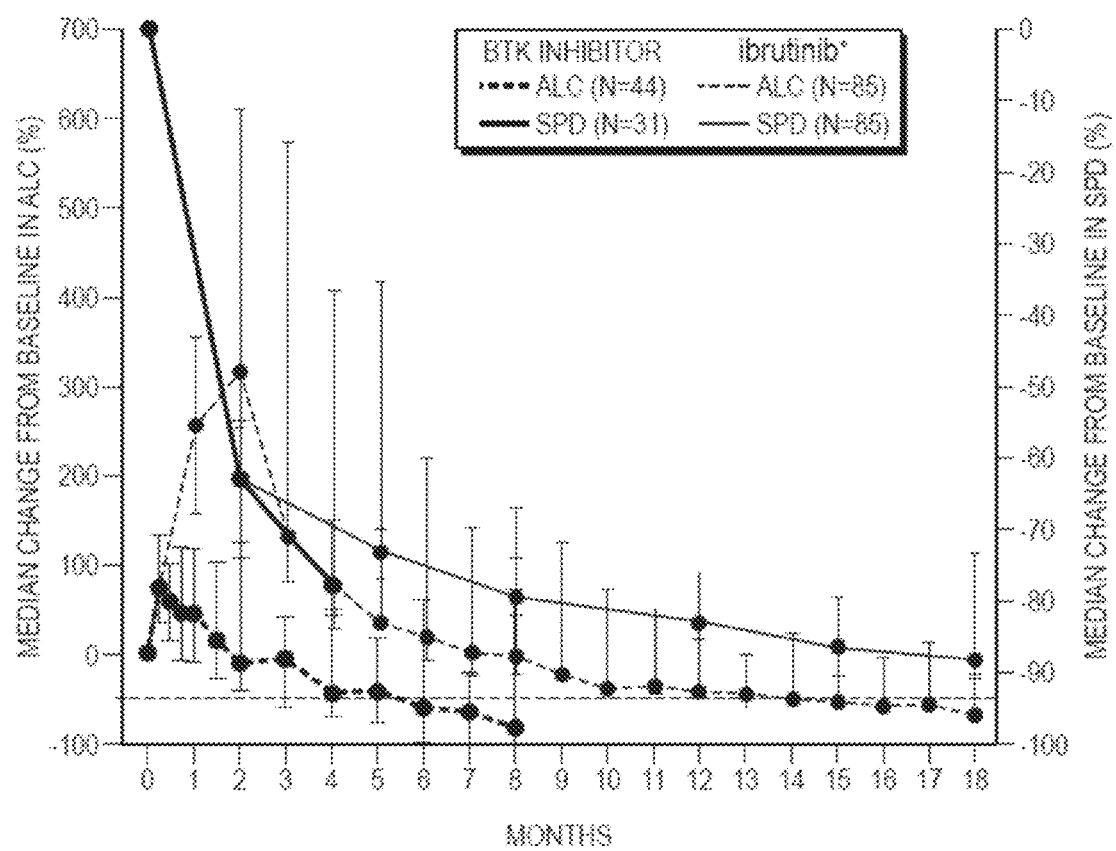

FIG. 102 illustrates the results of the clinical study of Formula (XVIII) (labeled "BTK inhibitor") in CLL, which are shown in comparison to the results reported for ibrutinib in FIG. 1A of Byrd, et al., *N. Engl. J. Med.* 2013, 369, 32-42.

The results show that the BTK inhibitor of Formula (XVIII) causes a much smaller relative increase and much faster decrease in absolute lymphocyte count (ALC) relative to the BTK inhibitor ibrutinib. The sum of the product of greatest diameters (SPD) also decreases more rapidly during treatment with the BTK inhibitor than with the BTK inhibitor ibrutinib.

Figure 103:
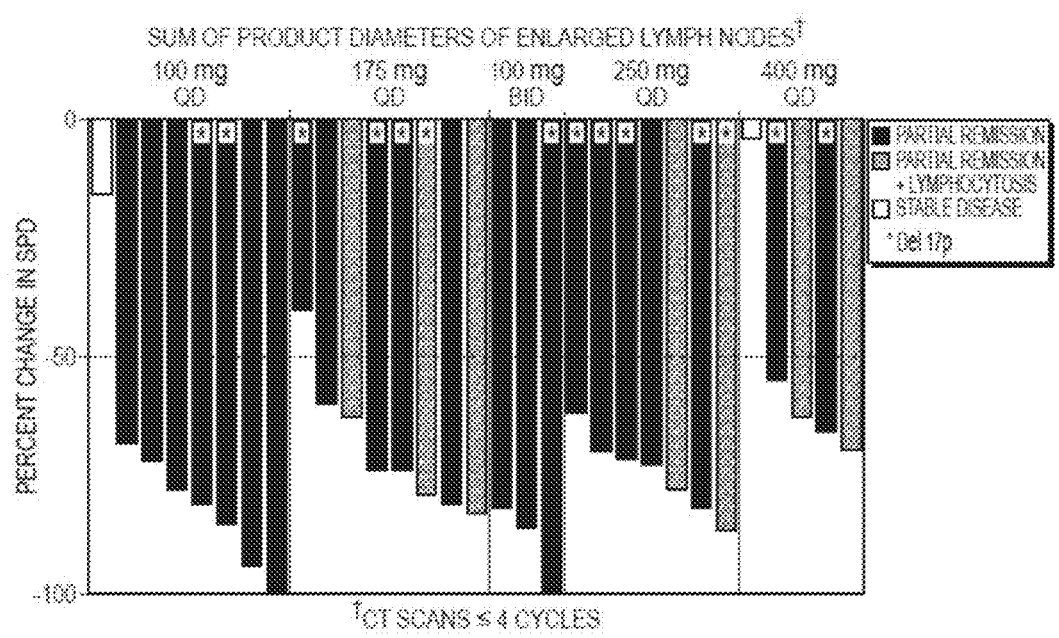

FIG. 103 shows overall response data shown by SPD of enlarged lymph nodes in CLL patients as a function of dose of the BTK inhibitor of Formula (XVIII).

Figure 104:
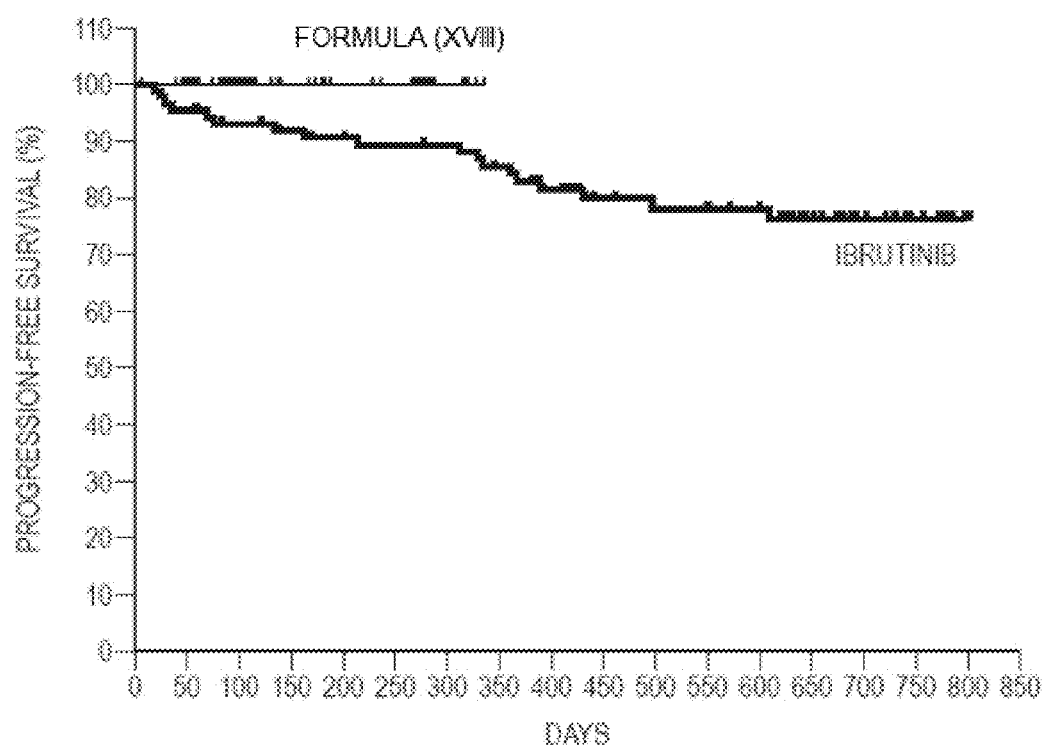

FIG. 104 shows a comparison of progression-free survival (PFS) in CLL patients treated with the BTK inhibitor ibrutinib or the BTK inhibitor of Formula (XVIII). The ibrutinib data is taken from Byrd, et al., *N. Engl. J. Med.* 2013, 369, 32-42. CLL patients treated with Formula (XVIII) for at least 8 days are included.

Figure 105:
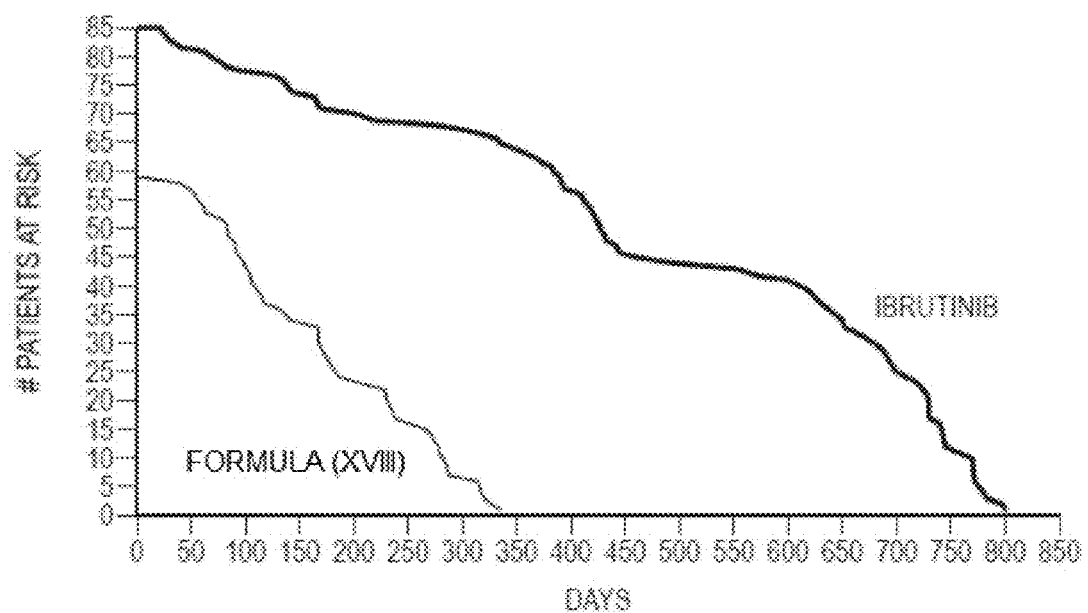

FIG. 105 shows a comparison of number of patients at risk in CLL patients treated with the BTK inhibitor ibrutinib or the BTK inhibitor of Formula (XVIII). CLL patients treated with Formula (XVIII) for at least 8 days are included.

Figure 106:
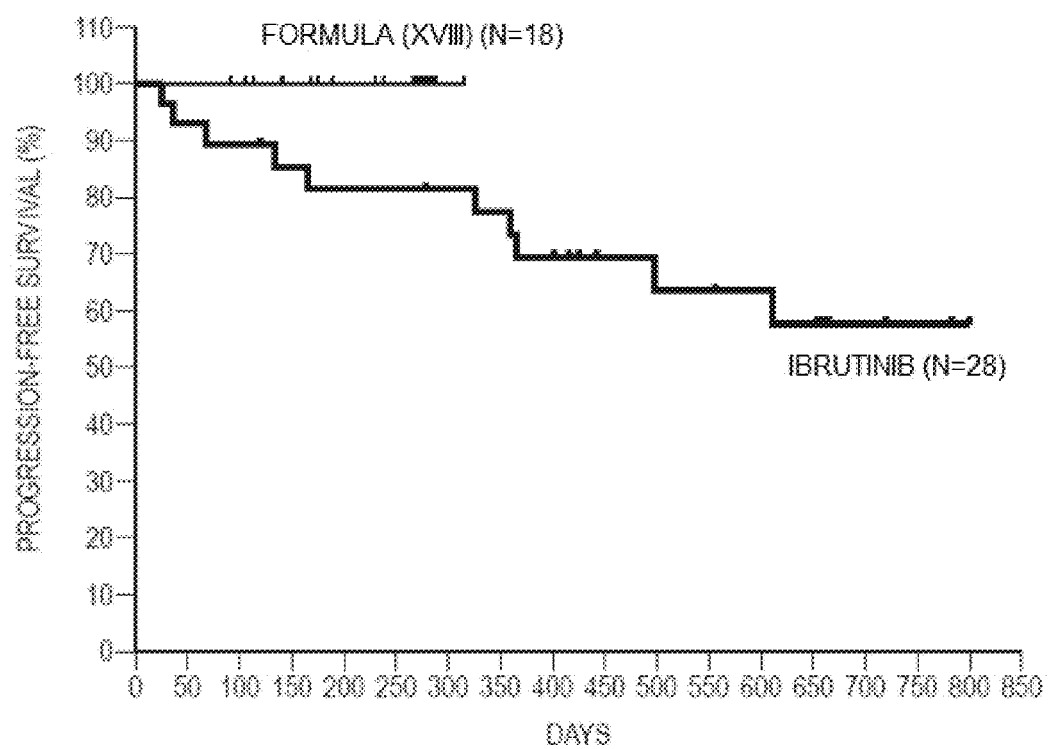

FIG. 106 shows a comparison of progression-free survival (PFS) in CLL patients exhibiting the 17p deletion and treated with the BTK inhibitor ibrutinib or the BTK inhibitor of Formula (XVIII). The ibrutinib data is taken from Byrd, et al., *N. Engl. J. Med.* 2013, 369, 32-42.

Figure 107:
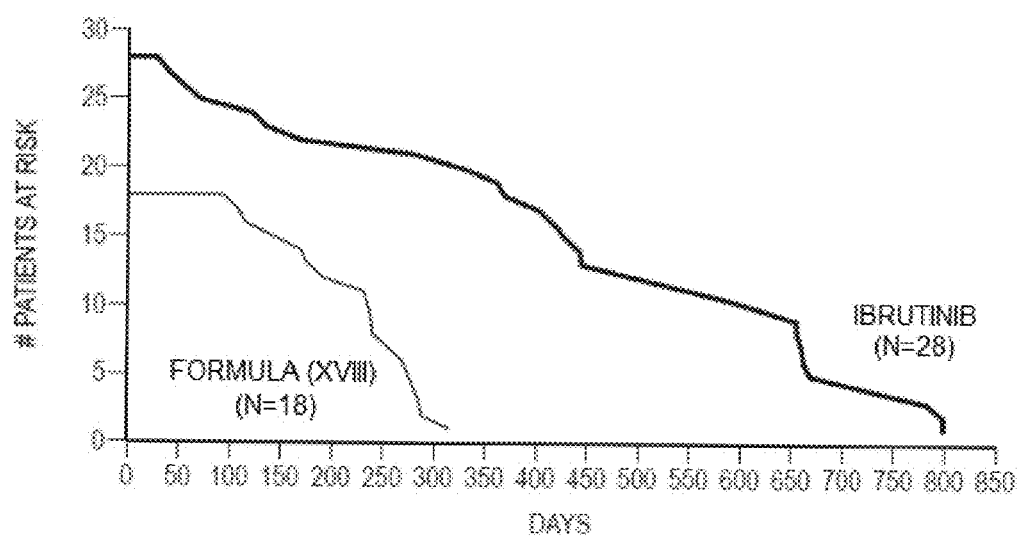

FIG. 107 shows a comparison of number of patients at risk in CLL patients exhibiting the 17p deletion and treated with the BTK inhibitor ibrutinib or the BTK inhibitor of Formula (XVIII). The ibrutinib data is taken from Byrd, et al., *N. Engl. J. Med.* 2013, 369, 32-42. CLL patients treated with Formula (XVIII) for at least 8 days are included.

Figure 108:
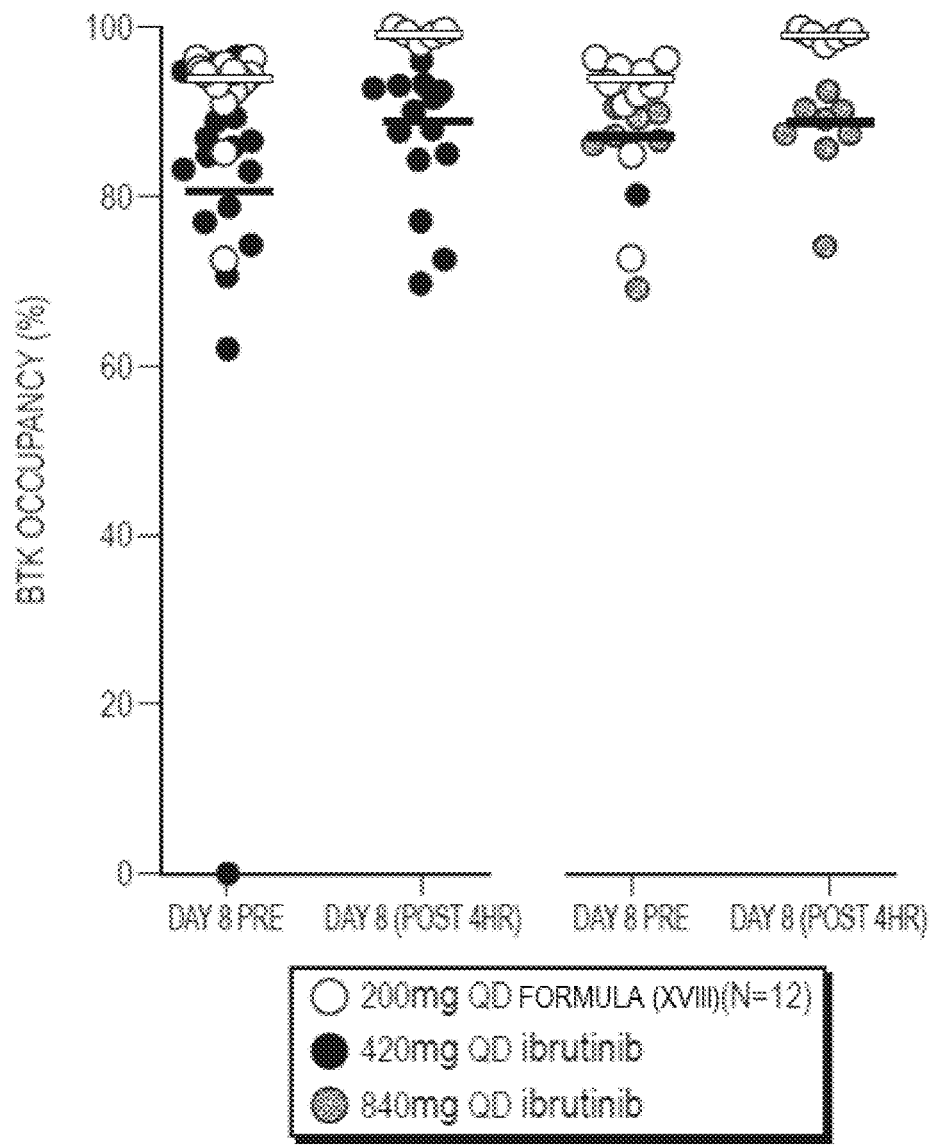

FIG. 108 shows improved BTK target occupancy of Formula (XVIII) at lower dosage versus ibrutinib in relapsed/refractory CLL patients.

Figure 109:
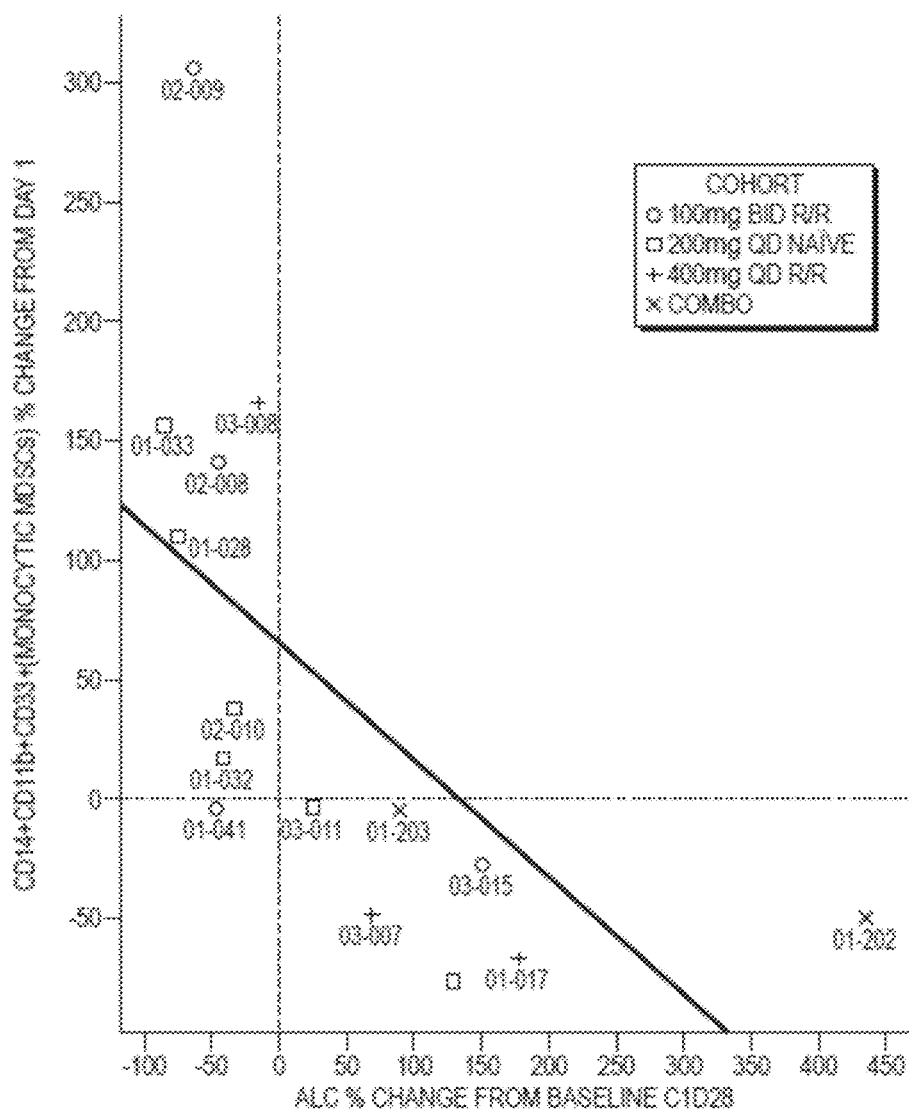

FIG. 109 shows the % change in myeloid-derived suppressor cell (MDSC) (monocytic) level over 28 days versus % ALC change at Cycle 1, day 28 (C1D28) with trendlines.

Figure 110:
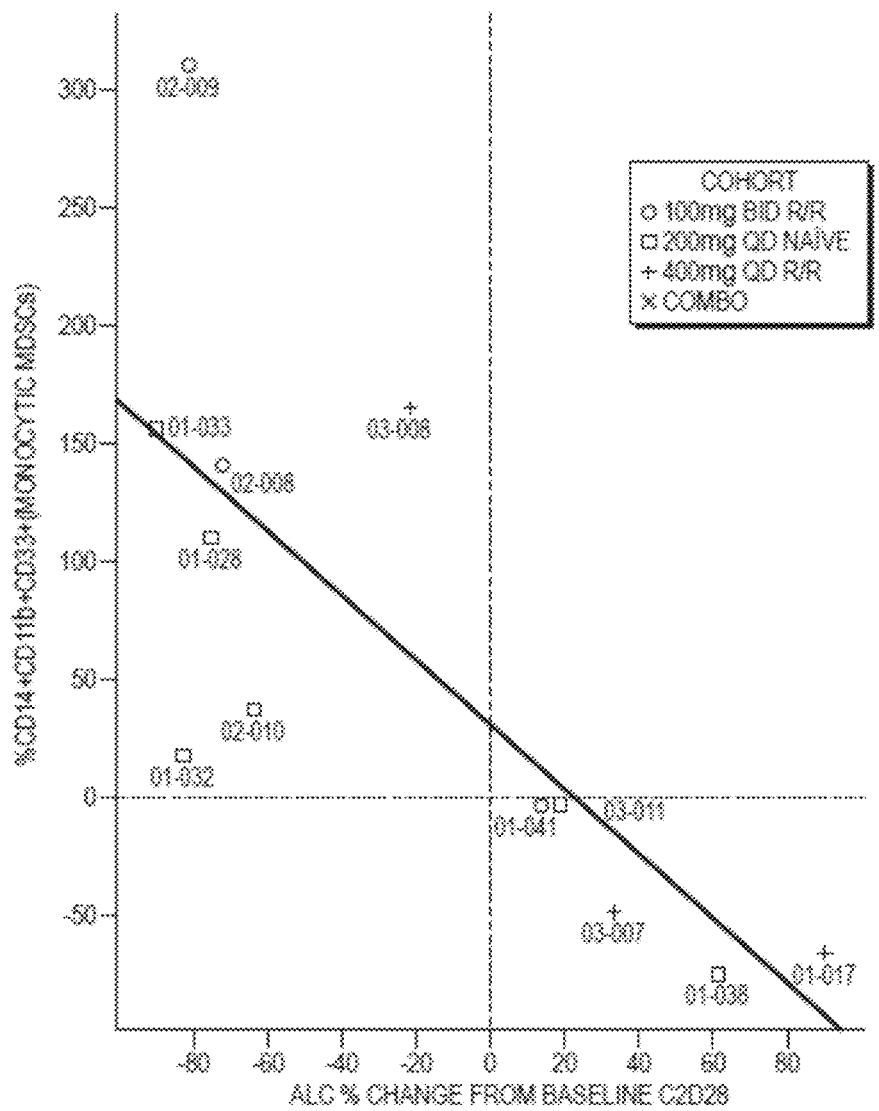

FIG. 110 shows the % change in MDSC (monocytic) level over 28 days versus % ALC change at Cycle 2, day 28 (C2D28) with trendlines.

Figure 111:
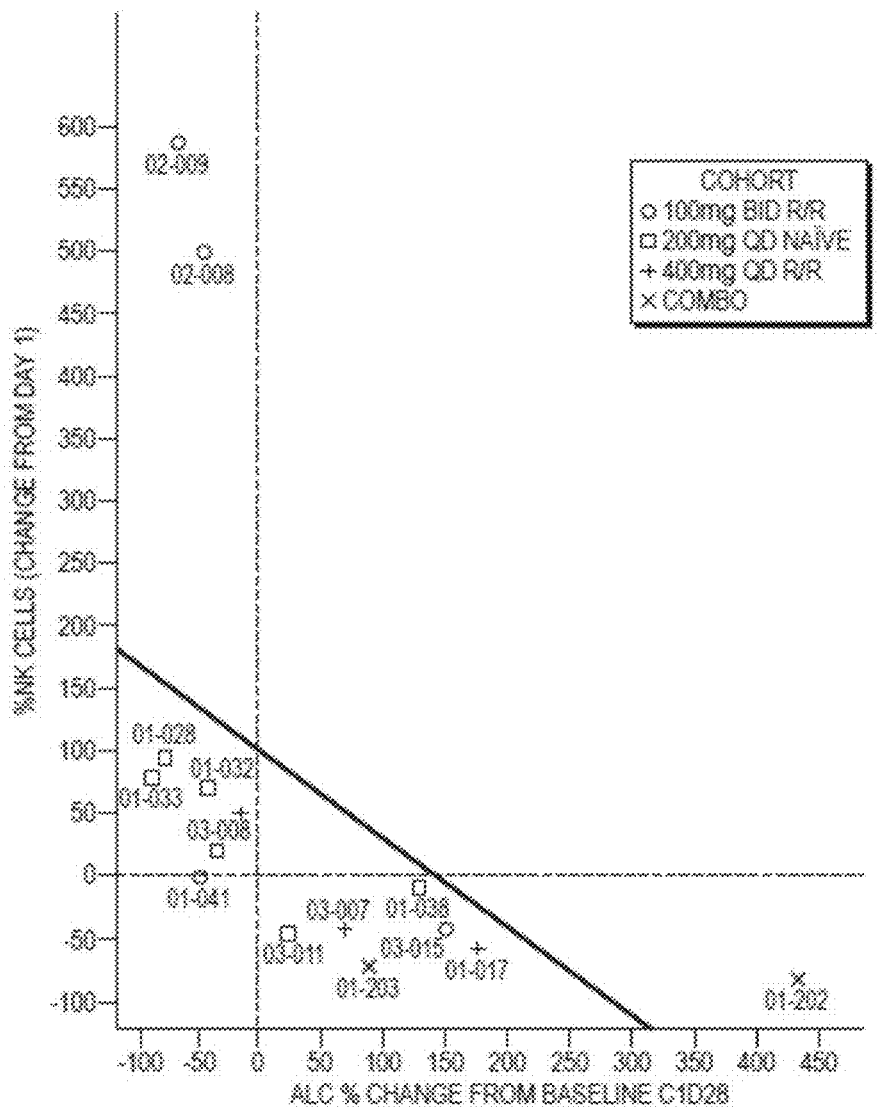

FIG. 111 shows the % change in natural killer (NK) cell level over 28 days versus % ALC change at Cycle 1, day 28 (C2D28) with trendlines.

Figure 112:
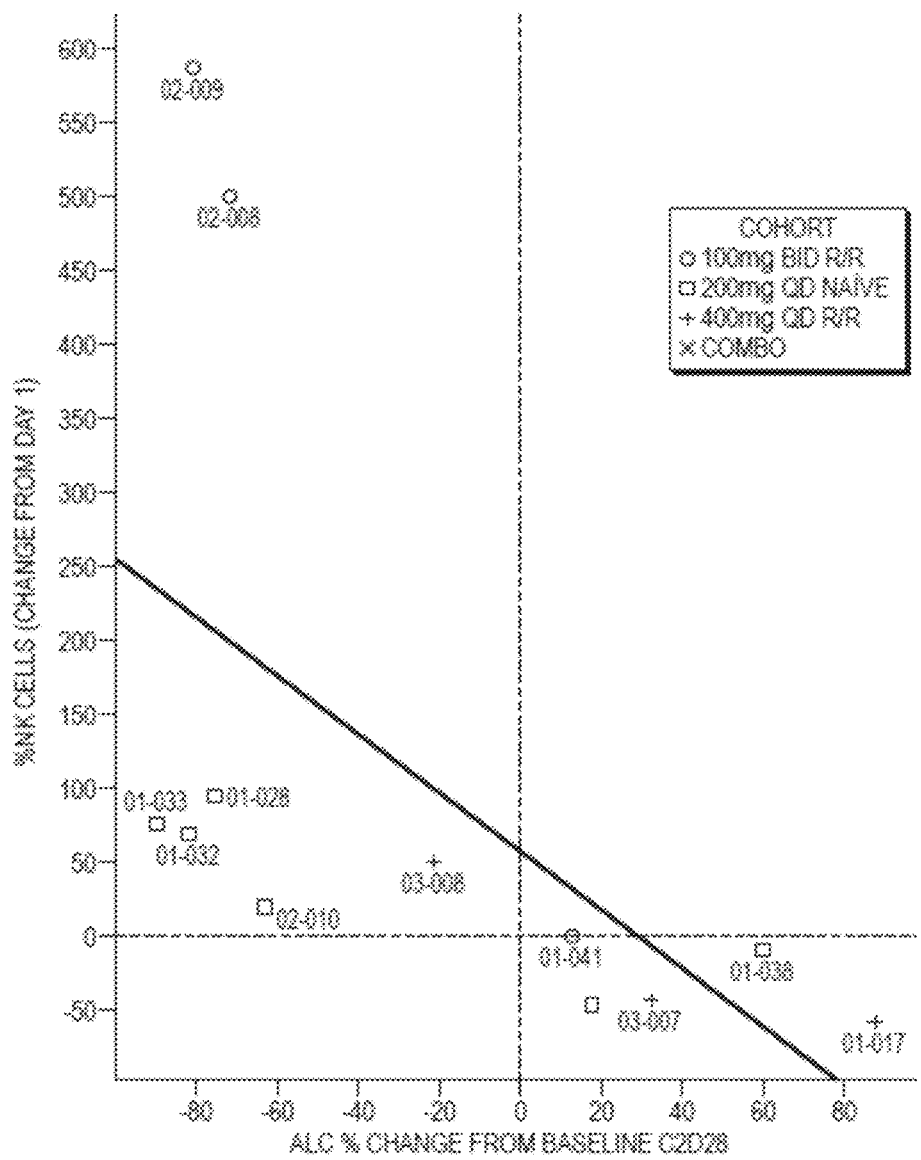

FIG. 112 shows the % change in NK cell level over 28 days versus % ALC change at Cycle 2, day 28 (C2D28) with trendlines.

Figure 113:
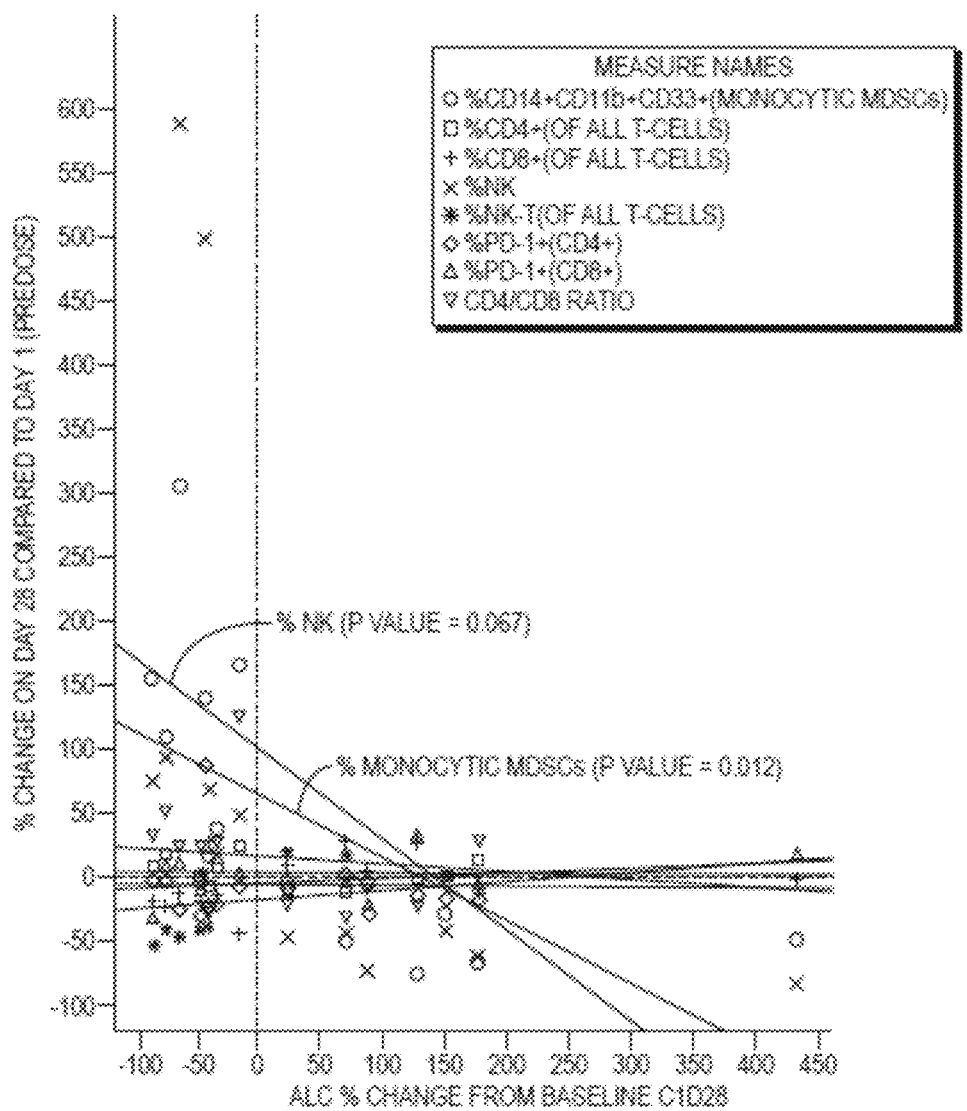

FIG. 113 compares the % change in MDSC (monocytic) level and % change in NK cell level over 28 days versus % ALC change with the % change in level of $CD4^+$ T cells, $CD8^+$ T cells, $CD4^+/CD8^+$ T cell ratio, NK-T cells, $PD-1^+$ $CD4^+$ T cells, and $PD-1^+CD8^+$ T cells, also versus % ALC change, at Cycle 1 day 28 (C1D28). Trendlines are shown for % change in MDSC (monocytic) level and % change in NK cell level.

Figure 114:
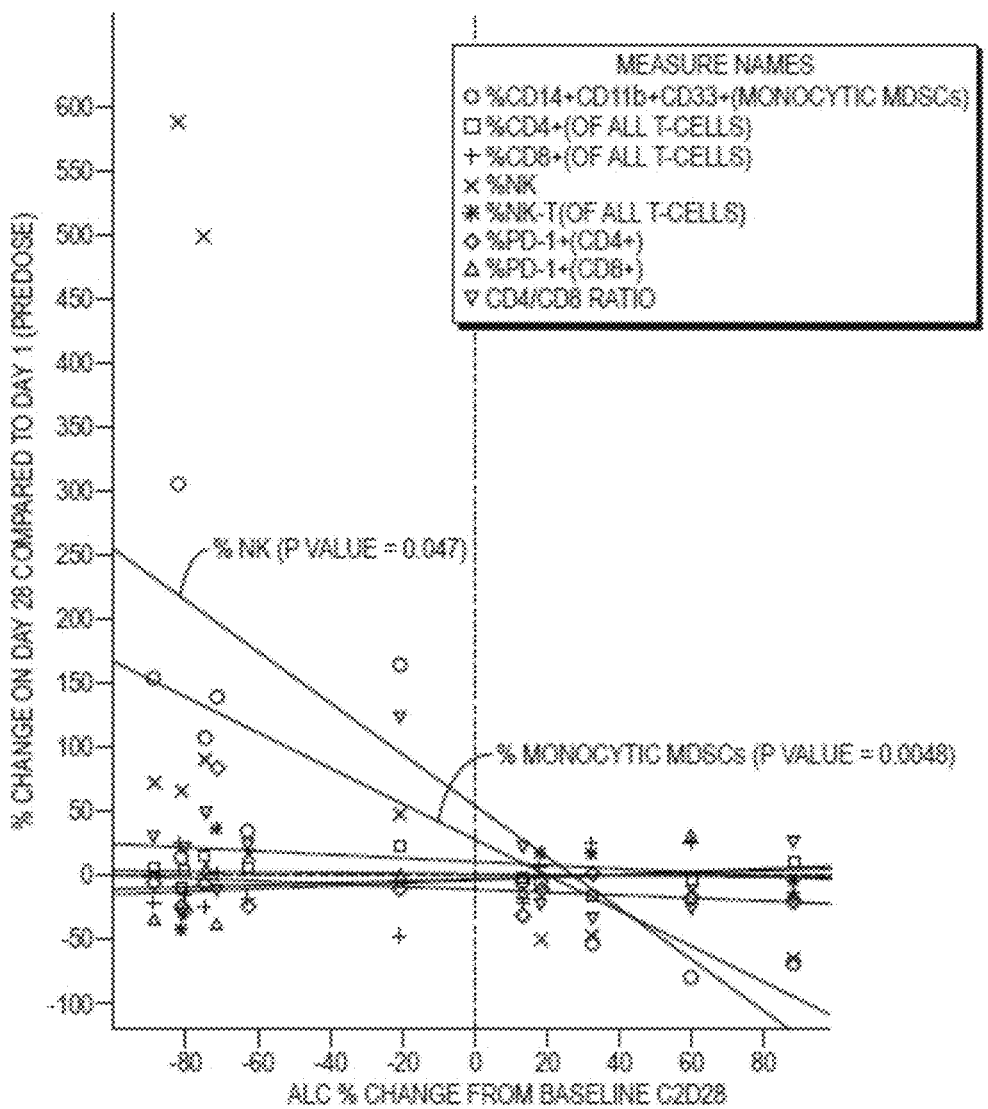

FIG. 114 compares the % change in MDSC (monocytic) level and % change in NK cell level over 28 days versus % ALC change with the % change in level of $CD4^+$ T cells, $CD8^+$ T cells, $CD4^+/CD8^+$ T cell ratio, NK-T cells, $PD-1^+$ $CD4^+$ T cells, and $PD-1^+CD8^+$ T cells, also versus % ALC change, at Cycle 2 day 28 (C2D28). Trendlines are shown for % change in MDSC (monocytic) level and % change in NK cell level.

Figure 115:
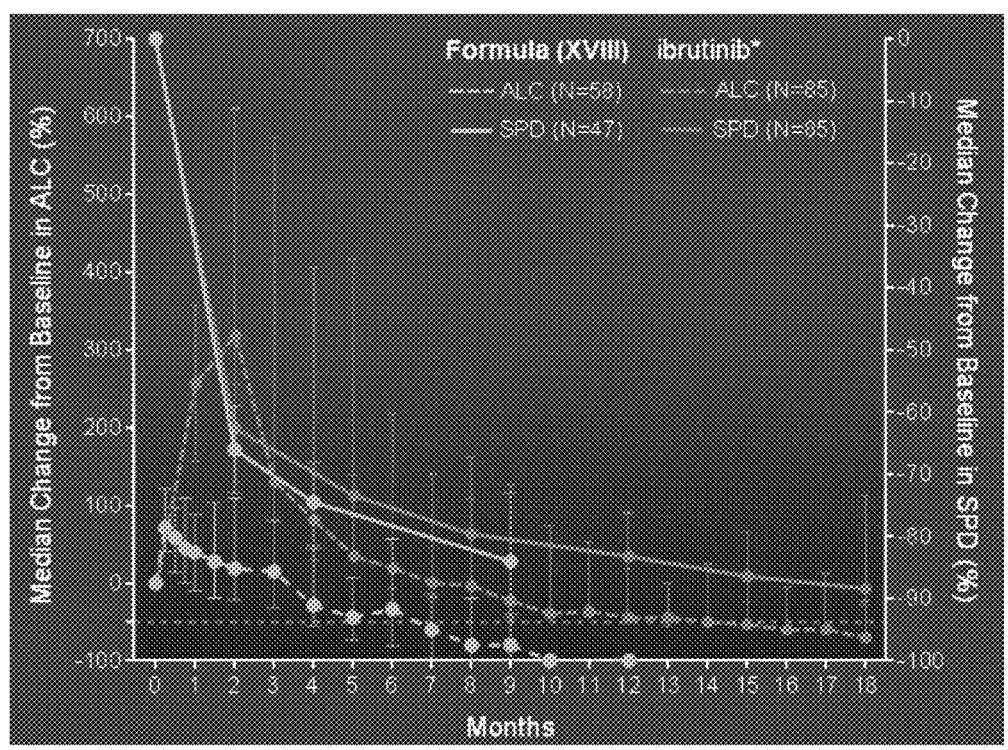

FIG. 115 shows an update of the data presented in FIG. 102.

Figure 116:
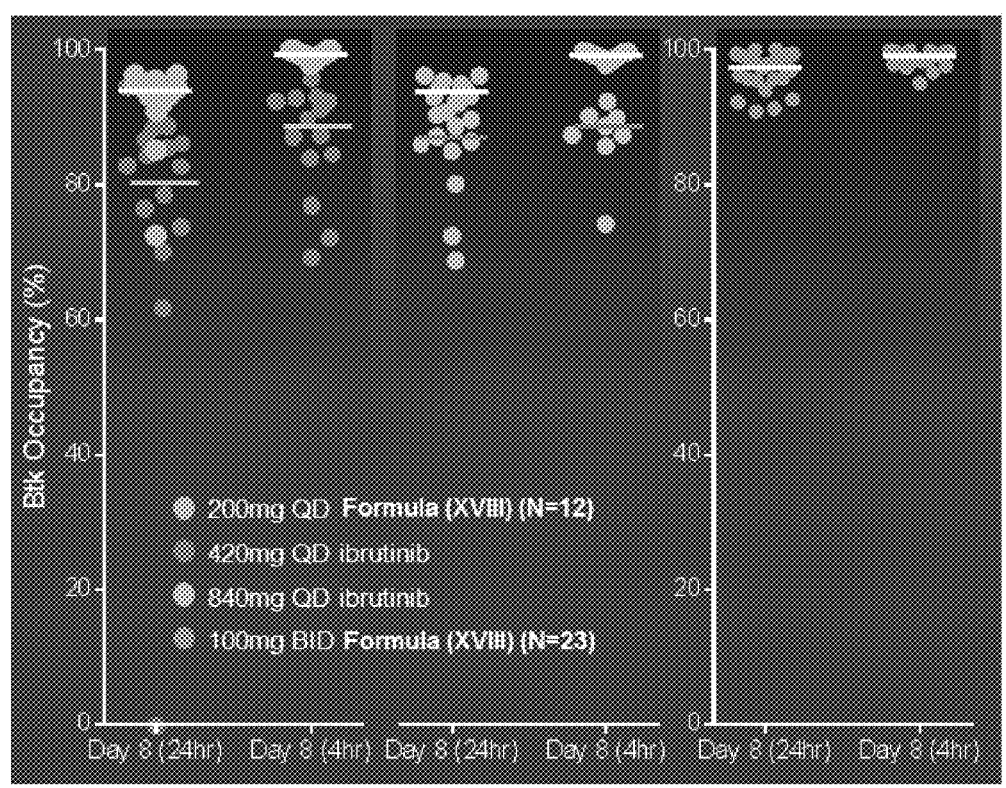

FIG. 116 shows an update of the data presented in FIG. 108, and includes BID dosing results.

Figure 117:
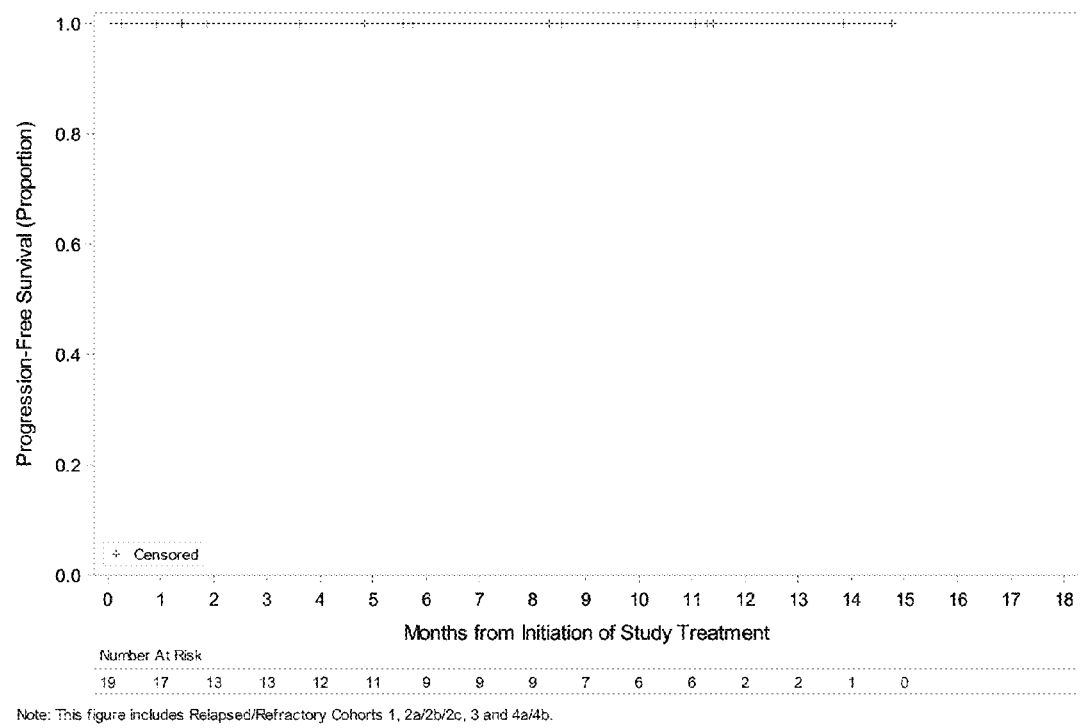

FIG. 117 illustrates PFS for patients with 11p deletion.

Figure 118:
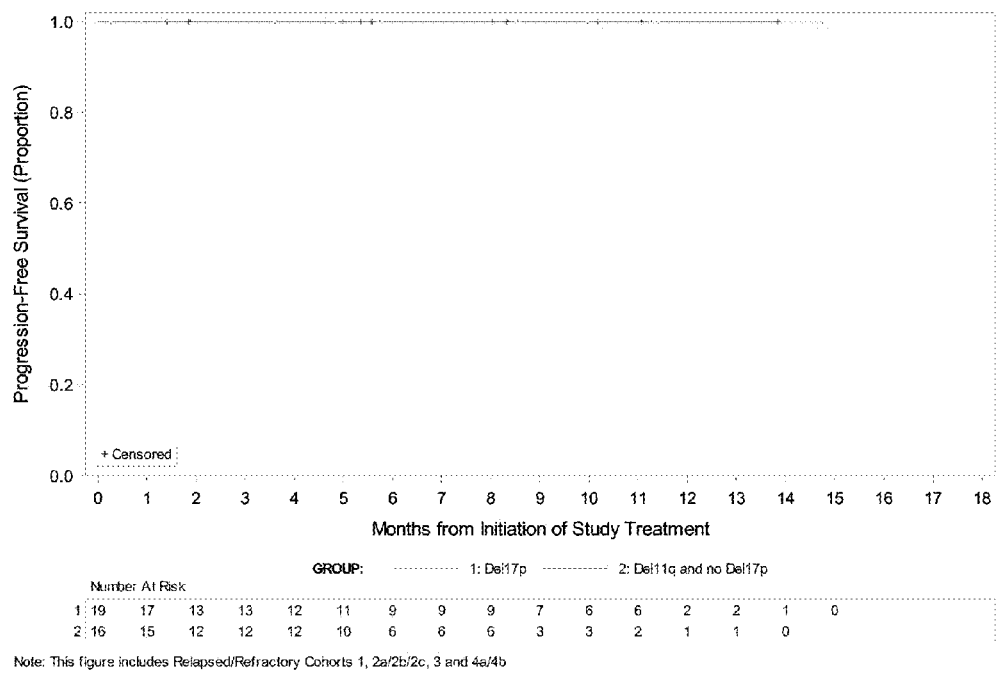

FIG. 118 illustrates PFS across relapsed/refractory patients with 11p deletion and with 17q deletion and no 11p deletion.

Figure 119:
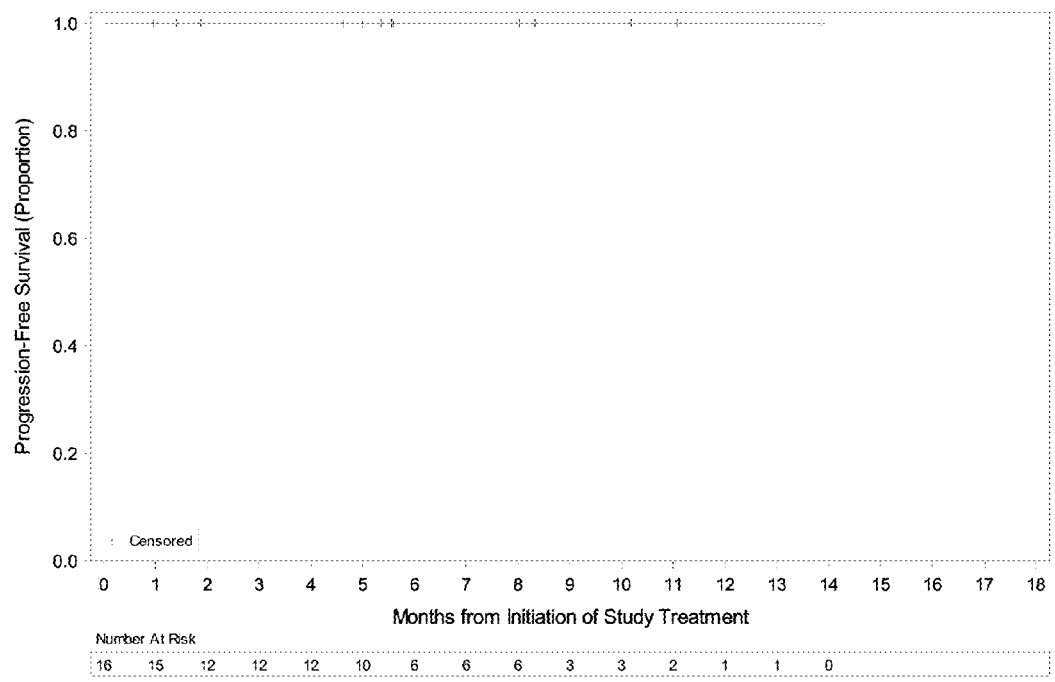

FIG. 119 illustrates PFS for patients with 17q deletion and no 11p deletion.

Figure 120:
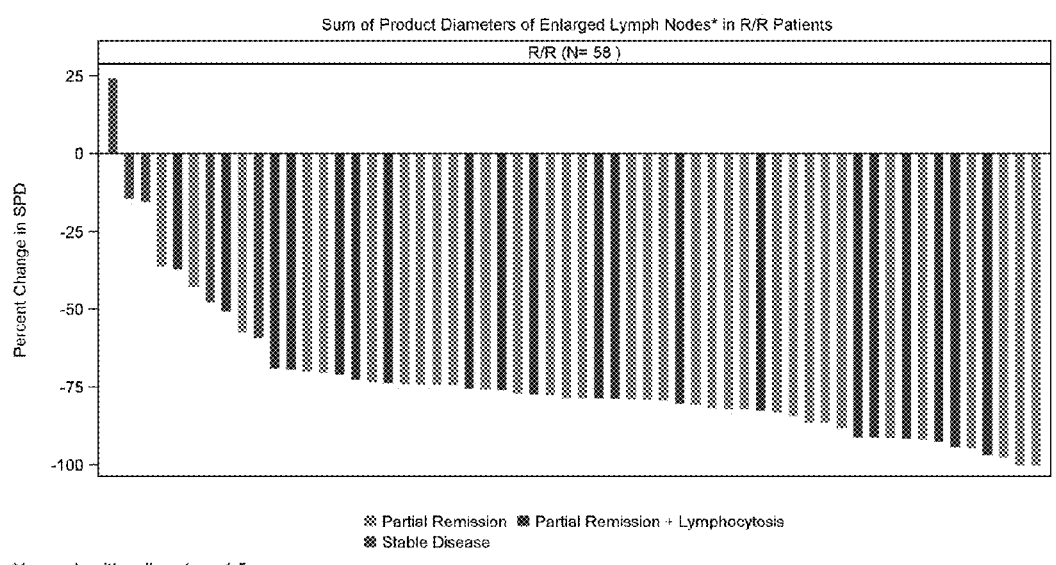

FIG. 120 illustrates updated SPD results from the clinical study of Formula (XVIII) in relapsed/refractory CLL patients.

Figure 121:
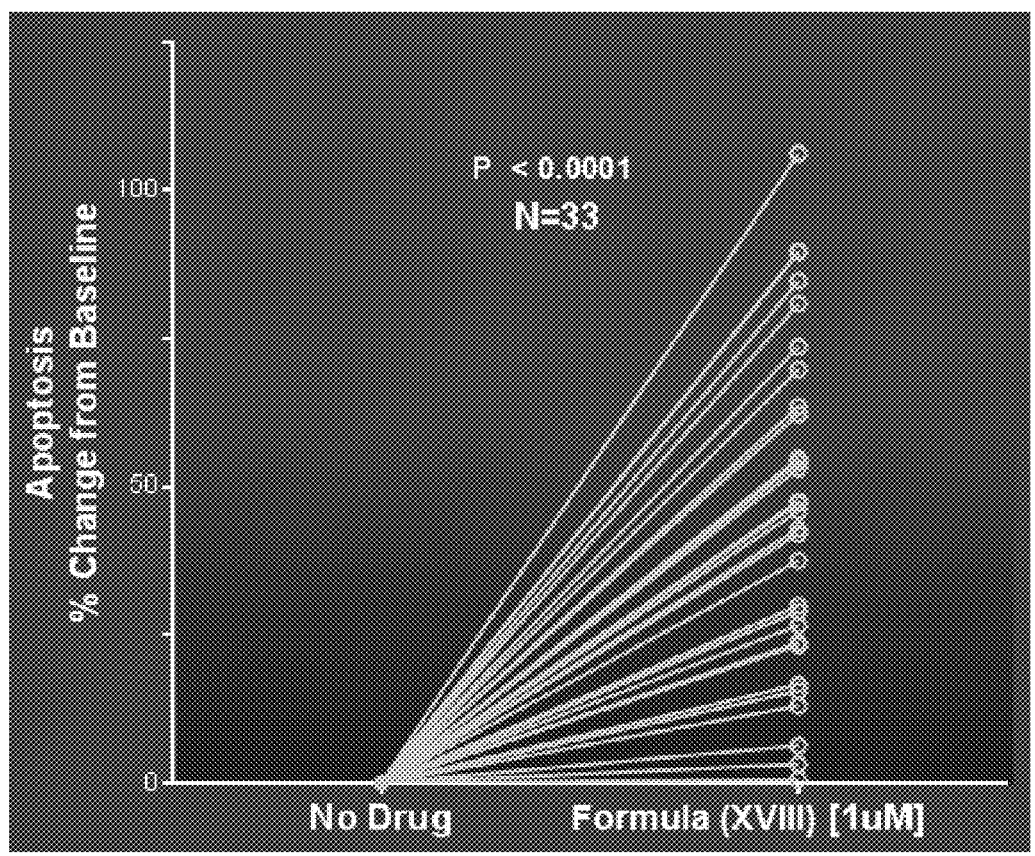

FIG. 121 illustrates that treatment of CLL patients with Formula (XVIII) resulted in increased apoptosis.

Figure 122:
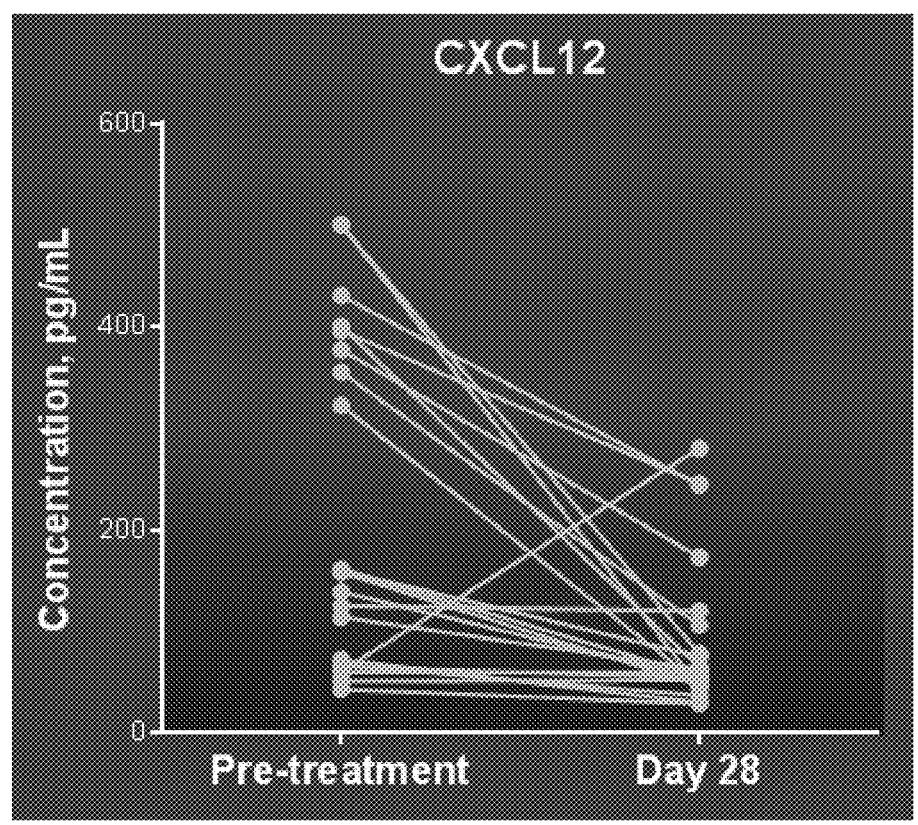

FIG. 122 illustrates a decrease in CXCL12 levels observed in patients treated with Formula (XVIII).

Figure 123:
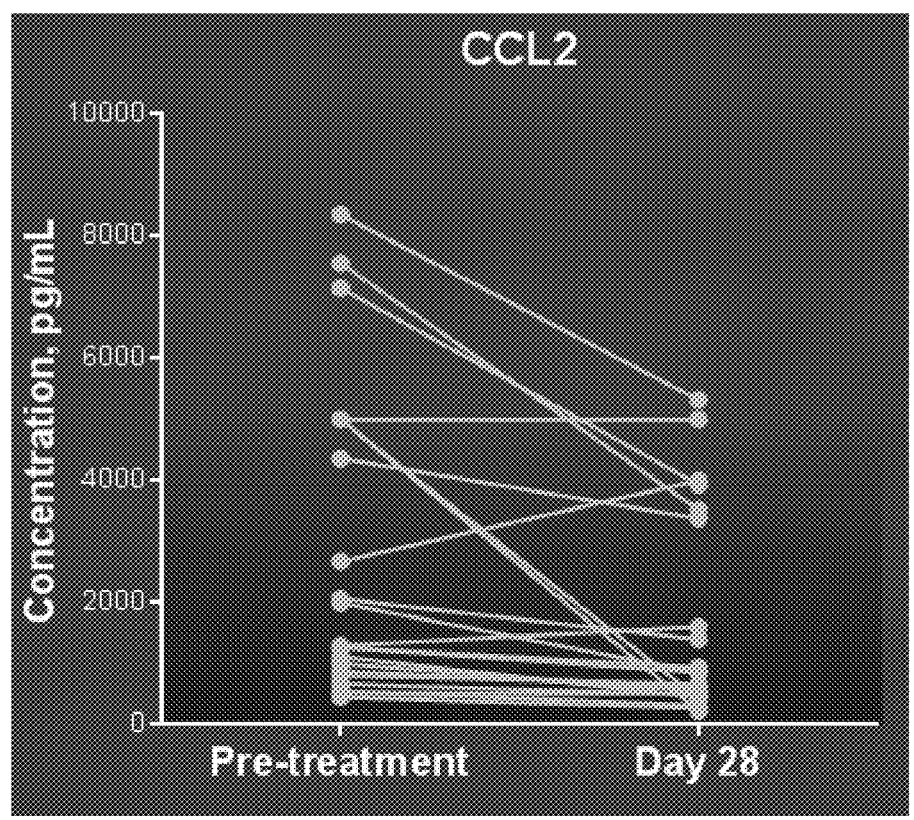

FIG. 123 illustrates a decrease in CCL2 levels observed in patients treated with Formula (XVIII).

Figure 124:
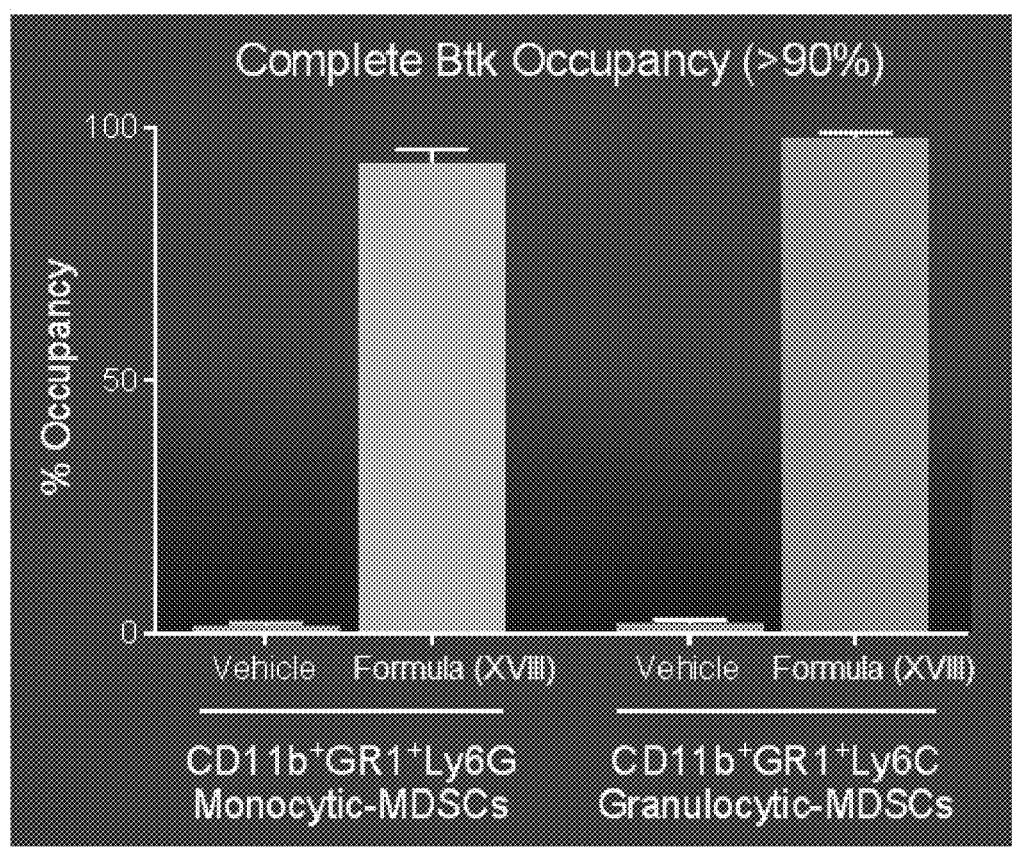

FIG. 124 illustrates BTK inhibitory effects on MDSCs.

Figure 125:
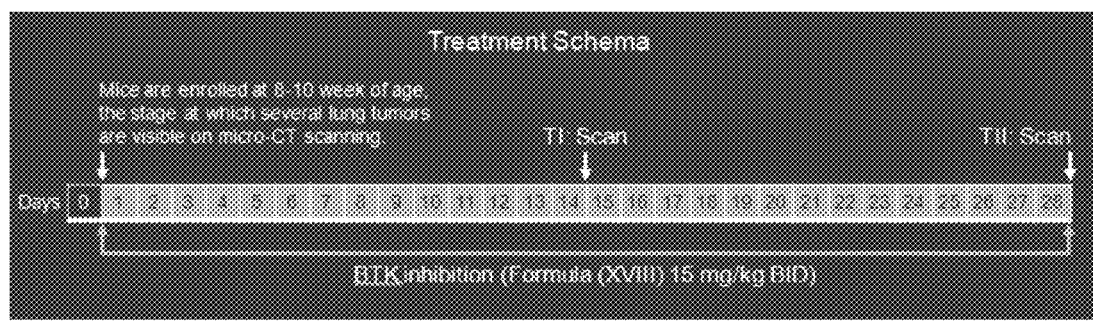

FIG. 125 illustrates the dosing schema used with the KrasLA2 non-small cell lung cancer (NSCLC) model.

BRIEF DESCRIPTION OF THE SEQUENCE LISTING

SEQ ID NO:1 is the heavy chain amino acid sequence of the anti-CD20 monoclonal antibody rituximab.

SEQ ID NO:2 is the light chain amino acid sequence of the anti-CD20 monoclonal antibody rituximab.

SEQ ID NO:3 is the heavy chain amino acid sequence of the anti-CD20 monoclonal antibody obinutuzumab.

SEQ ID NO:4 is the light chain amino acid sequence of the anti-CD20 monoclonal antibody obinutuzumab.

SEQ ID NO:5 is the variable heavy chain amino acid sequence of the anti-CD20 monoclonal antibody ofatumumab.

SEQ ID NO:6 is the variable light chain amino acid sequence of the anti-CD20 monoclonal antibody ofatumumab.

SEQ ID NO:7 is the Fab fragment heavy chain amino acid sequence of the anti-CD20 monoclonal antibody ofatumumab.

SEQ ID NO:8 is the Fab fragment light chain amino acid sequence of the anti-CD20 monoclonal antibody ofatumumab.

SEQ ID NO:9 is the heavy chain amino acid sequence of the anti-CD20 monoclonal antibody veltuzumab.

SEQ ID NO:10 is the light chain amino acid sequence of the anti-CD20 monoclonal antibody veltuzumab.

SEQ ID NO:11 is the heavy chain amino acid sequence of the anti-CD20 monoclonal antibody tositumomab.

SEQ ID NO:12 is the light chain amino acid sequence of the anti-CD20 monoclonal antibody tositumomab.

SEQ ID NO:13 is the heavy chain amino acid sequence of the anti-CD20 monoclonal antibody ibritumomab.

SEQ ID NO:14 is the light chain amino acid sequence of the anti-CD20 monoclonal antibody ibritumomab.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one JAK-2 inhibitor and at least one BTK inhibitor) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

As used herein, the term "warhead" or "warhead group" refers to a functional group present on a compound of the present invention wherein that functional group is capable of covalently binding to an amino acid residue present in the binding pocket of the target protein (such as cysteine, lysine, histidine, or other residues capable of being covalently modified), thereby irreversibly inhibiting the protein.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., (C$_{1-10}$)alkyl or C$_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $(C_{2-10})$alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., $(C_{2-10})$alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofuranzanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques.

When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Co-Administration of Compounds

An aspect of the invention is a composition, such as a pharmaceutical composition, comprising a combination of a PI3K inhibitor, a BTK inhibitor, and/or a JAK-2 inhbitor. Preferably, said composition comprises a combination of a BTK inhibitor and a JAK-2 inhibitor.

Another aspect is a kit containing any two or all three of a PI3K inhibitor, a BTK inhibitor, and a JAK-2 inhibitor, wherein each of the inhibitors is formulated into a separate pharmaceutical composition, and wherein said separate pharmaceutical compositions are formulated for co-administration. Preferably, said kit contains a BTK inhibitor and a JAK-2 inhibitor.

Another aspect of the invention is a method of treating a disease or condition in a subject, in particular a hyperproliferative disorder such as leukemia, lymphoma or a solid tumor cancer in a subject, comprising co-administering to the subject in need thereof a therapeutically effective amount of a combination of a PI3K inhibitor, a BTK inhibitor, and/or a JAK-2 inhibitor. In an embodiment, the foregoing method exhibits synergistic effects that may result in greater efficacy, less side effects, the use of less active pharmaceutical ingredient to achieve a given clinical result, or other synergistic effects. A combination of a BTK inhibitor and a JAK-2 inhibitor is a preferred embodiment. The pharmaceutical composition comprising the combination, and the kit, are both for use in treating such disease or condition.

In a preferred embodiment, the solid tumor cancer is selected from the group consisting of breast, lung, colorectal, thyroid, bone sarcoma, and stomach cancers.

In a preferred embodiment, the leukemia is selected from the group consisting of acute myelogenous leukemia (AML), chronic myelogenous leukemia (CML), acute lymphoblastic leukemia (ALL), B cell chronic lymphocytic leukemia (B-CLL), and chronic lymphoid leukemia (CLL).

In a preferred embodiment, the lymphoma is selected from the group consisting of Burkitt's lymphoma, mantle cell lymphoma, follicular lymphoma, indolent B-cell non-Hodgkin's lymphoma, histiocytic lymphoma, activated B-cell like diffuse large B cell lymphoma (DLBCL-ABC), germinal center B-cell like diffuse large B cell lymphoma (DLBCL-GCB), and diffuse large B cell lymphoma (DLBCL).

In an embodiment, the PI3K inhibitor is a PI3K-γ inhibitor.

In a preferred embodiment, the PI3K inhibitor is a PI3K-δ inhibitor.

In a preferred embodiment, the PI3K inhibitor is a PI3K-γ,δ inhibitor.

In an embodiment, the PI3K inhibitor is a selective PI3K inhibitor.

In an embodiment, the combination of the PI3K inhibitor, PI3K-γ inhibitor, PI3K-δ inhibitor, or PI3K-γ,δ inhibitor with the BTK inhibitor is administered by oral, intravenous, intramuscular, intraperitoneal, subcutaneous or transdermal means.

In an embodiment, the PI3K inhibitor, PI3K-γ inhibitor, PI3K-δ inhibitor, or PI3K-γ,δ inhibitor is in the form of a pharmaceutically acceptable salt, solvate, hydrate, complex, derivative, prodrug (such as an ester or phosphate ester), or cocrystal.

In an embodiment, the BTK inhibitor is in the form of a pharmaceutically acceptable salt, solvate, hydrate, complex, derivative, prodrug (such as an ester or phosphate ester), or cocrystal.

In an embodiment, the JAK-2 inhibitor is in the form of a pharmaceutically acceptable salt, solvate, hydrate, complex, derivative, prodrug (such as an ester or phosphate ester), or cocrystal.

In an embodiment, the PI3K inhibitor, which is preferably selected from the group consisting of a PI3K-γ inhibitor, a PI3K-δ inhibitor, and a PI3K-γ,δ inhibitor, is administered to the subject before administration of the BTK inhibitor.

In an embodiment, the PI3K inhibitor, which is preferably selected from the group consisting of a PI3K-γ inhibitor, a PI3K-δ inhibitor, and a PI3K-γ,δ inhibitor is administered concurrently with the administration of the BTK inhibitor.

In an embodiment, the PI3K inhibitor, which is preferably selected from the group consisting of a PI3K-γ inhibitor, a PI3K-δ inhibitor, and a PI3K-γ,δ inhibitor is administered to the subject after administration of the BTK inhibitor.

In an embodiment, the JAK-2 inhibitor is administered to the subject before administration of the BTK inhibitor.

In an embodiment, the JAK-2 inhibitor is administered concurrently with the administration of the BTK inhibitor.

In an embodiment, the JAK-2 inhibitor is administered to the subject after administration of the BTK inhibitor.

In an embodiment, the JAK-2 inhibitor is administered to the subject after administration of the BTK inhibitor.

In an embodiment, the JAK-2 inhibitor is administered to the subject before administration of the PI3K inhibitor.

In an embodiment, the JAK-2 inhibitor is administered concurrently with the administration of the PI3K inhibitor.

In a preferred embodiment, the BTK inhibitor, JAK-2 inhibitor, and/or PI3K inhibitor are administered concurrently.

In a preferred embodiment, the subject is a mammal, such as a human. In an embodiment, the subject is a human. In an embodiment, the subject is a companion animal. In an embodiment, the subject is a canine, feline, or equine.

PI3K Inhibitors

The PI3K inhibitor may be any PI3K inhibitor known in the art. In particular, it is one of the PI3K inhibitors described in more detail in the following paragraphs. Preferably, it is a PI3K inhibitor selected from the group consisting of a PI3K-γ inhibitor, a PI3K-δ inhibitor, and a PI3K-γ,δ inhibitor. In one specific embodiment, it is a PI3K-δ inhibitor.

In an embodiment, the PI3K inhibitor, which is preferably selected from the group consisting of a PI3K-γ inhibitor, a PI3K-δ inhibitor, and a PI3K-γ,δ inhibitor, is a compound selected from the structures disclosed in U.S. Pat. Nos. 8,193,182 and 8,569,323, and U.S. Patent Application Publication Nos. 2012/0184568 A1, 2013/0344061 A1, and 2013/0267521 A1, the disclosures of which are incorporated by reference herein. In an embodiment, the PI3K inhibitor (which may be a PI3K-γ inhibitor, PI3K-δ inhibitor, or PI3K-γ,δ inhibitor) is a compound of Formula (I):

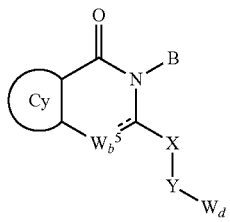

Formula (I)

or a pharmaceutically acceptable salt, solvate, hydrate, cocrystal or prodrug thereof, wherein:

Cy is aryl or heteroaryl substituted by 0 or 1 occurrences of $R^3$ and 0, 1, 2, or 3 occurrences of $R^5$;

$W_b^5$ is $CR^8$, $CHR^8$, or N;

$R^8$ is hydrogen, alkyl, alkenyl, alkynyl, cycloalkyl, heteroalkyl, alkoxy, amido, amino, acyl, acyloxy, sulfonamido, halo, cyano, hydroxyl or nitro;

B is hydrogen, alkyl, amino, heteroalkyl, cycloalkyl, heterocyclyl, aryl, or heteroaryl, each of which is substituted with 0, 1, 2, 3, or 4 occurrences of $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea, or carbonate;

X is —(CH($R^9$))$_z$—;

Y is —N($R^9$)—C(=O)—, —C(=O)—N($R^9$)—, —C(=O)—N($R^9$)—(CHR$^9$)—, —N($R^9$)—S(=O)—, —S(=O)—N($R^9$)—, S(=O)$_2$—N($R^9$)—, —N($R^9$)—C(=O)—N($R^9$) or —N($R^9$)S(=O)$_2$—;

z is an integer of 1, 2, 3, or 4;

$R^3$ is alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, aryl, heteroaryl, hydroxyl, or nitro;

each $R^5$ is independently alkyl, alkenyl, alkynyl, cycloalkyl, heteroalkyl, alkoxy, amido, amino, acyl, acyloxy, sulfonamido, halo, cyano, hydroxyl, or nitro;

each $R^9$ is independently hydrogen, alkyl, cycloalkyl, heterocyclyl, or heteroalkyl; or two adjacent occurrences of $R^9$ together with the atoms to which they are attached form a 4- to 7-membered ring;

$W_d$ is heterocyclyl, aryl, cycloalkyl, or heteroaryl, each of which is substituted with one or more $R^{10}$, $R^{11}$, $R^{12}$ or $R^{13}$, and $R^{10}$, $R^{11}$, $R^{12}$ and $R^{13}$ are each independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate or NR'R" wherein R' and R" are taken together with nitrogen to form a cyclic moiety.

In an embodiment, the PI3K inhibitor (which may be a PI3K-γ inhibitor, PI3K-δ inhibitor, or PI3K-γ,δ inhibitor) is a compound of Formula (I-1):

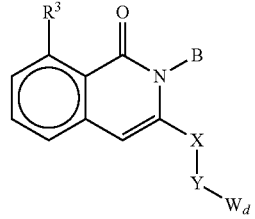

Formula (II)

or a pharmaceutically acceptable salt, solvate, hydrate, cocrystal, or prodrug thereof, wherein:

B is a moiety of Formula (II-A):

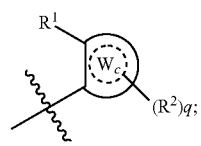

Formula (II-A)

$W_c$ is aryl, heteroaryl, heterocycloalkyl, or cycloalkyl;

q is an integer of 0, 1, 2, 3, or 4;

X is a bond or —(CH($R^9$))$_z$—, and z is an integer of 1, 2, 3 or 4;

Y is a bond, —N($R^9$)—, —O—, —S—, —S(=O)—, —S(=O)$_2$—, —C(=O)—, —C(=O)(CHR$^9$)$_z$—, —N($R^9$)—C(=O)—, —N($R^9$)—C(=O)NH— or —N($R^9$)C($R^9$)$_2$—;

z is an integer of 1, 2, 3, or 4;

$W_d$ is:

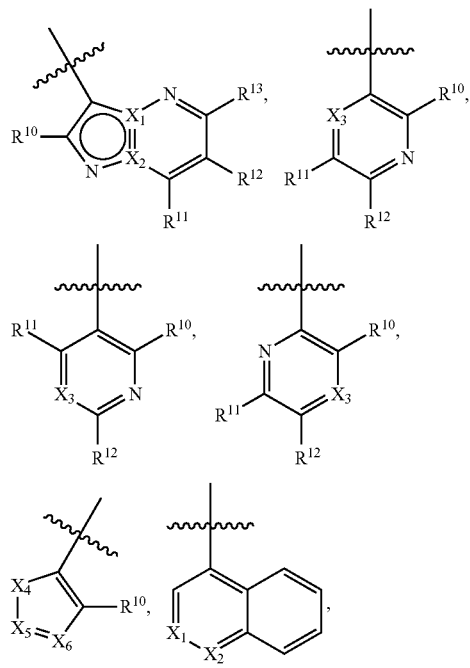

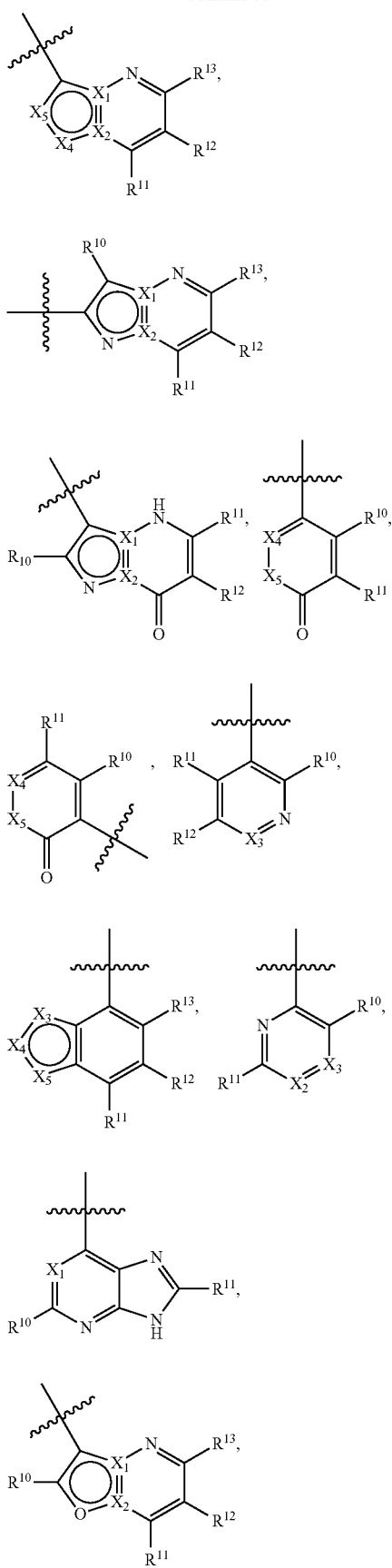

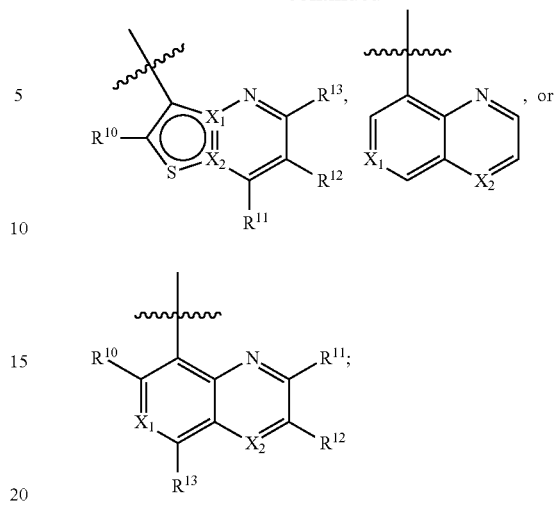

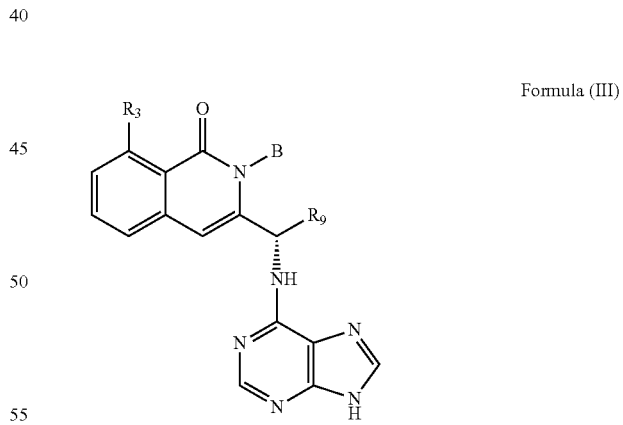

$X_1$, $X_2$ and $X_3$ are each independently C, $CR^{13}$ or N; and $X_4$, $X_5$ and $X_6$ are each independently N, NH, $CR^{13}$, S or O;

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy or nitro;

$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro; and each instance of $R^9$ is independently hydrogen, alkyl, or heterocycloalkyl.

In a preferred embodiment, the PI3K inhibitor (which may be a PI3K-γ inhibitor, PI3K-δ inhibitor, or PI3K-γ,δ inhibitor) is a compound of Formula (III):

Formula (III)

or a pharmaceutically acceptable salt, solvate, hydrate, cocrystal, or prodrug thereof, where B is a moiety of Formula (II-A), $R^2$ is alkyl, alkenyl, alkynyl, cycloalkyl, heterocycloalkyl, aryl, heteroaryl, heteroarylalkyl, alkoxy, amino, halo, cyano, hydroxy or nitro; and $R^9$ is hydrogen, alkyl, or heterocycloalkyl.

In a preferred embodiment, the PI3K-γ,δ inhibitor is a compound of Formula (III-A):

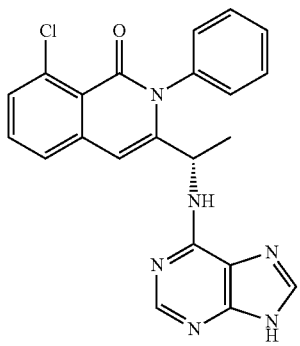

Formula (III-A)

or a pharmaceutically acceptable salt, solvate, hydrate, cocrystal, or prodrug thereof. Formula (III-A) is also known as IPI-145 or duvelisib (Infinity Pharmaceuticals) and has been studied at doses of 5 mg and 25 mg in clinical trials, including those described in Flinn, et al., *Blood,* 2014, 124, 802, and O'Brien, et al., *Blood,* 2014, 124, 3334.

In a preferred embodiment, the PI3K inhibitor is a compound of Formula (IV):

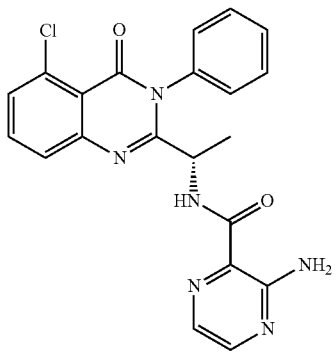

Formula (IV)

or a pharmaceutically acceptable salt, solvate, hydrate, cocrystal, or prodrug thereof.

In a preferred embodiment, the PI3K inhibitor is (S)-3-(1-((9H-purin-6-yl)amino)ethyl)-8-chloro-2-phenylisoquinolin-1(2H)-one or a pharmaceutically acceptable salt, solvate, hydrate, cocrystal, or prodrug thereof.

In a preferred embodiment, the PI3K inhibitor is (S)-3-amino-N-(1-(5-chloro-4-oxo-3-phenyl-3,4-dihydroquinazolin-2-yl)ethyl)pyrazine-2-carboxamide or a pharmaceutically acceptable salt, solvate, hydrate, cocrystal, or prodrug thereof.

In an embodiment, the PI3K inhibitor (which may be a PI3K-γ inhibitor, PI3K-δ inhibitor, or PI3K-γ,δ inhibitor) is a compound selected from the structures disclosed in U.S. Pat. Nos. 8,193,199, 8,586,739, and 8,901,135, the disclosure of each of which is incorporated by reference herein. In an embodiment, the PI3K inhibitor or PI3K-δ inhibitor is a compound of Formula (V):

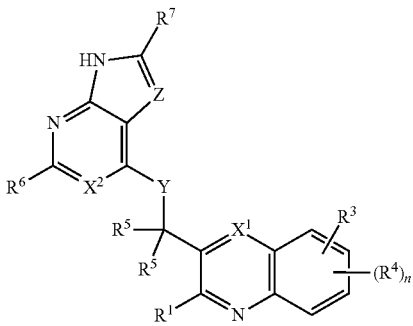

Formula (V)

or a pharmaceutically acceptable salt, solvate, hydrate, cocrystal, or prodrug thereof, wherein:

$X^1$ is $C(R^9)$ or N;
$X^2$ is $C(R^{10})$ or N;
Y is $N(R^{11})$, O or S;
Z is $CR^8$ or N;
n is 0, 1, 2 or 3;
$R^1$ is a direct-bonded or oxygen-linked saturated, partially saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $(C_{1-4})$alkyl, $O(C_{1-4})$alkyl, $O(C_{1-4})$haloalkyl, $NHC_{1-4}$, $N((C_{1-4})$alkyl$)(C_{1-4})$alkyl and $(C_{1-4})$haloalkyl;

$R^2$ is selected from halo, $(C_{1-4})$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$. —OC(=O)N($R^a$)S(=O)$_2R^a$, —O$(C_{2-6})$alkylN$R^aR^a$, —O$(C_{2-6})$alkylO$R^a$, —S$R^a$, OS(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a(C_{2-6}$ alkylN$R^aR^a$ and —N$R^a(C_{2-6})$alkylO$R^a$; or $R^2$ is selected from $(C_{1-6})$alkyl, phenyl, benzyl, heteroaryl, heterocycle, —(($C_{1-3}$)alkyl)heteroaryl, —(($C_{1-3}$)alkyl)heterocycle, —O(($C_{1-3}$)alkyl)heteroaryl, —O(($C_{1-3}$)alkyl)heterocycle, —N$R^a$(($C_{1-3}$)alkyl)heteroaryl, —N$R^a$(($C_{1-3}$)alkyl)heterocycle, —($C_{1-3}$)alkyl)phenyl, —O(($C_{1-3}$)alkyl)phenyl and —N$R^a$(($C_{1-3}$)alkyl)phenyl all of which are substituted by 0, 1, 2 or 3 substituents selected from $(C_{1-4})$haloalkyl, $O(C_{1-4})$alkyl, Br, Cl, F, I and $(C_{1-4})$alkyl;

$R^3$ is selected from H, halo, $(C_{1-4})$haloalkyl, cyano, nitro, —C(=O)$R^a$, —C(=O)$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^2$, —O$(C_{2-6})$alkylN$R^aR^a$, —O$(C_{2-6})$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$) S(=O)$_2R^a$, —N($R^a$)S(=O)$_2$N$R^aR^a$, —N$R^a(C_{2-6})$alkylO$R^a$, $(C_{1-6})$alkyl, phenyl, benzyl, heteroaryl and heterocycle, wherein the $(C_{1-6})$alkyl, phenyl, benzyl, heteroaryl and heterocycle are additionally substituted by 0, 1, 2 or 3 substituents selected from $(C_{1-6})$haloalkyl, $O(C_{1-6})$alkyl, Br, Cl, F, I and $(C_{1-6})$alkyl;

$R^4$ is, independently, in each instance, halo, nitro, cyano, $(C_{1-4})$alkyl, $O(C_{1-4})$alkyl, $O(C_{1-4})$haloalkyl, $NH(C_{1-4})$alkyl, $N((C_{1-4})alkyl)(C_{1-4})$alkyl or $(C_{1-4})$haloalkyl;

$R^5$ is, independently, in each instance, H, halo, $(C_{1-6})$alkyl, $(C_{1-4})$haloalkyl, or $(C_{1-6})$alkyl substituted by 1, 2 or 3 substituents selected from halo, cyano, OH, $O(C_{1-4})$alkyl, $(C_{1-4})$alkyl, $(C_{1-3})$haloalkyl, $O(C_{1-4})$alkyl, $NH_2$, $NHC_{1-4}$alkyl, $N(C_{1-4})alkyl(C_{1-4})$alkyl; or both $R^5$ groups together form a $(C_{3-6})$spiroalkyl substituted by 0, 1, 2 or 3 substituents selected from halo, cyano, OH, $O(C_{1-4})$alkyl, $(C_{1-4})$alkyl, $(C_{1-3})$haloalkyl, $O(C_{1-4})$alkyl, $NH_2$, NH $(C_{1-4})$alkyl, $N((C_{1-4})alkyl)(C_{1-4})$alkyl;

$R^6$ is selected from H, halo, $(C_{1-6})$alkyl, $(C_{1-4})$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$ N($R^a$)C(=O)O$R^a$, —S(=O)$_2$N($R^a$)C(=O)N$R^aR^a$;

$R^7$ is selected from H, halo, $(C_{1-6})$alkyl, $(C_{1-4})$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$ N($R^a$)C(=O)O$R^a$, —S(=O)$_2$N($R^a$)C(=O)N$R^aR^a$;

$R^8$ is selected from H, $(C_{1-6})$haloalkyl, Br, Cl, F, I, O$R^a$, N$R^aR^a$, $(C_{1-6})$alkyl, phenyl, benzyl, heteroaryl and heterocycle, wherein the $(C_{1-6})$alkyl, phenyl, benzyl, heteroaryl and heterocycle are additionally substituted by 0, 1, 2 or 3 substituents selected from $(C_{1-6})$haloalkyl, $O(C_{1-6})$alkyl, Br, Cl, F, I and $(C_{1-6})$alkyl;

$R^9$ is selected from H, halo, $(C_{1-4})$haloalkyl, cyano, nitro, —C(=O)$R^a$, —C(=O)O$R^a$, —C(=O)N$R^aR^a$C(=N$R^a$)N$R^aR^a$, —O$R^a$, —OC(=O)$R^a$, —OC(=O)N$R^aR^a$, —OC(=O)N($R^a$)S(=O)$_2R^a$, —O(C$_{2-6}$)alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, N$R^aR^a$, —N($R^a$)C(=O)$R^a$, —N($R^a$)C(=O)O$R^a$, —N($R^a$)C(O)N$R^aR^a$N($R^a$C(=N$R^a$)N$R^aR^a$, —N($R^a$)S(=O)$_2R^a$, —N($R^a$)S(=O)$_2$N$R^aR^a$, —N$R^a$(C$_{2-6}$ alkylN$R^aR^a$, —N$R^a$(C$_{1-6}$)alkyl, phenyl, benzyl, heteroaryl and heterocycle, wherein the $(C_{1-6}$ alkyl, phenyl, benzyl, heteroaryl and heterocycle are additionally substituted by 0, 1, 2 or 3 substituents selected from halo, $(C_{1-4})$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O(C$_{2-6}$)alkylN$R^aR^a$, —O(C$_{2-6}$)alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$(C$_{2-6}$)alkylO$R^a$, —N$R^a$(C$_{2-6}$)alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $(C_{1-4})$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O(C$_{2-6}$)alkylN$R^aR^a$, —O(C$_{2-6}$)alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$(C$_{2-6}$)alkylNR$^a$R$^a$ and —NR$^a$(C$_{2-6}$)alkylOR$^a$;

$R^{10}$ is H, $(C_{1-3})$alkyl, $(C_{1-3})$haloalkyl, cyano, nitro, CO$_2$R$^a$, C(=O)NR$^a$R$^a$, —C(=NR$^a$)NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —S(=O)R$^b$, S(=O)$_2$R$^b$ or S(=O)$_2$NR$^a$R$^a$;

$R^{11}$ is H or $(C_{1-4})$alkyl;

$R^a$ is independently, at each instance, H or R$^b$; and $R^b$ is independently, at each instance, phenyl, benzyl or $(C_{1-6})$alkyl, the phenyl, benzyl and $(C_{1-6})$alkyl being substituted by 0, 1, 2 or 3 substituents selected from halo, $(C_{1-4})$alkyl, $(C_{1-3})$haloalkyl, —O(C$_{1-4}$)alkyl, —NH$_2$, —NHC$_{1-4}$)alkyl, —N((C$_{1-4}$)alkyl)(C$_{1-4}$)alkyl.

In another embodiment, the PI3K inhibitor (which may be a PI3K-γ inhibitor, PI3K-δ inhibitor, or PI3K-γ,δ inhibitor) is a compound of Formula (VI):

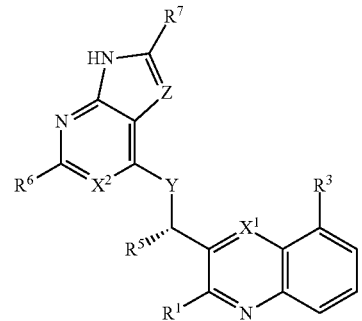

Formula (VI)

or a pharmaceutically acceptable salt, solvate, hydrate, cocrystal, or prodrug thereof, wherein:

$X^1$ is C(R$^9$) or N;

$X^2$ is C(R$^{10}$) or N;

Y is N(R$^{11}$), O or S;

Z is CR$^8$ or N;

$R^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1, 2 or 3 substituents independently selected from halo, nitro, cyano, $(C_{1-4})$alkyl, O(C$_{1-4}$)alkyl, O(C$_{1-4}$)haloalkyl, (NHC$_{1-4}$)alkyl, N(C$_{1-4}$ alkyl)(C$_{1-4}$)alkyl and (C$_{1-4}$)haloalkyl;

$R^2$ is selected from halo, $(C_{1-4})$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —O(C$_{2-6}$)alkylNR$^a$R$^a$, —O(C$_{2-6}$)alkylOR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$ N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$(C$_{2-6}$ alkylNR$^a$R$^a$ and —NR$^a$(C$_{2-6}$)alkylOR$^a$; or R$^2$ is selected from $(C_{1-6})$alkyl, phenyl, benzyl, heteroaryl, heterocycle, —((C$_{1-3}$)alkyl)heteroaryl, —((C$_{1-3}$)alkyl)heterocycle, —O((C$_{1-3}$)alkyl)heteroaryl, —O((C$_{1-3}$)alkyl)heterocycle, —NR$^a$((C$_{1-3}$)alkyl)heteroaryl, —NR$^a$((C$_{1-3}$)alkyl)heterocycle, —O((C$_{1-3}$)alkyl)phenyl, —O((C$_{1-3}$)alkyl)phenyl and —NR$^a$(C$_{1-3}$ alkyl)phenyl all of which are substituted by 0, 1, 2 or 3 substituents selected from (C$_{1-4}$)haloalkyl, O(C$_{1-4}$)alkyl, Br, Cl, F, I and (C$_{1-4}$)alkyl;

R$^3$ is selected from H, halo, (C$_{1-4}$)haloalkyl, cyano, nitro, —C(=O)R$^a$, —C(=O)OR$^a$, C(=O)NR$^a$R$^a$C(=NR$^a$)NR$^a$, —OR$^a$, —OC(=O)R$^a$, —OC(=O)NR$^a$R$^a$, —OC(=O)N(R$^a$)S(=O)$_2$R$^a$, —O(C$_{2-6}$)alkylNR$^a$R$^a$, —O(C$_{2-6}$) alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$ N(R$^a$)C(=O)OR$^a$, —S(=O)$_2$N(R$^a$)C(=O)NR$^a$R$^a$, NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$) S(=O)$_2$R$^a$, —N(R$^a$)S(=O)$_2$NR$^a$R$^a$, —NR$^a$(C$_{2-6}$)alkylOR$^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from (C$_{1-6}$) haloalkyl, O(C$_{1-6}$)alkyl, Br, Cl, F, I and (C$_{1-6}$)alkyl;

R$^5$ is, independently, in each instance, H, halo, (C$_{1-6}$)alkyl, (C$_{1-4}$)haloalkyl, or (C$_{1-6}$)alkyl substituted by 1, 2 or 3 substituents selected from halo, cyano, OH, O(C$_{1-4}$)alkyl, (C$_{1-4}$)alkyl, (C$_{1-3}$)haloalkyl, O(C$_{1-4}$)alkyl, NH$_2$, (NHC$_{1-4}$)alkyl, N(C$_{1-4}$)alkyl(C$_{1-4}$)alkyl; or both R$^5$ groups together form a C$_{3-6}$-spiroalkyl substituted by 0, 1, 2 or 3 substituents selected from halo, cyano, OH, O(C$_{1-4}$)alkyl, (C$_{1-4}$)alkyl, (C$_{1-3}$)haloalkyl, O(C$_{1-4}$)alkyl, NH$_2$, (NHC$_{1-4}$)alkyl, N((C$_{1-4}$)alkyl)(C$_{1-4}$)alkyl;

R$^6$ is selected from H, halo, (C$_{1-6}$)alkyl, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$ N(R$^a$)C(=O)OR$^a$, —S(=O)$_2$N(R$^a$)C(=O)NR$^a$R$^a$;

R$^7$ is selected from H, halo, (C$_{1-6}$)alkyl, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$S(=O)$_2$R$^a$, —S(=O)$_2$NR$^a$R$^a$, —S(=O)$_2$N(R$^a$)C(=O)R$^a$, —S(=O)$_2$ N(R$^a$)C(=O)OR$^a$, —S(=O)$_2$N(R$^a$)C(=O)NR$^a$R$^a$;

R$^8$ is selected from H, (C$_{1-6}$)haloalkyl, Br, Cl, F, I, OR$^a$, NR$^a$R$^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from (C$_{1-6}$)haloalkyl, O(C$_{1-6}$ alkyl, Br, Cl, F, I and (C$_{1-6}$)alkyl;

R$^9$ is selected from H, halo, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, OC(=O)NR$^a$R$^a$, —OC(=O)N(R$^a$)S(=O)$_2$R$^a$, —O(C$_{2-6}$)alkylNR$^a$R$^a$, —O(C$_{2-6}$)alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$(C$_{2-6}$)alkylNR$^a$R$^a$, —NR$^a$(C$_{2-6}$)alkylOR$^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from halo, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —O(C$_{2-6}$)alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, NR$^a$R$^a$,
—N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$ R$^a$, —N(R$^a$)S(=O)$_2$NR$^a$R$^a$, —NR$^a$(C$_{2-6}$)alkyl-NR$^a$, —NR$^a$(C$_{2-6}$)alkylOR$^a$; or R$^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —O(C$_{2-6}$)alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$) S(=O)$_2$R$^a$, —N(R$^a$)S(=O)$_2$NR$^a$R$^a$, —NR$^a$(C$_{2-6}$ alkylNR$^a$R$^a$ and —NR$^a$(C$_{2-6}$)alkylOR$^a$;

R$^{10}$ is H, (C$_{1-3}$)alkyl, (C$_{1-3}$)haloalkyl, cyano, nitro, CO$_2$R$^a$, C(=O)NR$^a$R$^a$, —C(=NR$^a$)NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —S(=O)R$^b$, S(=O)$_2$R$^b$ or S(=O)$_2$NR$^a$R$^a$; —R$^{11}$ is H or (C$_{1-4}$)alkyl;

R$^a$ is independently, at each instance, H or R$^b$; and

R$^b$ is independently, at each instance, phenyl, benzyl or (C$_{1-6}$)alkyl, the phenyl, benzyl and (C$_{1-6}$)alkyl being substituted by 0, 1, 2 or 3 substituents selected from halo, (C$_{1-4}$)alkyl, (C$_{1-3}$) haloalkyl, —O(C$_{1-4}$)alkyl, —NH$_2$, —NH(C$_{1-4}$)alkyl, —N(C$_{1-4}$)alkyl(C$_{1-4}$)alkyl.

In another embodiment, the PI3K inhibitor (which may be a PI3K-γ inhibitor, PI3K-δ inhibitor, or PI3K-γ,δ inhibitor) is a compound of Formula (VII):

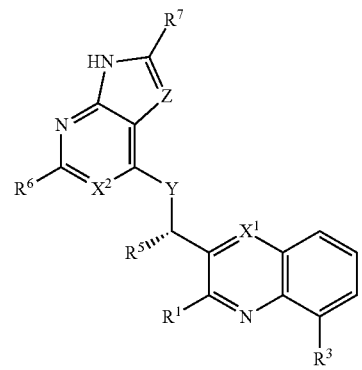

Formula (VII)

or a pharmaceutically acceptable salt, solvate, hydrate, cocrystal, or prodrug thereof, wherein:

X$^1$ is C(R$^9$) or N;
X$^2$ is C(R$^{10}$) or N;
Y is N(R$^{11}$), O or S;
Z is CR$^8$ or N;
R$^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1 or 2 or 3 substituents independently selected from halo, nitro, cyano, (C$_{1-4}$)alkyl, O(C₁₋₄)alkyl, O(C₁₋₄)haloalkyl, NH(C₁₋₄)alkyl, N(C₁₋₄)alkyl(C₁₋₄)alkyl and (C₁₋₄)haloalkyl;

R² is selected from halo, (C₁₋₄)haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆)alkylNRᵃRᵃ, —OC₂₋₆)alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃ(C₂₋₆ alkylNRᵃRᵃ and —NRᵃ(C₂₋₆)alkylORᵃ; or R² is selected from (C₁₋₆)alkyl, phenyl, benzyl, heteroaryl, heterocycle, —(C₁₋₃ alkyl)heteroaryl, —(C₁₋₃ alkyl)heterocycle, —O(C₁₋₃ alkyl)heteroaryl, —O((C₁₋₃) alkyl)heterocycle, —NRᵃ(C₁₋₃ alkyl)heteroaryl, —NRᵃ(C₁₋₃ alkyl)heterocycle, —(C₁₋₃ alkyl)phenyl, —O(C₁₋₃ alkyl)phenyl and —NRᵃ(C₁₋₃ alkyl)phenyl all of which are substituted by 0, 1, 2 or 3 substituents selected from (C₁₋₄)haloalkyl, O(C₁₋₄)alkyl, Br, Cl, F, I and (C₁₋₄)alkyl;

R³ is selected from H, halo, (C₁₋₄)haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆)alkylNRᵃRᵃ, —OC₂₋₆)alkylOR¹, —SRᵃ, —S(=O)Rᵃ, —S(=O)₂Rᵃ, —S(O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃ(C₂₋₆)alkylNRᵃRᵃ, —NRᵃ(C₂₋₆)alkylORᵃ, (C₁₋₆)alkyl, phenyl, benzyl, heteroaryl and heterocycle, wherein the (C₁₋₆)alkyl, phenyl, benzyl, heteroaryl and heterocycle are additionally substituted by 0, 1, 2 or 3 substituents selected from (C₁₋₆)haloalkyl, O(C₁₋₆)alkyl, Br, Cl, F, I and (C₁₋₆)alkyl;

R⁵ is, independently, in each instance, H, halo, (C₁₋₆)alkyl, (C₁₋₄)haloalkyl, or (C₁₋₆)alkyl substituted by 1, 2 or 3 substituents selected from halo, cyano, OH, O(C₁₋₄)alkyl, (C₁₋₄)alkyl, (C₁₋₃)haloalkyl, O(C₁₋₄)alkyl, NH₂, NHC₁₋₄)alkyl, N(C₁₋₄)alkyl(C₁₋₄)alkyl; or both R⁵ groups together form a C₃₋₆-spiroalkyl substituted by 0, 1, 2 or 3 substituents selected from halo, cyano, OH, O(C₁₋₄)alkyl, (C₁₋₄)alkyl, (C₁₋₃)haloalkyl, O(C₁₋₄)alkyl, NH₂, NHC₁₋₄) alkyl, N(C₁₋₄)alkyl)C₁₋₄)alkyl;

R⁶ is selected from H, halo, (C₁₋₆)alkyl, (C₁₋₄haloalkyl, cyano, nitro, —C(=O)Rᵃ, —C(=O)ORᵃ, —C(=O)NRᵃRᵃ, —C(=NRᵃ)NRᵃRᵃ, —S(=O)RᵃS(=O)₂Rᵃ, —S(=O)₂NRᵃRᵃ, —S(=O)₂N(Rᵃ)C(=O)Rᵃ, —S(=O)₂ N(Rᵃ)C(=O)ORᵃ, —S(=O)₂N(Rᵃ)C(=O)NRᵃRᵃ;

R⁷ is selected from H, halo, (C₁₋₆)alkyl, (C₁₋₄haloalkyl, cyano, nitro, —C(=O)Rᵃ, —C(=O)ORᵃ, —C(=O)NRᵃRᵃ, —C(=NRᵃ)NRᵃRᵃ, —S(=O)RᵃS(=O)₂Rᵃ, —S(=O)₂NRᵃRᵃ, —S(=O)₂N(Rᵃ)C(=O)Rᵃ, —S(=O)₂ N(Rᵃ)C(=O)ORᵃ, —S(=O)₂N(Rᵃ)C(=O)NRᵃRᵃ;

R⁸ is selected from H, (C₁₋₆)haloalkyl, Br, Cl, F, I, ORᵃ, NRᵃRᵃ, (C₁₋₆)alkyl, phenyl, benzyl, heteroaryl and heterocycle, wherein the (C₁₋₆)alkyl, phenyl, benzyl, heteroaryl and heterocycle are additionally substituted by 0, 1, 2 or 3 substituents selected from (C₁₋₆)haloalkyl, O(C₁₋₆)alkyl, Br, Cl, F, I and (C₁₋₆)alkyl;

R⁹ is selected from H, halo, (C₁₋₄)haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆)alkylNRᵃRᵃ, —OC₂₋₆)alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃ(C₂₋₆)alkylNRᵃRᵃ, —NRᵃ(C₂₋₆)alkylORᵃ, (C₁₋₆)alkyl, phenyl, benzyl, heteroaryl and heterocycle, wherein the (C₁₋₆)alkyl, phenyl, benzyl, heteroaryl and heterocycle are additionally substituted by 0, 1, 2 or 3 substituents selected from halo, (C₁₋₄)haloalkyl, cyano, nitro, —C(=O)Rᵃ, —C(=O)ORᵃ, —C(=O)NRᵃRᵃ, —C(=NRᵃ)NRᵃRᵃ, —OR⁸, —OC(=O)R⁸, —OC(=O)NR²R⁸, —OC(=O)N(Rᵃ)S(=O)₂Rᵃ, —OC₂₋₆)alkylNRᵃRᵃ, —OC₂₋₆)alkylORᵃ, —SRᵃ, —S(=O)Rᵃ, —S(=O)₂R⁸, —S(=O)₂NRᵃRᵃ, —S(=O)₂ N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂ Rᵃ, —N(Rᵃ)S(=O)₂NRᵃRᵃ, —NRᵃ(C₂₋₆)alkylNRᵃRᵃ, —NRᵃ(C₂₋₆)alkylORᵃ; or R⁹ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, (C₁₋₄)haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆)alkylNRᵃRᵃ, —OC₂₋₆)alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂ Rᵃ, —N(Rᵃ)S(=O)₂NRᵃRᵃ, —NRᵃ(C₂₋₆)alkylNRᵃRᵃ and —NRᵃ(C₂₋₆)alkylORᵃ;

R¹⁰ is H, (C₁₋₃ alkyl, (C₁₋₃)haloalkyl, cyano, nitro, CO₂Rᵃ, C(=O)NRᵃRᵃ, —C(=NRᵃ)NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —S(=O)Rᵇ, S(=O)₂Rᵇ or S(=O)₂NRᵃRᵃ;

R¹¹ is H or (C₁₋₄)alkyl;

Rᵃ is independently, at each instance, H or Rᵇ; and

Rᵇ is independently, at each instance, phenyl, benzyl or (C₁₋₆)alkyl, the phenyl, benzyl and (C₁₋₆)alkyl being substituted by 0, 1, 2 or 3 substituents selected from halo, (C₁₋₄)alkyl, (C₁₋₃)haloalkyl, —O(C₁₋₄)alkyl, —NH₂, —NHC₁₋₄)alkyl, —N(C₁₋₄)alkyl(C₁₋₄)alkyl.

In another embodiment, the PI3K inhibitor (which may be a PI3K-γ inhibitor, PI3K-δ inhibitor, or PI3K-γ,δ inhibitor) is a compound of Formula (VIII):

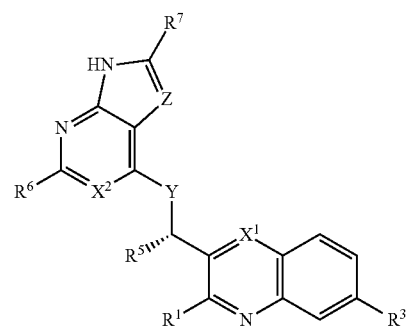

Formula (VIII)

or a pharmaceutically acceptable salt, solvate, hydrate, cocrystal, or prodrug thereof, wherein:

$X^1$ is $C(R^9)$ or N;

$X^2$ is $C(R^{10})$ or N;

Y is $N(R^{11})$, O or S;

Z is $CR^8$ or N;

$R^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $(C_{1-4})$alkyl, $O(C_{1-4})$alkyl, $O(C_{1-4})$haloalkyl, $NH(C_{1-4})$alkyl, $N(C_{1-4}$alkyl$)C_{1-4})$alkyl and $(C_{1-4})$haloalkyl;

$R^2$ is selected from halo, $(C_{1-4})$haloalkyl, cyano, nitro, —C(=O)$R^a$, —C(=O)O$R^a$, —C(=O)N$R^aR^a$—C(=N$R^a$)N$R^aR^a$, —O$R^a$, —OC(=O)$R^a$, OC(=O)N$R^aR^a$, —OC(=O)N($R^a$)S(=O)$_2R^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a(C_{2-6}$alkylN$R^aR^a$ and —N$R^a(C_{2-6}$alkylO$R^a$; or $R^2$ is selected from $(C_{1-6}$alkyl, phenyl, benzyl, heteroaryl, heterocycle, —(C$_{1-3}$ alkyl)heteroaryl, —(C$_{1-3}$ alkyl)heterocycle, —O(C$_{1-3}$ alkyl)heteroaryl, —O(C$_{1-3}$ alkyl)heterocycle, —N$R^a$(C$_{1-3}$ alkyl)heteroaryl, —N$R^a$(C$_{1-3}$ alkyl)heterocycle, —(C$_{1-3}$ alkyl)phenyl, —O(C$_{1-3}$ alkyl)phenyl and —N$R^a$(C$_{1-3}$ alkyl)phenyl all of which are substituted by 0, 1, 2 or 3 substituents selected from (C$_{1-4}$ haloalkyl, O(C$_{1-4}$)alkyl, Br, Cl, F, I and (C$_{1-4}$)alkyl;

$R^3$ is selected from H, halo, $(C_{1-4})$haloalkyl, cyano, nitro, —C(=O)$R^a$, —C(=O)O$R^a$, —C(=O)N$R^aR^a$—C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2 R^a$, —N($R^a$)S(=O)$_2$N$R^a$N$R^a$, —N$R^a$, —N$R^a$(C$_{2-6}$)alkylO$R^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from (C$_{1-6}$)haloalkyl, O(C$_{1-6}$)alkyl, Br, Cl, F, I and (C$_{1-6}$)alkyl;

$R^5$ is, independently, in each instance, H, halo, (C$_{1-6}$)alkyl, (C$_{1-4}$)haloalkyl, or (C$_{1-6}$)alkyl substituted by 1, 2 or 3 substituents selected from halo, cyano, OH, O(C$_{1-4}$)alkyl, (C$_{1-4}$)alkyl, (C$_{1-3}$)haloalkyl, O(C$_{1-4}$)alkyl, NH$_2$, NH(C$_{1-4}$)alkyl, N(C$_{1-4}$)alkyl(C$_{1-4}$)alkyl; or both $R^5$ groups together form a C$_{3-6}$-spiroalkyl substituted by 0, 1, 2 or 3 substituents selected from halo, cyano, OH, O(C$_{1-4}$)alkyl, (C$_{1-4}$)alkyl, (C$_{1-3}$)haloalkyl, O(C$_{1-4}$)alkyl, NH$_2$, NH(C$_{1-4}$) alkyl, N(C$_{1-4}$)alkyl(C$_{1-4}$)alkyl;

$R^6$ is selected from H, halo, (C$_{1-6}$)alkyl, (C$_{1-4}$)haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$ N($R^a$)C(=O)O$R^a$, —S(=O)$_2$N($R^a$)C(=O)N$R^aR^a$;

$R^7$ is selected from H, halo, (C$_{1-6}$)alkyl, (C$_{1-4}$)haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$ N($R^a$)C(=O)O$R^a$, —S(=O)$_2$N($R^a$)C(=O)N$R^aR^a$;

$R^8$ is selected from H, (C$_{1-6}$)haloalkyl, Br, Cl, F, I, O$R^a$, N$R^aR^a$, (C$_{1-6}$alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from (C$_{1-6}$)haloalkyl, OC$_{1-6}$ alkyl, Br, Cl, F, I and (C$_{1-6}$)alkyl;

$R^9$ is selected from H, halo, (C$_{1-4}$)haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$(C$_{2-6}$ alkylN$R^aR^a$, —N$R^a$(C$_{2-6}$alkylO$R^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from halo, (C$_{1-4}$)haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2 R^a$, —N($R^a$)S(=O)$_2$N$R^aR^a$, —N$R^a$(C$_{2-6}$alkylN$R^aR^a$, —N$R^a$(C$_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, (C$_{1-4}$)haloalkyl, cyano, nitro, —C(O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2 R^a$, —N($R^a$)S(=O)$_2$N$R^aR^a$, —N$R^a$(C$_{2-6}$ alkylN$R^aR^a$ and —N$R^a$(C$_{2-6}$alkylO$R^a$;

$R^{10}$ is H, (C$_{1-3}$ alkyl, (C$_{1-3}$)haloalkyl, cyano, nitro, CO$_2R^a$, C(=O)N$R^aR^a$, —C(=N$R^a$)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —S(=O)$R^b$, —S(=O)$_2R^b$ or S(=O)$_2$N$R^aR^a$;

$R^{11}$ is H or (C$_{1-4}$)alkyl;

$R^a$ is independently, at each instance, H or $R^b$; and $R^b$ is independently, at each instance, phenyl, benzyl or (C$_{1-6}$)alkyl, the phenyl, benzyl and (C$_{1-6}$) alkyl being substituted by 0, 1, 2 or 3 substituents selected from halo, (C$_{1-4}$)alkyl, (C$_{1-3}$ haloalkyl, —O(C$_{1-4}$)alkyl, —NH$_2$, —NH(C$_{1-4}$)alkyl, —N(C$_{1-4}$)alkyl(C$_{1-4}$)alkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $X^1$ is $C(R^9)$ and $X^2$ is N.

In a preferred embodiment, the PI3K inhibitor (which may be a PI3K-γ inhibitor, PI3K-δ inhibitor, or PI3K-γ,δ inhibitor) is a compound of Formula (VIII) wherein $X^1$ is $C(R^9)$ and $X^2$ is $C(R^{10})$.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is phenyl substituted by 0, 1, 2, or 3 independently selected $R^2$ substituents.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is phenyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is selected from 2-methylphenyl, 2-chlorophenyl, 2-trifluoromethylphenyl, 2-fluorophenyl and 2-methoxyphenyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is phenoxy.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is a direct-bonded or oxygen-linked saturated, partially-saturated or unsaturated 5-, 6- or 7-membered monocyclic ring containing 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}$alkyl)$C_{1-4}$alkyl and $C_{1-4}$haloalkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is an unsaturated 5- or 6-membered monocyclic ring containing 1, 2, 3 or 4 atoms selected from N, O and S, but containing no more than one O or S, wherein the ring is substituted by 0 or 1 $R^2$ substituents, and the ring is additionally substituted by 0, 1 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}$alkyl)$C_{1-4}$alkyl and $C_{1-4}$haloalkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is an unsaturated 5- or 6-membered monocyclic ring containing 1, 2, 3 or 4 atoms selected from N, O and S, but containing no more than one O or S, wherein the ring is substituted by 0 or 1 $R^2$ substituents, and the ring is additionally substituted by 1, 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}$alkyl)$C_{1-4}$alkyl and $C_{1-4}$ haloalkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is an unsaturated 5- or 6-membered monocyclic ring containing 1, 2, 3 or 4 atoms selected from N, O and S.

In a preferred embodiment, the PI3K inhibitor (which may be a PI3K-γ inhibitor, PI3K-δ inhibitor, or PI3K-γ,δ inhibitor) is a compound of Formula (VIII) wherein $R^1$ is selected from pyridyl and pyrimidinyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^3$ is selected from halo, $C_{1-4}$haloalkyl, cyano, nitro, —C(O)$R^a$, —C(=O)O$R^a$, —C(=O)N$R^aR^a$, —C(N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)N$R^aR^a$, —S(=O)$_2$N($R^a$)C(=O)$R^a$, —S(=O)$_2$N($R^a$)C(O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$(C$_{2-6}$alkylN$R^aR^a$, —N$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$)haloalkyl, $OC_{1-6}$alkyl, Br, Cl, F, I and $C_{1-6}$alkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^3$ is H.

In a preferred embodiment, the PI3K inhibitor (which may be a PI3K-γ inhibitor, PI3K-δ inhibitor, or PI3K-γ,δ inhibitor) is a compound of Formula (VIII) wherein $R^3$ is selected from F, Cl, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$)haloalkyl, $OC_{1-6}$alkyl, Br, Cl, F, I and $C_{1-6}$alkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, $OC_{1-4}$)alkyl, $C_{1-4}$)alkyl, $C_{1-3}$)haloalkyl, $OC_{1-4}$)alkyl, $NH_2$, $NHC_{1-4}$)alkyl, $N(C_{1-4}$alkyl)$C_{1-4}$)alkyl; or both $R^5$ groups together form a $C_{3-6}$spiroalkyl substituted by 0, 1, 2 or 3 substituents selected from halo, cyano, OH, $OC_{1-4}$)alkyl, $C_{1-4}$)alkyl, $C_{1-3}$)haloalkyl, $OC_{1-4}$)alkyl, $NH_2$, $NHC_{1-4}$)alkyl, $N(C_{1-4}$alkyl)$C_{1-4}$)alkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^5$ is H.

In a preferred embodiment, the PI3K inhibitor (which may be a PI3K-γ inhibitor, PI3K-δ inhibitor, or PI3K-γ,δ inhibitor) is a compound of Formula (VIII) wherein one $R^5$ is S-methyl, the other is H.

In a preferred embodiment, the PI3K inhibitor (which may be a PI3K-γ inhibitor, PI3K-δ inhibitor, or PI3K-γ,δ inhibitor) is a compound of Formula (VIII) wherein at least one $R^5$ is halo, $C_{1-6}$alkyl, $C_{1-4}$haloalkyl, or $C_{1-6}$alkyl substituted by 1, 2 or 3 substituents selected from halo, cyano, OH, $OC_{1-4}$)alkyl, $C_{1-4}$)alkyl, $C_{1-3}$)haloalkyl, $OC_{1-4}$)alkyl, $NH_2$, $NHC_{1-4}$)alkyl, $N(C_{1-4}$alkyl)$C_{1-4}$)alkyl.

In a preferred embodiment, the PI3K inhibitor (which may be a PI3K-γ inhibitor, PI3K-δ inhibitor, or PI3K-γ,δ inhibitor) is a compound of Formula (VIII) wherein $R^6$ is H.

In a preferred embodiment, the PI3K inhibitor (which may be a PI3K-γ inhibitor, PI3K-δ inhibitor, or PI3K-γ,δ inhibitor) is a compound of Formula (VIII) wherein $R^6$ is F, Cl, cyano or nitro.

In a preferred embodiment, the PI3K inhibitor (which may be a PI3K-γ inhibitor, PI3K-δ inhibitor, or PI3K-γ,δ inhibitor) is a compound of Formula (VIII) wherein $R^7$ is H.

In a preferred embodiment, the PI3K inhibitor (which may be a PI3K-γ inhibitor, PI3K-δ inhibitor, or PI3K-γ,δ inhibitor) is a compound of Formula (VIII) wherein $R^7$ is F, Cl, cyano or nitro.

In a preferred embodiment, the PI3K inhibitor (which may be a PI3K-γ inhibitor, PI3K-δ inhibitor, or PI3K-γ,δ inhibitor) is a compound of Formula (VIII) wherein $R^8$ is selected from H, $CF_3$, $C_{1-3}$ alkyl, Br, Cl and F.

In a preferred embodiment, the PI3K inhibitor (which may be a PI3K-γ inhibitor, PI3K-δ inhibitor, or PI3K-γ,δ inhibitor) is a compound of Formula (VIII) wherein $R^8$ is selected from H.

In a preferred embodiment, the PI3K inhibitor (which may be a PI3K-γ inhibitor, PI3K-δ inhibitor, or PI3K-γ,δ inhibitor) is a compound of Formula (VIII) wherein $R^8$ is selected from $CF_3$, $C_{1-3}$ alkyl, Br, Cl and F.

In a preferred embodiment, the PI3K inhibitor (which may be a PI3K-γ inhibitor, PI3K-δ inhibitor, or PI3K-γ,δ inhibitor) is a compound of Formula (VIII) wherein $R^9$ is H.

In a preferred embodiment, the PI3K inhibitor (which may be a PI3K-γ inhibitor, PI3K-δ inhibitor, or PI3K-γ,δ inhibitor) is a compound of Formula (VIII) wherein $R^9$ is selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$($C_{2-6}$alkylN$R^a R^a$, —N$R^a$($C_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$($C_{2-6}$alkylN$R^a R^a$, —N$R^a$($C_{2-6}$alkylO$R^a$.

In a preferred embodiment the PI3K inhibitor (which may be a PI3K-γ inhibitor, PI3K-δ inhibitor, or PI3K-γ,δ inhibitor) is a compound of Formula (VIII) wherein $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —O$C_{2-6}$alkylN$R^a R^a$, —O$C_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$($C_{2-6}$alkylN$R^a R^a$ and —N$R^a$($C_{2-6}$alkylO$R^a$.

In a preferred embodiment, the PI3K inhibitor (which may be a PI3K-γ inhibitor, PI3K-δ inhibitor, or PI3K-γ,δ inhibitor) is a compound of Formula (VIII) wherein $R^{10}$ is H.

In a preferred embodiment, the PI3K inhibitor (which may be a PI3K-γ inhibitor, PI3K-δ inhibitor, or PI3K-γ,δ inhibitor) is a compound of Formula (VIII) wherein $R^{10}$ is cyano, nitro, $CO_2 R^a$, C(=O)N$R^a R^a$, —C(=N$R^a$)N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, S(=O)$R^b$, S(=O)$_2 R^b$ or S(=O)$_2$N$R^a R^a$.

In a preferred embodiment, the PI3K inhibitor (which may be a PI3K-γ inhibitor, PI3K-δ inhibitor, or PI3K-γ,δ inhibitor) is a compound of Formula (VIII) wherein $R^{11}$ is H.

In a preferred embodiment, the PI3K-δ inhibitor is a compound of Formula (IX):

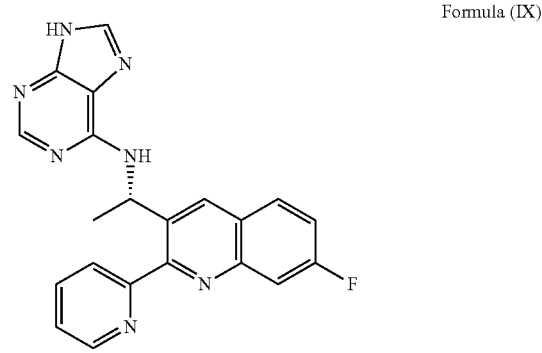 [SMILES: C[C@H](Nc1ncnc2[nH]cnc12)c1cc2ccc(F)cc2nc1-c1ccccn1]

Formula (IX)

or a pharmaceutically acceptable salt, solvate, hydrate, cocrystal, or prodrug thereof.

In a preferred embodiment, the PI3K inhibitor or PI3K-δ inhibitor is (S)—N-(1-(7-fluoro-2-(pyridin-2-yl)quinolin-3-yl)ethyl)-9H-purin-6-amine or a pharmaceutically acceptable salt, solvate, hydrate, cocrystal, or prodrug thereof.

In a preferred embodiment, the PI3K-δ inhibitor is a compound of Formula (X):

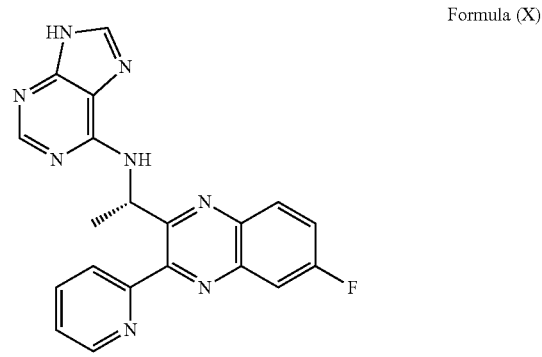 [SMILES: C[C@H](Nc1ncnc2[nH]cnc12)c1nc2ccc(F)cc2nc1-c1ccccn1]

Formula (X)

or a pharmaceutically acceptable salt, solvate, hydrate, cocrystal, or prodrug thereof.

In a preferred embodiment, the PI3K inhibitor or PI3K-δ inhibitor is (S)—N-(1-(6-fluoro-3-(pyridin-2-yl)quinoxalin-2-yl)ethyl)-9H-purin-6-amine or a pharmaceutically acceptable salt, solvate, hydrate, cocrystal, or prodrug thereof.

In a preferred embodiment, the PI3K-δ inhibitor is a compound of Formula (XI):

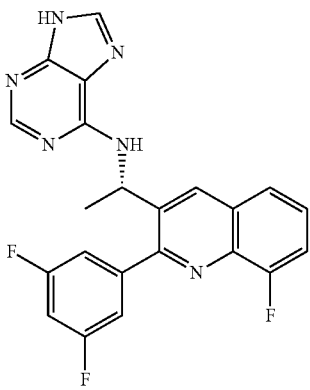

Formula (XI)

or a pharmaceutically acceptable salt, solvate, hydrate, cocrystal, or prodrug thereof.

In a preferred embodiment, the PI3K-δ inhibitor is (S)—N-(1-(2-(3,5-difluorophenyl)-8-fluoroquinolin-3-yl)ethyl)-9H-purin-6-amine or a pharmaceutically-acceptable salt, solvate, hydrate, cocrystal, or prodrug thereof.

In a preferred embodiment, the PI3K-δ inhibitor is a compound of Formula (XII):

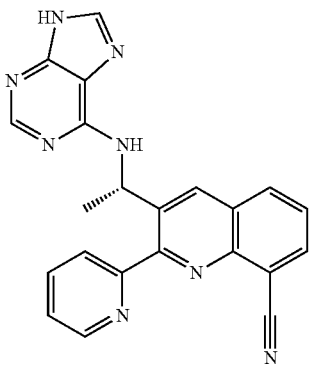

Formula (XII)

or a pharmaceutically acceptable salt, solvate, hydrate, cocrystal, or prodrug thereof.

In a preferred embodiment, the PI3K-δ inhibitor is (S)-3-(1-((9H-purin-6-yl)amino)ethyl)-2-(pyridin-2-yl)quinoline-8-carbonitrile or a pharmaceutically acceptable salt, solvate, hydrate, cocrystal, or prodrug thereof.

In a preferred embodiment, the PI3K-δ inhibitor is a compound of Formula (XIII):

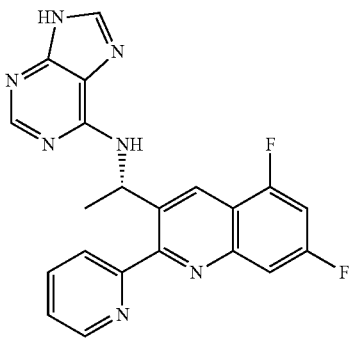

Formula (XIII)

or a pharmaceutically acceptable salt, solvate, hydrate, cocrystal, or prodrug thereof In a preferred embodiment, the PI3K-δ inhibitor is (S)—N-(1-(5,7-difluoro-2-(pyridin-2-yl)quinolin-3-yl)ethyl)-9H-purin-6-amine or a pharmaceutically acceptable salt, solvate, hydrate, cocrystal, or prodrug thereof.

In an embodiment, the PI3K inhibitor or PI3K-δ inhibitor is a compound selected from the structures disclosed in U.S. Pat. Nos. 7,932,260 and 8,207,153, the disclosure of which is incorporated by reference herein. In an embodiment, the PI3K inhibitor or PI3K-δ inhibitor is a compound of Formula (XIV):

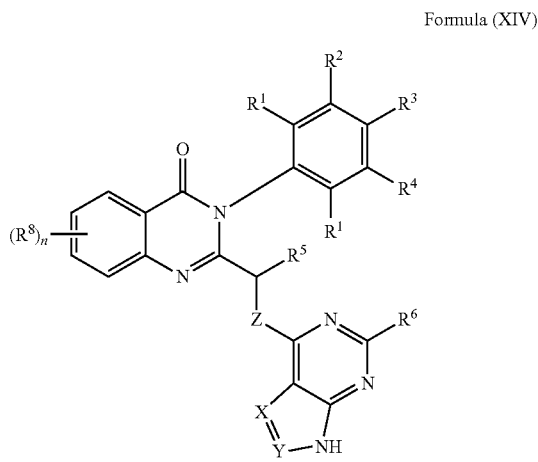

Formula (XIV)

wherein

X and Y, independently, are N or CH;

Z is N—$R^7$ or O;

$R^1$ are the same and are hydrogen, halo, or $C_{1-3}$ alkyl;

$R^2$ and $R^3$, independently, are hydrogen, halo, or $C_{1-3}$ alkyl;

$R^4$ is hydrogen, halo, $OR^a$, CN, $C_{2-6}$alkynyl, $C(=O)R^a$, $C(=O)NR^aR^b$, $C_{3-6}$heterocycloalkyl, $C_{1-3}$ alkyleneC$_{3-6}$ heterocycloalkyl, $O(C_{1-3})$alkyleneOR$^a$, $O(C_{1-3})$alkyleneNR$^a$R$^b$, $O(C_{1-3})$alkyleneC$_{3-6}$ cycloalkyl, OC$_{3-6}$heterocycloalkyl, $O(C_{1-3})$alkyleneC≡CH, or $O(C_{1-3})$alkyleneC(=O)NR$^a$R$^b$;

$R^5$ is $(C_{1-3})$alkyl, $CH_2CF_3$, phenyl, $CH_2C≡CH$, $(C_{1-3})$alkyleneOR$^e$, $(C_{1-4})$alkyleneNR$^a$R$^b$, or $C_{1-4}$ alkyleneNHC(=O)OR$^a$, $R^6$ is hydrogen, halo, or NR$^a$R$^b$;

$R^7$ is hydrogen or $R^5$ and $R^7$ are taken together with the atoms to which they are attached to form a five- or six-membered saturated ring;

$R^8$ is $C_{1-3}$ alkyl, halo, $CF_3$, or $CH_2C_{3-6}$heterocycloalkyl;

n is 0, 1, or 2;

$R^a$ is hydrogen, $(C_{1-4})$alkyl, or $CH_2C_6H_5$;

$R^b$ is hydrogen or $C_{1-3}$ alkyl; and $R^c$ is hydrogen, $C_{1-3}$ alkyl, or halo, wherein when the $R^1$ groups are different from hydrogen, $R^2$ and $R^4$ are the same; or a pharmaceutically acceptable salt, solvate, hydrate, cocrystal, or prodrug thereof.

In a preferred embodiment, the PI3K inhibitor or PI3K-δ inhibitor is an enantiomer of Formula (XIV), as shown in Formula (XV):

Formula (XV)

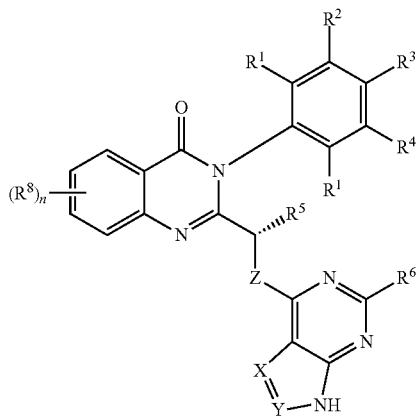

wherein X, Y, Z, R$^1$ through R$^8$, R$^a$, R$^b$, R$^c$, and n are as defined above for Formula (XIV).

In various embodiments exhibiting increased potency relative to other compounds, n=1, 2, or 3 and R$^8$ is C$_{1-3}$alkyl, F, Cl, or CF$_3$. Alternatively, in such embodiments, n is 0 (such that there is no R$^8$ substituent).

In further embodiments exhibiting increased potency, X is N and Y is CH. Alternatively, X and Y may also both be CH.

In further embodiments exhibiting increased potency, R$^6$ is hydrogen, halo, or NH$_2$. Preferably, R$^6$ is hydrogen.

In preferred embodiments exhibiting increased potency, n is 0 or 1; R$^8$ (if n is 1) is C$_{1-3}$ alkyl, F, Cl, or CF$_3$; R$^6$ is hydrogen; X is N and Y is CH or X and Y are both CH; Z is NH; R$^1$ are the same and are hydrogen, halo, or C$_{1-3}$alkyl; and R$^2$ and R$^3$, independently, are hydrogen, halo, or C$_{1-3}$alkyl. Preferably, R$^1$, R$^2$, and R$^3$ are hydrogen.

Unexpectedly, potency against PI3K-δ is conserved when R$^1$ is the same. In structural formulae (I) and (II), R$^2$ and R$^4$ may differ provided that R$^1$ is H. When R$^1$ is H, free rotation is unexpectedly permitted about the bond connecting the phenyl ring substituent to the quinazoline ring, and the compounds advantageously do not exhibit atropisomerism (i.e., multiple diastereomer formation is avoided). Alternatively, R$^2$ and R$^4$ can be the same such that the compounds advantageously do not exhibit atropisomerism.

In preferred embodiments, Z is N—R$^7$, and the bicyclic ring system containing X and Y is:

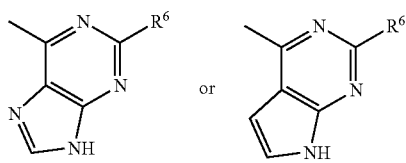

In other preferred embodiments of Formula (XIV) or Formula (XV), X, Y, Z, R$^a$, R$^b$, and R$^c$ are as defined above for Formula (XIV), and R$^1$ is hydrogen, fluoro, chloro, methyl, or

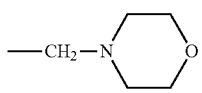

and R$^2$ is hydrogen, methyl, chloro, or fluoro; R$^3$ is hydrogen or fluoro; R$^6$ is NH$_2$, hydrogen, or fluoro; R$^7$ is hydrogen or R$^5$ and R$^7$ are taken together to form

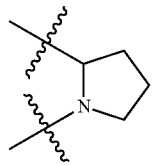 [SMILES: *C1CCCN1*]

R$^8$ is methyl, trifluoromethyl, chloro, or fluoro; R$^4$ is hydrogen, fluoro, chloro, OH, OCH$_3$, OCH$_2$C≡CH, O(CH$_2$)$_2$N(CH$_3$)$_2$, C(=O)CH$_3$, C≡CH, CN, C(=O)NH$_2$, OCH$_2$C(=O)NH$_2$, O(CH$_2$)$_2$OCH$_3$, O(CH$_2$)$_2$N(CH$_3$)$_2$,

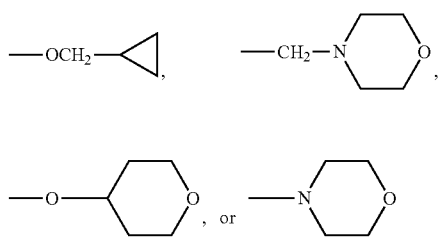

and R$^5$ is methyl, ethyl, propyl, phenyl, CH$_2$OH, CH$_2$OCH$_2$C$_6$H$_5$, CH$_2$CF$_3$, CH$_2$OC(CH$_3$)$_3$, CH$_2$C≡CH, (CH$_2$)$_3$N(C$_2$H$_5$)$_2$, (CH$_2$)$_3$NH$_2$, (CH$_2$)$_4$NH$_2$, (CH$_2$)$_3$NHC(=O)OCH$_2$C$_6$H$_5$, or (CH$_2$)$_4$NHC(=O)OCH$_2$C$_6$H$_5$; R$^c$ is hydrogen, methyl, fluoro, or bromo; and n is 0 or 1.

As used with respect to Formula (XIV) and Formula (XV), the term "alkyl" is defined as straight chained and branched hydrocarbon groups containing the indicated number of carbon atoms, e.g., methyl, ethyl, and straight chain and branched propyl and butyl groups. The terms "(C$_{1-3}$) alkylene" and "(C$_{1-4}$)alkylene" are defined as hydrocarbon groups containing the indicated number of carbon atoms and one less hydrogen than the corresponding alkyl group. The term "(C$_{2-6}$)alkynyl" is defined as a hydrocarbon group containing the indicated number of carbon atoms and a carbon-carbon triple bond. The term "(C$_{3-6}$)cycloalkyl" is defined as a cyclic hydrocarbon group containing the indicated number of carbon atoms. The term "(C$_{2-6}$)heterocycloalkyl" is defined similarly as cycloalkyl except the ring contains one or two heteroatoms selected from the group consisting of O, NR$^a$, and S. The term "halo" is defined as fluoro, bromo, chloro, and iodo.

In a preferred embodiment, the PI3K inhibitor (which may be a PI3K-γ inhibitor, PI3K-δ inhibitor, or PI3K-γ,δ inhibitor) is idelalisib. In a preferred embodiment, the PI3K inhibitor (which may be a PI3K-γ inhibitor, PI3K-δ inhibitor, or PI3K-γ,δ inhibitor) is the compound of Formula (XVI):

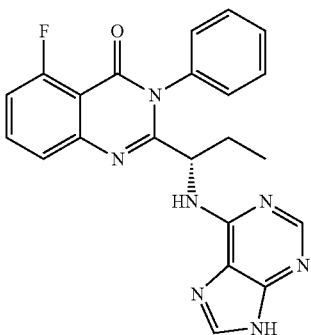

Formula (XVI)

or a pharmaceutically acceptable salt, solvate, hydrate, cocrystal, or prodrug thereof.

In a preferred embodiment, the PI3K inhibitor (which may be a PI3K-γ inhibitor, PI3K-δ inhibitor, or PI3K-γ,δ inhibitor) is (S)-2-(1-((9H-purin-6-yl)amino)propyl)-5-fluoro-3-phenylquinazolin-4(3H)-one or a pharmaceutically acceptable salt, solvate, hydrate, cocrystal, or prodrug thereof.

In an embodiment, the PI3K inhibitor (which may be a PI3K-γ inhibitor, PI3K-δ inhibitor, or PI3K-γ,δ inhibitor) is 4(3H)-quinazolinone, 5-fluoro-3-phenyl-2-[(1S)-1-(9H-purin-6-ylamino)propyl]-5-fluoro-3-phenyl-2-{(1S)-1-[(7H-purin-6-yl)amino]propyl}quinazolin-4(3H)-one or a pharmaceutically acceptable salt, solvate, hydrate, cocrystal, or prodrug thereof In an embodiment, the PI3K inhibitor (which may be a PI3K-γ inhibitor, PI3K-δ inhibitor, or PI3K-γ,δ inhibitor) is GS-9901. Other PI3K inhibitors suitable for use in the described combination with a BTK inhibitor also include, but are not limited to, those described in, for example, U.S. Pat. No. 8,193,182 and U.S. Published Application Nos. 2013/0267521; 2013/0053362; 2013/0029984; 2013/0029982; 2012/0184568; and 2012/0059000, the disclosures of each of which are incorporated by reference in their entireties.

BTK Inhibitors

The BTK inhibitor may be any BTK inhibitor known in the art. In particular, it is one of the BTK inhibitors described in more detail in the following paragraphs.

In an embodiment, the BTK inhibitor is a compound of Formula (XVII):

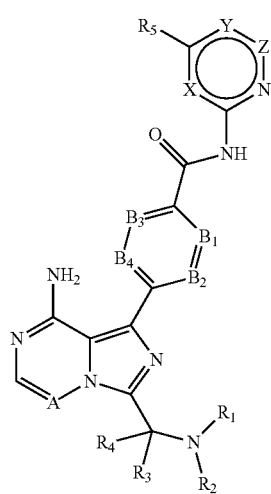

Formula (XVII)

or a pharmaceutically acceptable salt, solvate, hydrate, cocrystal, or prodrug thereof, wherein:

X is CH, N, O or S;
Y is $C(R_6)$, N, O or S;
Z is CH, N or bond;
A is CH or N;
$B_1$ is N or $C(R_7)$;
$B_2$ is N or $C(R_8)$;
$B_3$ is N or $C(R_9)$;
$B_4$ is N or $C(R_{10})$;
$R_1$ is $R_{11}C(=O)$, $R_{12}S(=O)$, $R_{13}S(=O)_2$ or $(C_{1-6})$alkyl optionally substituted with $R_{14}$;
$R_2$ is H, $(C_{1-3})$alkyl or $(C_{3-7})$cycloalkyl;
$R_3$ is H, $(C_{1-6})$alkyl or $(C_{3-7})$cycloalkyl); or
$R_2$ and $R_3$ form, together with the N and C atom they are attached to, a $(C_{3-7})$heterocycloalkyl optionally substituted with one or more fluorine, hydroxyl, $(C_{1-3})$alkyl, $(C_{1-3})$alkoxy or oxo;
$R_4$ is H or $(C_{1-3})$alkyl;
$R_5$ is H, halogen, cyano, $(C_{1-4})$alkyl, $(C_{1-3})$alkoxy, $(C_{3-6})$cycloalkyl, any alkyl group of which is optionally substituted with one or more halogen; or $R_5$ is $(C_{6-10})$aryl or $(C_{2-6})$heterocycloalkyl;
$R_6$ is H or $(C_{1-3})$alkyl; or
$R_5$ and $R_6$ together may form a $(C_{3-7})$cycloalkenyl or $(C_{2-6})$heterocycloalkenyl, each optionally substituted with $(C_{1-3})$alkyl or one or more halogens;
$R_7$ is H, halogen, $CF_3$, $(C_{1-3})$alkyl or $(C_{1-3})$alkoxy;
$R_8$ is H, halogen, $CF_3$, $(C_{1-3})$alkyl or $(C_{1-3})$alkoxy; or
$R_7$ and $R_R$ together with the carbon atoms they are attached to, form $(C_{6-10})$aryl or $(C_{1-9})$heteroaryl;
$R_9$ is H, halogen, $(C_{1-3})$alkyl or $(C_{1-3})$alkoxy;
$R_{10}$ is H, halogen, $(C_{1-3})$alkyl or $(C_{1-3})$alkoxy;
$R_{11}$ is independently selected from the group consisting of $(C_{1-6})$alkyl, $(C_{2-6})$alkenyl and $(C_{2-6})$alkynyl, where each alkyl, alkenyl or alkynyl is optionally substituted with one or more substituents selected from the group consisting of hydroxyl, $(C_{1-4})$alkyl, $(C_{3-7})$cycloalkyl, $[(C_{1-4})$alkyl]amino, di$[(C_{1-4})$alkyl]amino, $(C_{1-3})$alkoxy, $(C_{3-7})$cycloalkoxy, $(C_{6-10})$aryl and $(C_{3-7})$heterocycloalkyl; or $R_{11}$ is $(C_{1-3})$alkyl-C(O)—S—$(C_{1-3})$alkyl; or
$R_{11}$ is $(C_{1-5})$heteroaryl optionally substituted with one or more substituents selected from the group consisting of halogen or cyano;
$R_{12}$ and $R_{13}$ are independently selected from the group consisting of $(C_{2-6})$alkenyl or $(C_{2-6})$alkynyl, both optionally substituted with one or more substituents selected from the group consisting of hydroxyl, $(C_{1-4})$alkyl, $(C_{3-7})$cycloalkyl, $[(C_{1-4})$alkyl]amino, di$[(C_{1-4})$alkyl]amino, $(C_{1-3})$alkoxy, $(C_{3-7})$cycloalkoxy, $(C_{6-10})$aryl and $(C_{3-7})$heterocycloalkyl; or a $(C_{1-5})$heteroaryl optionally substituted with one or more substituents selected from the group consisting of halogen and cyano; and
$R_{14}$ is independently selected from the group consisting of halogen, cyano, $(C_{2-6})$alkenyl and $(C_{2-6})$alkynyl, both optionally substituted with one or more substituents selected from the group consisting of hydroxyl, $(C_{1-4})$alkyl, $(C_{3-7})$cycloalkyl, $(C_{1-4})$alkylamino, di$[(C_{1-4})$alkyl]amino, $(C_{1-3})$alkoxy, $(C_{3-7})$cycloalkoxy, $(C_{6-10})$aryl, $(C_{1-5})$heteroaryl and $(C_{3-7})$heterocycloalkyl; with the proviso that:
0 to 2 atoms of X, Y, Z can simultaneously be a heteroatom;
when one atom selected from X, Y is O or S, then Z is a bond and the other atom selected from X, Y can not be O or S;
when Z is C or N then Y is $C(R_6)$ or N and X is C or N;
0 to 2 atoms of $B_1$, $B_2$, $B_3$ and $B_4$ are N;

with the terms used having the following meanings:

(C$_{1-2}$)alkyl means an alkyl group having 1 to 2 carbon atoms, being methyl or ethyl, (C$_{1-3}$)alkyl means a branched or unbranched alkyl group having 1-3 carbon atoms, being methyl, ethyl, propyl or isopropyl;

(C$_{1-4}$)alkyl means a branched or unbranched alkyl group having 1-4 carbon atoms, being methyl, ethyl, propyl, isopropyl, butyl, isobutyl, sec-butyl and tert-butyl, (C$_{1-3}$) alkyl groups being preferred;

(C$_{1-5}$)alkyl means a branched or unbranched alkyl group having 1-5 carbon atoms, for example methyl, ethyl, propyl, isopropyl, butyl, isobutyl, sec-butyl, tert-butyl, pentyl and isopentyl, (C$_{1-4}$)alkyl groups being preferred. (C$_{1-6}$)Alkyl means a branched or unbranched alkyl group having 1-6 carbon atoms, for example methyl, ethyl, propyl, isopropyl, butyl, tert-butyl, n-pentyl and n-hexyl. (C$_{1-5}$)alkyl groups are preferred, (C$_{1-4}$)alkyl being most preferred;

(C$_{1-2}$)alkoxy means an alkoxy group having 1-2 carbon atoms, the alkyl moiety having the same meaning as previously defined;

(C$_{1-3}$)alkoxy means an alkoxy group having 1-3 carbon atoms, the alkyl moiety having the same meaning as previously defined. (C$_{1-2}$)alkoxy groups are preferred;

(C$_{1-4}$)alkoxy means an alkoxy group having 1-4 carbon atoms, the alkyl moiety having the same meaning as previously defined. (C$_{1-3}$)alkoxy groups are preferred, (C$_{1-2}$)alkoxy groups being most preferred;

(C$_{2-4}$)alkenyl means a branched or unbranched alkenyl group having 2-4 carbon atoms, such as ethenyl, 2-propenyl, isobutenyl or 2-butenyl;

(C$_{2-6}$)alkenyl means a branched or unbranched alkenyl group having 2-6 carbon atoms, such as ethenyl, 2-butenyl, and n-pentenyl, (C$_{2-4}$)alkenyl groups being most preferred;

(C$_{2-4}$)alkynyl means a branched or unbranched alkynyl group having 2-4 carbon atoms, such as ethynyl, 2-propynyl or 2-butynyl;

(C$_{2-6}$)alkynyl means a branched or unbranched alkynyl group having 2-6 carbon atoms, such as ethynyl, propynyl, n-butynyl, n-pentynyl, isopentynyl, isohexynyl or n-hexynyl. (C$_{2-4}$)alkynyl groups are preferred; (C$_{3-6}$)cycloalkyl means a cycloalkyl group having 3-6 carbon atoms, being cyclopropyl, cyclobutyl, cyclopentyl or cyclohexyl;

(C$_{3-7}$)cycloalkyl means a cycloalkyl group having 3-7 carbon atoms, being cyclopropyl, cyclobutyl, cyclopentyl, cyclohexyl or cycloheptyl;

(C$_{2-6}$)heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; also preferred are piperidine, morpholine, pyrrolidine and piperazine; with the most preferred (C$_{2-6}$)heterocycloalkyl being pyrrolidine; the heterocycloalkyl group may be attached via a heteroatom if feasible;

(C$_{3-7}$)heterocycloalkyl means a heterocycloalkyl group having 3-7 carbon atoms, preferably 3-5 carbon atoms, and one or two heteroatoms selected from N, O and/or S. Preferred heteroatoms are N or O; preferred (C$_{3-7}$) heterocycloalkyl groups are azetidinyl, pyrrolidinyl, piperidinyl, homopiperidinyl or morpholinyl; more preferred (C$_{3-7}$)heterocycloalkyl groups are piperidine, morpholine and pyrrolidine; and the heterocycloalkyl group may be attached via a heteroatom if feasible;

(C$_{3-7}$)cycloalkoxy means a cycloalkyl group having 3-7 carbon atoms, with the same meaning as previously defined, attached via a ring carbon atom to an exocyclic oxygen atom;

(C$_{6-10}$)aryl means an aromatic hydrocarbon group having 6-10 carbon atoms, such as phenyl, naphthyl, tetrahydronaphthyl or indenyl; the preferred (C$_{6-10}$)aryl group is phenyl;

(C$_{1-5}$)heteroaryl means a substituted or unsubstituted aromatic group having 1-5 carbon atoms and 1-4 heteroatoms selected from N, O and/or S; the (C$_{1-5}$)heteroaryl may optionally be substituted; preferred (C$_{1-5}$)heteroaryl groups are tetrazolyl, imidazolyl, thiadiazolyl, pyridyl, pyrimidyl, triazinyl, thienyl or furyl, a more preferred (C$_{1-5}$)heteroaryl is pyrimidyl;

(C$_{1-9}$)heteroaryl means a substituted or unsubstituted aromatic group having 1-9 carbon atoms and 1-4 heteroatoms selected from N, O and/or S; the (C$_{1-9}$)heteroaryl may optionally be substituted; preferred (C$_{1-9}$)heteroaryl groups are quinoline, isoquinoline and indole;

[(C$_{1-4}$)alkyl]amino means an amino group, monosubstituted with an alkyl group containing 1-4 carbon atoms having the same meaning as previously defined; preferred [(C$_{1-4}$)alkyl]amino group is methylamino;

di[(C$_{1-4}$)alkyl]amino means an amino group, disubstituted with alkyl group(s), each containing 1-4 carbon atoms and having the same meaning as previously defined; preferred di[(C$_{1-4}$)alkyl]amino group is dimethylamino;

halogen means fluorine, chlorine, bromine or iodine;

(C$_{1-3}$)alkyl-C(O)—S—(C$_{1-3}$)alkyl means an alkyl-carbonyl-thio-alkyl group, each of the alkyl groups having 1 to 3 carbon atoms with the same meaning as previously defined;

(C$_{3-7}$)cycloalkenyl means a cycloalkenyl group having 3-7 carbon atoms, preferably 5-7 carbon atoms; preferred (C$_{3-7}$)cycloalkenyl groups are cyclopentenyl or cyclohexenyl; cyclohexenyl groups are most preferred;

(C$_{2-6}$)heterocycloalkenyl means a heterocycloalkenyl group having 2-6 carbon atoms, preferably 3-5 carbon atoms; and 1 heteroatom selected from N, O and/or S; preferred (C$_{2-6}$)heterocycloalkenyl groups are oxycyclohexenyl and azacyclohexenyl group.

In the above definitions with multifunctional groups, the attachment point is at the last group.

When, in the definition of a substituent, it is indicated that "all of the alkyl groups" of said substituent are optionally substituted, this also includes the alkyl moiety of an alkoxy group.

A circle in a ring of Formula (XVII) indicates that the ring is aromatic.

Depending on the ring formed, the nitrogen, if present in X or Y, may carry a hydrogen.

In a preferred embodiment, the BTK inhibitor is a compound of Formula (XVII) or a pharmaceutically acceptable salt thereof, wherein:

X is CH or S;
Y is C(R$_6$);
Z is CH or bond;
A is CH;
B$_1$ is N or C(R$_7$);
B$_2$ is N or C(R$_8$);
B$_3$ is N or CH;
B$_4$ is N or CH;
R$_1$ is R$_{11}$C(=O),
R$_2$ is (C$_{1-3}$)alkyl;
R$_3$ is (C$_{1-3}$)alkyl; or R$_2$ and R$_3$ form, together with the N and C atom they are attached to, a (C$_{3-7}$)heterocycloalkyl ring selected from the group consisting of azetidinyl, pyrrolidinyl, piperidinyl, and morpholinyl, optionally substituted with one or more fluorine, hydroxyl, (C$_{1-3}$)alkyl, or (C$_{1-3}$)alkoxy;

R$_4$ is H;

R$_5$ is H, halogen, cyano, (C$_{1-4}$)alkyl, (C$_{1-3}$)alkoxy, (C$_{3-6}$)cycloalkyl, or an alkyl group which is optionally substituted with one or more halogen;

R$_6$ is H or (C$_{1-3}$)alkyl;

R$_7$ is H, halogen or (C$_{1-3}$)alkoxy;

R$_8$ is H or (C$_{1-3}$)alkyl; or

R$_7$ and R$_8$ form, together with the carbon atom they are attached to a (C$_{6-10}$)aryl or (C$_{1-9}$)heteroaryl;

R$_5$ and R$_6$ together may form a (C$_{3-7}$)cycloalkenyl or (C$_{2-6}$)heterocycloalkenyl, each optionally substituted with (C$_{1-3}$)alkyl or one or more halogen;

R$_{11}$ is independently selected from the group consisting of (C$_{2-6}$)alkenyl and (C$_{2-6}$)alkynyl, where each alkenyl or alkynyl is optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl;

with the proviso that 0 to 2 atoms of B$_1$, B$_2$, B$_3$ and B$_4$ are N.

In an embodiment of Formula (XVII), B$_1$ is C(R$_7$); B$_2$ is C(R$_8$); B$_3$ is C(R$_9$); B$_4$ is C(R$_{10}$); R$_7$, R$_9$, and R$_{10}$ are each H; and R$_8$ is hydrogen or methyl.

In an embodiment of Formula (XVII), the ring containing X, Y and Z is selected from the group consisting of pyridyl, pyrimidyl, pyridazyl, triazinyl, thiazolyl, oxazolyl and isoxazolyl.

In an embodiment of Formula (XVII), the ring containing X, Y and Z is selected from the group consisting of pyridyl, pyrimidyl and pyridazyl.

In an embodiment of Formula (XVII), the ring containing X, Y and Z is selected from the group consisting of pyridyl and pyrimidyl.

In an embodiment of Formula (XVII), the ring containing X, Y and Z is pyridyl.

In an embodiment of Formula (XVII), R$_5$ is selected from the group consisting of hydrogen, fluorine, methyl, methoxy and trifluoromethyl.

In an embodiment of Formula (XVII), R$_5$ is hydrogen.

In an embodiment of Formula (XVII), R$_2$ and R$_3$ together form a heterocycloalkyl ring selected from the group consisting of azetidinyl, pyrrolidinyl, piperidinyl, homopiperidinyl and morpholinyl, optionally substituted with one or more of fluoro, hydroxyl, (C$_{1-3}$)alkyl and (C$_{1-3}$)alkoxy.

In an embodiment of Formula (XVII), R$_2$ and R$_3$ together form a heterocycloalkyl ring selected from the group consisting of azetidinyl, pyrrolidinyl and piperidinyl.

In an embodiment of Formula (XVII), R$_2$ and R$_3$ together form a pyrrolidinyl ring.

In an embodiment of Formula (XVII), R$_1$ is independently selected from the group consisting of (C$_{1-6}$)alkyl, (C$_{2-6}$)alkenyl or (C$_{2-6}$)alkynyl, each optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl] amino, (C$_{1-3}$)alkoxy, (C$_{3-7}$)cycloalkoxy, (C$_{6-10}$)aryl and (C$_{3-7}$)heterocycloalkyl.

In an embodiment of Formula (XVII), B$_1$, B$_2$, B$_3$ and B$_4$ are CH; X is N; Y and Z are CH; R$_5$ is CH$_3$; A is N; R$_2$, R$_3$ and R$_4$ are H; and R$_1$ is CO—CH$_3$.

In an embodiment of Formula (XVII), B$_1$, B$_2$, B$_3$ and B$_4$ are CH; X and Y are N; Z is CH; R$_5$ is CH$_3$; A is N; R$_2$, R$_3$ and R$_4$ are H; and R$_1$ is CO—CH$_3$.

In an embodiment of Formula (XVII), B$_1$, B$_2$, B$_3$ and B$_4$ are CH; X and Y are N; Z is CH; R$_5$ is CH$_3$; A is CH; R$_2$ and R$_3$ together form a piperidinyl ring; R$_4$ is H; and R$_1$ is CO-ethenyl.

In an embodiment of Formula (XVII), B$_1$, B$_2$, B$_3$ and B$_4$ are CH; X, Y and Z are CH; R$_5$ is H; A is CH; R$_2$ and R$_3$ together form a pyrrolidinyl ring; R$_4$ is H; and R$_1$ is CO-propynyl.

In an embodiment of Formula (XVII), B$_1$, B$_2$, B$_3$ and B$_4$ are CH; X, Y and Z are CH; R$_5$ is CH$_3$; A is CH; R$_2$ and R$_3$ together form a piperidinyl ring; R$_4$ is H; and R$_1$ is CO-propynyl.

In an embodiment of Formula (XVII), B$_1$, B$_2$, B$_3$ and B$_4$ are CH; X and Y are N; Z is CH; R$_5$ is H; A is CH; R$_2$ and R$_3$ together form a morpholinyl ring; R$_4$ is H; and R$_1$ is CO-ethenyl.

In an embodiment of Formula (XVII), B$_1$, B$_2$, B$_3$ and B$_4$ are CH; X and Y are N; Z is CH; R$_5$ is CH$_3$; A is CH; R$_2$ and R$_3$ together form a morpholinyl ring; R$_4$ is H; and R$_1$ is CO-propynyl.

In a preferred embodiment, the BTK inhibitor is a compound of Formula (XVIII):

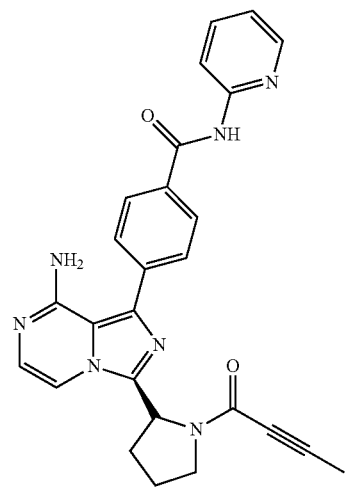

Formula (XVIII)

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In a preferred embodiment, the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or pharmaceutically acceptable salt, solvate, hydrate, cocrystal, or prodrug therof.

In a preferred embodiment, the BTK inhibitor is a compound of Formula (XVIII-A):

Formula (XVIII-A)

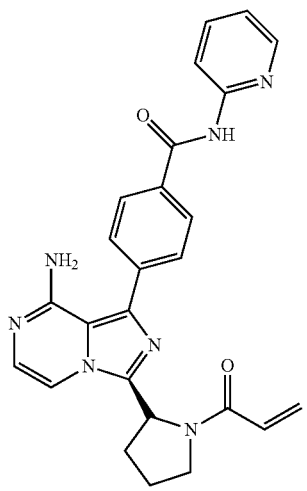

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In a preferred embodiment, the BTK inhibitor is a compound of Formula (XVIII-B):

Formula (XVIII-B)

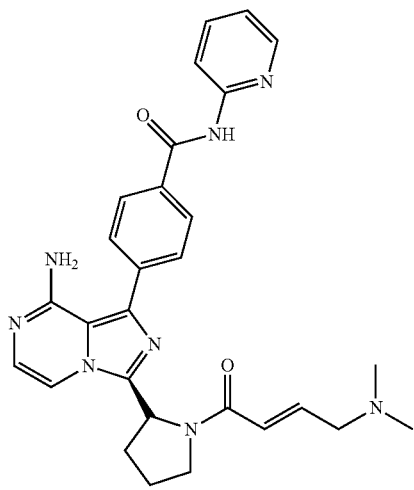

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In a preferred embodiment, the BTK inhibitor is a compound of Formula (XVIII-C):

Formula (XVIII-C)

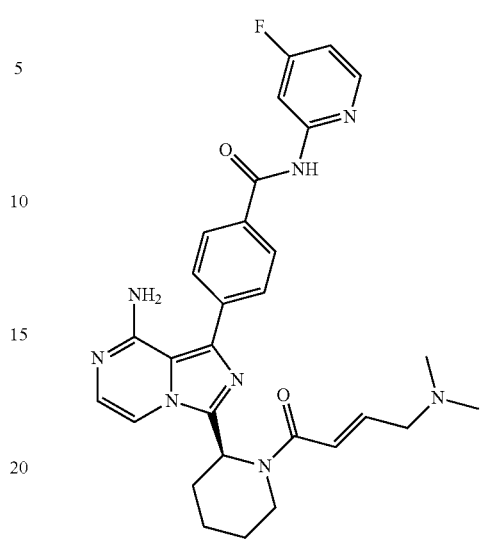

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In a preferred embodiment, the BTK inhibitor is a compound of Formula (XVIII-D):

Formula (XVIII-D)

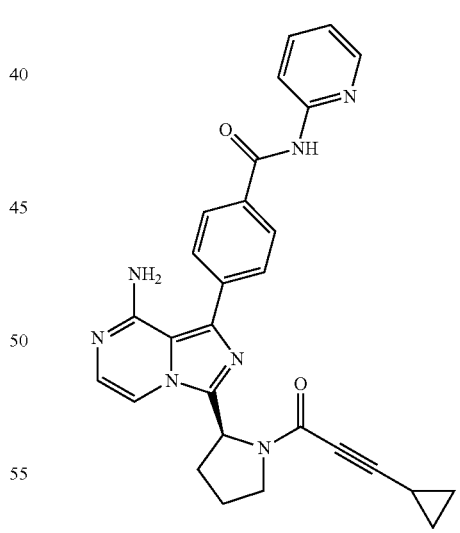

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In a preferred embodiment, the BTK inhibitor is a compound of Formula (XVIII-E):

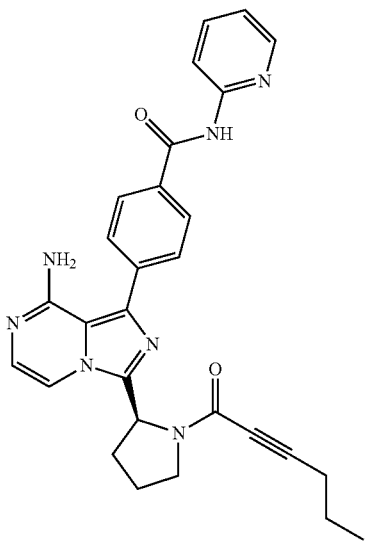

Formula (XVIII-E)

or a pharmaceutically acceptable salt, solvate, hydrate, cocrystal, or prodrug thereof. The preparation of this compound is described in International Patent Application Publication No. WO 2013/010868, the disclosure of which is incorporated herein by reference.

In other embodiments, the BTK inhibitors include, but are not limited to, those compounds described in International Patent Application Publication No. WO 2013/010868, the disclosures of each of which are specifically incorporated by reference herein.

In an embodiment, the BTK inhibitor is a compound of Formula (XIX) or a pharmaceutically acceptable salt, solvate, hydrate, cocrystal, or prodrug of a compound of Formula (XIX):

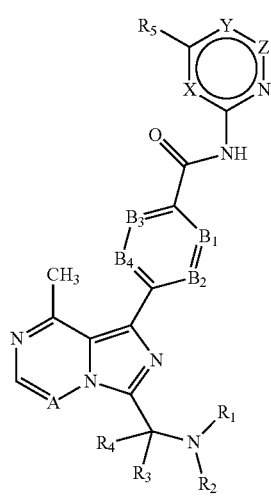

Formula (XIX)

In Formula (XIX) the substituents are defined as
X is CH, N, O or S;
Y is C($R_6$), N, O or S;
Z is CH, N or bond;
A is CH or N;
$B_1$ is N or C($R_7$);
$B_2$ is N or C($R_8$);
$B_3$ is N or C($R_9$);
$B_4$ is N or C($R_{10}$);
$R_1$ is $R_{11}$C(O), $R_{12}$S(O), $R_{13}$SO$_2$ or ($C_{1-6}$)alkyl optionally substituted with $R_{14}$;
$R_2$ is H, ($C_{1-3}$)alkyl or ($C_{3-7}$)cycloalkyl;
$R_3$ is H, ($C_{1-6}$)alkyl or ($C_{3-7}$)cycloalkyl); or
$R_2$ and $R_3$ form, together with the N and C atom they are attached to, a ($C_{3-7}$)heterocycloalkyl optionally substituted with one or more fluorine, hydroxyl, ($C_{1-3}$)alkyl, ($C_{1-3}$)alkoxy or oxo;
$R_4$ is H or ($C_{1-3}$)alkyl;
$R_5$ is H, halogen, cyano, ($C_{1-4}$)alkyl, ($C_{1-3}$)alkoxy, ($C_{3-6}$)cycloalkyl; all alkyl groups of R5 are optionally substituted with one or more halogen; or $R_5$ is ($C_{6-10}$)aryl or ($C_{2-6}$)heterocycloalkyl;
$R_6$ is H or ($C_{1-3}$)alkyl; or $R_5$ and $R_6$ together may form a ($C_{3-7}$)cycloalkenyl, or ($C_{2-6}$)heterocycloalkenyl; each optionally substituted with ($C_{1-3}$)alkyl, or one or more halogen;
$R_7$ is H, halogen, CF$_3$, ($C_{1-3}$)alkyl or ($C_{1-3}$)alkoxy;
$R_8$ is H, halogen, CF$_3$, ($C_{1-3}$)alkyl or ($C_{1-3}$)alkoxy; or
$R_7$ and $R_8$ together with the carbon atoms they are attached to, form ($C_{6-10}$)aryl or ($C_{1-5}$)heteroaryl;
$R_9$ is H, halogen, ($C_{1-3}$)alkyl or ($C_{1-3}$)alkoxy;
$R_{10}$ is H, halogen, ($C_{1-3}$)alkyl or ($C_{1-3}$)alkoxy;
$R_{11}$ is independently selected from a group consisting of ($C_{1-6}$)alkyl, ($C_{2-6}$)alkenyl and ($C_{2-6}$)alkynyl each alkyl, alkenyl or alkynyl optionally substituted with one or more groups selected from hydroxyl, ($C_{1-4}$)alkyl, ($C_{3-7}$)cycloalkyl, [($C_{1-4}$)alkyl]amino, di[($C_{1-4}$)alkyl]amino, ($C_{1-3}$)alkoxy, ($C_{3-7}$)cycloalkoxy, ($C_{6-10}$)aryl or ($C_{3-7}$)heterocycloalkyl, or
$R_{11}$ is ($C_{1-3}$)alkyl-C(O)—S—($C_{1-3}$)alkyl; or
$R_{11}$ is ($C_{1-5}$)heteroaryl optionally substituted with one or more groups selected from halogen or cyano.
$R_{12}$ and $R_{13}$ are independently selected from a group consisting of ($C_{2-6}$)alkenyl or ($C_{2-6}$)alkynyl both optionally substituted with one or more groups selected from hydroxyl, ($C_{1-4}$)alkyl, ($C_{3-7}$)cycloalkyl, [($C_{1-4}$)alkyl]amino, di[($C_{1-4}$)alkyl]amino, ($C_{1-3}$)alkoxy, ($C_{3-7}$)cycloalkoxy, ($C_{6-10}$)aryl, or ($C_{3-7}$)heterocycloalkyl; or
($C_{1-5}$)heteroaryl optionally substituted with one or more groups selected from halogen or cyano;
$R_{14}$ is independently selected from a group consisting of halogen, cyano or ($C_{2-6}$)alkenyl or ($C_{2-6}$)alkynyl both optionally substituted with one or more groups selected from hydroxyl, ($C_{1-4}$)alkyl, ($C_{3-7}$)cycloalkyl, [($C_{1-4}$)alkyl]amino, di[($C_{1-4}$)alkyl]amino, ($C_{1-3}$)alkoxy, ($C_{3-7}$)cycloalkoxy, ($C_{6-10}$)aryl, ($C_{1-5}$)heteroaryl or ($C_{3-7}$)heterocycloalkyl;
with the proviso that
0 to 2 atoms of X, Y, Z can simultaneously be a heteroatom;
when one atom selected from X, Y is O or S, then Z is a bond and the other atom selected from X, Y can not be O or S;
when Z is C or N then Y is C($R_6$) or N and X is C or N;
0 to 2 atoms of $B_1$, $B_2$, $B_3$ and $B_4$ are N;
with the terms used having the following meanings:
($C_{1-3}$)alkyl means a branched or unbranched alkyl group having 1-3 carbon atoms, being methyl, ethyl, propyl or isopropyl;
($C_{1-4}$)alkyl means a branched or unbranched alkyl group having 1-4 carbon atoms, being methyl, ethyl, propyl, isopropyl, butyl, isobutyl, sec-butyl and tert-butyl, ($C_{1-3}$)alkyl groups being preferred;

($C_{1-6}$)alkyl means a branched or unbranched alkyl group having 1-6 carbon atoms, for example methyl, ethyl, propyl, isopropyl, butyl, tert-butyl, n-pentyl and n-hexyl. ($C_{1-5}$)alkyl groups are preferred, ($C_{1-4}$)alkyl being most preferred;

($C_{1-2}$)alkoxy means an alkoxy group having 1-2 carbon atoms, the alkyl moiety having the same meaning as previously defined;

($C_{1-3}$)alkoxy means an alkoxy group having 1-3 carbon atoms, the alkyl moiety having the same meaning as previously defined, with ($C_{1-2}$)alkoxy groups preferred;

($C_{2-3}$)alkenyl means an alkenyl group having 2-3 carbon atoms, such as ethenyl or 2-propenyl;

($C_{2-4}$)alkenyl means a branched or unbranched alkenyl group having 2-4 carbon atoms, such as ethenyl, 2-propenyl, isobutenyl or 2-butenyl;

($C_{2-6}$)alkenyl means a branched or unbranched alkenyl group having 2-6 carbon atoms, such as ethenyl, 2-butenyl, and n-pentenyl, with ($C_{2-4}$)alkenyl groups preferred, and ($C_{2-3}$)alkenyl groups even more preferred;

($C_{2-4}$)alkynyl means a branched or unbranched alkynyl group having 2-4 carbon atoms, such as ethynyl, 2-propynyl or 2-butynyl;

($C_{2-3}$)alkynyl means an alkynyl group having 2-3 carbon atoms, such as ethynyl or 2-propynyl;

($C_{2-6}$)alkynyl means a branched or unbranched alkynyl group having 2-6 carbon atoms, such as ethynyl, propynyl, n-butynyl, n-pentynyl, isopentynyl, isohexynyl or n-hexynyl, with ($C_{2-4}$)alkynyl groups preferred, and ($C_{2-3}$)alkynyl groups more preferred;

($C_{3-6}$)cycloalkyl means a cycloalkyl group having 3-6 carbon atoms, being cyclopropyl, cyclobutyl, cyclopentyl or cyclohexyl;

($C_{3-7}$)cycloalkyl means a cycloalkyl group having 3-7 carbon atoms, being cyclopropyl, cyclobutyl, cyclopentyl, cyclohexyl or cycloheptyl;

($C_{2-6}$)heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; preferred groups are piperidine, morpholine, pyrrolidine and piperazine; a most preferred ($C_{2-6}$)heterocycloalkyl is pyrrolidine; and the heterocycloalkyl group may be attached via a heteroatom if feasible;

($C_{3-7}$)heterocycloalkyl means a heterocycloalkyl group having 3-7 carbon atoms, preferably 3-5 carbon atoms, and one or two heteroatoms selected from N, O and/or S; preferred heteroatoms are N or O; preferred ($C_{3-7}$) heterocycloalkyl groups are azetidinyl, pyrrolidinyl, piperidinyl, homopiperidinyl or morpholinyl; more preferred ($C_{3-7}$)heterocycloalkyl groups are piperidine, morpholine and pyrrolidine; even more preferred are piperidine and pyrrolodine; and the heterocycloalkyl group may be attached via a heteroatom if feasible;

($C_{3-7}$)cycloalkoxy means a cycloalkyl group having 3-7 carbon atoms, with the same meaning as previously defined, attached via a ring carbon atom to an exocyclic oxygen atom;

($C_{6-10}$)aryl means an aromatic hydrocarbon group having 6-10 carbon atoms, such as phenyl, naphthyl, tetrahydronaphthyl or indenyl; the preferred ($C_{6-10}$)aryl group is phenyl;

($C_{1-5}$)heteroaryl means a substituted or unsubstituted aromatic group having 1-5 carbon atoms and 1-4 heteroatoms selected from N, O and/or S, wherein the ($C_{1-5}$)heteroaryl may optionally be substituted; preferred ($C_{1-5}$)heteroaryl groups are tetrazolyl, imidazolyl, thiadiazolyl, pyridyl, pyrimidyl, triazinyl, thienyl or furyl, and the more preferred ($C_{1-5}$)heteroaryl is pyrimidyl;

[($C_{1-4}$)alkyl]amino means an amino group, monosubstituted with an alkyl group containing 1-4 carbon atoms having the same meaning as previously defined; the preferred [($C_{1-4}$)alkyl]amino group is methylamino;

di[($C_{1-4}$)alkyl]amino means an amino group, disubstituted with alkyl group(s), each containing 1-4 carbon atoms and having the same meaning as previously defined; the preferred di[($C_{1-4}$)alkyl]amino group is dimethylamino;

halogen means fluorine, chlorine, bromine or iodine;

($C_{1-3}$)alkyl-C(O)—S—($C_{1-3}$)alkyl means an alkyl-carbonyl-thio-alkyl group, each of the alkyl groups having 1 to 3 carbon atoms with the same meaning as previously defined;

($C_{3-7}$)cycloalkenyl means a cycloalkenyl group having 3-7 carbon atoms, preferably 5-7 carbon atoms; preferred ($C_{3-7}$)cycloalkenyl groups are cyclopentenyl or cyclohexenyl; and cyclohexenyl groups are most preferred;

($C_{2-6}$)heterocycloalkenyl means a heterocycloalkenyl group having 2-6 carbon atoms, preferably 3-5 carbon atoms; and 1 heteroatom selected from N, O and/or S; the preferred ($C_{2-6}$)heterocycloalkenyl groups are oxycyclohexenyl and azacyclohexenyl groups.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

A circle in a ring of Formula (XIX) indicates that the ring is aromatic.

Depending on the ring formed, the nitrogen, if present in X or Y, may carry a hydrogen.

In a preferred embodiment, the invention relates to a compound according to Formula (XIX) wherein $B_1$ is $C(R_7)$; $B_2$ is $C(R_8)$; $B_3$ is $C(R_9)$ and $B_4$ is $C(R_{10})$.

In other embodiments, the BTK inhibitors include, but are not limited to, those compounds described in International Patent Application Publication No. WO 2013/010869, the disclosures of each of which are specifically incorporated by reference herein.

In an embodiment, the BTK inhibitor is a compound of Formula (XX):

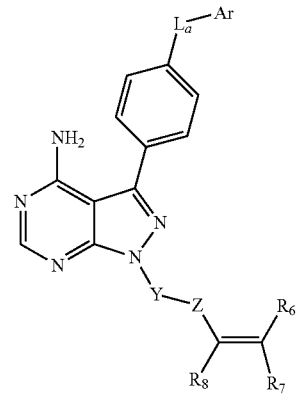

Formula (XX)

or a pharmaceutically acceptable salt, solvate, hydrate, cocrystal, or prodrug thereof, wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O)$_x$, where x is 1 or 2;

$R^7$ and $R^8$ are each independently H; or $R^7$ and $R^8$ taken together form a bond;

$R^6$ is H; and

R is H or $(C_{1-6})$alkyl.

In an embodiment, the BTK inhibitor is ibrutinib or a pharmaceutically acceptable salt, solvate, hydrate, cocrystal, or prodrug thereof. In an exemplary embodiment, the BTK inhibitor is (R)-1-(3-(4-amino-3-(4-phenoxyphenyl)-1H-pyrazolo[3,4-d]pyrimidin-1-yl)piperidin-1-yl)prop-2-en-1-one. In an exemplary embodiment, the BTK inhibitor is 1-[(3R)-3-[4-amino-3-(4-phenoxyphenyl)-1H-pyrazolo[3,4-d]pyrimidin-1-yl]piperidin-1-yl]prop-2-en-1-one. In an exemplary embodiment, the BTK inhibitor is (S)-1-(3-(4-amino-3-(4-phenoxyphenyl)-1H-pyrazolo[3,4-d]pyrimidin-1-yl)piperidin-1-yl)prop-2-en-1-one. In an exemplary embodiment, the BTK inhibitor has the structure of Formula (XX-A), or an enantiomer thereof, or a pharmaceutically acceptable salt, solvate, hydrate, cocrystal, or prodrug thereof.

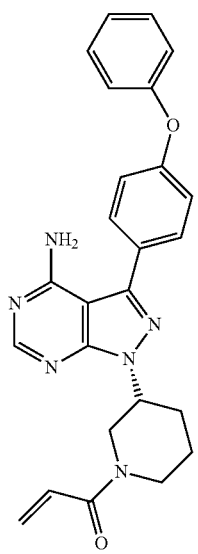

Formula (XX-A)

In an exemplary embodiment, the BTK inhibitor is a compound of Formula (XXI):

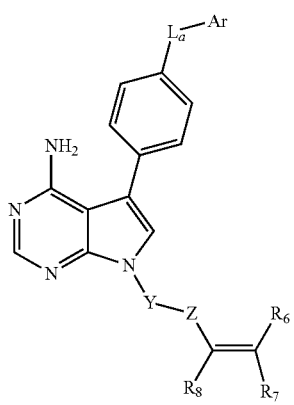

Formula (XXI)

or a pharmaceutically acceptable salt, solvate, hydrate, cocrystal, or prodrug thereof, wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O)$_x$, where x is 1 or 2;

$R^7$ and $R^8$ are each H; or $R^7$ and $R^8$ taken together form a bond;

$R^6$ is H, and

R is H or $(C_{1-6})$alkyl.

In an embodiment, the BTK inhibitor is a compound of Formula (XXII):

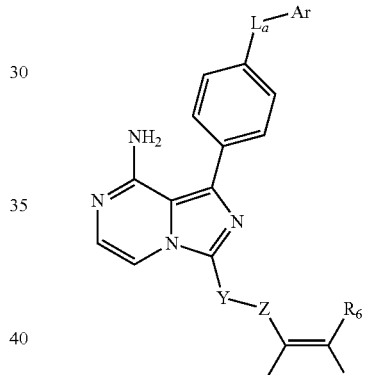

Formula (XXII)

or a pharmaceutically acceptable salt, solvate, hydrate, cocrystal, or prodrug thereof, wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O)$_x$, where x is 1 or 2;

$R^7$ and $R^8$ are each H; or $R^7$ and $R^8$ taken together form a bond;

$R^6$ is H; and

R is H or $(C_{1-6})$alkyl.

In an embodiment, the BTK inhibitor is a compound of Formula (XXIII):

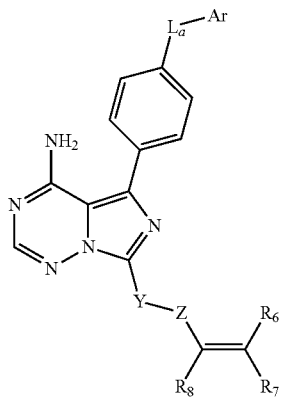

Formula (XXIII)

or a pharmaceutically acceptable salt, solvate, hydrate, cocrystal, or prodrug thereof, wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O)$_x$, where x is 1 or 2;

$R^7$ and $R^8$ are each H; or $R^7$ and $R^8$ taken together form a bond;

$R^6$ is H; and

R is H or ($C_{1-6}$)alkyl.

In an embodiment, the BTK inhibitor is a compound disclosed in U.S. Pat. No. 7,459,554, the disclosure of which is specifically incorporated herein by reference. In an embodiment, the BTK inhibitor is a compound of Formula (XXIV):

Formula (XXIV)

or a pharmaceutically acceptable salt, solvate, hydrate, cocrystal, or prodrug thereof, wherein:

$Q^1$ is aryl$^1$, heteroaryl$^1$, cycloalkyl, heterocyclyl, cycloalkenyl, or heterocycloalkenyl, any of which is optionally substituted by one to five independent $G^1$ substituents;

$R^1$ is alkyl, cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents;

$G^1$ and $G^{41}$ are each independently halo, oxo, —$CF_3$, —$OCF_3$, —$OR^2$, —$NR^2R^3(R^{3a})_{j1}$, —C(O)$R^2$, —$CO_2R^2$, —$CONR^2R^3$, —$NO_2$, —CN, —S(O)$_{j1}R^2$, —$SO_2NR^2R^3$, $NR^2(C=O)R^3$, $NR^2(C=O)OR^3$, $NR^2(C=O)NR^2R^3$, $NR^2S(O)_{j1}R^3$, —(C=S)O$R^2$, —(C=O)S$R^2$, —$NR^2(C=NR^3)NR^{2a}R^{3a}$, —$NR^2(C=NR^3)OR^{2a}$, —$NR^2(C=NR^3)SR^{3a}$, —O(C=O)O$R^2$, —O(C=O)NR$^2R^3$, —O(C=O)SR$^2$, —S(C=O)OR$^2$, —S(C=O)NR$^2R^3$, ($C_{0-10}$)alkyl, ($C_{2-10}$)alkenyl, ($C_{2-10}$)alkynyl, ($C_{1-10}$) alkoxy($C_{1-10}$)alkyl, ($C_{1-10}$)alkoxy($C_{2-10}$)alkenyl, ($C_{1-10}$) alkoxy($C_{2-10}$)alkynyl, ($C_{1-10}$)alkylthio($C_{1-10}$) alkyl, ($C_{1-10}$)alkylthio($C_{2-10}$)alkenyl, ($C_{1-10}$)alkylthio($C_{2-10}$) alkynyl, cyclo($C_{3-8}$)alkyl, cyclo($C_{3-8}$)alkenyl, cyclo($C_{3-8}$) alkyl($C_{1-10}$)alkyl, cyclo($C_{3-8}$)alkenyl($C_{1-10}$)alkyl, cyclo ($C_{3-8}$) alkyl($C_{2-10}$)alkenyl, cyclo($C_{3-8}$)alkenyl($C_{2-10}$) alkenyl, cyclo($C_{3-8}$)alkyl($C_{2-10}$)alkynyl, cyclo($C_{3-8}$) alkenyl($C_{2-10}$)alkynyl, heterocyclyl-($C_{0-10}$)alkyl, heterocyclyl-($C_{2-10}$)alkenyl, or heterocyclyl-($C_{2-10}$)alkynyl, any of which is optionally substituted with one or more independent halo, oxo, —$CF_3$, —$OCF_3$, —$OR^{222}$, —$NR^{222}R^{333}(R^{333}a)_{j1a}$, —C(O)$R^{222}$, —$CO_2R^{222}$, —$CONR^{222}R^{333}$, —$NO_2$, —CN, —S(O)$_{j1a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, —(C=S)O$R^{222}$, —(C=O)SR$^{222}$, —$NR^{222}(C=NR^{333})NR^{222a}R^{333a}$, —$NR^{222}(C=NR^{333})OR^{222a}$, —$NR^{222}(C=NR^{333})SR^{333a}$, —O(C=O)O$R^{222}$, —O(C=O)NR$^{222}R^{333}$, —O(C=O)SR$^{222}$, —S(C=O)OR$^{222}$, or —S(C=O)NR$^{222}R^{333}$ substituents; or —(X$^1$)$_n$—(Y$^1$)$_m$— $R^4$; or aryl-($C_{0-10}$)alkyl, aryl-($C_{2-10}$)alkenyl, or aryl-($C_{2-10}$) alkynyl, any of which is optionally substituted with one or more independent halo, —$CF_3$, —$OCF_3$, —$OR^{222}$, —$NR^{222}R^{333}(R^{333a})_{j2a}$, —C(O)$R^{222}$, —$CO_2R^{222}$, —$CONR^{222}R^{333}$, —$NO_2$, —CN, —S(O)$_{j2a}$ $R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j2a}R^{333}$, —(C=S)O$R^{222}$, —(C=O)SR$^{222}$, —$NR^{222}(C=NR^{333})NR^{222a}R^{333a}$, —$NR^{222}(C=NR^{333})OR^{222a}$, —$NR^{222}(C=NR^{333})SR^{333a}$, —O(C=O)O$R^{222}$, —O(C=O)NR$^{222}R^{333}$, —O(C=O)SR$^{222}$, —S(C=O) OR$^{222}$, or —S(C=O)NR$^{222}R^{333}$ substituents; or hetaryl-($C_{0-10}$)alkyl, hetaryl-($C_{2-10}$)alkenyl, or hetaryl-($C_{2-10}$) alkynyl, any of which is optionally substituted with one or more independent halo, —$CF_3$, —$OCF_3$, —$OR^{222}$, —$NR^{222}$, $R^{333}(R^{333a})_{j3a}$, —C(O)$R^{222}$, —$CO_2R^{222}$, —$CONR^{222}R^{333}$, —$NO_2$, —CN, —S(O)$_{j3a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j3a}R^{333}$, —(C=S)O$R^{222}$, —(C=O)SR$^{222}$, —$NR^{222}(C=NR^{333})$ $N^{222}aR^{333}a$, —$NR^{222}(C=NR^{333})OR^{222a}$, —$NR^{222}(C=NR^{333})SR^{333}a$, —O(C=O)O$R^{222}$, —O(C=O)NR$^{222}R^{333}$, —O(C=O)SR$^{222}$, —S(C=O)OR$^{222}$, or —S(C=O)NR$^{222}R^{333}$ substituents;

$G^{11}$ is halo, oxo, —$CF_3$, —$OCF_3$, —$OR^{21}$, —$NR^{21}R^{31}$ $(R^{3a1})_{j4}$, —C(O)$R^{21}$, —$CO_2R^{21}$, —$CONR^{21}R^{31}$, —$NO_2$, —CN, —S(O)$_{j4}R^{21}$, —$SO_2NR^{21}R^{31}$, $NR^{21}(C=O)R^{31}$, $NR^{21}(C=O)OR^{31}$, $N^{21}(C=O)NR^{21}R^{31}$, $NR^{21}S(O)_{j4}R^{31}$, —(C=S)O$R^{21}$, —(C=O)SR$^{21}$, —$NR^{21}(C=NR^{31})NR^{2a1}R^{3a1}$, —$NR^{21}(C=NR^{31})OR^{2a1}$, —$NR^{21}(C=NR^{31})SR^{3a1}$, —O(C=O)OR$^{21}$, —O(C=O)NR$^{21}R^{31}$, —O(C=O)SR$^{21}$, —S(C=O)OR$^{21}$, —S(C=O)NR$^{21}R^{31}$, —P(O)OR$^{21}$OR$^{31}$, ($C_{0-10}$)alkyl, ($C_{2-10}$)alkenyl, ($C_{2-10}$)alkynyl, ($C_{1-10}$) alkoxy($C_{1-10}$) alkyl, ($C_{1-10}$)alkoxy($C_{2-10}$)alkenyl, ($C_{1-10}$)alkoxy($C_{2-10}$) alkynyl, ($C_{1-10}$) alkylthio($C_{1-10}$)alkyl, ($C_{1-10}$)alkylthio ($C_{2-10}$)alkenyl, ($C_{1-10}$)alkylthio($C_{2-10}$)alkynyl, cyclo ($C_{3-8}$)alkyl, cyclo($C_{3-8}$)alkenyl, cyclo($C_{3-8}$)alkyl($C_{1-10}$) alkyl, cyclo($C_{3-8}$)alkenyl($C_{1-10}$) alkyl, cyclo($C_{3-8}$)alkyl ($C_{2-10}$)alkenyl, cyclo($C_{3-8}$)alkenyl($C_{2-10}$)alkenyl, cyclo ($C_{3-8}$) alkyl($C_{2-10}$) alkynyl, cyclo($C_{3-8}$)alkenyl($C_{2-10}$) alkynyl, heterocyclyl-($C_{0-10}$)alkyl, heterocyclyl-($C_{2-10}$) alkenyl, or heterocyclyl-($C_{2-10}$)alkynyl, any of which is optionally substituted with one or more independent halo, oxo, —$CF_3$, —$OCF_3$, —$OR^{2221}$, —$N^{2221}R^{3331}$ $(R^{333a1})_{j4a}$, —C(O)$R^{2221}$, —$CO_2R^{2221}$, —$CONR^{2221}R^{3331}$, —$NO_2$, —CN, —S(O)$_{j4a}R^{2221}$, —$SO_2NR^{2221}R^{3331}$, $NR^{2221}(C=O)R^{3331}$, $NR^{2221}(C=O)$ OR$^{3331}$, —NR$^{2221}$(C=O)NR$^{2221}$R$^{3331}$, —NR$^{2221}$S(O)$_{j4a}$ R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$) OR$^{222a1}$, —NR$^{2221}$(C=NR$^{3331}$)SR$^{333a1}$, —O(C=O) OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O) NR$^{2221}$R$^{3331}$ substituents; or aryl-(C$_{0-10}$)alkyl, aryl-(C$_{2-10}$)alkenyl, or aryl-(C$_{2-10}$)alkynyl, any of which is optionally substituted with one or more independent halo, —CF$_3$, —OCF$_3$, —OR$^{2221}$, —N$^{2221}$R$^{3331}$(R$^{333a1}$)$_{j5a}$, —C(O)R$^{2221}$, —CO$_2$R$^{2221}$, —CONR$^{2221}$R$^{3331}$, —NO$_2$, —CN, —S(O)$_{j5a}$R$^{2221}$, —SO$_2$NR$^{2221}$R$^{3331}$, —NR$^{2221}$(C=O)R$^{3331}$, NR$^{2221}$(C=O)OR$^{3331}$, —NR$^{2221}$(C=O) NR$^{2221}$R$^{3331}$, NR$^{2221}$S(O)$_{j5a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O) OR$^{2221}$R$^{3331}$, or —S(C=O)NR$^{2221}$R$^{3331}$ substituents; or hetaryl-(C$_{0-10}$) alkyl, hetaryl-(C$_{2-10}$)alkenyl, or hetaryl-(C$_{2-10}$)alkynyl, any of which is optionally substituted with one or more independent halo, —CF$_3$, —OCF$_3$, —OR$^{2221}$, —NR$^{2221}$R$^{3331}$(R$^{333a}$)$_{j6a}$, —C(O)R$^{2221}$, —CO$_2$R$^{2221}$, —CONR$^{2221}$R$^{3331}$, —NO$_2$, —CN, —S(O)$_{j6a}$ R$^{2221}$, —SO$_2$NR$^{2221}$R$^{3331}$, —NR$^{2221}$(C=O) R$^{3331}$, NR$^{2221}$(C=O)OR$^{3331}$, —NR$^{2221}$(C=O) NR$^{2221}$R$^{3331}$, NR$^{2221}$S(O)$_{j6a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O) OR$^{2221}$OR$^{3331}$, or —S(C=O)NR$^{2221}$R$^{3331}$ substituents; or G$^{11}$ is taken together with the carbon to which it is attached to form a double bond which is substituted with R$^5$ and G$^{11}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{333a1}$ are each independently equal to (C$_{0-10}$)alkyl, (C$_{2-10}$)alkenyl, (C$_{2-10}$)alkynyl, (C$_{1-10}$)alkoxy(C$_{1-10}$)alkyl, (C$_{1-10}$)alkoxy(C$_{2-10}$)alkenyl, (C$_{1-10}$)alkoxy(C$_{2-10}$)alkynyl, (C$_{1-10}$)alkylthio(C$_{1-10}$) alkyl, (C$_{1-10}$)alkylthio(C$_{2-10}$)alkenyl, (C$_{1-10}$)alkylthio (C$_{2-10}$)alkynyl, cyclo(C$_{3-8}$)alkyl, cyclo(C$_{3-8}$)alkenyl, cyclo(C$_{3-8}$)alkyl(C$_{1-10}$)alkyl, cyclo(C$_{3-8}$)alkenyl(C$_{1-10}$) alkyl, cyclo(C$_{3-8}$)alkyl(C$_{2-10}$)alkenyl, cyclo(C$_{3-8}$)alkenyl (C$_{2-10}$)alkenyl, cyclo(C$_{3-8}$)alkyl(C$_{2-10}$)alkynyl, cyclo (C$_{3-8}$)alkenyl(C$_{2-10}$)alkynyl, heterocyclyl-(C$_{0-10}$)alkyl, heterocyclyl-(C$_{2-10}$)alkenyl, or heterocyclyl-(C$_{2-10}$)alkynyl, any of which is optionally substituted by one or more G$^{111}$ substituents; or aryl-(C$_{0-10}$)alkyl, aryl-(C$_{2-10}$)alkenyl, or aryl-(C$_{2-10}$)alkynyl, hetaryl-(C$_{0-10}$)alkyl, hetaryl-(C$_{2-10}$)alkenyl, or hetaryl-(C$_{2-10}$)alkynyl, any of which is optionally substituted by one or more G$^{111}$ substituents; or in the case of —NR$^2$R$^3$(R$^{3a}$)$_{j1}$ or —NR$^{222}$R$^{333}$(R$^{333}$a)$_{j1a}$ or —NR$^{222}$R$^{333}$(R$^{333}$a)$_{j2a}$ or —NR$^{2221}$R$^{3331}$(R$^{333a1}$)$_{j3a}$ or —NR$^{2221}$R$^{3331}$(R$^{333a1}$)$_{j4a}$ or —NR$^{2221}$R$^{3331}$(R$^{333a1}$)$_{j5a}$ or —NR$^{2221}$R$^{3331}$(R$^{333a1}$)$_{j6a}$, R$^2$ and R$^3$ or R$^{222}$ and R$^{333}$, or R$^{2221}$ and R$^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more G$^{111}$ substituents;

X$^1$ and Y$^1$ are each independently —O—, —NR$^7$—, —S(O)$_{j7}$—, —CR$^5$R$^6$—, —N(C(O)OR$^7$)—, —N(C(O) R$^7$)—, —N(SO$_2$R$^7$)—, —CH$_2$O—, —CH$_2$S—, —CH$_2$N (R$^7$)—, —CH(NR$^7$)—, —CH$_2$N(C(O)R$^7$)—, —CH$_2$N(C (O)OR$^7$)—, —CH$_2$N(SO$_2$R$^7$)—, —CH(NHR$^7$)—, —CH (NHC(O)R$^7$)—, —CH(NHSO$_2$R$^7$)—, —CH(NHC(O) OR$^7$)—, —CH(OC(O)R$^7$)—, —CH(OC(O)NHR$^7$)—, —CH=CH—, —C.ident.C—, —C(=NOR$^7$)—, —C(O)—, —CH(OR$^7$)—, —C(O)N(R$^7$)—, —N(R$^7$)C (O)—, —N(R$^7$)S(O)—, —N(R$^7$)S(O)$_2$—, —OC(O)N (R$^7$)—, —N(R$^7$)C(O)N(R$^7$)—, —NR$^7$C(O)O—, —S(O) N(R$^7$)—, —S(O)$_2$N(R$^7$)—, —N(C(O)R$^7$)S(O)—, —N(C (O)R$^7$)S(O)$_2$—, —N(R$^7$)S(O)N(R$^7$)—, —N(R$^7$)S(O)$_2$N (R$^7$)—, —C(O)N(R$^7$)C(O)—, —S(O)N(R$^7$)C(O)—, —S(O)$_2$N(R$^7$)C(O)—, —OS(O)N(R$^7$)—, —OS(O)$_2$N (R$^7$)—, —N(R$^7$)S(O)O—, —N(R$^7$)S(O)$_2$O—, —N(R$^7$)S (O)C(O)—, —N(R$^7$)S(O)$_2$C(O)—, —SON(C(O)R$^7$)—, —SO$_2$N(C(O)R$^7$)—, —N(R$^7$)SON(R$^7$)—, —N(R$^7$) SO$_2$N(R$^7$)—, —C(O)O—, —N(R$^7$)P(OR$^8$)O—, —N(R$^7$) P(OR$^8$)—, —N(R$^7$)P(O)(OR$^8$)O—, —N(R$^7$)P(O) (OR$^8$)—, —N(C(O)R$^7$)P(OR$^8$)O—, —N(C(O)R$^7$)P (OR$^8$)—, —N(C(O)R$^7$)P(O)(OR$^8$)O—, —N(C(O)R$^7$)P (OR$^8$)—, —CH(R$^7$)S(O)—, —CH(R$^7$)S(O)$_2$—, —CH (R$^7$)N(C(O)OR$^7$)—, —CH(R$^7$)N(C(O)R$^7$)—, —CH(R$^7$) N(SO$_2$R$^7$)—, —CH(R$^7$)O—, —CH(R$^7$)S—, —CH(R$^7$)N (R$^7$)—, —CH(R$^7$)NC(O)R$^7$)—, —CH(R$^7$) NC(O)R$^7$)—, —CH(R$^7$)N(SO$_2$R$^7$)—, —CH(R$^7$)C(=NOR$^7$)—, —CH (R$^7$)C(O)—, —CH(R$^7$)CH(OR$^7$)—, —CH(R$^7$)C(O)N (R$^7$)—, —CH(R$^7$)N(R$^7$)C(O)—, —CH(R$^7$)N(R$^7$)S(O)—, —CH(R$^7$)N(R$^7$)S(O)$_2$—, —CH(R$^7$)OC(O)N(R$^7$)—, —CH(R$^7$)N(R$^7$)C(O)N(R$^7$)—, —CH(R$^7$)NR$^7$C(O)O—, —CH(R$^7$)S(O)N(R$^7$)—, —CH(R$^7$)S(O)$_2$N(R$^7$)—, —CH (R$^7$)N(C(O)R$^7$)S(O)—, —CH(R$^7$)N(C(O)R$^7$)S(O)—, —CH(R$^7$)N(R$^7$)S(O)N(R$^7$)—, —CH(R$^7$)N(R$^7$)S(O)$_2$N (R$^7$)—, —CH(R$^7$)C(O)N(R$^7$)C(O)—, —CH(R$^7$)S(O)N (R$^7$)C(O)—, —CH(R$^7$)S(O)$_2$N(R$^7$)C(O)—, —CH(R$^7$) OS(O)N(R$^7$)—, —CH(R$^7$)OS(O)$_2$N(R$^7$)—, —CH(R$^7$)N (R$^7$)S(O)O—, —CH(R$^7$)N(R$^7$)S(O)$_2$O—, —CH(R$^7$)N (R$^7$)S(O)C(O)—, —CH(R$^7$)N(R$^7$)S(O)$_2$C(O)—, —CH (R$^7$)SON(C(O)R$^7$)—, —CH(R$^7$)SO$_2$N(C(O)R$^7$)—, —CH(R$^7$)N(R$^7$) SON(R$^7$)—, —CH(R$^7$)N(R$^7$)SO$_2$N (R$^7$)—, —CH(R$^7$)C(O)O—, —CH(R$^7$)N(R$^7$)P(OR$^8$) O—, —CH(R$^7$)N(R$^7$)P(OR$^8$)—, —CH(R$^7$)N(R$^7$)P(O) (OR$^8$)O—, —CH(R$^7$)N(R$^7$)P(O)(OR$^8$)—, —CH(R$^7$)N(C (O)R$^7$)P(OR$^8$)O—, —CH(R$^7$)N(C(O)R$^7$)P(OR$^8$)—, —CH(R$^7$)N(C(O)R$^7$)P(O)(OR$^8$)O—, or —CH(R$^7$)N(C (O)R$^7$)P(OR$^8$)—;

or X$^1$ and Y$^1$ are each independently represented by one of the following structural formulas:

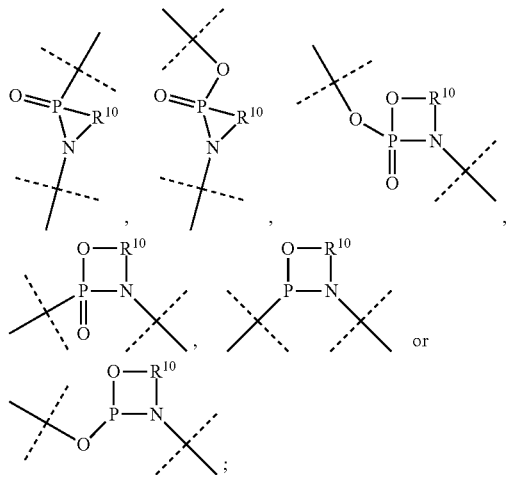

R$^{10}$, taken together with the phosphinamide or phosphonamide, is a 5-, 6-, or 7-membered aryl, heteroaryl or heterocyclyl ring system;

$R^5$, $R^6$, and $G^{111}$ are each independently a $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C{=}O)R^{87}$, $NR^{77}(C{=}O)OR^{87}$, $NR^{77}(C{=}O)NR^{78}R^{87}$, $NR^{77}S(O)_{j5a}R^{87}$, —$(C{=}S)OR^{77}$, —$(C{=}O)SR^{77}$, —$NR^{77}(C{=}NR^{87})NR^{78}R^{88}$, —$NR^{77}(C{=}NR^{87})OR^{78}$, —$NR^{77}(C{=}NR^{87})SR^{78}$, —$O(C{=}O)OR^{77}$, —$O(C{=}O)NR^{77}R^{87}$, —$O(C{=}O)SR^{77}$, —$S(C{=}O)OR^{77}$, —$P(O)OR^{77}OR^{87}$, or —$S(C{=}O)NR^{77}R^{87}$ substituents; or aryl-$(C_{0-10})$alkyl, aryl-$(C_{2-10})$alkenyl, or aryl-$(C_{2-10})$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C{=}O)R^{87}$, $NR^{77}(C{=}O)OR^{87}$, $NR^{77}(C{=}O)NR^{78}R^{87}$, $NR^{77}S(O)_{j5a}R^{87}$, —$(C{=}S)OR^{77}$, —$(C{=}O)SR^{77}$, —$NR^{77}(C{=}NR^{87})NR^{78}R^{88}$, —$NR^{77}(C{=}NR^{87})OR^{78}$, —$NR^{77}(C{=}NR^{87})SR^{78}$, —$O(C{=}O)OR^{77}$, —$O(C{=}O)NR^{77}R^{87}$, —$O(C{=}O)SR^{77}$, —$S(C{=}O)OR^{77}$, —$P(O)OR^{77}OR^{87}$, or —$S(C{=}O)NR^{77}R^{87}$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C{=}O)R^{87}$, $NR^{77}(C{=}O)OR^{87}$, $NR^{77}(C{=}O)NR^{78}R^{87}$, $NR^{77}S(O)_{j5a}R^{87}$, —$(C{=}S)OR^{77}$, —$(C{=}O)SR^{77}$, —$NR^{77}(C{=}NR^{87})NR^{78}R^{88}$, —$NR^{77}(C{=}NR^{87})OR^{78}$, —$NR^{77}(C{=}NR^{87})SR^{78}$, —$O(C{=}O)OR^{77}$, —$O(C{=}O)NR^{77}R^{87}$, —$O(C{=}O)SR^{77}$, —$S(C{=}O)OR^{77}$, —$P(O)OR^{77}OR^{87}$, or —$S(C{=}O)NR^{77}R^{87}$ substituents; or $R^5$ with $R^6$ taken together with the respective carbon atom to which they are attached, form a 3-10 membered saturated or unsaturated ring, wherein said ring is optionally substituted with $R^{69}$; or $R^5$ with $R^6$ taken together with the respective carbon atom to which they are attached, form a 3-10 membered saturated or unsaturated heterocyclic ring, wherein said ring is optionally substituted with $R^{69}$;

$R^7$ and $R^8$ are each independently H, acyl, alkyl, alkenyl, aryl, heteroaryl, heterocyclyl or cycloalkyl, any of which is optionally substituted by one or more $G^{111}$ substituents;

$R^4$ is H, alkyl, alkenyl, alkynyl, aryl, heteroaryl, cycloalkyl, heterocyclyl, cycloalkenyl, or heterocycloalkenyl, any of which is optionally substituted by one or more $G^{41}$ substituents;

$R^{69}$ is equal to halo, —$OR^{78}$, —$SH$, —$NR^{78}R^{88}$, —$CO_2R^{78}$, —$CONR^{78}R^{88}$, —$NO_2$, —$CN$, —$S(O)_{j8}R^{78}$, —$SO_2NR^{78}R^{88}$, $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, cyano, nitro, —$OR^{778}$, —$SO_2NR^{778}R^{888}$, or —$NR^{778}R^{888}$ substituents; or aryl-$(C_{0-10})$alkyl, aryl-$(C_{2-10})$alkenyl, or aryl-$(C_{2-10})$alkynyl, any of which is optionally substituted with one or more independent halo, cyano, nitro, —$OR^{778}$, $(C_{1-10})$alkyl, $(C_{2-10})$alkenyl, $(C_{2-10})$alkynyl, halo$(C_{1-10})$alkyl, halo$(C_{2-10})$alkenyl, halo$(C_{2-10})$alkynyl, —COOH, $(C_{1-4})$alkoxycarbonyl, —$CONR^{778}R^{888}$, —$SO_2NR^{778}R^{888}$, or —$NR^{778}R^{888}$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, cyano, nitro, —$OR^{778}$, $(C_{1-10})$alkyl, $(C_{2-10})$alkenyl, $(C_{2-10})$alkynyl, halo$(C_{1-10})$alkyl, halo$(C_{2-10})$alkenyl, halo$(C_{2-10})$alkynyl, —COOH, $(C_{1-4})$alkoxycarbonyl, —$CONR^{778}R^{888}$, —$SO_2NR^{778}R^{888}$, or —$NR^{778}R^{888}$ substituents; or mono$(C_{1-6}$alkyl)amino$(C_{1-6})$alkyl, di$((C_{1-6})$alkyl)amino$(C_{1-6})$alkyl, mono(aryl)amino$(C_{1-6})$alkyl, di(aryl)amino$(C_{1-6})$alkyl, or —N$((C_{1-6})$ alkyl)-$(C_{1-6})$alkyl-aryl, any of which is optionally substituted with one or more independent halo, cyano, nitro, —$OR^{778}$, $(C_{1-10})$alkyl, $(C_{2-10})$alkenyl, $(C_{2-10})$alkynyl, halo$(C_{1-10})$alkyl, halo$(C_{2-10})$alkenyl, halo$(C_{2-10})$alkynyl, —COOH, $(C_{1-4})$alkoxycarbonyl, —$CONR^{778}R^{888}SO_2NR^{778}R^{888}$, or —$NR^{778}R^{888}$ substituents; or in the case of —$NR^{78}R^{88}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $(C_{1-10})$alkoxy, —$SO_2NR^{778}R^{888}$, or —$NR^{778}R^{888}$ substituents;

$R^{77}$, $R^{78}$, $R^{87}$, $R^{88}$, $R^{778}$, and $R^{888}$ are each independently $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$C_{2-10})$alkenyl, $(C_{1-10})$alkoxy$(C_{2-10})$alkynyl, $(C_{1-10})$alkylthio$(C_{1-10})$alkyl, $(C_{1-10})$ alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, heterocyclyl-$(C_{2-10})$alkynyl, $(C_{1-10})$alkylcarbonyl, $(C_{2-10})$alkenylcarbonyl, $(C_{2-10})$alkynylcarbonyl, $(C_{1-10})$alkoxycarbonyl, $(C_{1-10})$alkoxycarbonyl$(C_{1-10})$alkyl, mono$(C_{1-6})$alkylaminocarbonyl, di$(C_{1-6})$alkylaminocarbonyl, mono(aryl)aminocarbonyl, di(aryl)aminocarbonyl, or $(C_{1-10})$alkyl(aryl)aminocarbonyl, any of which is optionally substituted with one or more independent halo, cyano, hydroxy, nitro, $(C_{1-10})$alkoxy, —$SO_2N((C_{0-4})$alkyl$)((C_{0-4})$alkyl), or —N$((C_{0-4})$alkyl$)((C_{0-4})$alkyl) substituents; or aryl-$(C_{0-10})$alkyl, aryl-$(C_{2-10})$alkenyl, or aryl-$(C_{2-10})$alkynyl, any of which is optionally substituted with one or more independent halo, cyano, nitro, —O$((C_{0-4})$alkyl), $(C_{1-10})$alkyl, $(C_{2-10})$alkenyl, $(C_{2-10})$alkynyl, halo$(C_{1-10})$alkyl, halo$(C_{2-10})$alkenyl, halo$(C_{2-10})$alkynyl, —COOH, $(C_{1-4})$alkoxycarbonyl, —CON$((C_{0-4})$alkyl$)((C_{0-10})$alkyl), —$SO_2N((C_{0-4})$alkyl$)((C_{0-4})$alkyl), or —N$((C_{0-4})$alkyl$)((C_{0-4})$alkyl) substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, cyano, nitro, —O$((C_{0-4})$alkyl), $(C_{1-10})$alkyl, $(C_{2-10})$alkenyl, $(C_{2-10})$alkynyl, halo$(C_{1-10})$alkyl, halo$(C_{2-10})$alkenyl, halo$(C_{2-10})$alkynyl, —COOH, $(C_{1-4})$alkoxycarbonyl, —CON$((C_{0-4})$ alkyl)((C$_{0-4}$)alkyl), —SO$_2$N((C$_{0-4}$)alkyl)((C$_{0-4}$)alkyl), or —N((C$_{0-4}$)alkyl)((C$_{0-4}$)alkyl) substituents; or mono ((C$_{1-6}$)alkyl)amino(C$_{1-6}$)alkyl, di((C$_{1-6}$)alkyl)amino (C$_{1-6}$)alkyl, mono(aryl)amino(C$_{1-6}$)alkyl, di(aryl)amino (C$_{1-6}$)alkyl, or —N((C$_{1-6}$)alkyl)-(C$_{1-6}$)alkyl-aryl, any of which is optionally substituted with one or more independent halo, cyano, nitro, —O((C$_{0-4}$)alkyl), (C$_{1-10}$)alkyl, (C$_{2-10}$)alkenyl, (C$_{2-10}$)alkynyl, halo(C$_{1-10}$)alkyl, halo (C$_{2-10}$)alkenyl, halo(C$_{2-10}$)alkynyl, —COOH, (C$_{1-4}$) alkoxycarbonyl, —CON((C$_{0-4}$)alkyl)((C$_{0-4}$)alkyl), —SO$_2$N((C$_{0-4}$)alkyl)((C$_{0-4}$)alkyl), or —N((C$_{0-4}$)alkyl) ((C$_{0-4}$)alkyl) substituents; and n, m, j1, j1a, j2a, j3a, j4, j4a, j5a, j6a, j7, and j8 are each independently equal to 0, 1, or 2.

In an embodiment, the BTK inhibitor is a compound selected from the structures disclosed in U.S. Pat. Nos. 8,450,335 and 8,609,679, and U.S. Patent Application Publication Nos. 2010/0029610 A1, 2012/0077832 A1, 2013/0065879 A1, 2013/0072469 A1, and 2013/0165462 A1, the disclosures of which are incorporated by reference herein. In an embodiment, the BTK inhibitor is a compound of Formula (XXV) or Formula (XXVI):

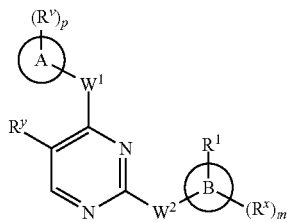

Formula (XXV)

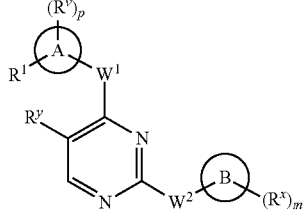

Formula (XXVI)

or a pharmaceutically acceptable salt, solvate, hydrate, cocrystal, or prodrug thereof, wherein:

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

R$^1$ is a warhead group;

R$^y$ is hydrogen, halogen, —CN, —CF$_3$, C$_{1-4}$ aliphatic, C$_{1-4}$ haloaliphatic, —OR, —C(O)R, or —C(O)N(R)$_2$;

each R group is independently hydrogen or an optionally substituted group selected from C$_{1-6}$ aliphatic, phenyl, an optionally substituted 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

W$^1$ and W$^2$ are each independently a covalent bond or a bivalent C$_{1-3}$ alkylene chain wherein one methylene unit of W$^1$ or W$^2$ is optionally replaced by —NR$^2$—, —N(R$^2$) C(O)—, —C(O)N(R$^2$)—, —N(R$^2$)SO$_2$—, —SO$_2$N(R$^2$), —O—, —C(O)—, —OC(O)—, —C(O)O—, —S—, —SO— or —SO$_2$—;

R$^2$ is hydrogen, optionally substituted C$_{1-6}$ aliphatic, or —C(O)R, or:

R$^2$ and a substituent on Ring A are taken together with their intervening atoms to form a 4-6 membered saturated, partially unsaturated, or aromatic fused ring, or:

R$^2$ and R$^y$ are taken together with their intervening atoms to form an optionally substituted 4-7 membered partially unsaturated or aromatic fused ring;

m and p are independently 0-4; and

R$^x$ and R$^v$ are independently selected from —R, halogen, —OR, —O(CH$_2$)$_q$OR, —CN, —NO$_2$, —SO$_2$R, —SO$_2$N (R)$_2$, —SOR, —C(O)R, —CO$_2$R, —C(O)N(R)$_2$, —NRC (O)R, —NRC(O)NR$_2$, —NRSO$_2$R, or —N(R)$_2$, wherein q is 1-4; or:

R$^x$ and R$^1$ when concurrently present on Ring B are taken together with their intervening atoms to form an optionally substituted 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic; or R$^v$ and R$^1$ when concurrently present on Ring A are taken together with their intervening atoms to form an optionally substituted 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic.

In an embodiment, the BTK inhibitor is a compound of Formula (XXV) or Formula (XXVI), wherein:

Ring A is selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, NO$_2$, halogen, CN, or $C_{1-6}$ aliphatic, wherein:

Q is a covalent bond or a bivalent $C_{1-6}$ saturated or unsaturated, straight or branched, hydrocarbon chain, wherein one or two methylene units of Q are optionally and independently replaced by —NR—, —S—, —O—, —C(O)—, —SO—, or —SO$_2$—; and Z is hydrogen or $C_{1-6}$ aliphatic optionally substituted with oxo, halogen, or CN;

$R^y$ is hydrogen, halogen, —CN, —CF$_3$, $C_{1-4}$ aliphatic, $C_{1-4}$ haloaliphatic, —OR, —C(O)R, or —C(O)N(R)$_2$;

each R group is independently hydrogen or an optionally substituted group selected from $C_{1-6}$ aliphatic, phenyl, an optionally substituted 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent $C_{1-3}$ alkylene chain wherein one methylene unit of $W^1$ or $W^2$ is optionally replaced by —NR$^2$—, —N(R$^2$)C(O)—, —C(O)N(R$^2$)—, —N(R$^2$)SO$_2$—, —SO$_2$N(R$^2$)—, —O—, —C(O)—, —OC(O)—, —C(O)O—, —S—, —SO— or —SO$_2$—;

$R^2$ is hydrogen, optionally substituted $C_{1-6}$ aliphatic, or —C(O)R, or:

$R^2$ and a substituent on Ring A are taken together with their intervening atoms to form a 4-6 membered partially unsaturated or aromatic fused ring; or $R^2$ and $R^y$ are taken together with their intervening atoms to form a 4-6 membered saturated, partially unsaturated, or aromatic fused ring;

m and p are independently 0-4; and $R^x$ and $R^v$ are independently selected from —R, halogen, —OR, —O(CH$_2$)$_q$OR, —CN, —NO$_2$, —SO$_2$R, —SO$_2$N(R)$_2$, —SOR, —C(O)R, —CO$_2$R, —C(O)N(R)$_2$, —NRC(O)R, —NRC(O)NR$_2$, —NRSO$_2$R, or —N(R)$_2$, wherein R is independently selected from the group consisting of hydrogen, cycloalkyl, alkenyl, cycloalkenyl, alkynyl, aryl, heteroaryl, and heterocycly; or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic.

As defined generally above, Ring A is selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In preferred embodiments, Ring A is an optionally substituted phenyl group. In some embodiments, Ring A is an optionally substituted naphthyl ring or an optionally substituted bicyclic 8-10 membered heteroaryl ring having 1-4 heteroatoms independently selected from nitrogen, oxygen, or sulfur. In certain other embodiments, Ring A is an optionally substituted 3-7 membered carbocyclic ring. In yet other embodiments, Ring A is an optionally substituted 4-7 membered heterocyclic ring having 1-3 heteroatoms independently selected from nitrogen, oxygen, or sulfur. In preferred embodiments, Ring B is an optionally substituted phenyl group.

In certain embodiments, Ring A in Formula (XXV) or Formula (XXVI) is substituted as defined herein. In some embodiments, Ring A is substituted with one, two, or three groups independently selected from halogen, $R^o$, or —(CH$_2$)$_{0-4}$OR$^o$, or —O(CH$_2$)$_{0-4}$R$^o$, wherein each $R^o$ is independently selected from the group consisting of cycloalkyl, alkenyl, cycloalkenyl, alkynyl, aryl, heteroaryl, and heterocyclyl. Exemplary substituents on Ring A include Br, I, Cl, methyl, —CF$_3$, —C≡CH, —OCH$_2$phenyl, —OCH$_2$(fluorophenyl), or —OCH$_2$pyridyl.

In a preferred embodiment, the BTK inhibitor is CC-292, or a pharmaceutically acceptable salt, solvate, hydrate, cocrystal, or prodrug thereof, preferably a hydrochloride salt or a besylate salt thereof. In a preferred embodiment, the BTK inhibitor is a compound of Formula (XXVII):

Formula (XXVII)

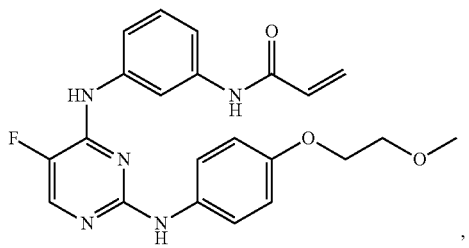

which is N-(3-((5-fluoro-2-((4-(2-methoxyethoxy)phenyl)amino)pyrimidin-4-yl)amino)phenyl)acrylamide, or a pharmaceutically acceptable salt, solvate, hydrate, cocrystal, or prodrug thereof, or in an exemplary embodiment is a hydrochloride salt or a besylate salt thereof. The preparation of this compound is described in U.S. Patent Application Publication No. 2010/0029610 A1 at Example 20, the disclosure of which is incorporated by reference herein. The preparation of the besylate salt of this compound is described in U.S. Patent Application Publication No. 2012/0077832 A1, the disclosure of which is incorporated by reference herein. In an embodiment, the BTK inhibitor is a compound selected from the structures disclosed in U.S. Patent Application Publication No. 2010/0029610 A1 or No. 2012/0077832 A1, the disclosures of which are incorporated by reference herein.

In a preferred embodiment, the BTK inhibitor is N-(3-((5-fluoro-2-((4-(2-methoxyethoxy)phenyl)amino)pyrimidin-4-yl)amino)phenyl)acrylamide or a pharmaceutically acceptable salt, solvate, hydrate, cocrystal, or prodrug thereof, or a hydrochloride salt thereof. The preparation of this compound is described in U.S. Patent Application Publication Nos. 2010/0029610 A1 and 2012/0077832 A1, the disclosure of which is incorporated by reference herein.

In a preferred embodiment, the BTK inhibitor is (N-(3-(5-fluoro-2-(4-(2-methoxyethoxy)phenylamino)pyrimidin-4-ylamino)phenyl)acrylamide), or a pharmaceutically acceptable salt, solvate, hydrate, cocrystal, or prodrug thereof, or preferably a besylate salt thereof. The preparation of this compound is described in U.S. Patent Application Publication No. 2010/0029610 A1 at Example 20, the disclosure of which is incorporated by reference herein. The preparation of its besylate salt is described in U.S. Patent Application Publication No. 2012/0077832 A1, the disclosure of which is incorporated by reference herein.

In an embodiment, the BTK inhibitor is a compound of Formula (XXVIII):

or a pharmaceutically acceptable salt, hydrate, solvate, cocrystal, or prodrug thereof, wherein L represents (1) —O—, (2) —S—, (3) —SO—, (4) —SO$_2$— (5) —NH—, (6) —C(O)—, (7) —CH$_2$O—, (8) —O—CH$_2$—, (9) —CH$_2$—, or (10) —CH(OH)—;

$R^1$ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;

ring1 represents a 4- to 7-membered cyclic group, which may be substituted by from one to five substituents each independently selected from the group consisting of (1) halogen atoms, (2) $C_{1-4}$ alkyl groups, (3) $C_{1-4}$ alkoxy groups, (4) nitrile, (5) $C_{1-4}$ haloalkyl groups, and (6) $C_{1-4}$ haloalkoxy groups, wherein when two or more substituents are present on ring1, these substituents may form a 4- to 7-membered cyclic group together with the atoms in ring1 to which these substituents are bound;

ring2 represents a 4- to 7-membered saturated heterocycle, which may be substituted by from one to three -K-$R^2$; K represents (1) a bond, (2) a $C_{1-4}$ alkylene, (3) —C(O)—, (4) —C(O)—CH$_2$—, (5) —CH$_2$—C(O)—, (6) —C(O)O—, or (7) —SO$_2$— (wherein the bond on the left is bound to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) NR$^3$R$^4$, (2) halogen atoms, (3) CONR$^5$R$^6$, (4) CO$_2$R$^7$, and (5) OR$^8$;

$R^3$ and $R^4$ each independently represent (1) a hydrogen atom, or (2) a $C_{1-4}$ alkyl group which may be substituted by OR$^9$ or CONR$^{10}$R$^{11}$; R$^3$ and R$^4$ may, together with the nitrogen atom to which they are bound, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group; $R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another).

In an exemplary embodiment, the BTK inhibitor is a compound of Formula (XXVIII-A):

Formula (XXVIII)

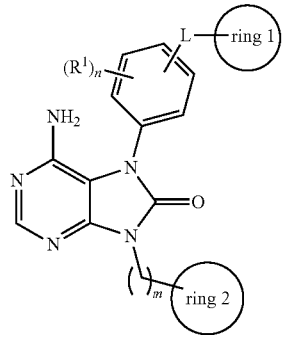

Formula (XXVIII-A)

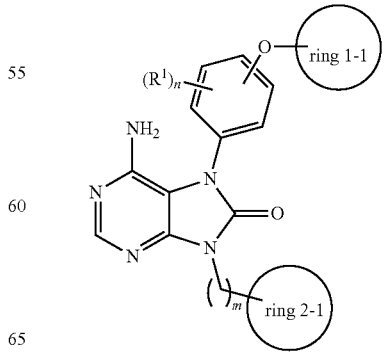

or a pharmaceutically acceptable salt, hydrate, solvate, cocrystal, or prodrug thereof, wherein R¹ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;

ring1 represents a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, (5) $CF_3$;

ring2 represents a 4- to 7-membered nitrogenous saturated heterocycle, which may be substituted by from one to three -K-R²; wherein K represents (1) a bond, (2) a $C_{1-4}$ alkylene, (3) —C(O)—, (4) —C(O)—$CH_2$—, (5) —$CH_2$—C(O)—, (6) —C(O)O—, or (7) —$SO_2$— (wherein the bond on the left is bound to the ring2);

R² represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

R³ and R⁴ each independently represent (1) a hydrogen atom, or (2) a $C_{1-4}$ alkyl group which may be substituted by $OR^9$ or $CONR^{10}R^{11}$; R³ and R⁴ may, together with the nitrogen atom to which they are bound, form a 4- to 7-membered nitrogenous saturated heterocycle, which may be substituted by an oxo group or a hydroxyl group;

R⁵ and R⁶ each independently represent (1) a hydrogen atom, (2) $C_{1-4}$ alkyl group, or (3) a phenyl group;

R⁷ represents (1) a hydrogen atom or (2) a $C_{1-4}$ alkyl group;

R⁸ represents (1) a hydrogen atom, (2) a $C_{1-4}$ alkyl group, (3) a phenyl group, or (4) a benzotriazolyl group; R⁹ represents (1) a hydrogen atom or (2) a $C_{1-4}$ alkyl group;

R¹⁰ and R¹¹ each independently represent (1) a hydrogen atom or (2) a $C_{1-4}$ alkyl group;

n represents an integer from 0 to 4;

m represents an integer from 0 to 2; and when n is two or more, the R¹'s may be the same as each other or may differ from one another).

In a preferred embodiment, the BTK inhibitor is a compound of Formula (XXVIII-B):

Formula (XXVIII-B)

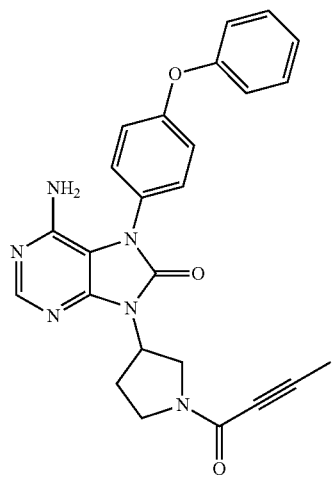

or a pharmaceutically acceptable salt, solvate, hydrate, cocrystal, or prodrug thereof, preferably a hydrochloride salt thereof. The preparation of this compound is described in International Patent Application Publication No. WO 2013/081016 A1, the disclosure of which is incorporated by reference herein. In an embodiment, the BTK inhibitor is 6-amino-9-(1-(but-2-ynoyl)pyrrolidin-3-yl)-7-(4-phenoxyphenyl)-7,9-dihydro-8H-purin-8-one or a pharmaceutically acceptable salt, solvate, hydrate, cocrystal, or prodrug thereof, or preferably a hydrochloride salt thereof. In an embodiment, the BTK inhibitor is 6-amino-9-[(3S)-1-(2-butynoyl)-3-pyrrolidinyl]-7-(4-phenoxyphenyl)-7,9-dihydro-8H-purin-8-one or a pharmaceutically acceptable salt, solvate, hydrate, cocrystal, or prodrug thereof, or a hydrochloride salt thereof.

The R-enantiomer of Formula (XXVIII-B) is also known as ONO-4059, and is given by Formula (XXVIII-R). In a preferred embodiment, the BTK inhibitor is a compound of Formula (XXVIII-R):

Formula (XXVIII-R)

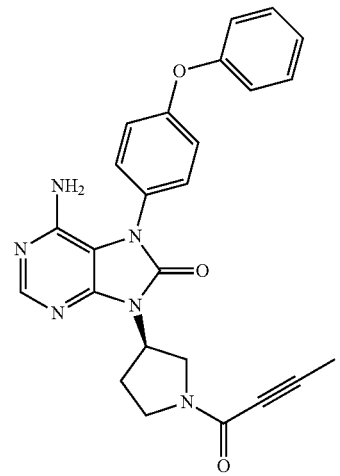

or a pharmaceutically acceptable salt, solvate, hydrate, cocrystal, or prodrug thereof, preferably a hydrochloride salt thereof.

In an embodiment, the BTK inhibitor is 6-amino-9-[(3R)-1-(2-butynoyl)-3-pyrrolidinyl]-7-(4-phenoxyphenyl)-7,9-dihydro-8H-purin-8-one or a pharmaceutically acceptable salt, solvate, hydrate, cocrystal, or prodrug thereof, preferably a hydrochloride salt thereof.

The preparation of Formula (XXVII-R) is described in International Patent Application Publication No. WO 2013/081016 A1, the disclosure of which is incorporated by reference herein. In brief, the BTK inhibitor of Formula (XXVIII-R) can be prepared by the following procedure.

Step 1: A solution of dibenzylamine (10.2 g) in dichloromethane (30 mL) is dripped into a solution of 4,6-dichloro-5-nitropyrimidine (10 g) in dichloromethane (70 mL) on an ice bath. Then triethylamine (14.4 mL) is added, and the mixture is stirred for 1 hour. Water is added to the reaction mixture, the organic layer is washed with a saturated aqueous sodium chloride solution and dried over anhydrous sodium sulfate, and the solvent is concentrated under reduced pressure to obtain N,N-dibenzyl-6-chloro-5-nitropyrimidine-4-amine (19.2 g).

Step 2: The compound prepared in Step 1 (19 g) and tert-butyl (3R)-3-aminopyrrolidine-1-carboxylate (10.5 g) are dissolved in dioxane (58 mL). Triethylamine (8.1 mL) is added, and the mixture is stirred for 5 hours at 50° C. The reaction mixture is returned to room temperature, the solvent is distilled off, water is added, and extraction is performed with ethyl acetate. The organic layer is washed with saturated aqueous sodium chloride solution, then dried over anhydrous sodium sulfate, and the solvent is distilled off. The residue is purified by silica gel column chromatography to obtain tert-butyl (3R)-3-{[6-(dibenzylamino)-5-nitropyrimidin-4-yl]amino}pyrrolid-ine-1-carboxylate (27.0 g).

Step 3: An ethyl acetate (360 mL) solution of the compound prepared in Step 2 (17.5 g) is dripped into a mixture of zinc (23.3 g) and a 3.0 M aqueous ammonium chloride solution (11.4 g) on an ice bath, and the temperature is immediately raised to room temperature. After stirring for 2 hours, the reaction mixture is filtered through CELITE and the solvent is distilled off. The residue is purified by silica gel column chromatography to obtain tert-butyl (3R)-3-{[5-amino-6-(dibenzylamino)pyrimidin-4-yl]amino}pyrrolidine-1-carboxylate (12.4 g).

Step 4: The compound prepared in Step 3 (8.4 g) and 1,1'-carbonyl diimidazole (5.9 g) are dissolved in tetrahydrofuran (120 mL) and the solution is stirred for 15 hours at 60° C. The solvent is distilled off from the reaction mixture, water is added, and extraction with ethyl acetate is performed. The organic layer is washed with saturated aqueous sodium chloride solution, dried over anhydrous sodium sulfate, and the solvent is distilled off. The residue is purified by silica gel column chromatography to obtain tert-butyl (3R)-3-[6-(dibenzylamino)-8-oxo-7,8-dihydro-9H-purin-9-yl]pyrrolidin-1-carboxylate (7.8 g).

Step 5: The compound prepared in Step 4 (7.8 g) is dissolved in methanol (240 mL) and ethyl acetate (50 mL), 20% Pearlman's catalyst (Pd(OH)$_2$/C) (8.0 g, 100 wt %) is added, hydrogen gas replacement is carried out, and stirring is performed for 7.5 hours at 60° C. The reaction mixture is filtered through CELITE and the solvent is distilled off to obtain tert-butyl (3R)-3-(6-amino-8-oxo-7,8-dihydro-9H-purin-9-yl)pyrrolidine-1-carboxylate (5.0 g).

Step 6: At room temperature p-phenoxy phenyl boronic acid (2.1 g), copper(II) acetate (1.48 g), molecular sieve 4A (2.5 g), and pyridine (0.82 mL) are added to a dichloromethane suspension (200 mL) of the compound prepared in Step 5 (2.5 g), followed by stirring for 21 hours. The reaction mixture is filtered through CELITE and the residue is purified by silica gel column chromatography to obtain tert-butyl (3R)-3-[6-amino-8-oxo-7-(4-phenoxyphenyl)-7,8-dihydro-9H-purin-9-yl]pyrrolidine-1-carboxylate (1.3 g).

Step 7: At room temperature 4 N HCl/dioxane (13 mL) is added to a methanol (13 mL) suspension of the compound prepared in Step 6 (1.3 g 2.76 mmol, 1.0 equivalent), and the mixture is stirred for 1 hour. The solvent is then distilled off to obtain (3R)-6-amino-9-pyrrolidin-3-yl-7-(4-phenoxyphenyl)-7,9-dihydro-8H-purin-8-one dihydrochloride (1.5 g).

Step 8: After 2-butylnoic acid (34 mg), 1-ethyl-3-(3-dimethylaminopropyl) carbodiimide hydrochloride (EDC) (78 mg), 1-hydroxybenzotriazole (HOBt) (62 mg), and triethylamine (114 mL) are added to a solution of the compound prepared in Step 7 (100 mg) in dimethyl formamide (3 mL), the mixture is stirred at room temperature for 3 hours. Water is added to the reaction mixture and extraction with ethyl acetate is performed. The organic layer is washed with saturated sodium carbonate solution and saturated aqueous sodium chloride solution, then dried over anhydrous sodium sulfate, and the solvent is distilled off. The residue is purified by thin layer chromatography (dichloromethane:methanol:28% ammonia water=90:10:1) to obtain 6-amino-9-[(3R)-1-(2-butynoyl)-3-pyrrolidinyl]-7-(4-phenoxyphenyl)-7,9-dihydro-8H-purin-8-one (Formula (XXVIII-R)) (75 mg).

The hydrochloride salt of the compound of Formula (XXVIII-R) can be prepared as follows: 6-amino-9-[(3R)-1-(2-butynoyl)-3-pyrrolidinyl]-7-(4-phenoxyphenyl)-7,9-dihydro-8H-purin-8-one (3.0 g) (which may be prepared as described above) is placed in a 300 mL 3-neck pear-shaped flask, ethyl acetate (30 mL) and 1-propanol (4.5 mL) are added, and the external temperature is set at 70° C. (internal temperature 61° C.). After it is confirmed that the compound prepared in Step 8 has dissolved completely, 10% HCl/methanol (3.5 mL) is added, and after precipitation of crystals is confirmed, the crystals are ripened by the following sequence: external temperature 70° C. for 30 min, external temperature 60° C. for 30 min, external temperature 50° C. for 60 min, external temperature 40° C. for 30 min, room temperature for 30 min, and an ice bath for 30 min. The resulting crystals are filtered, washed with ethyl acetate (6 mL), and dried under vacuum at 50° C. to obtain white crystals of 6-amino-9-[(3R)-1-(2-butynoyl)-3-pyrrolidinyl]-7-(4-phenoxyphenyl)-7,9-dihydro-8H-purin-8-one hydrochloride (2.76 g).

In an embodiment, the BTK inhibitor is a compound selected from the structures disclosed in U.S. Patent Application Publication No. US 2014/0330015 A1, the disclosure of which is incorporated by reference herein.

In an embodiment, the BTK inhibitor is a compound of Formula (B):

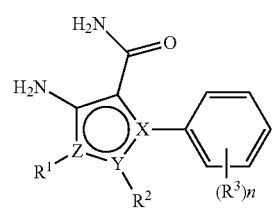

Formula (B)

or a pharmaceutically acceptable salt, solvate, hydrate, cocrystal, or prodrug thereof, wherein:

X—Y—Z is N—C—C and $R^2$ is present, or C—N—N and $R^2$ is absent;

$R^1$ is a 3-8 membered, N-containing ring, wherein the N is unsubstituted or substituted with $R^4$;

$R^2$ is H or lower alkyl, particularly methyl, ethyl, propyl or butyl; or $R^1$ and $R^2$ together with the atoms to which they are attached, form a 4-8 membered ring, preferably a 5-6 membered ring, selected from cycloalkyl, saturated or unsaturated heterocycle, aryl, and heteroaryl rings unsubstituted or substituted with at least one substituent L-$R^4$;

$R^3$ is in each instance, independently halogen, alkyl, S-alkyl, CN, or OR$^5$;

n is 1, 2, 3, or 4, preferably 1 or 2;

L is a bond, NH, heteroalkyl, or heterocyclyl;

$R^4$ is COR', CO$_2$R', or SO$_2$R', wherein R' is substituted or unsubstituted alkyl, substituted or unsubstituted alkenyl, substituted or unsubstituted alkynyl;

$R^5$ is H or unsubstituted or substituted heteroalkyl, alkyl, cycloalkyl, saturated or unsaturated heterocyclyl, aryl, or heteroaryl.

In some embodiments, the BTK inhibitor is one of the following particular embodiments of Formula B:

X—Y—Z is C—N—N and $R^2$ is absent; and $R^1$ is 3-8 membered, N-containing ring, N-substituted with $R^4$;

X—Y—Z is N—C—C and $R^2$ is present, $R^1$ is 3-8 membered, N-containing ring, N-substituted with $R^4$; and $R^2$ is H or lower alkyl;

X—Y—Z is N—C—C and $R^2$ is present; and $R^1$ and $R^2$ together with the atoms to which they are attached, form a 4-8 membered ring selected from cycloalkyl, saturated or unsaturated heterocycle, aryl, and heteroaryl rings unsubstituted or substituted with at least one substituent L-$R^4$, wherein preferred rings of $R^1$ and $R^2$ are 5-6-membered, particularly dihydropyrrole, tetrahydropyridine, tetrahydroazepine, phenyl, or pyridine;

X—Y—Z is N—C—C and $R^2$ is present; and $R^1$ and $R^2$ together with the atoms to which they are attached, form a 5-6 membered ring, preferably (a) phenyl substituted with a single -L-$R^4$, or (b) dihydropyrrole or tetrahydropyridine, N-substituted with a single -L-$R^4$ wherein L is bond;

$R^1$ is piperidine or azaspiro[3.3]heptane, preferably N-substituted with $R^4$;

$R^4$ is COR' or $SO_2R'$, particularly wherein R' is substituted or unsubstituted alkenyl, particularly substituted or unsubstituted ethenyl; or $R^5$ is unsubstituted or substituted alkyl or aryl, particularly substituted or unsubstituted phenyl or methyl, such as cyclopropyl-substituted methyl with or tetrabutyl-substituted phenyl.

In some embodiments, the BTK inhibitor is one of the following particular embodiments of Formula B:

$R^1$ is piperidine or azaspiro[3.3]heptane, N-substituted with $R^4$, wherein $R^4$ is H, COR' or $SO_2R'$, and R' is substituted or unsubstituted alkenyl, particularly substituted or unsubstituted ethenyl;

$R^3$ is —$OR^5$, $R^5$ is phenyl, and n is 1;

$R^1$ and $R^2$, together with the atoms to which they are attached, form a 5-6 membered ring, preferably (a) phenyl substituted with a single -L-$R^4$, or (b) dihydropyrrole or tetrahydropyridine, N-substituted with a single -L-$R^4$ wherein L is bond; $R^3$ is —$OR^5$; n is 1; $R^4$ is COR', and R' is ethenyl; and $R^5$ is phenyl; and X—Y—Z is C—N—N and $R^2$ is absent; $R^1$ is piperidine, N-substituted with $R^4$; $R^3$ is —$OR^5$; n is 1; $R^4$ is COR', and R' is unsubstituted or substituted alkenyl, particularly ethenyl; and $R^5$ is substituted or unsubstituted aryl, particularly phenyl.

In an exemplary embodiment, the BTK inhibitor is a compound of Formula (B1), Formula (B1-2), or Formula (B1-3):

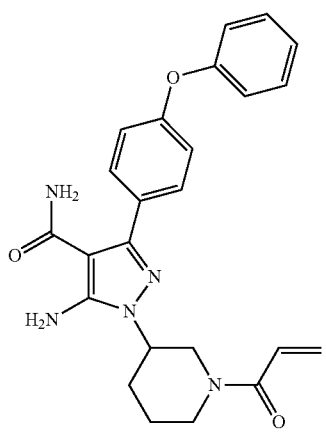

Formula (B1)

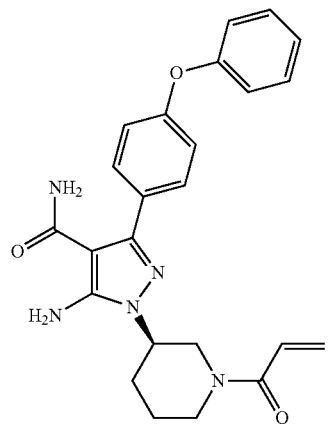

Formula (B1-2)

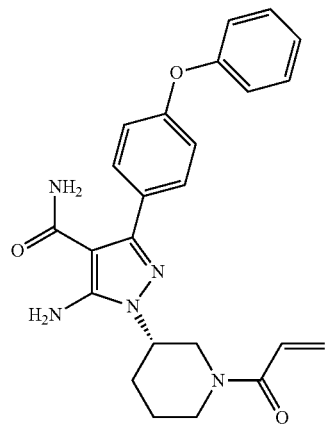

Formula (B1-3)

or a pharmaceutically acceptable salt, solvate, hydrate, cocrystal, or prodrug thereof. Formula (B1-2) is also known as BGB-3111. The preparation of these compounds is described in International Patent Application Publication No. WO 2014/173289 A1 and U.S. Patent Application Publication No. US 2015/0005277 A1, the disclosure of which is incorporated by reference herein.

In brief, the BTK inhibitor of Formula (B1) can be prepared by the following procedure.

Step 1. Preparation of 2-(hydroxy(4-phenoxyphenyl)methylene)malononitrile

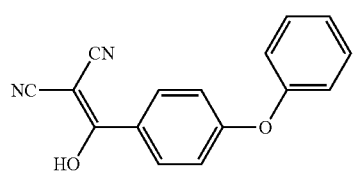 [SMILES: N#CC(C#N)=C(O)c1ccc(Oc2ccccc2)cc1]

A solution of 4-phenoxybenzoic acid (300 g, 1.4 mol) in $SOCl_2$ (1.2 L) is stirred at 80° C. under $N_2$ for 3 hours. The mixture is concentrated in vacuum to give the intermediate (315 g) which is used for next step without further purification.

To a solution of propanedinitrile (89.5 g, 1355 mmol) and DIEA (350 g, 2710 mmol) in THF (800 mL) is dropwise a solution of the intermediate (315 g) in toluene (800 mL) at 0-5° C. over 2 hours. The resultant mixture is allowed to warm to RT and stirred for 16 hours. The reaction is quenched with water (2.0 L) and extracted with of EA (2.0 L×3). The combined organic layers are washed with 1000 mL of 3 N HCl aqueous solution, brine (2.0 L×3), dried over Na₂SO₄ and concentrated to give the crude product (330 g, 93%).

Step 2. Preparation of 2-(Methoxy(4-phenoxyphenyl)methylene)malononitrile

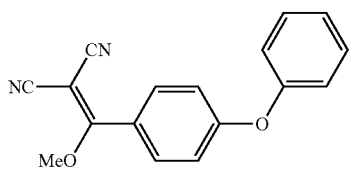 [SMILES: COC(=C(C#N)C#N)c1ccc(Oc2ccccc2)cc1]

A solution of 2-(hydroxy(4-phenoxyphenyl)methylene) malononitrile (50 g, 190.8 mmol) in CH(OMe₃) (500 mL) is heated to 75° C. for 16 hours. Then the mixture is concentrated to a residue and washed with MeOH (50 mL) to give 25 g (47.5%) of 2-(methoxy(4-phenoxyphenyl)methylene) malononitrile as a yellow solid.

Step 3. Preparation of 5-amino-3-(4-phenoxyphenyl)-1H-pyrazole-4-carbonitrile

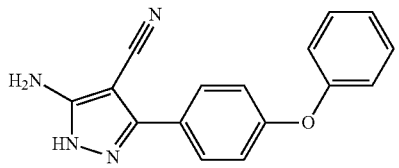 [SMILES: N#Cc1c(-c2ccc(Oc3ccccc3)cc2)n[nH]c1N]

To a solution of 2-(methoxy(4-phenoxyphenyl)methylene)malononitrile (80 g, 290 mmol) in ethanol (200 mL) is added hydrazine hydrate (20 mL). The mixture is stirred at RT for 16 hours then is concentrated to give the crude product and washed with MeOH (30 mL) to afford 55 g (68.8%) of 5-amino-3-(4-phenoxyphenyl)-1H-pyrazole-4-carbonitrile as a off-white solid.

Step 4. Preparation of tert-butyl 3-(tosyloxy)piperidine-1-carboxylate

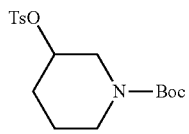

wherein "Boc" represents a tert-butyloxycarbonyl protecting group.

To a solution of tert-butyl 3-hydroxypiperidine-1-carboxylate (1.05 g, 5.0 mmol) in pyridine (8 mL) is added TsCl (1.425 g, 7.5 mmol). The mixture is stirred at RT under N₂ for two days. The mixture is concentrated and partitioned between 100 mL of EA and 100 mL of HCl (1 N) aqueous solution. The organic layer is separated from aqueous layer, washed with saturated NaHCO₃ aqueous solution (100 mL×2), brine (100 mL×3) and dried over Na₂SO₄. The organic layer is concentrated to afford 1.1 g (60%) of tert-butyl 3-(tosyloxy)piperidine-1-carboxylate as a colorless oil.

Step 5. Preparation of tert-butyl 3-(5-amino-4-cyano-3-(4-phenoxyphenyl)-1H-pyrazol-1-yl)piperidine-1-carboxylate

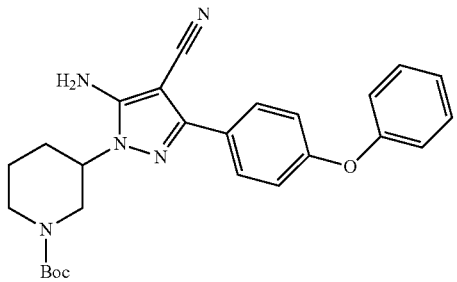 [SMILES: CC(C)(C)OC(=O)N1CCCC(n2nc(-c3ccc(Oc4ccccc4)cc3)c(C#N)c2N)C1]

To a solution of tert-butyl 3-(tosyloxy)piperidine-1-carboxylate (355 mg, 1.0 mmol) and 5-amino-3-(4-phenoxyphenyl)-1H-pyrazole-4-carbonitrile (276 mg, 1.0 mmol) in 5 mL of DMF is added Cs₂CO₃ (650 mg, 2.0 mmol). A tosyloxy leaving group is employed in this reaction. The mixture is stirred at RT for 16 hours, 75° C. for 3 hours and 60° C. for 16 hours. The mixture is concentrated washed with brine (100 mL×3) and dried over Na₂SO₄. The material is concentrated and purified by chromatography column on silica gel (eluted with petroleum ether/ethyl actate=3/1) to afford 60 mg (13%) of tert-butyl 3-(5-amino-4-cyano-3-(4-phenoxyphenyl)-1H-pyrazol-1-yl)piperidine-1-carboxylate as a yellow oil.

Step 6. Preparation of tert-butyl 3-(5-amino-4-carbamoyl-3-(4-phenoxyphenyl)-1H-pyrazol-1-yl)piperidine-1-carboxylate

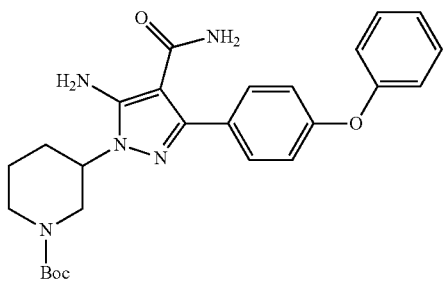 [SMILES: CC(C)(C)OC(=O)N1CCCC(n2nc(-c3ccc(Oc4ccccc4)cc3)c(C(N)=O)c2N)C1]

To a solution of tert-butyl 3-(5-amino-4-cyano-3-(4-phenoxyphenyl)-1H-pyrazol-1-yl)piperidine-1-carboxylate (100 mg, 0.22 mmol) in DMSO (2 mL) and ethanol (2 mL) was added the solution of NaOH (200 mg, 5 mmol) in water (1 mL) and H₂O₂(1 mL). The mixture is stirred at 60° C. for 15 min and concentrated to remove EtOH, after which 10 mL of water and 50 mL of ethyl acetate are added. The organic layer is separated from aqueous layer, washed with brine (30 mL×3) and dried over Na₂SO₄. After concentration, 50 mg of residue is used directly in the next step, wherein 50 mg of residue is purified by pre-TLC (eluted with petroleum ether/ethyl actate=1/1) to afford 12 mg (30%) of tert-butyl 3-(5-amino-4-carbamoyl-3-(4-phenoxyphenyl)-1H-pyrazol-1-yl)piperidine-1-carboxylate as a white solid.

Step 7. Preparation of 5-amino-3-(4-phenoxyphenyl)-1-(piperidin-3-yl)-1H-pyrazole-4-carboxamide

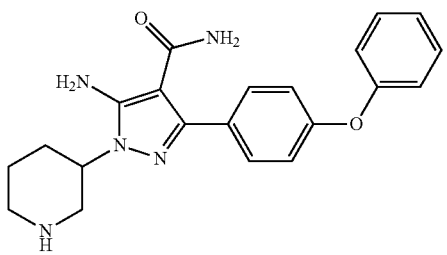 [SMILES: NC(=O)c1c(-c2ccc(Oc3ccccc3)cc2)nn(C2CCCNC2)c1N]

To a solution of tert-butyl 3-(5-amino-4-carbamoyl-3-(4-phenoxyphenyl)-1H-pyrazol-1-yl)piperidine-1-carboxylate (50 mg, 0.11 mmol) in ethyl acetate (1 mL) is added concentrated HCl (0.75 mL). The mixture is stirred at RT for 1 hour. Then saturated $NaHCO_3$ is added until pH >7, followed by ethyl acetate (50 mL). The organic layer is separated from aqueous layer, washed with brine (50 mL×3) and dried over $Na_2SO_4$. The resulting product is concentrated and purified by Pre-TLC (eluted with dichloromethane/MeOH/$NH_3$—$H_2O$=5/1/0.01) to afford 10 mg (25%) of 5-amino-3-(4-phenoxyphenyl)-1-(piperidin-3-yl)-1H-pyrazole-4-carboxamide as a white solid.

Step 8. Preparation of 1-(1-acryloylpiperidin-3-yl)-5-amino-3-(4-phenoxyphenyl)-1H-pyrazole-4-carboxamide

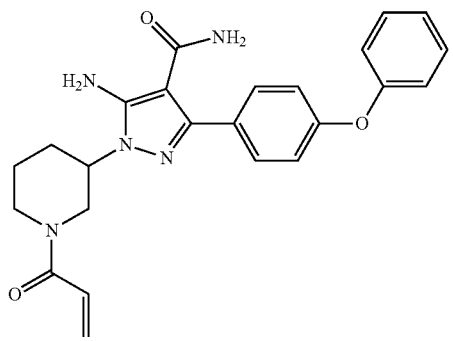 [SMILES: C=CC(=O)N1CCCC(n2nc(-c3ccc(Oc4ccccc4)cc3)c(C(N)=O)c2N)C1]

To a solution of 5-amino-3-(4-phenoxyphenyl)-1-(piperidin-3-yl)-1H-pyrazole-4-carboxamide (63 mg, 0.17 mmol) in dichloromethane (4 mL) is added pyridine (27 mg, 0.34 mmol). Then a solution of acryloyl chloride (12 mg, 0.17 mmol) in dichloromethane (1 mL) is added dropwise. After stirring at RT for 4 hours, the mixture is partitioned between 100 mL of dichloromethane and 100 mL of brine. The organic layer is separated from aqueous layer, washed with brine (100 mL×2) and dried over $Na_2SO_4$. The material is concentrated and purified by Pre-TLC (eluted with dichloromethane/MeOH=10/1) to afford 4 mg (5.5%) of 1-(1-acryloylpiperidin-3-yl)-5-amino-3-(4-phenoxyphenyl)-1H-pyrazole-4-carboxamide as a white solid.

The enantiomers of Formula (B1) provided by the procedure above may be prepared from 5-amino-3-(phenoxyphenyl)-1H-pyrazole-4-carbonitrile and (S)-tert-butyl 3-hydroxypiperidine-1-carboxylate using a similar procedure (step 4 to 8) for Formula (B1-2), or from (R)-tert-butyl 3-hydroxypiperidine-1-carboxylate using a similar procedure (step 4 to 8) for Formula (B1-3). Under appropriate conditions recognized by one of ordinary skill in the art, a racemic mixture of Formula (B1) may be separated by chiral HPLC, the crystallization of chiral salts, or other means described above to yield Formula (B1-2) and Formula (B1-3) of high enantiomeric purity.

In an embodiment, the BTK inhibitor is a compound selected from the structures disclosed in U.S. Patent Application Publication No. US 2015/0005277A1, the disclosure of which is incorporated by reference herein.

Other BTK inhibitors suitable for use in the described combination with a JAK-2 inhibitor or a PI3K inhibitor, the PI3K inhibitor being preferably selected from the group consisting of a PI3K-γ inhibitor, a PI3K-δ inhibitor, and a PI3K-γ,δ inhibitor, also include, but are not limited to, those described in, for example, International Patent Application Publication Nos. WO 2013/010868, WO 2012/158843, WO 2012/135944, WO 2012/135937, U.S. Patent Application Publication No. 2011/0177011, and U.S. Pat. Nos. 8,501,751, 8,476,284, 8,008,309, 7,960,396, 7,825,118, 7,732,454, 7,514,444, 7,459,554, 7,405,295, and 7,393,848, the disclosures of each of which are incorporated herein by reference.

JAK-2 Inhibitors

The JAK-2 inhibitor may be any JAK-2 inhibitor known in the art. In particular, it is one of the JAK-2 inhibitors described in more detail in the following paragraphs. In preferred embodiments, the compositions described herein provide a combination of a JAK-2 inhibitor with a BTK inhibitor, or methods of using a combination of a JAK-2 inhibitor with a BTK inhibitor. In some embodiments, the JAK-2 inhibitors provided herein are selective for JAK-2, in that the compounds bind or interact with JAK-2 at substantially lower concentrations than they bind or interact with other JAK receptors, including the JAK-3 receptor. In certain embodiments, the compounds bind to the JAK-3 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the JAK-2 receptor.

In an embodiment, the JAK-2 inhibitor is a compound of Formula (XXIX):

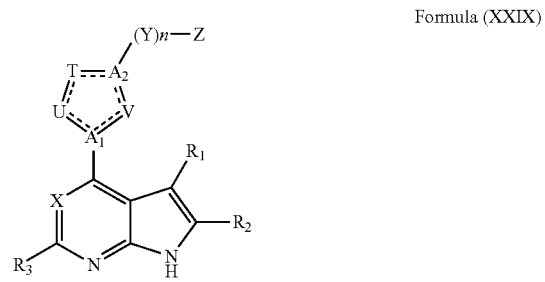

Formula (XXIX)

or a pharmaceutically acceptable salt, solvate, hydrate, cocrystal, or prodrug thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^cC(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$)R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$ $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$)R^b$, and $S(O)_2NR^cR^d$;

wherein when Z is H, n is 1;

or the —$(Y)_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$, $A^2$, U, T, and V, wherein said 4- to 20-membered aryl, cycloalkyl, heteroaryl, or heterocycloalkyl ring is optionally substituted by 1, 2, 3, 4, or 5 substituents independently selected from -$(W)_m$-Q;

W is $C_{1-8}$ alkylenyl, $C_{2-8}$ alkenylenyl, $C_{2-8}$ alkynylenyl, O, S, C(O), $C(O)NR^{c'}$, C(O)O, OC(O), $OC(O)NR^{c'}$, $NR^{c'}$, $NR^{c'}C(O)NR^{d'}$, S(O), $S(O)NR^{c'}$, $S(O)_2$, or $S(O)_2NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}OC(O)NR^{c''}R^{d''}$, $NR^{c''}R^{d''}$, $NR^{c''}C(O)R^{b''}$, $NR^{c''}C(O)OR^{a''}$, $NR^{c''}S(O)R^{b''}$, $NR^{c''}S(O)_2R^{b''}$, $S(O)R^{b''}$, $S(O)NR^{c''}R^{d''}$, $S(O)_2R^{b''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, halosulfanyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7OC(O)R^8$, $OC(O)NR^9R^{10}$, $NR^9R^{11}$, $NR^9C(O)R^8$, $NR^9C(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is H, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$;

$R^6$ is H, $C_{1-4}$ alkyl, $C_{2-4}$ alkenyl, $C_{2-4}$ alkynyl, $C_{1-4}$ haloalkyl, $OR^7$, $C(O)R^8$, $C(O)NR^9R^{10}$, $C(O)OR^7$, $S(O)R^8$, $S(O)NR^9R^{10}$, $S(O)_2R^8$, or $S(O)_2NR^9R^{10}$;

$R^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, arylcarbonyl, $C_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H and -$E^1$-$E^2$-$E^3$-$E^4$;

$D^1$ and $E^1$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^2$ and $E^2$ are independently absent or independently selected from $C_{1-6}$ alkylene, $C_{2-6}$ alkenylene, $C_{2-6}$ alkynylene, $(C_{1-6}$ alkylene$)_r$-O—$(C_{1-6}$ alkylene$)_s$, $(C_{1-6}$ alkylene$)_r$-S—$(C_{1-6}$ alkylene$)_s$, $(C_{1-6}$ alkylene$)_s$, —$NR^e$—$(C_{1-6}$ alkylene$)_s$, $(C_{1-6}$ alkylene$)_r$-CO—$(C_{1-6}$ alkylene$)_s$, $(C_{1-6}$ alkylene$)_r$-COO—$(C_{1-6}$ alkylene$)_s$, $(C_{1-6}$ alkylene$)_r$-$CONR^e$—$(C_{1-6}$ alkylene$)_s$, $(C_{1-6}$ alkylene$)_r$-SO—$(C_{1-6}$ alkylene$)_s$, $(C_{1-6}$ alkylene$)_r$-$SO_2$—$(C_{1-6}$ alkylene$)_s$, $(C_{1-6}$ alkylene$)_r$-$SONR^e$—$(C_{1-6}$ alkylene$)_s$, and $(C_{1-6}$ alkylene$)_r$- $NR^eCONR^f$—$(C_{1-6}$ alkylene$)_s$, wherein each of the $C_{1-6}$ alkylene, $C_{2-6}$ alkenylene, and $C_{2-6}$ alkynylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^3$ and $E^3$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^4$ and $E^4$ are independently selected from H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$)R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, —$C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$;

$R^a$ is H, $Cy^1$, —$(C_{1-6}$ alkyl$)$-$Cy^1$, $C_{1-6}$ alkyl, $C_{1-6}$ haloalkyl, $C_{2-6}$ alkenyl, $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

$R^b$ is H, $Cy^1$, —$(C_{1-6}$ alkyl$)$-Cy, $C_{1-6}$ alkyl, $C_{1-6}$ haloalkyl, $C_{2-6}$ alkenyl, $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{a'}$ and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

$R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^c$ and $R^d$ are independently selected from H, $Cy^1$, —$(C_{1-6}$ alkyl$)$-$Cy^1$, $C_{1-10}$ alkyl, $C_{1-6}$ haloalkyl, $C_{2-6}$ alkenyl, $C_{2-6}$ alkynyl, wherein said $C_{1-10}$ alkyl, $C_{1-6}$ haloalkyl, $C_{2-6}$ alkenyl, or $C_{2-6}$ alkynyl, is optionally substituted with 1, 2, or 3 substituents independently selected from $Cy^1$, —$(C_{1-6}$ alkyl$)$-$Cy^1$, OH, CN, amino, halo, $C_{1-6}$ alkyl, $C_{1-6}$ haloalkyl, $C_{1-6}$ haloalkyl, and halosulfanyl;

or $R^c$ and $R^d$ together with the N atom to which they are attached form a 4-, 5-, 6- or 7-membered heterocycloalkyl group optionally substituted with 1, 2, or 3 substituents independently selected from $Cy^1$, —$(C_{1-6}$ alkyl$)$-$Cy^1$, OH, CN, amino, halo, $C_{1-6}$ alkyl, $C_{1-6}$ haloalkyl, $C_{1-6}$ haloalkyl, and halosulfanyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^i$ is H, CN, $NO_2$, or $C_{1-6}$ alkyl;
$R^e$ and R are independently selected from H and $C_{1-6}$ alkyl;
$R^i$ is H, CN, or $NO_2$;
m is 0 or 1;
n is 0 or 1;
p is 0, 1, 2, 3, 4, 5, or 6;
q is 0, 1, 2, 3, 4, 5 or 6;
r is 0 or 1; and
s is 0 or 1.

In some embodiments, when X is N, n is 1, and the moiety formed by $A^1$, $A^2$, U, T, V, and —$(Y)_n$—Z has the formula:

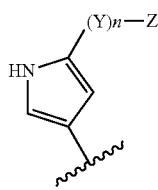

then Y is other than $(CR^{11}R^{12})_pC(O)NR^c(CR^{11}R^{12})_q$.

In some embodiments, when X is N, the 5-membered ring formed by $A^1$, $A^2$, U, T, and V is other than pyrrolyl.

In some embodiments, when X is CH, n is 1, and the moiety formed by $A^1$, $A^2$, U, T, V, and $-(Y)_n-Z$ has the formula:

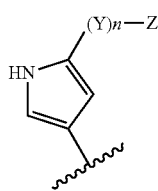

then $-(Y)_n-Z$ is other than COOH.

In some embodiments, when X is CH or C-halo, $R^1$, $R^2$, and $R^3$ are each H, n is 1, and the moiety formed by $A^1$, $A^2$, U, T, V, and $-(Y)_n-Z$ has the formula:

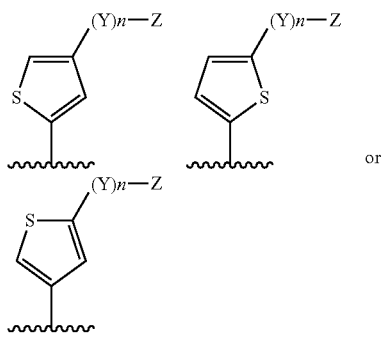

then Y is other than $(CR^{11}R^{12})_pC(O)NR^c(CR^{11}R^{12})_q$ or $(CR^{11}R^{12})_pC(O)(CR^{11}R^{12})_q$.

In some embodiments, when X is CH or C-halo, $R^1$, $R^2$, and $R^3$ are each H, n is 0, and the moiety formed by $A^1$, $A^2$, U, T, V, and $-(Y)_n-Z$ has the formula:

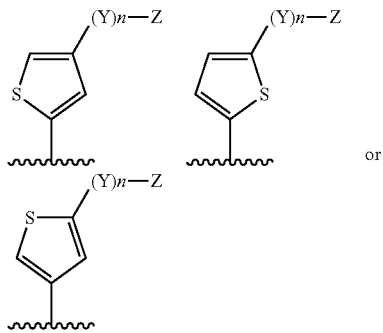

then Z is other than CN, halo, or $C_{1-4}$ alkyl.

In some embodiments, when X is CH or C-halo, $R^1$, $R^2$, and $R^3$ are each H, n is 1, and the moiety formed by $A^1$, $A^2$, U, T, V, and $-(Y)_n-Z$ has the formula:

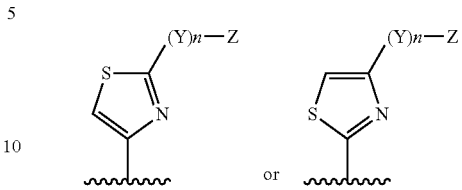

then Y is other than $(CR^{11}R^{12})_pC(O)NR^c(CR^{11}R^{12})_q$ or $(CR^{11}R^{12})_pC(O)(CR^{11}R^{12})_q$.

In some embodiments, when X is CH or C-halo, $R^1$, $R^2$, and $R^3$ are each H, n is 1, and the moiety formed by $A^1$, $A^2$, U, T, V, and $-(Y)_n-Z$ has the formula:

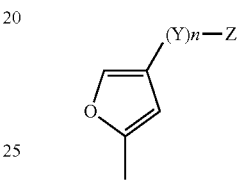

then Y is other than $(CR^{11}R^{12})_pNR^c(CR^{11}R^{12})_q$.

In some embodiments, when X is CH or C-halo and $R^1$, $R^2$, and $R^3$ are each H, then the moiety formed by $A^1$, $A^2$, U, T, V, and $-(Y)_n-Z$ has a formula other than:

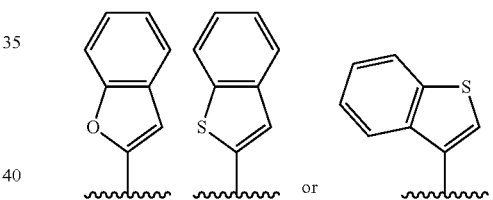

In some embodiments:

Z is H, halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$;

Q is H, halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2 NR^{c'}R^{d'}$;

$Cy^1$ and $Cy^1$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)OR^{a''}$, $NR^{c''}S(O)R^{b''}$, $NR^{c''}S(O)_2R^{b''}$, $S(O)R^{b''}$, $S(O)NR^{c''}R^{d''}$, $S(O)_2R^{b''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7 OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is H, halo, $C_{1-4}$ alkyl, $C_{2-4}$ alkenyl, $C_{2-4}$ alkynyl, $C_{1-4}$ haloalkyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$;

$R^6$ is H, $C_{1-4}$ alkyl, $C_{2-4}$ alkenyl, $C_{2-4}$ alkynyl, $C_{1-4}$ haloalkyl, $OR^7$, $C(O)R^8$, $C(O)NR^9R^{10}$, $C(O)OR^7$, $S(O)R^8$, $S(O)NR^9R^{10}$, $S(O)_2R^8$, or $S(O)_2NR^9R^{10}$;

$R^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, arylcarbonyl, $C_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H, halo, OH, CN, $C_{1-4}$ alkyl, $C_{1-4}$ haloalkyl, $C_{2-4}$ alkenyl, $C_{2-4}$ alkynyl, $C_{1-4}$ hydroxyalkyl, $C_{1-4}$ cyanoalkyl, aryl, heteroaryl, cycloalkyl, and heterocycloalkyl;

$R^a$, $R^{a'}$, and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^b$, $R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl.

In some embodiments, X is N.

In some embodiments, X is $CR^4$.

In some embodiments, $A^1$ is C.

In some embodiments, $A^1$ is N.

In some embodiments, $A^2$ is C.

In some embodiments, $A^2$ is N.

In some embodiments, at least one of $A^1$, $A^2$, U, T, and V is N.

In some embodiments, the 5-membered ring formed by $A^1$, $A^2$, U, T, and V is pyrrolyl, pyrazolyl, imidazolyl, oxazolyl, thiazolyl, or oxadiazolyl.

In some embodiments, the 5-membered ring formed by $A^1$, $A^2$, U, T, and V is selected from:

113

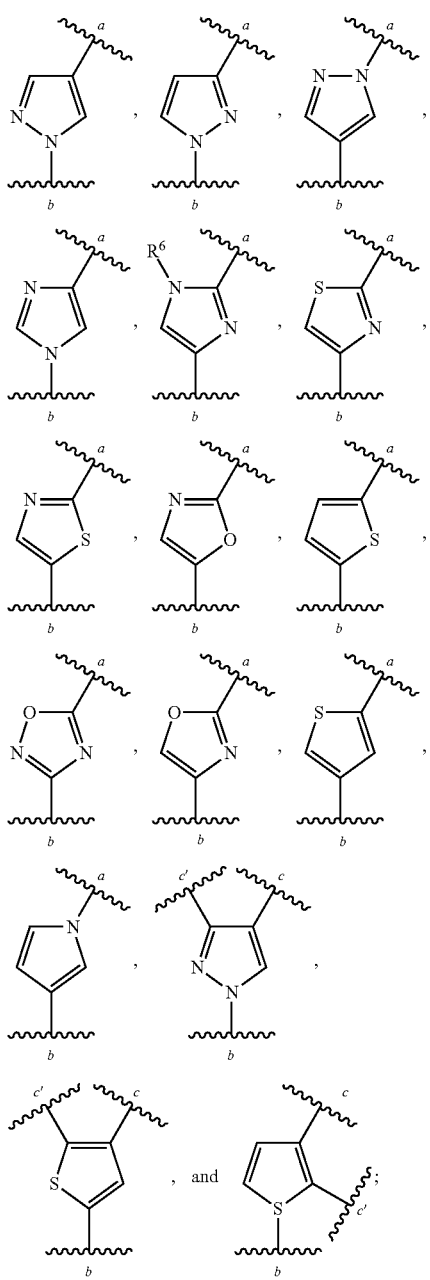

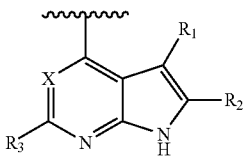

wherein:
a designates the site of attachment of moiety —(Y)$_n$—Z;
b designates the site of attachment to the core moiety:

and
c and c' designate the two site of attachment of the fused 4- to 20-membered aryl, cycloalkyl, heteroaryl, or heterocycloalkyl ring.

114

In some embodiments, the 5-membered ring formed by $A^1$, $A^2$, U, T, and V is:

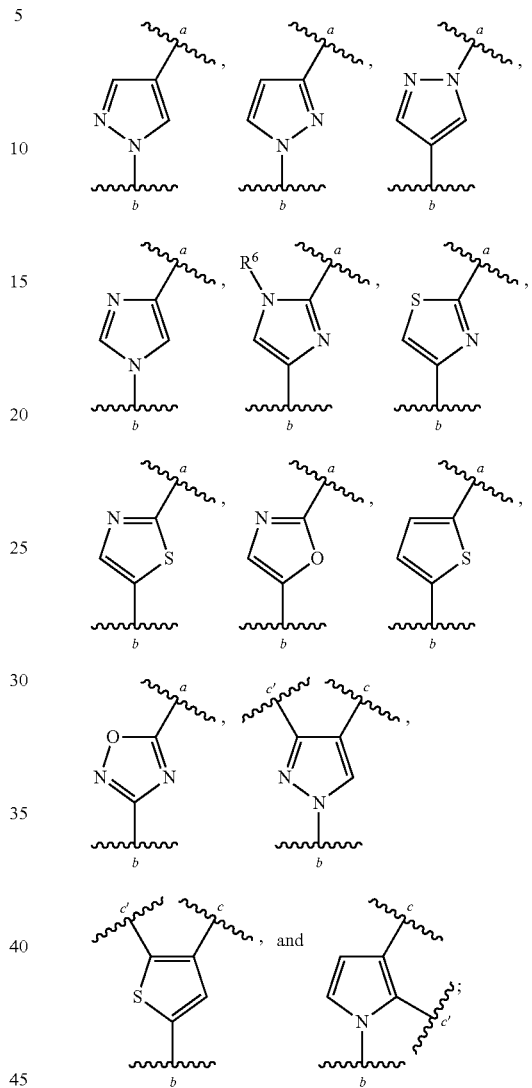

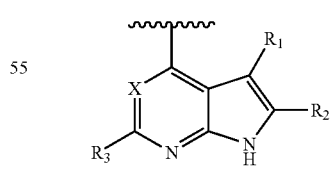

wherein:
a designates the site of attachment of moiety —(Y)$_n$—Z;
b designates the site of attachment to the core moiety.

and
c and c' designate the two sites of attachment of the fused 4- to 20-membered aryl, cycloalkyl, heteroaryl, or heterocycloalkyl ring.

In some embodiments, the 5-membered ring formed by $A^1$, $A^2$, U, T, and V is selected from:

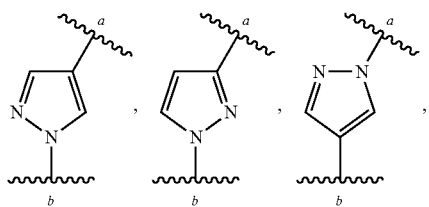

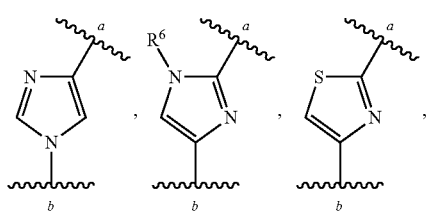

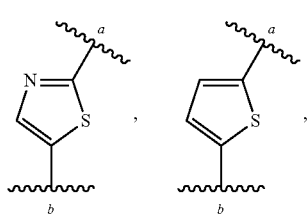

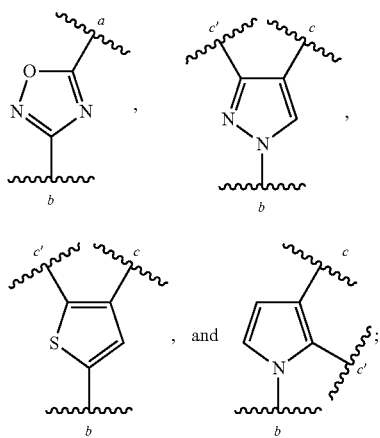

wherein:
a designates the site of attachment of moiety —(Y)$_n$—Z;
b designates the site of attachment to the core moiety:

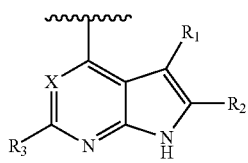

and
c and c' designate the two sites of attachment of the fused 4- to 20-membered aryl, cycloalkyl, heteroaryl, or heterocycloalkyl ring.

In some embodiments, the 5-membered ring formed by A$^1$, A$^2$, U, T, and V is selected from:

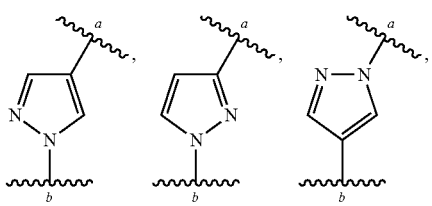

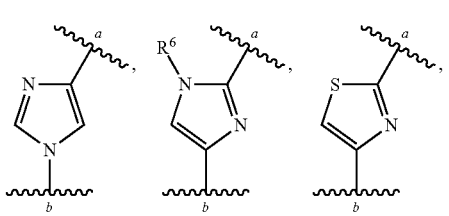

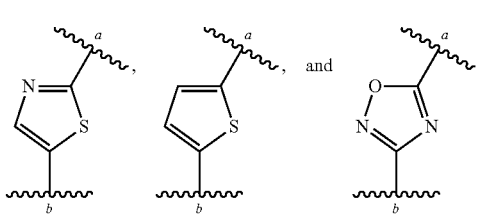

wherein:
a designates the site of attachment of moiety —(Y)$_n$—Z;
b designates the site of attachment to the core moiety:

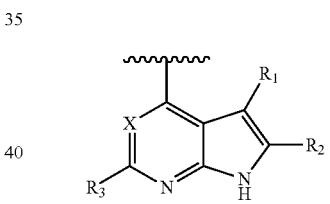

In some embodiments, the 5-membered ring formed by A$^1$, A$^2$, U, T, and V is selected from:

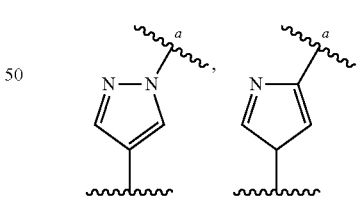

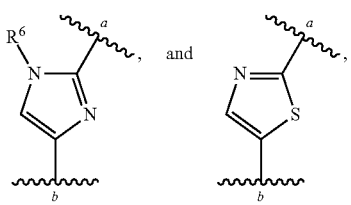

wherein:
a designates the site of attachment of moiety —(Y)$_n$—Z;

b designates the site of attachment to the core moiety:

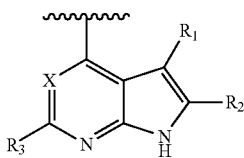

In some embodiments, the 5-membered ring formed by $A^1$, $A^2$, U, T, and V is selected from:

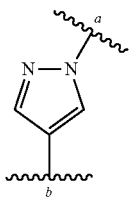

wherein:
a designates the site of attachment of moiety —$(Y)_n$—Z;
b designates the site of attachment to the core moiety:

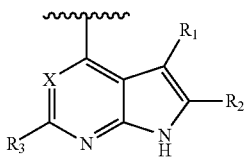

In some embodiments, n is 0.
In some embodiments, n is 1.
In some embodiments, n is 1 and Y is $C_{1-8}$ alkylene, $C_{2-8}$ alkenylene, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, wherein said $C_{1-8}$ alkylene or $C_{2-8}$ alkenylene, is optionally substituted with 1, 2, or 3 halo, OH, CN, amino, $C_{1-4}$ alkylamino, or $C_{2-8}$ dialkylamino.

In some embodiments, n is 1 and Y is $C_{1-8}$ alkylene, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, wherein said $C_{1-8}$ alkylene is optionally substituted with 1, 2, or 3 halo, OH, CN, amino, $C_{1-4}$ alkylamino, or $C_{2-8}$ dialkylamino.

In some embodiments, n is 1 and Y is $C_{1-8}$ alkylene optionally substituted with 1, 2, or 3 halo, OH, CN, amino, $C_{1-4}$ alkylamino, or $C_{2-8}$ dialkylamino.

In some embodiments, n is 1 and Y is ethylene optionally substituted with 1, 2, or 3 halo, OH, CN, amino, $C_{1-4}$ alkylamino, or $C_{2-8}$ dialkylamino.

In some embodiments, n is 1 and Y is $(CR^{11}R^{12})_pC(O)(CR^{11}R^{12})_q$, $(CR^{11}R^{12})_pC(O)NR^c(CR^{11}R^{12})_q$, or $(CR^{11}R^{12})_pC(O)O(CR^{11}R^{12})_q$.

In some embodiments, Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, or $(CR^{11}R^{12})_pS(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$.

In some embodiments, Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, or $(CR^{11}R^{12})_pS(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from $D^4$.

In some embodiments, Y is $C_{1-8}$ alkylene, $C_{2-8}$ alkenylene, $C_{2-8}$ alkynylene, or $(CR^{11}R^{12})_p$—$(C_{3-10}$ cycloalkylene)-$(CR^{11}R^{12})_q$, wherein said $C_{1-8}$ alkylene, $C_{2-8}$ alkenylene, $C_{2-8}$ alkynylene, or cycloalkylene, is optionally substituted with 1, 2, or 3 substituents independently selected from -$D^1$-$D^2$-$D^3$-$D^4$.

In some embodiments, Y is $C_{1-8}$ alkylene, $C_{2-8}$ alkenylene, $C_{2-8}$ alkynylene, or $(CR^{11}R^{12})_p$—$(C_{3-10}$ cycloalkylene)-$(CR^{11}R^{12})_q$, wherein said $C_{1-8}$ alkylene, $C_{2-8}$ alkenylene, $C_{2-8}$ alkynylene, or cycloalkylene, is optionally substituted with 1, 2, or 3 substituents independently selected from $D^4$.

In some embodiments, Y is $C_{1-8}$ alkylene, $C_{2-8}$ alkenylene, or $C_{2-8}$ alkynylene, each optionally substituted with 1, 2, or 3 substituents independently selected from -$D^1$-$D^2$-$D^3$-$D^4$ In some embodiments, Y is $C_{1-8}$ alkylene optionally substituted with 1, 2, or 3 substituents independently selected from -$D^1$-$D^2$-$D^3$-$D^4$.

In some embodiments, Y is $C_{1-8}$ alkylene optionally substituted with 1, 2, or 3 substituents independently selected from $D^4$.

In some embodiments, Y is $C_{1-8}$ alkylene, $C_{2-8}$ alkenylene, $C_{2-8}$ alkynylene, $(CR^{11}R^{12})_pO$—$(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_p NR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene is optionally substituted with 1, 2, or 3 substituents independently selected from halo, OH, CN, amino, $C_{1-4}$ alkylamino, and $C_{2-8}$ dialkylamino.

In some embodiments, Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_p OC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from halo, OH, CN, amino, $C_{1-4}$ alkylamino, and $C_{2-8}$ dialkylamino.

In some embodiments, p is 0.
In some embodiments, p is 1.
In some embodiments, p is 2.
In some embodiments, q is 0.
In some embodiments, q is 1.

In some embodiments, q is 2.

In some embodiments, one of p and q is 0 and the other of p and q is 1, 2, or 3.

In some embodiments, Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl)$R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl))$R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $—C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NRS(O)_2R^b$, and $S(O)_2NR^cR^d$.

In some embodiments, Z is aryl or heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $—C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^c$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NRS(O)_2R^b$, and $S(O)_2NR^cR^d$.

In some embodiments, Z is cycloalkyl or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is cyclopropyl, cyclobutyl, cyclopentyl, cyclohexyl, or cycloheptyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$. In some embodiments, Z is $C_{1-8}$ alkyl, $C_{2-8}$ alkenyl, or $C_{2-8}$ alkynyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2 R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$, hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$ $NR^cC(O)R^b$ $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, 3, 4, 5, or 6 substituents independently selected from halo, $C_{1-4}$ alkyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, 3, 4, 5, or 6 substituents independently selected from halo, $C_{1-4}$ alkyl, $C_{1-4}$ haloalkyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, or 3 substituents independently selected from halo, $C_{1-4}$ alkyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, or 3 substituents independently selected from halo, $C_{1-4}$ alkyl, $C_{1-4}$ haloalkyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is substituted with at least one substituent comprising at least one CN group.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each substituted with at least one CN or $C_{1-4}$ cyanoalkyl and optionally substituted with 1, 2, 3, 4, or 5 further substituents selected from halo, $C_{1-4}$ alkyl, $C_{2-8}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each substituted with at least one CN or C$_{1-4}$ cyanoalkyl and optionally substituted with 1, 2, 3, 4, or 5 further substituents selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, wherein the —(Y)$_n$—Z moiety is taken together with i) A$^2$ to which said moiety is attached, ii) R$^5$ or R$^6$ of either T or V, and iii) the C or N atom to which said R$^5$ or R$^6$ of either T or V is attached to form a 4- to 20-membered aryl, cycloalkyl, heteroaryl, or heterocycloalkyl ring fused to the 5-membered ring formed by A$^1$, A$^2$, U, T, and V, wherein said 4- to 20-membered aryl, cycloalkyl, heteroaryl, or heterocycloalkyl ring is optionally substituted by 1, 2, 3, 4, or 5 substituents independently selected from -(W)$_m$-Q.

In some embodiments, wherein the —(Y)$_n$—Z moiety is taken together with i) A$^2$ to which said moiety is attached, ii) R$^5$ or R$^6$ of either T or V, and iii) the C or N atom to which said R$^5$ or R$^6$ of either T or V is attached to form a 4- to 8-membered aryl, cycloalkyl, heteroaryl, or heterocycloalkyl ring fused to the 5-membered ring formed by A$^1$, A$^2$, U, T, and V, wherein said 4- to 8-membered aryl, cycloalkyl, heteroaryl, or heterocycloalkyl ring is optionally substituted by 1, 2, 3, 4, or 5 substituents independently selected from -(W)$_m$-Q.

In some embodiments, the —(Y)$_n$—Z moiety is taken together with i) A$^2$ to which said moiety is attached, ii) R$^5$ or R$^6$ of either T or V, and iii) the C or N atom to which said R$^5$ or R$^6$ of either T or V is attached to form a 6-membered aryl, cycloalkyl, heteroaryl, or heterocycloalkyl ring fused to the 5-membered ring formed by A$^1$, A$^2$, U, T, and V, wherein said 6-membered aryl, cycloalkyl, heteroaryl, or heterocycloalkyl ring is optionally substituted by 1, 2, or 3 substituents independently selected from halo, CN, NO$_2$, C$_{1-8}$ alkyl, C$_{2-8}$ alkenyl, C$_{2-8}$ alkynyl, C$_{1-8}$ haloalkyl, aryl, cycloalkyl, heteroaryl, or heterocycloalkyl wherein said C$_{1-8}$ alkyl, C$_{2-8}$ alkenyl, C$_{2-8}$ alkynyl, C$_{1-8}$ haloalkyl, aryl, cycloalkyl, heteroaryl, or heterocycloalkyl is optionally substituted by 1, 2 or 3 CN.

In some embodiments, Cy$^1$ and Cy$^2$ are independently selected from aryl, heteroaryl, cycloalkyl, and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$, S(O)R$^{b''}$, S(O)NR$^{c''}$R$^{d''}$, S(O)$_2$R$^{b''}$, and S(O)$_2$NR$^{c''}$R$^{d''}$.

In some embodiments, Cy$^1$ and Cy$^2$ are independently selected from aryl, heteroaryl, cycloalkyl, and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$S(O)R$^{b''}$, S(O)NR$^{c''}$R$^{d''}$, S(O)$_2$R$^{b''}$, and S(O)$_2$NR$^{c''}$R$^{d''}$.

In some embodiments, Cy$^1$ and Cy$^2$ are independently selected from cycloalkyl and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$OC(O)NR$^{c''}$R$^{d''}$, NR$^{c''}$R$^{d''}$, NR$^{c''}$C(O)R$^{b''}$, NR$^{c''}$C(O)OR$^{a''}$, S(O)R$^{b''}$, S(O)NR$^{c''}$R$^{d''}$, S(O)$_2$R$^{b''}$, and S(O)$_2$NR$^{c''}$R$^{d''}$.

In some embodiments, Cy$^1$ and Cy$^2$ are independently selected from cycloalkyl optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$S(O)R$^{b''}$, S(O)NR$^{c''}$R$^{d''}$, S(O)$_2$R$^{b''}$, and S(O)$_2$NR$^{c''}$R$^{d''}$.

In some embodiments, R$^1$, R$^2$, R$^3$, and R$^4$ are independently selected from H, halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^7$, SR$^7$, C(O)R$^8$, C(O)NR$^9$R$^{10}$, C(O)OR$^7$OC(O)R$^8$, OC(O)NR$^9$R$^{10}$, NR$^9$R$^{10}$, NR$^9$C(O)R$^8$, NR$^c$C(O)OR$^7$, S(O)R$^8$, S(O)NR$^9$R$^{10}$, S(O)$_2$R$^8$, NR$^9$S(O)$_2$R$^8$, and S(O)$_2$NR$^9$R$^{10}$.

In some embodiments, R$^1$, R$^2$, R$^3$, and R$^4$ are independently selected from H, halo, and C$_{1-4}$ alkyl.

In some embodiments, R$^1$, R$^2$, R$^3$, and R$^4$ are each H.

In some embodiments, R$^1$ is H, halo, or C$_{1-4}$ alkyl.

In some embodiments, R$^5$ is H, halo, C$_{1-4}$ alkyl, C$_{2-4}$ alkenyl, C$_{2-4}$ alkynyl, C$_{1-4}$ haloalkyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, or S(O)$_2$NR$^9$R$^{10}$.

In some embodiments, R$^5$ is H, halo, C$_{1-4}$ alkyl, C$_{1-4}$ haloalkyl, halosulfanyl, CN, or NR$^9$R$^{10}$.

In some embodiments, R$^5$ is H, halo, C$_{1-4}$ alkyl, C$_{1-4}$ haloalkyl, CN, or NR$^9$R$^{10}$.

In some embodiments, R$^5$ is H.

In some embodiments, R$^6$ is H or C$_{1-4}$ alkyl.

In some embodiments, R$^6$ is H.

In some embodiments, R$^{11}$ and R$^{12}$ are independently selected from H, halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl)R$^b$, and S(O)$_2$NR$^c$R$^d$, wherein said C$_{1-8}$ alkyl, C$_{2-8}$ alkenyl, or C$_{2-8}$ alkynyl, is optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$.

In some embodiments, R$^{11}$ and R$^{12}$ are independently selected from H, halo, OH, CN, (C$_{1-4}$)alkyl, (C$_{1-4}$)haloalkyl, halosulfanyl, SCN, (C$_{2-4}$)alkenyl, (C$_{2-4}$)alkynyl, (C$_{1-4}$)hydroxyalkyl, (C$_{1-4}$)cyanoalkyl, aryl, heteroaryl, cycloalkyl, and heterocycloalkyl.

In some embodiments, R$^{11}$ and R$^{12}$ are independently selected from H, halo, OH, CN, (C$_{1-4}$)alkyl, (C$_{1-4}$)haloalkyl, (C$_{2-4}$)alkenyl, (C$_{2-4}$)alkynyl, (C$_{1-4}$)hydroxyalkyl, (C$_{1-4}$)cyanoalkyl, aryl, heteroaryl, cycloalkyl, and heterocycloalkyl.

In a preferred embodiment, the JAK-2 inhibitor is ruxolitinib (available from Incyte Corp. and Novartis AG). In a preferred embodiment, the JAK-2 inhibitor is ruxolitinib phosphate (available from Incyte Corp. and Novartis AG). In a preferred embodiment, the JAK-2 inhibitor is (R)-3-(4-(7H-pyrrolo[2,3-d]pyrimidin-4-yl)-1H-pyrazol-1-yl)-3-cyclopentylpropanenitrile. In a preferred embodiment, the JAK-2 inhibitor is the phosphate salt of (R)-3-(4-(7H-pyrrolo[2,3-d]pyrimidin-4-yl)-1H-pyrazol-1-yl)-3-cyclopentylpropanenitrile. In a preferred embodiment, the JAK-2 inhibitor is (3R)-3-cyclopentyl-3-[4-(7H-pyrrolo[2,3-d]pyrimidin-4-yl)-1H-pyrazol-1-yl]propanenitrile. In a preferred embodiment, the JAK-2 inhibitor is a compound of Formula (XXX):

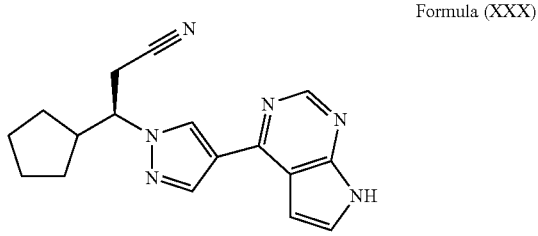 [SMILES: N#CC[C@H](C1CCCC1)n1cc(-c2ncnc3[nH]ccc23)cn1]

Formula (XXX)

or a pharmaceutically acceptable salt, solvate, hydrate, cocrystal, or prodrug thereof. The preparation of this compound is described in U.S. Pat. Nos. 8,604,043, 7,834,022, 8,486,902, 8,530,485, 7,598,257, 8,541,425, and 8,410,265 and U.S. Patent Application Publication Nos. 2010/0298355 A1, 2008/0312258 A1, 2011/0082159 A1, 2011/0086810 A1, 2013/0345157 A1, 2014/0018374 A1, 2014/0005210 A1, 2011/0223210 A1, 2011/0224157 A1, 2007/0135461 A1, 2010/0022522 A1, 2013/0253193 A1, 2013/0253191 A1, 2013/0253190 A1, 2010/0190981 A1, 2013/0338134 A1, 2008/0312259 A1, 2014/0094477 A1, and 2014/0094476 A1, the disclosures of which are incorporated by reference herein. In an embodiment, the JAK-2 inhibitor is a compound selected from the structures disclosed in U.S. Pat. Nos. 8,604,043, 7,834,022, 8,486,902, 8,530,485, 7,598,257, 8,541,425, and 8,410,265 and U.S. Patent Application Publication Nos. 2010/0298355 A1, 2008/0312258 A1, 2011/0082159 A1, 2011/0086810 A1, 2013/0345157 A1, 2014/0018374 A1, 2014/0005210 A1, 2011/0223210 A1, 2011/0224157 A1, 2007/0135461 A1, 2010/0022522 A1, 2013/0253193 A1, 2013/0253191 A1, 2013/0253190 A1, 2010/0190981 A1, 2013/0338134 A1, 2008/0312259 A1, 2014/0094477 A1, and 2014/0094476 A1, the disclosures of which are incorporated by reference herein.

Ruxolitinib may be prepared according to the procedures given in the references above, or by the procedure of Example 67 of U.S. Pat. No. 7,598,257, the disclosure of which is specifically incorporated by reference herein. Briefly, the preparation is as follows:

Step 1. (2E)- and (2Z)-3-Cyclopentylacrylonitrile. To a solution of 1.0 M potassium tert-butoxide in THF (235 mL) at 0° C. was added dropwise a solution of diethyl cyanomethylphosphonate (39.9 mL, 0.246 mol) in TBF (300 mL). The cold bath was removed and the reaction was warmed to room temperature followed by recooling to 0° C., at which time a solution of cyclopentanecarbaldehyde (22.0 g, 0.224 mol) in THF (60 mL) was added dropwise. The bath was removed and the reaction warmed to ambient temperature and stirred for 64 hours. The mixture was partitioned between diethyl ether and water, the aqueous was extracted with three portions of ether, followed by two portions of ethyl acetate. The combined extracts were washed with brine, then dried over sodium sulfate, filtered and concentrated in vacuo to afford a mixture containing 24.4 g of olefin isomers which was used without further purification (89%). $^1$H NMR (400 MHz, CDCl3): δ 6.69 (dd, 1H, trans olefin), 6.37 (t, 1H, cis olefin), 5.29 (dd, 1H, trans olefin), 5.20 (d, 1H, cis olefin), 3.07-2.95 (m, 1H, cis product), 2.64-2.52 (m, 1H, trans product), 1.98-1.26 (m, 16H).

Step 2. (3R)- and (3S)-3-Cyclopentyl-3-[4-(7-[2-(trimethylsilyl)ethoxy]methyl-7H-pyrrolo[2,3-d]-pyrimidin-4-yl)-1H-pyrazol-1-yl]propanenitrile. To a solution of 4-(1H-pyrazol-4-yl)-7-[2-(trimethylsilyl)ethoxy]methyl-7H-pyrrolo[2,3-d]-pyrimidine (15.0 g, 0.0476 mol) in ACN (300 mL) was added 3-cyclopentylacrylonitrile (15 g, 0.12 mol) (as a mixture of cis and trans isomers), followed by DBU (15 mL, 0.10 mol). The resulting mixture was stirred at room temperature overnight. The ACN was evaporated. The mixture was diluted with ethyl acetate, and the solution was washed with 1.0 N HCl. The aqueous layer was back-extracted with three portions of ethyl acetate. The combined organic extracts were washed with brine, dried over sodium sulfate, filtered and concentrated. The crude product was purified by silica gel chromatography (gradient of ethyl acetate/hexanes) to yield a viscous clear syrup, which was dissolved in ethanol and evaporated several times to remove ethyl acetate, to afford 19.4 g of racemic adduct (93%). The enantiomers were separated by preparative-HPLC, (OD-H column, 15% ethanol/hexanes) and used separately in the next step to generate their corresponding final product. The final products (see Step 3) stemming from each of the separated enantiomers were found to be active JAK inhibitors; however, the final product stemming from the second peak to elute from the preparative-HPLC was more active than its enantiomer. The products may be isolated by preparative HPLC or other means known to those of skill in the art for use in Step 3 below. $^1$H NMR (300 MHz, CDCl3): δ 8.85 (s, 1H), 8.32 (s, 2H), 7.39 (d, 1H), 6.80 (d, 1H), 5.68 (s, 2H), 4.26 (dt, 1H), 3.54 (t, 2H), 3.14 (dd, 1H), 2.95 (dd, 1H), 2.67-2.50 (m, 1H), 2.03-1.88 (m, 1H), 1.80-1.15 (m, 7H), 0.92 (t, 2H), −0.06 (s, 9H); MS(ES): 437 (M+1).

Step 3. To a solution of 3-cyclopentyl-3-[4-(7-[2-(trimethylsilyl)ethoxy]methyl-7H-pyrrolo[2,3-d]-pyrimidin-4-yl)-1H-pyrazol-1-yl]propanenitrile (6.5 g, 0.015 mol, R or S enantiomer as isolated above) in DCM (40 mL) was added TFA (16 mL) and this was stirred for 6 hours. The solvent and TFA were removed in vacuo. The residue was dissolved in DCM and concentrated using a rotary evaporator two further times to remove as much as possible of the TFA. Following this, the residue was stirred with ethylenediamine (4 mL, 0.06 mol) in methanol (30 mL) overnight. The solvent was removed in vacuo, water was added and the product was extracted into three portions of ethyl acetate. The combined extracts were washed with brine, dried over sodium sulfate, decanted and concentrated to afford the crude product which was purified by flash column chromatography (eluting with a gradient of methanol/DCM). The resulting mixture was further purified by preparative-HPLC/MS (C18 eluting with a gradient of ACN/H2O containing 0.15% NH4OH) to afford product (2.68 g, 58%). $^1$H NMR (400 MHz, D6-dmso): δ 12.11 (br s, 1H), 8.80 (s, 1H), 8.67 (s, 1H), 8.37 (s, 1H), 7.60 (d, 1H), 6.98 (d, 1H), 4.53 (dt, 1H), 3.27 (dd, 1H), 3.19 (dd, 1H), 2.48-2.36 (m, 1H), 1.86-1.76 (m, 1H), 1.68-1.13 (m, 7H); MS(ES): 307 (M+1).

Ruxolitinib prepared according to the steps above, or any other procedure, may be used as its free base for the compositions and methods described heren. Ruxolitinib may also be used in a salt form. For example, a crystalline phosphoric acid salt of (R)-3-(4-(7H-pyrrolo[2,3-d]pyrimidin-4-yl)-1H-pyrazol-1-yl)-3-cyclopentylpropanenitrile may be prepared from the free base as follows according to the procedure given in Example 2 of U.S. Pat. No. 8,722,693, the disclosure of which is specifically incorporated herein by reference. To a test tube was added (R)-3-(4-(7H-pyrrolo[2,3-d]pyrimidin-4-yl)-1H-pyrazol-1-yl)-3-cyclopentylpropanenitrile (153.5 mg) and phosphoric acid (56.6 mg) followed by isopropyl alcohol (IPA) (5.75 mL). The resulting mixture was heated to clear, cooled to room temperature, and then stirred for another 2 hours. The precipitate was collected by filtration and the cake was washed with 0.6 mL of cold IPA. The cake was dried under vacuum to constant weight to provide the final salt product (171.7 mg). The phosphroic acid salt is a 1:1 salt by $^1$H NMR and crystallinity is confirmed by X-ray powder diffraction (XRPD). Differential scanning calorimetry (DSC) of the produce yields a sharp melting peak at about 198.7° C.

In an embodiment, the JAK-2 inhibitor is a compound of Formula (XXXI):

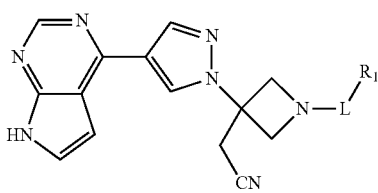

Formula (XXXI)

or a pharmaceutically acceptable salt, solvate, hydrate, cocrystal, or prodrug thereof, wherein:

L is $SO_2$ or CO;

$R^1$ is $C_{1-6}$ alkyl, $C_{3-7}$ cycloalkyl, phenyl, 5- or 6-membered heteroaryl, indolyl, $NR^2R^3$, or $OR^4$, wherein said alkyl, cycloalkyl, phenyl, or heteroaryl is optionally substituted with 1, 2, or 3 substituents independently selected from F, CN, and $C_{1-4}$ alkyl;

$R^2$ and $R^3$ are independently selected from H, $C_{1-4}$ alkyl, and phenyl; and $R^4$ is $C_{1-6}$ alkyl, phenyl, or benzyl.

In some embodiments, when L is $SO_2$, then $R^1$ is other than $OR^4$.

In some embodiments, when L is $SO_2$, then $R^1$ is $C_{1-6}$ alkyl, $C_{3-7}$ cycloalkyl, phenyl, 5- or 6-membered heteroaryl, or $NR^2R^3$, wherein said alkyl, cycloalkyl, phenyl, or heteroaryl is optionally substituted with 1, 2, or 3 substituents independently selected from F and $C_{1-4}$ alkyl.

In some embodiments, when L is CO, then $R^1$ is $C_{3-7}$ cycloalkyl, phenyl, 5- or 6-membered heteroaryl, indolyl, $NR^2R^3$, or $OR^4$, wherein said cycloalkyl, phenyl, or heteroaryl is optionally substituted with 1, 2, or 3 substituents independently selected from CN and $C_{1-4}$ alkyl.

In some embodiments, L is $SO_2$.
In some embodiments, L is CO.
In some embodiments, $R^1$ is methyl, ethyl, n-propyl, isopropyl, n-butyl, t-butyl, 2-methylprop-1-yl, 1-methylprop-1-yl, each optionally substituted with 1, 2, or 3 F.
In some embodiments, $R^1$ is $C_{1-4}$ alkyl.
In some embodiments, $R^1$ is ethyl.
In some embodiments, $R^1$ is $C_{3-7}$ cycloalkyl optionally substituted by $C_{1-4}$ alkyl.
In some embodiments, $R^1$ is phenyl optionally substituted with F, methyl, or CN.
In some embodiments, $R^1$ is 5-membered heteroaryl selected from thienyl, pyrazolyl, pyrrolyl, 1,2,4-oxadiazolyl, and isoxazolyl, each optionally substituted with $C_{1-4}$ alkyl.
In some embodiments, $R^1$ is pyridinyl.
In some embodiments, $R^1$ is $NR^2R^3$ or $OR^4$.

In some embodiments, L is $SO_2$ and $R^1$ is $C_{1-6}$ alkyl.

In an embodiment, the JAK-2 inhibitor is baricitinib (available from Incyte Corp. and Eli Lilly & Co.). In an embodiment, the JAK-2 inhibitor is 2-(3-(4-(7H-pyrrolo[2,3-d]pyrimidin-4-yl)-1H-pyrazol-1-yl)-1-(ethylsulfonyl)azetidin-3-yl)acetonitrile. In an embodiment, the JAK-2 inhibitor is a compound of Formula (XXXII):

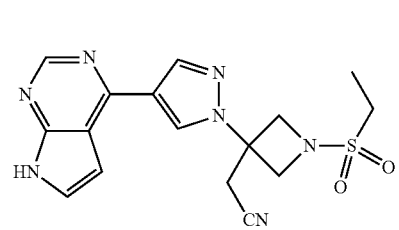

Formula (XXXII)

or a pharmaceutically acceptable salt, solvate, hydrate, cocrystal, or prodrug thereof. The preparation of this compound is described in U.S. Pat. Nos. 8,158,616 and 8,420,629, U.S. Patent Application Publication Nos. 2009/0233903 A1; 2013/0225556 A1; and, 2012/0077798 A1, and International Patent Application Publication No. WO 2014/0028756, the disclosures of which are incorporated by reference herein. In an embodiment, the JAK-2 inhibitor is a compound described in U.S. Pat. Nos. 8,158,616 and 8,420,629, U.S. Patent Application Publication Nos. 2009/0233903 A1; 2013/0225556 A1; and, 2012/0077798 A1, and International Patent Application Publication No. WO 2014/0028756, the disclosures of which are incorporated by reference herein.

In an embodiment, the JAK-2 inhibitor is a compound of Formula (XXXIII):

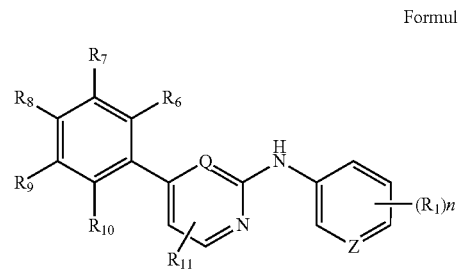

Formula (XXXIII)

or a pharmaceutically acceptable salt, solvate, hydrate, cocrystal, or prodrug thereof, wherein:

Q and Z are independently selected from N and $CR^1$; n is 1, 2 or 3;

$R^1$ is independently selected from hydrogen, halogen, $R^2$, $OR^2$, OH, $R^4$, $OR^4$, CN, $CF_3$, $(CH_2)_nN(R^2)_2$, $NO_2$, $R^2R^4$, $SO_2R^4$, $NR^2SO_2R^3$, $COR^4$, $NR^2COR^3$, $CO_2H$, $CO_2R^2$, $NR^2COR^4$, $R^2CN$, $R^2CN$, $R^2OH$, $R^2OR^3$ and $OR^5R^4$; or two $R^1$ substituents together with the carbons which they are attached to form an unsaturated 5 or 6 membered heterocyclyl;

$R^2$ is substituted or unsubstituted $C_{1-4}$alkyl or substituted or unsubstituted $C_{1-4}$ alkylene where up to 2 carbon atoms can be optionally replaced with CO, $NR^Y$, $CONR^Y$, S, $SO_2$ or O;

$R^3$ is $R^2$, $C_{2-4}$ alkenyl or substituted or unsubstituted aryl;

$R^4$ is $NH_2$, $NHR^2$, $N(R')_2$, substituted or unsubstituted morpholino, substituted or unsubstituted thiomorpholino, substituted or unsubstituted thiomorpholino-1-oxide, substituted or unsubstituted thiomorpholino-1, 1-dioxide, substituted or unsubstituted piperazinyl, substituted or unsubstituted piperidinyl, substituted or unsubstituted pyridinyl, substituted or unsubstituted pyrrolidinyl, substituted or unsubstituted pyrrolyl, substituted or unsubstituted oxazolyl, substituted or unsubstituted imidazolyl, substituted or unsubstituted tetrahydrofuranyl and substituted or unsubstituted tetrahydropyranyl;

$R^5$ is substituted or unsubstituted $C_{1-4}$alkylene;

$R^6$-$R^{10}$ are independently selected from H, $R^X$CN, halogen, substituted or unsubstituted $C_M$alkyl, $OR^1$, $CO_2R^1$, $N(R')_2$, $NO_2$, $CON(R')_2$, $SO_2N(R^Y)_2$, $N(SO_2R^{\wedge})_2$, substituted or unsubstituted piperazinyl, $N(R^Y)SO_2R^2$ and $CF_3$; $R^x$ is absent or substituted or unsubstituted $C_{i-6}$alkylene wherein up to 2 carbon atoms can be optionally replaced with CO, $NSO_2R^1$, $NR^Y$, $CONR^Y$, S, $SO_2$ or O; $R^y$ is H or substituted or unsubstituted $C_{1-4}$ alkyl; and $R^{11}$ is selected from H, halogen, substituted or unsubstituted $C_{1-4}$ alkyl, $OR^2$, $CO_2R^2$, CN, $CON(R')_2$ and $CF_3$, or an enantiomer thereof.

In a preferred embodiment, the JAK-2 inhibitor is momelotinib (Gilead Sciences). Momelotinib is also known as CYT-387. In a preferred embodiment, the JAK-2 inhibitor is N-(cyanomethyl)-4-(2-((4-morpholinophenyl)amino)pyrimidin-4-yl)benzamide. In a preferred embodiment, the JAK-2 inhibitor is a compound of Formula (XXXIV):

Formula (XXXIV)

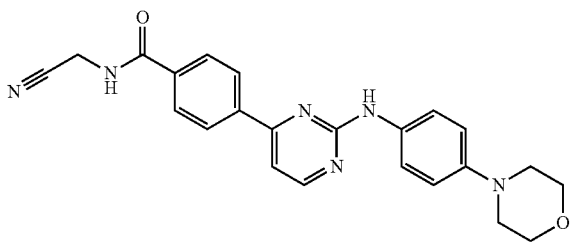

or a pharmaceutically acceptable salt, solvate, hydrate, cocrystal, or prodrug thereof. The preparation of this compound is described in U.S. Pat. No. 8,486,941 and U.S. Patent Application Publication Nos. 2010/0197671 A1; 2014/0005180 A1; 2014/0011803 A1; and, 2014/0073643 A1, the disclosures of which are incorporated by reference herein. In an embodiment, the JAK-2 inhibitor is a compound described in U.S. Pat. No. 8,486,941 and U.S. Patent Application Publication Nos. 2010/0197671 A1; 2014/0005180 A1; 2014/0011803 A1; and, 2014/0073643 A1, the disclosures of which are incorporated by reference herein.

In an embodiment, the JAK-2 inhibitor is a compound of Formula (XXXV):

Formula (XXXV)

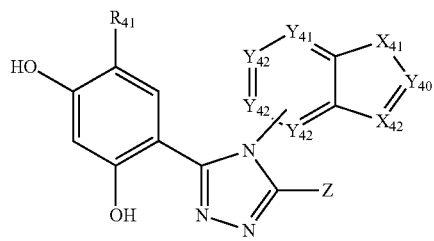

or a tautomer thereof, or a clathrate thereof, or a pharmaceutically acceptable salt, solvate, hydrate, cocrystal, or prodrug thereof, wherein:

$X_{41}$ is O, S, or $NR_{42}$
$X_{42}$ is $CR_{44}$ or N;
$Y_{40}$ is N or $CR_{43}$;
$Y_{41}$ is N or $CR_{45}$;
$Y_{42}$, for each occurrence, is independently N, C or $CR_{46}$;
Z is OH SH, or $NHR_7$;
$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —$NR_{10}R_{11}$, —$OR_7$, —C(O)$R_7$, —C(O)$OR_7$, —C(S)$R_7$, —C(O)$SR_7$, —C(S)$SR_7$, —C(S)$OR_7$, —C(S)$NR_{10}R_{11}$, —C($NR_8$)$OR_7$, —C($NR_8$)$R_7$, —C($NR_8$)$NR_{10}R_{11}$, —C($NR_8$)$SR_7$, —OC(O)$R_7$, —OC(O)$OR_7$, —OC(S)$OR_7$, —OC$_{(8)}$$OR_7$, —SC(O)$R_7$, —SC(O)$OR_7$, —SC($NR_8$)$OR_7$, —OC(S)$R_7$, —SC(S)$R_7$, —SC(S)$OR_7$, —OC(O)$NR_{10}R_{11}$, —OC(S)$NR_{10}R_{11}$, —OC($NR_8$)$NR_{10}R_{11}$, —SC(O)$NR_{10}R_{11}$, —SC($NR_8$)$NR_{10}R_{11}$, —SC(S)$NR_{10}R_{11}$, —OC($NR_8$)$R_7$, —SC($NR_8$)$R_7$, —C(O)$NR_{10}R_{11}$, —$NR_8$C(O)$R_7$, —$NR_7$C(S)$R_7$, —$NR_7$C(S)$OR_7$, —$NR_7$C($NR_8$)$R_7$, —$NR_7$C(O)$OR_7$, —$NR_7$C($NR_8$)$OR_7$, —$NR_7$C(O)$NR_{10}R_{11}$, —$NR_7$C(S)$NR_{10}R_{11}$, —$NR_7$C($NR_8$)$NR_{10}R_{11}$, —$SR_7$, —S(O)$_p$$R_7$, —OS(O)$_p$$R_7$, —OS(O)$_p$$OR_7$, —OS(O)$_p$$NR_{10}R_{11}$, —S(O)$_p$ $OR_7$, —$NR_8$S(O)$_p$$R_7$, —$NR_7$S(O)$_p$$NR_{10}R_{11}$, —$NR_7$S(O)$_p$$OR_7$, —S(O)$_p$$NR_{10}R_{11}$, —SS(O)$_p$$R_7$, —SS(O)$_p$$OR_7$, —SS(O)$_p$$NR_{10}R_{11}$, —OP(O)($OR_7$)$_2$, or —SP(O)($OR_7$)$_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —C(O)$R_7$, —(CH$_2$)$_m$C(O)$OR_7$, —C(O)$OR_7$, —OC(O)$R_7$, —C(O)$NR_{10}R_{11}$, —S(O)$_p$$R_7$, —S(O)$_p$$OR_7$, or —S(O)$_p$$NR_{10}R_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —C(O)$R_7$, —C(O)$OR_7$, —OC(O)$R_7$, —C(O)$NR_{10}R_{11}$, —$NR_8$C(O)$R_7$, —$SR_7$, —S(O)$_p$$R_7$, —OS(O)$_p$$R_7$, —S(O)$_p$$OR_7$, —$NR_8$S(O)$_p$$R_7$, —S(O)$_p$$NR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —$NR_7$H, —$OR_{26}$, —$SR_{26}$, —$NHR_{26}$, —O(CH$_2$)$_m$OH, —O(CH$_2$)$_m$SH, —O(CH$_2$)$_m$$NR_7$H, —S(CH$_2$)$_m$OH, —S(CH$_2$)$_m$SH, —S(CH$_2$)$_m$$NR_7$H, —OC(O)$NR_{10}R_{11}$, —SC(O)$NR_{10}R_{11}$, —$NR_7$C(O)$NR_{10}R_{11}$, —OC(O)$R_7$, —SC(O)$R_7$, —$NR_7$C(O)$R_7$, —OC(O)$OR_7$, —SC(O)$OR_7$, —$NR_7$C(O)$OR_7$,

—OCH$_2$C(O)R$_7$, —SCH$_2$C(O)R$_7$, —NR$_7$CH$_2$C(O)R$_7$, —OCH$_2$C(O)OR$_7$, —SCR$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(N$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, or —NR$_7$C(N$_8$)NR$_{10}$R$_{11}$;

R$_{46}$, for each occurrence, is independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

R$_7$ and R$_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$, for each occurrence is, is independently, a lower alkyl;
p, for each occurrence, is, independently, 1 or 2; and
m, for each occurrence, is independently, 1, 2, 3, or 4.

In an embodiment, the JAK-2 inhibitor is a compound of Formula (XXXVI):

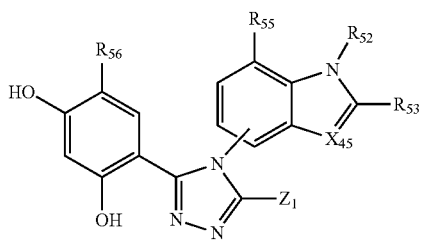

Formula (XXXVI)

or a tautomer thereof, or a clathrate thereof, or a pharmaceutically acceptable salt, solvate, hydrate, cocrystal, or prodrug thereof, wherein:
X$_{45}$ is CR$_{54}$ or N;
Z1 is —OH or —SH;
R$_{56}$ is selected from the group consisting of —H, methyl, ethyl, isopropyl, and cyclopropyl;

R$_{52}$ is selected from the group consisting of —H, methyl, ethyl, n-propyl, isopropyl, n-butyl, n-pentyl, n-hexyl, —(CH$_2$)$_2$OCH$_3$, —CH$_2$C(O)OH, and —C(O)N(CH$_3$)$_2$;

R$_{53}$ and R$_{54}$ are each, independently, —H, methyl, ethyl, or isopropyl; or R$_{53}$ and R$_{54}$ taken together with the carbon atoms to which they are attached form a phenyl, cyclohexenyl, or cyclooctenyl ring; and R$_{55}$ is selected from the group consisting of —H, —OH, —OCH$_3$, and —OCH$_2$CH$_3$.

In a preferred embodiment, the JAK-2 inhibitor is ganetespib. In a preferred embodiment, the JAK-2 inhibitor is 5-(2,4-dihydroxy-5-isopropylphenyl)-4-(1-methyl-1H-indol-5-yl)-2,4-dihydro-3H-1,2,4-triazol-3-one. In a preferred embodiment, the JAK-2 inhibitor is a compound of Formula (XXXVII):

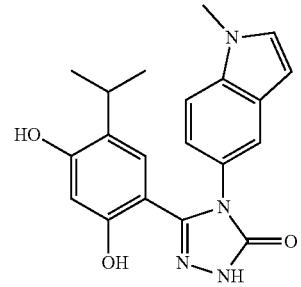

Formula (XXXVII)

or a pharmaceutically acceptable salt, solvate, hydrate, cocrystal, or prodrug thereof. The preparation of this compound is described in U.S. Pat. Nos. 7,825,148 and 8,628,752, U.S. Patent Application Publication Nos. 2006/0167070 A1; 2014/0024030 A1; 2014/0051665 A1; 2014/0045908 A1; 2012/0128665 A1; 2013/0109045 A1, and 2014/0079636 A1, and, International Patent Application Publication No. WO 2013/170182; WO 2013/028505; WO 2013/067162; WO 2013/173436; WO 2013/006864; WO 2012/162584; WO 2013/170159; WO 2013/067165; WO 2013/074594; WO 2012/162372; WO 2012/162293; and WO 2012/155063, the disclosures of which are incorporated by reference herein. In an embodiment, the JAK-2 inhibitor is a compound described in U.S. Pat. Nos. 7,825,148 and 8,628,752, U.S. Patent Application Publication Nos. 2006/0167070 A1; 2014/0024030 A1; 2014/0051665 A1; 2014/0045908 A1; 2012/0128665 A1; 2013/0109045 A1, and 2014/0079636 A1, and, International Patent Application Publication No. WO 2013/170182; WO 2013/028505; WO 2013/067162; WO 2013/173436; WO 2013/006864; WO 2012/162584; WO 2013/170159; WO 2013/067165; WO 2013/074594; WO 2012/162372; WO 2012/162293; and WO 2012/155063, the disclosures of which are incorporated by reference herein.

In an embodiment, the JAK-2 inhibitor is a compound of Formula (XXXVIII):

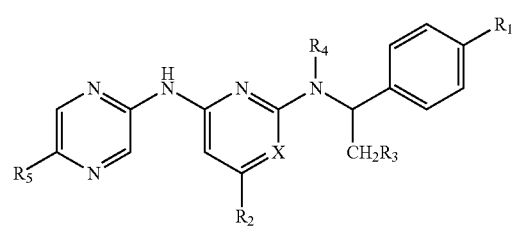

Formula (XXXVIII)

or a pharmaceutically acceptable salt, solvate, hydrate, cocrystal, or prodrug thereof, wherein the compound is defined by the following (I) or (II).
(I): X represents CH or N; $R_1$ represents a halogen;
$R_2$ represents: (1) H, (2) a halogen, (3) cyano, (4) a group represented by the following general formula [2]:

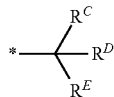

[2]

(wherein * indicates the binding position; and $R^C$, $R^D$ and $R^E$ are the same or different and each represents (a) H, or (b) alkyl optionally substituted by hydroxy or alkoxy, or alternatively two of $R^C$, $R^D$ and $R^E$ are taken together with the adjacent C to represent a N-containing saturated heterocyclic group and the other one is H, the saturated heterocyclic group optionally substituted by alkylsulfonyl),
(5) a group represented by the following general formula [3]:

[3]

(wherein * has the same meaning as described above; and $R^F$ and $R^G$ are the same or different and each represents (a) H, (b) alkyl optionally substituted by one or two groups selected from the group consisting of hydroxy, amino, dialkylamino, a saturated cyclic amino group, alkylcarbonylamino, alkylsulfonylamino, aryl, heteroaryl optionally substituted by alkyl, tetrahydrofuranyl, and carbamoyl, (c) alkylcarbonyl, (d) alkylsulfonyl, (e) carbamoyl, or (f) heteroaryl optionally substituted by alkyl, or alternatively $R^F$ and $R^G$ are taken together with the adjacent N to represent a saturated cyclic amino group, which may optionally be substituted by one or two groups selected from the group consisting of (a) halogen, (b) cyano, (c) hydroxy, (d) alkyl optionally substituted by one or two groups selected from the group consisting of hydroxy, alkoxy, amino, alkoxycarbonylamino, alkylsulfonylamino, and alkylcarbonylamino, (e) cycloalkyl, (f) haloalkyl, (g) alkoxy, (h) oxo, (i) a group represented by the following general formula [4]:

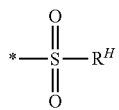

[4]

(wherein * has the same meaning as described above; and $R^H$ represents alkyl or aryl), (j) a group represented by the following general formula [5]:

[5]

(wherein * has the same meaning as described above; and $R^I$ and $R^J$ are the same or different and each represents H, alkyl, carbamoyl, alkylcarbonyl, or alkylsulfonyl), (k) a group represented by the following general formula [6]:

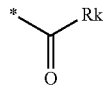

[6]

(wherein * has the same meaning as described above; and $R^K$ represents alkyl, hydroxy, amino, alkylamino, dialkylamino, cycloalkylamino, (cycloalkyl)alkylamino, (hydroxyalkyl)amino, (alkoxyalkyl)amino, alkoxy, alkylsulfonylamino, or a saturated cyclic amino group), and (1) a saturated cyclic amino group optionally substituted by hydroxy; and the saturated cyclic amino group, which is formed by combining $R^F$, $R^G$ and the adjacent N, may form a spiro-linkage with a group represented by the following general formula [7A] or [7B]:

[7A]

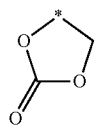

[7B]

(wherein has the same meaning as described above)),
(6) a group represented by the following general formula [8]:

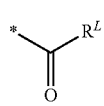

[8]

(wherein * has the same meaning as described above; and $R^L$ represents (a) alkyl, (b) hydroxy, (c) alkoxy, (d) saturated cyclic amino group optionally substituted by alkyl or alkylsulfonyl, or (e) an amino optionally substituted by one or two groups selected from the group consisting of alkyl, cycloalkyl, (cycloalkyl)alkyl, aralkyl; haloalkyl, dialkylaminoalkyl, alkoxyalkyl, and hydroxyalkyl),
(7) a group represented by the following general formula [9]:

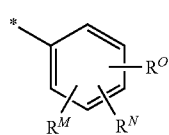

[9]

(wherein * has the same meaning as described above; and $R^M$, $R^N$ and $R^O$ are the same or different and each represents H, halogen, cyano, alkoxy, carbamoyl, sulfamoyl, monoalkylaminosulfonyl, or alkylsulfonyl, or alternatively two of $R^M$, $R^N$ and $R^O$ are taken together to represent methylenedioxy), (8) —$OR^P$ ($R^P$ represents an alkyl optionally substituted by a group selected from the group consisting of hydroxy, dialkylamino, alkoxy, tetrahydrofuranyl, and cycloalkyl, or an optionally O-containing saturated cyclic group optionally substituted by hydroxy), or (9) a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl;

$R_3$ represents H or hydroxy;
$R_2$ represents H or alkyl; and
$R_5$ represents H or alkyl;

(II): X represents —$CR^A$;
$R^A$ represents a group represented by the following general formula [10]:

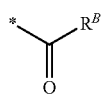
[10]

(wherein * has the same meaning as described above; and $R^B$ represents (a) amino optionally substituted by one or two groups selected from the group consisting of alkyl, cycloalkyl, (cycloalkyl)alkyl, and alkoxyalkyl, (b) alkoxy, (c) hydroxy, or (d) a saturated cyclic amino group);

$R_1$ represents a halogen;
$R_2$ represents H;
$R_3$ represents E or hydroxy;
$R_4$ represents H or alkyl; and
$R_5$ represents H or alkyl.

In a preferred embodiment, the JAK-2 inhibitor is NS-018. In an embodiment, the JAK-2 inhibitor is (S)—$N^2$-(1-(4-fluorophenyl)ethyl)-6-(1-methyl-1H-pyrazol-4-yl)-$N^4$-(pyrazin-2-yl)pyrimidine-2,4-diamine. NS-018 has been described in Nakaya, et al., *Blood Cancer J.* 2014, 4, e174. In an embodiment, the JAK-2 inhibitor has the chemical structure shown in Formula (XXXIX):

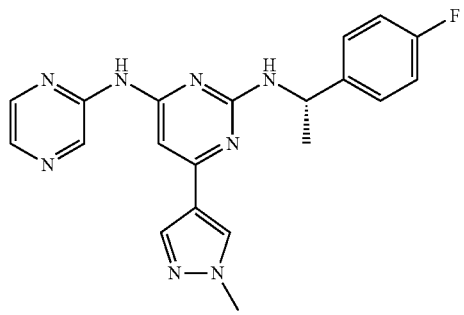

Formula (XXXIX)

or a pharmaceutically acceptable salt, solvate, hydrate, cocrystal, or prodrug thereof. The preparation of this compound is described in U.S. Pat. Nos. 8,673,891 and 8,586,591, U.S. Patent Application Publication Nos. 2011/0288065 A1 and 2013/0131082 A1, and International Patent Application Publication No. WO 2012/020787 and WO 2012/020786, the disclosures of which are incorporated by reference herein. In an embodiment, the JAK-2 inhibitor is a compound described in U.S. Pat. Nos. 8,673,891 and 8,586,591, U.S. Patent Application Publication Nos. 2011/0288065 A1 and 2013/0131082 A1, and International Patent Application Publication No. WO 2012/020787 and WO 2012/020786, the disclosures of which are incorporated by reference herein.

In an embodiment, the JAK-2 inhibitor is a compound of Formula (XL):

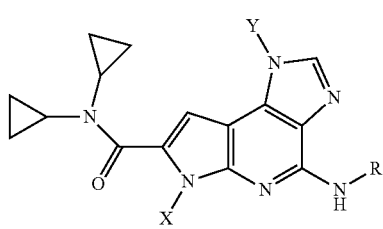

Formula (XL)

or a stereoisomer, tautomer, or pharmaceutically acceptable salt, solvate, hydrate, cocrystal, or prodrug thereof, wherein:
Y is $C_{1-4}$ alkyl;
X is $C_{1-4}$ alkyl;
R is

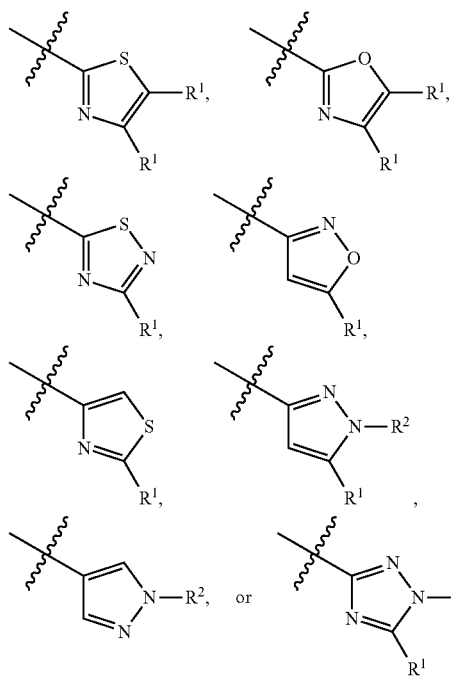

any of which are optionally fused with a 5 or 6 membered carbocycle or heterocycle having one heteroatom selected from $NR^3$ or S, said fused carbocycle or heterocycle being optionally substituted with 0-3 $R^1$.

$R^1$ is H, halo, CN, $C_{1-6}$ alkyl substituted with 0-3 $R^c$, $CF_3$, $CONR^aR^a$, $NR^aR^a$, $COOR^b$, $SO_2$—($C_{1-4}$)alkyl, $C(O)R^d$, cycloalkyl substituted with 0-3 $R^e$, furanyl, tetrahydropyranyl, or pyridinyl;

$R^2$ is absent, H, $C_{1-6}$ alkyl substituted with 0-3 $R^c$, $C(O)$O—($C_{1-4}$)alkyl, $SO_2$—($C_{1-4}$)alkyl, cycloalkyl substituted with 0-3 $R^e$, or tetrahydropyranyl;

$R^3$ is absent, H, or $C(O)O$—($C_{1-4}$)alkyl;

$R^a$ is H, $C_{1-6}$ alkyl substituted with 0-3 $R^e$, $C_{3-6}$ cycloalkyl substituted with 0-3 $R^e$, tetrahydropyranyl, or dioxotetrahydrothiophenyl;

$R^b$ is H or $C_{1-6}$ alkyl;

$R^c$ is H, halo, CN, OH, O—($C_{1-4}$)alkyl, O—($C_{1-4}$)alkyl-O—($C_{1-4}$)alkyl, $NH_2$, $N(C_{1-4}$ alkyl$)_2$, $C(O)N(C_{1-4}$ alkyl$)_2$, $SO_2$—($C_{1-4}$)alkyl, or morpholinyl or piperazinyl, either of which are optionally substituted with 0-1 $C_{1-4}$ alkyl;

$R^d$ is $C_{1-6}$ alkyl, or azeridinyl, azetidinyl, pyrrolidinyl, piperidinyl, morpholinyl, piperazinyl, dioxidothiomorpholinyl or tetrahydropyranyl, any of which are substituted with 0-2 $R^e$; and $R^e$ is H, halo, CN, $C_{1-4}$ alkyl, OH, O—($C_{1-4}$)alkyl, $SO_2$—($C_{1-4}$)alkyl, NHC(O)—($C_{1-4}$)alkyl, morpholinyl, OC(O)—($C_{1-4}$)alkyl, $C(O)N(C_{1-4}$ alkyl$)_2$, or O—($C_{1-4}$)alkyl-O—($C_{1-4}$)alkyl.

In an embodiment, the JAK-2 inhibitor is a compound of Formula (XL), wherein:

R is:

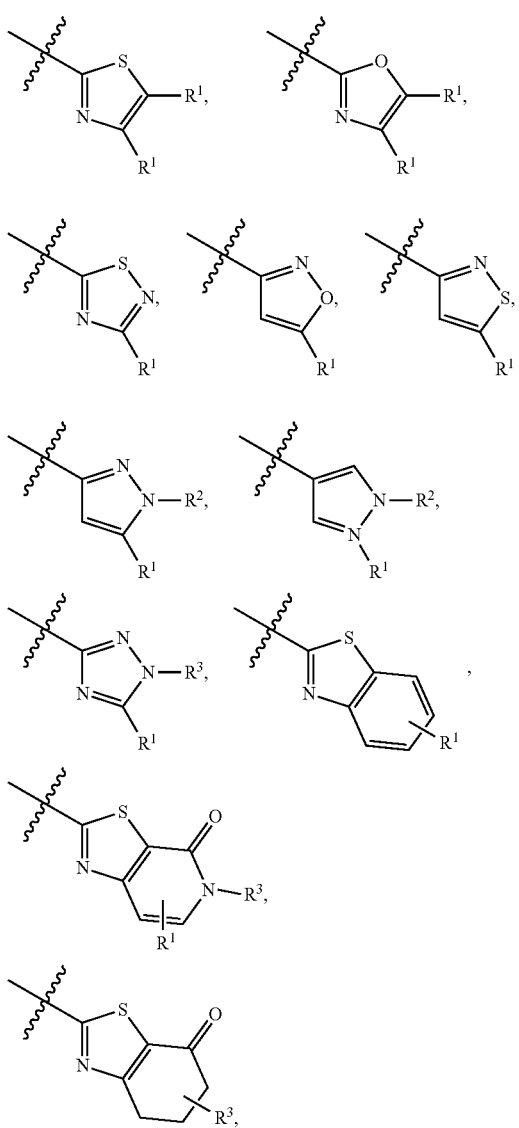

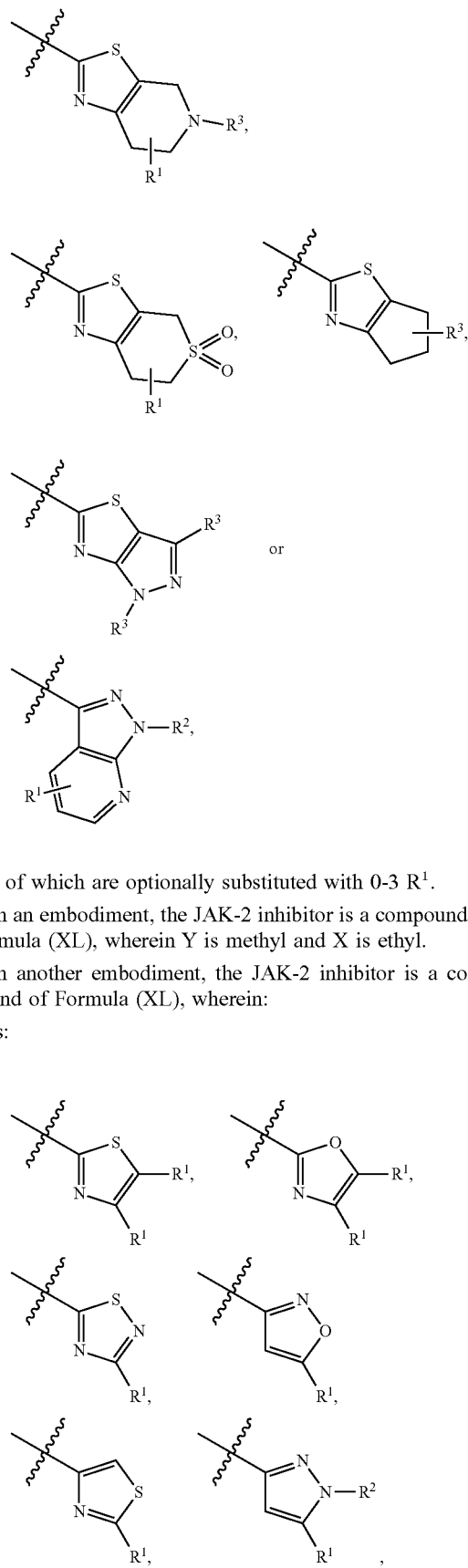

any of which are optionally substituted with 0-3 $R^1$.

In an embodiment, the JAK-2 inhibitor is a compound of Formula (XL), wherein Y is methyl and X is ethyl.

In another embodiment, the JAK-2 inhibitor is a compound of Formula (XL), wherein:

R is:

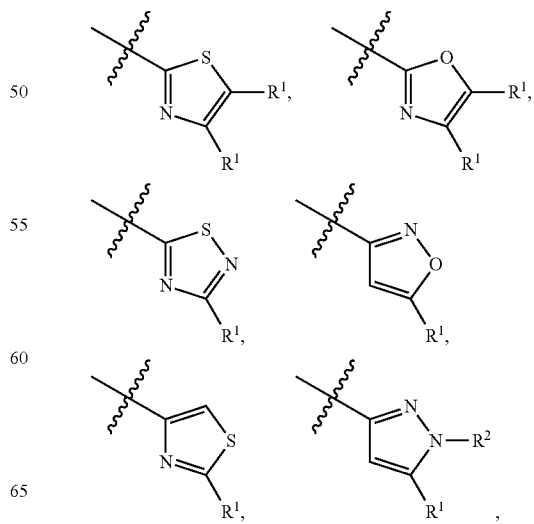

-continued

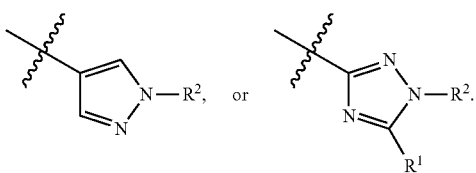

In an embodiment, the JAK-2 inhibitor is a compound of Formula (XL), wherein:
R is:

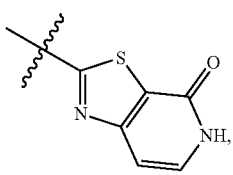

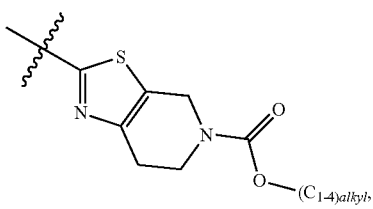

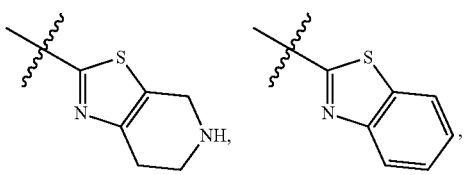

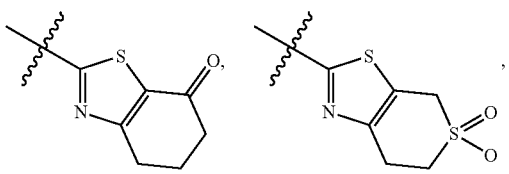

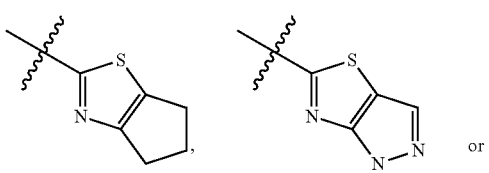

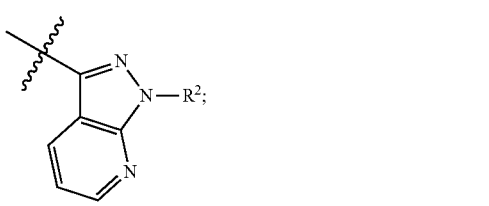

any of which are optionally substitute with 0-2 $R^1$.

In an embodiment, the JAK-2 inhibitor is a compound of Formula (XL), wherein

R is:

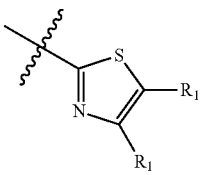

$R^1$ is H, halo, CN, $C_{1-6}$ alkyl substituted with 0-3 $R^e$, $CF_3$, $CONR^aR^a$, $COOR^b$, $SO_2$—$(C_{1-4})$alkyl, $C(O)R^d$, cycloalkyl substituted with 0-3 $R^e$, or pyridinyl;

$R^a$ is H, $C_{1-6}$ alkyl substituted with 0-3 $R^e$, $C_{3-6}$ cycloalkyl substituted with 0-3 $R^e$, tetrahydropyranyl or dioxotetrahydrothiophenyl;

$R^b$ is H or $C_{1-6}$ alkyl;

$R^c$ is H, halo, OH, O—$(C_{1-4})$alkyl, $SO_2$—$(C_{1-4})$alkyl or morpholinyl;

$R^d$ is $C_{1-6}$ alkyl, or azetidinyl, pyrrolidinyl, morpholinyl, piperazinyl or dioxidothiomorpholinyl, any of which are substituted with 0-2 $R^e$;

$R^e$ is H, halo, CN, OH, O—$(C_{1-4})$alkyl, $SO_2$—$(C_{1-4})$alkyl, NHC(O)—$(C_{1-4})$alkyl or morpholinyl.

In an embodiment, the JAK-2 inhibitor is a compound of Formula (XL), wherein:
R is:

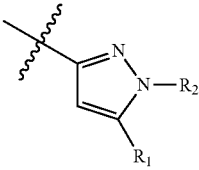

$R^1$ is H, halo, $C_{1-6}$ alkyl substituted with 0-3 $R^c$, $CF_3$, $CONR^aR^a$, $COOR^b$, $C(O)R^d$, cycloalkyl substituted with 0-3 $R^e$ or furanyl;

$R^2$ is H, $C_{1-6}$ alkyl substituted with 0-3 $R^c$, $SO_2$—$(C_{1-4})$alkyl, cycloalkyl substituted with 0-3 $R^e$, or tetrahydropyranyl;

$R^a$ is H, or $C_{1-6}$ alkyl substituted with 0-3 $R^e$;

$R^b$ is H or $C_{1-6}$ alkyl;

$R^c$ is H, halo, CN, OH, O—$(C_{1-4})$alkyl, O—$(C_{1-4})$alkyl-O—$(C_{1-4})$alkyl, $NH_2$, $N(C_{1-4}$ alkyl$)_2$, $C(O)N(C_{1-4}$ alkyl$)_2$, $SO_2$—$(C_{1-4})$alkyl, or morpholinyl or piperazinyl, either of which are optionally substituted with 0-1 $C_{1-4}$ alkyl;

$R^d$ is $C_{1-6}$ alkyl, or morpholinyl, piperazinyl or dioxidothiomorpholinyl, any of which are substituted with 0-2 $R^e$; and $R^e$ is H, $C_{1-4}$ alkyl, CN, OH, NHC(O)—$(C_{1-4})$alkyl or morpholinyl.

In an embodiment, the JAK-2 inhibitor is a compound of Formula (XL), wherein:
R is:

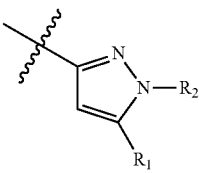

$R^1$ is $C_{1-6}$ alkyl substituted with 0-3 $R^c$; and
$R^2$ is $C_{1-6}$ alkyl.

In a preferred embodiment, the JAK-2 inhibitor is BMS-911543. In a preferred embodiment, the JAK-2 inhibitor is N,N-dicyclopropyl-4-((1,5-dimethyl-1H-pyrazol-3-yl)amino)-6-ethyl-1-methyl-1,6-dihydroimidazo[4,5-d]pyrrolo[2,3-b]pyridine-7-carboxamide. In a preferred embodiment, the JAK-2 inhibitor is a compound of Formula (XLI):

Formula (XLI)

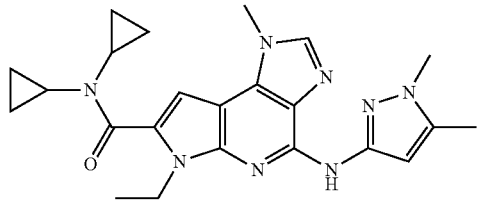

or a pharmaceutically acceptable salt, solvate, hydrate, cocrystal, or prodrug thereof. The preparation of this compound is described in U.S. Pat. Nos. 8,673,933 and 8,202,881 and U.S. Patent Application Publication Nos. 2013/0225551 A1 and 2011/0059943 A1, the disclosures of which are incorporated by reference herein. In an embodiment, the JAK-2 inhibitor is a compound described in U.S. Pat. Nos. 8,673,933 and 8,202,881 and U.S. Patent Application Publication Nos. 2013/0225551 A1 and 2011/0059943 A1, the disclosures of which are incorporated by reference herein.

In a preferred embodiment, the JAK-2 inhibitor is gandotinib. In a preferred embodiment, the JAK-2 inhibitor is 3-(4-chloro-2-fluorobenzyl)-2-methyl-N-(5-methyl-1H-pyrazol-3-yl)-8-(morpholinomethyl)imidazo[1,2-b]pyridazin-6-amine. In a preferred embodiment, the JAK-2 inhibitor is a compound of Formula (XLII):

Formula (XLII)

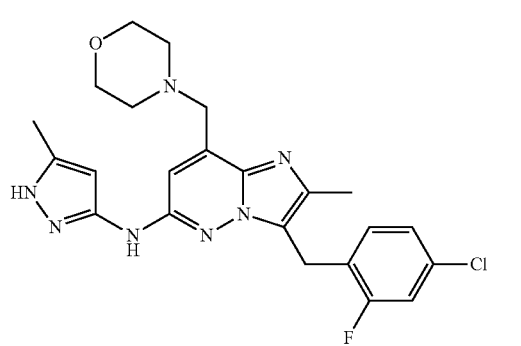

or a pharmaceutically acceptable salt, solvate, hydrate, cocrystal, or prodrug thereof. The preparation of this compound is described in U.S. Pat. No. 7,897,600 and U.S. Patent Application Publication Nos. 2010/0152181 A1 and 2010/0286139 A1, the disclosures of which are incorporated by reference herein. In an embodiment, the JAK-2 inhibitor is a compound described in U.S. Pat. No. 7,897,600 and U.S. Patent Application Publication Nos. 2010/0152181 A1 and 2010/0286139 A1, the disclosures of which are incorporated by reference herein.

In an embodiment, the JAK-2 inhibitor is a compound of Formula (XLIII):

Formula (XLIII)

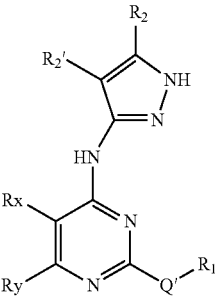

or a pharmaceutically acceptable salt, solvate, hydrate, cocrystal, or prodrug thereof, wherein:

$R^x$ and $R^y$ are independently selected from the group consisting of -T-$R^3$ and -L-Z—$R^3$;

Q' is selected from the group consisting of —$CR^{6''}$=$CR^{6''}$— and wherein said —$CR^{6''}$=$CR^{6''}$— may be a cis or trans double bond or a mixture thereof, $R^1$ is -T-(Ring D);

Ring D is a 5-7 membered monocyclic ring or 8-10 membered bicyclic ring selected from the group consisting of aryl, heteroaryl, heterocyclyl, and carbocyclyl, said heteroaryl or heterocyclyl ring having 1-4 ring heteroatoms selected from the group consisting of nitrogen, oxygen, and sulfur, wherein each substitutable ring carbon of Ring D is independently substituted by oxo, -T-$R^5$ or -V-Z—$R^5$, and each substitutable ring nitrogen of Ring D is independently substituted by —$R^4$;

T is a valence bond or —(C($R^{6'}$)$_2$)-A-;

A is a valence bond or a $C_1$-$C_3$ alkylidene chain wherein a methylene unit of said $C_{1-3}$ alkylidene chain is optionally replaced by —O—, —S—, —N($R^4$)—, —CO—, —CONH—, —NHCO—, —SO$_2$—, —SO$_2$NH—, —NHSO$_2$—, —CO$_2$—, —OC(O)—, —OC(O)NH—, or —NHCO$_2$—;

Z is a $C_{1-4}$ alkylidene chain;

L is selected from the group consisting of —O—, —S—, —SO—, —SO$_2$—, —N($R^6$)SO$_2$—SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$—O—, —C($R^6$)$_2$—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, and —C($R^6$)$_2$N($R^6$)CON($R^6$)—;

$R^2$ and $R^{2'}$ are independently selected from the group consisting of —R and -T-W-$R^6$, or $R^2$ and $R^{2'}$ taken together with their intervening atoms form a fused, 5-8 membered, unsaturated or partially unsaturated ring having 0-3 ring heteroatoms selected from the group consisting of nitrogen, oxygen, and sulfur, wherein each substitutable ring carbon of said fused ring formed by $R^2$ and $R^{2'}$ is independently substituted by halo, oxo, —CN, —NO$_2$, $R^7$, or -V-$R^6$, and each substitutable ring nitrogen of said ring formed by $R^2$ and $R^{2'}$ is independently substituted by —$R^4$;

$R^3$ is selected from the group consisting of —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$($C_{1-6}$ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, and —OC(=O)N(R)₂;

each R is independently hydrogen or an optionally substituted group selected from the group consisting of C₁₋₆ aliphatic, C₆₋₁₀ aryl, a heteroaryl ring having 5-10 ring atoms, and a heterocyclyl ring having 5-10 ring atoms;

each R⁴ is independently selected from the group consisting of —R⁷, —COR⁷, —CO₂(optionally substituted C₁₋₆ aliphatic), —CON(R⁷)₂, and —SO₂R⁷;

each R⁵ is independently selected from the group consisting of —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴) COR, —N(R⁴)CO₂ (optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, and —OC(=O)N(R⁴)₂;

V is selected from the group consisting of —O—, —S—, —SO—, —SO₂—, —N(R⁶)SO₂—, —SO₂N(R⁶)—, —N(R⁶)—, —CO—, —CO₂—, —N(R⁶)CO—, —N(R⁶) C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂ SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N (R⁶)N(R⁶)—, —C(R⁶)₂N(R⁶)SO₂N(R⁶)—, and —C(R⁶)₂ N(R⁶)CON(R⁶)—;

W is selected from the group consisting of —C(R⁶)₂O—, —C(R⁶)₂S—, —C(R⁶)₂SO—, —C(R⁶)₂SO₂—, —C(R⁶)₂ SO₂N(R⁶)—, —C(R⁶)₂N(R⁶)—, —CO—, —CO₂—, —C(R⁶)OC(O)—, —C(R⁶)OC(O)N(R⁶)—, C(R⁶)₂N(R⁶) CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N (R⁶)SO₂N(R⁶)—, —C(R⁶)₂N(R⁶)CON(R⁶)—, and —CON(R⁶)—;

each R⁶ is independently selected from the group consisting of hydrogen and an optionally substituted C₁₋₄ aliphatic group, or two R⁶ groups on the same nitrogen atom may be taken together with the nitrogen atom to form a 3-6 membered heterocyclyl or heteroaryl ring;

each R⁶' is independently selected from the group consisting of hydrogen and a C₁₋₄ aliphatic group, or two R⁶' on the same carbon atom are taken together to form a 3-8 membered carbocyclic ring;

each R⁶'' is independently selected from the group consisting of hydrogen, a C₁₋₄ aliphatic group, halogen, optionally substituted aryl, and optionally substituted heteroaryl, or two R⁶ on adjacent carbon atoms are taken together to form a 5-7 membered carbocyclic ring; and each R⁷ is independently selected from the group consisting of hydrogen and an optionally substituted C₁₋₆ aliphatic group, or two R⁷ on the same nitrogen are taken together with the nitrogen to form a 5-8 membered heterocyclyl or heteroaryl ring.

In a preferred embodiment, the JAK-2 inhibitor is ENMD-2076. In a preferred embodiment, the JAK-2 inhibitor is (E)-N-(5-methyl-1H-pyrazol-3-yl)-6-(4-methylpiperazin-1-yl)-2-styrylpyrimidin-4-amine. In a preferred embodiment, the JAK-2 inhibitor is a compound of Formula (XLIV):

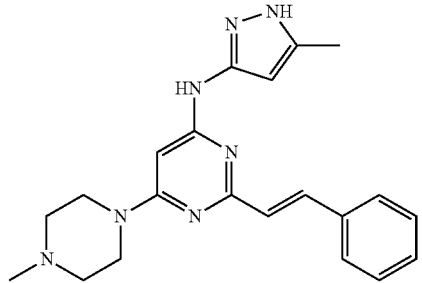

Formula (XLIV)

or a pharmaceutically acceptable salt, solvate, hydrate, cocrystal, or prodrug thereof. The preparation of this compound is described in U.S. Pat. Nos. 8,153,630; 7,563,787; and, 8,114,870 and U.S. Patent Application Publication Nos. 2008/0200485 A1; 2007/0142368 A1; 2009/0264422 A1; 2011/0318393 A1; and, 2009/0029992 A1, the disclosures of which are incorporated by reference herein. In an embodiment, the JAK-2 inhibitor is a compound described in U.S. Pat. Nos. 8,153,630; 7,563,787; and, 8,114,870 and U.S. Patent Application Publication Nos. 2008/0200485 A1; 2007/0142368 A1; 2009/0264422 A1; 2011/0318393 A1; and, 2009/0029992 A1, the disclosures of which are incorporated by reference herein.

In an embodiment, the JAK-2 inhibitor is a compound of Formula (XLV):

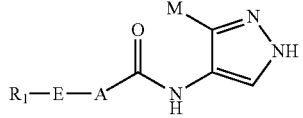

Formula (XLV)

or a pharmaceutically acceptable salt, solvate, hydrate, cocrystal, prodrug, tautomer or N-oxide thereof,
wherein M is selected from a group D1 and a group D2:

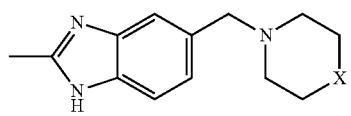

D1

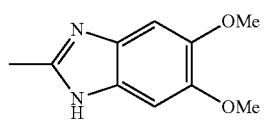

D2 and wherein:
(A) when M is a group D1:
X is selected from O, NH and NCH₃;
A is selected from a bond and a group NR₂ where R₂ is hydrogen or methyl;
E is selected from a bond, CH₂, CH(CN) and C(CH₃)₂;
R₁ is selected from:
(i) a cycloalkyl group of 3 to 5 ring members optionally substituted by hydroxy, fluorine, amino, methylamino, methyl or ethyl;
(ii) a saturated heterocyclic group of 4 to 6 ring members containing 1 or 2 heteroatom ring members selected from O, N, S and SO$_2$, the heterocyclic group being optionally substituted by (C$_{1-4}$)alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl;

(iii) a 2,5-substituted phenyl group of the formula:

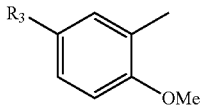

wherein (a) when X is NH or N—CH$_3$, R$_3$ is selected from chlorine and cyano;
and (b) when X is O, R$_3$ is CN;

(iv) a group CR$_6$R$_7$R$_8$ wherein R$_6$ and R$_7$ are each selected from hydrogen and methyl, and R$_8$ is selected from hydrogen, methyl, (C$_{1-4}$)alkylsulphonylmethyl, hydroxymethyl and cyano;

(v) a pyridazin-4-yl group optionally substituted by one or two substituents selected from methyl, ethyl, methoxy and ethoxy;

(vi) a substituted imidazothiazole group wherein the substituents are selected from methyl, ethyl, amino, fluorine, chlorine, amino and methylamino; and (vii) an optionally substituted 1,3-dihydro-isoindol-2-yl or optionally substituted 2,3-dihydro-indol-1-yl group wherein the optional substituents in each case are selected from halogen, cyano, amino, C$_{1-4}$ mono- and dialkylamino, CONH$_2$ or CONH—(C$_{1-4}$)alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino;

(viii) 3-pyridyl optionally substituted by one or two substituents selected from hydroxy, halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino, but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide;

(ix) thiomorpholine or an S-oxide or S,S-dioxide thereof optionally substituted by one or two substituents selected from halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino; and when E-A is NR$_2$, R$_1$ is additionally selected from:

(x) 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl;

(xi) a group NR$_{10}$R$_{11}$ where R$_{10}$ and R$_{11}$ are each C$_{1-4}$ alkyl or R$_{10}$ and R$_{11}$ are linked so that NR$_{10}$R$_{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy;

(xii) pyridone optionally substituted by one or two substituents selected from hydroxy, halogen, cyano, amino, C$_{1-4}$ mono- and dialkylamino, CONH2, CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino;

when E-A is C(CH$_3$)$_2$NR$_2$ or CH$_2$—NR$_2$, R$_1$ is additionally selected from:

(xiii) unsubstituted 2-furyl and 2,6-difluorophenyl; and when E-A is C(CH3)$_2$NR$_2$, R$_1$ is additionally selected from:

(xiv) unsubstituted phenyl; and when E is CH$_2$, R$_1$ is additionally selected from:

(xv) unsubstituted tetrahydropyran-4-yl; and (B) when M is a group D2:

A is selected from a bond and a group NR$_2$ where R$_2$ is hydrogen or methyl;

E is selected from a bond, CH$_2$, CH(CN) and C(CH$_3$)$_2$;

R$_1$ is selected from:

(xvi) a 2-substituted 3-furyl group of the formula:

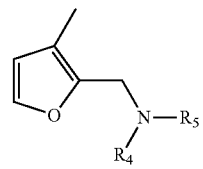

wherein R$_4$ and R$_5$ are the same or different and are selected from hydrogen and C$_{1-4}$ alkyl, or R$_4$ and R$_5$ are linked so that NR$_4$R$_5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl; (xvii) a 5-substituted 2-furyl group of the formula:

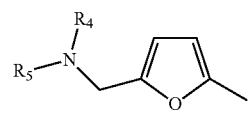

wherein R$_4$ and R$_5$ are the same or different and are selected from hydrogen and C$_{1-4}$ alkyl, or R$_4$ and R$_5$ are linked so that NR$_4$R$_5$ forms a 5- or 6-membered saturated heterocyclic group optionally containing a second heteroatom or group selected from O, NH, NMe, S or SO$_2$, the 5- or 6-membered saturated heterocyclic group being optionally substituted by hydroxy, fluorine, amino, methylamino, methyl or ethyl;

with the proviso that the compound is not 5-piperidin-1-ylmethyl-furan-2-carboxylic acid [3-(5,6-dimethoxy-1H-benzoimidazol-2-yl)-1H-pyrazol-4-yl]-amide;

(xviii) a group of the formula:

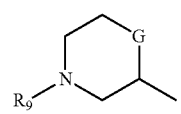

wherein R$_9$ is hydrogen, methyl, ethyl or isopropyl; G is CH, O, S, SO, SO$_2$ or NH and the group is optionally substituted by one, two or three substituents selected from C$_{1-4}$ hydrocarbyl, hydroxy, C$_{1-4}$ hydrocarbyloxy, fluorine, amino, mono- and di-C$_{1-4}$ alkylamino and wherein the C$_{1-4}$ hydrocarbyl and $C_{1-4}$ hydrocarbyloxy groups are each optionally substituted by hydroxy, fluorine, amino, mono- or di-$C_{1-4}$ alkylamino; and (xix) a 3,5-disubstituted phenyl group of the formula:

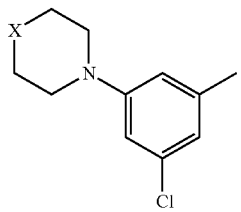

wherein X is selected from O, NH and $NCH_3$; and (C) when M is a group D1:
and X is O; A is a group $NR_2$ where $R_2$ is hydrogen; E is a bond; and $R_1$ is 2,6-difluorophenyl; then the compound of the Formula (XLV) is an acid addition salt selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (-)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

In a preferred embodiment, the JAK-2 inhibitor is AT-9283. In a preferred embodiment, the JAK-2 inhibitor is 1-cyclopropyl-3-(3-(5-(morpholinomethyl)-1H-benzo[d]imidazol-2-yl)-1H-pyrazol-4-yl)urea. In a preferred embodiment, the JAK-2 inhibitor is a compound of Formula (XLVI):

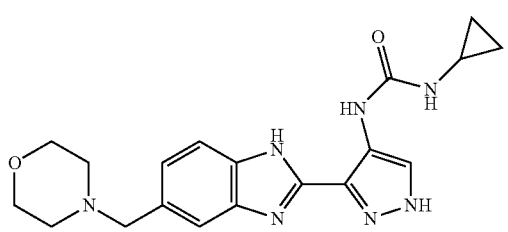

Formula (XLVI)

or a pharmaceutically acceptable salt, solvate, hydrate, cocrystal, or prodrug thereof. The preparation of this compound is described in U.S. Pat. Nos. 8,399,442 and 7,977,477 and U.S. Patent Application Publication Nos. 2010/0004232 A1; 2014/0010892 A1; 2011/0224203 A1; and, 2007/0135477, the disclosures of which are incorporated by reference herein. In an embodiment, the JAK-2 inhibitor is a compound described in U.S. Pat. Nos. 8,399,442 and 7,977,477 and U.S. Patent Application Publication Nos. 2010/0004232 A1; 2014/0010892 A1; 2011/0224203 A1; and, 2007/0135477, the disclosures of which are incorporated by reference herein.

In an embodiment, the JAK-2 inhibitor is a compound of Formula (XLVII):

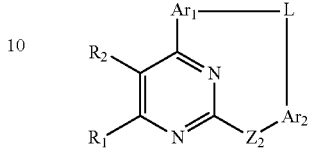

Formula (XLVII)

or a pharmaceutically acceptable salt, solvate, hydrate, cocrystal, or prodrug thereof, wherein:

$R^1$ and $R^2$ are each independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —$COR^3$, —$COOR^3$, —$CONHR^3$, —$NHCOR^3$, —$NHCOOR^3$, —$NHCONHR^3$, alkoxycarbonyl, alkylaminocarbonyl, sulfonyl, alkylsulfonyl, alkylsulfinyl, arylsulfonyl, arylsulfinyl, aminosulfonyl, —$SR^3$, $R^4S(O)R^6$—, $R^4S(O)_2R^6$—, $R^4C(O)N(R^5)R^6$—, $R^4SO_2N(R^5)R^6$—, $R^4N(R^5)C(O)R^6$—, $R^4N(R^5)SO_2R^6$—, $R^4N(R^5)C(O)N(R^5)R^6$— and acyl, each of which may be optionally substituted;

each $R^3$, $R^4$, and $R^5$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^6$ is independently selected from the group consisting of a bond, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

$Z^2$ is independently selected from the group consisting of a bond, O, S, —$N(R^7)$—, —$N(R^7)C_{1-2}alkyl$-, and —$C_{1-2}alkylN(R^7)$—;

each $R^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

$Ar^1$ and $Ar^2$ are each independently selected from the group consisting of aryl and heteroaryl, each of which may be optionally substituted;

L is a group of formula:

—$X^1$—Y—$X^2$— wherein $X^1$ is attached to $Ar^1$ and $X^2$ is attached to $Ar^2$, and wherein $X^1$, $X^2$ and Y are selected such that the group L has between 5 and 15 atoms in the normal chain, $X^1$ and $X^2$ are each independently a heteroalkyl group containing at least one oxygen atom in the normal chain, Y is a group of formula —CR$^a$=CR$^b$— or an optionally substituted cycloalkyl group,
wherein R$^a$ and R$^b$ are each independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted, or
R$^a$ and R$^b$ may be joined such that when taken together with the carbon atoms to which they are attached they form a cycloalkenyl or cycloheteroalkenyl group;
or a pharmaceutically acceptable salt, solvate, hydrate, cocrystal, or prodrug thereof, or an N-oxide thereof.
In certain embodiments Z$^2$ is selected from the group consisting of a bond, —N(R$^7$)—, and —S—. In one specific embodiment Z$^2$ is —N(R$^7$)—. In an even more specific embodiment Z$^2$ is —N(H)—.
Ar$^1$ and Ar$^2$ are each independently selected from the group consisting of aryl and heteroaryl and may be monocyclic, bicyclic or polycyclic moieties. In certain embodiments each of Ar$^1$ and Ar$^2$ is a monocyclic or bicyclic moiety. In certain embodiments each of Ar$^1$ and Ar$^2$ are a monocyclic moiety.
In certain embodiments Ar$^1$ is selected from the group consisting of:

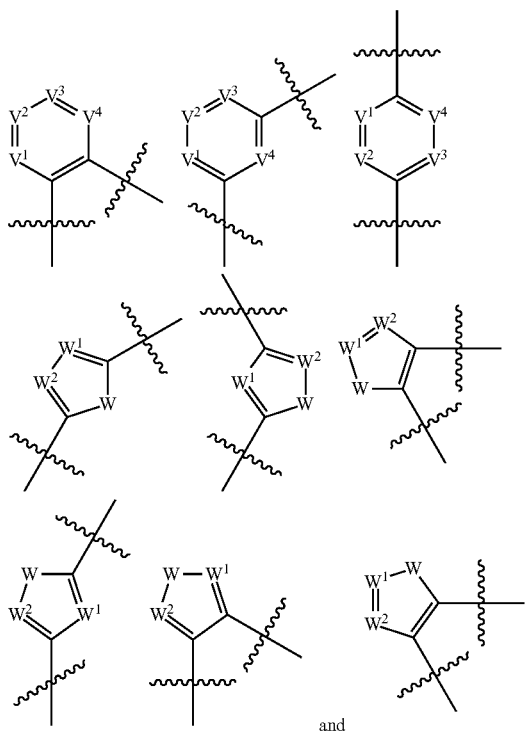

wherein V$^1$, V$^2$, V$^3$ and V$^4$ are each independently selected from the group consisting of N, and C(R$^{10}$);
W is selected from the group consisting of O, S and NR$^{10}$;
W$^1$ and W$^2$ are each independently selected from the group consisting of N and CR$^{10}$;
wherein each R$^{10}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted,
wherein R$^3$, R$^4$, R$^5$ and R$^6$ are as defined above.
In certain embodiments Ar$^1$ is selected from the group consisting of:

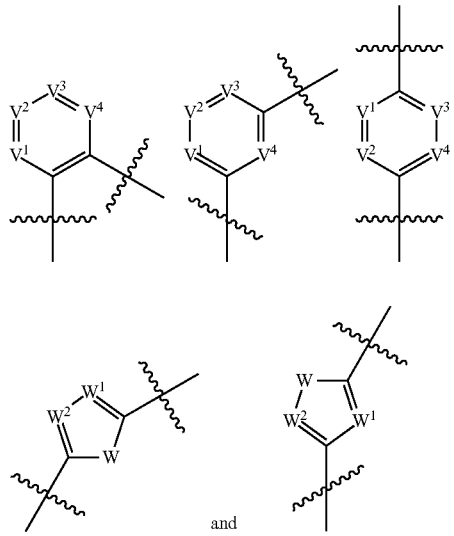

wherein V$^1$, V$^2$, V$^3$, V$^4$, W, W$^1$, W$^2$, R$^3$, R$^4$, R$^5$ and R$^6$ are as defined above.
In yet an even further embodiment Ar$^1$ is selected from the group consisting of:

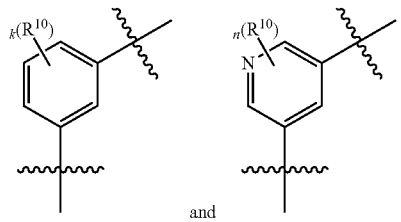

wherein each R$^{10}$ is independently as defined above,
k is an integer selected from the group consisting of 0, 1, 2, 3, and 4; and
n is an integer selected from the group consisting of 0, 1, and 2.
In yet an even further embodiment Ar$^1$ is selected from the group consisting of:

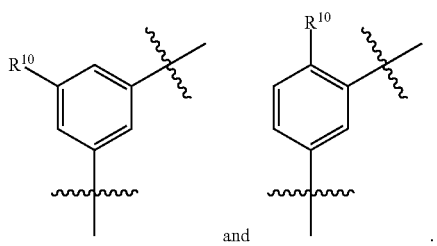

and

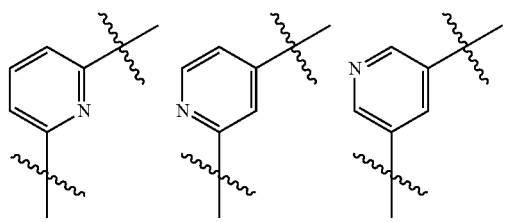

wherein $R^{10}$ is as defined above.

In certain embodiments $Ar^1$ is selected from the group consisting of:

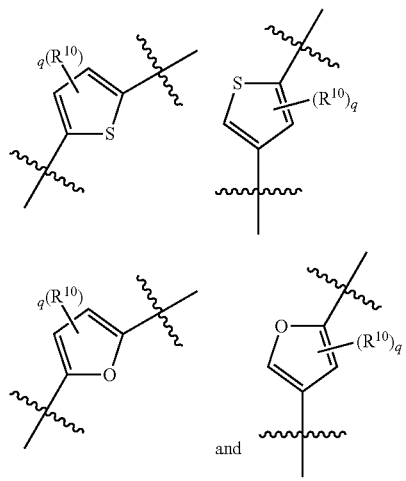

and wherein each $R^{10}$ is independently as defined above, and q is an integer selected from the group consisting of 0, 1 and 2.

In certain embodiments $Ar^1$ is selected from the group consisting of:

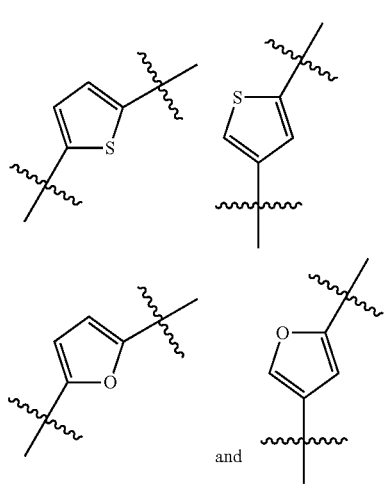

and

In certain embodiments $Ar^1$ is selected from the group consisting of:

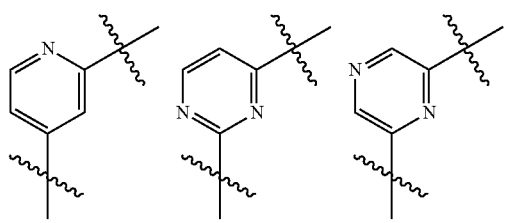

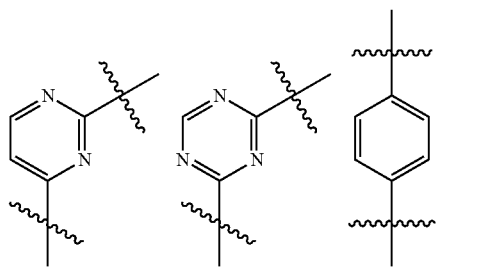

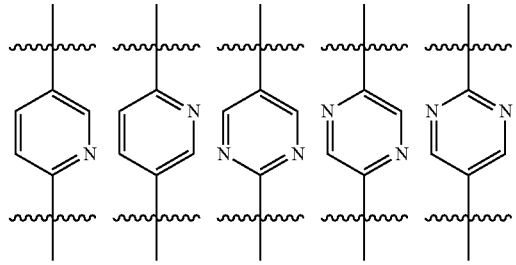

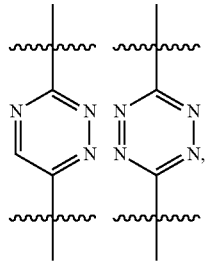

In certain embodiments $Ar^2$ is selected from the group consisting of:

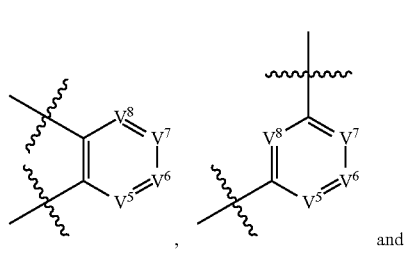

, and

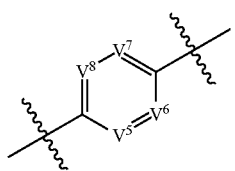

wherein $V^5$, $V^6$, $V^7$ and $V^8$ are independently selected from the group consisting of N, and $C(R^{11})$;

wherein each $R^{11}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted.

In certain embodiments Ar$^2$ is selected from the group consisting of:

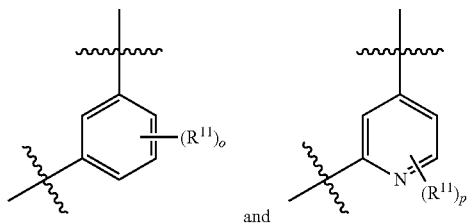

and wherein each $R^{11}$ is independently as defined above o is an integer selected from the group consisting of 0, 1, 2, 3, and 4; and p is an integer selected from the group consisting of 0, 1, 2, and 3.

In certain embodiments Ar$^2$ is selected from the group consisting of:

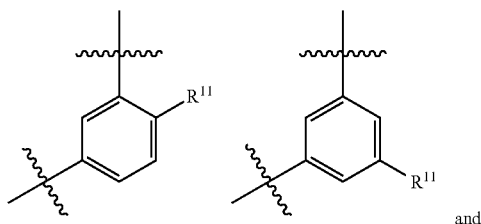

and

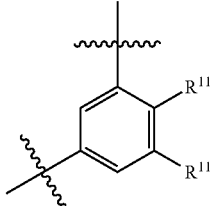

wherein each $R^{11}$ is as defined above.

In a further embodiment Ar$^2$ is selected from the group consisting of:

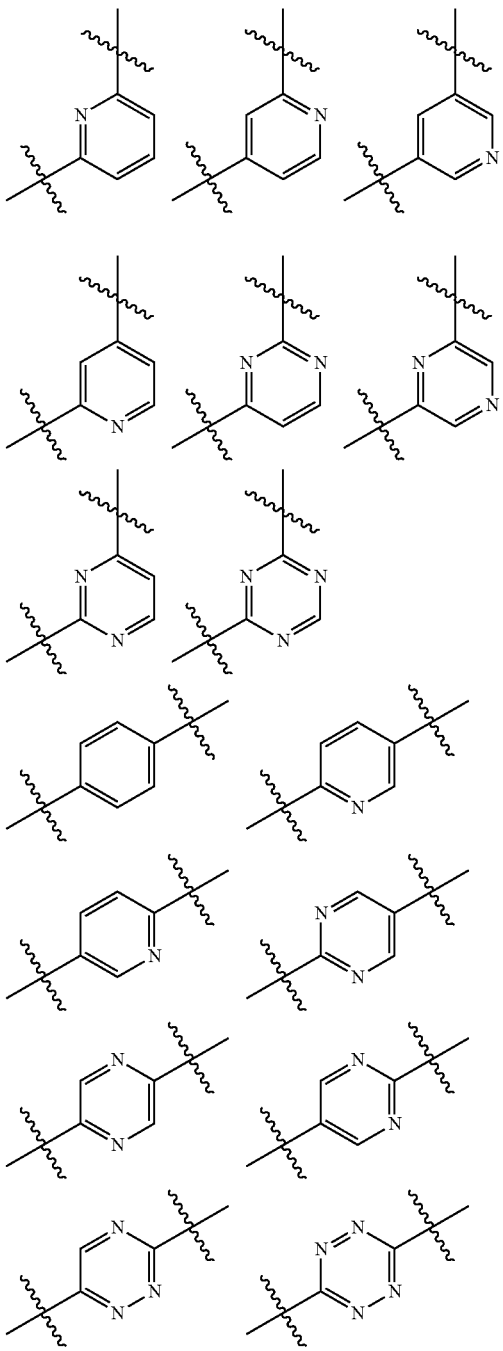

In an embodiment, the JAK-2 inhibitor is a compound of Formula (XLVIII):

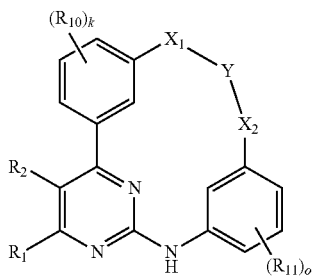

Formula (XLVIII)

or a pharmaceutically acceptable salt, solvate, hydrate, cocrystal, or prodrug thereof
wherein $R^1$, $R^2$, $R^{10}$, $R^{11}$, $X^1$, $X^2$, Y, k and o are as defined above.

In an embodiment, the JAK-2 inhibitor is a compound of Formula (XLIX):

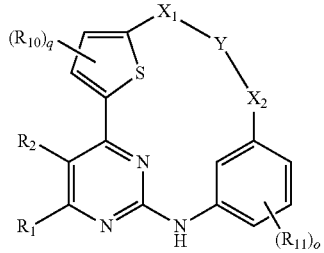

Formula (XLIX)

or a pharmaceutically acceptable salt, solvate, hydrate, cocrystal, or prodrug thereof
wherein $R^1$, $R^2$, $R^{10}$, $R^{11}$, $X^1$, $X^2$, Y, q and o are as defined above.

In an embodiment, the JAK-2 inhibitor is a compound of Formula (L):

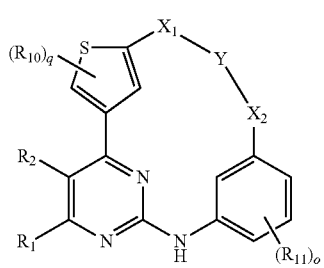

Formula (L)

or a pharmaceutically acceptable salt, solvate, hydrate, cocrystal, or prodrug thereof
wherein $R^1$, $R^2$, $R^{10}$, $R^{11}$, $X^1$, $X^2$, Y, q and o are as defined above.

In an embodiment, the JAK-2 inhibitor is a compound of Formula (LI):

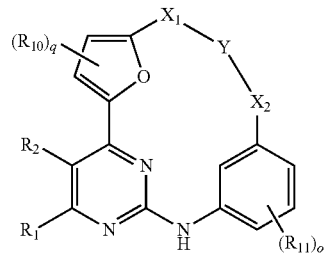

Formula (LI)

or a pharmaceutically acceptable salt, solvate, hydrate, cocrystal, or prodrug thereof
wherein $R^1$, $R^2$, $R^{10}$, $R^{11}$, $X^1$, $X^2$, Y, q and o are as defined above.

In an embodiment, the JAK-2 inhibitor is a compound of Formula (LII):

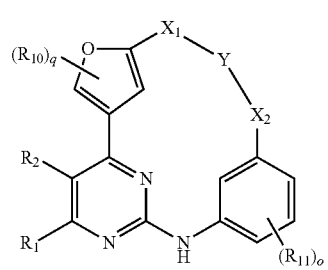

Formula (LII)

or a pharmaceutically acceptable salt, solvate, hydrate, cocrystal, or prodrug thereof
wherein $R^1$, $R^2$, $R^{10}$, $R^{11}$, $X^1$, $X^2$, Y, q and o are as defined above.

In an embodiment, the JAK-2 inhibitor is a compound of Formula (LIII):

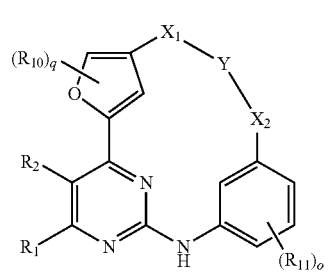

Formula (LIII)

or a pharmaceutically acceptable salt, solvate, hydrate, cocrystal, or prodrug thereof
wherein $R^1$, $R^2$, $R^{10}$, $R^{11}$, $X^1$, $X^2$, Y, q and o are as defined above.

In embodiments where the JAK-2 inhibitor is a compound of Formulas (XLVII)-(LIII), $X^1$, $X^2$ and Y are chosen such that there are between 5 and 15 atoms in the normal chain. In one embodiment, $X^1$, $X^2$ and Y are chosen such that there are between 6 and 15 atoms in the normal chain. In one specific embodiment, $X^1$, $X^2$ and Y are chosen such that there are 7 atoms in the normal chain. In another specific embodiment, $X^1$, $X^2$ and Y are chosen such that there are 8 atoms in the normal chain.

In embodiments where the JAK-2 inhibitor is a compound of Formulas (XLVII)-(LIII), $X^1$ and $X^2$ are each independently a heteroalkyl group containing at least one oxygen atom in the normal chain. In certain embodiments $X^1$ is selected from the group consisting of: (a) —O($C_{1-5}$)alkyl-, (b) —($C_{1-5}$)alkylO—, and (c) —($C_{1-5}$)alkylO($C_{1-5}$)alkyl. In certain embodiments $X^1$ is selected from the group consisting of: (a) —OCH$_2$— (b) —CH$_2$O—, (c) —OCH$_2$CH$_2$—, (d) —CH$_2$CH$_2$O—, (e) —CH$_2$OCH$_2$—, and (f) —CH$_2$CH$_2$OCH$_2$—. In one specific embodiment $X^1$ is —OCH$_2$—. In another specific embodiment $X^1$ is —CH$_2$O—. In another specific embodiment $X^1$ is —OCH$_2$CH$_2$—. In another specific embodiment $X^1$ is —CH$_2$CH$_2$O—. In another specific embodiment $X^1$ is —CH$_2$OCH$_2$—. In another specific embodiment $X^1$ is —CH$_2$CH$_2$OCH$_2$—. In certain embodiments $X^2$ is selected from the group consisting of: (a) —O($C_{1-5}$)alkyl-, (b) —($C_{1-5}$)alkylO—, and (c) —($C_{1-5}$)alkylO($C_{1-5}$)alkyl. In certain embodiments $X^2$ is selected from the group consisting of: (a) —OCH$_2$— (b) —CH$_2$O—, (c) —OCH$_2$CH$_2$—, (d) —CH$_2$CH$_2$O—, (e) —CH$_2$OCH$_2$—, and (f) —CH$_2$CH$_2$OCH$_2$—. In one specific embodiment $X^2$ is —OCH$_2$—. In another specific embodiment $X^1$ is —CH$_2$O—. In another specific embodiment $X^2$ is —OCH$_2$CH$_2$—. In another specific embodiment $X^2$ is —CH$_2$CH$_2$O—. In another specific embodiment $X^2$ is —CH$_2$OCH$_2$—. In another specific embodiment $X^2$ is —CH$_2$CH$_2$OCH$_2$—.

In a preferred embodiment, the JAK-2 inhibitor is pacritinib. Pacritinib is also known as SB1518. In a preferred embodiment, the JAK-2 inhibitor is (E)-$4^4$-(2-(pyrrolidin-1-yl)ethoxy)-6,11-dioxa-3-aza-2(4,2)-pyrimidina-1,4(1,3)-dibenzenacyclododecaphan-8-ene. In a preferred embodiment, the JAK-2 inhibitor is 14,19-dioxa-5,7,27-triazatetracyclo[19.3.1.1$^{2,6}$.1$^{8,12}$]heptacosa-1 (25),2,4,6(27), 8,10,12(26),16,21,23-decaene, 11-[2-(1-pyrrolidinyl) ethoxy]-, (16E)-. In a preferred embodiment, the JAK-2 inhibitor is (16E)-11-[2-(pyrrolidin-1-yl)ethoxy]-14,19-dioxa-5,7,27-triazatetracyclo[19.3.1.1$^{2,6}$.1$^{8,12}$]heptacosa-1 (24),2,4,6,8,10,12(26),16,21(25),22-decaene. In an embodiment, the JAK-2 inhibitor is a compound of Formula (LIV):

Formula (LIV)

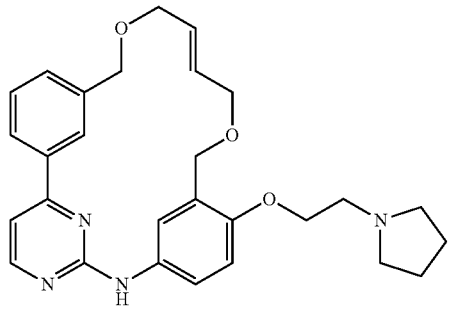

or a pharmaceutically acceptable salt, solvate, hydrate, cocrystal, or prodrug thereof. In an embodiment, the structure of Formula (LIV) may be a tautomeric form. The preparation of Formula (LIV) is described in U.S. Pat. Nos. 8,143,255; 8,153,632; and, 8,415,338 and U.S. Patent Application Publication Nos. 2009/0258886 A1; 2012/0142680 A1; 2012/0196855 A1; and 2013/0172338 A1, the disclosures of which are incorporated by reference herein. The preparation and properties of this JAK-2 inhibitor are known to those of ordinary skill in the art, and for example are described in: Hart, et al., SB1518, a novel macrocyclic pyrimidine-based JAK2 inhibitor for the treatment of myeloid and lymphoid malignancies, *Leukemia* 2011, 25, 1751-1759; Hart, et al., Pacritinib (SB1518), a JAK2/FLT3 inhibitor for the treatment of acute myeloid leukemia, *Blood Cancer J.,* 2011, 1(11), e44; William, et al., Discovery of the macrocycle 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8, 10,12(27),16,21,23-decaene (SB1518), a potent Janus kinase 2/fms-like tyrosine kinase-3 (JAK2/FLT3) inhibitor for the treatment of myelofibrosis and lymphoma. *J. Med. Chem.* 2011, 54, 4638-4658; Poulsen, et al. Structure-based design of oxygen-linked macrocyclic kinase inhibitors: discovery of SB1518 and SB1578, potent inhibitors of Janus kinase 2 (JAK2) and Fms-like tyrosine kinase-3 (FLT3). *J. Comput. Aided Mol. Des.* 2012, 26, 437-450.

In an embodiment, the JAK-2 inhibitor is selected from the structures disclosed in U.S. Pat. Nos. 8,143,255; 8,153, 632; and 8,415,338 and U.S. Patent Application Publication Nos. 2009/0258886 A1; 2012/0142680 A1; 2012/0196855 A1; and 2013/0172338 A1, the disclosures of which are incorporated by reference herein.

In a preferred embodiment, the JAK-2 inhibitor is (E)-$4^4$-(2-(pyrrolidin-1-yl)ethoxy)-6,11-dioxa-3-aza-2(4,2)-pyrimidina-1(2,5)-furana-4(1,3)-benzenacyclododecaphan-8-ene. In a preferred embodiment, the JAK-2 inhibitor is (9E)-15-(2-(pyrrolidin-1-yl)ethoxy)-7,12,25-trioxa-19,21, 24-triaza-tetracyclo[18.3.1.1(2,5).1(14,18)]hexacosa-1(24), 2,4,9,14(26),15,17,20,22-nonaene. In a preferred embodiment, the JAK-2 inhibitor is a compound of Formula (LIV-A):

Formula (LIV-A)

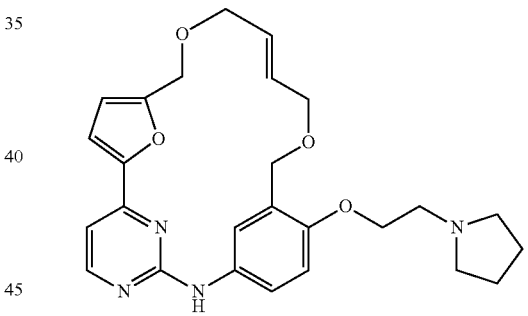

or a pharmaceutically acceptable salt, solvate, hydrate, cocrystal, or prodrug thereof. The preparation and properties of this JAK-2 inhibitor are known to those of ordinary skill in the art, and for example are described in: Madan et al., SB1578, a novel inhibitor of JAK2, FLT3, and c-Fms for the treatment of rheumatoid arthritis, *J. Immunol.* 2012, 189, 4123-4134 and William et al., Discovery of the macrocycle (9E)-15-(2-(pyrrolidin-1-yl)ethoxy)-7,12,25-trioxa-19,21, 24-triaza-tetracyclo[18.3.1.1(2,5).1(14,18)]hexacosa-1 (24), 2,4,9,14(26),15,17,20,22-nonaene (SB1578), a potent inhibitor of janus kinase 2/fms-like tyrosine kinase-3 (JAK2/ FLT3) for the treatment of rheumatoid arthritis. *J. Med. Chem.* 2012, 55, 2623-2640.

In an embodiment, the JAK-2 inhibitor is a compound selected from the structures disclosed in U.S. Pat. No. 8,349,851 and U.S. Patent Application Publication Nos. 2010/0317659 A1, 2013/0245014, 2013/0296363 A1, the disclosures of which are incorporated by reference herein. In an embodiment, the JAK-2 inhibitor is a compound of Formula (LV):

Formula (LV)

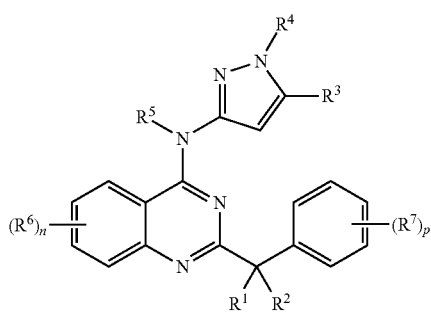

or a pharmaceutically acceptable salt, solvate, hydrate, cocrystal, or prodrug thereof, wherein
$R^1$ and $R^2$ are selected from (i), (ii), (iii), (iv), and (v) as follows:
(i) $R^1$ and $R^2$ together form =O, =S, =$NR^9$ or =$CR^{10}R^{11}$;
(ii) $R^1$ and $R^2$ are both —$OR^8$, or $R^1$ and $R^2$, together with the carbon atom to which they are attached, form dioxacycloalkyl;
(iii) $R^1$ is hydrogen or halo; and $R^2$ is halo; and
(iv) $R^1$ is alkyl, alkenyl, alkynyl, cycloalkyl or aryl, wherein the alkyl, alkenyl, alkynyl, cycloalkyl and aryl is optionally substituted with one or more substituents selected from halo, cyano, alkyl, —$R^xOR^w$, —$R^xS(O)_qR^v$, —$R^xNR^yR^z$ and —C(O)$OR^w$; and $R^2$ is halo or —$OR^8$; and
(v) $R^1$ is halo, deutero, —$OR^{12}$, —$NR^{13}R^{14}$, or —$S(O)_qR^{15}$; and $R^2$ is hydrogen, deutero, alkyl, alkenyl, alkynyl, cycloalkyl or aryl, wherein the alkyl, alkenyl, alkynyl, cycloalkyl and aryl, is optionally substituted with one or more substituents selected from halo, cyano, alkyl, —$R^xOR^w$, —$R^xS(O)_qR^v$ and —$R^xNR^yR^z$;
$R^3$ is hydrogen, halo, alkyl, cyano, haloalkyl, cycloalkyl, cycloalkylalkyl, hydroxy or alkoxy;
$R^4$ and $R^5$ are each independently hydrogen or alkyl;
each $R^6$ is independently selected from halo, alkyl, alkenyl, alkynyl, haloalkyl, cycloalkyl, —$R^xOR^{18}$, —$R^xNR^{19}R^{20}$, and —$R^xS(O)_qR^v$;
each $R^7$ is independently halo, alkyl, haloalkyl or —$R^xOR^w$;
$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)$OR^8$;
$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)$R^v$, —C(O)$OR^w$ and —C(O)$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;
$R^{13}$ and $R^{14}$ are selected as follows:
(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)$R^v$, —C(O)$OR^w$, —C(O)$NR^yR^z$ and —S(O)$_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or
(ii) $R^{13}$ and $R^{14}$, together with the nitrogen atom to which they are attached, form heterocyclyl or heteroaryl wherein the heterocyclyl or heteroaryl is optionally substituted with one or more substituents independently selected from halo, alkyl, hydroxy, alkoxy, amino and alkylthio and wherein the heterocyclyl is also optionally substituted with oxo;
$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)$NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;
$R^{18}$ is hydrogen, alkyl, haloalkyl, hydroxy($C_{2-6}$)alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, alkoxysulfonyl, hydroxycarbonyl, cycloalkyl, heterocyclyl, aryl, heteroaryl, haloaryl and amino;
$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which is optionally substituted with 1 to 2 groups each independently selected from halo, alkyl, haloalkyl, hydroxyl and alkoxy;
each $R^x$ is independently alkylene or a direct bond;
$R^v$ is hydrogen, alkyl, alkenyl or alkynyl;
$R^w$ is independently hydrogen, alkyl, alkenyl, alkynyl or haloalkyl;
$R^y$ and $R^z$ are selected as follows:
(i) $R^y$ and $R^z$ are each independently hydrogen, alkyl, alkenyl, alkynyl, cycloalkyl or haloalkyl;
(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy;
n is 0-4;
p is 0-5; and
each q is independently 0, 1 or 2.

In a preferred embodiment, the JAK-2 inhibitor is AC-410 (available from Ambit Biosciences). In a preferred embodiment, the JAK-2 inhibitor is (S)-(4-fluorophenyl)(4-((5-methyl-1H-pyrazol-3-yl)amino)quinazolin-2-yl)methanol.

In a preferred embodiment, the JAK-2 inhibitor is a compound of Formula (LVI):

Formula (LVI)

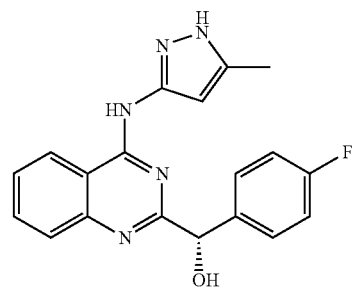

or a pharmaceutically acceptable salt, solvate, hydrate, cocrystal, or prodrug thereof. The preparation of racemic (4-fluorophenyl)(4-((5-methyl-1H-pyrazol-3-yl)amino)quinazolin-2-yl)methanol hydrochloride is described in Examples 3 and 12 of U.S. Pat. No. 8,349,851, the disclosure of which is incorporated by reference herein. Other preparation methods known to one of skill in the art also may be used. The preparation of the compound of Formula (LVI) is also described in the following paragraphs.

The preparation of (4-fluorophenyl)(4-(5-methyl-1H-pyrazol-3-ylamino)quinazolin-2-yl)methanone is accomplished by the following two steps (A and B). Step A: To a solution of ethyl 4-chloroquinazoline-2-carboxylate (0.6 g, 2.53 mmol) in THF (6 mL) at −40° C., was added dropwise a 1 M solution of 4-fluorophenylmagnesium bromide in THF (3 mL, 3.0 mmol, 1.2 eq). The mixture was stirred at −40° C. for 4 h. The reaction was quenched by adding 0.5 N HCl solution (5 mL) and the mixture was extracted with EtOAc (2×10 mL). The combined organic layers were washed with brine and dried over $MgSO_4$. The crude product was purified on a silica gel column using a mixture of EtOAc-hexanes as eluent. (4-chloroquinazoline-2-yl)(4-fluorophenyl)methanone was obtained as a light yellow solid (440 mg, 60%). $^1$H NMR (300 MHz, DMSO-d6) δ 7.45-740 (m, 2H), 8.07-8.03 (m, 1H), 8.17-8.13 (m, 2H), 8.23 (m, 2H), 8.42 (d, 1H); LC-MS (ESI) m/z 287 $(M+H)^+$. Step B: To a solution of (4-chloroquinazolin-2-yl)(4-fluorophenyl) methanone (84 mg, 0.30 mmol) in DMF (3 mL) were added DIEA (0.103 mL, 0.6 mmol) and 5-methyl-1H-pyrazol-3-amine (88 mg, 0.9 mmol at rt. The reaction mixture was heated at 40° C. overnight. The reaction was quenched by adding water and the yellow precipitate was collected by filtration and washed with water. The crude product was purified by silica gel chromatography eluting with DCM/MeOH to give (4-fluorophenyl)(4-(5-methyl-1H-pyrazol-3-ylamino)quinazolin-2-yl)methanone (30 mg, 29%). $^1$H NMR (300 MHz, DMSO-d6) δ 2.19 (s, 3H), 6.54 (s, 1H), 7.40 (m, 2H), 7.68 (t, 1H), 7.9-7.7 (m, 2H), 8.08 (m, 2H), 8.74 (d, 1H), 10.66 (s, 1H), 12.20 (s, 1H); LC-MS (ESI) m/z 348 $(M+H)^+$.

To a solution of 4-fluorophenyl)(4-(5-methyl-1H-pyrazol-3-ylamino)quinazolin-2-yl)methanone (60 mg, 0.172 mmol) in 1:1 MeOH/THF (10 mL) at 0° C., was added $NaBH_4$ (64 mg, 1.69 mmol). The reaction mixture was stirred at 0° C. for 1.5 h. The reaction mixture was quenched by adding a few drops of acetone and concentrated to dryness. The crude solid was purified on HPLC to afford (4-fluorophenyl)(4-(5-methyl-1H-pyrazol-3-ylamino)quinazolin-2-yl)methanol (18 mg, 30%); $^1$H NMR (300 MHz, DMSO-d6) δ 2.25 (s, 3H), 5.67 (s, 1H), 5.83 (bs, 1H), 6.40 (bs, 1H), 7.13 (m, 2H), 7.55-7.53 (m, 3H), 7.79 (s, 2H), 8.57 (bs, 1H), 10.43 (s, 1H), 12.12 (bs, 1H); LC-MS (ESI) m/z 350 $(M+H)^-$.

To a suspension of (4-fluorophenyl)(4-(5-methyl-1H-pyrazol-3-ylamino)quinazolin-2-yl)methanone (2.3 g) in 30% MeOH/DCM (60 mL) at 0° C. was added dropwise 4M HCl/1,4-dioxane (10 mL). After all solid material had dissolved, the mixture was concentrated under reduced pressure, and to the residue was added 30% $CH_3CN/H_2O$ (80 mL) and the mixture was sonicated until all solid material had dissolved. The mixture was frozen and lyophilized overnight to afford (4-fluorophenyl)(4-(5-methyl-1H-pyrazol-3-ylamino)quinazolin-2-yl)methanol hydrochloride (100%). $^1$H NMR (300 MHz, DMSO-d6) δ 2.25 (s, 3H), 6.02 (s, 1H), 6.20 (s, 1H), 7.27 (t, 2H), 7.60 (qt, 2H), 7.80 (t, 1H), 8.08 (t, 1H), 8.23 (d, 1H), 8.83 (d, 1H), 12.16 (s, 1H), 14.51 (b, 1H); LC-MS (ESI) m/z 350 $(M+H)^+$. The compound of Formula (LVI), (S)-(4-fluorophenyl)(4-((5-methyl-1H-pyrazol-3-yl)amino)quinazolin-2-yl)methanol, may be obtained from this preparation by chiral liquid chromatographic separation of the enantiomers, or by other well known techniques for resolution of enantiomers, such as those described in: Eliel et al., *Stereochemistry of organic Compounds*, Wiley-Interscience, New York, 1994.

In a preferred embodiment, the JAK-2 inhibitor is (R)-(4-fluorophenyl)(4-((5-methyl-1H-pyrazol-3-yl)amino)quinazolin-2-yl)methanol, which is also known in the art to be active as a JAK-2 inhibitor. In a preferred embodiment, the JAK-2 inhibitor is racemic (4-fluorophenyl)(4-((5-methyl-1H-pyrazol-3-yl)amino)quinazolin-2-yl)methanol, which is also known in the art to be active as a JAK-2 inhibitor.

In some preferred embodiments, JAK-2 inhibitors having Formula (LV) or Formula (LVI) can be prepared, isolated, or obtained by any method known to one of skill in the art, including, but not limited to, synthesis from a suitable optically pure precursor, asymmetric synthesis from an achiral starting material, or resolution of a racemic or enantiomeric mixture, for example, chiral chromatography, recrystallization, resolution, diastereomeric salt formation, or derivatization into diastereomeric adducts followed by separation.

A method for preparation of the compound of Formula (LVI) comprises resolving racemic (4-fluorophenyl)(4-(5-methyl-1H-pyrazol-3-ylamino)quinazolin-2-yl)methanol with chiral chromatography. In certain embodiments, the two individual enantiomers are separated using a chiral column, wherein the stationary phase is silica gel coated with a chiral selector such as tris-(3,5-dimethylphenyl)carbamoyl cellulose.

A method for preparation of the compound of Formula (LVI) comprises the step of reducing the achiral ketone (4-fluorophenyl)(4-(5-methyl-1H-pyrazol-3-ylamino)quinazolin-2-yl)methanone, prepared as described above or by other methods known to one of skill in the art, with hydrogen in the present of a chiral catalyst. The achiral ketone (4-fluorophenyl)(4-(5-methyl-1H-pyrazol-3-ylamino)quinazolin-2-yl)methanone may be reduced to predominantly a single enantiomeric product with a chiral reducing system of "type A" or "type B," wherein type A and type B differ from each other solely by having chiral auxiliaries of opposite chiralities. In certain embodiments, the chiral catalyst is [(S)—P-Phos $RuCl_2$ (S)-DAIPEN].

The reduction of the achiral ketone (4-fluorophenyl)(4-(5-methyl-1H-pyrazol-3-ylamino)quinazolin-2-yl)methanone in presence of a chiral catalyst may be carried out in isopropyl alcohol as a solvent. The reduction of achiral ketone (4-fluorophenyl)(4-(5-methyl-1H-pyrazol-3-ylamino)quinazolin-2-yl)methanone in the presence of a chiral catalyst is carried out in isopropyl alcohol and water mixture as a solvent. Isopropyl alcohol and water are used in a ratio of 1:1, 8:1 or 9:1. DMSO is used as a cosolvent in the reaction. Alternatively, DMSO is used in amounts of 10, 20 or 30% based on the total amount of isopropyl alcohol and water mixture. Alternatively, isopropyl alcohol, DMSO and water are used in a ratio of 1:1:1, 4:4:0.5, 8:1:1, 47:47:6, 41:58:1, 44:50:6, or 18:79:3. Alternatively, isopropyl alcohol, DMSO and water are used in a ratio of 41:58:1. Alternatively, isopropyl alcohol, and DMSO are used in a ratio of 1:1. Alternatively, the reduction is carried out in presence of a base, such as potassium hydroxide, potassium tert butoxide and others. Alternatively, the base is used in 2-15 mol %, in one embodiment, 2 mol %, 5 mol %, 10 mol %, 12.5 mol % or 15 mol %. Alternatively, the reduction is carried out at a temperature of 40-80° C., in one embodiment, 40° C., 50° C., 60° C., 70° C. or 80° C. Alternatively, the reduction is carried out at a temperature of 70° C. Alternatively, the reduction is carried out at a pressure of 4 bar to 30 bar, in one embodiment, 4, 5, 10, 15, 20, 25 or 30 bar. Alternatively, the reduction is carried out at a pressure of 4 bar. Alternatively, the catalyst loading in the reaction is 100/1, 250/1, 500/1, 1000/1, 2000/1, 3000/1, 4000/1, 5000/1, 7000/1, 10,0000/1 or 20,000/1. In certain embodiments, the catalyst loading in the reaction is 2000/1 or 4000/1.

A method for preparation of the compound of Formula (LVI) comprises the step of reducing the achiral ketone (4-fluorophenyl)(4-(5-methyl-1H-pyrazol-3-ylamino)quinazolin-2-yl)methanone with a ketoreductase (e.g., alcohol dehydrogenase). See Moore, et al., *Acc. Chem. Res.* 2007, 40, 1412-1419; Daussmann, et al., *Engineering in Life Sciences* 2006, 6, 125-129; Schlummer, et al., *Specialty Chemicals Magazine* 2008, 28, 48-49; Osswald, et al., *Chimica Oggi* 2007, 25(Suppl.), 16-18; and Kambourakis, et al., *PharmaChem* 2006, 5(9), 2-5.

An alternative method for preparation of the compound of Formula (LVI) comprises the step of reducing the achiral ketone (4-fluorophenyl)(4-(5-methyl-1H-pyrazol-3-ylamino)quinazolin-2-yl)methanone with a reducing reagent (e.g., borane or borohydride reagents) in the presence of a chiral catalyst. In certain embodiments, the reducing agent is borane or a borohydride reagent. In certain embodiments, the chiral catalyst is a chiral oxazaborolidine. Cory, et al., *Tetrahedron Letters* 1996, 37, 5675; Cho, *Chem. Soc. Rev.* 2009, 38, 443.

Another method for preparation of the compound of Formula (LVI) comprises the step of reducing the achiral ketone (4-fluorophenyl)(4-(5-methyl-1H-pyrazol-3-ylamino)quinazolin-2-yl)methanone via asymmetric hydrosilylation, as described in U.S. Patent Application Publication No. 2008/0269490, the disclosure of which is specifically incorporated herein by reference.

Another method for preparation of the compound of Formula (LVI) comprises the step of reducing the achiral ketone (4-fluorophenyl)(4-(5-methyl-1H-pyrazol-3-ylamino)quinazolin-2-yl)methanone via transfer hydrogenation catalyzed by an iridium complex, as described in Malacea, et al., *Coord. Chem. Rev.* 2010, 254, 729-752.

The starting materials used in the synthesis of the compound of Formula (LVI) provided herein are either commercially available or can be prepared by a method known to one of skill in the art. For example, the achiral ketone (4-fluorophenyl)(4-(5-methyl-1H-pyrazol-3-ylamino)quinazolin-2-yl)methanone can be prepared according to the methods described in U.S. Pat. No. 8,349,851, issued Jan. 8, 2013, and U.S. Pat. No. 8,703,943, issued Apr. 22, 2014, the disclosures of which are incorporated herein by reference in their entireties.

In an embodiment, the JAK-2 inhibitor is a JAK-2 inhibitor described in U.S. Patent Application Publication No. US 2013/0225614 A1, the disclosure of which are specifically incorporated herein by reference. In an embodiment, the JAK-2 inhibitor is a compound of Formula (LV-A):

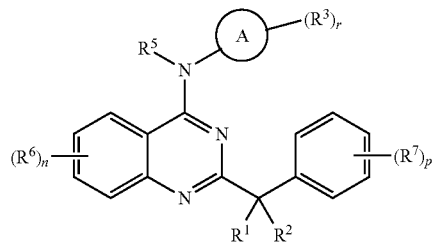

Formula (LV-A)

or a pharmaceutically acceptable salt, solvate, hydrate, cocrystal, or prodrug thereof, wherein A is azolyl other than pyrazolyl;

$R^1$ and $R^2$ are selected from (i), (ii), (iii), (iv) and (v) as follows:

(i) $R^1$ and $R^2$ together form =O, =S, =$NR^9$ or =$CR^{10}R^n$;

(ii) $R^1$ and $R^2$ are both —$OR^8$, or $R^1$ and $R^2$, together with the carbon atom to which they are attached, form cycloalkyl or heterocyclyl wherein the cycloalkyl is substituted with one to four substituents selected from halo, deutero, alkyl, haloalkyl, —OR, —$N(R)_2$, and —$S(O)_qR$ and wherein the heterocyclyl contains one to two heteroatoms wherein each heteroatom is independently selected from O, $NR^{24}$, S, S(O) and $S(O)_2$;

(iii) $R^1$ is hydrogen or halo; and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one to four substituents selected from halo, deutero, alkyl, cycloalkyl, heterocyclyl, aryl, heteroaryl, cyano, =O, =N—$OR^{21}$, —$R^xOR^{21}$, —$R^XN(R^{22})_2$, —$R^xS(O)_qR^{23}$, —$C(O)R^{21}$, —$C(O)OR^{21}$ and —$C(O)N(R^{22})_2$; and (v) $R^1$ is halo, deutero, —$OR^{12}$, —$NR^{13}R^{14}$, or —$S(O)_qR^{15}$, and $R^2$ is hydrogen, deutero, alkyl, alkenyl, alkynyl, cycloalkyl or aryl, wherein the alkyl, alkenyl, alkynyl, cycloalkyl and aryl are each optionally substituted with one to four substituents selected from halo, cyano, alkyl, —$R^xOR^w$, —$R^xS(O)_qR^v$ and —$R^xNR^yR^z$;

$R^3$ is hydrogen, deutero, halo, alkyl, cyano, haloalkyl, deuteroalkyl, cycloalkyl, cycloalkylalkyl, hydroxy or alkoxy;

$R^5$ is hydrogen or alkyl; each $R^6$ is independently selected from halo, alkyl, alkenyl, alkynyl, haloalkyl, cycloalkyl, —$R^xOR^{18}$, —$R^XNR^{19}R^{20}$, and —$R^xS(O)_qR^v$;

each $R^7$ is independently halo, alkyl, haloalkyl or —$R^xOR^w$;

R is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —$C(O)OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^v$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:

(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —$C(O)R^v$, —$C(O)OR^w$, —$C(O)NR^yR^z$ and —$S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo; $R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)NR$^y$R$^z$ or —NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:
(i) $R^y$ and $R^z$ are each independently hydrogen, alkyl, alkenyl, alkynyl, cycloalkyl or haloalkyl; or
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;
p is 0-5;
each q is independently 0, 1 or 2; and
r is 1-3.

In an embodiment, the JAK-2 inhibitor of Formula (LV-A) is a compound of Formula (LV-B):

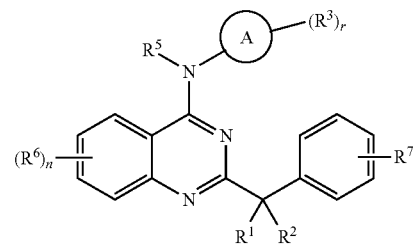

Formula (LV-B)

or a pharmaceutically acceptable salt, solvate, hydrate, cocrystal, or prodrug thereof, wherein A is imidazolyl, oxazolyl, thiazolyl, thiadiazolyl, or triazolyl;

$R^3$ is hydrogen, alkyl, haloalkyl or cycloalkyl;

each $R^6$ is independently selected from halo, alkyl, alkenyl, alkynyl, haloalkyl, cycloalkyl, —R$^x$OR$^{18}$, —R$^x$NR$^{19}$R$^{20}$, and —R$^x$S(O)$_q$R$^v$;

$R^7$ is halo;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

each $R^x$ is independently alkylene or a direct bond;

$R^v$ is hydrogen, alkyl, alkenyl or alkynyl;

$R^y$ and $R^z$ are selected as follows:
(i) $R^y$ and $R^z$ are each independently hydrogen, alkyl, alkenyl, alkynyl, cycloalkyl or haloalkyl; or
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-3;
each q is independently 0, 1 or 2; and
r is 1-3.

In a preferred embodiment of the JAK-2 inhibitor of Formula (LV-A) or (LV-B), $R^3$ is hydrogen or alkyl.

In a preferred embodiment of the JAK-2 inhibitor of Formula (LV-A) or (LV-B), A is imidazolyl, oxazolyl, thiazolyl, thiadiazolyl, or triazolyl.

In a preferred embodiment of the JAK-2 inhibitor of Formula (LV-A) or (LV-B), $R^7$ is fluro.

In a preferred embodiment of the JAK-2 inhibitor of Formula (LV-A) is a compound of Formula (LV-C):

Formula (LV-C)

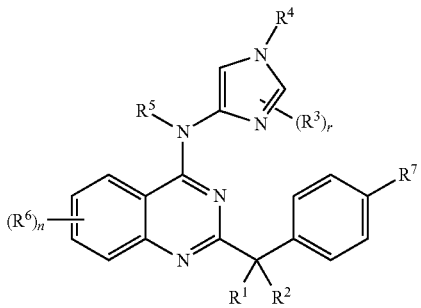

or a pharmaceutically acceptable salt, solvate, hydrate, cocrystal, or prodrug thereof, where
$R^1$ and $R^2$ are selected as follows:
(i) $R^1$ and $R^2$ together form =O;
(ii) $R^1$ and $R^2$, together with the carbon atom to which they are attached, form dioxacycloalkyl or cycloalkyl wherein the cycloalkyl is substituted with one to four substituents selected from halo, deutero, alkyl, cycloalkyl, heterocyclyl, aryl, heteroaryl, cyano, =O, and hydroxy;
(iii) $R^1$ is hydrogen or halo; and $R^2$ is halo;
(iv) $R^1$ is alkyl, and $R^2$ is hydrogen, alkyl, halo, hydroxy or alkoxy; or
(v) $R^1$ is halo, hydroxy or alkoxy; and $R^2$ is hydrogen or alkyl;
$R^3$ is hydrogen, alkyl or cycloalkyl,
$R^4$ is hydrogen or alkyl;
$R^5$ is hydrogen or alkyl;
$R^7$ is halo; and
n is 0-3.

In a preferred embodiment of the JAK-2 inhibitor of Formula (LV-C), n is 0.

In an embodiment, JAK-2 inhibitor of Formula (LV-A) has the structure of Formula (LV-D):

Formula (LV-D)

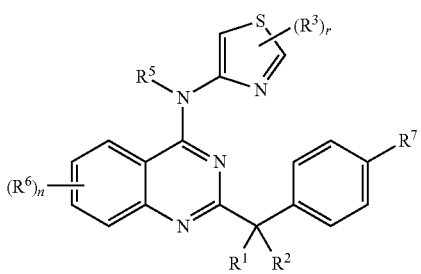

or a pharmaceutically acceptable salt, solvate, hydrate, cocrystal, or prodrug thereof, where
$R^1$ and $R^2$ are selected as follows:
(i) $R^L$ and $R^2$ together form =O;
(ii) $R^1$ and $R^2$, together with the carbon atom to which they are attached, form dioxacycloalkyl or cycloalkyl wherein the cycloalkyl is substituted with one to four substituents selected from halo, deutero, alkyl, cycloalkyl, heterocyclyl, aryl, heteroaryl, cyano, =O, and hydroxy;
(iii) $R^1$ is hydrogen or halo; and $R^2$ is halo;
(iv) $R^1$ is alkyl, and $R^2$ is hydrogen, alkyl, halo, hydroxy or alkoxy; or
(v) $R^1$ is halo, hydroxy or alkoxy; and $R^2$ is hydrogen or alkyl; $R^3$ is hydrogen, alkyl or cycloalkyl,
$R^5$ is hydrogen or alkyl;
$R^7$ is halo; and
n is 0-3.

In a preferred embodiment of the JAK-2 inhibitor of Formula (LV-D), n is 0.

In a preferred embodiment, JAK-2 inhibitor of Formula (LV-D) is selected from the group consisting of:
(4-fluorophenyl)(4-((1-methyl-1H-imidazol-4-yl)amino)quinazolin-2-yl)methanol; (4-((1H-imidazol-4-yl)amino)quinazolin-2-yl)(4-fluorophenyl)methanol;
(4-fluorophenyl)(4-(thiazol-4-ylamino)quinazolin-2-yl) methanol;
(4-fluorophenyl)(4-((5-methylthiazol-2-yl)amino)quinazolin-2-yl)methanol; and 2-(difluoro(4-fluorophenyl) methyl)-N-(1-methyl-1H-imidazol-4-yl)quinazolin-4-amine, or a pharmaceutically acceptable salt, solvate, hydrate, cocrystal, or prodrug thereof.

In an embodiment, the JAK-2 inhibitor is a compound of Formula (LVII):

Formula (LVII)

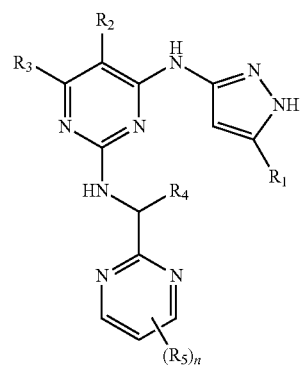

or a pharmaceutically acceptable salt, solvate, hydrate, cocrystal, or prodrug thereof, wherein:
$R^1$ is selected from hydrogen, hydroxy, amino, mercapto, $C_{1-6}$alkyl, $C_{2-6}$alkenyl, $C_{2-6}$alkynyl, $C_{1-6}$ alkoxy, $C_{1-6}$alkanoyloxy, N—($C_{1-6}$alkyl)amino, N,N—($C_{1-6}$alkyl)$_2$ amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;
$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$ alkanoyl, $C_{1-6}$alkanoyloxy, N—($C_{1-6}$ alkyl)amino, N,N—($C_{1-6}$alkyl)$_2$-amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$ sulphamoyl, ($C_{1-6}$alkyl)$_2$N—S(O)$_2$—NH—, ($C_{1-6}$alkyl) NH—S(O)$_2$—NH—, NH$_2$—S(O)$_2$—NH—, ($C_{1-6}$alkyl)$_2$ N—S(O)$_2$—N($C_{1-6}$alkyl)-, ($C_{1-6}$alkyl)NH—S(O)$_2$—N ($C_{1-6}$alkyl)-, NH$_2$—S(O)$_2$—N($C_{1-6}$alkyl)-, N—($C_{1-6}$ alkyl)-N—($C_{1-6}$alkylsulphonyl)amino, $C_{1-6}$ alkylsulphonylamino, carbocyclyl-$R^{19}$— or heterocyclyl-$R^{21}$; wherein $R^2$ and $R^3$ independently of each other may be optionally substituted on carbon by one or more $R^8$;

and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$ alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethyl sulphamoyl or N-methyl-N-ethylsulphamoyl; and $R^{19}$ and $R^{21}$ are independently selected from a direct bond, —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt, solvate, hydrate, cocrystal, or prodrug thereof.

In an embodiment, the JAK-2 inhibitor is a compound of Formula (LVII), wherein:

$R^1$ is selected from hydrogen, hydroxy, amino, mercapto, $C_{1-6}$alkyl, $C_{2-6}$alkenyl, $C_{2-6}$alkynyl, $C_{1-6}$ alkoxy, $C_{1-6}$alkanoyloxy, N—($C_{1-6}$alkyl)amino, N,N—($C_{1-6}$alkyl)$_2$amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$ alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$ alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^2$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$ alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$ alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^8$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt, solvate, hydrate, cocrystal, or prodrug thereof.

In an embodiment, the JAK-2 inhibitor is a compound of Formula (LVII), wherein:

$R^1$ is selected from hydrogen, hydroxy, amino, mercapto, $C_{1-6}$alkyl, $C_{2-6}$alkenyl, $C_{2-6}$alkynyl, $C_{1-6}$ alkoxy, $C_{1-6}$alkanoyloxy, N—($C_{1-6}$alkyl)amino, N,N—($C_{1-6}$alkyl)$_2$amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$ alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, N—($C_{1-6}$alkyl)-N—($C_{1-6}$alkylsulphonyl)amino, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$ alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from ($C_{1-6}$)alkyl, ($C_{1-6}$)alkanoyl, ($C_{1-6}$)alkylsulphonyl, ($C_{1-6}$)alkoxycarbonyl, carbamoyl, N—(($C_{1-6}$)alkyl)carbamoyl, N,N—(($C_{1-6}$)alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $(C_{1-6})$alkyl, $(C_{2-6})$alkenyl, $(C_{2-6})$alkynyl, $(C_{1-6})$alkoxy, $(C_{1-6})$alkanoyl, $(C_{1-6})$alkanoyloxy, N—$((C_{1-6})$alkyl)amino, N,N—$((C_{1-6})$alkyl)$_2$amino, $(C_{1-6})$ alkanoylamino, N—$((C_{1-6})$alkyl)carbamoyl, N,N—$((C_{1-6})$alkyl)$_2$carbamoyl, $(C_{1-6})$alkylS(O)$_a$ wherein a is 0 to 2, $(C_{1-6})$alkoxycarbonyl, N—$((C_{1-6})$alkyl)sulphamoyl, N,N—$((C_{1-6})$alkyl)$_2$sulphamoyl, $(C_{1-6})$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from a direct bond, —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $(C_{1-6})$alkyl and s is 0-2;

$R^{18}$ is selected from $(C_{1-6})$alkyl, $(C_{1-6})$alkanoyl, $(C_{1-6})$alkylsulphonyl, $(C_{1-6})$alkoxycarbonyl, carbamoyl, N—$(C_{1-6}$ alkyl)carbamoyl, N,N—$((C_{1-6})$alkyl)carbamoyl, benzyl, benzyloxycarbonyl, benzoyl and phenylsulphonyl;

or a pharmaceutically acceptable salt, solvate, hydrate, cocrystal, or prodrug thereof.

Particular values of the variable groups contained in Formula (LVII) are as follows. Such values may be used, where appropriate, with any of the definitions, claims or embodiments defined hereinbefore or hereinafter in relation to compounds of Formula (LVII).

$R^1$ is selected from $(C_{1-6})$alkyl, $(C_{1-6})$alkoxy, 3-5-membered carbocyclyl, and N,N—$((C_{1-6})$alkyl)$_2$amino, wherein $R^1$ may be optionally substituted on carbon by one or more $R^6$; and wherein $R^6$ is halo, $R^1$ is $(C_{1-6})$alkoxy or 3-5-membered carbocyclyl.

$R^1$ is selected from $(C_{1-6})$alkyl, $(C_{1-6})$alkoxy or 3-5-membered carbocyclyl.

$R^1$ is $(C_{1-6})$alkyl or $(C_{1-6})$alkoxy.

$R^1$ is 3-5 membered carbocyclyl.

$R^1$ is N,N$((C_{1-6})$alkyl)$_2$amino.

$R^1$ is $(C_{1-6})$alkyl.

$R^1$ is $(C_{1-4})$alkyl.

$R^1$ is $(C_{1-6})$alkoxy.

$R^1$ is selected from methyl, methoxy, trifluoroethoxy, isopropoxy, cyclopropyl, and N,N-dimethylamino;

$R^1$ is isopropoxy or cyclopropyl.

$R^1$ is methyl, methoxy, isopropoxy or cyclopropyl.

$R^1$ is selected from methyl, methoxy, isopropoxy, N,N-dimethylamino, and cyclopropyl.

$R^1$ is isopropoxy.

$R^1$ is methyl.

$R^1$ is ethyl.

$R^1$ is selected from methyl, ethyl, propyl, and butyl.

$R^1$ is selected from $(C_{1-4})$alkyl, $(C_{1-4})$alkoxy, and cyclopropyl.

$R^1$ is methoxy.

$R^1$ is cyclopropyl. $R^1$ is N,N-dimethylamino.

$R^2$ is selected from hydrogen, halo, nitro, and $(C_{1-6})$alkyl, wherein $R^2$ may be optionally substituted on carbon by one or more $R^8$; and wherein $R^8$ is halo.

$R^2$ is selected from hydrogen, chloro, fluoro, bromo, nitro, and trifluoromethyl.

$R^2$ is halo.

$R^2$ is $(C_{1-6})$alkyl, wherein $R^2$ may be optionally substituted on carbon by one or more $R^8$; and wherein $R^8$ is halo.

$R^2$ and $R^3$ are independently selected from hydrogen, halo, nitro, cyano, hydroxy, amino, carboxy, carbamoyl, mercapto, sulphamoyl, $(C_{1-6})$alkyl, $(C_{2-6})$alkenyl, $(C_{2-6})$alkynyl, $(C_{1-6})$alkoxy, $(C_{1-6})$alkanoyl, $(C_{1-6})$alkanoyloxy, N—$((C_{1-6})$alkyl)amino, N,N—$((C_{1-6})$alkyl)$_2$amino, $(C_{1-6})$alkanoylamino, N—$((C_{1-6})$alkyl)carbamoyl, N,N—$((C_{1-6})$alkyl)$_2$carbamoyl, $(C_{1-6})$alkylS(O)$_a$ wherein a is 0 to 2, $(C_{1-6})$alkoxycarbonyl, N—$((C_{1-6})$alkyl)sulphamoyl, N,N—$((C_{1-6})$alkyl)$_2$sulphamoyl, $(C_{1-6})$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$.

$R^2$ and $R^3$ are independently selected from hydrogen, halo, nitro, cyano, hydroxy, amino, carboxy, carbamoyl, mercapto, sulphamoyl, $(C_{1-6})$alkyl, $(C_{2-6})$alkenyl, $(C_{2-6})$alkynyl, $(C_{1-6})$alkoxy, $(C_{1-6})$alkanoyl, $(C_{1-6})$alkanoyloxy, N—$((C_{1-6})$alkyl)amino, N,N—$((C_{1-6})$alkyl)$_2$amino, $(C_{1-6})$alkanoylamino, N—$((C_{1-6})$alkyl)carbamoyl, N,N—$((C_{1-6})$alkyl)$_2$carbamoyl, $(C_{1-6})$alkylS(O)$_a$ wherein a is 0 to 2, $(C_{1-6})$alkoxycarbonyl, N-( )$C_{1-6}$alkyl)sulphamoyl, N,N—$((C_{1-6})$alkyl)$_2$sulphamoyl, N—$((C_{1-6})$alkyl)-N—$((C_{1-6})$alkylsulphonyl)amino, $(C_{1-6})$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$.

$R^2$ and $R^3$ are independently selected from hydrogen, halo, N—$((C_{1-6})$alkyl)-N—$((C_{1-6})$alkylsulphonyl)amino, or heterocyclyl-$R^{21}$—; wherein $R^{21}$ is a direct bond.

$R^2$ and $R^3$ are independently selected from hydrogen and halo.

$R^2$ and $R^3$ are independently selected from hydrogen and chloro.

$R^2$ and $R^3$ are independently selected from hydrogen, fluoro, chloro, bromo, N-methyl-N-mesylamino and morpholino.

$R^2$ is halo and $R^3$ is hydrogen.

$R^2$ is chloro and $R^3$ is hydrogen.

$R^2$ is chloro or fluoro and $R^3$ is hydrogen. $R^3$ is selected from hydrogen, halo, cyano, N—$((C_{1-6})$alkyl)-N—$((C_{1-6})$alkylsulphonyl)amino, $(C_{1-6})$alkyl, $((C_{1-6})$alkyl)$_2$N—S(O)$_2$—N($(C_{1-6})$alkyl)-, and heterocyclyl-$R^{21}$—, wherein $R^3$ may be optionally substituted on carbon by one or more $R^8$; wherein $R^8$ is halo; and wherein $R^{21}$ is a bond.

$R^3$ is hydrogen.

$R^3$ is halo.

$R^3$ is selected from N—$((C_{1-6})$alkyl)-N—$((C_{1-6})$alkylsulphonyl)amino and $((C_{1-6})$alkyl)$_2$N—S(O)$_2$—N($(C_{1-6})$alkyl)-.

R³ is selected from heterocyclyl-R²¹—, wherein R³ may be optionally substituted on carbon by one or more R⁵; wherein R⁵ is halo; and wherein R²¹ is a bond.

R³ is selected from hydrogen, chloro, cyano, trifluoromethyl, $(CH_3)_2N-S(O)_2-N(CH_3)-$, N-methyl-N-mesylamino, and morpholino.

R³ is $(CH_3)_2N-S(O)_2-N(CH_3)-$.

R³ is N-methyl-N-mesylamino,

R³ is morpholino.

R⁴ is $(C_{1-6})$alkyl.

R⁴ is methyl.

R⁵ is halo.

R⁵ is fluoro.

n=1.

R¹⁹ and R²¹ are independently selected from —O—, —N(R²²)—, —C(O)—, —N(I²³)C(O)—, —C(O)N(R²⁴)—, —S(O)$_s$—, —SO₂N(R²⁵)— or —N(R²⁶)SO₂—; wherein R²², R²³, R²⁴, R²⁵ and R²⁶ are independently selected from hydrogen or $(C_{1-6})$alkyl and s is 0-2.

Therefore in a further aspect of the invention there is provided a compound of Formula (LVII) (as depicted herein above) wherein:

R¹ is selected from $(C_{1-6})$alkyl, $(C_{1-6})$alkoxy or 3-5-membered carbocyclyl;

R¹ and R³ are independently selected from hydrogen, halo, N—(($C_{1-6}$)alkyl)-N—(($C_{1-6}$)alkylsulphonyl)amino, or heterocyclyl-R²¹—;

R⁴ is $(C_{1-6})$alkyl;

R⁵ is halo;

n=1;

R²¹ is a direct bond;

or a pharmaceutically acceptable salt, solvate, hydrate, cocrystal, or prodrug thereof.

Therefore, in an embodiment of the invention, the JAK-2 inhibitor is a compound of Formula (LVII) wherein:

R¹ is $(C_{1-6})$alkoxy;

R² and R³ are independently selected from hydrogen and halo;

R⁴ is $(C_{1-6})$alkyl;

R⁵ is halo;

n=1;

or a pharmaceutically acceptable salt, solvate, hydrate, cocrystal, or prodrug thereof.

Therefore, in an embodiment of the invention, the JAK-2 inhibitor is a compound of Formula (LVII) wherein:

R¹ is methyl, methoxy, isopropoxy or cyclopropyl;

R² and R³ are independently selected from hydrogen, fluoro, chloro, bromo, N-methyl-N-mesylamino and morpholino;

R⁴ is methyl;

R⁵ is fluoro; and n=1;

or a pharmaceutically acceptable salt, solvate, hydrate, cocrystal, or prodrug thereof.

Therefore, in an embodiment of the invention, the JAK-2 inhibitor is a compound of Formula (LVII) wherein:

R¹ is selected from $(C_{1-6})$alkyl, $(C_{1-6})$alkoxy, 3-5-membered carbocyclyl, and N,N—(($C_{1-6}$)alkyl)₂amino, wherein R¹ may be optionally substituted on carbon by one or more R⁶;

R² is selected from hydrogen, halo, nitro, and $(C_{1-6})$alkyl, wherein R² may be optionally substituted on carbon by one or more R⁸;

R³ is selected from hydrogen, halo, cyano, N—(($C_{1-6}$)alkyl)-N—(($C_{1-6}$)alkylsulphonyl)amino, $(C_{1-6})$alkyl, $((C_{1-6})$alkyl)₂N—S(O)₂—N(($C_{1-6}$)alkyl)-, and heterocyclyl-R²¹—, wherein R³ may be optionally substituted on carbon by one or more R⁸;

R⁴ is $(C_{1-6})$alkyl;

R⁵ is halo;

R⁶ is halo;

R⁸ is halo;

R²¹ is a bond; and n=1;

or a pharmaceutically acceptable salt, solvate, hydrate, cocrystal, or prodrug thereof.

Therefore, in an embodiment of the invention, the JAK-2 inhibitor is a compound of Formula (LVII) wherein:

R¹ is selected from methyl, methoxy, trifluoroethoxy, isopropoxy, cyclopropyl, and N,N-dimethylamino;

R² is selected from hydrogen, chloro, fluoro, bromo, nitro, and trifluoromethyl;

R³ is selected from hydrogen, chloro, cyano, trifluoromethyl, $(CH_3)_2N-S(O)_2-N(CH_3)-$, N-methyl-N-mesylamino, and morpholino;

R⁴ is methyl;

R⁵ is fluoro; and n is 1;

or a pharmaceutically acceptable salt, solvate, hydrate, cocrystal, or prodrug thereof.

Therefore, in an embodiment of the invention, the JAK-2 inhibitor is a compound of Formula (LVII) wherein:

R¹ is selected from $(C_{1-6})$alkoxy, wherein R¹ may be optionally substituted on carbon by one or more R⁶;

R² is selected from hydrogen and halo;

R³ is selected from hydrogen, halo, and heterocyclyl-R²¹—;

R⁴ is $(C_{1-6})$alkyl;

R⁵ is halo;

R⁶ is halo;

R²¹ is a bond;

n is 1;

or a pharmaceutically acceptable salt, solvate, hydrate, cocrystal, or prodrug thereof.

Therefore, in an embodiment of the invention, the JAK-2 inhibitor is a compound of Formula (LVII) wherein:

R¹ is selected from $(C_{1-4})$alkyl, $(C_{1-4})$alkoxy, and cyclopropyl;

R² is selected from hydrogen, halo, nitro, and $(C_{1-6})$alkyl, wherein R² may be optionally substituted on carbon by one or more R⁸;

R³ is selected from hydrogen, halo, cyano, N—(($C_{1-6}$)alkyl)-N—(($C_{1-6}$)alkylsulphonyl)amino, $(C_{1-6})$alkyl, $((C_{1-6})$alkyl)₂N—S(O)₂—N(($C_{1-6}$)alkyl)-, and heterocyclyl-R²¹—, wherein R³ may be optionally substituted on carbon by one or more R⁸;

R⁴ is $(C_{1-6})$alkyl;

R⁵ is halo;

R⁶ is halo;

R⁸ is halo;

R²¹ is a bond; and n=1;

or a pharmaceutically acceptable salt, solvate, hydrate, cocrystal, or prodrug thereof.

In a preferred embodiment, the JAK-2 inhibitor is AZD-1480. In a preferred embodiment, the JAK-2 inhibitor is (S)-5-chloro-N²-(1-(5-fluoropyrimidin-2-yl)ethyl)-N⁴-(5-methyl-1H-pyrazol-3-yl)pyrimidine-2,4-diamine. In a preferred embodiment, the JAK-2 inhibitor has the chemical structure shown in Formula (LVIII):

Formula (LVIII)

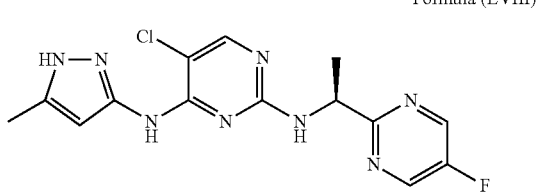

or a pharmaceutically acceptable salt, solvate, hydrate, cocrystal, or prodrug thereof. The preparation of this compound is described in U.S. Pat. No. 8,088,784 and U.S. Patent Application Publication Nos. 2008/0287475 A1; 2010/0160325 A1; and, 2012/0071480 A1, the disclosures of which are incorporated by reference herein. In an embodiment, the JAK-2 inhibitor is selected from the compounds described in U.S. Pat. No. 8,088,784 and U.S. Patent Application Publication Nos. 2008/0287475 A1; 2010/0160325 A1; and, 2012/0071480 A1, the disclosures of which are incorporated by reference herein.

In an embodiment, the JAK-2 inhibitor is a compound of Formula (LIX):

Formula (LIX)

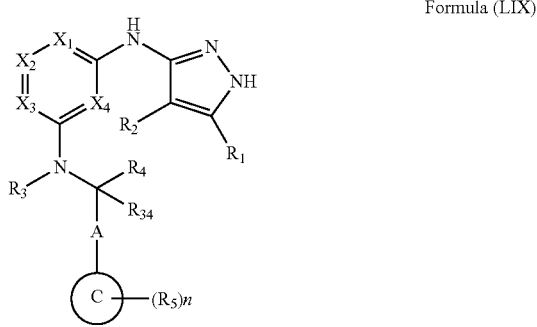

or a pharmaceutically acceptable salt, solvate, hydrate, cocrystal, or prodrug thereof, wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$alkyl)amino, N,N—($C_{1-6}$ alkyl)$_2$-amino, $C_{1-6}$ alkanoylamino, N—($C_{1-6}$ alkyl)carbamoyl, N,N—($C_{1-6}$ alkyl)$_2$-carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, carbocyclyl or heterocyclyl; wherein $R^1$ and $R^2$ independently of each other may be optionally substituted on carbon by one or more $R^6$; and wherein if said heterocyclyl contains an —NH— moiety that nitrogen may be optionally substituted by a group selected from $R^7$;

one of $X^1$, $X^2$, $X^3$ and $X^4$ is =N—, the other three are independently selected from =CR$^8$—, =CR$^9$— and =CR$^{10}$—;

$R^3$ is hydrogen or optionally substituted $C_{1-6}$ alkyl; wherein said optional substituents are selected from one or more $R^{11}$;

$R^4$ and $R^{34}$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$ alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, carbocyclyl or heterocyclyl; wherein $R^4$ and $R^{34}$ may be independently optionally substituted on carbon by one or more $R^{12}$; and wherein if said heterocyclyl contains an —NH— moiety that nitrogen may be optionally substituted by a group selected from $R^{13}$;

A is a direct bond or $C_{1-2}$alkylene; wherein said $C_{1-2}$alkylene may be optionally substituted by one or more $R^{14}$;

Ring C is carbocyclyl or heterocyclyl; wherein if said heterocyclyl contains an —NH— moiety that nitrogen may be optionally substituted by a group selected from $R^{15}$;

$R^5$ is selected from halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, carbocyclyl-$R^{37}$— or heterocyclyl-$R^{38}$—; wherein $R^5$ may be optionally substituted on carbon by one or more $R^{16}$; and wherein if said heterocyclyl contains an —NH— moiety that nitrogen may be optionally substituted by a group selected from $R^{17}$;

n is 0, 1, 2 or 3; wherein the values of $R^5$ may be the same or different;

$R^8$, $R^9$ and $R^{10}$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$ alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, carbocyclyl-$R^{25}$— or heterocyclyl-$R^{26}$—; wherein $R^8$, $R^9$ and $R^{10}$ independently of each other may be optionally substituted on carbon by one or more $R^{18}$; and wherein if said heterocyclyl contains an —NH— moiety that nitrogen may be optionally substituted by a group selected from $R^{19}$;

$R^6$, $R^{11}$, $R^{12}$, $R^{14}$, $R^{16}$ and $R^{18}$ are independently selected from halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, carbocyclyl-$R^{27}$— or heterocyclyl-$R^{28}$—; wherein $R^6$, $R^{11}$, $R^{12}$, $R^{14}$, $R^{16}$ and $R^{18}$ independently of each other may be optionally substituted on carbon by one or more $R^{20}$; and wherein if said heterocyclyl contains an —NH— moiety that nitrogen may be optionally substituted by a group selected from $R^{21}$;

$R^7$, $R^{13}$, $R^{15}$, $R^{17}$, $R^{19}$ and $R^{21}$ are independently selected from $C_{1-6}$ alkyl, $C_{1-6}$ alkanoyl, $C_{1-6}$ alkylsulphonyl, $C_{1-6}$ alkoxycarbonyl, carbamoyl, N—($C_{1-6}$ alkyl)carbamoyl, N,N—($C_{1-6}$ alkyl)carbamoyl, benzyl, benzyloxycarbonyl, benzoyl and phenylsulphonyl; wherein $R^7$, $R^{13}$, $R^{15}$, $R^{17}$, $R^{19}$ and $R^{21}$ independently of each other may be optionally substituted on carbon by on or more $R^{22}$;

$R^{20}$ and $R^{22}$ are independently selected from halo, nitro, cyano, hydroxy, trifluoromethoxy, amino, carboxy, carbamoyl, mercapto, sulphamoyl, $C_{1-3}$alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, $C_{1-6}$ alkylsulphonyl-N—($C_{1-6}$ alkyl)amino, carbocyclyl-$R^{35}$— or heterocyclyl-$R^{36}$—; wherein $R^{20}$ and $R^{22}$ independently of each other may be optionally substituted on carbon by one or more $R^{23}$; and wherein if said heterocyclyl contains an —NH— moiety that nitrogen may be optionally substituted by a group selected from $R^{24}$;

$R^{25}$, $R^{26}$, $R^{27}$, $R^{28}$, $R^{35}$, $R^{36}$, $R^{37}$ and $R^{38}$ are independently selected from a direct bond, —O—, —N($R^{29}$)—, —C(O)—, —N($R^{30}$)C(O)—, —C(O)N($R^{31}$)—, —S(O)$_s$—, —NH=CH—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$ alkyl and s is 0-2;

$R^{23}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethyl sulphamoyl or phenyl; and $R^{24}$ is selected from $C_{1-6}$ alkyl, $C_{1-6}$ alkanoyl, $C_{1-6}$ alkylsulphonyl, $C_{1-6}$ alkoxycarbonyl, carbamoyl, N—($C_{1-6}$ alkyl)carbamoyl, N,N—($C_{1-6}$ alkyl)carbamoyl, benzyl, benzyloxycarbonyl, benzoyl and phenylsulphonyl;

or a pharmaceutically acceptable salt, solvate, hydrate, cocrystal, or prodrug thereof.

In a preferred embodiment, the JAK-2 inhibitor is (S)-5-fluoro-2-((1-(4-fluorophenyl)ethyl)amino)-6-((5-methyl-1H-pyrazol-3-yl)amino)nicotinonitrile. In a preferred embodiment, the JAK-2 inhibitor is a compound of Formula (LX):

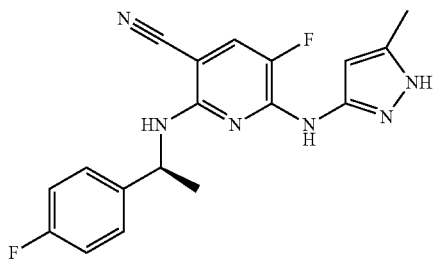

Formula (LX)

or a pharmaceutically acceptable salt, solvate, hydrate, cocrystal, or prodrug thereof. The preparation of this compound is described in U.S. Pat. No. 8,324,252 and U.S. Patent Application Publication Nos. 2008/0139561 A1 and 2013/0090358 A1, the disclosures of which are incorporated by reference herein. In an embodiment, the JAK-2 inhibitor is selected from the compounds described in U.S. Pat. No. 8,324,252 and U.S. Patent Application Publication Nos. 2008/0139561 A1 and 2013/0090358 A1, the disclosures of which are incorporated by reference herein.

In an embodiment, the JAK-2 inhibitor is a compound of Formula (LXII):

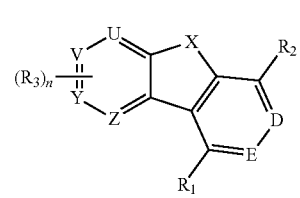

Formula (LXII)

or a pharmaceutically acceptable salt, solvate, hydrate, cocrystal, or prodrug thereof, or a stereoisomer thereof, wherein:

D is CH or N;
E is CH or N;
X is CH$_2$, NR$_4$, O or S;
U is CH or N;
V is CH or N;
Y is CH or N;
Z is CH or N;
R1 is NR$_5$R$_6$, CR5R$_6$R$_7$, SR$_5$ or OR$_5$;
R$_2$ is (C=O)OH, (C=O)NH$_2$, (C=O)NHR$_4$ or heterocyclyl;
R$_3$ is
  (a) hydrogen;
  (b) $C_{1-6}$ alkyl, which is optionally substituted with halo, hydroxyl, amino, phenyl, heterocyclyl, $C_{1-6}$ alkyl or R$_{10}$;
  (c) $C_{2-6}$ alkenyl, which is optionally substituted with halo, hydroxyl, amino, phenyl, heterocyclyl, $C_{1-6}$ alkyl or R$_4$;
  (d) $C_{3-10}$ cycloalkyl, which is optionally substituted with $C_{1-6}$ alkyl, OR$_4$, NR$_8$R$_4$, phenyl (which is optionally substituted with $C_{1-6}$ alkyl, OR$_4$ or NR$_8$R$_4$), halo, R$_{10}$ or heterocyclyl;
  (e) —(CO)R$_8$;
  (f) —(CO)—NR$_8$R$_9$;
  (g) $C_{4-10}$ heterocyclyl, which is optionally substituted on either the carbon or the heteroatom with C1-6 alkyl, halo, R$_{10}$, OR$_4$, NR$_8$R$_4$, phenyl (which is optionally substituted with C1-6 alkyl, OR$_4$ or NR$_8$R$_4$), —(CO)R$_8$ or —(CO)—NR$_8$R$_9$;
  (h) OR$_4$;
  (i) NR$_8$R$_4$;
  (j) halo;
  (k) Aryl, which is optionally substituted with one or more groups selected from $C_{1-6}$ alkyl (which is optionally substituted with one to three halo), halo or R$_{10}$;
  (l) Heteroaryl, which is optionally substituted with one or more groups selected from $C_{1-6}$ alkyl (which is optionally substituted with one to three halo), halo or R$_{10}$;
  (m) O-aryl, which is optionally substituted with one or more groups selected from $C_{1-6}$ alkyl, halo or R$_{10}$;
  (n) O—$C_{1-6}$ alkyl, which is optionally substituted with $C_{1-6}$ alky, halo or R$_{10}$; or
  (o) L-A-R$_{10}$;
R$_4$ is
  (a) hydrogen;
  (b) $C_{1-6}$ alkyl, which is optionally substituted with halo, hydroxyl, amino, aryl or heterocyclyl;

(c) $C_{3-10}$ cycloalkyl, which is optionally substituted with $C_{1-6}$ alkyl, $OR_{11}$, $NR_8R_{11}$, phenyl (which is optionally substituted with $C_{1-6}$ alkyl, $OR_{11}$ or $NR_8R_{11}$), heterocyclyl, aryl or heteroaryl;

(d) —(CO)$R_8$;

(e) —(CO)—$NR_8R_9$;

(f) $C_{4-10}$ heterocyclyl, which is optionally substituted on either the carbon or the heteroatom with $C_{1-6}$ alkyl, $OR_{11}$, $NR_8R_{11}$, phenyl (which is optionally substituted with $C_{1-6}$ alkyl, $OR_{11}$ or $NR_8R_{11}$), heterocyclyl, —(CO)$R_8$ or —(CO)—$NR_8R_9$;

(g) $OR_{11}$;

(h) $NR_8R_{11}$;

(i) Aryl, which is optionally substituted with one to five halo or $R_{10}$;

(j) Heteroaryl (wherein the heteroaryl has 5 or 6 members in which 1, 2, 3, or 4 of the atoms is a heteroatom selected from N, S and O), which is optionally substituted with one to five halo or $R_{10}$;

$R_5$ is (a) hydrogen;

(b) $C_{1-8}$ alkyl, which is optionally substituted with halo, hydroxyl, amino, aryl, cycloalkyl or heterocyclyl;

(c) $C_{3-10}$ cycloalkyl, which is optionally substituted with $C_{1-6}$ alkyl, ($C_{1-6}$ alkyl)aryl, ($C_{1-6}$ alkyl)$OR_9$, $OR_4$, $NR_8R_4$, phenyl (which is optionally substituted with $C_{1-6}$ alkyl, $OR_4$, $NR_8R_4$, heterocyclyl, —(CO)R8 or —(CO)—$NR_8R_9$);

(d) —(CO)$R_8$;

(e) —(CO)—$NR_8R_9$;

(f) $C_{1-6}$ alkyl(C=O)$NR_8CR_9$(C=O)$NR_8R_9$;

(g) $C_{4-10}$ heterocyclyl which is optionally substituted on either the carbon or the heteroatom with one to three substituents selected from $C_{1-6}$ alkyl, halo, $OR_4$, $NR_8R_4$, —(CO)$R_8$, (CO)—$NR_8R_9$ or phenyl (which is optionally substituted with $C_{1-6}$ alkyl, $OR_4$, $NR_8R_4$, heterocyclyl, —(CO)$R_8$ or —(CO)—$NR_8R_9$);

$R_6$ is (a) hydrogen;

(b) $C_{1-8}$ alkyl, which is optionally substituted with halo, hydroxyl, amino, aryl, cycloalkyl or heterocyclyl;

(c) $C_{3-10}$ cycloalkyl, which is optionally substituted with $C_{1-6}$ alkyl, ($C_{1-6}$ alkyl)aryl, ($C_{1-6}$ alkyl)$OR_9$, $OR_4$, $NR_8R_4$, phenyl (which is optionally substituted with $C_{1-6}$ alkyl, $OR_4$, $NR_8R_4$, heterocyclyl, —(CO)$R_8$ or —(CO)—$NR_8R_9$);

(d) —(CO)$R_8$;

(e) —(CO)—$NR_8R_9$;

(f) $C_{1-6}$ alkyl(C=O)$NR_8CR_9$(C=O)$NR_8R_9$;

(g) $C_{4-10}$ heterocyclyl which is optionally substituted on either the carbon or the heteroatom with one to three substituents selected from $C_{1-6}$ alkyl, halo, $OR_4$, $NR_8R_4$, —(CO)$R_8$, (CO)—$NR_8R_9$ or phenyl (which is optionally substituted with $C_{1-6}$ alkyl, $OR_4$, $NR_8R_4$, heterocyclyl, —(CO)$R_8$ or —(CO)—$NR_8R_9$);

$R_7$ is (a) hydrogen;

(b) $C_{1-6}$ alkyl, which is optionally substituted with halo, hydroxyl, amino, phenyl or heterocyclyl;

(c) $C_{3-10}$ cycloalkyl, which is optionally substituted with $C_{1-6}$ alkyl, $OR_4$, $NR_8R_4$, phenyl (which is optionally substituted with $C_{1-6}$ alkyl, $OR_4$, $NR_8R_4$, heterocyclyl, —(CO)$R_8$ or —(CO)—$NR_8R_9$);

(d) $C_{4-10}$ heterocyclyl which is optionally substituted on either the carbon or the heteroatom with $C_{1-6}$ alkyl, $OR_4$, $NR_8R_4$, phenyl (which is optionally substituted with $C_{1-6}$ alkyl, $OR_4$, $NR_8R_4$, heterocyclyl, —(CO)$R_8$ or —(CO)—$NR_8R_9$);

Or $R_5$ and $R_6$, together with the atoms between them, can form a three to ten membered heterocyclic or heteroaryl ring which is optionally substituted with $C_{1-6}$ alkyl, ($C_{1-6}$ alkyl)aryl, ($C_{1-6}$ alkenyl)aryl, ($C_{1-6}$ alkyl)$OR_9$, $OR_4$, $NR_8R_4$, phenyl (which is optionally substituted with $C_{1-6}$ alkyl, $OR_4$, $NR_8R_4$, heterocyclyl, —(CO)$R_8$ or —(CO)—$NR_8R_9$), —(CO)$R_8$; —(CO)—NR8R9, or heterocyclyl;

$R_8$ is hydrogen or $C_{1-6}$ alkyl, —(CO)$R_{11}$, —(CO)N($R_{11})_{12}$;

$R_9$ is hydrogen or $C_{1-6}$ alkyl;

$R_{10}$ is:

(a) hydrogen;

(b) $CO_2R_{11}$;

(c) $C(O)R_{11}$;

(d) $NHR_1$;

(e) $NR_{11}R_{12}$;

(f) $NHS(O)_2R_{11}$;

(g) $NHC(O)R_{11}$;

(h) $NHC(O)OR_{11}$;

(i) NH—C=(NH)$NH_2$;

(j) $NHC(O)NH_2$;

(k) $NHC(O)NHR_{11}$;

(l) $NHC(O)NR_{11}R_{12}$;

(m) NC3-6cycloalkyl;

(n) $C(O)NHR_{11}$;

(o) $C(O)NR_{11}R_{12}$;

(p) $SO_2NHR_{11}$;

(q) $SO_2NHC(O)R_{12}$; or (r) $SO_2R_{11}$;

$R_{11}$ is selected from the group consisting of:

(a) hydrogen, (b) $C_{3-6}$cycloalkyl, which is optionally substituted with aryl, heteroaryl or one to five halo;

(c) $C_{1-6}$ alkyl, which is optionally substituted with aryl, heteroaryl, or one to five halo;

(d) Aryl, which is optionally substituted with one to five halo;

(e) Heteroaryl (wherein the heteroaryl has 5 or 6 members in which 1, 2, 3, or 4 of the atoms is a heteroatom selected from N, S and O), which is optionally substituted with one to five halo;

$R_{12}$ is selected from the group consisting of:

(a) hydrogen, (b) $C_{1-6}$alkyl, which is optionally substituted with aryl, heteroaryl or one to five halo;

(c) $C_{3-6}$cycloalkyl, which is optionally substituted with aryl, heteroaryl or one to five halo;

(d) Aryl, which is optionally substituted with one to five halo;

(e) Heteroaryl (wherein the heteroaryl has 5 or 6 members in which 1, 2, 3, or 4 of the atoms is a heteroatom selected from N, S and O), which is optionally substituted with one to five halo;

A is absent or is selected from the group consisting of: aryl or heteroaryl (wherein the heteroaryl is a monocyclic ring of 5 or 6 atoms or a bicyclic ring of 9 or 10 atoms in which 1, 2, 3, or 4 of the atoms is a heteroatom selected from N, S and O), wherein said aryl or heteroaryl is optionally substituted with one or more substituents selected from halo, ($C_{1-3}$) alkyl, —C(O)OH, $CF_3$, —$SO_2(C_{1-3})$alkyl, $SO_2N(C_{1-3})$alkyl, $SO_2NHC(O)$—($C_{1-3}$)alkyl or N($CH_3)_2$;

L is absent or is selected from the group consisting of: —(CH$_2$)k-W-, —Z—(CH$_2$)k-, —C≡C—, —$C_{1-6}$alkyl-, —$C_{3-6}$cycloalkyl- and —$C_{2-5}$alkene-, wherein the alkene is optionally substituted with one or more groups selected from $C_{1-6}$alkyl or $C_{1-6}$cycloalkyl;

W is selected from the group consisting of: O, NH, $NC_{1-6}$alkyl and S(O)m, with the proviso that when W is O, S(O)m, NH or $NC_{1-6}$alkyl and simultaneously A is absent then $R_{10}$ is $CO_2R_{11}$, $COR_{11}$, $CONHR_{11}$ or $CONR_{11}R_{12}$;

k=0, 1, 2, 3, 4, or 5;

m=0, 1, or 2; and n=0, 1, 2, or 3.

In a preferred embodiment, the JAK-2 inhibitor is ((R)-7-(2-aminopyrimidin-5-yl)-1-((1-cyclopropyl-2,2,2-trifluoroethyl)amino)-5H-pyrido[4,3-b]indole-4-carboxamide, which is also named 7-(2-aminopyrimidin-5-yl)-1-{[(1R)-1-cyclopropyl-2,2,2-trifluoroethyl]amino}-5H-pyrido[4,3-b]indole-4-carboxamide. In a preferred embodiment, the JAK-2 inhibitor is a compound of Formula (LXII):

Formula (LXII)

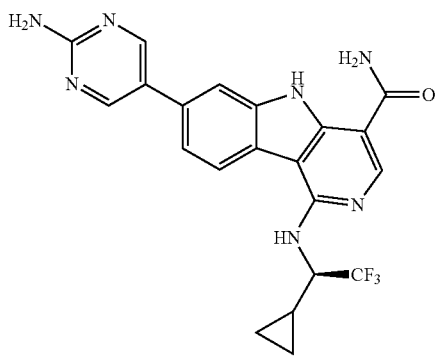

or a pharmaceutically acceptable salt, solvate, hydrate, cocrystal, or prodrug thereof. The preparation of this compound is known to those of ordinary skill in the art, and is described in Lim, et al., Discovery of 1-amino-5H-pyrido[4,3-b]indol-4-carboxamide inhibitors of Janus kinase-2 (JAK2) for the treatment of myeloproliferative disorders, *J. Med. Chem.* 2011, 54, 7334-7349, the disclosure of which is incorporated by reference herein.

In an embodiment, the JAK-2 inhibitor is a compound selected from the JAK-2 inhibitors disclosed in U.S. Patent No. U.S. Pat. No. 8,518,964 or U.S. Patent Application Publication Nos. 2010/0048551 A1, the disclosures of which are incorporated by reference herein.

Pharmaceutical Compositions

In one embodiment, the invention provides a pharmaceutical composition for use in the treatment of the diseases and conditions described herein. In a preferred embodiment, the invention provides pharmaceutical compositions, including those described below, for use in the treatment of a hyperproliferative disease. In a preferred embodiment, the invention provides pharmaceutical compositions, including those described below, for use in the treatment of cancer.

In some embodiments, the invention provides pharmaceutical compositions for treating solid tumor cancers, lymphomas and leukemia.

In preferred embodiments, the invention provides a composition comprising therapeutically effective amounts of (1) a JAK-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof, for use in the treatment of cancer. This composition is typically a pharmaceutical composition.

In preferred embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K inhibitor or a pharmaceutically acceptable salt, solvate, hydrate, cocrystal, or prodrug thereof. This composition is typically a pharmaceutical composition.

In preferred embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof. This composition is typically a pharmaceutical composition.

In preferred embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In preferred embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a compound selected from the group consisting of gemcitabine, albumin-bound paclitaxel, bendamustine, fludarabine, cyclophosphamide, chlorambucil, an anticoagulant or antiplatelet active pharmaceutical ingredient, or combinations thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; and (4) a compound selected from the group consisting of gemcitabine, albumin-bound paclitaxel, bendamustine, fludarabine, cyclophosphamide, chlorambucil, an anticoagulant or antiplatelet active pharmaceutical ingredient, and combinations thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) a compound selected from the group consisting of gemcitabine, albumin-bound paclitaxel, bendamustine, fludarabine, cyclophosphamide, chlorambucil, an anticoagulant or antiplatelet active pharmaceutical ingredient, and combinations thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof, for use in the treatment of cancer; (3) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, biosimilars thereof, and combinations thereof; and (4) a compound selected from the group consisting of gemcitabine, albumin-bound paclitaxel, bendamustine, fludarabine, cyclophosphamide, chlorambucil, an anticoagulant or antiplatelet active pharmaceutical ingredient, and combinations thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, biosimilars thereof, and combinations thereof; and (5) a compound selected from the group consisting of gemcitabine, albumin-bound paclitaxel, bendamustine, fludarabine, cyclophosphamide, chlorambucil, an anticoagulant or antiplatelet active pharmaceutical ingredient, and combinations thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof; and (5) a compound selected from the group consisting of gemcitabine, albumin-bound paclitaxel, bendamustine, fludarabine, cyclophosphamide, chlorambucil, an anticoagulant or antiplatelet active pharmaceutical ingredient, and combinations thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; and (2) a BTK inhibitor having the structure:

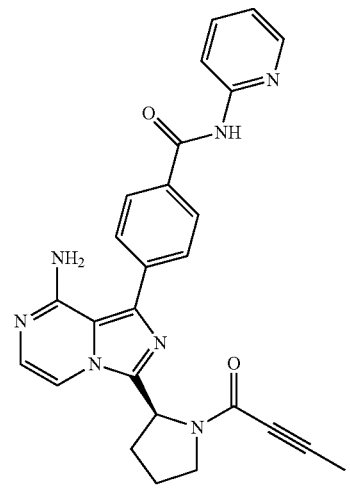

or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof, (2) a BTK inhibitor having the structure:

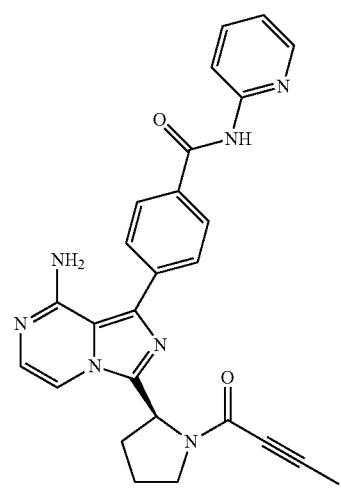 [SMILES: CC#CC(=O)N1CCC[C@H]1c1nc(-c2ccc(C(=O)Nc3ccccn3)cc2)c2c(N)nccn12]

or a pharmaceutically acceptable salt, solvate, hydrate, cocrystal, or prodrug thereof; and (3) a PI3K inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor having the structure:

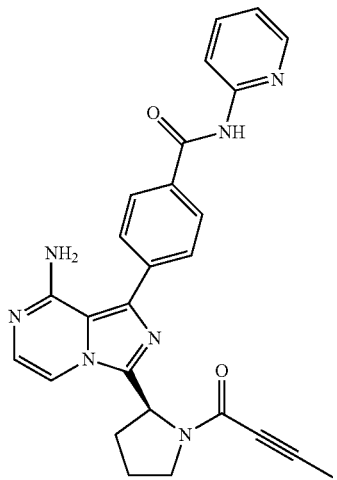 [SMILES: CC#CC(=O)N1CCC[C@H]1c1nc(-c2ccc(C(=O)Nc3ccccn3)cc2)c2c(N)nccn12]

or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor having the structure:

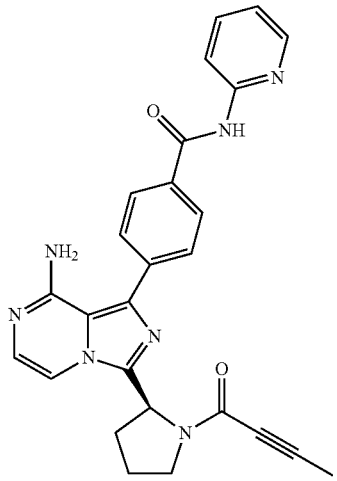 [SMILES: CC#CC(=O)N1CCC[C@H]1c1nc(-c2ccc(C(=O)Nc3ccccn3)cc2)c2c(N)nccn12]

or a pharmaceutically acceptable salt, solvate, hydrate, cocrystal, or prodrug thereof; and (3) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor having the structure:

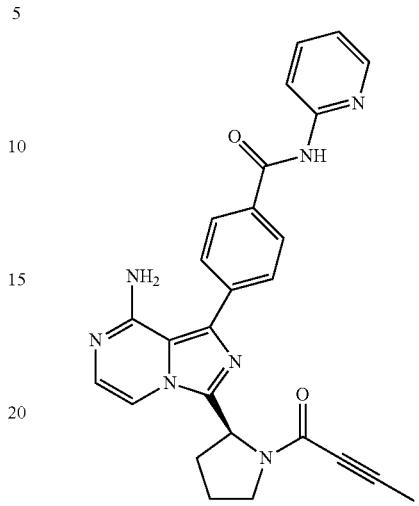

or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor having the structure:

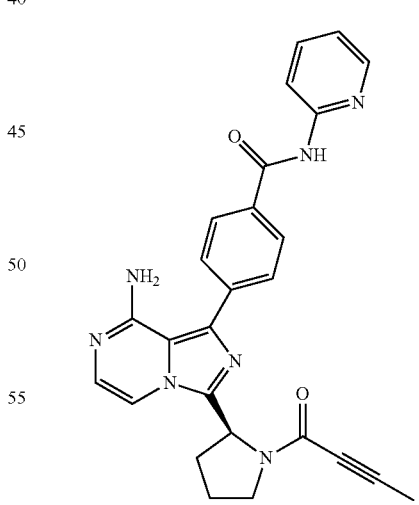

or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; and (2) a BTK inhibitor selected from the group consisting of:

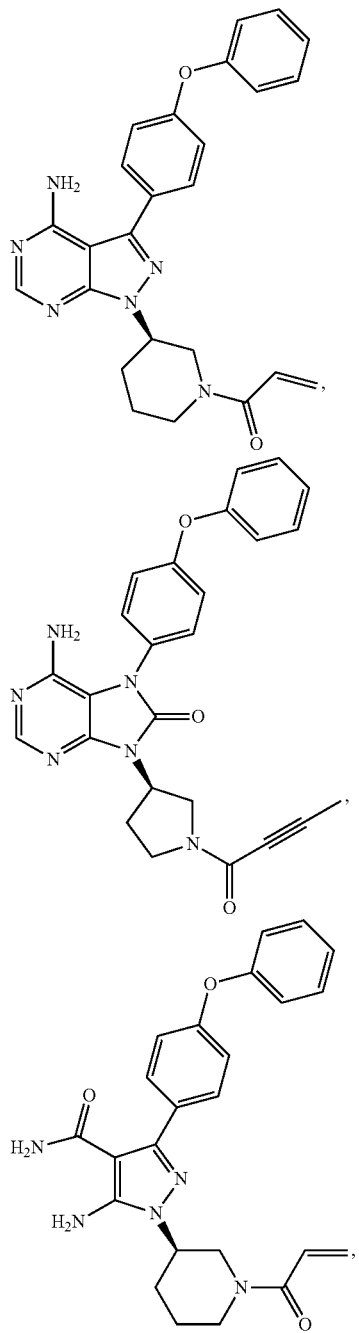

and pharmaceutically-acceptable salts, cocrystals, hydrates, solvates, and prodrugs thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor selected from the group consisting of:

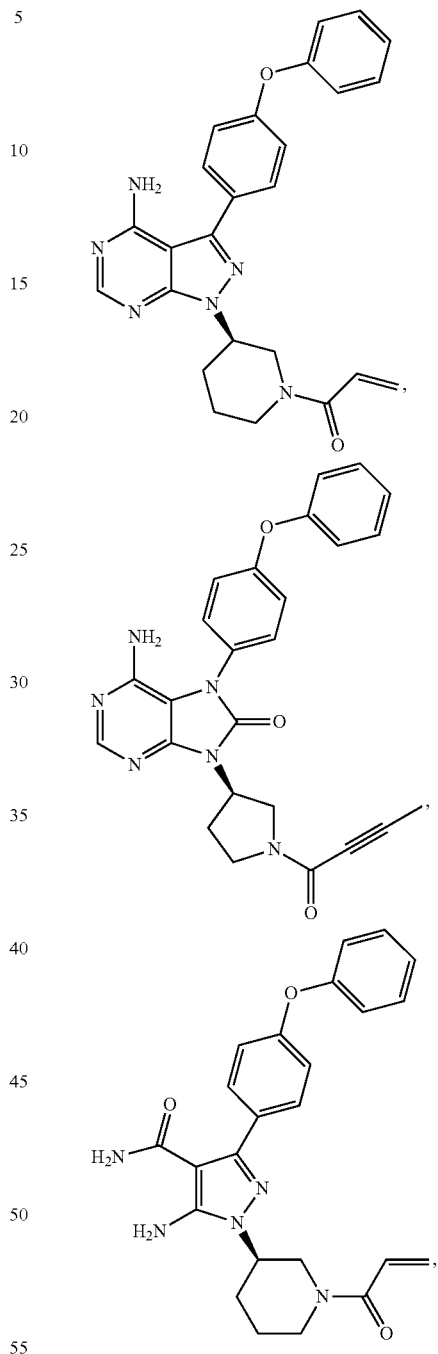

and pharmaceutically-acceptable salts, cocrystals, hydrates, solvates, and prodrugs thereof; and (3) a PI3K inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor selected from the group consisting of:

191

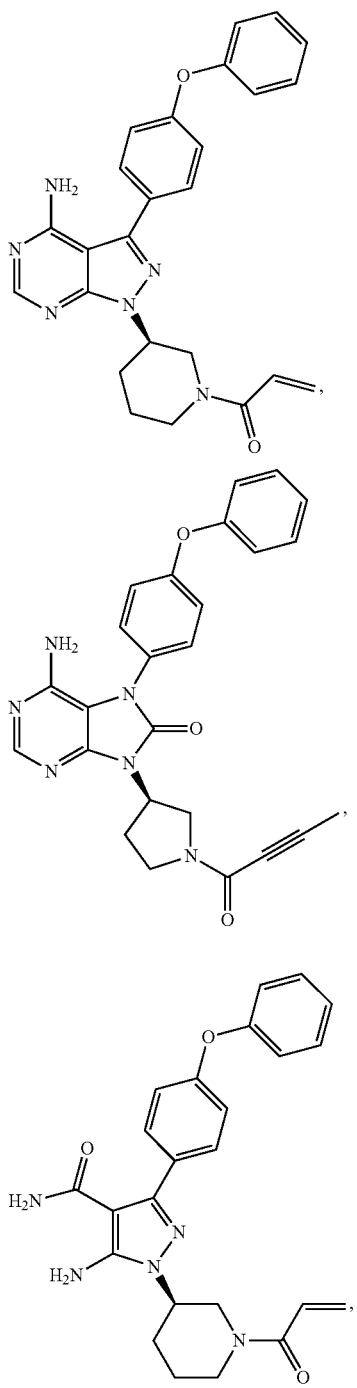

and pharmaceutically-acceptable salts, cocrystals, hydrates, solvates, and prodrugs thereof; and (3) a PI3K-δ inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor selected from the group consisting of:

192

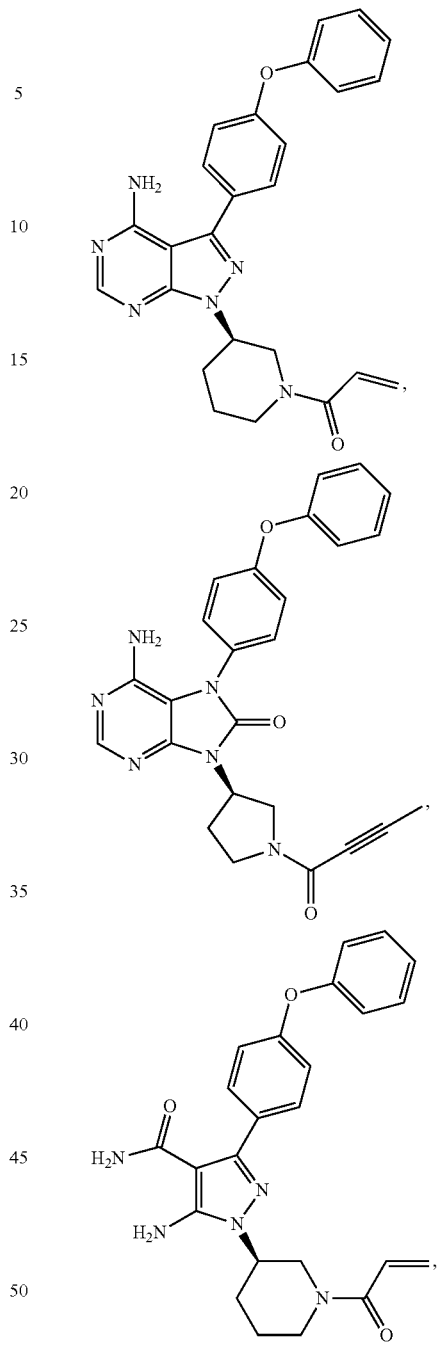

and pharmaceutically-acceptable salts, cocrystals, hydrates, solvates, and prodrugs thereof, and (3) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor selected from the group consisting of:

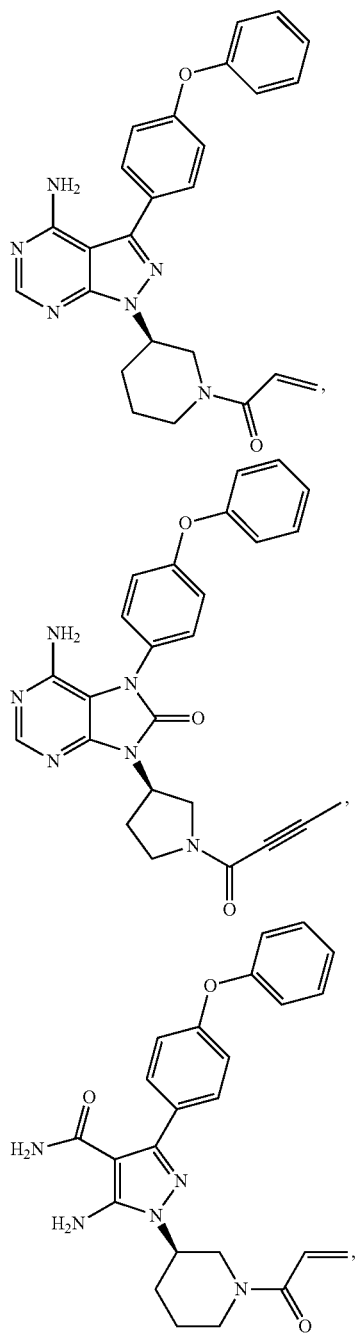

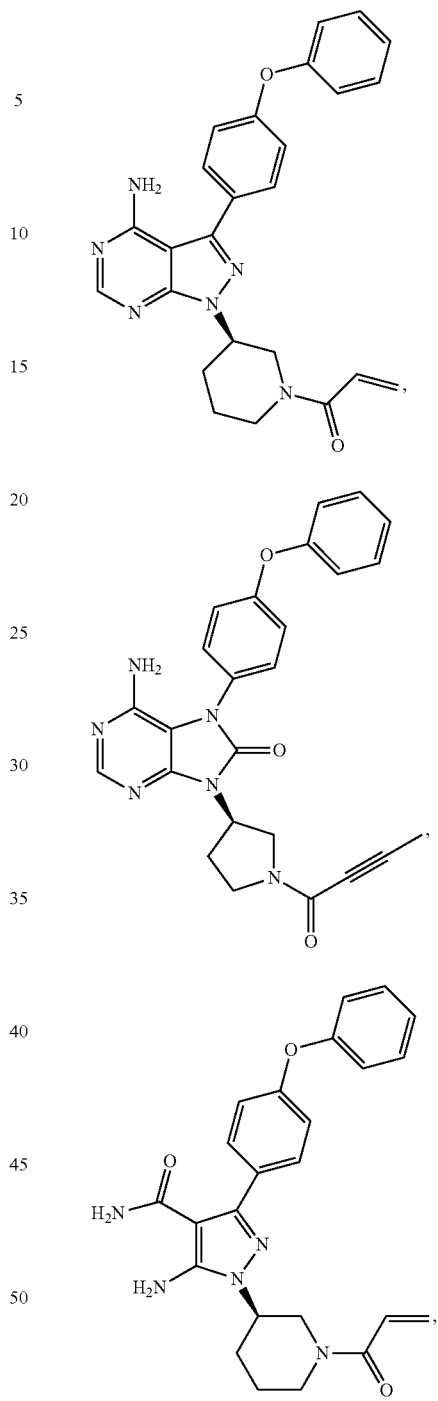

and pharmaceutically-acceptable salts, cocrystals, hydrates, solvates, and prodrugs thereof; (3) a PI3K inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor selected from the group consisting of:

and pharmaceutically-acceptable salts, cocrystals, hydrates, solvates, and prodrugs thereof, (3) a PI3K-δ inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor selected from the group consisting of ruxolitinib, pacritinib, and pharmaceutically-acceptable salts, cocrystals, hydrates, solvates, and prodrugs thereof; and (2) a BTK inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor selected from the group consisting of:

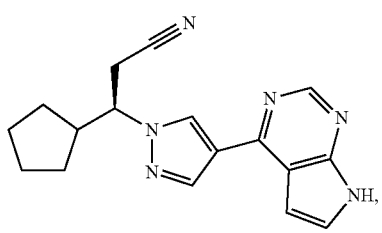

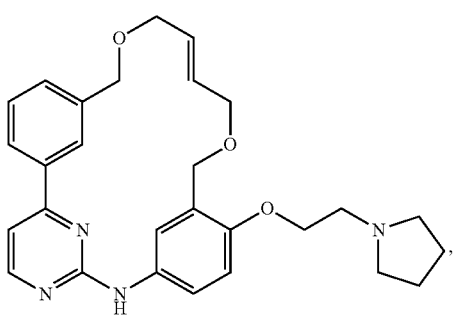

and pharmaceutically-acceptable salts, cocrystals, hydrates, solvates, and prodrugs thereof; and (2) a BTK inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor selected from the group consisting of ruxolitinib, pacritinib, and pharmaceutically-acceptable salts, cocrystals, hydrates, solvates, and prodrugs thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof. This composition is typically a pharmaceutical composition.

In some embodiments, the invention provides a composition comprising therapeutically effective amounts of (1) a JAK-2 inhibitor selected from the group consisting of:

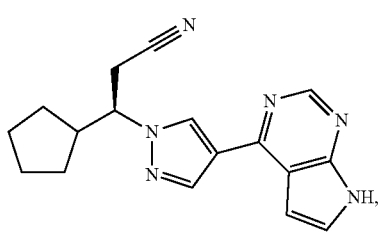

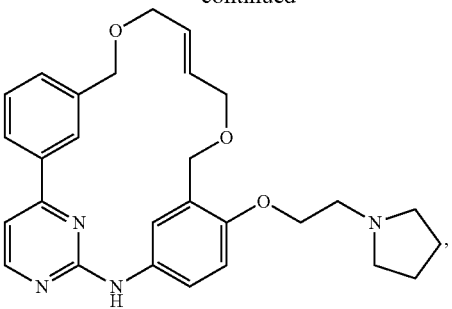

and pharmaceutically-acceptable salts, cocrystals, hydrates, solvates, and prodrugs thereof; (2) a BTK inhibitor or a pharmaceutically acceptable salt, solvate, hydrate, cocrystal, or prodrug thereof, for use in the treatment of cancer; and (3) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor selected from the group consisting of ruxolitinib, pacritinib, and pharmaceutically-acceptable salts, cocrystals, hydrates, solvates, and prodrugs thereof; (2) a BTK inhibitor or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; and (4) an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor selected from the group consisting of ruxolitinib, pacritinib, and pharmaceutically-acceptable salts, cocrystals, hydrates, solvates, or prodrugs thereof; (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K inhibitor selected from the group consisting of:

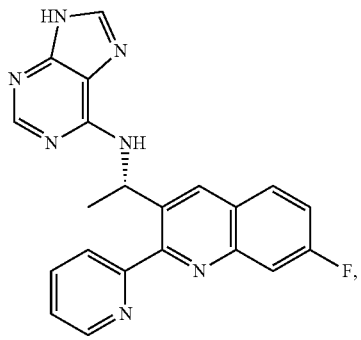

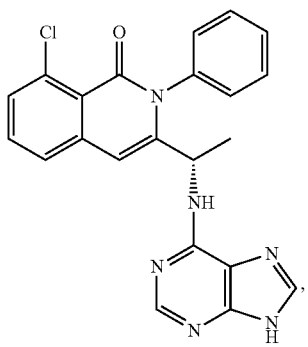

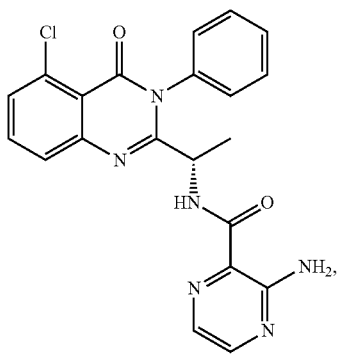

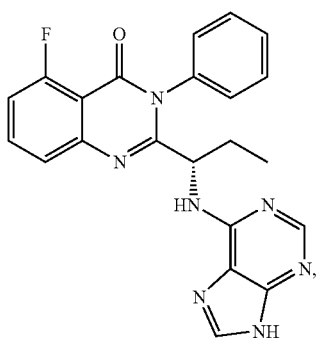

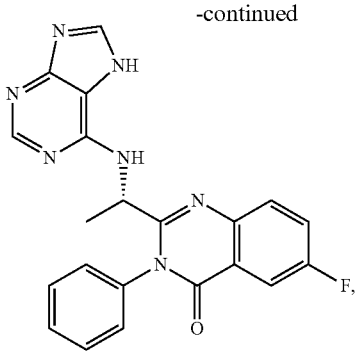

and pharmaceutically acceptable salts, solvates, hydrates, cocrystals, and prodrugs thereof. This composition is typically a pharmaceutical composition.

In some embodiments, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor selected from the group consisting of:

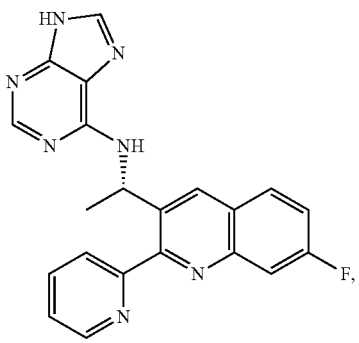

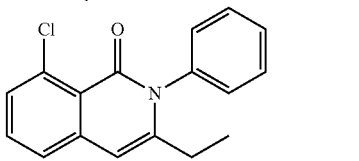

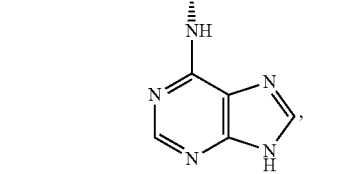

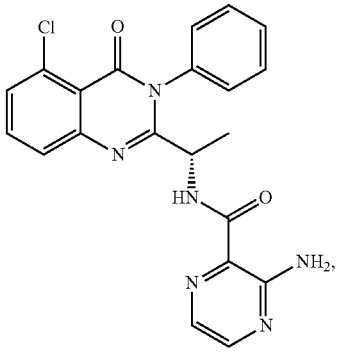

-continued

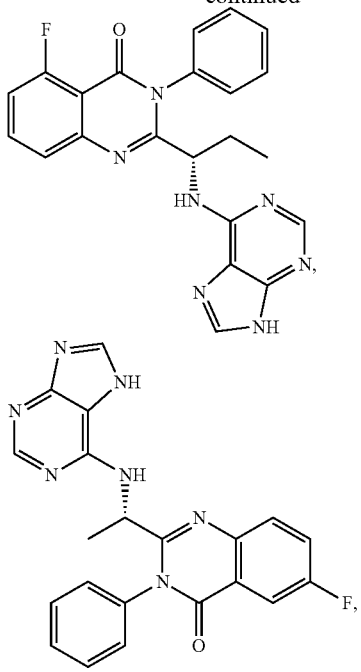

and pharmaceutically acceptable salts, solvates, hydrates, cocrystals, and prodrugs thereof. This composition is typically a pharmaceutical composition.

In one embodiment, the invention provides a composition comprising therapeutically effective amounts of (1) a JAK-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor selected from the group consisting of:

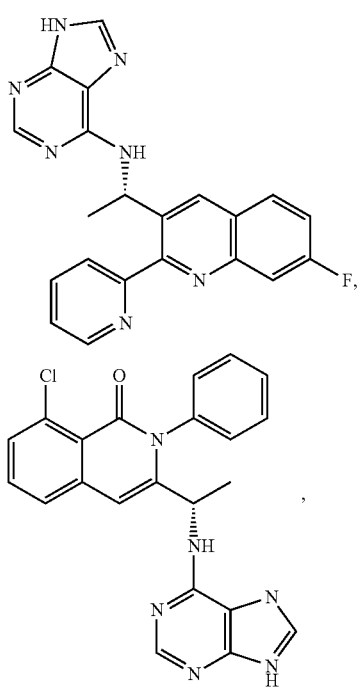

-continued

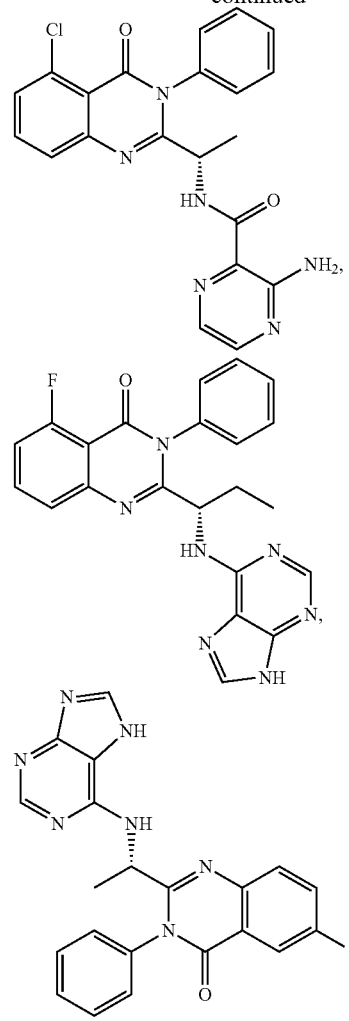

and pharmaceutically acceptable salts, solvates, hydrates, cocrystals, and prodrugs thereof; and (4) a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. This composition is typically a pharmaceutical composition.

The pharmaceutical compositions are typically formulated to provide a therapeutically effective amount of a combination as described herein, i.e., a combination of a PI3K inhibitor, including a PI3K-γ or PI3K-δ inhibitor, a JAK-2 inhibitor, and/or a BTK inhibitor as the active ingredients, or pharmaceutically acceptable salts, prodrugs, solvates, or hydrates thereof. Where desired, the pharmaceutical compositions contain a pharmaceutically acceptable salt and/or coordination complex of one or more of the active ingredients. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

The pharmaceutical compositions described above are preferably for use in the treatment of the diseases and conditions described below. In a preferred embodiment, the pharmaceutical compositions are for use in the treatment of cancer. In preferred embodiments, the pharmaceutical compositions are for use in treating solid tumor cancers, lymphomas, and leukemias.

In a preferred embodiment, the pharmaceutical compositions of the present invention are for use in the treatment of cancer. In one embodiment, the pharmaceutical compositions of the present invention are for use in the treatment of a cancer selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, esophageal cancer, testicular cancer, gynecological cancer, thyroid cancer, aquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

The pharmaceutical compositions are administered as a combination of a JAK-2 inhibitor with a PI3K inhibitor, which may be a PI3K-γ or PI3K-δ inhibitor, and/or a BTK inhibitor. Where desired, other active pharmaceutical ingredient(s) may be mixed into a preparation or two or more components of the combination may be formulated into separate preparations for use in combination separately or at the same time. A kit containing the components of the combination, formulated into separate preparations for said use, in also provided by the invention.

In an embodiment, the molar ratio of the JAK-2 inhibitor to the BTK inhibitor in the pharmaceutical compositions is in the range from 10:1 to 1:10, preferably from 2.5:1 to 1:2.5, and more preferably about 1:1. In an embodiment, the molar ratio of the JAK-2 inhibitor to the PI3K inhibitor in the pharmaceutical compositions is in the range from 10:1 to 1:10, preferably from 2.5:1 to 1:2.5, and more preferably about 1:1. In an embodiment, the weight ratio of the JAK-2 inhibitor to the BTK inhibitor in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the JAK-2 inhibitor to the PI3K inhibitor in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

In some embodiments, the concentration of each of the PI3K, JAK-2, and BTK inhibitors provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of each of the PI3K, JAK-2, and BTK inhibitors provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the PI3K, JAK-2 and BTK inhibitors provided in the pharmaceutical compositions is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of each of the PI3K, JAK-2, and BTK inhibitors provided in the pharmaceutical compositions is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of each of the PI3K, JAK-2, and BTK inhibitors provided in the pharmaceutical compositions is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the PI3K, JAK-2, and BTK inhibitors provided in the pharmaceutical compositions is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the PI3K, JAK-2, and BTK inhibitors according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

In a preferred embodiment, the pharmaceutical compositions of the present invention are for use in the treatment of cancer. In a preferred embodiment, the pharmaceutical compositions of the present invention are for use in the treatment of a cancer selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, esophageal cancer, testicular cancer, gynecological cancer, thyroid cancer, aquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

Described below are non-limiting pharmaceutical compositions and methods for preparing the same.

Pharmaceutical Compositions for Oral Administration

In preferred embodiments, the invention provides a pharmaceutical composition for oral administration containing the combination of a PI3K, JAK-2, and BTK inhibitor, and a pharmaceutical excipient suitable for oral administration.

In preferred embodiments, the invention provides a solid pharmaceutical composition for oral administration containing: (i) an effective amount of each of a PI3K, JAK-2, and BTK inhibitor in combination and (ii) a pharmaceutical excipient suitable for oral administration. In some embodiments, the composition further contains (iii) an effective amount of a fourth active pharmaceutical ingredient.

In some embodiments, the invention provides a solid pharmaceutical composition for oral administration containing: (i) an effective amount of a JAK-2 inhibitor in combination with a PI3K inhibitor and (ii) a pharmaceutical excipient suitable for oral administration. In selected embodiments, the composition further contains (iii) an effective amount of a third active pharmaceutical ingredient.

In preferred embodiments, the invention provides a solid pharmaceutical composition for oral administration containing: (i) an effective amount of a JAK-2 inhibitor in combination with a BTK inhibitor and (ii) a pharmaceutical excipient suitable for oral administration. In selected embodiments, the composition further contains (iii) an effective amount of a third active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the PI3K, JAK-2, and BTK inhibitors as active ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanol amine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In preferred embodiments, the invention provides a pharmaceutical composition for injection containing the combination of the PI3K, JAK-2, and BTK inhibitors, most preferably a combination of the JAK-2 and BTK inhibitors, and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating the combination of the PI3K, JAK-2, and BTK inhibitors in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In preferred embodiments, the invention provides a pharmaceutical composition for transdermal delivery containing the combination of the PI3K, JAK-2, and BTK inhibitors, most preferably a combination of the JAK-2 and BTK inhibitors, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of the combination of the PI3K, JAK-2, and BTK inhibitors in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of the combination of the PI3K, JAK-2, and BTK inhibitors or pharmaceutical composition of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g. PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. The combination of the JAK-2, PI3K, and/or BTK inhibitors may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. The combination of the PI3K, JAK-2, and BTK inhibitors may additionally be administered intravascularly from a balloon used during angioplasty. Extravascular administration of the combination of the PI3K, JAK-2, and BTK inhibitors via the pericard or via advential application of formulations of the invention may also be performed to decrease restenosis.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include each of the PI3K, JAK-2, and BTK inhibitors, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, the PI3K, JAK-2, and BTK inhibitors and another active pharmaceutical ingredient are provided as separate compositions in separate containers within the kit. In selected embodiments, the PI3K, JAK-2, and BTK inhibitors and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit comprising (1) a composition comprising a therapeutically effective amount of a JAK-2 inhibitor or a pharmaceutically acceptable salt, solvate, hydrate, cocrystal, or prodrug thereof; and (2) a composition comprising a therapeutically effective amount of a BTK inhibitor or a pharmaceutically acceptable salt, solvate, hydrate, cocrystal, or prodrug thereof. These compositions are typically pharmaceutical compositions. The kit is for co-administration of the JAK-2 and the BTK inhibitors, either simultaneously or separately.

In some embodiments, the invention provides a kit comprising (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; and (3) a composition comprising a therapeutically effective amount of a PI3K inhibitor or a pharmaceutically acceptable salt, solvate, hydrate, cocrystal, or prodrug thereof. These compositions are typically pharmaceutical compositions. The kit is for co-administration of the JAK-2, the BTK, and the PI3K inhibitors, either simultaneously or separately.

In some embodiments, the invention provides a kit comprising (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; and (3) a composition comprising a therapeutically effective amount of a PI3K-δ inhibitor or a pharmaceutically acceptable salt, solvate, hydrate, cocrystal, or prodrug thereof. These compositions are typically pharmaceutical compositions. The kit is for co-administration of the JAK-2, the BTK, and the PI3K-δ inhibitors, either simultaneously or separately.

In some embodiments, the invention provides a kit comprising (1) a composition comprising a therapeutically effective amount of JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; and (3) a composition comprising a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. These compositions are typically pharmaceutical compositions. The kit is for co-administration of the JAK-2 inhibitor, the BTK inhibitor, and the anti-CD20 antibody, either simultaneously or separately.

In some embodiments, the invention provides a kit comprising, (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of a PI3K inhibitor or a pharmaceutically acceptable salt, solvate, hydrate, cocrystal, or prodrug thereof; and (4) a composition comprising a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. These compositions are typically pharmaceutical compositions. The kit is for co-administration of the JAK-2 inhibitor, the BTK inhibitor, and the anti-CD20 antibody, either simultaneously or separately.

In some embodiments, the invention provides a kit comprising, (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of a PI3K-δ inhibitor or a pharmaceutically acceptable salt, solvate, hydrate, cocrystal, or prodrug thereof; and (4) a composition comprising a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof. These compositions are typically pharmaceutical compositions. The kit is for co-administration of the JAK-2 inhibitor, the BTK inhibitor, the PI3K-δ inhibitor and the anti-CD20 antibody, either simultaneously or separately.

In some embodiments, the invention provides a kit comprising (1) a composition comprising a therapeutically effective amount of a JAK-2 inhibitor or a pharmaceutically acceptable salt, solvate, hydrate, cocrystal, or prodrug thereof, (2) a composition comprising a therapeutically effective amount of a BTK inhibitor or a pharmaceutically acceptable salt, solvate, hydrate, cocrystal, or prodrug thereof; and (3) a composition comprising a therapeutically effective amount of gemcitabine, albumin-bound paclitaxel, bendamustine, fludarabine, cyclophosphamide, chlorambucil, an anticoagulant or antiplatelet active pharmaceutical ingredient, or combinations thereof. These compositions are typically pharmaceutical compositions. The kit is for co-administration of the JAK-2 inhibitor, BTK inhibitor, gemcitabine, albumin-bound paclitaxel, bendamustine, fludarabine, cyclophosphamide, chlorambucil, and/or the anticoagulant or the antiplatelet active pharmaceutical ingredient, either simultaneously or separately.

In some embodiments, the invention provides a kit comprising, (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of a PI3K inhibitor or a pharmaceutically acceptable salt, solvate, hydrate, cocrystal, or prodrug thereof; and (4) a composition comprising a therapeutically effective amount of gemcitabine, albumin-bound paclitaxel, bendamustine, an anticoagulant or antiplatelet active pharmaceutical ingredient, or combinations thereof. These compositions are typically pharmaceutical compositions. The kit is for co-administration of the JAK-2 inhibitor, BTK inhibitor, PI3K inhibitor, gemcitabine, albumin-bound paclitaxel, bendamustine, fludarabine, cyclophosphamide, chlorambucil, and/or the anticoagulant or the antiplatelet active pharmaceutical ingredient, either simultaneously or separately.

In some embodiments, the invention provides a kit comprising, (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of a PI3K-δ inhibitor or a pharmaceutically acceptable salt, solvate, hydrate, cocrystal, or prodrug thereof; and (4) a composition comprising a therapeutically effective amount of gemcitabine, albumin-bound paclitaxel, bendamustine, fludarabine, cyclophosphamide, chlorambucil, and/or an anticoagulant or antiplatelet active pharmaceutical ingredient. These compositions are typically pharmaceutical compositions. The kit is for co-administration of the JAK-2 inhibitor, BTK inhibitor, PI3K-δ inhibitor, gemcitabine, albumin-bound paclitaxel, bendamustine, fludarabine, cyclophosphamide, chlorambucil, and/or the anticoagulant or the antiplatelet active pharmaceutical ingredient, either simultaneously or separately.

In some embodiments, the invention provides a kit comprising (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, biosimilars thereof, and combinations thereof; and (4) a composition comprising a therapeutically effective amount of gemcitabine, albumin-bound paclitaxel, bendamustine, fludarabine, cyclophosphamide, chlorambucil, an anticoagulant or antiplatelet active pharmaceutical ingredient, or combinations thereof. These compositions are typically pharmaceutical compositions. The kit is for co-administration of the JAK-2 inhibitor, BTK inhibitor, anti-CD20 antibody, gemcitabine, albumin-bound paclitaxel, bendamustine, fludarabine, cyclophosphamide, chlorambucil, and/or the anticoagulant or the antiplatelet active pharmaceutical ingredient, either simultaneously or separately.

In some embodiments, the invention provides a kit comprising, (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of a PI3K inhibitor or a pharmaceutically acceptable salt, solvate, hydrate, cocrystal, or prodrug thereof; (4) a composition comprising a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, biosimilars thereof, and combinations thereof; and (5) a composition comprising a therapeutically effective amount of gemcitabine, albumin-bound paclitaxel, bendamustine, fludarabine, cyclophosphamide, chlorambucil, and/or an anticoagulant or antiplatelet active pharmaceutical ingredient. These compositions are typically pharmaceutical compositions. The kit is for co-administration of the JAK-2 inhibitor, BTK inhibitor, PI3K inhibitor, anti-CD20 antibody, gemcitabine, albumin-bound paclitaxel, bendamustine, fludarabine, cyclophosphamide, chlorambucil, and/or the anticoagulant or the antiplatelet active pharmaceutical ingredient, either simultaneously or separately.

In some embodiments, the invention provides a kit comprising, (1) a composition comprising a therapeutically effective amount of a JAK-2 inhibitor or a pharmaceutically acceptable salt, solvate, hydrate, cocrystal, or prodrug thereof; (2) a composition comprising a therapeutically effective amount of a BTK inhibitor or a pharmaceutically acceptable salt, solvate, hydrate, cocrystal, or prodrug thereof; (3) a composition comprising a therapeutically effective amount of a PI3K-δ inhibitor or a pharmaceutically acceptable salt, solvate, hydrate, cocrystal, or prodrug thereof; (4) a composition comprising a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, biosimilars thereof, and combinations thereof; and (5) a composition comprising a therapeutically effective amount of gemcitabine, albumin-bound paclitaxel, bendamustine, fludarabine, cyclophosphamide, chlorambucil, and/or an anticoagulant or antiplatelet active pharmaceutical ingredient. These compositions are typically pharmaceutical compositions. The kit is for co-administration of the JAK-2 inhibitor, BTK inhibitor, PI3K-δ inhibitor, anti-CD20 antibody, gemcitabine, albumin-bound paclitaxel, bendamustine, fludarabine, cyclophosphamide, chlorambucil, and/or the anticoagulant or the antiplatelet active pharmaceutical ingredient, either simultaneously or separately.

The kits described above are preferably for use in the treatment of the diseases and conditions described herein. In a preferred embodiment, the kits are for use in the treatment of cancer. In preferred embodiments, the kits are for use in treating solid tumor cancers, lymphomas and leukemias.

In a preferred embodiment, the kits of the present invention are for use in the treatment of cancer. In a preferred embodiment, the kits of the present invention are for use in the treatment of a cancer selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, esophageal cancer, testicular cancer, gynecological cancer, thyroid cancer, aquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

Dosages and Dosing Regimens

The amounts of BTK inhibitors, PI3K inhibitors, and JAK-2 inhibitors administered will be dependent on the human or mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect— e.g., by dividing such larger doses into several small doses for administration throughout the day. The dosage of BTK inhibitors, PI3K inhibitors, and JAK-2 inhibitors may be provided in units of mg/kg of body mass or in mg/m$^2$ of body surface area. In an embodiment, the ratio of the dose of the JAK-2 inhibitor to the dose of the BTK inhibitor in mg/kg or in mg/m$^2$ is in the range from 10:1 to 1:10, preferably from 2.5:1 to 1:2.5, and more preferably about 1:1. In an embodiment, the ratio of the dose of the JAK-2 inhibitor to the dose of the PI3K inhibitor in mg/kg or in mg/m$^2$ is in the range from 10:1 to 1:10, preferably from 2.5:1 to 1:2.5, and more preferably about 1:1. In an embodiment, the ratio of the JAK-2 inhibitor to the BTK inhibitor in mg/kg or in mg/m$^2$ is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the JAK-2 inhibitor to the PI3K inhibitor in mg/kg or in mg/m$^2$ is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

In some embodiments, the combination of the PI3K, JAK-2, and/or BTK inhibitors is administered in a single dose. Such administration may be by injection, e.g., intravenous injection, in order to introduce the PI3K, JAK-2, and/or BTK inhibitors quickly. However, other routes, including the preferred oral route, may be used as appropriate. A single dose of the combination of the PI3K, JAK-2, and/or BTK inhibitors may also be used for treatment of an acute condition.

In some embodiments, the combination of the PI3K, JAK-2, and/or BTK inhibitors is administered in multiple doses. In a preferred embodiment, the combination of the JAK-2 and BTK inhibitors is administered in multiple doses. Dosing may be once, twice, three times, four times, five times, six times, or more than six times per day. Dosing may be once a month, once every two weeks, once a week, or once every other day. In other embodiments, the combination of the PI3K, JAK-2, and/or BTK inhibitors is administered about once per day to about 6 times per day. In some embodiments, the combination of the PI3K, JAK-2, and/or BTK inhibitors is administered once daily, while in other embodiments, the combination of the PI3K, JAK-2, and/or BTK inhibitors is administered twice daily, and in other embodiments the combination of the PI3K, JAK-2, and/or BTK inhibitors is administered three times daily. In some embodiments, a BTK inhibitor disclosed herein is administered in combination with a PI3K-δ inhibitor and/or a JAK-2 inhibitor once daily, while in other embodiments a BTK inhibitor disclosed herein is administered in combination with a PI3K-δ inhibitor and/or a JAK-2 inhibitor twice daily, and in other embodiments a BTK inhibitor disclosed herein is administered in combination with a PI3K-δ inhibitor and/or a JAK-2 inhibitor three times daily. In some embodiments a PI3K-δ inhibitor disclosed herein is administered in combination with a BTK inhibitor and/or a JAK-2 inhibitor once daily, while in other embodiments a PI3K-δ inhibitor disclosed herein is administered in combination with a BTK inhibitor and/or a JAK-2 inhibitor twice daily, and in other embodiments a PI3K-δ inhibitor disclosed herein is administered in combination with a BTK inhibitor and/or a JAK-2 inhibitor three times daily. In some embodiments a JAK-2 inhibitor disclosed herein is administered in combination with a BTK inhibitor and/or a PI3K-δ inhibitor once daily, while in other embodiments a JAK-2 inhibitor disclosed herein is administered in combination with a BTK inhibitor and/or a PI3K-δ inhibitor twice daily, and in other embodiments a JAK-2 inhibitor disclosed herein is administered in combination with a BTK inhibitor and/or a PI3K-δ inhibitor three times daily.

Administration of the active pharmaceutical ingredients of the invention may continue as long as necessary. In selected embodiments, the combination of the PI3K, JAK-2, and/or BTK inhibitors is administered for more than 1, 2, 3, 4, 5, 6, 7, 14, or 28 days. In some embodiments, the combination of the PI3K, JAK-2, and BTK inhibitors is administered for less than 28, 14, 7, 6, 5, 4, 3, 2, or 1 day. In selected embodiments, the combination of the PI3K, JAK-2, and/or BTK inhibitors is administered chronically on an ongoing basis—e.g., for the treatment of chronic effects. In another embodiment the administration of the combination of the PI3K, JAK-2, and/or BTK inhibitors continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of a BTK inhibitor disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a BTK inhibitor disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a BTK inhibitor disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a BTK inhibitor disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, an effective dosage of a PI3K inhibitor disclosed herein is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg. In some embodiments, an effective dosage of a PI3K inhibitor disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a PI3K inhibitor disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.01 mg/kg to about 0.7 mg/kg, about 0.07 mg/kg to about 0.65 mg/kg, about 0.15 mg/kg to about 0.6 mg/kg, about 0.2 mg/kg to about 0.5 mg/kg, about 0.3 mg/kg to about 0.45 mg/kg, about 0.3 mg/kg to about 0.4 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg to about 1.6 mg/kg, about 1.35 mg/kg to about 1.5 mg/kg, about 1.4 mg/kg to about 1.45 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a PI3K inhibitor disclosed herein is about 0.4 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, an effective dosage of a JAK-2 inhibitor disclosed herein is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg. In some embodiments, an effective dosage of a JAK-2 inhibitor disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a JAK-2 inhibitor disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.01 mg/kg to about 0.7 mg/kg, about 0.07 mg/kg to about 0.65 mg/kg, about 0.15 mg/kg to about 0.6 mg/kg, about 0.2 mg/kg to about 0.5 mg/kg, about 0.3 mg/kg to about 0.45 mg/kg, about 0.3 mg/kg to about 0.4 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg to about 1.6 mg/kg, about 1.35 mg/kg to about 1.5 mg/kg, about 1.4 mg/kg to about 1.45 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a JAK-2 inhibitor disclosed herein is about 0.4 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a combination of a BTK inhibitor and a PI3K inhibitor is administered at a dosage of 10 to 200 mg BID, including 50, 60, 70, 80, 90, 100, 150, or 200 mg BID, for the BTK inhibitor, and 10 to 200 mg BID, including 25, 50, 75, 100, 150, or 200 mg BID for the PI3K inhibitor.

In some embodiments, a combination of a BTK inhibitor and a JAK-2 inhibitor is administered at a dosage of 10 to 200 mg BID, including 50, 60, 70, 80, 90, 100, or 150 mg BID, for the BTK inhibitor, and 10 to 500 mg BID, including 1, 5, 10, 15, 25, 50, 75, 100, 150, 200, 300, 400, or 500 mg BID for the JAK-2 inhibitor.

In some embodiments, a combination of a PI3K inhibitor and a JAK-2 inhibitor is adminstered at a dosage of 10 to 200 mg BID, including 50, 60, 70, 80, 90, 100, or 150 mg BID, for the PI3K inhibitor, and 10 to 500 mg BID, including 1, 5, 10, 15, 25, 50, 75, 100, 150, 200, 300, 400, or 500 mg BID for the JAK-2 inhibitor.

In some embodiments, a combination of a a BTK inhibitor, a PI3K inhibitor, and a JAK-2 inhibitor is adminstered at a dosage of 10 to 200 mg BID, including 50, 60, 70, 80, 90, 100, or 150 mg BID, for the BTK inhibitor, 10 to 200 mg BID, including 50, 60, 70, 80, 90, 100, or 150 mg BID, for the PI3K inhibitor, and 10 to 500 mg BID, including 1, 5, 10, 15, 25, 50, 75, 100, 150, 200, 300, 400, or 500 mg BID for the JAK-2 inhibitor.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of the combination of the PI3K, JAK-2, and BTK inhibitors may be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, or as an inhalant.

Methods of Treating Solid Tumor Cancers, Hematological Malignancies, and Other Diseases The compositions and combinations of inhibitors described above can be used in a method for treating diseases. In a preferred embodiment, they are for use in treating hyperproliferative disorders. They may also be used in treating other disorders as described herein and in the following paragraphs.

In some embodiments, the invention provides a method of treating a hyperproliferative disorder in a mammal that comprises administering to said mammal a therapeutically effective amount of a PI3K inhibitor (or a PI3K-γ inhibitor, PI3K-δ inhibitor, or PI3K-γ,δ inhibitor) and a BTK inhibitor, or a pharmaceutically acceptable salt, solvate, hydrate, cocrystal, or prodrug of either or both the PI3K inhibitor (or a PI3K-γ inhibitor, PI3K-δ inhibitor, or PI3K-γ,δ inhibitor) or the BTK inhibitor. In some embodiments, the invention provides a method of treating a hyperproliferative disorder in a mammal that comprises administering to said mammal a therapeutically effective amount of a JAK-2 inhibitor and a BTK inhibitor, or a pharmaceutically acceptable salt, solvate, hydrate, cocrystal, or prodrug of either or both the JAK-2 inhibitor or the BTK inhibitor. In some embodiments, the invention provides a method of treating a hyperproliferative disorder in a mammal that comprises administering to said mammal a therapeutically effective amount of a JAK-2 inhibitor and a PI3K inhibitor, or a pharmaceutically acceptable salt, solvate, hydrate, cocrystal, or prodrug of either or both the JAK-2 inhibitor or the PI3K inhibitor. In some embodiments, the invention provides a method of treating a hyperproliferative disorder in a mammal that comprises administering to said mammal a therapeutically effective amount of a JAK-2 inhibitor, a BTK inhibitor, and a PI3K inhibitor, or a pharmaceutically acceptable salt, solvate, hydrate, cocrystal, or prodrug of the JAK-2 inhibitor, the BTK inhibitor, and/or the PI3K inhibitor.

In some embodiments, the hyperproliferative disorder is cancer. In selected embodiments, the cancer is selected from the group consisting of non-Hodgkin's lymphomas (such as diffuse large B-cell lymphoma), acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, bone (e.g., metastatic bone), esophageal, testicular, gynecological, thyroid, CNS, PNS, AIDS-related (e.g. lymphoma and Kaposi's sarcoma), viral-induced cancers such as cervical carcinoma (human papillomavirus), B-cell lymphoproliferative disease and nasopharyngeal carcinoma (Epstein-Barr virus), Kaposi's sarcoma and primary effusion lymphomas (Kaposi's sarcoma herpesvirus), hepatocellular carcinoma (hepatitis B and hepatitis C viruses), and T-cell leukemias (Human T-cell leukemia virus-1), B cell acute lymphoblastic leukemia, Burkitt's leukemia, juvenile myelomonocytic leukemia, hairy cell leukemia, Hodgkin's disease, multiple myeloma, mast cell leukemia, and mastocytosis. In selected embodiments, the method relates to the treatment of a non-cancerous hyperproliferative disorder such as benign hyperplasia of the skin (e.g., psoriasis), restenosis, or prostate conditions (e.g., benign prostatic hypertrophy (BPH)).

In some embodiments, the hyperproliferative disorder is an inflammatory, immune, or autoimmune disorder. In some embodiments, the hyperproliferative disorder is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's disease, lupus, and lupus nephritis.

In some embodiments, the invention provides pharmaceutical compositions of a combination of a PI3K inhibitor, including a PI3K-γ, PI3K-δ, or PI3K-γ,δ inhibitor, a JAK-2 inhibitor, and/or a BTK inhibitor for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., lymphoma and Kaposi's sarcoma) or viral-induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, the invention provides pharmaceutical compositions of a combination of a PI3K inhibitor, including a PI3K-γ, PI3K-δ, or PI3K-γ,δ inhibitor, a JAK-2 inhibitor, and/or a BTK inhibitor for the treatment of disorders such as myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL1-positive), chronic neutrophilic leukemia, chronic eosinophilic leukemia, or mastocytosis.

The invention further provides a composition as described herein for the prevention of blastocyte implantation in a mammal.

The invention also provides a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In one embodiment, provided herein is a method of treating, preventing and/or managing asthma. As used herein, "asthma" encompasses airway constriction regardless of the cause. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction and mucus production.

Efficacy of the compounds and combinations of compounds described herein in treating, preventing and/or managing the indicated diseases or disorders can be tested using various animal models known in the art. Efficacy in treating, preventing and/or managing asthma can be assessed using the ova induced asthma model described, for example, in Lee, et al., *J. Allergy Clin. Immunol.* 2006, 118, 403-9. Efficacy in treating, preventing and/or managing arthritis (e.g., rheumatoid or psoriatic arthritis) can be assessed using the autoimmune animal models described in, for example, Williams, et al., *Chem. Biol.* 2010, 17, 123-34, WO 2009/088986, WO 2009/088880, and WO 2011/008302. Efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke, et al., *Clinics in Dermatology*, 2007, 25, 596-605. Efficacy in treating, preventing and/or managing fibrosis or fibrotic conditions can be assessed using the unilateral ureteral obstruction model of renal fibrosis, which is described, for example, in Chevalier, et al., *Kidney International* 2009, 75, 1145-1152; the bleomycin induced model of pulmonary fibrosis described in, for example, Moore, et al., *Am. J. Physiol. Lung. Cell. Mol. Physiol.* 2008, 294, L152-L160; a variety of liver/biliary fibrosis models described in, for example, Chuang, et al., *Clin. Liver Dis.* 2008, 12, 333-347 and Omenetti, et al., *Laboratory Investigation*, 2007, 87, 499-514 (biliary duct-ligated model); or any of a number of myelofibrosis mouse models such as described in Varicchio, et al., *Expert Rev. Hematol.* 2009, 2(3), 315-334. Efficacy in treating, preventing and/or managing scleroderma can be assessed using a mouse model induced by repeated local injections of bleomycin described, for example, in Yamamoto, et al., *J. Invest. Dermatol.* 1999, 112, 456-462. Efficacy in treating, preventing and/or managing dermatomyositis can be assessed using a myositis mouse model induced by immunization with rabbit myosin as described, for example, in Phyanagi, et al., *Arthritis & Rheumatism*, 2009, 60(10), 3118-3127. Efficacy in treating, preventing and/or managing lupus can be assessed using various animal models described, for example, in Ghoreishi, et al., *Lupus*, 2009, 19, 1029-1035; Ohl, et al., *J. Biomed. Biotechnol.*, 2011, Article ID 432595; Xia, et al., *Rheumatology*, 2011, 50, 2187-2196; Pau, et al., *PLoS ONE*, 2012, 7(5), e36761; Mustafa, et al., *Toxicology*, 2011, 290, 156-168; Ichikawa, et al., *Arthritis & Rheumatism*, 2012, 62(2), 493-503; Rankin, et al., *J. Immunology*, 2012, 188, 1656-1667. Efficacy in treating, preventing and/or managing Sjögren's syndrome can be assessed using various mouse models described, for example, in Chiorini, et al., *J. Autoimmunity*, 2009, 33, 190-196.

In selected embodiments, the invention provides a method of treating a solid tumor cancer with a composition including a combination of a PI3K inhibitor (e.g., a PI3K-γ or PI3K-δ inhibitor), a JAK-2 inhibitor, and/or a BTK inhibitor, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In selected embodiments, the invention provides a method of treating pancreatic cancer, breast cancer, ovarian cancer, melanoma, lung cancer, squamous cell carcinoma including head and neck cancer, and colorectal cancer using a combination of a BTK inhibitor, a PI3K inhibitor, and/or a JAK-2 inhibitor, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In an embodiment, the invention provides a method for treating pancreatic cancer, breast cancer, ovarian cancer, melanoma, lung cancer, head and neck cancer, and colorectal cancer using a combination of a BTK inhibitor, a PI3K inhibitor, and/or a JAK-2 inhibitor and gemcitabine, or a pharmaceutically-acceptable salt, cocrystal, hydrate, solvate, or prodrug thereof. In an embodiment, the invention provides a method for treating pancreatic cancer, breast cancer, ovarian cancer, melanoma, lung cancer, head and neck cancer, and colorectal cancer using a combination of a BTK inhibitor, a PI3K inhibitor, and/or a JAK-2 inhibitor and gemcitabine, or a pharmaceutically-acceptable salt, cocrystal, hydrate, solvate, or prodrug thereof, wherein the BTK inhibitor is a compound of Formula (XVIII). Efficacy of the compounds and combinations of compounds described herein in treating, preventing and/or managing the indicated diseases or disorders can be tested using various models known in the art. For example, models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development*, 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32. Models for determining efficacy of treatments for colorectal cancer, including the CT26 model, are described below in the examples.

Methods of Treating Patients Intolerant to Bleeding Events

In selected embodiments, the invention provides a method of treating a cancer in a human sensitive to or intolerant to bleeding events, comprising the step of administering a therapeutically effective amount of a BTK inhibitor, or a pharmaceutically-acceptable salt, cocrystal, hydrate, solvate, or prodrug thereof, and a JAK-2 inhibitor and/or a PI3K inhibitor, or a pharmaceutically-acceptable salt, cocrystal, hydrate, solvate, or prodrug thereof. In a preferred embodiment, the invention provides a method of treating a cancer in a human sensitive to or intolerant to bleeding events, comprising the step of administering a therapeutically effective amount of a BTK inhibitor, wherein the BTK inhibitor is selected from the group consisting of Formula (XVIII), Formula (XVIII-A), Formula (XVIII-B), Formula (XVIII-C), Formula (XVIII-D), and Formula (XVIII-E), and a pharmaceutically-acceptable salt, cocrystal, hydrate, solvate, and prodrug thereof. In a preferred embodiment, the invention provides a method of treating a cancer in a human sensitive to or intolerant to bleeding events, comprising the step of administering a therapeutically effective amount of a BTK inhibitor and a JAK-2 inhibitor, wherein the BTK inhibitor is selected from the group consisting of Formula (XVIII), Formula (XVIII-A), Formula (XVIII-B), Formula (XVIII-C), Formula (XVIII-D), and Formula (XVIII-E), and a pharmaceutically-acceptable salt, cocrystal, hydrate, solvate, and prodrug thereof, and wherein the JAK-2 inhibitor is selected from the group consisting of ruxolitinib, pacritinib, and a pharmaceutically-acceptable salt, cocrystal, hydrate, solvate, and prodrug thereof.

In an embodiment, the invention provides a method of treating a cancer in a human intolerant to bleeding events, comprising the step of administering a therapeutically effective amount of a BTK inhibitor, wherein the BTK inhibitor is Formula (XVIII), or a pharmaceutically-acceptable salt, cocrystal, hydrate, solvate, or prodrug thereof, and a JAK-2 inhibitor, or a pharmaceutically-acceptable salt, cocrystal, hydrate, solvate, or prodrug thereof, further comprising the step of administering a therapeutically effective amount of an anticoagulant or antiplatelet active pharmaceutical ingredient.

In selected embodiments, the invention provides a method of treating a cancer in a human intolerant to bleeding events, comprising the step of administering a therapeutically effective amount of a BTK inhibitor, wherein the BTK inhibitor is preferably a compound of Formula (XVIII), and wherein the cancer is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, colorectal cancer, esophageal cancer, testicular cancer, gynecological cancer, thyroid cancer, aquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hogkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In some embodiments, the invention provides a method of treating a cancer in a human intolerant to platelet-mediated thrombosis comprising the step of administering a therapeutically effective amount of a BTK inhibitor, wherein the BTK inhibitor is Formula (XVIII), or a pharmaceutically-acceptable salt, cocrystal, hydrate, solvate, or prodrug thereof, and a JAK-2 inhibitor, or a pharmaceutically-acceptable salt, cocrystal, hydrate, solvate, or prodrug thereof.

In some embodiments, the BTK inhibitor and the anticoagulant or the antiplatelet active pharmaceutical ingredient are administered sequentially. In some embodiments, the BTK inhibitor and the anticoagulant or the antiplatelet active pharmaceutical ingredient are administered concomitantly. In selected embodiments, the BTK inhibitor is administered before the anticoagulant or the antiplatelet active pharmaceutical ingredient. In selected embodiments, the BTK inhibitor is administered after the anticoagulant or the antiplatelet active pharmaceutical ingredient. In selected embodiments, a JAK-2 inhibitor is co-administered with the BTK inhibitor and the anticoagulant or the antiplatelet active pharmaceutical ingredient at the same time or at different times.

Selected anti-platelet and anticoagulant active pharmaceutical ingredients for use in the methods of the present invention include, but are not limited to, cyclooxygenase inhibitors (e.g., aspirin), adenosine diphosphate (ADP) receptor inhibitors (e.g., clopidogrel and ticlopidine), phosphodiesterase inhibitors (e.g., cilostazol), glycoprotein IIb/IIIa inhibitors (e.g., abciximab, eptifibatide, and tirofiban), and adenosine reuptake inhibitors (e.g., dipyridamole). In other embodiments, examples of anti-platelet active pharmaceutical ingredients for use in the methods of the present invention include anagrelide, aspirin/extended-release dipyridamole, cilostazol, clopidogrel, dipyridamole, prasugrel, ticagrelor, ticlopidine, vorapaxar, tirofiban HCl, eptifibatide, abciximab, argatroban, bivalirudin, dalteparin, desirudin, enoxaparin, fondaparinux, heparin, lepirudin, apixaban, dabigatran etexilate mesylate, rivaroxaban, and warfarin.

In an embodiment, the invention provides a method of treating a cancer, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and a JAK-2 inhibitor, or pharmaceutically acceptable salt, solvate, hydrate, cocrystal, or prodrug thereof, further comprising the step of administering a therapeutically effective amount of an anticoagulant or antiplatelet active pharmaceutical ingredient, wherein the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, prodrugs thereof, and combinations thereof.

Combinations of BTK Inhibitors, PI3K Inhibitors, and JAK-2 Inhibitors

Non-limiting, exemplary embodiments of combinations of the PI3K inhibitors, BTK inhibitors, and JAK-2 inhibitors described above are given in the following paragraphs. The disclosure encompassed herein should in no way be construed as being limited to these examples, but rather should be construed to encompass any and all variations which become evident as a result of the teachings provided herein.

In an embodiment, the invention provides a method of treating leukemia, lymphoma, or a solid tumor cancer, comprising co-administering, to a mammal in need thereof, a composition comprising therapeutically effective amounts of (1) a PI3K inhibitor or a pharmaceutically acceptable salt, solvate, hydrate, cocrystal, or prodrug thereof, (2) a JAK-2 inhibitor or a pharmaceutically acceptable salt, solvate, hydrate, cocrystal, or prodrug thereof, and (3) a BTK inhibitor or a pharmaceutically acceptable salt, solvate, hydrate, cocrystal, or prodrug thereof.

In an embodiment, the invention provides a method of treating leukemia, lymphoma, or a solid tumor cancer, comprising co-administering, to a mammal in need thereof, a composition comprising therapeutically effective amounts of (1) a PI3K inhibitor or a pharmaceutically acceptable salt, solvate, hydrate, cocrystal, or prodrug thereof, and (2) a BTK inhibitor or a pharmaceutically acceptable salt, solvate, hydrate, cocrystal, or prodrug thereof.

In an embodiment, the invention provides a method of treating leukemia, lymphoma, or a solid tumor cancer, comprising co-administering, to a mammal in need thereof, a composition comprising therapeutically effective amounts of (1) a JAK-2 inhibitor or a pharmaceutically acceptable salt, solvate, hydrate, cocrystal, or prodrug thereof, and (2) a BTK inhibitor or a pharmaceutically acceptable salt, solvate, hydrate, cocrystal, or prodrug thereof.

In an embodiment, the invention provides the method as in any of the preceding paragraphs, wherein the composition is administered by oral, intravenous, intramuscular, intraperitoneal, subcutaneous or transdermal means.

In an embodiment, the invention provides the method as in any of the preceding paragraphs, wherein the PI3K inhibitor is a PI3K-γ inhibitor, a PI3K-δ inhibitor, or a PI3K-γ,δ inhibitor.

In an embodiment, the invention provides the method of any of the preceding paragraphs, wherein the leukemia is selected from the group consisting of chronic lymphocytic leukemia, acute myeloid leukemia, and B cell acute lymphoblastic leukemia. In an embodiment, the invention provides the method of any of the preceding paragraphs, wherein the lymphoma is selected from the group consisting of Burkitt's lymphoma, mantle cell lymphoma, follicular lymphoma, indolent B-cell non-Hodgkin's lymphoma, histiocytic lymphoma, activated B-cell like diffuse large B cell lymphoma, and germinal center B-cell like diffuse large B cell lymphoma. In an embodiment, the invention provides the method of any of the preceding paragraphs, wherein the solid tumor cancer is selected from the group consisting of breast, lung, colorectal, thyroid, bone sarcoma, and stomach cancers.

In an embodiment, the invention provides the method of any of the preceding paragraphs, wherein the PI3K inhibitor is administered to the subject before administration of the BTK inhibitor. In an embodiment, the invention provides the method of any of the preceding paragraphs, wherein the PI3K inhibitor is administered concurrently with the administration of the BTK inhibitor. In an embodiment, the invention provides the method of any of preceding paragraphs, wherein the PI3K inhibitor is administered to the subject after administration of the BTK inhibitor.

In an embodiment, the invention provides the method of any of the preceding paragraphs, wherein the JAK-2 inhibitor is administered to the subject before administration of the BTK inhibitor. In an embodiment, the invention provides the method of any of the preceding paragraphs, wherein the JAK-2 inhibitor is administered concurrently with the administration of the BTK inhibitor. In an embodiment, the invention provides the method of any of the preceding paragraphs, wherein the JAK-2 inhibitor is administered to the subject after administration of the BTK inhibitor.

In an embodiment, the invention provides the method of any of the preceding paragraphs, wherein the JAK-2 inhibitor is administered to the subject before administration of the PI3K inhibitor. In an embodiment, the invention provides the method of any of the preceding paragraphs, wherein the JAK-2 inhibitor is administered concurrently with the administration of the PI3K inhibitor. In an embodiment, the invention provides the method of any of the preceding paragraphs, wherein the JAK-2 inhibitor is administered to the subject after administration of the PI3K inhibitor.

In an embodiment, the invention provides the method of any of the preceding paragraphs, wherein the PI3K inhibitor is a compound according to:

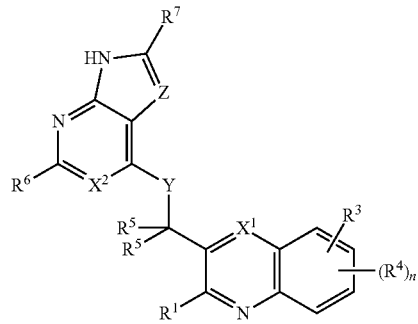

or any pharmaceutically-acceptable salt, solvate, hydrate, cocrystal, or prodrug thereof, wherein:

$X^1$ is $C(R^9)$ or N;
$X^2$ is $C(R_{10})$ or N;
Y is $N(R^{11})$, O or S;
Z is $CR^8$ or N;
n is 0, 1, 2 or 3;
$R^1$ is a direct-bonded or oxygen-linked saturated, partially saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $(C_{1-4})$alkyl, $O(C_{1-4})$alkyl, $O(C_{1-4})$haloalkyl, $NH(C_{1-4})$, $N((C_{1-4})$alkyl$)(C_{1-4})$alkyl and $(C_{1-4})$haloalkyl;
$R^2$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$. —OC(=O)N($R^a$)S(=O)$_2R^a$, —OC$_{2-6}$ alkylN$R^aR^a$, —OC$_{2-6}$alkylO$R^a$, —S$R^a$, OS(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$ alkylN$R^aR^a$ and —N$R^a(C_{2-6})$alkylO$R^a$; or $R^2$ is selected from $(C_{1-6})$alkyl, phenyl, benzyl, heteroaryl, heterocycle, —(($C_{1-3}$)alkyl)heteroaryl, —(($C_{1-3}$)alkyl)heterocycle, —O(($C_{1-3}$)alkyl)heteroaryl, —O(($C_{1-3}$)alkyl)heterocycle, —NR$^a$(($C_{1-3}$)alkyl)heteroaryl, —NR$^a$(($C_{1-3}$)alkyl)heterocycle, —(($C_{1-3}$)alkyl)phenyl, —O(($C_{1-3}$)alkyl)phenyl and —NR$^a$(($C_{1-3}$)alkyl)phenyl all of which are substituted by 0, 1, 2 or 3 substituents selected from $(C_{1-4})$haloalkyl, $O(C_{1-4})$alkyl, Br, Cl, F, I and $(C_{1-4})$alkyl;
$R^3$ is selected from H, halo, $(C_{1-4})$haloalkyl, cyano, nitro, —C(=O)$R^a$, —C(=O)$R^a$, —C(=O)N$R^aR^a$, —C(=N$R^a$)

NR$^a$R$^a$, —OR$^a$, —OC(=O)R$^a$, —OC(=O)NR$^a$R$^a$, —OC(=O)N(R$^a$)S(=O)$_2$R$^2$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$NR$^a$R$^a$, —NR$^a$(C$_{2-6}$)alkylOR$^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from (C$_{1-6}$)haloalkyl, O(C$_{1-6}$)alkyl, Br, Cl, F, I and (C$_{1-6}$)alkyl;

R$^4$ is, independently, in each instance, halo, nitro, cyano, (C$_{1-4}$)alkyl, O(C$_{1-4}$)alkyl, O(C$_{1-4}$)haloalkyl, NH(C$_{1-4}$)alkyl, N((C$_{1-4}$)alkyl)(C$_{1-4}$)alkyl or (C$_{1-4}$)haloalkyl;

R$^5$ is, independently, in each instance, H, halo, (C$_{1-6}$)alkyl, (C$_{1-4}$)haloalkyl, or (C$_{1-6}$)alkyl substituted by 1, 2 or 3 substituents selected from halo, cyano, OH, O(C$_{1-4}$)alkyl, (C$_{1-4}$)alkyl, (C$_{1-3}$)haloalkyl, O(C$_{1-4}$)alkyl, NH$_2$, NH(C$_{1-4}$)alkyl, N((C$_{1-4}$)alkyl)(C$_{1-4}$)alkyl; or both R$^5$ groups together form a (C$_{3-6}$)spiroalkyl substituted by 0, 1, 2 or 3 substituents selected from halo, cyano, OH, O(C$_{1-4}$)alkyl, (C$_{1-4}$)alkyl, (C$_{1-3}$)haloalkyl, O(C$_{1-4}$)alkyl, NH$_2$, NH(C$_{1-4}$)alkyl, N((C$_{1-4}$)alkyl)(C$_{1-4}$)alkyl;

R$^6$ is selected from H, halo, (C$_{1-6}$)alkyl, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$;

R$^7$ is selected from H, halo, (C$_{1-6}$)alkyl, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$;

R$^8$ is selected from H, (C$_{1-6}$)haloalkyl, Br, Cl, F, I, OR$^a$, NR$^a$R$^a$, (C$_{1-6}$)alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from (C$_{1-6}$)haloalkyl, O(C$_{1-6}$)alkyl, Br, Cl, F, I and (C$_{1-6}$)alkyl;

R$^9$ is selected from H, halo, (C$_{1-4}$)haloalkyl, cyano, nitro, —C(=O)R$^a$, —C(=O)OR$^a$, —C(=O)NR$^a$R$^a$C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —O(C$_{2-6}$)alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, NR$^a$R$^a$, —N(R$^a$)C(=O)R$^a$, —N(R$^a$)C(=O)OR$^a$, —N(R$^a$)C(O)NR$^a$R$^a$N(R$^a$C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$, —NR$^a$C$_{1-6}$alkyl, phenyl, benzyl, heteroaryl and heterocycle, wherein the (C$_{1-6}$)alkyl, phenyl, benzyl, heteroaryl and heterocycle are additionally substituted by 0, 1, 2 or 3 substituents selected from halo, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, OC(=O)NR$^a$R$^a$, —OC(=O)N(R$^a$)S(=O)$_2$R$^a$, —O(C$_{2-6}$)alkylNR$^a$R$^a$, —O(C$_{2-6}$)alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$(C$_{2-6}$)alkylOR$^a$, —NR$^a$(C$_{2-6}$)alkylOR$^a$; or R$^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, (C$_{1-4}$)haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —O(C$_{2-6}$)alkylNR$^a$R$^a$, —O(C$_{2-6}$)alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$(C$_{2-6}$)alkylNR$^a$R$^a$ and —NR$^a$(C$_{2-6}$)alkylOR$^a$;

R$^{10}$ is H, (C$_{1-3}$)alkyl, (C$_{1-3}$)haloalkyl, cyano, nitro, CO$_2$R$^a$, C(=O)NR$^a$R$^a$, —C(=NR$^a$)NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —S(=O)R$^b$, S(=O)$_2$R$^b$ or S(=O)$_2$NR$^a$R$^a$;

R$^{11}$ is H or (C$_{1-4}$)alkyl;

R$^a$ is independently, at each instance, H or R$^b$; and R$^b$ is independently, at each instance, phenyl, benzyl or (C$_{1-6}$)alkyl, the phenyl, benzyl and (C$_{1-6}$)alkyl being substituted by 0, 1, 2 or 3 substituents selected from halo, (C$_{1-4}$)alkyl, (C$_{1-3}$)haloalkyl, —O(C$_{1-4}$)alkyl, —NH$_2$, —NH(C$_{1-4}$)alkyl, —N((C$_{1-4}$)alkyl)(C$_{1-4}$)alkyl.

In an embodiment, the invention provides the method of any of the preceding paragraphs, wherein the PI3K inhibitor is a compound according to:

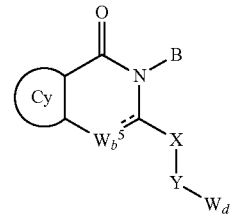

or an enantiomer, a mixture of enantiomers, or a mixture of two or more diastereomers thereof, or a pharmaceutically acceptable salt, hydrate, solvate, cocrystal, or prodrug thereof, wherein Cy is aryl or heteroaryl substituted by 0 or 1 occurrence of R$^3$ and 0, 1, 2, or 3 occurrence(s) of R$^5$;

$W_b^5$ is CR$^8$, CHR$^8$, or N;

R$^8$ is hydrogen, alkyl, alkenyl, alkynyl, cycloalkyl, heteroalkyl, alkoxy, amido, amino, acyl, acyloxy, sulfonamido, halo, cyano, hydroxyl or nitro; B is hydrogen, alkyl, amino, heteroalkyl, cycloalkyl, heterocyclyl, aryl, or heteroaryl, each of which is substituted with 0, 1, 2, 3, or 4 occurrence(s) of R$^2$;

each R$^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea, or carbonate;

X is —(CH(R$^9$))$_z$—;

Y is —N(R$^9$)—C(=O)—, —C(=O)—N(R$^9$)—, —C(=O)—N(R$^9$)—(CHR$^9$)—, —N(R$^9$)—S(=O)—, —S(=O)—N(R$^9$)—, —S(=O)$_2$—N(R$^9$)—, —N(R$^9$)—C(=O)—N(R$^9$) or —N(R$^9$)S(=O)$_2$—;

z is an integer of 1, 2, 3, or 4;

R$^3$ is alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, aryl, heteroaryl, hydroxyl, or nitro;

each $R^5$ is independently alkyl, alkenyl, alkynyl, cycloalkyl, heteroalkyl, alkoxy, amido, amino, acyl, acyloxy, sulfonamido, halo, cyano, hydroxyl, or nitro;

each $R^9$ is independently hydrogen, alkyl, cycloalkyl, heterocyclyl, or heteroalkyl; or two adjacent occurrences of $R^9$ together with the atoms to which they are attached form a 4- to 7-membered ring;

$W_d$ is heterocyclyl, aryl, cycloalkyl, or heteroaryl, each of which is substituted with one or more $R^{10}$, $R^{11}$, $R^{12}$ or $R^{13}$, and $R^{10}$, $R^{11}$, $R^{12}$ and $R^{13}$ are each independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate or NR'R" wherein R' and R" are taken together with nitrogen to form a cyclic moiety.

In an embodiment, the invention provides the method of any of the preceding paragraphs, wherein the PI3K inhibitor is a compound according to:

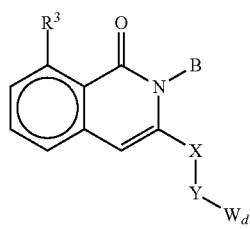

or a pharmaceutically acceptable salt, solvate, hydrate, cocrystal, or prodrug thereof, wherein B is:

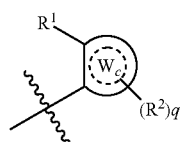

wherein $W_c$ is aryl, heteroaryl, heterocycloalkyl, or cycloalkyl, and q is an integer of 0, 1, 2, 3, or 4;

X is a bond or —(CH($R^9$))$_z$—, and z is an integer of 1;

Y is —N($R^9$)—;

$W_d$ is:

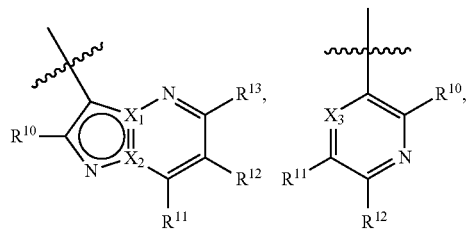

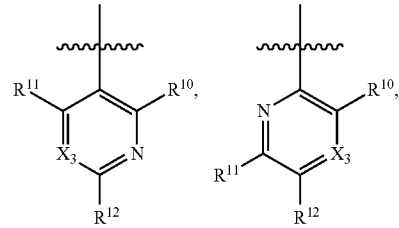

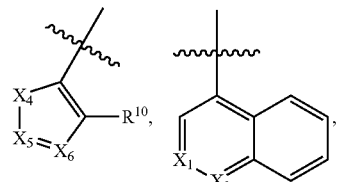

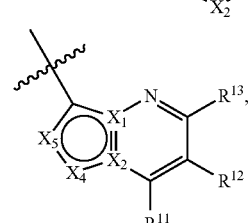

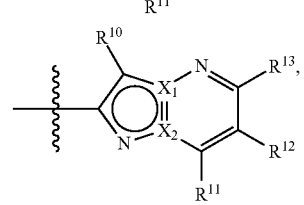

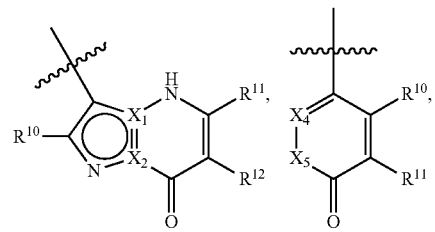

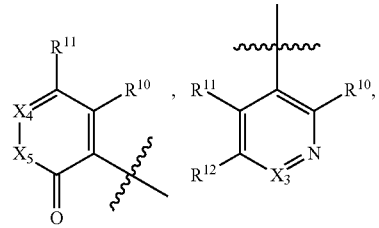

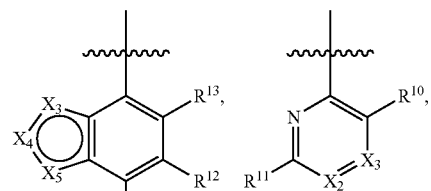

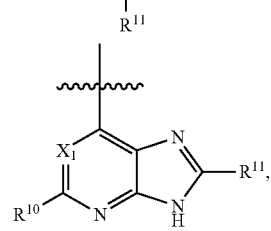

-continued

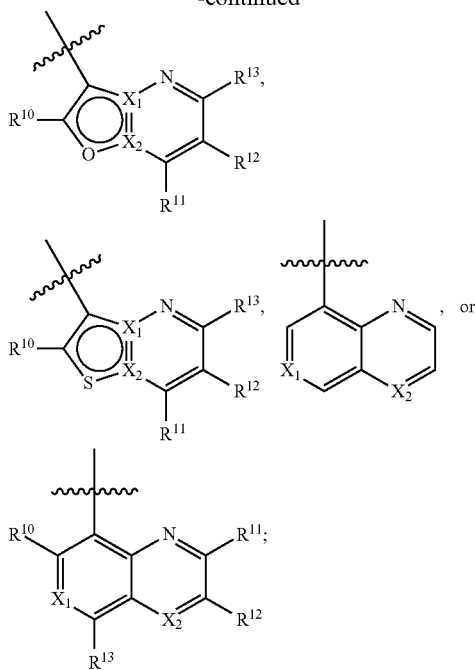

$X_1$, $X_2$ and $X_3$ are each independently C, $CR^{13}$ or N; and $X_4$, $X_5$ and $X_6$ are each independently N, NH, $CR^{13}$, S or O;

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy or nitro; $R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro; and each instance of $R^9$ is independently hydrogen, alkyl, or heterocycloalkyl.

In an embodiment, the invention provides the method of any of the preceding paragraphs, wherein the BTK inhibitor is a compound according to:

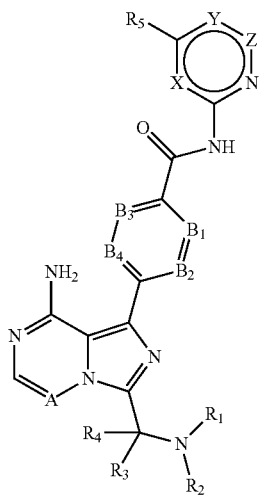

or a pharmaceutically acceptable salt, hydrate, solvate, cocrystal, or prodrug thereof, wherein X is CH, N, O or S;
Y is $C(R_6)$, N, O or S;
Z is CH, N or bond;
A is CH or N;
$B_1$ is N or $C(R_7)$;
$B_2$ is N or $C(R_8)$;
$B_3$ is N or $C(R_9)$;
$B_4$ is N or $C(R_{10})$;
$R_1$ is $R_{11}C(O)$, $R_{12}S(O)$, $R_{13}SO_2$ or $(C_{1-6})$alkyl optionally substituted with $R_{14}$;
$R_2$ is H, $(C_{1-3})$alkyl or $(C_{3-7})$cycloalkyl;
$R_3$ is H, $(C_{1-6})$alkyl or $(C_{3-7})$cycloalkyl; or
$R_2$ and $R_3$ form, together with the N and C atom they are attached to, a $(C_{3-7})$heterocycloalkyl optionally substituted with one or more fluorine, hydroxyl, $(C_{1-3})$alkyl, $(C_{1-3})$alkoxy or oxo;
$R_4$ is H or $(C_{1-3})$alkyl;
$R_5$ is H, halogen, cyano, $(C_{1-4})$alkyl, $(C_{1-3})$alkoxy, $(C_{3-6})$cycloalkyl, any alkyl group of which is optionally substituted with one or more halogen; or $R_5$ is $(C_{6-10})$aryl or $(C_{2-6})$heterocycloalkyl;
$R_6$ is H or $(C_{1-3})$alkyl; or
$R_5$ and $R_6$ together may form a $(C_{3-7})$cycloalkenyl, or $(C_{2-6})$heterocycloalkenyl; each optionally substituted with $(C_{1-3})$alkyl, or one or more halogen;
$R_7$ is H, halogen, $CF_3$, $(C_{1-3})$alkyl or $(C_{1-3})$alkoxy;
$R_8$ is H, halogen, $CF_3$, $(C_{1-3})$alkyl or $(C_{1-3})$alkoxy; or
$R_7$ and $R_8$ together with the carbon atoms they are attached to, form $(C_{6-10})$aryl or $(C_{1-9})$heteroaryl;
$R_9$ is H, halogen, $(C_{1-3})$alkyl or $(C_{1-3})$alkoxy;
$R_{10}$ is H, halogen, $(C_{1-3})$alkyl or $(C_{1-3})$alkoxy;
$R_{11}$ is independently selected from a group consisting of $(C_{1-6})$alkyl, $(C_{1-6})$alkenyl and $(C_{2-6})$alkynyl each alkyl, alkenyl or alkynyl optionally substituted with one or more groups selected from hydroxyl, $(C_{1-4})$alkyl, $(C_{3-7})$cycloalkyl, [$(C_{1-4})$alkyl]amino, di[$(C_{1-4})$alkyl]amino, $(C_{1-3})$alkoxy, $(C_{3-7})$cycloalkoxy, $(C_{6-10})$aryl or $(C_{3-7})$heterocycloalkyl; or $R_{11}$ is $(C_{1-3})$alkyl-C(O)—S—$(C_{1-3})$alkyl; or
$R_{11}$ is $(C_{1-5})$heteroaryl optionally substituted with one or more groups selected from halogen or cyano;
$R_{12}$ and $R_{13}$ are independently selected from a group consisting of $(C_{2-6})$alkenyl or $(C_{2-6})$alkynyl both optionally substituted with one or more groups selected from hydroxyl, $(C_{1-4})$alkyl, $(C_{3-7})$cycloalkyl, [$(C_{1-4})$alkyl]amino, di[$(C_{1-4})$alkyl]amino, $(C_{1-3})$alkoxy, $(C_{3-7})$cycloalkoxy, $(C_{6-10})$aryl or $(C_{3-7})$heterocycloalkyl; or
$(C_{1-5})$heteroaryl optionally substituted with one or more groups selected from halogen or cyano; and
$R_{14}$ is independently selected from a group consisting of halogen, cyano or $(C_{2-6})$alkenyl or $(C_{2-6})$alkynyl both optionally substituted with one or more groups selected from hydroxyl, $(C_{1-4})$alkyl, $(C_{3-7})$cycloalkyl, $(C_{1-4})$alkylamino, di[$(C_{1-4})$alkyl]amino, $(C_{1-3})$alkoxy, $(C_{3-7})$cycloalkoxy, $(C_{6-10})$aryl, $(C_{1-5})$heteroaryl or $(C_{3-7})$heterocycloalkyl.

In an embodiment, the invention provides the method of any of the preceding paragraphs, wherein the BTK inhibitor is a compound according to:

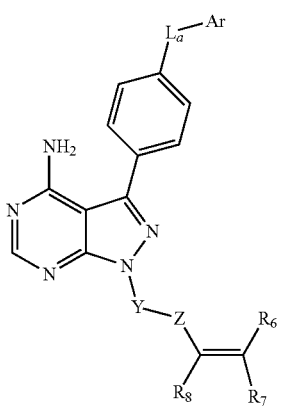

or a pharmaceutically acceptable salt, hydrate, solvate, cocrystal, or prodrug thereof, wherein
$L_a$ is $CH_2$, O, NH or S;
Ar is a substituted or unsubstituted aryl, or a substituted or unsubstituted heteroaryl;
Y is an optionally substituted group selected from the group consisting of alkyl, heteroalkyl, cycloalkyl, heterocycloalkyl, aryl and heteroaryl;
Z is C(=O), OC(=O), NRC(=O), C(=S), S(=O)$_x$, OS(=O)$_x$, NRS(=O)$_x$, where x is 1 or 2;
$R_7$ and $R_8$ are each H; or $R_7$ and $R_8$ taken together form a bond;
$R_6$ is H; and
R is H or ($C_1$-$C_6$)alkyl.

In an embodiment, the invention provides the method of any of the preceding paragraphs, wherein the BTK inhibitor is a compound according to:

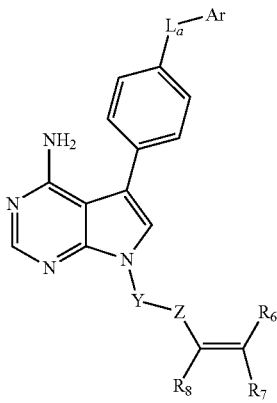

or a pharmaceutically acceptable salt, hydrate, solvate, cocrystal, or prodrug thereof, wherein
$L_a$ is $CH_2$, O, NH or S;
Ar is a substituted or unsubstituted aryl, or a substituted or unsubstituted heteroaryl;
Y is an optionally substituted group selected from the group consisting of alkyl, heteroalkyl, cycloalkyl, heterocycloalkyl, aryl and heteroaryl;
Z is C(=O), OC(=O), NRC(=O), C(=S), S(=O)$_x$, OS(=O)$_x$, NRS(=O)$_x$, where x is 1 or 2;
$R_7$ and $R_8$ are each H; or $R_7$ and $R_8$ taken together form a bond;
$R_6$ is H; and
R is H or ($C_1$-$C_6$)alkyl.

In an embodiment, the invention provides the method of any of the preceding paragraphs, wherein the BTK inhibitor is a compound according to:

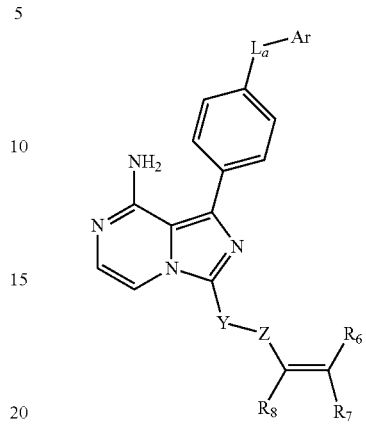

or a pharmaceutically acceptable salt, hydrate, solvate, cocrystal, or prodrug thereof, wherein
$L_a$ is $CH_2$, O, NH or S;
Ar is a substituted or unsubstituted aryl, or a substituted or unsubstituted heteroaryl;
Y is an optionally substituted group selected from the group consisting of alkyl, heteroalkyl, cycloalkyl, heterocycloalkyl, aryl and heteroaryl;
Z is C(=O), OC(=O), NRC(=O), C(=S), S(=O)$_x$, OS(=O)$_x$, NRS(=O)$_x$, where x is 1 or 2;
$R_7$ and $R_8$ are each H; or $R_7$ and $R_8$ taken together form a bond;
$R_6$ is H; and
R is H or ($C_1$-$C_6$)alkyl.

In an embodiment, the invention provides the method of any of the preceding paragraphs, wherein the BTK inhibitor is a compound according to:

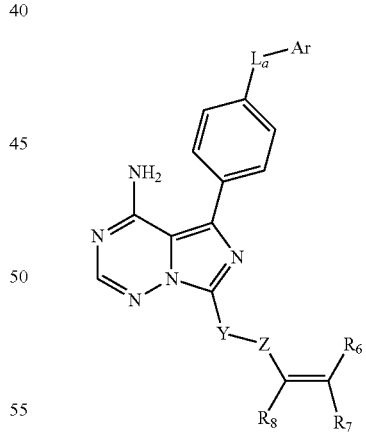

or a pharmaceutically acceptable salt, hydrate, solvate, cocrystal, or prodrug thereof, wherein
$L_a$ is $CH_2$, O, NH or S;
Ar is a substituted or unsubstituted aryl, or a substituted or unsubstituted heteroaryl;
Y is an optionally substituted group selected from the group consisting of alkyl, heteroalkyl, cycloalkyl, heterocycloalkyl, aryl and heteroaryl;
Z is C(=O), OC(=O), NRC(=O), C(=S), S(=O)$_x$, OS(=O)$_x$, NRS(=O)$_x$, where x is 1 or 2;

$R_7$ and $R_8$ are each H; or $R_7$ and $R_8$ taken together form a bond;

$R_6$ is H; and

R is H or $(C_1-C_6)$alkyl.

In an embodiment, the invention provides the method of any of the preceding paragraphs, wherein the BTK inhibitor is a compound according to:

or a pharmaceutically acceptable salt, hydrate, solvate, cocrystal, or prodrug thereof, wherein:

$Q^1$ is aryl$^1$, heteroaryl$^1$, cycloalkyl, heterocyclyl, cycloalkenyl, or heterocycloalkenyl, any of which is optionally substituted by one to five independent $G^1$ substituents;

$R^1$ is alkyl, cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents;

$G^1$ and $G^{41}$ are each independently halo, oxo, —$CF_3$, —$OCF_3$, —$OR^2$, —$NR^2R^3(R^{3a})_{j1}$, —$C(O)R^2$, —$CO_2R^2$, —$CONR^2R^3$, —$NO_2$, —CN, —$S(O)_{j1}R^2$, —$SO_2NR^2R^3$, $NR^2(C=O)R^3$, $NR^2(C=O)OR^3$, $NR^2(C=O)NR^2R^3$, $NR^2S(O)_{j1}R^3$, —$(C=S)OR^2$, —$(C=O)SR$, —$NR^2(C=NR^3)NR^{2a}R^{3a}$, —$NR^2(C=NR^3)OR^{2a}$, —$NR^2(C=NR^3)SR^{3a}$, —$O(C=O)OR^2$, —$O(C=O)NR^2R^3$, —$O(C=O)SR^2$, —$S(C=O)OR^2$, —$S(C=O)NR^2R^3$, $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, oxo, —$CF_3$, —$OCF_3$, —$OR^{222}$, —$NR^{222}R^{333}(R^{333}a)_{j1a}$, —$C(O)R^{222}$, —$CO_2R^{222}$, —$CONR^{222}R^{333}$, —$NO_2$, —CN, —$S(O)_{j1a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, —$(C=S)OR^{222}$, —$(C=O)SR^{222}$, —$NR^{222}(C=NR^{333})R^{222a}R^{333a}$, —$NR^{222}(C=NR^{333})OR^{222a}$, —$NR^{222}(C=NR^{333})SR^{333a}$, —$O(C=O)OR^{222}$, —$O(C=O)NR^{222}R^{333}$, —$O(C=O)SR^{222}$, —$S(C=O)OR^{222}$, or —$S(C=O)NR^{222}R^{333}$ substituents; or —$(X^1)_n$—$(Y^1)_m$—$R^4$; or aryl-$(C_{0-10})$alkyl, aryl-$(C_{2-10})$alkenyl, or aryl-$(C_{2-10})$alkynyl, any of which is optionally substituted with one or more independent halo, —$CF_3$, —$OCF_3$, —$OR^{222}$, —$NR^{222}R^{333}(R^{333a})_{j2a}$, —$C(O)R^{222}$, —$CO_2R^{222}$, —$CONR^{222}R^{333}$, —$NO_2$, —CN, —$S(O)_{j2a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j2a}R^{333}$, —$(C=S)OR^{222}$, —$(C=O)SR^{222}$, —$NR^{222}(C=NR^{333})NR^{222a}R^{333a}$, —$NR^{222}(C=NR^{333})OR^{222a}$, —$NR^{222}(C=NR^{333})SR^{333a}$, —$O(C=O)OR^{222}$, —$O(C=O)NR^{222}R^{333}$, —$O(C=O)SR^{222}$, —$S(C=O)OR^{222}$, or —$S(C=O)NR^{222}R^{333}$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, —$CF_3$, —$OCF_3$, —$OR^{222}$, —$NR^{222}R^{333}(R^{333}a)_{j3a}$, —$C(O)R^{222}$, —$CO_2R^{222}$, —$CONR^{222}R^{333}$, —$NO_2$, —CN, —$S(O)_{j3a}R^{222}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j3a}R^{333}$, —$(C=S)OR^{222}$, —$(C=O)SR^{222}$, —$NR^{222}(C=NR^{333})NR^{222a}R^{333}a$, —$NR^{222}(C=NR^{333})OR^{222a}$, —$NR^{222}(C=NR^{333})SR^{333a}$, —$O(C=O)OR^{222}$, —$O(C=O)NR^{222}R^{333}$, —$O(C=O)SR^{222}$, —$S(C=O)OR^{222}$, or —$S(C=O)NR^{222}R^{333}$ substituents;

$G^{11}$ is halo, oxo, —$CF_3$, —$OCF_3$, —$OR^{21}$, —$NR^{21}R^{31}(R^{3a1})_{j4}$, —$C(O)R^{21}$, —$CO_2R^{21}$, —$CONR^{21}R^{31}$, —$NO_2$, —CN, —$S(O)_{j4}R^{21}$, —$SO_2NR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, —$(C=S)OR^{21}$, —$(C=O)SR^{21}$, —$NR^{21}(C=NR^{31})NR^{2a1}R^{3a1}$, —$NR^{21}(C=NR^{31})OR^{2a1}$, —$NR^{21}(C=NR^{31})SR^{3a1}$, —$O(C=O)OR^{21}$, —$O(C=O)NR^{21}R^{31}$, —$O(C=O)SR^{21}$, —$S(C=O)OR^{21}$, —$S(C=O)NR^{21}R^{31}$, —$P(O)OR^{21}OR^{31}$, $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, oxo, —$CF_3$, —$OCF_3$, —$OR^{2221}$, $NR^{2221}R^{3331}(R^{333a1})_{j4a}$, —$C(O)R^{2221}$, —$CO_2R^{2221}$, —$CONR^{2221}R^{3331}$, —$NO_2$, —CN, —$S(O)_{j4a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, —$P(O)OR^{2221}OR^{3331}$, or —$S(C=O)NR^{2221}R^{3331}$ substituents; or aryl-$(C_{0-10})$alkyl, aryl-$(C_{2-10})$alkenyl, or aryl-$(C_{2-10})$alkynyl, any of which is optionally substituted with one or more independent halo, —$CF_3$, —$OCF_3$, —$OR^{2221}$, —$N^{2221}R^{3331}(R^{333a1})_{j5a}$, —$C(O)R^{2221}$, —$CO_2R^{2221}$, —$CONR^{2221}R^{3331}$, —$NO_2$, —CN, —$S(O)_{j5a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j5a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, —$P(O)OR^{2221}R^{3331}$, or —$S(C=O)NR^{2221}R^{3331}$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, —$CF_3$, —$OCF_3$, —$OR^{2221}$, —$NR^{2221}R^{3331}(R^{333a1})_{j6a}$, —$C(O)R^{2221}$, —$C_2R^{2221}$, —$CONR^{2221}R^{3331}$, —$N_2$, —CN, —$S(O)_{j6a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j6a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, —$P(O)OR^{2221}OR^{3331}$, or —$S(C=O)NR^{2221}R^{3331}$ substituents; or $G^{11}$ is taken together with the carbon to which it is attached to form a double bond which is substituted with $R^5$ and $G^{111}$;

$R^2$, $R^{2a}$, $R^3$, $R^{3a}$, $R^{222}$, $R^{222}a$, $R^{333}$, $R^{333a}$, $R^{21}$, $R^{2a1}$, $R^{31}$, $R^{3a1}$, $R^{2221}$, $R^{222a1}$, $R^{3331}$, and $R^{333a1}$ are each independently equal to $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted by one or more $G^{111}$ substituents; or aryl-$(C_{0-10})$alkyl, aryl-$(C_{2-10})$alkenyl, or aryl-$(C_{2-10})$alkynyl, hetaryl-$(C_{0-10})$alkyl, hetaryl-$(C_{2-10})$alkenyl, or hetaryl-$(C_{2-10})$alkynyl, any of which is optionally substituted by one or more $G^{111}$ substituents; or in the case of $-NR^2R^3(R^{3a})_{j1}$ or $-NR^{222}R^{333}(R^{333}a)_{j1}a$ or $-NR^{222}R^{333}(R^{333}a)j2a$ or $-NR^{2221}R^{3331}(R^{333a1})_{j3a}$ or $-NR^{2221}R^{3331}(R^{333a1})_{j4a}$ or $-NR^{2221}R^{3331}(R^{333a1})_{j5a}$ or $-NR^{2221}R^{3331}(R^{333a1})_{j6a}$, $R^2$ and $R^3$ or $R^{222}$ and $R^{333}$ or $R^{2221}$ and $R^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more $G^{111}$ substituents;

$X^1$ and $Y^1$ are each independently $-O-$, $-NR^7-$, $-S(O)_{j7}-$, $-CR^5R^6-$, $-N(C(O)OR^7)-$, $-N(C(O)R^7)-$, $-N(SO_2R^7)-$, $-CH_2O-$, $-CH_2S-$, $-CH_2N(R^7)-$, $-CH(NR^7)-$, $-CH_2N(C(O)R^7)-$, $-CH_2N(C(O)OR^7)-$, $-CH_2N(SO_2R^7)-$, $-CH(NHR^7)-$, $-CH(NHC(O)R^7)-$, $-CH(NHSO_2R^7)-$, $-CH(NHC(O)OR^7)-$, $-CHOC(O)R^7)-$, $-CHOC(O)NHR^7)-$, $-CH=CH-$, $-C\text{.ident.}C-$, $-C(=NOR^7)-$, $-C(O)-$, $-CH(OR^7)-$, $-C(O)N(R^7)-$, $-N(R^7)C(O)-$, $-N(R^7)S(O)-$, $-N(R^7)S(O)_2-$, $-OC(O)N(R^7)-$, $-N(R^7)C(O)N(R^7)-$, $-NR^7C(O)O-$, $-S(O)N(R^7)-$, $-S(O)_2N(R^7)-$, $-N(C(O)R^7)S(O)-$, $-N(C(O)R^7)S(O)_2-$, $-N(R^7)S(O)N(R^7)-$, $-N(R^7)S(O)_2N(R^7)-$, $-C(O)N(R^7)C(O)-$, $-S(O)N(R^7)C(O)-$, $-S(O)_2N(R^7)C(O)-$, $-OS(O)N(R^7)-$, $-OS(O)_2N(R^7)-$, $-N(R^7)S(O)O-$, $-N(R^7)S(O)_2O-$, $-N(R^7)S(O)C(O)-$, $-N(R^7)S(O)_2C(O)-$, $-SON(C(O)R^7)-$, $-SO_2N(C(O)R^7)-$, $-N(R^7)SON(R^7)-$, $-N(R^7)SO_2N(R^7)-$, $-C(O)O-$, $-N(R^7)P(O^8)O-$, $-N(R^7)P(OR^8)-$, $-N(R^7)P(O)(OR^8)O-$, $-N(R^7)P(O)(OR^8)-$, $-N(C(O)R^7)P(OR^8)-$, $-N(C(O)R^7)P(O)(OR^8)O-$, $-N(C(O)R^7)P(OR^8)-$, $-N(C(O)R^7)P(O)(OR^8)O-$, $-N(C(O)R^7)P(OR^8)-$, $-CH(R^7)S(O)-$, $-CH(R^7)S(O)_2-$, $-CH(R^7)N(C(O)OR^7)-$, $-CH(R^7)N(C(O)R^7)-$, $-CH(R^7)N(SO_2R^7)-$, $-CH(R^7)O-$, $-CH(R^7)S-$, $-CH(R^7)N(R^7)-$, $-CH(R^7)N(C(O)R^7)-$, $-CH(R^7)N(C(O)OR^7)-$, $-CH(R^7)N(SO_2R^7)-$, $-CH(R^7)C(=NOR^7)-$, $-CH(R^7)C(O)-$, $-CH(R^7)CH(OR^7)-$, $-CH(R^7)C(O)N(R^7)-$, $-CH(R^7)N(R^7)C(O)-$, $-CH(R^7)N(R^7)S(O)-$, $-CH(R^7)N(R^7)S(O)_2-$, $-CH(R^7)OC(O)N(R^7)-$, $-CH(R^7)N(R^7)C(O)N(R^7)-$, $-CH(R^7)NR^7C(O)O-$, $-CH(R^7)S(O)N(R^7)-$, $-CH(R^7)S(O)_2N(R^7)-$, $-CH(R^7)N(C(O)R^7)S(O)-$, $-CH(R^7)N(C(O)R^7)S(O)-$, $-CH(R^7)N(R^7)S(O)N(R^7)-$, $-CH(R^7)N(R^7)S(O)_2N(R^7)-$, $-CH(R^7)C(O)N(R^7)C(O)-$, $-CH(R^7)S(O)N(R^7)C(O)-$, $-CH(R^7)S(O)_2N(R^7)C(O)-$, $-CH(R^7)OS(O)N(R^7)-$, $-CH(R^7)OS(O)_2N(R^7)-$, $-CH(R^7)N(R^7)S(O)O-$, $-CH(R^7)N(R^7)S(O)_2O-$, $-CH(R^7)N(R^7)S(O)C(O)-$, $-CH(R^7)N(R^7)S(O)_2C(O)-$, $-CH(R^7)SON(C(O)R^7)-$, $-CH(R^7)SO_2N(C(O)R^7)-$, $-CH(R^7)N(R^7)SON(R^7)-$, $-CH(R^7)N(R^7)SO_2N(R^7)-$, $-CH(R^7)C(O)O-$, $-CH(R^7)N(R^7)P(O^8)O-$, $-CH(R^7)N(R^7)P(OR^8)-$, $-CH(R^7)N(R^7)P(O)(OR^8)O-$, $-CH(R^7)N(R^7)P(o)(OR^8)-$, $-CH(R^7)N(C(O)R^7)P(OR^8)O-$, $-CH(R^7)N(C(O)R^7)P(OR^8)-$, $-CH(R^7)N(C(O)R^7)P(O)(OR^8)O-$, or $-CH(R^7)N(C(O)R^7)P(OR^8)-$; or $X^1$ and $Y^1$ are each independently represented by one of the following structural formulas:

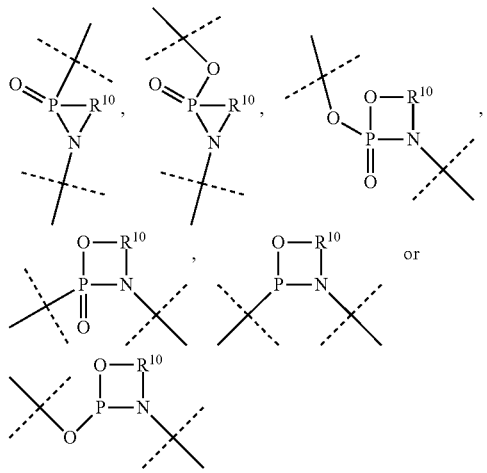

$R^{10}$, taken together with the phosphinamide or phosphonamide, is a 5-, 6-, or 7-membered aryl, heteroaryl or heterocyclyl ring system;

$R^5$, $R^6$, and $G^{111}$ are each independently a $(C_{0-10})$alkyl, $(C_{2-10})$alkenyl, $(C_{2-10})$alkynyl, $(C_{1-10})$alkoxy$(C_{1-10})$alkyl, $(C_{1-10})$alkoxy$(C_{2-10})$alkenyl, $(C_{1-10})$alkoxy$(C_{2-10})$alkynyl, $(C_{1-10})$alkylthio$(C_{1-10})$alkyl, $(C_{1-10})$alkylthio$(C_{2-10})$alkenyl, $(C_{1-10})$alkylthio$(C_{2-10})$alkynyl, cyclo$(C_{3-8})$alkyl, cyclo$(C_{3-8})$alkenyl, cyclo$(C_{3-8})$alkyl$(C_{1-10})$alkyl, cyclo$(C_{3-8})$alkenyl$(C_{1-10})$alkyl, cyclo$(C_{3-8})$alkyl$(C_{2-10})$alkenyl, cyclo$(C_{3-8})$alkenyl$(C_{2-10})$alkenyl, cyclo$(C_{3-8})$alkyl$(C_{2-10})$alkynyl, cyclo$(C_{3-8})$alkenyl$(C_{2-10})$alkynyl, heterocyclyl-$(C_{0-10})$alkyl, heterocyclyl-$(C_{2-10})$alkenyl, or heterocyclyl-$(C_{2-10})$alkynyl, any of which is optionally substituted with one or more independent halo, $-CF_3$, $-OCF_3$, $-OR^{77}$, $-NR^{77}R^{87}$, $-C(O)R^{77}$, $-CO_2R^{77}$, $-CONR^{77}R^{87}$, $-NO_2$, $-CN$, $-S(O)_{j5a}R^{77}$, $-SO_2NR^{77}R^{87}$, $NR^{77}(C=O)R^{87}$, $NR^{77}(C=O)OR^{87}$, $NR^{77}(C=O)NR^{78}R^{87}$, $NR^{77}S(O)_{j5a}R^{87}$, $-(C=S)OR^{77}$, $-(C=O)SR^{77}$, $-NR^{77}(C=NR^{87})NR^{78}R^{88}$, $-NR^{77}(C=NR^{87})OR^{78}$, $-NR^{77}(C=NR^{87})SR^{78}$, $-O(C=O)OR^{77}$, $-O(C=O)NR^{77}R^{87}$, $-O(C=O)SR^{77}$, $-S(C=O)OR^{77}$, $-P(O)OR^{77}OR^{87}$, or $-S(C=O)NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, $-CF_3$, $-OCF_3$, $-OR^{77}$, $-NR^{77}R^{87}$, $-C(O)R^{77}$, $-CO_2R^{77}$, $-CONR^{77}R^{87}$, $-NO_2$, $-CN$, $-S(O)_{j5a}R^{77}$, $-SO_2NR^{77}R^{87}$, $NR^{77}(C=O)R^{87}$, $NR^{77}(C=O)OR^{87}$, $NR^{77}(C=O)NR^{78}R^{87}$, $NR^{77}S(O)_{j5a}R^{87}$, $-(C=S)OR^{77}$, $-(C=O)SR^{77}$, $-NR^{77}(C=NR^{87})NR^{78}R^{88}$, $-NR^{77}(C=NR^{87})OR^{78}$, $-NR^{77}(C=NR^{87})SR^{78}$, $-O(C=O)OR^{77}$, $-O(C=O)NR^{77}R^{87}$, $-O(C=O)SR^{77}$, $-S(C=O)OR^{77}$, $-P(O)OR^{77}R^{87}$, or $-S(C=O)NR^{77}R^{87}$ substituents; or hetaryl-$(C_{0-10})$alkyl, hetaryl-$(C_{2-10})$alkenyl, or hetaryl-$(C_{2-10})$alkynyl, any of which is optionally substituted with one or more independent halo, $-CF_3$, $-OCF_3$, $-OR^{77}$, $-NR^{77}R^{87}$, $-C(O)R^{77}$, $-CO_2R^{77}$, $-CONR^{77}R^{87}$, $-NO_2$, $-CN$, $-S(O)_{j5a}R^{77}$, $-SO_2NR^{77}R^{87}$, $NR^{77}(C=O)R^{87}$, $NR^{77}(C=O)OR^{87}$, $NR^{77}$ (C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$OR$^{87}$, or —S(C=O)NR$^{77}$R$^{87}$ substituents; or R$^5$ with R$^6$ taken together with the respective carbon atom to which they are attached, form a 3-10 membered saturated or unsaturated ring, wherein said ring is optionally substituted with R$^{69}$; or R$^5$ with R$^6$ taken together with the respective carbon atom to which they are attached, form a 3-10 membered saturated or unsaturated heterocyclic ring, wherein said ring is optionally substituted with R$^{69}$;

R$^7$ and R$^8$ are each independently H, acyl, alkyl, alkenyl, aryl, heteroaryl, heterocyclyl or cycloalkyl, any of which is optionally substituted by one or more G$^{111}$ substituents;

R$^4$ is H, alkyl, alkenyl, alkynyl, aryl, heteroaryl, cycloalkyl, heterocyclyl, cycloalkenyl, or heterocycloalkenyl, any of which is optionally substituted by one or more G$^{41}$ substituents;

R$^{69}$ is equal to halo, —OR$^{78}$, —SH, —NR$^{78}$R$^{88}$, —CO$_2$R$^{78}$, —CONR$^{78}$R$^{88}$, —NO$_2$, —CN, —S(O)$_{j8}$R$^{78}$, —SO$_2$NR$^{78}$R$^{88}$, (C$_{0-10}$)alkyl, (C$_{2-10}$)alkenyl, (C$_{2-10}$)alkynyl, (C$_{1-10}$)alkoxy(C$_{1-10}$)alkyl, (C$_{1-10}$)alkoxy(C$_{2-10}$)alkenyl, (C$_{1-10}$)alkoxy(C$_{2-10}$)alkynyl, (C$_{1-10}$)alkylthio(C$_{1-10}$)alkyl, (C$_{1-10}$)alkylthio(C$_{2-10}$)alkenyl, (C$_{1-10}$)alkylthio(C$_{2-10}$)alkynyl, cyclo(C$_{3-8}$)alkyl, cyclo(C$_{3-8}$)alkenyl, cyclo(C$_{3-8}$)alkyl(C$_{1-10}$)alkyl, cyclo(C$_{3-8}$)alkenyl(C$_{1-10}$)alkyl, cyclo(C$_{3-8}$)alkyl(C$_{2-10}$)alkenyl, cyclo(C$_{3-8}$)alkenyl(C$_{2-10}$)alkenyl, cyclo(C$_{3-8}$)alkyl(C$_{2-10}$)alkynyl, cyclo(C$_{3-8}$)alkenyl(C$_{2-10}$)alkynyl, heterocyclyl-(C$_{0-10}$)alkyl, heterocyclyl-(C$_{2-10}$)alkenyl, or heterocyclyl-(C$_{2-10}$)alkynyl, any of which is optionally substituted with one or more independent halo, cyano, nitro, —OR$^{778}$, —SO$_2$NR$^{778}$R$^{888}$, or —NR$^{778}$R$^{888}$ substituents; or aryl-(C$_{0-10}$)alkyl, aryl-(C$_{2-10}$)alkenyl, or aryl-(C$_{2-10}$)alkynyl, any of which is optionally substituted with one or more independent halo, cyano, nitro, —OR$^{778}$, (C$_{1-10}$)alkyl, (C$_{2-10}$)alkenyl, (C$_{2-10}$)alkynyl, halo(C$_{1-10}$)alkyl, haloC$_{2-10}$alkenyl, haloC$_{2-10}$alkynyl, —COOH, (C$_{1-4}$)alkoxycarbonyl, —CONR$^{788}$R$^{888}$, —SO$_2$NR$^{778}$R$^{888}$, or —NR$^{778}$R$^{888}$ substituents; or hetaryl-(C$_{0-10}$)alkyl, hetaryl-(C$_{2-10}$)alkenyl, or hetaryl-(C$_{2-10}$)alkynyl, any of which is optionally substituted with one or more independent halo, cyano, nitro, —OR$^{778}$, (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CONR$^{778}$R$^{888}$, —SO$_2$NR$^{778}$R$^{888}$, or —NR$^{778}$R$^{888}$ substituents; or mono((C$_{1-6}$)alkyl)amino(C$_{1-6}$)alkyl, di((C$_{1-6}$)alkyl)amino(C$_{1-6}$)alkyl, mono(aryl)amino(C$_{1-6}$)alkyl, di(aryl)amino(C$_{1-6}$)alkyl, or —N((C$_{1-6}$)alkyl)-(C$_{1-6}$)alkyl-aryl, any of which is optionally substituted with one or more independent halo, cyano, nitro, —OR$^{778}$, (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CONR$^{778}$R$^{888}$SO$_2$NR$^{778}$R$^{888}$, or —NR$^{778}$R$^{888}$ substituents; or in the case of —NR$^{78}$R$^{88}$, R$^{78}$ and R$^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, (C$_{1-10}$)alkoxy, —SO$_2$NR$^{778}$R$^{888}$, or —NR$^{778}$R$^{888}$ substituents;

R$^{77}$, R$^{78}$, R$^{87}$, R$^{88}$, R$^{778}$, and R$^{888}$ are each independently (C$_{0-10}$)alkyl, (C$_{2-10}$)alkenyl, (C$_{2-10}$)alkynyl, (C$_{1-10}$)alkoxy(C$_{1-10}$)alkyl, (C$_{1-10}$)alkoxy(C$_{2-10}$)alkenyl, (C$_{1-10}$)alkoxy(C$_{2-10}$)alkynyl, (C$_{1-10}$)alkylthio(C$_{1-10}$)alkyl, (C$_{1-10}$)alkylthio(C$_{2-10}$)alkenyl, (C$_{1-10}$)alkylthio(C$_{2-10}$)alkynyl, cyclo(C$_{3-8}$)alkyl, cyclo(C$_{3-8}$)alkenyl, cyclo(C$_{3-8}$)alkyl(C$_{1-10}$) alkyl, cyclo(C$_{3-8}$)alkenyl(C$_{1-10}$)alkyl, cyclo(C$_{3-8}$)alkyl(C$_{2-10}$)alkenyl, cyclo(C$_{3-8}$)alkenyl(C$_{2-10}$)alkenyl, cyclo(C$_{3-8}$)alkyl(C$_{2-10}$)alkynyl, cyclo(C$_{3-8}$)alkenyl(C$_{2-10}$)alkynyl, heterocyclyl-(C$_{0-10}$)alkyl, heterocyclyl-(C$_{2-10}$)alkenyl, heterocyclyl-(C$_{2-10}$)alkynyl, (C$_{1-10}$)alkylcarbonyl, (C$_{2-10}$)alkenylcarbonyl, (C$_{2-10}$)alkynylcarbonyl, (C$_{1-10}$)alkoxycarbonyl, (C$_{1-10}$)alkoxycarbonyl(C$_{1-10}$)alkyl, mono(C$_{1-6}$)alkylaminocarbonyl, di(C$_{1-6}$)alkylaminocarbonyl, mono(aryl)aminocarbonyl, di(aryl)aminocarbonyl, or (C$_{1-10}$)alkyl(aryl)aminocarbonyl, any of which is optionally substituted with one or more independent halo, cyano, hydroxy, nitro, (C$_{1-10}$)alkoxy, —SO$_2$N((C$_{0-4}$)alkyl)((C$_{0-4}$)alkyl), or —N((C$_{0-4}$)alkyl)((C$_{0-4}$)alkyl) substituents; or aryl-(C$_{0-10}$)alkyl, aryl-(C$_{2-10}$)alkenyl, or aryl-(C$_{2-10}$)alkynyl, any of which is optionally substituted with one or more independent halo, cyano, nitro, —O((C$_{0-4}$)alkyl), (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CON((C$_{0-4}$)alkyl)((C$_{0-10}$)alkyl), —SO$_2$N((C$_{0-4}$)alkyl)((C$_{0-4}$)alkyl), or —N((C$_{0-4}$)alkyl)((C$_{0-4}$)alkyl) substituents; or hetaryl-(C$_{0-10}$)alkyl, hetaryl-(C$_{2-10}$)alkenyl, or hetaryl-(C$_{2-10}$)alkynyl, any of which is optionally substituted with one or more independent halo, cyano, nitro, —O((C$_{0-4}$)alkyl), (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CON((C$_{0-4}$)alkyl)((C$_{0-4}$)alkyl), —SO$_2$N((C$_{0-4}$)alkyl)((C$_{0-4}$)alkyl), or —N((C$_{0-4}$)alkyl)((C$_{0-4}$)alkyl) substituents; or mono((C$_{1-6}$)alkyl)amino(C$_{1-6}$)alkyl, di((C$_{1-6}$)alkyl)amino(C$_{1-6}$)alkyl, mono(aryl)amino(C$_{1-6}$)alkyl, di(aryl)amino(C$_{1-6}$)alkyl, or —N((C$_{1-6}$)alkyl)-(C$_{1-6}$)alkyl-aryl, any of which is optionally substituted with one or more independent halo, cyano, nitro, —O((C$_{0-4}$)alkyl), (C$_{1-10}$)alkyl, (C$_{2-10}$)alkenyl, (C$_{2-10}$)alkynyl, halo(C$_{1-10}$)alkyl, halo(C$_{2-10}$)alkenyl, halo(C$_{2-10}$)alkynyl, —COOH, (C$_{1-4}$)alkoxycarbonyl, —CON((C$_{0-4}$)alkyl)((C$_{0-4}$)alkyl), —SO$_2$N((C$_{0-4}$)alkyl)((C$_{0-4}$)alkyl), or —N((C$_{0-4}$)alkyl)((C$_{0-4}$)alkyl) substituents; and n, m, j1, j1a, j2a, j3a, j4, j4a, j5a, j6a, j7, and j8 are each independently equal to 0, 1, or 2.

In an embodiment, the invention provides the method of any of the preceding paragraphs, wherein the BTK inhibitor is a compound according to:

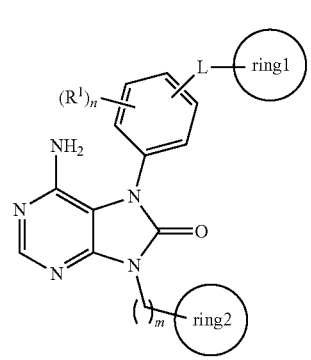

or a pharmaceutically acceptable salt, hydrate, solvate, cocrystal, or prodrug thereof, wherein L represents (1) —O—, (2) —S—, (3) —SO—, (4) —SO$_2$— (5) —NH—, (6) —C(O)—, (7) —CH$_2$O—, (8) —O—CH$_2$—, (9) —CH$_2$—, or (10) —CH(OH)—;

R$^1$ represents (1) a halogen atom, (2) a C$_{1-4}$ alkyl group, (3) a C$_{1-4}$ alkoxy group, (4) a C$_{1-4}$ haloalkyl group, or (5) a C$_{1-4}$ haloalkoxy group;

ring1 represents a 4- to 7-membered cyclic group, which may be substituted by from one to five substituents each independently selected from the group consisting of (1) halogen atoms, (2) $C_{1-4}$ alkyl groups, (3) $C_{1-4}$ alkoxy groups, (4) nitrile, (5) $C_{1-4}$ haloalkyl groups, and (6) $C_{1-4}$ haloalkoxy groups, wherein when two or more substituents are present on ring1, these substituents may form a 4- to 7-membered cyclic group together with the atoms in ring1 to which these substituents are bound;

ring2 represents a 4- to 7-membered saturated heterocycle, which may be substituted by from one to three -K-$R^2$; K represents (1) a bond, (2) a $C_{1-4}$ alkylene, (3) —C(O)—, (4) —C(O)—CH$_2$—, (5) —CH$_2$—C(O)—, (6) —C(O)O—, or (7) —SO$_2$— (wherein the bond on the left is bound to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

$R^3$ and $R^4$ each independently represent (1) a hydrogen atom, or (2) a $C_{1-4}$ alkyl group which may be substituted by $OR^9$ or $CONR^{10}R^{11}$; $R^3$ and $R^4$ may, together with the nitrogen atom to which they are bound, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group; $R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another).

In an embodiment, the invention provides the method of any of the preceding paragraphs, wherein the JAK-2 inhibitor is a compound according to:

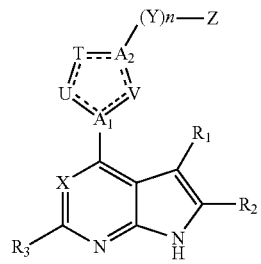

or a pharmaceutically acceptable salt, solvate, hydrate, cocrystal, or prodrug thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O$ $(CR^{11}R^{12})_q$, $(CR^{11}R^{12})_pOC(O)(CR^{11}R^{12})_q$, $(CR^{11}R^{12})_p$ $OC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)$ $(CR^{11}R^{12})_q$, $(CR^{11}R^{12})_pS(O)NR^c(CR^{11}R^{12})_q$, $(CR^{11}R^{12})_p$ $S(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)$ $NR^cR^d$, $NR^cR^d$, $NR^cC(O)R^b$, $NR^cC(O)NR^cR^d$, $NR^cC(O)$ $OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl)$R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)$ $NR^cR^d$, $NR^cC(=NR^i)NR^cR^d$, $S(O)R^b$, $S(O)NR^cR^d$, $S(O)_2$ $R^b$, $NR^cS(O)_2R^b$, $C(=NOH)R^b$, $C(=NO(C_{1-6}$ alkyl)$R^b$, and $S(O)_2NR^cR^d$;

wherein when Z is H, n is 1;

or the —(Y)$_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$, $A^2$, U, T, and V, wherein said 4- to 20-membered aryl, cycloalkyl, heteroaryl, or heterocycloalkyl ring is optionally substituted by 1, 2, 3, 4, or 5 substituents independently selected from -(W)$_m$-Q;

W is $C_{1-8}$ alkylenyl, $C_{2-8}$ alkenylenyl, $C_{2-8}$ alkynylenyl, O, S, C(O), C(O)$NR^{c'}$, C(O)O, OC(O), OC(O)$NR^{c'}$, $NR^{c'}$, $NR^{c'}$-C(O)$NR^{d'}$, S(O), S(O)$NR^{c'}$, $S(O)_2$, or $S(O)_2NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S$ $(O)_2R^{b'}$, and $S(O)_2NR^{c'}R^{d'}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}OC(O)NR^{c''}R^{d''}$, $NR^{c''}R^{d''}$, $NR^{c''}C$ $(O)R^{b''}$, $NR^{c''}C(O)OR^{a''}$, $NR^{c''}S(O)R^{b''}$, $NR^{c''}S(O)_2R^{b''}$, $S(O)R^{b''}$, $S(O)NR^{c''}R^{d''}$, $S(O)_2R^{b''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, halosulfanyl, aryl, cycloalkyl, heteroaryl, heterocycloalkyl, CN, NO$_2$, OR$^7$, SR$^7$, C(O)R$^8$, C(O)NR$^9$R$^{10}$, C(O)OR$^7$OC(O)R$^8$, OC(O)NR$^9$R$^{10}$, NR$^9$R$^{10}$, NR$^9$C(O)R$^8$, NR$^c$C(O)OR$^7$, S(O)R$^8$, S(O)NR$^9$R$^{10}$, S(O)$_2$R$^8$, NR$^9$S(O)$_2$R$^8$, and S(O)$_2$NR$^9$R$^{10}$;

R$^5$ is H, halo, C$_{1-4}$ alkyl, C$_{2-4}$ alkenyl, C$_{2-4}$ alkynyl, C$_{1-4}$ haloalkyl, halosulfanyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, or S(O)$_2$NR$^9$R$^{10}$;

R$^6$ is H, C$_{1-4}$ alkyl, C$_{2-4}$ alkenyl, C$_{2-4}$ alkynyl, C$_{1-4}$ haloalkyl, OR$^7$, C(O)R$^8$, C(O)NR$^9$R$^{10}$, C(O)OR$^7$, S(O)R$^8$, S(O)NR$^9$R$^{10}$, S(O)$_2$R$^8$, or S(O)$_2$NR$^9$R$^{10}$;

R$^7$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^8$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^9$ and R$^{10}$ are independently selected from H, C$_{1-10}$ alkyl, C$_{1-6}$ haloalkyl, C$_{2-6}$ alkenyl, C$_{2-6}$ alkynyl, C$_{1-6}$ alkylcarbonyl, arylcarbonyl, C$_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl; or R$^9$ and R$^{10}$ together with the N atom to which they are attached form a 4-, 5-, 6- or 7-membered heterocycloalkyl group;

R$^{11}$ and R$^{12}$ are independently selected from H and -E$^1$-E$^2$-E$^3$-E$^4$;

D$^1$ and E$^1$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^2$ and E$^2$ are independently absent or independently selected from C$_{1-6}$ alkylene, C$_{2-6}$ alkenylene, C$_{2-6}$ alkynylene, (C$_{1-6}$ alkylene)$_r$-O—(C$_{1-6}$ alkylene)$_s$, (C$_{1-6}$ alkylene)$_r$-S—(C$_{1-6}$ alkylene)$_s$, (C$_{1-6}$ alkylene)$_s$, —NR$^e$—(C$_{1-6}$ alkylene)$_s$, (C$_{1-6}$ alkylene)$_r$-CO—(C$_{1-6}$ alkylene)$_s$, (C$_{1-6}$ alkylene)$_r$-COO—(C$_{1-6}$ alkylene)$_s$, (C$_{1-6}$ alkylene)$_r$-CONR$^e$—(C$_{1-6}$ alkylene)$_s$, (C$_{1-6}$ alkylene)$_r$-SO—(C$_{1-6}$ alkylene)$_s$, (C$_{1-6}$ alkylene)$_r$-SO$_2$—(C$_{1-6}$ alkylene)$_s$, (C$_{1-6}$ alkylene)$_r$-SONR$^e$—(C$_{1-6}$ alkylene)$_s$, and (C$_{1-6}$ alkylene)$_r$- NR$^e$CONR$^f$—(C$_{1-6}$ alkylene)$_s$, wherein each of the C$_{1-6}$ alkylene, C$_{2-6}$ alkenylene, and C$_{2-6}$ alkynylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^3$ and E$^3$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^4$ and E$^4$ are independently selected from H, halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl)R$^b$, and S(O)$_2$NR$^c$R$^d$, wherein said C$_{1-8}$ alkyl, C$_{2-8}$ alkenyl, or C$_{2-8}$ alkynyl, is optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, —C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$;

R$^a$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^b$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{a\prime}$ and R$^{a\prime\prime}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^{b\prime}$ and R$^{b\prime\prime}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^c$ and R$^d$ are independently selected from H, Cy$^1$, —(C$_{1-6}$ alkyl)-Cy$^1$, C$_{1-10}$ alkyl, C$_{1-6}$ haloalkyl, C$_{2-6}$ alkenyl, C$_{2-6}$ alkynyl, wherein said C$_{1-10}$ alkyl, C$_{1-6}$ haloalkyl, C$_{2-6}$ alkenyl, or C$_{2-6}$ alkynyl, is optionally substituted with 1, 2, or 3 substituents independently selected from Cy$^1$, —(C$_{1-6}$ alkyl)-Cy$^1$, OH, CN, amino, halo, C$_{1-6}$ alkyl, C$_{1-6}$ haloalkyl, C$_{1-6}$ haloalkyl, and halosulfanyl; or R$^c$ and R$^d$ together with the N atom to which they are attached form a 4-, 5-, 6- or 7-membered heterocycloalkyl group optionally substituted with 1, 2, or 3 substituents independently selected from Cy¹, —(C$_{1-6}$ alkyl)-Cy¹, OH, CN, amino, halo, C$_{1-6}$ alkyl, C$_{1-6}$ haloalkyl, C$_{1-6}$ haloalkyl, and halosulfanyl;

R$^{c'}$ and R$^{d'}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

or R$^{c'}$ and R$^{d'}$ together with the N atom to which they are attached form a 4-, 5-, 6- or 7-membered heterocycloalkyl group optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{c''}$ and R$^{d''}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, C$_{1-6}$ haloalkyl, aryl, arylalkyl, heteroaryl, heteroarylalkyl, cycloalkyl and heterocycloalkyl;

or R$^{c''}$ and R$^{d''}$ together with the N atom to which they are attached form a 4-, 5-, 6- or 7-membered heterocycloalkyl group optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^i$ is H, CN, NO$_2$, or C$_{1-6}$ alkyl;
R$^e$ and R$^f$ are independently selected from H and C$_{1-6}$ alkyl;
R$^i$ is H, CN, or NO$_2$;
m is 0 or 1;
n is 0 or 1;
p is 0, 1, 2, 3, 4, 5, or 6;
q is 0, 1, 2, 3, 4, 5 or 6;
r is 0 or 1; and
s is 0 or 1.

In an embodiment, the invention provides the method of any of the preceding paragraphs, wherein the JAK-2 inhibitor is a compound according to:

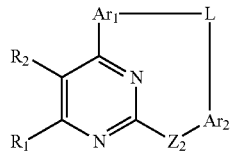

or a pharmaceutically acceptable salt, solvate, hydrate, cocrystal, or prodrug thereof, wherein:
R$^1$ and R$^2$ are each independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted;

each R$^3$, R$^4$, and R$^5$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^6$ is independently selected from the group consisting of a bond, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

Z$^2$ is independently selected from the group consisting of a bond, O, S, —N(R$^7$)—, —N(R$^7$)C$_{1-2}$ alkyl-, and —C$_{1-2}$alkylN(R$^7$)—;

each R$^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

Ar$^1$ and Ar$^2$ are each independently selected from the group consisting of aryl and heteroaryl, each of which may be optionally substituted;

L is a group of formula:

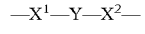

wherein X$^1$ is attached to Ar$^1$ and X$^2$ is attached to Ar$^2$, and wherein X$^1$, X$^2$ and Y are selected such that the group L has between 5 and 15 atoms in the normal chain, X$^1$ and X$^2$ are each independently a heteroalkyl group containing at least one oxygen atom in the normal chain, Y is a group of formula —CR$^a$=CR$^b$— or an optionally substituted cycloalkyl group, wherein R$^a$ and R$^b$ are each independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted, or R$^a$ and R$^b$ may be joined such that when taken together with the carbon atoms to which they are attached they form a cycloalkenyl or cycloheteroalkenyl group;

or a pharmaceutically acceptable salt, solvate, hydrate, cocrystal, or prodrug thereof, or an N-oxide thereof.

In certain embodiments Z$^2$ is selected from the group consisting of a bond, —N(R$^7$)—, and —S—. In one specific embodiment Z$^2$ is —N(R$^7$)—. In an even more specific embodiment Z$^2$ is —N(H)—.

Ar$^1$ and Ar$^2$ are each independently selected from the group consisting of aryl and heteroaryl and may be monocyclic, bicyclic or polycyclic moieties. In certain embodiments each of $Ar^1$ and $Ar^2$ is a monocyclic or bicyclic moiety. In certain embodiments each of $Ar^1$ and $Ar^2$ are a monocyclic moiety.

In certain embodiments $Ar^1$ is selected from the group consisting of:

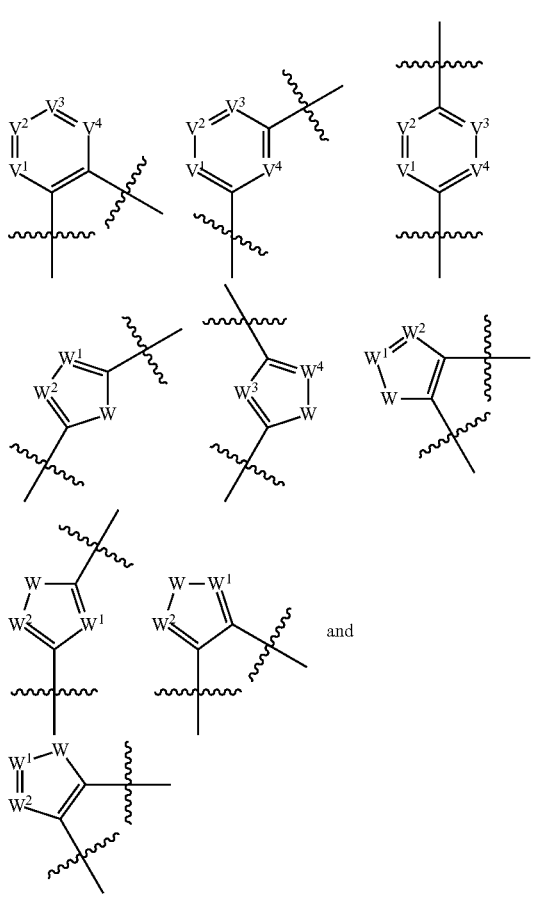

wherein $V^1$, $V^2$, $V^3$ and $V^4$ are each independently selected from the group consisting of N, and $C(R^{10})$;

W is selected from the group consisting of O, S and $NR^{10}$;

$W^1$ and $W^2$ are each independently selected from the group consisting of N and $CR^{10}$;

wherein each $R^{10}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$, R$^4$N(R$^5$)SO$_2$R$^6$—, R$^4$N(R$^5$)C(O)N(R$^5$)R$^6$— and acyl, each of which may be optionally substituted, wherein $R^3$, $R^4$, $R^5$ and $R^6$ are as defined above.

In certain embodiments $Ar^1$ is selected from the group consisting of:

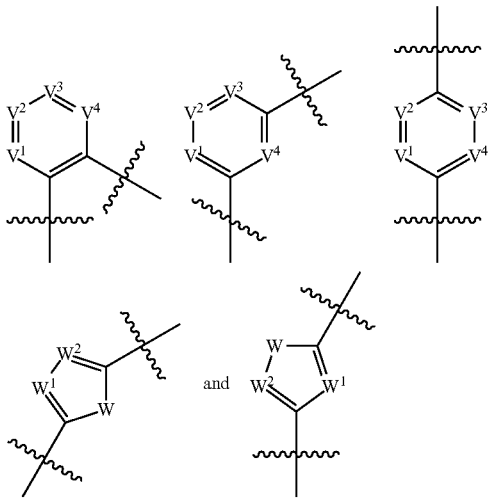

wherein $V^1$, $V^2$, $V^3$, $V^4$, W, $W^1$, $W^2$, $R^3$, $R^4$, $R^5$ and $R^6$ are as defined above.

In certain embodiments $Ar^1$ is selected from the group consisting of:

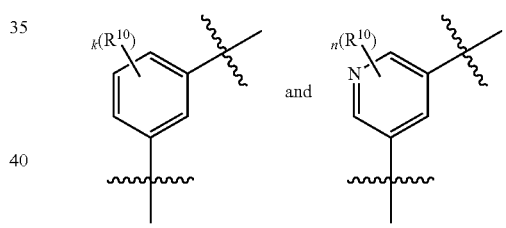

wherein each $R^{10}$ is independently as defined above, k is an integer selected from the group consisting of 0, 1, 2, 3, and 4; and n is an integer selected from the group consisting of 0, 1, and 2.

In yet an even further embodiment $Ar^1$ is selected from the group consisting of:

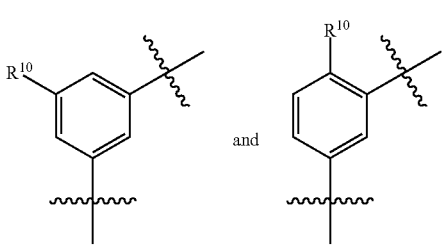

wherein $R^{10}$ is as defined above.

In certain embodiments $Ar^1$ is selected from the group consisting of:

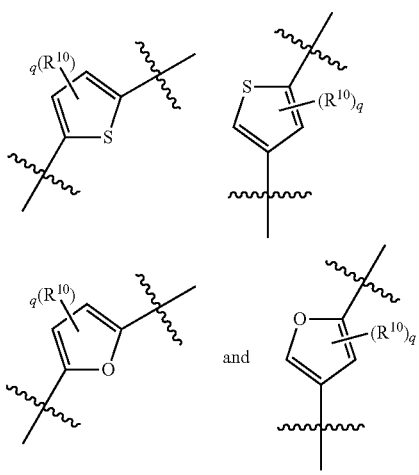

wherein each $R^{10}$ is independently as defined above, and q is an integer selected from the group consisting of 0, 1 and 2.

In certain embodiments $Ar^1$ is selected from the group consisting of:

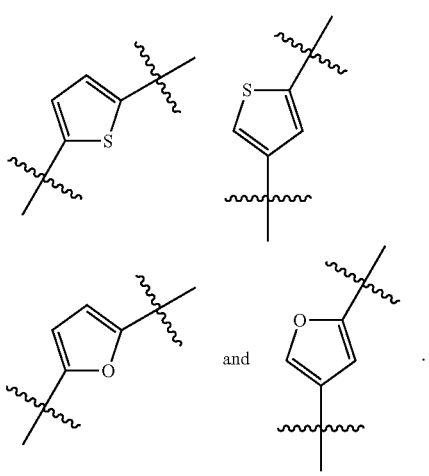

In certain embodiments $Ar^1$ is selected from the group consisting of:

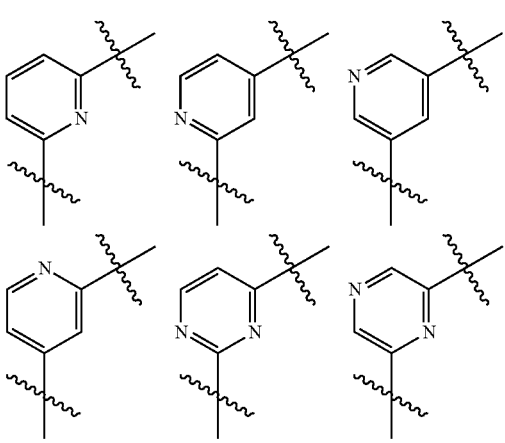

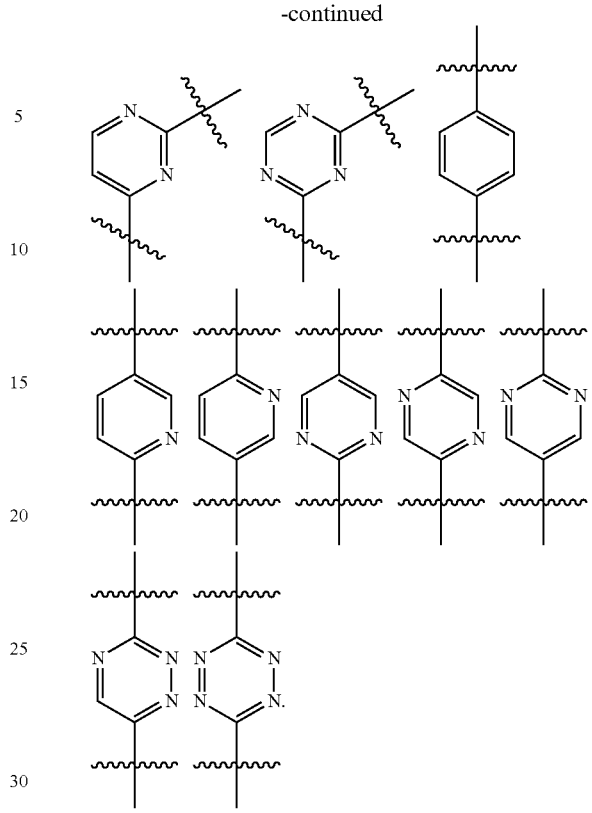

In certain embodiments $Ar^2$ is selected from the group consisting of:

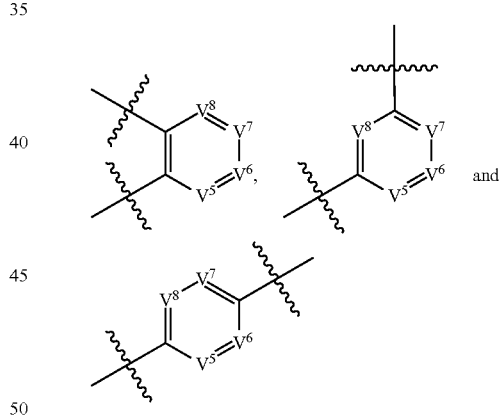

wherein $V^5$, $V^6$, $V^7$ and $V^8$ are independently selected from the group consisting of N, and $C(R^{11})$;

wherein each $R^{11}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted.

In certain embodiments Ar$^2$ is selected from the group consisting of:

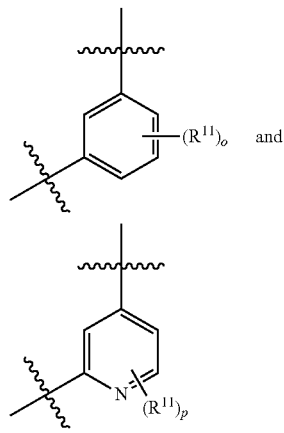

wherein each R$^{11}$ is independently as defined above
o is an integer selected from the group consisting of 0, 1, 2, 3, and 4; and
p is an integer selected from the group consisting of 0, 1, 2, and 3.

In certain embodiments Ar$^2$ is selected from the group consisting of:

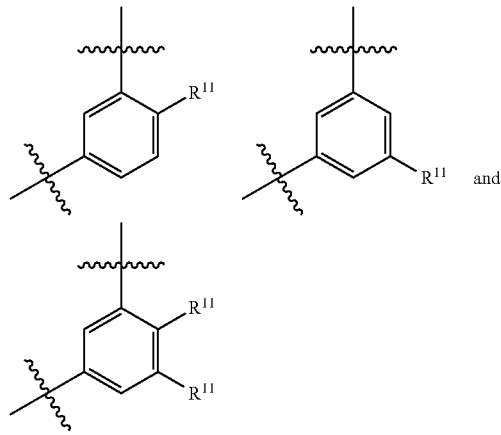

wherein each R$^{11}$ is as defined above.

In an even further embodiment Ar$^2$ is selected from the group consisting of:

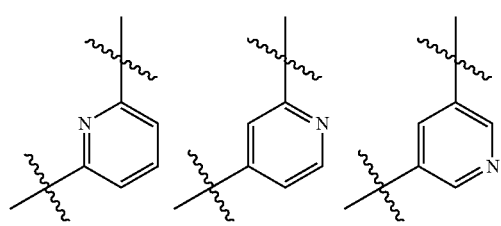

-continued

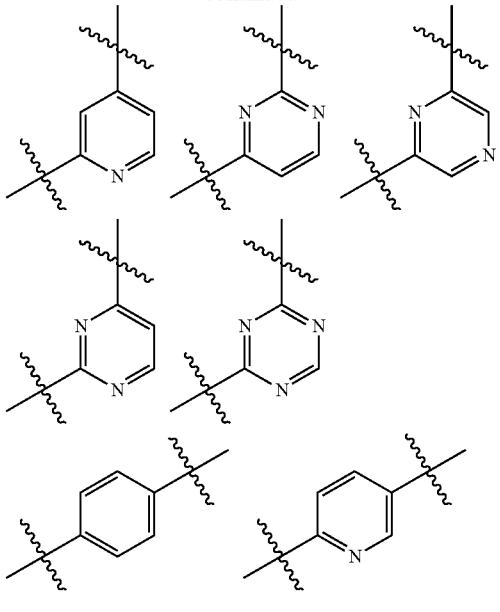

In an embodiment, the invention provides the method of any of the preceding paragraphs, wherein the BTK inhibitor is selected from the group consisting of:

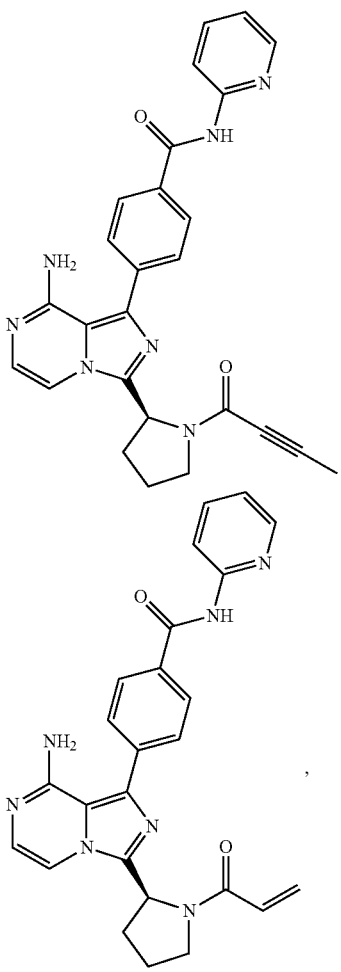

255
-continued
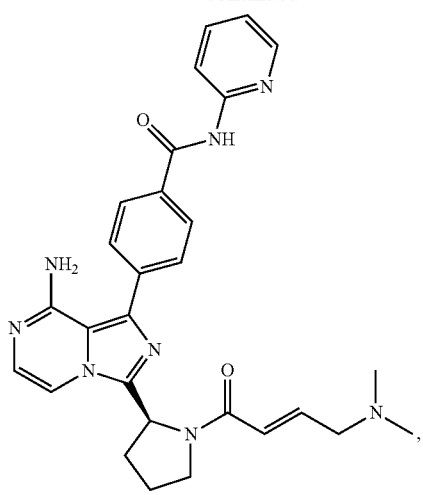
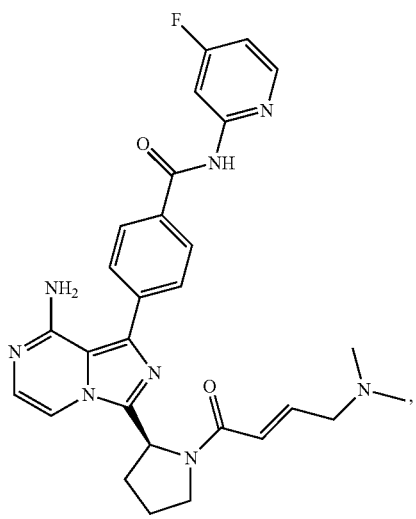
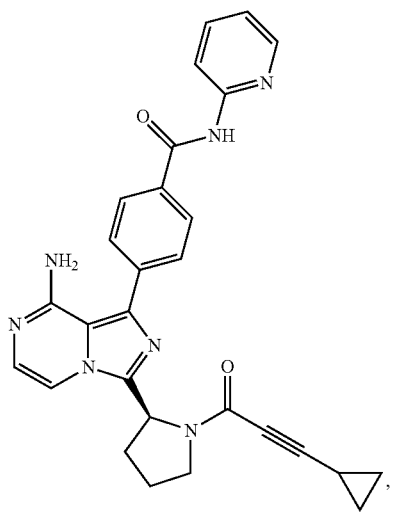
256
-continued
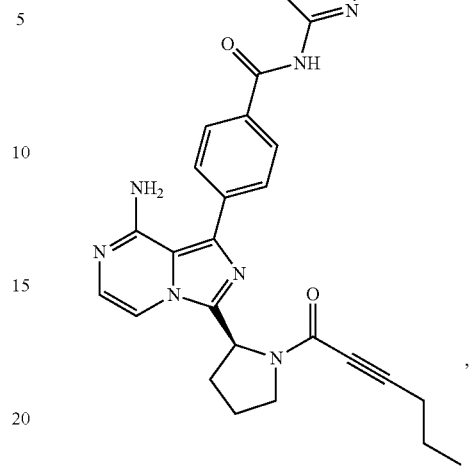
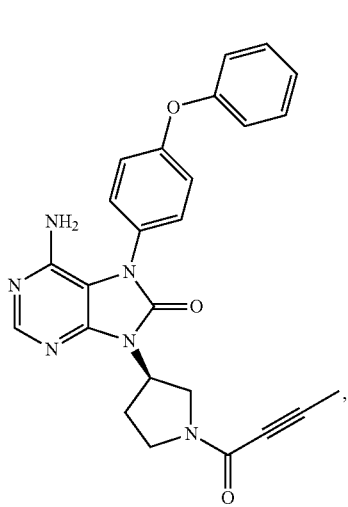

-continued

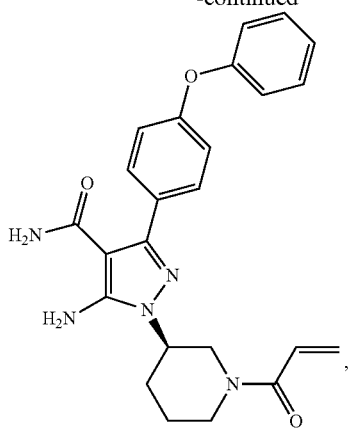

and pharmaceutically acceptable salts, solvates, hydrates, cocrystals, and prodrugs thereof; and the JAK-2 inhibitor is selected from the group consisting of:

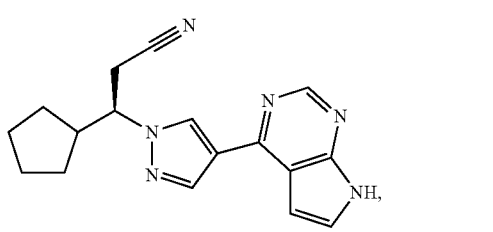

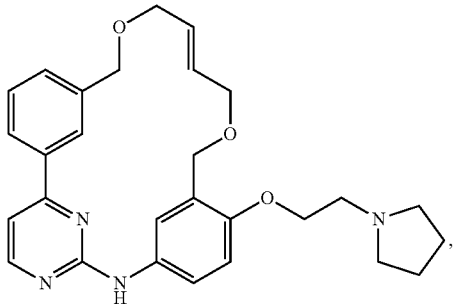

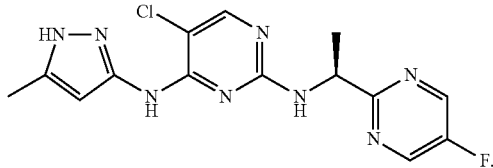

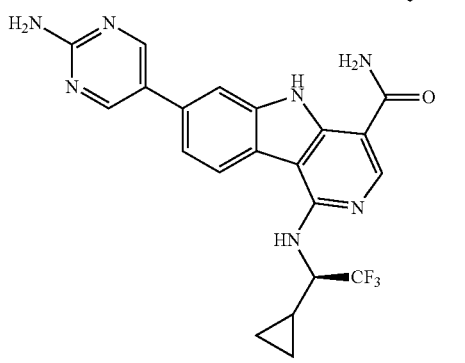

and pharmaceutically acceptable salts, solvates, hydrates, cocrystals, and prodrugs thereof.

In an embodiment, the invention provides the method of any of the preceding paragraphs, wherein the BTK inhibitor is selected from the group consisting of:

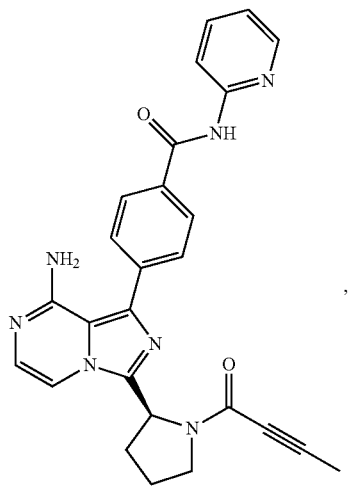

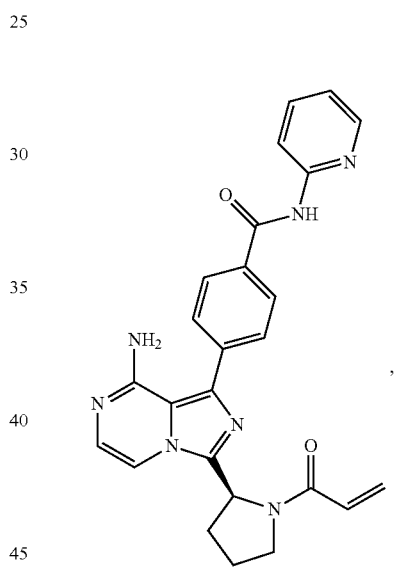

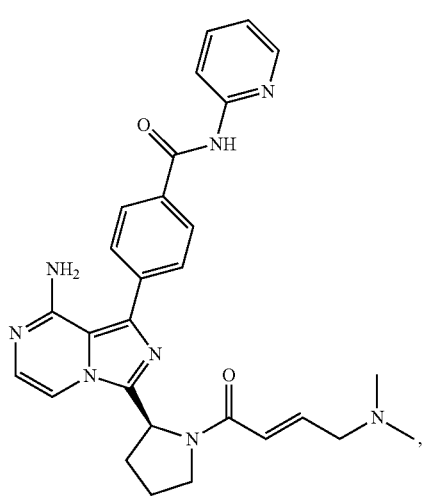

259
-continued
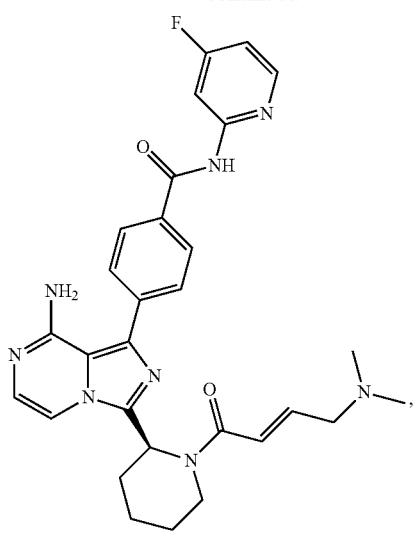
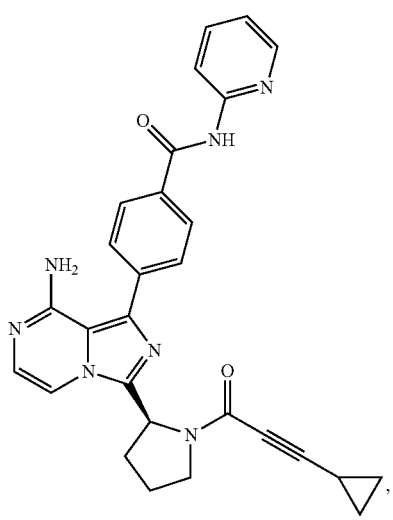
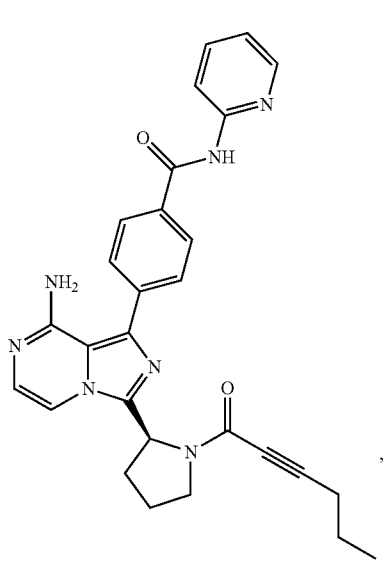
260
-continued
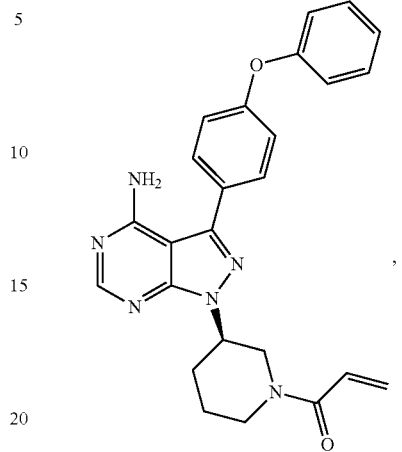
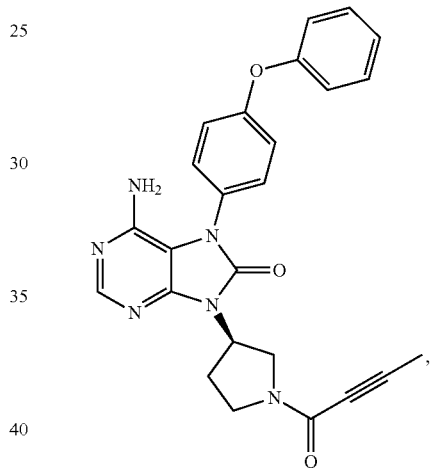
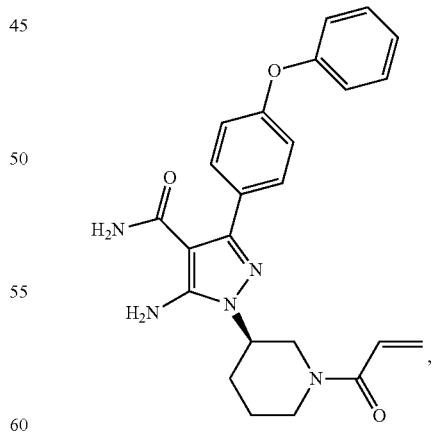
and pharmaceutically acceptable salts, solvates, hydrates, cocrystals, and prodrugs thereof, and the JAK-2 inhibitor is selected from the group consisting of:

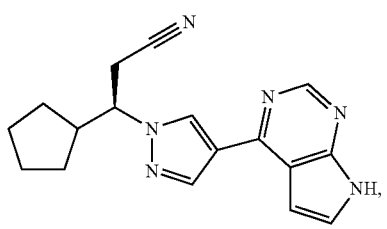

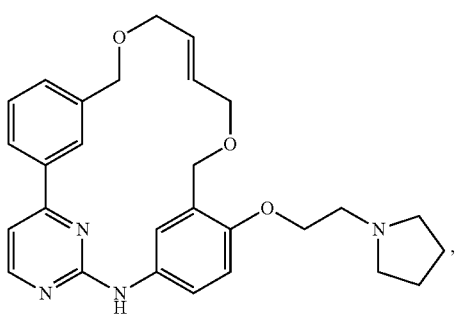

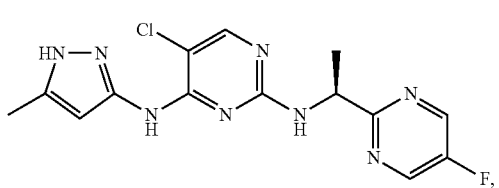

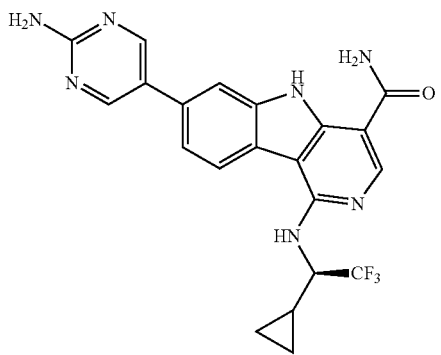

and pharmaceutically acceptable salts, solvates, hydrates, cocrystals, and prodrugs thereof; and a PI3K inhibitor selected from the group consisting of:

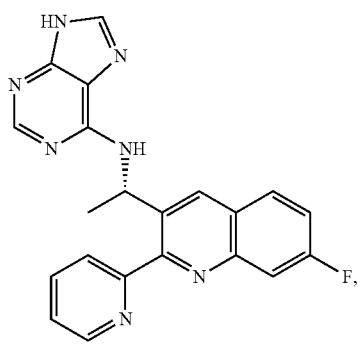

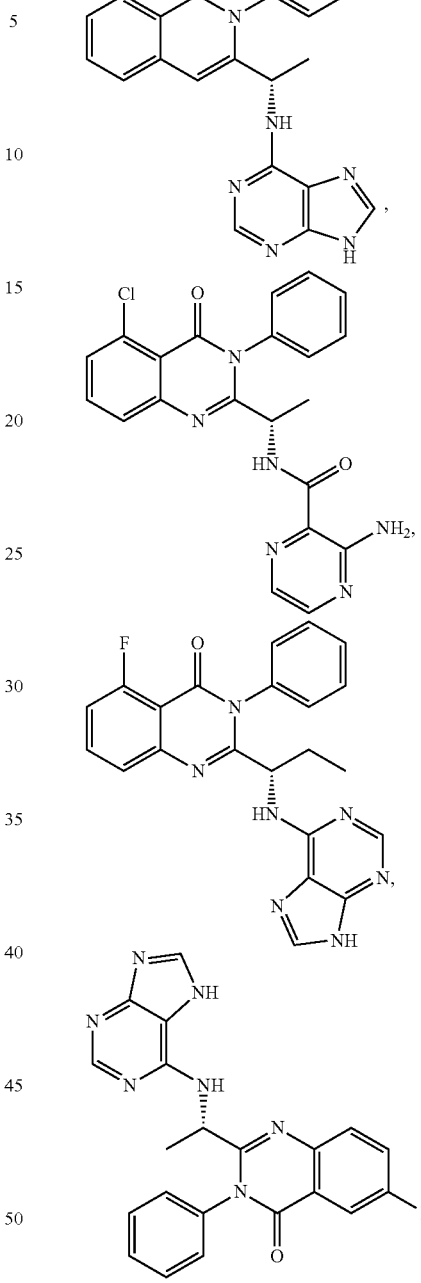

and pharmaceutically acceptable salts, solvates, hydrates, cocrystals, and prodrugs thereof.

In an embodiment, the invention provides a method of treating a solid tumor cancer in a human comprising administering a therapeutically effective amount of a BTK inhibitor, a JAK-2 inhibitor, and/or a PI3K-δ inhibitor, wherein the dose is effective to inhibit signaling between the cells of the solid tumor cancer and at least one tumor microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In an embodiment, the solid tumor cancer is selected from the group consisting of pancreatic cancer, ovarian cancer, colon carcinoma, breast cancer, lung cancer, colorectal cancer, thyroid cancer, bone sarcoma, and stomach cancers. In an embodiment, the invention provides the method of any of the preceding paragraphs, wherein the dose is further effective to increase immune system recognition and rejection of the solid tumor by the human.

Combinations of BTK Inhibitors, PI3K Inhibitors, and/or JAK-2 Inhibitors with Anti-CD20 Antibodies The BTK inhibitors of the present invention and combinations of the BTK inhibitors with PI3K inhibitors and/or JAK-2 inhibitors may also be safely co-administered with immunotherapeutic antibodies such as the anti-CD20 antibodies rituximab, obinutuzumab, ofatumumab, veltuzumab, tositumomab, and ibritumomab, and or antigen-binding fragments, derivatives, conjugates, variants, and radioisotope-labeled complexes thereof, which may be given alone or with conventional chemotherapeutic active pharmaceutical ingredients such as those described herein. In an embodiment, the foregoing combinations exhibit synergistic effects that may result in greater efficacy, less side effects, the use of less active pharmaceutical ingredient to achieve a given clinical result, or other synergistic effects.

In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is a monoclonal antibody or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is an anti-CD20 monoclonal antibody or an antigen-binding fragment, derivative, conjugate, variant, or radioisotope-labeled complex thereof, and wherein the anti-CD20 antibody specifically binds to human CD20 with a $K_D$ selected from the group consisting of $1 \times 10^{-7}$ M or less, $5 \times 10^{-8}$ M or less, $1 \times 10^{-8}$ M or less, and $5 \times 10^{-9}$ M or less. Anti-CD20 monoclonal antibodies are classified as Type I or Type II, as described in Klein, et al., *mAbs* 2013, 5, 22-33. Type I anti-CD20 monoclonal antibodies are characterized by binding to the Class I epitope, localization of CD20 to lipid rafts, high complement-dependent cytotoxicity, full binding capacity, weak homotypic aggregation, and moderate cell death induction. Type II anti-CD20 monoclonal antibodies are characterized by binding to the Class I epitope, a lack of localization of CD20 to lipid rafts, low complement-dependent cytotoxicity, half binding capacity, homotypic aggregation, and strong cell death induction. Both Type I and Type II anti-CD20 monoclonal antibodies exhibit antibody-dependent cytotoxiticy (ADCC) and are thus useful with BTK inhibitors described herein. Type I anti-CD20 monoclonal antibodies include but are not limited to rituximab, ocrelizumab, and ofatumumab. Type II anti-CD20 monoclonal antibodies include but are not limited to obinutuzumab and tositumomab. In an embodiment, the foregoing methods exhibit synergistic effects that may result in greater efficacy, less side effects, the use of less active pharmaceutical ingredient to achieve a given clinical result, or other synergistic effects.

In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is a monoclonal antibody or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is an anti-CD20 monoclonal antibody or an antigen-binding fragment, derivative, conjugate, variant, or radioisotope-labeled complex thereof, and wherein the anti-CD20 antibody specifically binds to human CD20 with a $K_D$ selected from the group consisting of $1 \times 10^{-7}$ M or less, $5 \times 10^{-8}$ M or less, $1 \times 10^{-8}$ M or less, and $5 \times 10^{-9}$ M or less.

In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an Type I anti-CD20 antibody, or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an Type II anti-CD20 antibody, or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and a JAK-2 inhibitor or a pharmaceutically acceptable salt, solvate, hydrate, cocrystal, or prodrug thereof, and further comprising the step of administering an Type I anti-CD20 antibody, or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and a JAK-2 inhibitor or a pharmaceutically acceptable salt, solvate, hydrate, cocrystal, or prodrug thereof, and further comprising the step of administering an Type II anti-CD20 antibody, or an antigen-binding fragment, derivative, conjugate, variant, or radioisotope-labeled complex thereof.

In selected embodiments, the BTK inhibitors of the present invention and combinations of the BTK inhibitors with PI3K inhibitors, and/or JAK-2 inhibitors, and the anti-CD20 monoclonal antibody are administered sequentially. In selected embodiments, the BTK inhibitors of the present invention and combinations of the BTK inhibitors with PI3K inhibitors, and/or JAK-2 inhibitors, and the anti-CD20 monoclonal antibody are administered concomitantly. In selected embodiments, the BTK inhibitors of the present invention and combinations of the BTK inhibitors with PI3K inhibitors and/or JAK-2 inhibitors is administered before the anti-CD20 monoclonal antibody. In selected embodiments, the BTK inhibitors of the present invention and combinations of the BTK inhibitors with PI3K inhibitors and/or JAK-2 inhibitors is administered after the anticoagulant or the antiplatelet active pharmaceutical ingredient. In selected embodiments, the BTK inhibitors of the present invention and combinations of the BTK inhibitors with PI3K inhibitors and/or JAK-2 inhibitors and the anti-CD20 monoclonal antibody are administered over the same time period, and the BTK inhibitor administration continues after the anti-CD20 monoclonal antibody administration is completed.

In an embodiment, the anti-CD20 monoclonal antibody is rituximab, or an antigen-binding fragment, derivative, conjugate, variant, or radioisotope-labeled complex thereof. Rituximab is a chimeric murine-human monoclonal antibody directed against CD20, and its structure comprises an IgG1 kappa immunoglobulin containing murine light- and heavy-chain variable region sequences and human constant region sequences. Rituximab is composed of two heavy chains of 451 amino acids and two light chains of 213 amino acids. The amino acid sequence for the heavy chains of rituximab is set forth in SEQ ID NO:1. The amino acid sequence for the light chains of rituximab is set forth in SEQ ID NO:2. Rituximab is commercially available, and its properties and use in cancer and other diseases is described in more detail in Rastetter, et al., *Ann. Rev. Med.* 2004, 55, 477-503, and in Plosker and Figgett, *Drugs*, 2003, 63, 803-43. In an embodiment, the anti-CD20 monoclonal antibody is an anti-CD20 biosimilar monoclonal antibody approved by drug regulatory authorities with reference to rituximab. In an embodiment, the anti-CD20 monoclonal antibody has a heavy chain sequence identity of greater than 90% to SEQ ID NO:1. In an embodiment, the anti-CD20 monoclonal antibody has a light chain sequence identity of greater than 90% to SEQ ID NO:2. In an embodiment, the anti-CD20 monoclonal antibody has a heavy chain sequence identity of greater than 95% to SEQ ID NO:1. In an embodiment, the anti-CD20 monoclonal antibody has a light chain sequence identity of greater than 95% to SEQ ID NO:2. In an embodiment, the anti-CD20 monoclonal antibody has a heavy chain sequence identity of greater than 98% to SEQ ID NO:1. In an embodiment, the anti-CD20 monoclonal antibody has a light chain sequence identity of greater than 98% to SEQ ID NO:2. In an embodiment, the anti-CD20 monoclonal antibody has a heavy chain sequence identity of greater than 99% to SEQ ID NO:1. In an embodiment, the anti-CD20 monoclonal antibody has a light chain sequence identity of greater than 99% to SEQ ID NO:2.

In an embodiment, the anti-CD20 monoclonal antibody is obinutuzumab, or an antigen-binding fragment, derivative, conjugate, variant, or radioisotope-labeled complex thereof. Obinutuzumab is also known as afutuzumab or GA-101. Obinutuzumab is a humanized monoclonal antibody directed against CD20. The amino acid sequence for the heavy chains of obinutuzumab is set forth in SEQ ID NO:3. The amino acid sequence for the light chains of obinutuzumab is set forth in SEQ ID NO:4. Obinutuzumab is commercially available, and its properties and use in cancer and other diseases is described in more detail in Robak, *Curr. Opin. Investig. Drugs* 2009, 10, 588-96. In an embodiment, the anti-CD20 monoclonal antibody is an anti-CD20 biosimilar monoclonal antibody approved by drug regulatory authorities with reference to obinutuzumab. In an embodiment, the anti-CD20 monoclonal antibody has a heavy chain sequence identity of greater than 90% to SEQ ID NO:3. In an embodiment, the anti-CD20 monoclonal antibody has a light chain sequence identity of greater than 90% to SEQ ID NO:4. In an embodiment, the anti-CD20 monoclonal antibody has a heavy chain sequence identity of greater than 95% to SEQ ID NO:3. In an embodiment, the anti-CD20 monoclonal antibody has a light chain sequence identity of greater than 95% to SEQ ID NO:4. In an embodiment, the anti-CD20 monoclonal antibody has a heavy chain sequence identity of greater than 98% to SEQ ID NO:3. In an embodiment, the anti-CD20 monoclonal antibody has a light chain sequence identity of greater than 98% to SEQ ID NO:4. In an embodiment, the anti-CD20 monoclonal antibody has a heavy chain sequence identity of greater than 99% to SEQ ID NO:3. In an embodiment, the anti-CD20 monoclonal antibody has a light chain sequence identity of greater than 99% to SEQ ID NO:4. In an embodiment, the anti-CD20 monoclonal antibody obinutuzumab is an immunoglobulin G1, anti-(human B-lymphocyte antigen CD20 (membrane-spanning 4-domains subfamily A member 1, B-lymphocyte surface antigen B1, Leu-16 or Bp35)), humanized mouse monoclonal obinutuzumab des-CH3107-K-γ1 heavy chain (222-219')-disulfide with humanized mouse monoclonal obinutuzumab κ light chain dimer (228-228":231-231")-bisdisulfide antibody.

In an embodiment, the anti-CD20 monoclonal antibody is ofatumumab, or an antigen-binding fragment, derivative, conjugate, variant, or radioisotope-labeled complex thereof. Ofatumumab is described in Cheson, *J. Clin. Oncol.* 2010, 28, 3525-30. The crystal structure of the Fab fragment of ofatumumab has been reported in Protein Data Bank reference 3GIZ and in Du, et al., *Mol. Immunol.* 2009, 46, 2419-2423. Ofatumumab is commercially available, and its preparation, properties, and use in cancer and other diseases are described in more detail in U.S. Pat. No. 8,529,202 B2, the disclosure of which is incorporated herein by reference. In an embodiment, the anti-CD20 monoclonal antibody is an anti-CD20 biosimilar monoclonal antibody approved by drug regulatory authorities with reference to ofatumumab. In an embodiment, the anti-CD20 monoclonal antibody has a variable heavy chain sequence identity of greater than 90% to SEQ ID NO:5. In an embodiment, the anti-CD20 monoclonal antibody has a variable light chain sequence identity of greater than 90% to SEQ ID NO:6. In an embodiment, the anti-CD20 monoclonal antibody has a variable heavy chain sequence identity of greater than 95% to SEQ ID NO:5. In an embodiment, the anti-CD20 monoclonal antibody has a variable light chain sequence identity of greater than 95% to SEQ ID NO:6. In an embodiment, the anti-CD20 monoclonal antibody has a variable heavy chain sequence identity of greater than 98% to SEQ ID NO:5. In an embodiment, the anti-CD20 monoclonal antibody has a variable light chain sequence identity of greater than 98% to SEQ ID NO:6. In an embodiment, the anti-CD20 monoclonal antibody has a variable heavy chain sequence identity of greater than 99% to SEQ ID NO:5. In an embodiment, the anti-CD20 monoclonal antibody has a variable light chain sequence identity of greater than 99% to SEQ ID NO:6. In an embodiment, the anti-CD20 monoclonal antibody has a Fab fragment heavy chain sequence identity of greater than 90% to SEQ ID NO:7. In an embodiment, the anti-CD20 monoclonal antibody has a Fab fragment light chain sequence identity of greater than 90% to SEQ ID NO:8. In an embodiment, the anti-CD20 monoclonal antibody has a Fab fragment heavy chain sequence identity of greater than 95% to SEQ ID NO:7. In an embodiment, the anti-CD20 monoclonal antibody has a Fab fragment light chain sequence identity of greater than 95% to SEQ ID NO:8. In an embodiment, the anti-CD20 monoclonal antibody has a Fab fragment heavy chain sequence identity of greater than 98% to SEQ ID NO:7. In an embodiment, the anti-CD20 monoclonal antibody has a Fab fragment light chain sequence identity of greater than 98% to SEQ ID NO:8. In an embodiment, the anti-CD20 monoclonal antibody has a Fab fragment heavy chain sequence identity of greater than 99% to SEQ ID NO:7. In an embodiment, the anti-CD20 monoclonal antibody has a Fab fragment light chain sequence identity of greater than 99% to SEQ ID NO:8. In an embodiment, the anti-CD20 monoclonal antibody ofatumumab is an immunoglobulin G1, anti-(human B-lymphocyte antigen CD20 (membrane-spanning 4-domains subfamily A member 1, B-lymphocyte surface antigen B1, Leu-16 or Bp35)); human monoclonal ofatumumab-CD20 γ1 heavy chain (225-214')-disulfide with human monoclonal ofatumumab-CD20 κ light chain, dimer (231-231":234-234")-bisdisulfide antibody.

In an embodiment, the anti-CD20 monoclonal antibody is veltuzumab, or an antigen-binding fragment, derivative, conjugate, variant, or radioisotope-labeled complex thereof. Veltuzumab is also known as hA20. Veltuzumab is described in Goldenberg, et al., *Leuk. Lymphoma* 2010, 51, 747-55. In an embodiment, the anti-CD20 monoclonal antibody is an anti-CD20 biosimilar monoclonal antibody approved by drug regulatory authorities with reference to veltuzumab. In an embodiment, the anti-CD20 monoclonal antibody has a heavy chain sequence identity of greater than 90% to SEQ ID NO:9. In an embodiment, the anti-CD20 monoclonal antibody has a light chain sequence identity of greater than 90% to SEQ ID NO:10. In an embodiment, the anti-CD20 monoclonal antibody has a heavy chain sequence identity of greater than 95% to SEQ ID NO:9. In an embodiment, the anti-CD20 monoclonal antibody has a light chain sequence identity of greater than 95% to SEQ ID NO:10. In an embodiment, the anti-CD20 monoclonal antibody has a heavy chain sequence identity of greater than 98% to SEQ ID NO:9. In an embodiment, the anti-CD20 monoclonal antibody has a light chain sequence identity of greater than 98% to SEQ ID NO:10. In an embodiment, the anti-CD20 monoclonal antibody has a heavy chain sequence identity of greater than 99% to SEQ ID NO:9. In an embodiment, the anti-CD20 monoclonal antibody has a light chain sequence identity of greater than 99% to SEQ ID NO:10. In an embodiment, the anti-CD20 monoclonal antibody ofatumumab is an immunoglobulin G1, anti-(human B-lymphocyte antigen CD20 (membrane-spanning 4-domains subfamily A member 1, Leu-16, Bp35)); [218-arginine,360-glutamic acid,362-methionine]humanized mouse monoclonal hA20 γ1 heavy chain (224-213')-disulfide with humanized mouse monoclonal hA20 κ light chain (230-230":233-233")-bisdisulfide dimer In an embodiment, the anti-CD20 monoclonal antibody is tositumomab, or an antigen-binding fragment, derivative, conjugate, variant, or radioisotope-labeled complex thereof. In an embodiment, the anti-CD20 monoclonal antibody is $^{131}$I-labeled tositumomab. In an embodiment, the anti-CD20 monoclonal antibody is an anti-CD20 biosimilar monoclonal antibody approved by drug regulatory authorities with reference to tositumomab. In an embodiment, the anti-CD20 monoclonal antibody has a heavy chain sequence identity of greater than 90% to SEQ ID NO:11. In an embodiment, the anti-CD20 monoclonal antibody has a light chain sequence identity of greater than 90% to SEQ ID NO:12. In an embodiment, the anti-CD20 monoclonal antibody has a heavy chain sequence identity of greater than 95% to SEQ ID NO:11. In an embodiment, the anti-CD20 monoclonal antibody has a light chain sequence identity of greater than 95% to SEQ ID NO:12. In an embodiment, the anti-CD20 monoclonal antibody has a heavy chain sequence identity of greater than 98% to SEQ ID NO:11. In an embodiment, the anti-CD20 monoclonal antibody has a light chain sequence identity of greater than 98% to SEQ ID NO:12. In an embodiment, the anti-CD20 monoclonal antibody has a heavy chain sequence identity of greater than 99% to SEQ ID NO:11. In an embodiment, the anti-CD20 monoclonal antibody has a light chain sequence identity of greater than 99% to SEQ ID NO:12.

In an embodiment, the anti-CD20 monoclonal antibody is ibritumomab, or an antigen-binding fragment, derivative, conjugate, variant, or radioisotope-labeled complex thereof. The active form of ibritumomab used in therapy is ibritumomab tiuxetan. When used with ibritumomab, the chelator tiuxetan (diethylene triamine pentaacetic acid) is complexed with a radioactive isotope such as $^{90}$Y or $^{111}$In. In an embodiment, the anti-CD20 monoclonal antibody is ibritumomab tiuxetan, or radioisotope-labeled complex thereof. In an embodiment, the anti-CD20 monoclonal antibody is an anti-CD20 biosimilar monoclonal antibody approved by drug regulatory authorities with reference to tositumomab. In an embodiment, the anti-CD20 monoclonal antibody has a heavy chain sequence identity of greater than 90% to SEQ ID NO:13. In an embodiment, the anti-CD20 monoclonal antibody has a light chain sequence identity of greater than 90% to SEQ ID NO:14. In an embodiment, the anti-CD20 monoclonal antibody has a heavy chain sequence identity of greater than 95% to SEQ ID NO:13. In an embodiment, the anti-CD20 monoclonal antibody has a light chain sequence identity of greater than 95% to SEQ ID NO:14. In an embodiment, the anti-CD20 monoclonal antibody has a heavy chain sequence identity of greater than 98% to SEQ ID NO:13. In an embodiment, the anti-CD20 monoclonal antibody has a light chain sequence identity of greater than 98% to SEQ ID NO:14. In an embodiment, the anti-CD20 monoclonal antibody has a heavy chain sequence identity of greater than 99% to SEQ ID NO:13. In an embodiment, the anti-CD20 monoclonal antibody has a light chain sequence identity of greater than 99% to SEQ ID NO:14.

In an embodiment, an anti-CD20 antibody selected from the group consisting of obinutuzumab, ofatumumab, veltuzumab, tositumomab, and ibritumomab, and or antigen-binding fragments, derivatives, conjugates, variants, and radioisotope-labeled complexes thereof, is administered to a subject by infusing a dose selected from the group consisting of about 10 mg, about 20 mg, about 25 mg, about 50 mg, about 75 mg, 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg. In an embodiment, the anti-CD20 antibody is admininstered weekly. In an embodiment, the anti-CD20 antibody is admininstered every two weeks. In an embodiment, the anti-CD20 antibody is admininstered every three weeks. In an embodiment, the anti-CD20 antibody is admininstered monthly. In an embodiment, the anti-CD20 antibody is administered at a lower initial dose, which is escalated when administered at subsequent intervals admininstered monthly. For example, the first infusion can deliver 300 mg of anti-CD20 antibody, and subsequent weekly doses could deliver 2,000 mg of anti-CD20 antibody for eight weeks, followed by monthly doses of 2,000 mg of anti-CD20 antibody. During any of the foregoing embodiments, the BTK inhibitors of the present invention and combinations of the BTK inhibitors with PI3K inhibitors and/or JAK-2 inhibitors may be administered daily, twice daily, or at different intervals as described above, at the dosages described above.

In an embodiment, the invention provides a kit comprising a first composition comprising a BTK inhibitor and/or combinations of the BTK inhibitor with PI3K inhibitor and/or JAK-2 inhibitor and a second composition comprising an anti-CD20 antibody selected from the group consisting of rituximab, obinutuzumab, ofatumumab, veltuzumab, tositumomab, and ibritumomab, or an antigen-binding fragment, derivative, conjugate, variant, or radioisotope-labeled complex thereof, for use in the treatment of CLL or SLL, hematological malignancies, B cell malignancies or, or any of the other diseases described herein. The compositions are typically both pharmaceutical compositions. The kit is for use in co-administration of the anti-CD20 antibody and the BTK inhibitor, either simultaneously or separately, in the treatment of CLL or SLL, hematological malignancies, B cell malignancies, or any of the other diseases described herein.

Combinations of BTK Inhibitors with Chemotherapeutic Active Pharmaceutical Ingredients The combinations of the BTK inhibitors with PI3K inhibitors and/or JAK-2 inhibitors may also be safely co-administered with chemotherapeutic active pharmaceutical ingredients such as gemcitabine, albumin-bound paclitaxel (nab-paclitaxel), and bendamustine or bendamustine hydrochloride. In a preferred embodiment, the invention provides a method of treating a hematological malignancy or a solid tumor cancer in a human comprising the step of administering to said human a BTK inhibitor, a PI3K inhibitor, and/or a JAK-2 inhibitor, and further comprising the step of administering a therapeutically-effective amount of gemcitabine, or a pharmaceutically acceptable salt, prodrug, cocrystal, solvate or hydrate thereof. In an embodiment, the invention provides a method of treating a hematological malignancy or a solid tumor cancer in a human comprising the step of administering to said human a BTK inhibitor of Formula (XVIII), or a pharmaceutically acceptable salt, prodrug, cocrystal, solvate or hydrate thereof, and further comprising the step of administering a therapeutically-effective amount of gemcitabine, or a pharmaceutically acceptable salt, prodrug, cocrystal, solvate or hydrate thereof. In an embodiment, the solid tumor cancer in any of the foregoing embodiments is pancreatic cancer.

In an embodiment, the invention provides a method of treating a hematological malignancy or a solid tumor cancer in a human comprising the step of administering to said human a BTK inhibitor, a PI3K inhibitor, and/or a JAK-2 inhibitor, and further comprising the step of administering a therapeutically-effective amount of albumin-bound paclitaxel. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering a therapeutically-effective amount of albumin-boundpaclitaxel. In an embodiment, the solid tumor cancer in any of the foregoing embodiments is pancreatic cancer.

In an embodiment, the invention provides a method of treating a hematological malignancy or a solid tumor cancer in a human comprising the step of administering to said human a BTK inhibitor, a PI3K inhibitor, and/or a JAK-2 inhibitor, and further comprising the step of administering a therapeutically-effective amount of bendamustine hydrochloride. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering a therapeutically-effective amount of bendamustine hydrochloride. In an embodiment, the hematological malignancy in any of the foregoing embodiments is CLL or SLL. In an embodiment, the invention provides the treatment of a hematological malignancy, including CLL or SLL, comprising the step of administering to said human a BTK inhibitor and/or a JAK-2 inhibitor, an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof, and further comprising the step of administering a therapeutically-effective amount of bendamustine or bendamustine hydrochloride.

The anti-CD20 antibody sequences referenced in the foregoing are summarized in Table 1.

TABLE 1

Anti-CD20 antibody sequences.

| Identifier | Sequence (One-Letter Amino Acid Symbols) | | | | | |
|---|---|---|---|---|---|---|
| SEQ ID NO: 1 | QVQLQQPGAE | LVKPGASVKM | SCKASGYTFT | SYNMHWVKQT | PGRGLEWIGA | IYPGNGDTSY | 60 |
| | NQKFKGKATL | TADKSSSTAY | MQLSSLTSED | SAVYYCARST | YYGGDWYFNV | WGAGTTVTVS | 120 |
| | AASTKGPSVF | PLAPSSKSTS | GGTAALGCLV | KDYFPEPVTV | SWNSGALTSG | VHTFPAVLQS | 180 |
| | SGLYSLSSVV | TVPSSSLGTQ | TYICNVNHKP | SNTKVDKKVE | PKSCDKTHTC | PPCPAPELLG | 240 |
| | GPSVFLFPPK | PKDTLMISRT | PEVTCVVVDV | SHEDPEVKFN | WYVDGVEVHN | AKTKPREEQY | 300 |
| | NSTYRVVSVL | TVLHQDWLNG | KEYKCKVSNK | ALPAPIEKTI | SKAKGQPREP | QVYTLPPSRD | 360 |
| | ELTKNQVSLT | CLVKGFYPSD | IAVEWESNGQ | PENNYKTTPP | VLDSDGSFFL | YSKLTVDKSR | 420 |
| | WQQGNVFSCS | VMHEALHNHY | TQKSLSLSPG | K | | | 451 |
| SEQ ID NO: 2 | QIVLSQSPAI | LSASPGEKVT | MTCRASSSVS | YIHWFQQKPG | SSPKPWIYAT | SNLASGVPVR | 60 |
| | FSGSGSGTSY | SLTISRVEAE | DAATYYCQQW | TSNPPTFGGG | TKLEIKRTVA | APSVFIFPPS | 120 |
| | DEQLKSGTAS | VVCLLNNFYP | REAKVQWKVD | NALQSGNSQE | SVTEQDSKDS | TYSLSSTLTL | 180 |
| | SKADYEKHKV | YACEVTHQGL | SSPVTKSFNR | GEC | | | 213 |

TABLE 1-continued

Anti-CD20 antibody sequences.

| Identifier | Sequence (One-Letter Amino Acid Symbols) | |
|---|---|---|
| SEQ ID NO: 3 | QVQLVQSGAE VKKPGSSVKV SCKASGYAFS YSWINWVRQA PGQGLEWMGR IPPGDGDTDY | 60 |
| | NGKFKGRVTI TADKSTSTAY MELSSLRSED TAVYYCARNV FDGYWLVYWG QGTLVTVSSA | 120 |
| | STKGPSVFPL APSSKSTSGG TAALGCLVKD YFPEPVTVSW NSGALTSGVH TFPAVLQSSG | 180 |
| | LYSLSSVVTV PSSSLGTQTY ICNVNHKPSN TKVDKKVEPK SCDKTHTCPP CPAPELLGGP | 240 |
| | SVFLFPPKPK DTLMISRTPE VTCVVVDVSH EDPEVKFNWY VDGVEVHNAK TKPREEQYNS | 300 |
| | TYRVVSVLTV LHQDWLNGKE YKCKVSNKAL PAPIEKTISK AKGQPREPQV YTLPPSRDEL | 360 |
| | TKNQVSLTCL VKGFYPSDIA VEWESNGQPE NNYKTTPPVL DSDGSFFLYS KLTVDKSRWQ | 420 |
| | QGNVFSCSVM HEALHNHYTQ KSLSLSPGK | 449 |
| SEQ ID NO: 4 | DIVMTQTPLS LPVTPGEPAS ISCRSSKSLL HSNGITYLYW YLQKPGQSPQ LLIYQMSNLV | 60 |
| | SGVPDRFSGS GSGTDFTLKI SRVEAEDVGV YYCAQNLELP YTFGGGTKVE IKRTVAAPSV | 120 |
| | FIFPPSDEQL KSGTASVVCL LNNFYPREAK VQWKVDNALQ SGNSQESVTE QDSKDSTYSL | 180 |
| | SSTLTLSKAD YEKHKVYACE VTHQGLSSPV TKSFNRGEC | 219 |
| SEQ ID NO: 5 | EVQLVESGGG LVQPGRSLRL SCAASGFTFN DYAMHWVRQA PGKGLEWVST ISWNSGSIGY | 60 |
| | ADSVKGRFTI SRDNAKKSLY LQMNSLRAED TALYYCAKDI QYGNYYYGMD VWGQGTTVTV | 120 |
| | SS | 122 |
| SEQ ID NO: 6 | EIVLTQSPAT LSTSPGERAT LSCRASQSVS SYLAWYQQKP GQAPRLLIYD ASNRATGIPA | 60 |
| | RFSGSGSGTD FTLTISSLEP EDFAVYYCQQ RSNWPITFGQ GTRLEIK | 107 |
| SEQ ID NO: 7 | EVQLVESGGG LVQPGRSLRL SCAASGFTFN DYAMHWVRQA PGKGLEWVST ISWNSGSIGY | 60 |
| | ADSVKGRFTI SRDNAKKSLY LQMNSLRAED TALYYCAKDI QYGNYYYGMD VWGQGTTVTV | 120 |
| | SSASTKGPSV FPLAPGSSKS TSGTAALGCL VKDYFPEPVT VSWNSGALTS GVHTFPAVLQ | 180 |
| | SSGLYSLSSV VTVPSSSLGT QTYICNVNHK PSNTKVDKKV EP | 222 |
| SEQ ID NO: 8 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPITFGQ GTRLEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN R | 211 |
| SEQ ID NO: 9 | QVQLQQSGAE VKKPGSSVKV SCKASGYTFT SYNMHWVKQA PGQGLEWIGA IYPGMGDTSY | 60 |
| | NQKFKGKATL TADESTNTAY MELSSLRSED TAFYYCARST YYGGDWYFDV WGQGTTVTVS | 120 |
| | SASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKRVE PKSCDKTHTC PPCPAPELLG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPAPIEKTI SKAKGQPREP QVYTLPPSRE | 360 |
| | EMTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 10 | DIQLTQSPSS LSASVGDRVT MTCRASSSVS YIHWFQQKPG KAPKPWIYAT SNLASGVPVR | 60 |
| | FSGSGSGTDY TFTISSLQPE DIATYYCQQW TSNPPTFGGG TKLEIKRTVA APSVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFNR GEC | 213 |
| SEQ ID NO: 11 | QAYLQQSGAE LVRPGASVKM SCKASGYTFT SYNMHWVKQT PRQGLEWIGA IYPGNGDTSY | 60 |
| | NQKFKGKATL TVDKSSSTAY MQLSSLTSED SAVYFCARVV YYSNSYWYFD VWGTGTTVTV | 120 |
| | SGPSVFPLAP SSKSTGGTA ALGCLVKDYF PEPVTVSWNS GALTSGVHTF PAVLQSSGLY | 180 |
| | SLSSVVTVPS SSLGTQTYIC NVNHKPSNTK VDKKAEPKSC DKTHTCPPCP APELLGGPSV | 240 |
| | FLFPPKPKDT LMISRTPEVT CVVVDVSHED PEVKFNWYVD GVEVHNAKTK PREEQYNSTY | 300 |
| | RVVSVLTVLH QDWLNGKEYK CKVSNKALPA PIEKTISKAK GQPREPQVYT LPPSRDELTK | 360 |
| | NQVSLTCLVK GFYPSDIAVE WESNGQPENN YKTTPPVLDS DGSFFLYSKL TVDKSRWQQG | 420 |
| | NVFSCSVMHE ALHNHYTQKS LSLSPGK | 447 |
| SEQ ID NO: 12 | QIVLSQSPAI LSASPGEKVT MTCRASSSVS YMHWYQQKPG SSPKPWIYAP SNLASGVPAR | 60 |
| | FSGSGSGTSY SLTISRVEAE DAATYYCQQW SFNPPTFGAG TKLELKRTVA APSVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFNR | 210 |
| SEQ ID NO: 13 | QAYLQQSGAE LVRPGASVKM SCKASGYTFT SYNMHWVKQT PRQGLEWIGA IYPGNGDTSY | 60 |
| | NQKFKGKATL TVDKSSSTAY MQLSSLTSED SAVYFCARVV YYSNSYWYFD VWGTGTTVTV | 120 |
| | SAPSVYPLAP VCGDTTGSSV TLGCLVKGYF PEPVTLTWNS GSLSSGVHTF PAVLQSDLYT | 180 |
| | LSSSVTVTSS TWPSQSITCN VAHPASSTKV DKKIEPRGPT IKPCPPCKCP APNLLGGPSV | 240 |
| | FIFPPKIKDV LMISLSPIVT CVVVDVSEDD PDVQISWFVN NVEVHTAQTQ THREDYNSTL | 300 |
| | RVVSALPIQH QDWMSGKEFK CKVNNKDLPA PIERTISKPK GSVRAPQVYV LPPPEEEMTK | 360 |
| | KQVILICMVT DFMPEDIYVE WTNNGKTELN YKNTEPVLDS DGSYFMYSKL RVEKKNWVER | 420 |
| | NSYSCSVVHE GLHNHHTTKS FSR | 443 |

TABLE 1-continued

Anti-CD20 antibody sequences.

| Identifier | Sequence (One-Letter Amino Acid Symbols) | |
|---|---|---|
| SEQ ID NO: 14 | QIVLSQSPAI LSASPGEKVT MTCRASSSVS YMHWYQQKPG SSPKPWIYAP SNLASGVPAR | 60 |
| | FSGSGSGTSY SLTISRVEAE DAATYYCQQW SFNPPTFGAG TKLELKRADA APTVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFN | 209 |

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Synergistic Combination of a BTK Inhibitor and a PI3K-δ Inhibitor

Ficoll purified mantle cell lymphoma (MCL) cells ($2 \times 10^5$) isolated from bone marrow or peripheral blood were treated with each drug alone and with six equimolar concentrations of a BTK inhibitor (Formula (XVIII)) and a PI3K-δ inhibitor (Formula (IX)) ranging from 0.01 nM to 10 μM on 96-well plates in triplicate. Plated cells were then cultured in HS-5 conditioned media at 37° C. with 5% $CO_2$. After 72 hours of culture, cell viability was determined using an (3-(4,5-dimethylthiazol-2-yl)-5-(3-carboxymethoxyphenyl)-2-(4-sulfophenyl)-2H-tetrazolium) (MTS) assay (Cell Titer 96, Promega). Viability data were used to generate cell viability curves for each drug alone and in combination for each sample. The potential synergy of the combination of the BTK inhibitor of Formula (XVIII) and the PI3K-δ inhibitor of Formula (IX) at a given equimolar concentration was determined using the median effect model as described in Chou and Talalay, Adv Enzyme Regul. 1984, 22, 27-55. The statistical modeling was run in R using a script that utilizes the median effect model as described in Lee et al., J. Biopharm. Slat. 2007, 17, 461-80. A value of 1, less than 1, and greater than 1 using R defines an additive interaction, a synergistic interaction, and an antagonistic interaction, respectively. The Lee et al. method calculates a 95% confidence interval for each data point. For each viability curve, to be considered synergistic, a data point must have an interaction index below 1 and the upper confidence interval must also be below 1. In order to summarize and demonstrate collective synergy results, an interaction dot blot was generated for the primary patient samples.

A similar approach was utilized to study diffuse large B cell lymphoma (DLBCL) (TMD8) and MCL (MINO) cell lines. Cells were treated with each drug alone and with six equimolar concentrations of the BTK inhibitor of Formula (XVIII) and the PI3K-δ inhibitor of Formula (IX) ranging from 0.003 nM to 1.0 μM (for TMD8) or 0.03 nM to 10 μM (for MINO) on 96-well plates in triplicate. Plated cells were then cultured in standard conditioned media plus FBS at 37° C. with 5% $CO_2$. After 72 hours of culture, viability was determined using an MTS assay (Cell Titer 96, Promega). Viability data were used to generate cell viability curves for each drug alone and in combination for each sample. The results of the experiments described in this example are shown in FIG. 1, FIG. 2, FIG. 3, and FIG. 4.

Example 2—Synergistic Combination of a BTK Inhibitor and a PI3K-δ Inhibitor

Combination experiments were performed to determine the synergistic, additive, or antagonistic behavior of drug combinations using the Chou/Talalay method/algorithm by defining combination indexes for drug combinations. Information about experimental design for evaluation of synergy is described in e.g. Chou and Talalay, Adv. Enzyme Regul. 1984, 22, 27-55 and more generally in e.g. Greco et al., Pharmacol. Rev. 1995, 47, 331-385. The study was performed using the BTK inhibitor of Formula (XVIII) and the PI3K-δ inhibitor of Formula (IX). Single drug activities were first determined in the various cell lines and subsequently, the combination indexes were established using equimolar ratios taking the single agent drug EC50s into consideration. For individual drugs that displayed no single drug activity, equimolar ratios were used at fixed concentrations to establish combination indexes. The readout from 72 hour proliferation assays using Cell TiterGlo (ATP content of remaining cells) determined the fraction of cells that were effected as compared to untreated cells (Fa=fraction affected=(1-((cells+inhibitor)-background signal)/((cells+DMSO)-background signal))).

The combination index obtained was ranked according to Table 2.

TABLE 2

Combination Index (CI) Ranking Scheme

| Range of CI | Description |
|---|---|
| <0.1 | Very strong synergism |
| 0.1-0.3 | Strong synergism |
| 0.3-0.7 | Synergism |
| 0.7-0.85 | Moderate synergism |
| 0.85-0.9 | Slight synergism |
| 0.9-1.1 | Nearly additive |
| 1.1-1.2 | Slight antagonism |
| 1.2-1.45 | Moderate antagonism |
| 1.45-3.3 | Antagonism |
| 3.3-10 | Strong antagonism |
| >10 | Very strong antagonism |

The detailed results of the cell line studies for the BTK inhibitor of Formula (XVIII) and the PI3K-δ inhibitor of Formula (IX) are given in FIG. 5 to FIG. 37. The results of the cell line studies are summarized in Table 3.

TABLE 3

Summary of results of the combination of a BTK inhibitor with a PI3K-δ inhibitor (S = synergistic, A = additive, X = no effect).

| Cell Line | Indication | ED25 | ED50 | ED75 | ED90 |
|---|---|---|---|---|---|
| Raji | Burkitt's | S | S | S | S |
| Ramos | Burkitt's | X | X | X | X |
| Daudi | Burkitt's | S | S | S | S |
| Mino | MCL | S | S | S | S |
| Pfeiffer | iNHL | S | S | S | S |
| DOHH | iNHL | S | S | S | S |
| REC-1 | iNHL | S | S | A | A |
| U937 | Myeloid | S | S | S | S |
| K562 | CML | X | X | X | X |
| SU-DHL-1 | ABC | S | A | X | X |
| SU-DHL-2 | ABC | S | S | S | S |
| HBL-1 | ABC | S | S | S | S |
| TMD8 | ABC | S | S | S | S |
| LY19 | GCB | X | X | X | X |
| LY7 | GCB | S | S | S | S |
| LY1 | GCB | X | X | X | X |
| SU-DHL-6 | GCB | S | S | S | S |
| SupB15 | B-ALL | S | S | S | S |
| CCRF | B-ALL | S | A/S | X | X |

Example 3—Synergistic Combination of a BTK Inhibitor and the JAK-2 Inhibitor Ruxolitinib Combination experiments were performed to determine the synergistic, additive, or antagonistic behavior of drug combinations using the methods described above in Example 2. The study was performed using the BTK inhibitor of Formula (XVIII) and the JAK-2 inhibitor of Formula XXX (ruxolitinib).

The detailed results of the cell line studies for the BTK inhibitor of Formula (XVIII) and the JAK-2 inhibitor of Formula XXX (ruxolitinib) are given in FIG. 38 to FIG. 65. The results of the cell line studies are summarized in Table 4.

TABLE 4

Summary of results of the combination of a BTK inhibitor with the JAK-2 inhibitor of Formula XXX (ruxolitinib) (S = synergistic, A = additive, X = no effect).

| Cell Line | Indication | ED25 | ED50 | ED75 | ED90 |
|---|---|---|---|---|---|
| Raji | Burkitt's | S | S | S | S |
| Ramos | Burkitt's | S | S | S | S |
| Daudi | Burkitt's | S | S | S | S |
| Mino | MCL | S | S | S | S |
| Pfeiffer | iNHL | S | S | S | S |
| DOHH | iNHL | S | S | S | S |
| REC-1 | iNHL | S | S | S | S |
| JVM-2 | CLL like | S | S | S | X |
| U937 | Myeloid | X | X | X | X |
| K562 | CML | X | X | X | X |
| SU-DHL-1 | ABC | S | S | S | S |
| SU-DHL-2 | ABC | S | S | S | X |
| HBL-1 | ABC | S | S | S | S |
| TMD8 | ABC | S | S | S | S |
| LY19 | GCB | X | X | X | X |
| LY7 | GCB | X | X | X | X |
| LY1 | GCB | X | X | X | X |
| SU-DHL-6 | GCB | S | S | X | X |
| SupB15 | B-ALL | X | X | X | X |
| CCRF | B-ALL | X | X | A | A |

Example 4—Synergistic Combination of a BTK Inhibitor and the JAK-2 Inhibitor Pacritinib Combination experiments were performed to determine the synergistic, additive, or antagonistic behavior of drug combinations using the methods described above in Example 2. The study was performed using the BTK inhibitor of Formula (XVIII) and the JAK-2 inhibitor of Formula LIV (pacritinib).

The detailed results of the cell line studies for the BTK inhibitor of Formula (XVIII) and the JAK-2 inhibitor of Formula LIV (pacritinib) are given in FIG. 66 to FIG. 94. The results of the cell line studies are summarized in Table 5.

TABLE 5

Summary of results of the combination of a BTK inhibitor with the JAK-2 inhibitor of Formula LIV (pacritinib) (S = synergistic, A = additive, X = no effect).

| Cell Line | Indication | ED25 | ED50 | ED75 | ED90 |
|---|---|---|---|---|---|
| Mino | MCL | S | S | S | S |
| JVM-2 | prolymphocytic leukemia | S | S | S | S |
| Maver-1 | B-ALL, MCL | S | S | S | S |
| Raji | B-ALL, Burkitt's | S | S | S | S |
| Daudi | Burkitt's | S | S | S | S |
| Rec-1 | FL | X | S | S | S |
| CCRF | B-ALL | S | S | S | S |
| Sup-B15 | B-ALL | S | S | A | A |
| SU-DHL-4 | DLBCL-ABC | S | S | S | S |
| EB3 | B-ALL, Burkitt's | S | S | S | S |
| CA46 | B-ALL, Burkitt's | S | S | S | S |
| Pfeiffer | FL | S | S | S | S |
| DB | B-ALL, MCL | S | S | S | S |
| DOHH2 | FL | S | S | S | S |
| Namalwa | B-ALL, Burkitt's | S | S | S | S |
| JVM-13 | B-ALL, MCL | S | S | S | S |
| SU-DHL-1 | DLBCL-ABC | S | S | S | S |
| SU-DHL-2 | DLBCL-ABC | S | S | S | X |
| Ramos | Burkitt's | S | S | S | S |
| SU-DHL-6 | DLBCL-GCB | S | S | S | A |
| TMD-8 | DLBCL-ABC | X | X | S | S |
| SU-DHL-10 | DLBCL-GCB | S | S | S | S |
| HBL-1 | DLBCL-ABC | S | S | S | X |
| OCI-Ly3 | DLBCL-ABC | S | S | S | S |
| OCI-Ly7 | DLBCL-ABC | S | S | S | S |
| Jeko | B-ALL, MCL | S | S | S | S |

Example 5—Effects of BTK Inhibitors on Thrombosis

Clinical studies have shown that targeting the BCR signaling pathway by inhibiting BTK produces significant clinical benefit (Byrd, et al., N. Engl. J. Med. 2013, 369(1), 32-42, Wang, et al., N. Engl. J. Med. 2013, 369(6), 507-16). However, in these studies, bleeding has been reported in up to 50% of ibrutinib-treated patients. Most bleeding events were of grade 1-2 (spontaneous bruising or petechiae) but, in 5% of patients, they were of grade 3 or higher after trauma. These results are reflected in the prescribing information for ibrutinib, where bleeding events of any grade, including bruising and petechiae, were reported in about half of patients treated with ibrutinib (IMBRUVICA package insert and prescribing information, revised July 2014, U.S. Food and Drug Administration).

Constitutive or aberrant activation of the BCR signaling cascade has been implicated in the propagation and maintenance of a variety of B cell malignancies. Small molecule inhibitors of BTK, a protein early in this cascade and specifically expressed in B cells, have emerged as a new class of targeted agents. There are several BTK inhibitors, including Formula XXVII (CC-292), and Formula XX-A (PCI-32765, ibrutinib), in clinical development. Importantly, early stage clinical trials have found ibrutinib to be particularly active in chronic lymphocytic leukemia (CLL)

and mantle cell lymphoma (MCL), suggesting that this class of inhibitors may play a significant role in various types of cancers (Aalipour and Advani, *Br. J. Haematol.* 2013, 163, 436-43). However, their effects are not limited to leukemia or lymphomas as platelets also rely on the Tec kinases family members BTK and Tec for signal transduction in response to various thrombogenic stimuli (Oda, et al., *Blood* 2000, 95(5), 1663-70; Atkinson, et al., *Blood* 2003, 102(10), 3592-99). In fact, both Tec and BTK play an important role in the regulation of phospholipase Cγ2 (PLCγ2) downstream of the collagen receptor glycoprotein VI (GPVI) in human platelets. In addition, BTK is activated and undergoes tyrosine phosphorylation upon challenge of the platelet thrombin receptor, which requires the engagement of αIIbβ3 integrin and PI3K activity (Laffargue, et al., *FEBS Lett.* 1999, 443(1), 66-70). It has also been implicated in GPIbα-dependent thrombus stability at sites of vascular injury (Liu, et al., *Blood* 2006, 108(8), 2596-603). Thus, BTK and Tec are involved in several processes important in supporting the formation of a stable hemostatic plug, which is critical for preventing significant blood loss in response to vascular injury. Hence, the effects of the BTK inhibitor of Formula (XVIII) and ibrutinib were evaluated on human platelet-mediated thrombosis by utilizing the in vivo human thrombus formation in the VWF HA1 mice model described in Chen, et al., *Nat. Biotechnol.* 2008, 26(1), 114-19.

Administration of anesthesia, insertion of venous and arterial catheters, fluorescent labeling and administration of human platelets ($5 \times 10^8$/ml), and surgical preparation of the cremaster muscle in mice have been previously described (Chen et al., *Nat Biotechnol.* 2008, 26(1), 114-19). Injury to the vessel wall of arterioles (~40-65 mm diameter) was performed using a pulsed nitrogen dye laser (440 nm, Photonic Instruments) applied through a 20× water-immersion Olympus objective (LUMPlanFI, 0.5 numerical aperature (NA)) of a Zeiss Axiotech vario microscope. Human platelet and wall interactions were visualized by fluorescence microscopy using a system equipped with a Yokogawa CSU-22 spinning disk confocal scanner, iXON EM camera, and 488 nm and 561 nm laser lines to detect BCECF-labeled and rhodamine-labeled platelets, respectively (Revolution XD, Andor Technology). The extent of thrombus formation was assessed for 2 minutes after injury and the area ($\mu m^2$) of coverage determined (Image IQ, Andor Technology). For the Formula (XVIII), Formula (XXVII) (CC-292), and Formula (XX-A) (ibrutinib) inhibition studies, the BTK inhibitors were added to purified human platelets for 30 minutes before administration.

The in vivo throbus effects of the BTK inhibitors, Formula (XVIII), Formula (XXVII) (CC-292), and Formula (XX-A) (ibrutinib), were evaluated on human platelet-mediated thrombosis by utilizing the in vivo human thrombus formation in the VWF HA1 mice model, which has been previously described (Chen, et al., *Nat Biotechnol.* 2008, 26(1), 114-19). Purified human platelets were preincubated with various concentrations of the BTK inhibitors (0.1 µM, 0.5 µM, or 1 µM) or DMSO and then administered to VWF HA1 mice, followed by laser-induced thrombus formation. The BTK inhibitor-treated human platelets were fluorescently labeled and infused continuously through a catheter inserted into the femoral artery. Their behavior in response to laser-induced vascular injury was monitored in real time using two-channel confocal intravital microscopy (Furie and Furie, *J. Clin. Invest.* 2005, 115(12), 2255-62). Upon induction of arteriole injury untreated platelets rapidly formed thrombi with an average thrombus size of 6,450±292 mm² (mean±s.e.m.), as shown in FIG. 95.

The objective of this study was to evaluate in vivo thrombus formation in the presence of BTK inhibitors. In vivo testing of novel antiplatelet agents requires informative biomarkers. By utilizing a genetic modified mouse von Willebrand factor (VWFR1326H) model that supports human but not mouse platelet-mediated thrombosis, we evaluated the effects of Formula (XVIII), Formula XXVII (CC-292), and Formula XX-A (ibrutinib) on thrombus formation. These results show that Formula (XVIII) had no significant effect on human platelet-mediated thrombus formation while Formula XX-A (ibrutinib) was able to limit this process, resulting in a reduction in maximal thrombus size by 61% compared with control. Formula XXVII (CC-292) showed an effect similar to Formula XX-A (ibrutinib). These results, which show reduced thrombus formation for ibrutinib at physiologically relevant concentrations, may provide some mechanistic background for the Grade ≥3 bleeding events (eg, subdural hematoma, gastrointestinal bleeding, hematuria and postprocedural hemorrhage) that have been reported in ≤6% of patients treated with Formula XX-A (ibrutinib).

GPVI platelet aggregation was measured for Formula (XVIII) and Formula XX-A (ibrutinib). Blood was obtained from untreated humans, and platelets were purified from plasma-rich protein by centrifugation. Cells were resuspended to a final concentration of 350,000/µL in buffer containing 145 mmol/L NaCl, 10 mmol/L HEPES, 0.5 mmol/L $Na_2HPO_4$, 5 mmol/L KCl, 2 mmol/L $MgCl_2$, 1 mmol/L $CaCl_2$, and 0.1% glucose, at pH 7.4. Stock solutions of Convulxin (CVX) GPVI were prepared on the day of experimentation and added to platelet suspensions 5 minutes (37° C., 1200 rpm) before the induction of aggregation. Aggregation was assessed with a Chronolog Lumi-Aggregometer (model 540 VS; Chronolog, Havertown, Pa.) and permitted to proceed for 6 minutes after the addition of agonist. The results are reported as maximum percent change in light transmittance from baseline with platelet buffer used as a reference. The results are shown in FIG. 96.

In FIG. 97, the results of CVX-induced (250 ng/mL) human platelet aggregation results before and 15 minutes after administration of the BTK inhibitors to 6 healthy individuals are shown.

The results depicted in FIG. 96 and FIG. 97 indicate that the BTK inhibitor of Formula XX-A (ibrutinib) significantly inhibits GPVI platelet aggregation, while the BTK inhibitor of Formula (XVIII) does not, further illustrating the surprising benefits of the latter compound. Furthermore, the combination of the BTK inhibitor of Formula (XVIII) with a JAK-2 inhibitor, including the JAK-2 inhibitors ruxolitinib and pacritinib, is suprisingly favorable because of the tendency of these JAK-2 inhibitors to cause thrombocytopenia and other disordered associated with increased bleeding.

Example 6—Study of a BTK Inhibitor and a Combination of a BTK Inhibitor and a PI3K Inhibitor in Canine Lymphoma Canine B cell lymphoma exists as a pathological entity that is characterized by large anaplastic, centroblastic or immunoblastic lymphocytes with high proliferative grade, significant peripheral lymphadenopathy and an aggressive clinical course. While some dogs respond initially to prednisone, most canine lymphomas progress quickly and must be treated with combination therapies, including cyclophosphamide, vincristine, doxorubicin, and prednisone (CHOP), or other cytotoxic agents. In their histopathologic features, clinical course, and high relapse rate after initial treatment, canine B cell lymphomas resemble diffuse large B cell lymphoma (DLBCL) in humans. Thus, responses of canine B cell lymphomas to experimental treatments are considered to provide proof of concept for therapeutic candidates in DLBCL.

In this example, companion dogs with newly diagnosed or relapsed/refractory B cell lymphoma were enrolled on a veterinary clinical trial of the BTK inhibitor of Formula (XVIII) ("Arm 1") or the BTK inhibitor of Formula (XVIII) and the PI3K-δ inhibitor of Formula (IX) ("Arm 2"). Enrollment has completed for both arms. The results show that combined treatment with the BTK inhibitor of Formula (XVIII) and the PI3K-δ inhibitor of Formula (IX) may have greater efficacy than treatment with the BTK inhibitor of Formula (XVIII) alone in aggressive lymphomas.

Twenty-one dogs were treated in Arm 1 with the BTK inhibitor of Formula (XVIII) at dosages of 2.5 mg/kg once daily to 20 mg/kg twice daily. Intra-subject dose escalation was allowed. Six of the 11 dogs that initiated at 2.5 or 5 mg/kg once daily were escalated and completed the study with dosages of 10 mg/kg twice daily. Among all the dose cohorts, 8 dogs had shrinkage of target lesions >20%; the best tumor responses were between 45-49% reduction in the sum of target lesions in two dogs. Complete responses ("CR", disappearance of all evidence of disease per evaluator judgment; and absence of new lesions) were not observed in Arm 1. CR were defined as disappearance of all evidence of disease per evaluator judgment, and absence of new lesions. Vali, et al., *Vet. Comp. Oncol.* 2010, 8, 28-37.

In the combination phase of the study (Arm 2), 10 dogs were treated with 10 mg/kg the BTK inhibitor of Formula (XVIII) and the PI3K-δ inhibitor of Formula (IX) at 2.5 or 3.5 mg/kg, on a twice daily schedule. Of these, 7 dogs had shrinkage of target lesions >20%, providing evidence of biological activity for the combination; four of these dogs achieved a PR. The best tumor responses were between 58-65% reduction in the sum of target lesions, with one sustained CR observed among the 10 dogs treated. The initial reductions in the sum of target lesions continued to deepen during the course of therapy in 7 of the 10 dogs. A summary of the results is presented in Table 6.

TABLE 6

Summary of the results of the canine lymphoma study.

| Response Metric | Formula (XVIII) and Formula (IX) | Formula (XVIII) monotherapy |
| --- | --- | --- |
| Sum LD$^a$ decreased by ≥20% | 7/10 (70%) | 8/21 (38%) |
| Sum LD$^a$ decreased by ≥30% (PR) | 4/10 (40%) | 6/21 (28.6%) |
| CR by investigator evaluation | 1/10 (10%) | 0/21 (0%) |
| Median time on study | 23 days | 24 days |
| Median time to best response | 18 days | 7 days |

$^a$LD, longest diameter, sum of up to 5 target lesions.

These data suggest that in companion dogs with naturally occurring B cell lymphomas, treatment with the combination of the BTK inhibitor of Formula (XVIII) and the PI3K-δ inhibitor of Formula (IX) may provide increased biological activity (tumor shrinkage and stable disease) and may possibly lead to deeper responses than treatment with the BTK inhibitor of Formula (XVIII) alone. The higher rate of biological responses and extended response duration (median time to best response), along with the observation of a CR in this aggressive disease setting, provide evidence of synergy between Formula (XVIII) and Formula (IX).

Example 7—Study of a Combination of a BTK Inhibitor and a PI3K Inhibitor in DLBCL Cell Lines To explore the role of PI3K signaling in diffuse large B-cell lymphoma ("DLBCL"), several DLBCL cell lines of varying molecular profiles may be utilized. In an exemplary embodiment, a cellular growth inhibition assay used five cell lines, including four GCB (SU-DHL-4, SU-DHL-6, OCI-LY-8 and WSU-DLCL-2) and one ABC (Ri-1) subtype. In an exemplary embodiment, a cellular growth inhibition assay used five cell lines that were OCI-LY-3, OCI-LY-7, Pfeiffer, Toledo and U2932. In an exemplary embodiment, evidence of PI3K pathway inhibition is measured by reduction in phospho (p)-AKT. In an exemplary embodiment, the kinetics of pathway modulation was characterized by examination of phosphorylation of AKT, PRAS40 and S6 following a time-course of treatment by a PI3K-inhibitor in selected cell lines. In one embodiment, upon B-cell receptor stimulation via antibody-induced crosslinking, some cell lines exhibited enhanced AKT phosphorylation.

In an exemplary embodiment, the combination effect of a PI3K inhibitor with a BTK inhibitor was observed in a cellular growth inhibition assay in the SU-DHL-4 cell line and in the OCI-LY-8 cell line with BCR crosslinking.

Example 8—Effects of BTK Inhibition on Antibody-Dependent NK Cell Mediated Cytotoxicity Using Obinutuzumab It has been shown above that ibrutinib undesirably antagonizes rituximab ADCC effects mediated by NK cells, and that Formula (XVIII) does not antagonize rituximab ADCC effects and instead allows for a synergistic combination. As noted previously, this may be due to ibrutinib's secondary irreversible binding to ITK, which is required for FcR-stimulated NK cell function including calcium mobilization, granule release, and overall ADCC. H. E. Kohrt, et al., *Blood* 2014, 123, 1957-60. The potential for ibrutinib antagonization of obinutuzumab (GA-101) ADCC as mediated by NK cells was also explored and compared to the effects of Formula (XVIII).

The NK cell degranulation/ADCC assay was performed using a whole blood assay with CLL targets added to normal donor whole blood, in the presence or absence of different doses of Formula (XVIII) and ibrutinib, followed by opsonization with the anti-CD20 antibody obinutuzumab. Ibrutinib was used as a control, and two blinded samples of BTK inhibitors, Formula (XVIII) and a second sample of ibrutinib, were provided to the investigators. Degranulation in whole blood was performed as follows. CLL targets (MEC-1 cells) were expanded in RPMI 1640 medium (Life Technologies, Inc.) with 10% fetal bovine serum (FBS). Exponentially growing cells were used. On the day of the experiment, 8 mL of blood was drawn from a normal volunteer into a test tube containing desirudin to obtain a final concentration of 50 µg/mL. A white blood cell (WBC) count of whole blood was performed. MEC-1 cells were re-suspended at the concentration of WBC in whole blood (e.g., if 6×10$^6$ WBC/mL was measured, MEC-1 cells were re-suspended at 6×10$^6$ cells/mL, to allow for a final WBC: MEC-1 cell ratio of 1:1). The ibrutinib control and two blinded BTK inhibitors were diluted in X-VIVO 15 serum-free hematopoietic cell medium (Lonza Group, Ltd.) to concentrations of 200 µM, 20 µM and 2 µM. 170 µL aliquots of unmanipulated whole blood were incubated with 10 µL BTK inhibitors or X-VIVO 15 medium for one hour into a plate. Cetuximab and obinutuzumab (GA-101) were diluted in X-VIVO 15 medium to a concentration of 20 µg/mL. Equal volumes of MEC-1 cells and antibodies were incubated for 5 minutes. After incubation, 20 µL of MEC-1 cells and antibodies was added to whole blood and the BTK inhibitors/X-VIVO 15 medium (for a final volume of 200 µL). The samples were placed in a 5% $CO_2$ incubator for 4 hours at 37° C. The experimental conditions thus achieved a WBC:MEC-1 cell ratio of 1:1, with final concentrations of the BTK inhibitors in the assay of 10 µM, 1 µM and 0.1 µM and final concentrations of the antibodies of 1 µg/mL.

After 4 hours, the samples were mixed gently and 50 µL aliquots were removed from each well and placed in fluorescence-activated cell sorting (FACS) test tubes. A 20 µL aliquot of anti-CD56-APC antibody and anti-CD107a-PE antibody was added. The samples were incubated for 20 minutes at room temperature in the dark. An aliquot of 2 mL of FACS lysing solution (BD Biosceinces) was added. The samples were again incubated for 5 minutes, and then centrifuged at 2000 rpm for 5 minutes. Supernatant was discarded and the cell pellet was resuspended in 500 µL of PBS. The samples were analyzed on the flow cytometer for $CD107a^+$ NK cells ($CD56^+$).

The NK cell degranulation results are summarized in FIG. 98 for n=3 experiments, which shows the effects on whole blood after pretreatment for 1 hour with the BTK inhibitors at the concentrations shown and subsequent stimulation with MEC-1 opsonised with obinutuzumab or cetuximab at 1 µg/mL for 4 hours. A strong reduction in the percentage of $CD56^+/CD107a^+$ NK cells is observed using ibrutinib (both as a control and blinded BTK inhibitor), which indicates that ibrutinib undesirably antagonizes NK cells. In contrast, Formula (XVIII) shows little antagonism towards NK cells, and had a minimal effect on obinutuzumab-stimulated NK cell degranulation while ibrutinib reduced obinutuzumab-stimulated NK degranulation by greater than 40%. These results support the synergistic combination of obinutuzumab and Formula (XVIII) in treatment of human B cell malignancies.

Example 9—Preclinical Characteristics of BTK Inhibitors

The BTK inhibitor ibrutinib ((1-[(3R)-3-[4-amino-3-(4-phenoxyphenyl)-1H-pyrazolo[3,4-d]pyrimidin-1-yl]piperidin-1-yl]prop-2-en-1-one) is a first-generation BTK inhibitor. In clinical testing as a monotherapy in subjects with hematologic malignancies, ibrutinib was generally well tolerated at dose levels through 840 mg (the highest dose tested). Advani, et al., *J. Clin. Oncol.* 2013, 31, 88-94; Byrd, et al., *N. Engl. J. Med.* 2013, 369, 32-42; Wang, et al., *N. Engl. J. Med.* 2013, 369, 507-16. No maximum tolerated dose (MTD) was apparent within the tested dose range. Furthermore, subjects typically found the drug tolerable over periods extending to >2 years. No subject had tumor lysis syndrome. No overt pattern of myelosuppression was associated with ibrutinib treatment. No drug-related reductions in circulating $CD4^+$ T cells or serum immunoglobulins were noted. Adverse events with an apparent relationship to study drug included diarrhea and rash.

In subjects with heavily pretreated non-Hodgkin lymphoma (NHL), ibrutinib showed substantial antitumor activity, inducing durable regressions of lymphadenopathy and splenomegaly in most subjects. Improvements in disease-associated anemia and thrombocytopenia were observed. The pattern of changes in subjects with CLL was notable. Single-active pharmaceutical ingredient ibrutinib caused rapid and substantial reductions in lymph node size concomitant with a redistribution of malignant sites into the peripheral blood. An asymptomatic absolute lymphocyte count (ALC) increase was observed that was maximal during the first few months of treatment and generally decreased thereafter but could be persistent in some subjects or could be seen repeatedly in subjects who had interruption and resumption of drug therapy.

Collectively, these data with ibrutinib support the potential benefits of selective BTK inhibition in the treatment of subjects with relapsed lymphoid cancers. However, while highly potent in inhibiting BTK, ibrutinib has also shown in vitro activity against other kinases with a cysteine in the same position as Cys481 in BTK, to which the drug covalently binds. For example, ibrutinib inhibits epidermal growth factor receptor (EGFR), which may be the cause of ibrutinib-related diarrhea and rash. In addition, it is a substrate for both cytochrome P450 (CYP) enzymes 3A4/5 and 2D6, which increases the possibility of drug-drug interactions. These liabilities support the development of alternative BTK inhibitors for use in the therapy of lymphoid cancer.

The preclinical selectivity and potency characteristics of the second-generation BTK inhibitor of Formula (XVIII) were compared to the first-generation BTK inhibitor ibrutinib. In Table 7, a kinome screen (performed by Life Technologies or based on literature data) is shown that compares these compounds.

TABLE 7

Kinome Screen for BTK Inhibitors ($IC_{50}$, nM)

| 3F-Cys Kinase | Formula (XVIII) | Ibrutinib (Formula (XX-A)) |
|---|---|---|
| Btk | 3.1 | 0.5 |
| Tec | 29 | 78 |
| Bmx | 39 | 0.80 |
| Itk | >1000 | 10.7 |
| Txk | 291 | 2.0 |
| EGFR | >1000 | 5.6 |
| ErbB2 | 912 | 9.4 |
| ErbB4 | 13.2 | 2.7 |
| Blk | >1000 | 0.5 |
| JAK-3 | >1000 | 16.1 |

The results shown in Table 7 are obtained from a 10 point biochemical assay generated from 10 point concentration curves. The BTK inhibitor of Formula (XVIII) shows much greater selectivity for BTK compared to other kinases than ibrutinib.

A comparison of the in vivo potency results for the BTK inhibitors of Formula (XVIII) and ibrutinib is shown in FIG. 99. CD86 and CD69 are cell surface proteins that are BCR activation markers. To obtain the in vivo potency results, mice were gavaged at increasing drug concentration and sacrificed at one time point (3 hours post-dose). BCR was stimulated with IgM and the expression of activation marker CD69 and CD86 are monitored by flow cytometry and to determine $EC_{50}$ values.

In vitro and in vivo safety pharmacology studies with Formula (XVIII) have demonstrated a favorable nonclinical safety profile. When screened at 10 LM in binding assays evaluating interactions with 80 known pharmacologic targets such as G-protein-coupled receptors, nuclear receptors, proteases, and ion channels, Formula (XVIII) shows significant activity only against the A3 adenosine receptor; follow-up dose-response experiments indicated a $IC_{50}$ of 2.7 µM, suggesting a low clinical risk of off-target effects. Formula (XVIII) at 10 μM showed no inhibition of in vitro EGFR phosphorylation in an A431 human epidermoid cancer cell line whereas ibrutinib had an $IC_{50}$ of 66 nM. The in vitro effect of Formula (XVIII) on human ether-à-go-go-related gene (hERG) channel activity was investigated in vitro in human embryonic kidney cells stably transfected with hERG. Formula (XVIII) inhibited hERG channel activity by 25% at 10 μM, suggesting a low clinical risk that Formula (XVIII) would induce clinical QT prolongation as predicted by this assay. Formula (XVIII) was well tolerated in standard in vivo Good Laboratory Practices (GLP) studies of pharmacologic safety. A functional observation battery in rats at doses through 300 mg/kg (the highest dose level) revealed no adverse effects on neurobehavioral effects or body temperature at any dose level. A study of respiratory function in rats also indicated no treatment-related adverse effects at doses through 300 mg/kg (the highest dose level). In a cardiovascular function study in awake telemeterized male beagle dogs, single doses of Formula (XVIII) at dose levels through 30 mg/kg (the highest dose level) induced no meaningful changes in body temperature, cardiovascular, or electrocardiographic (ECG) (including QT interval) parameters. The results suggest that Formula (XVIII) is unlikely to cause serious off-target effects or adverse effects on critical organ systems.

The drug-drug interaction potential of Formula (XVIII) was also evaluated. In vitro experiments evaluating loss of parent drug as catalyzed by CYPs indicated that Formula (XVIII) is metabolized by CYP3A4. In vitro metabolism studies using mouse, rat, dog, rabbit, monkey, and human hepatocytes incubated with $^{14}C$-labeled Formula (XVIII) indicated two mono-oxidized metabolites and a glutathione conjugate. No unique human metabolite was identified. Preliminary evaluations of metabolism in the plasma, bile, and urine of rats, dogs, and monkeys indicated metabolic processes of oxidation, glutathione binding, and hydrolysis. It was shown that Formula (XVIII) binds to glutathione but does not deplete glutathione in vitro. Nonclinical CYP interaction studies data indicate that Formula (XVIII) is very unlikely to cause clinical drug-drug interactions through alteration of the metabolism of drugs that are substrates for CYP enzymes.

The in vitro potency in whole blood of Formula (XVIII), ibrutinib and CC-292 in inhibiting signals through the B cell receptor was also assessed. Blood from four healthy donors was incubated for 2 hours with the compounds shown over a concentration range, and then stimulated with anti-human IgD [10 μg/mL] for 18 hours. The mean fluorescent intensity (MFI) of CD69 (and CD86, data not shown) on gated CD19+ B cells was measured by flow cytometry. MFI values were normalized so that 100% represents CD69 level in stimulated cells without inhibitor, while 0% represents the unstimulated/no drug condition. The results are shown in FIG. 100. The $EC_{50}$ values obtained were 8.2 nM (95% confidence interval: 6.5-10.3), 6.1 nM (95% confidence interval: 5.2-7.2), and 121 nM (95% confidence interval: 94-155) for Formula (XVIII), ibrutinib, and CC-292, respectively.

The EGF receptor phosphorylation in vitro was also determined for Formula (XVIII) and ibrutinib. Epidermoid carcinoma A431 cells were incubated for 2 h with a dose titration of Formula (XVIII) or ibrutinib, before stimulation with EGF (100 ng/mL) for 5 min to induce EGFR phosphorylation (p-EGFR). Cells were fixed with 1.6% paraformaldehyde and permeabilized with 90% MeOH. Phosphoflow cytometry was performed with p-EGFR (Y1069). MFI values were normalized so that 100% represents the p-EGFR level in stimulated cells without inhibitor, while 0% represents the unstimulated/no drug condition. The results are shown in FIG. 101. EGF-induced p-EGFR inhibition was determined to be 7% at 10 μM for Formula (XVIII), while ibrutinib has an $EC_{50}$ of 66 nM. The much more potent inhibition of EGF-induced p-EGFR by ibrutinib may be associated with increased side effects including diarrhea and rash.

Example 10—Clinical Study of a BTK Inhibitor in Leukemia/Lymphoma and Effects on Bone Marrow and Lymphoid Microenvironments Clinical studies have shown that targeting the BCR signaling pathway by inhibiting BTK produces significant clinical benefit in patients with non-Hodgkin's lymphoma (NHL). The second generation BTK inhibitor, Formula (XVIII), achieves significant oral bioavailability and potency, and has favorable preclinical characteristics, as described above. The purpose of this study is to evaluate the safety and efficacy of the second generation BTK inhibitor of Formula (XVIII) in treating subjects with chronic lymphocytic leukemia (CLL) and small lymphocytic lymphoma (SLL).

The design and conduct of this study is supported by an understanding of the history and current therapies for subjects with lymphoid cancers; knowledge of the activity and safety of a first-generation BTK inhibitor, ibrutinib, in subjects with hematologic cancers; and the available nonclinical information regarding Formula (XVIII). The collective data support the following conclusions. BTK expression plays an important role in the biology of lymphoid neoplasms, which represent serious and life-threatening disorders with continuing unmet medical need. Clinical evaluation of Formula (XVIII) as a potential treatment for these disorders has sound scientific rationale based on observations that the compound selectively abrogates BTK activity and shows activity in nonclinical models of lymphoid cancers. These data are supported by clinical documentation that ibrutinib, a first-generation BTK inhibitor, is clinically active in these diseases. Ibrutinib clinical data and Formula (XVIII) nonclinical safety pharmacology and toxicology studies support the safety of testing Formula (XVIII) in subjects with B cell malignancies.

The primary objectives of the clinical study are as follows: (1) establish the safety and the MTD of orally administered Formula (XVIII) in subjects with CLL/SLL; (2) determine pharmacokinetics (PK) of orally administered Formula (XVIII) and identification of its major metabolite(s); and (3) measure pharmacodynamic (PD) parameters including drug occupancy of BTK, the target enzyme, and effect on biologic markers of B cell function.

The secondary objective of the clinical study is to evaluate tumor responses in patients treated with Formula (XVIII).

This study is a multicenter, open-label, nonrandomized, sequential group, dose escalation study. The following dose cohorts will be evaluated:
Cohort 1: 100 mg/day for 28 days (=1 cycle)
Cohort 2: 175 mg/day for 28 days (=1 cycle)
Cohort 3: 250 mg/day for 28 days (=1 cycle)
Cohort 4: 350 mg/day for 28 days (=1 cycle)
Cohort 5: 450 mg/day for 28 days (=1 cycle)
Cohort 6: To be determined amount in mg/day for 28 days (=1 cycle)

Each cohort will be enrolled sequentially with 6 subjects per cohort. If ≤1 dose-limiting toxicity (DLT) is observed in the cohort during Cycle 1, escalation to the next cohort will proceed. Subjects may be enrolled in the next cohort if 4 of the 6 subjects enrolled in the cohort completed Cycle 1 without experiencing a DLT, while the remaining 2 subjects are completing evaluation. If ≥2 DLTs are observed during Cycle 1, dosing at that dose and higher will be suspended and the MTD will be established as the previous cohort. The MTD is defined as the largest daily dose for which fewer than 33% of the subjects experience a DLT during Cycle 1. Dose escalation will end when either the MTD is achieved or at 3 dose levels above full BTK occupancy, whichever occurs first. Full BTK occupancy is defined as Formula (XVIII) active-site occupancy of >80% (average of all subjects in cohort) at 24 hours postdose. Should escalation to Cohort 6 be necessary, the dose will be determined based on the aggregate data from Cohorts 1 to 5, which includes safety, efficacy, and PK/PD results. The dose for Cohort 6 will not exceed 900 mg/day.

Treatment with Formula (XVIII) may be continued for >28 days until disease progression or an unacceptable drug-related toxicity occurs. Subjects with disease progression will be removed from the study. All subjects who discontinue study drug will have a safety follow-up visit 30 (±7) days after the last dose of study drug unless they have started another cancer therapy within that timeframe. Radiologic tumor assessment will be done at screening and at the end of Cycle 2, Cycle 4, and Cycle 12 and at investigator discretion. Confirmation of complete response (CR) will require bone marrow analysis and radiologic tumor assessment. For subjects who remain on study for >11 months, a mandatory bone marrow aspirate and biopsy is required in Cycle 12 concurrent with the radiologic tumor assessment.

All subjects will have standard hematology, chemistry, and urinalysis safety panels done at screening. This study also includes pancreatic function assessment (serum amylase and serum lipase) due to the pancreatic findings in the 28-day GLP rat toxicity study. Once dosing commences, all subjects will be evaluated for safety once weekly for the first 4 weeks, every other week for Cycle 2, and monthly thereafter. Blood samples will be collected during the first week of treatment for PK/PD assessments. ECGs will be done at screening, and on Day 1-2, 8, 15, 22, 28 of Cycle 1, Day 15 and 28 of Cycle 2, and monthly thereafter through Cycle 6. ECGs are done in triplicate for screening only. Thereafter, single ECG tests are done unless a repeat ECG testing is required.

Dose-limiting toxicity is defined as any of the following events (if not related to disease progression): (1) any Grade ≥3 non-hematologic toxicity (except alopecia) persisting despite receipt of a single course of standard outpatient symptomatic therapy (e.g., Grade 3 diarrhea that responds to a single, therapeutic dose of Imodium® would not be considered a DLT); (2) grade ≥3 prolongation of the corrected QT interval (QTc), as determined by a central ECG laboratory overread; (3) grade 4 neutropenia (absolute neutrophil count [ANC] <500/μL) lasting >7 days after discontinuation of therapy without growth factors or lasting >5 days after discontinuation of therapy while on growth factors (i.e., Grade 4 neutropenia not lasting as long as specified will not be considered a DLT), (4) grade 4 thrombocytopenia (platelet count <20,000/μL) lasting >7 days after discontinuation of therapy or requiring transfusion (i.e., Grade 4 thrombocytopenia not lasting as long as specified will not be considered a DLT), and (5) dosing delay due to toxicity for >7 consecutive days.

The efficacy parameters for the study include overall response rate, duration of response, and progression-free survival (PFS). The safety parameters for the study include DLTs and MTD, frequency, severity, and attribution of adverse events (AEs) based on the Common Terminology Criteria for Adverse Events (CTCAE v4.03) for non-hematologic AEs. Hallek, et al., *Blood* 2008, 111, 5446-5456.

The schedule of assessments is as follows, with all days stated in the following meaning the given day or +/−2 days from the given day. A physical examination, including vital signs and weight, are performed at screening, during cycle 1 at 1, 8, 15, 22, and 28 days, during cycle 2 at 15 and 28 days, during cycles 3 to 24 at 28 days, and at follow up (after the last dose). The screening physical examination includes, at a minimum, the general appearance of the subject, height (screening only) and weight, and examination of the skin, eyes, ears, nose, throat, lungs, heart, abdomen, extremities, musculoskeletal system, lymphatic system, and nervous system. Symptom-directed physical exams are done thereafter. Vital signs (blood pressure, pulse, respiratory rate, and temperature) are assessed after the subject has rested in the sitting position. Eastern Cooperative Oncology Group (ECOG) status is assessed at screening, during cycle 1 at 1, 8, 15, 22, and 28 days, during cycle 2 at 15 and 28 days, during cycles 3 to 24 at 28 days, and at follow up, using the published ECOG performance status indications described in Oken, et al., *Am. J. Clin. Oncol.* 1982, 5, 649-655. ECG testing is performed at screening, during cycle 1 at 1, 2, 8, 15, 22, and 28 days, during cycle 2 at 15 and 28 days, during cycles 3 to 24 at 28 days, and at follow up. The 12-lead ECG test will be done in triplicate (≥1 minute apart) at screening. The calculated QTc average of the 3 ECGs must be <480 ms for eligibility. On cycle 1, day 1 and cycle 1, day 8, single ECGs are done predose and at 1, 2, 4, and 6 hours postdose. The single ECG on Cycle 1 Day 2 is done predose. On cycle 1, day 15, day 22, and day 28, a single ECG is done 2 hours post-dose. Starting with cycle 2, a single ECG is done per visit. Subjects should be in supine position and resting for at least 10 minutes before study-related ECGs. Two consecutive machine-read QTc >500 ms or >60 ms above baseline require central ECG review. Hematology, including complete blood count with differential and platelet and reticulocyte counts, is assesed at screening, during cycle 1 at 1, 8, 15, 22, and 28 days, during cycle 2 at 15 and 28 days, during cycles 3 to 24 at 28 days, and at follow up. Serum chemistry is assesed at screening, during cycle 1 at 1, 8, 15, 22, and 28 days, during cycle 2 at 15 and 28 days, during cycles 3 to 24 at 28 days, and at follow up. Serum chemistry includes albumin, alkaline phosphatase, ALT, AST, bicarbonate, blood urea nitrogen (BUN), calcium, chloride, creatinine, glucose, lactate dehydrogenase (LDH), magnesium, phosphate, potassium, sodium, total bilirubin, total protein, and uric acid. Cell counts and serum immunoglobulin are performed at screening, at cycle 2, day 28, and at every 6 months thereafter until last dose and include T/B/NK/monocyte cell counts (CD3, CD4, CD8, CD14, CD19, CD19, CD16/56, and others as needed) and serum immunoglobulin (IgG, IgM, IgA, and total immunoglobulin). Bone marrow aspirates are performed at cycle 12. Pharmacodynamics samples are drawn during cycle 1 at 1, 2, and 8 days, and at follow up. On days 1 and 8, pharmacodynamic samples are drawn pre-dose and 4 hours (±10 minutes) post-dose, and on day 2, pharmacodynamic samples are drawn pre-dose. Pharmacokinetics samples are drawn during cycle 1 at 1, 2, 8, 15, 22, and 28 days. Pharmacokinetic samples for Cycle 1 Day 1 are drawn pre-dose and at 0.5, 1, 2, 4, 6 and 24 hours (before dose on Day 2) post-dose. Samples for Cycle 1 Day 8 are drawn pre-dose and at 0.5, 1, 2, 4, and 6 hours post-dose. On Cycle 1 Day 15, 22, and 28, a PK sample is drawn pre-dose and the second PK sample must be drawn before (up to 10 minutes before) the ECG acquisition, which is 2 hours postdose. Pretreatment radiologic tumor assessments are performed within 30 days before the first dose. A computed tomography (CT) scan (with contrast unless contraindicated) is required of the chest, abdomen, and pelvis. In addition, a positron emission tomography (PET) or PET/CT must done for subjects with SLL. Radiologic tumor assessments are mandatory at the end of Cycle 2 (−7 days), Cycle 4 (−7 days), and Cycle 12 (−7 days). Otherwise, radiologic tumor assessments are done at investigator discretion. A CT (with contrast unless contraindicated) scan of the chest, abdomen, and pelvis is required for subjects with CLL. In addition, a PET/CT is required in subjects with SLL. Bone marrow and radiologic assessments are both required for confirmation of a complete response (CR). Clinical assessments of tumor response should be done at the end of Cycle 6 and every 3 months thereafter. Molecular markers are measured at screening, and include interphase cytogenetics, stimulated karyotype, IgHV mutational status, Zap-70 methylation, and beta-2 microglobulin levels. Urinalysis is performed at screening, and includes pH, ketones, specific gravity, bilirubin, protein, blood, and glucose. Other assessments, including informed consent, eligibility, medical history, and pregnancy test are done at the time of screening.

The investigator rates the subject's response to treatment based on recent guidelines for CLL, as given in Hallek, et al., *Blood* 2008, 111, 5446-56, and for SLL, as given in Cheson, et al., *J. Clin. Oncol.* 2007, 25, 579-586. The response assessment criteria for CLL are summarized in Table 8.

TABLE 8

Response Assessment Criteria for CLL.
Abbreviations:
ANC = absolute neutrophil count; CR = complete remission;
CRi = CR with incomplete blood count recovery; PR = partial remission.

| Response | Peripheral Blood | Bone Marrow (if performed) | Nodes, Liver, and Spleen[a] |
|---|---|---|---|
| CR | Lymphocytes <4 × $10^9$/L<br>ANC >1.5 × $10^9$/L[b]<br>Platelets >100 × $10^9$/L[b]<br>Hemoglobin >11.0 g/dL (untransfused)[b] | Normocellular<br><30% lymphocytes<br>No B-lymphoid nodules | Normal (e.g., no lymph nodes >1.5 cm) |
| CRi | Lymphocytes <4 × $10^9$/L<br>Persistent anemia, thrombocytopenia, or neutropenia related to drug toxicity | Hypocellular<br><30% lymphocytes | Normal (e.g., no lymph nodes >1.5 cm) |
| PR | Lymphocytes ≥50% decrease from baseline<br>ANC >1.5 × $10^9$/L<br>or<br>Platelets >100 × $10^9$/L or 50% improvement over baseline[b]<br>or<br>Hemoglobin >11.0 g/dL<br>or<br>50% improvement over baseline (untransfused)[b] | Not assessed | ≥50% reduction in lymphadenopathy[c] and/or in spleen or liver enlargement |

[a]Computed tomography (CT) scan of abdomen pelvis, and chest is required for this evaluation
[b]Without need for exogenous growth factors
[c]In the sum products of ≤6 lymph nodes or in the largest diameter of the enlarged lymph node(s) detected before therapy and no increase in any lymph node or new enlarged lymph nodes The response assessment criteria for SLL are summarized in Table 9.

TABLE 9

Response Assessment Criteria for SLL.
Abbreviations: CR = complete remission, CT = computed tomography,
FDG = [$^{18}$F]fluorodeoxyglucose, PET = positron-emission tomography,
PR = partial remission, SD = stable disease, SPD = sum of the product of the diameters.

| Response | Definition | Nodal Masses | Spleen, Liver | Bone Marrow |
|---|---|---|---|---|
| CR | Disappearance of all evidence of disease | (a) FDG-avid or PET positive prior to therapy; mass of any size permitted if PET negative<br>(b) Variably FDG-avid or PET negative; regression to normal size on CT | Not palpable, nodules disappeared | If infiltrate present at screening, infiltrate cleared on repeat biopsy; if indeterminate by morphology, immunohisto-chemistry should be negative |
| PR | Regression of measurable disease and no new sites | ≥50% decrease in SPD of up to 6 largest dominant masses; no increase in size of other nodes<br>(a) FDG-avid or PET positive prior to therapy; ≥1 PET positive at previously involved site<br>(b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or progressive disease | (a) FDG-avid or PET positive prior to therapy; PET positive at prior sites of disease, and no new sites on CT or PET | | |

TABLE 9-continued

Response Assessment Criteria for SLL.
Abbreviations: CR = complete remission, CT = computed tomography,
FDG = [$^{18}$F]fluorodeoxyglucose, PET = positron-emission tomography,
PR = partial remission, SD = stable disease, SPD = sum of the product of the diameters.

| Response | Definition | Nodal Masses | Spleen, Liver | Bone Marrow |
|---|---|---|---|---|
| | | (b) Variably FDG avid or PET negative; no change in size of previous lesions on CT | | |

The PK parameters of the study are as follows. The plasma PK of Formula (XVIII) and a metabolite is characterized using noncompartmental analysis. The following PK parameters are calculated, whenever possible, from plasma concentrations of Formula (XVIII):

$AUC_{(0-t)}$: Area under the plasma concentration-time curve calculated using linear trapezoidal summation from time 0 to time t, where t is the time of the last measurable concentration (Ct), $AUC_{(0-24)}$: Area under the plasma concentration-time curve from 0 to 24 hours, calculated using linear trapezoidal summation, $AUC_{(0-\infty)}$: Area under the plasma concentration-time curve from 0 to infinity, calculated using the formula: $AUC_{(0-\infty)} = AUC_{(0-t)} + Ct/\lambda z$, where $\lambda z$ is the apparent terminal elimination rate constant, $C_{max}$: Maximum observed plasma concentration, $T_{max}$: Time of the maximum plasma concentration (obtained without interpolation), $t_{1/2}$: Terminal elimination half-life (whenever possible), $\lambda_z$: Terminal elimination rate constant (whenever possible), Cl/F: oral clearance.

The PD parameters of the study are as follows. The occupancy of BTK by Formula (XVIII) are measured in peripheral blood mononuclear cells (PBMCs) with the aid of a biotin-tagged Formula (XVIII) analogue probe. The effect of Formula (XVIII) on biologic markers of B cell function will also be evaluated.

The statistical analysis used in the study is as follows. No formal statistical tests of hypotheses are performed. Descriptive statistics (including means, standard deviations, and medians for continuous variables and proportions for discrete variables) are used to summarize data as appropriate.

The following definitions are used for the safety and efficacy analysis sets: Safety analysis set: All enrolled subjects who receive ≥1 dose of study drug; Per-protocol (PP) analysis set: All enrolled subjects who receive ≥1 dose of study drug and with ≥1 tumor response assessment after treatment. The safety analysis set will be used for evaluating the safety parameters in this study. The PP analysis sets will be analyzed for efficacy parameters in this study.

No imputation of values for missing data is performed except for missing or partial start and end dates for adverse events and concomitant medication will be imputed according to prespecified, conservative imputation rules. Subjects lost to follow-up (or drop out) will be included in statistical analyses to the point of their last evaluation.

The safety endpoint analysis was performed as follows. Safety summaries will include summaries in the form of tables and listings. The frequency (number and percentage) of treatment emergent adverse events will be reported in each treatment group by Medical Dictionary for Regulatory Activities (MedDRA) System organ Class and Preferred Term. Summaries will also be presented by the severity of the adverse event and by relationship to study drug. Laboratory shift tables containing counts and percentages will be prepared by treatment assignment, laboratory parameter, and time. Summary tables will be prepared for each laboratory parameter. Figures of changes in laboratory parameters over time will be generated. Vital signs, ECGs, and physical exams will be tabulated and summarized.

Additional analyses include summaries of subject demographics, baseline characteristics, compliance, and concurrent treatments. Concomitant medications will be coded according to the World Health organization (WHO) Drug Dictionary and tabulated.

The analysis of efficacy parameters was performed as follows. The point estimate of the overall response rate will be calculated for the PP analysis set. The corresponding 95% confidence interval also will be derived. The duration of overall response is measured from the time measurement criteria are met for CR or PR (whichever is first recorded) until the first date that recurrent or progressive disease is objectively documented (taking as reference for progressive disease the smallest measurements recorded since the treatment started). Kaplan-Meier methodology will be used to estimate event-free curves and corresponding quantiles (including the median). Progression-free survival is measured from the time of first study drug administration until the first date that recurrent or progressive disease is objectively documented (taking as reference for progressive disease the smallest measurements recorded since the treatment started). Kaplan-Meier methodology will be used to estimate the event-free curves and corresponding quantiles (including the median).

The study scheme is a seqential cohort escalation. Each cohort consists of six subjects. The sample size of the study is 24 to 36 subjects, depending on dose escalation into subsequent cohorts. Cohort 1 (N=6) consists of Formula (XVIII), 100 mg QD for 28 days. Cohort 2 (N=6) consists of Formula (XVIII), 175 mg QD for 28 days. Cohort 3 (N=6) consists of Formula (XVIII), 250 mg QD for 28 days. Cohort 4 (N=6) consists of Formula (XVIII), 350 mg QD for 28 days. Cohort 5 (N=6) consists of Formula (XVIII), 450 mg QD for 28 days. Cohort 6 (N=6) consists of Formula (XVIII), at a dose to be determined QD for 28 days. The dose level for Cohort 6 will be determined based on the safety and efficacy of Cohorts 1 to 5, and will not exceed 900 mg/day. Escalation will end with either the MTD cohort or three levels above full BTK occupancy, whichever is observed first. An additional arm of the study will explore 100 mg BID dosing. Treatment with oral Formula (XVIII) may be continued for greater than 28 days until disease progression or an unacceptable drug-related toxicity occurs.

The inclusion criteria for the study are as follows: (1) men and women ≥18 years of age with a confirmed diagnosis of CLL/SLL, which has relapsed after, or been refractory to, ≥2 previous treatments for CLL/SLL; however, subjects with 17p deletion are eligible if they have relapsed after, or been refractory to, 1 prior treatment for CLL/SLL; (2) body weight ≥60 kg, (3) ECOG performance status of ≤2; (4) agreement to use contraception during the study and for 30 days after the last dose of study drug if sexually active and able to bear children; (5) willing and able to participate in all required evaluations and procedures in this study protocol including swallowing capsules without difficulty; or (6) ability to understand the purpose and risks of the study and provide signed and dated informed consent and authorization to use protected health information (in accordance with national and local subject privacy regulations).

The dosage form and strength of Formula (XVIII) used in the clinical study is a hard gelatin capsules prepared using standard pharmaceutical grade excipients (microcrystalline cellulose) and containing 25 mg of Formula (XVIII) each. The color of the capsules is Swedish orange. The route of administration is oral (per os, or PO). The dose regimen is once daily or twice daily, as defined by the cohort, on an empty stomach (defined as no food 2 hours before and 30 minutes after dosing).

The baseline characteristics for the patients enrolled in the clinical study are given in Table 10.

TABLE 10

Relapsed/refractory CLL baseline characteristics.

| Characteristic | CLL (N = 44) |
|---|---|
| Patient Demographics | |
| Age (years), median (range) | 62 (45-84) |
| Sex, men (%) | 33 (75) |
| Prior therapies, median (range), n | 3 (1-10) |
| ≥3 prior therapies, n (%) | 26 (59) |
| Clinical Details | |
| ECOG performance status ≥1 (%) | 28 (63) |
| Rai stage III/IV | 16 (36) |
| Bulky disease ≥5 cm, n (%) | 15 (34) |
| Cytopenia at baseline | 33 (75) |
| Cytogenic Status | |
| Chromosome 11q22.3 deletion (Del 11q), n (%) | 18 (41) |
| Chromosome 17p13.1 (Del 17p), n (%) | 19 (34) |
| IgV$_H$ status (unmutated), n (%) | 28 (64) |

The results of the clinical study in relapsed/refractory CLL patients are summarized in Table 11.

FIG. 100 shows the median % change in ALC and SPD from baseline in the clinical study of Formula (XVIII), plotted in comparison to the results reported for ibrutinib in FIG. 1A of Byrd, et al., N. Engl. J. Med. 2013, 369, 32-42. The results show that Formula (XVIII) leads to a more rapid patient response in CLL than corresponding treatment with ibrutinib. This effect is illustrated, for example, by the median % change in SPD, which achieved the same status in the present study at 7 months of treatment with Formula (XVIII) as compared to 18 months for ibrutinib. The % change in SPD observed in the different cohorts (i.e. by dose and dosing regimen) is shown in FIG. 101, and in all cases shows significant responses.

A Kaplan-Meier curve showing PFS from the clinical CLL study of Formula (XVIII) is shown in FIG. 102. A comparison of survival curves was performed using the Log-Rank (Mantle-Cox) test, with a p-value of 0.0206 indicating that the survival curves are different. The number of patients at risk is shown in FIG. 103. Both FIG. 102 and FIG. 103 show the results for Formula (XVIII) in comparison to the results reported for ibrutinib in Byrd, et al., N. Engl. J. Med. 2013, 369, 32-42. An improvement in survival and a reduction in risk are observed in CLL patients treated with Formula (XVIII) in comparison to patients treated with ibrutinib.

Based on the data and comparisons shown in FIG. 100 to FIG. 103, the CLL study with Formula (XVIII) showed that the efficacy of Formula (XVIII) was surprisingly superior to that of ibrutinib.

In the literature study of ibrutinib, increased disease progression was associated with patients with high-risk cytogenetic lesions (17p13.1 deletion or 11q22.3 deletion), as shown in FIG. 3A in Byrd, et al., N. Engl. J. Med. 2013, 369, 32-42, which shows ibrutinib PFS including PFS broken down by genetic abnormality. The 17p and 11q deletions are validated high-risk characteristics of CLL, and the 17p deletion is the highest risk. In FIG. 104, the PFS is shown for Formula (XVIII) in patients with the 17p deletion in comparison to the results obtained for ibrutinib in Byrd, et al., N. Engl. J. Med. 2013, 369, 32-42. A p-value of 0.0696 was obtained. In FIG. 105, the number of patients at risk with the 17p deletion is compared. To date, no 17p patients have progressed on Formula (XVIII).

The adverse events observed in the clinical study in relapsed/refractory CLL are given in Table 12. No DLTs were observed. The MTD was not reached. No treatment-related serious adverse events (SAEs) were observed. No prophylactic antivirals or antibiotics were needed.

TABLE 11

Activity of Formula (XVIII) in relapsed/refractory CLL.

n (%)

| | All Cohorts (N = 31) | 100 mg QD (N = 8) | 175 mg QD (N = 8) | 250 mg QD (N = 7) | 100 mg BID (N = 3) | 400 mg QD (N = 5) |
|---|---|---|---|---|---|---|
| PR | 22 (71) | 7 (88) | 5 (63) | 5 (71) | 3 (100) | 2 (40) |
| PR + L | 7 (23) | 0 (0) | 3 (37) | 2 (29) | 0 (0) | 2 (40) |
| SD | 2 (6) | 1 (12) | 0 (0) | 0 (0) | 0 (0) | 1 (20) |
| PD | 0 (0) | 0 (0) | 0 (0) | 0 (0) | 0 (0) | 0 (0) |
| Median (range) Cycles | | | | | | |
| | 7.3 (3.0-10.8) | 10.0 (9.0-10.8) | 8.6 (3.0-8.8) | 7.0 (7.0-7.3) | 5.2 (4.7-5.5) | 5.0 (4.8-5.5) |

(PR = partial response; PR + L = partial response with lymphocytosis; SD = stable disease; PD = progressive disease.)

TABLE 12

Treatment-related adverse events reported in the clinical study of Formula (XVIII) in relapsed/refractory CLL. (Reported in ≥5% of patients.)

| Adverse Events (Treatment-Related), n (%) | Grade | All (N = 44) |
|---|---|---|
| Headache | 1/2 | 7 (16) |
| Increased tendency to bruise | 1 | 6 (14) |
| Diarrhea | 1 | 4 (9) |
| Petechiae | 1 | 3 (7) |

The clinical study of Formula (XVIII) thus showed other unexpectedly superior results compared to ibrutinib therapy. A lack of lymphocytosis was observed in the study. Furthermore, only grade 1 AEs were observed, and these AEs were attributable to the high BTK selectivity of Formula (XVIII).

BTK target occupany was measured for relapsed/refractory CLL patients with the results shown in FIG. 106. For 200 mg QD dosing of the BTK inhibitor of Formula (XVIII), about 94%-99% BTK occupancy was observed, with superior 24 hour coverage and less inter-patient variability also observed. For 420 mg and 840 mg QD of the BTK inhibitor ibrutinib, 80%-90% BTK occupancy was observed, with more inter-patient variability and capped occupancy. These results indicate that the BTK inhibitor of Formula (XVIII) achieves superior BTK occupancy in CLL patients than ibrutinib.

The effects of Formula (XVIII) on cell subset percentages were also evaluated using flow cytometry analysis of peripheral blood, with the results shown in FIG. 107, FIG. 108, FIG. 109, FIG. 110, FIG. 111, and FIG. 112. PBMC samples from CLL patient samples drawn prior to (predose) and after 28 days of dosing with Formula (XVIII) were compared for potential changes in cell subsets. PBMCs were stained with monoclonal antibodies conjugated to fluorescent tags (flourochromes) to identify cell subsets via flow cytometry. Non-viable cells were excluded from the analysis using the dye 7-aminoactinomycin D (7-AAD). To produce the metric of percent change, the following steps were taken. First, each cell subset was defined by hierarchical flow cytometry gating. Then, the change in frequency (between day 1 and day 28) was calculated for each cell subset. MDSC subsets were measured as a % of all myeloid cells. T cell subsets were measured as a % of all CD3$^+$ cells, and NK cells were measured as a % of all live CD45$^+$ cells. In FIG. 107 and FIG. 108, the results show the % change in MDSC (monocytic) level over 28 days versus % ALC change at cycle 1 day 28 (C1D28) and at cycle 2 day 28 (C2D28). A cycle is 28 days. A trend is observed wherein patients with decreasing ALC % had increasing MDSC (monocytic) %. This may include patients who had quickly resolving lymphocytosis and those with no initial lymphocytosis. This provides evidence that treatment with Formula (XVIII) mobilizes MDSCs and thus affects the CLL tumor microenvironment in marrow and lymph nodes, which is an unexpected indication of superior efficacy. In FIG. 109 and FIG. 110, the results show the % change in NK cell level over 28 days versus % ALC change, measured at C1D28 or C2D28, and similar trends are observed wherein patients with decreasing ALC % had increasing NK cell %. This may include patients who had quickly resolving lymphocytosis and those having no initial lymphocytosis. The effects in FIG. 107 to FIG. 110 are observed in multiple cohorts, at doses including 100 mg BID, 200 mg QD, and 400 mg QD. In FIG. 111 and FIG. 112, the effects on NK cells and MDSC cells are compared to a number of other markers versus % change in ALC at C1D28 and C2D28. These other markers include CD4+ T cells, CD8+ T cells, CD4+/CD8+ T cell ratio, NK-T cells, PD-1+ CD4+ T cells, and PD-1+ CD8+ T cells. The effects on NK cells and MDSC cells are observed to be much more pronounced than on any of these other markers.

These results suggest that after Formula (XVIII) administration, the CLL microenvironment undergoes a change wherein NK cells and monocytic MDSC subsets increase in frequency in the peripheral blood in patients with falling ALC counts, an important clinical parameter in CLL. The NK cell increase may reflect an overall increase in cytolytic activity against B-CLL resulting in the ALC % to drop. The increase in MDSC % in the blood may be due to a movement of these cells out of the lymph nodes, spleen, and bone marrow, which are all possible sites of CLL proliferation. Fewer MDSCs at the CLL proliferation centers would likely result in a reduced immunosuppressive microenvironment leading to an increase in cell-mediated immunity against the tumor, decreased tumor proliferation, and eventually lower ALC % in the circulation.

Updated clinical results from the CLL study are shown in FIG. 115 to FIG. 120. FIG. 115 shows an update of the data presented in FIG. 102. FIG. 116 shows an update of the data presented in FIG. 108, and includes BID dosing results. Formula (XVIII) 200 mg QD dosing resulted in 94%-99% BTK occupancy, 24 hour coverage, and less inter-patient variability. Ibrutinib 420 mg and 840 mg QD dosing resulted in 80%-90% BTK occupancy, more inter-patient variability, and capped occupancy. Formula (XVIII) 100 mg BID dosing resulted in 97%-99% BTK occupancy, complete BTK coverage, and less inter-patient variability. The PFS for patients with 11p deletions and 17q deletions are illustrated in FIG. 117, FIG. 118, and FIG. 119. Updated SPD results are illustrated in FIG. 120.

Treatment of CLL patients with Formula (XVIII) also resulted in increased apoptotis, as illustrated in FIG. 121. Apoptotic B-CLL was defined by flow cytometry as having cleaved PARP$^+$, Caspase 3$^+$, CD19$^+$, and CD5$^+$ phenotypes. 82% of samples tested had a baseline change greater than 25%. Treatment of CLL patients also showed that Formula (XVIII) decreased plasma chemokines associated with MDSC homing and retention. A significant decrease in CXCL12 and CCL2 levels has been observed in patients treated with Formula (XVIII), as shown in FIG. 122 and FIG. 123, respectively.

Overall, Formula (XVIII) shows superior efficacy to first generation BTK inhibitors such as ibrutinib, or to monotherapy with PI3K-δ inhibitors such as idelalisib. Formula (XVIII) has better target occupancy and better pharmacokinetic and metabolic parameters than ibrutinib, leading to improved B cell apoptosis. Furthermore, unlike treatment with ibrutinib and PI3K-δ inhibitors, treatment with Formula (XVIII) does not affect NK cell function. Finally, treatment with Formula (XVIII) leads to a CLL tumor microenvironmental effect by excluding MDSC cells from the marrow and lymph nodes and reducing their number.

Example 11—Clinical Study of a BTK Inhibitor in Leukemia/Lymphoma in Combination with Obinutuzumab (GA-101)

The primary objectives of the study are (1) to determine the overall response rate (ORR) at 12 months with the combination of Formula (XVIII) and obinutuzumab in patients with relapsed or refractory CLL, (2) to determine the ORR at 12 months with the combination of Formula (XVIII) and obinutuzumab in patients with treatment-naive CLL, and (3) to establish the safety and feasibility of the combination of Formula (XVIII) and obinutuzumab.

The secondary objectives of this study are: (1) to determine the complete response (CR) rate and MRD-negative CR rate in previously untreated and relapsed and refractory CLL with this regimen; (2) to determine the progression-free survival (PFS), time to next treatment (TTNT), and overall survival (OS) with this regimen, (3) to perform baseline analysis of patients enrolled on this trial including fluorescence in situ hybridization (FISH), stimulated karyotype, Zap-70 methylation, and $IgV_H$ mutational status and describe relationships between these biomarkers and ORR or PFS for patients treated with this regimen; (4) to determine pharmacokinetics (PK) of orally administered Formula (XVIII); (5) to measure pharmacodynamic (PD) parameters including drug occupancy of BTK, change in miR and gene expression on day 8 and 29 of therapy of Formula (XVIII); (6) to determine the influence of Formula (XVIII) on NK cell and T cell function in vivo; (7) to assess for serial development of resistance by baseline and longitudinal assessment of mutations of BTK and PLCG2 at regular follow up intervals and by examining diagnosis to relapse samples by whole exome sequencing; (8) to determine the influence of Formula (XVIII) on emotional distress and quality of life in CLL patients; and (9) to determine trajectory of psychological and behavioral responses to Formula (XVIII) and covariation with response to therapy.

CLL is the most prevalent form of adult leukemia and has a variable clinical course, where many patients do not require treatment for years and have survival equal to age matched controls. Other patients, however, exhibit aggressive disease and have a poor prognosis despite appropriate therapy. Byrd, et al., Chronic lymphocytic leukemia. *Hematology Am. Soc. Hematol. Educ. Program.* 2004, 163-183. While patients with early disease have not been shown to have a survival advantage with early treatment, most patients will eventually require therapy for their disease with the onset of symptoms or cytopenias, and despite the relatively long life expectancy for early stage disease, CLL remains an incurable disease. Patients diagnosed with or progressing to advanced disease have a mean survival of 18 months to 3 years. Unfortunately these patients with advanced disease are also more refractory to conventional therapy.

The treatment of CLL has progressed significantly over the previous decades. While alkylator therapy was used in the past, randomized trials have demonstrated a higher response rate and longer progression free survival (PFS) with fludarabine and subsequently with fludarabine-and cyclophosphamide-based combinations. O'Brien, et al., Advances in the biology and treatment of B-cell chronic lymphocytic leukemia. *Blood* 1995, 85, 307-18; Rai, et al., Fludarabine compared with chlorambucil as primary therapy for chronic lymphocytic leukemia. *N. Engl. J. Med.* 2000, 343, 1750-57; Johnson, et al., Multicentre prospective randomised trial of fludarabine versus cyclophosphamide, doxorubicin, and prednisone (CAP) for treatment of advanced-stage chronic lymphocytic leukaemia. The French Cooperative Group on CLL. *Lancet* 1996, 347, 1432-38; Leporrier, et al., Randomized comparison of fludarabine, CAP, and ChOP in 938 previously untreated stage B and C chronic lymphocytic leukemia patients. *Blood* 2001, 98, 2319-25; Catovsky, et al., Assessment of fludarabine plus cyclophosphamide for patients with chronic lymphocytic leukaemia (the LRF CLL4 Trial): A randomised controlled trial. *Lancet* 2007, 370, 230-239; Eichhorst, et al., Fludarabine plus cyclophosphamide versus fludarabine alone in first-line therapy of younger patients with chronic lymphocytic leukemia. *Blood* 2006, 107, 885-91. At the same time, the chimeric anti-CD20 monoclonal antibody rituximab was introduced for the treatment of CLL. At high doses or with dose intensive treatment, single agent rituximab has shown efficacy; however complete responses and extended remissions are very rare. O'Brien, et al. Rituximab dose-escalation trial in chronic lymphocytic leukemia. *J. Clin. Oncol.* 2001, 19, 2165-70; Byrd, et al., Rituximab using a thrice weekly dosing schedule in B-cell chronic lymphocytic leukemia and small lymphocytic lymphoma demonstrates clinical activity and acceptable toxicity. *Clin. Oncol.* 2001, 19, 2153-64. The efficacy of rituximab has been improved by combining it with traditional cytotoxic agents such as fludarabine or fludarabine and cyclophosphamide, which have produced high CR rates and extended progression free survival (PFS) compared to historical controls. Indeed, a large randomized clinical trial reported by the German CLL study group has shown a benefit of the addition of antibody therapy with rituximab to fludarabine and cyclophosphamide in the prolongation of PFS and OS in patients with untreated CLL. Hallek, et al., Addition of rituximab to fludarabine and cyclophosphamide in patients with chronic lymphocytic leukaemia: a randomised, open-label, phase 3 trial. *Lancet* 2010, 376, 1164-74. This encouraging progress in therapy and our understanding of the disease has resulted in significantly improved response rates and PFS. However, significant improvements in overall survival (OS) and ultimately cure, remain elusive goals.

While fludarabine based chemoimmunotherapy is standard for younger patients, the therapy for older patients is less well defined. In the large Phase 2 and 3 trials outlined previously, median ages were typically in the early-60s, while the average age of patients diagnosed with CLL is 72, which calls into question whether these results are generalizable to the entire CLL population. In fact, the one randomized Phase 3 trial investigating primary CLL therapy in older patients demonstrated that in patients >65 years old, fludarabine is not superior to chlorambucil. Eichhorst, et al., First-line therapy with fludarabine compared with chlorambucil does not result in a major benefit for elderly patients with advanced chronic lymphocytic leukemia. *Blood* 2009, 114, 3382-91. This finding was corroborated by a large retrospective study of front-line trials performed by the Alliance for Clinical Trials in Oncology, which demonstrated again that fludarabine is not superior to chlorambucil in older patients, but also showed that the addition of rituximab to chemotherapy was beneficial regardless of age. Woyach, et al., Impact of age on outcomes after initial therapy with chemotherapy and different chemoimmunotherapy regimens in patients with chronic lymphocytic leukemia: Results of sequential cancer and leukemia group B studies. *J. Clin. Oncol.* 2013, 31, 440-7. Two studies have evaluated the combination of rituximab with chlorambucil, showing that this combination is safe and moderately effective. Hillmen, et al., rituximab plus chlorambucil in patients with CD20-positive B-cell chronic lymphocytic leukemia (CLL): Final response analysis of an open-label Phase II Study, ASH Annual Meeting Abstracts, *Blood* 2010, 116, 697; Foa, et al., A Phase II study of chlorambucil plus rituximab followed by maintenance versus observation in elderly patients with previously untreated chronic lymphocytic leukemia: Results of the first interim analysis, ASH Annual Meeting Abstracts, *Blood* 2010, 116, 2462.

Recently, the type II glycoengineered CD20 monoclonal antibody obinutuzumab was introduced. In a Phase 1 trial of previously treated CLL as monotherapy, this antibody has a 62% response rate including 1 MRD-negative complete response, suggesting that alone this antibody may be more active in CLL than rituximab. Morschhauser, et al., Phase I study of R05072759 (GA10) in relapsed/refractory chronic lymphocytic leukemia, ASH Annual Meeting Abstracts. Blood, 2009, 114, 884. The German CLL Study Group (GCLLSG) recently completed a Phase 3 trial of rituximab and chlorambucil or obinutuzumab and chlorambucil vs chlorambucil alone in patients with untreated CLL and significant comorbidities. In this population, obinutuzumab and chlorambucil (but not rituximab and chlorambucil) improved OS over chlorambucil alone (hazard ratio 0.41, p=0.002), and obinutuzumab and chlorambucil improved PFS over rituximab and chlorambucil (median PFS 26.7 months vs 14.9 months, p<0.001). Goede, et al., Obinutuzumab plus chlorambucil in patients with CLL and coexisting conditions, N. Engl. J. Med. 2014, 370, 1101-10. On the basis of these favorable data, the combination of obinutuzumab and chlorambucil is FDA approved as frontline therapy for CLL patients.

Many older patients are also treated with the combination of bendamustine plus rituximab (BR). Although BR has not been compared directly with chlorambucil and rituximab, results of a recent Phase 2 trial show an ORR of 88% with a median event free survival of 33.9 months and 90.5% OS at 27 months. Fischer, et al., Bendamustine in combination with rituximab for previously untreated patients with chronic lymphocytic leukemia: A multicenter phase II trial of the German Chronic Lymphocytic Leukemia Study Group. J. Clin. Oncol. 2012, 30, 3209-16. These results held for patients >70 years old, and compare favorably with results published for chlorambucil and rituximab. While results with this regimen appear to be improved over historical controls, outcomes are not as good as those observed in younger patients with chemoimmunotherapy. Therefore, the optimal therapy for older patients remains an unmet need in clinical trials.

Additionally, most patients eventually relapse with their disease and are frequently refractory to existing agents. Patients who relapse after combined chemoimmunotherapy have a poor outcome with subsequent standard therapies. While options for these patients include alemtuzumab, bendamustine, high dose corticosteroids, ofatumumab, and combination based approaches, none of these therapies produces durable remissions that exceed that observed with first line chemoimmunotherapy. Keating, et al., Therapeutic role of alemtuzumab (Campath-1H) in patients who have failed fludarabine: results of a large international study. Blood 2002, 99, 3554-61; Bergmann, et al., Efficacy of bendamustine in patients with relapsed or refractory chronic lymphocytic leukemia: results of a phase I/II study of the German CLL Study Group. Haematologica 2005, 90, 1357-64; Thornton P D, Matutes E, Bosanquet A G, et al. High dose methylprednisolone can induce remissions in CLL patients with p53 abnormalities. Ann. Hematology 2003, 82, 759-65; Coiffier, et al., Safety and efficacy of ofatumumab, a fully human monoclonal anti-CD20 antibody, in patients with relapsed or refractory B-cell chronic lymphocytic leukemia: A phase 1-2 study. Blood 2008, 111, 1094-1100; Tsimberidou, et al., Phase I-II study of oxaliplatin, fludarabine, cytarabine, and rituximab combination therapy in patients with Richter's syndrome or fludarabine-refractory chronic lymphocytic leukemia. J. Clin. Oncol. 2008, 26, 196-203. Several of these therapies including alemtuzumab and high dose steroids are also associated with significant toxicities and sustained immunosuppression. Lozanski G, Heerema N A, Flinn IW, et al. Alemtuzumab is an effective therapy for chronic lymphocytic leukemia with p53 mutations and deletions. Blood 2004, 103, 3278-81; Osuji, et al., The efficacy of alemtuzumab for refractory chronic lymphocytic leukemia in relation to cytogenetic abnormalities of p53. Haematologica 2005, 90, 1435-36; Thornton, et al., High dose methyl prednisolone in refractory chronic lymphocytic leukaemia. Leuk. Lymphoma 1999, 34, 167-70; Bowen, et al. Methylprednisolone-rituximab is an effective salvage therapy for patients with relapsed chronic lymphocytic leukemia including those with unfavorable cytogenetic features. Leuk Lymphoma 2007, 48, 2412-17; Castro, et al., Rituximab in combination with high-dose methylprednisolone for the treatment of fludarabine refractory high-risk chronic lymphocytic leukemia. Leukemia 2008, 22, 2048-53.

In an ongoing Phase 1b/2 study, the BTK inhibitor ibrutinib has shown activity in patients with relapsed or refractory CLL. In patients with relapsed or refractory CLL and measurable lymphadenopathy, the rate of lymph node shrinkage >50% is 89%. With a median follow-up of 4 months, ORR was 48% due to asymptomatic lymphocytosis, and with longer follow-up of 26 months in patients receiving the 420 mg dose, has improved to 71%, with an additional 20% of patients achieving a partial response with lymphocytosis (PR-L). Byrd, et al., Activity and tolerability of the Bruton's tyrosine kinase (Btk) inhibitor PCI-32765 in patients with chronic lymphocytic leukemia/small lymphocytic lymphoma (CLL/SLL): Interim results of a phase Ib/II study. J. Clin. Oncol. ASCO Annual Meeting Abstracts, 2011, 29, Abstract 6508; Byrd, et al. Targeting BTK with ibrutinib in relapsed chronic lymphocytic leukemia. N. Engl. J. Med. 2013, 369, 32-42. This lymphocytosis is likely related to B cell release from lymph node, spleen and marrow microenvironment due to disruption of homing signals or chemoattractants that are relevant to usual lymphocyte circulation dynamics. Lymphocytosis with ibrutinib is seen within 1-2 weeks of starting therapy, reaches plateau within the first 2-3 cycles, and has resolved over time in virtually all patients. The duration of lymphocytosis does not appear to be related to the depth of eventual response nor to response duration. Woyach, et al., Prolonged lymphocytosis during ibrutinib therapy is associated with distinct molecular characteristics and does not indicate a suboptimal response to therapy. Blood 2014, 123, 1810-7. Response to ibrutinib occurs independently of high-risk genomic features including $IgV_H$ mutational status and del(17p13.1). Responses to this drug have been durable as well, with an estimated 26 month PFS of 76% and OS of 83% for these relapsed and refractory patients. This study also included a cohort of 31 previously untreated patients. With 16.6 months of follow-up, ORR is 71%, with an additional 10% of patients having persistent lymphocytosis; estimated 22 month PFS is 96%. This agent is currently in Phase 3 trials in treatment-naïve disease and is currently FDA approved for the treatment of relapsed CLL. These data with ibrutinib support the potential benefits of selective BTK inhibition in CLL. However, while highly potent in inhibiting BTK, ibrutinib has also shown in vitro activity against other kinases (e.g., epidermal growth factor receptor), which may be the cause of ibrutinib-related diarrhea and rash. Honigberg, et al., The Bruton tyrosine kinase inhibitor PCI-32765 blocks B-cell activation and is efficacious in models of autoimmune disease and B-cell malignancy. Proc. Natl. Acad. Sci. USA 2010, 107, 13075-13080. In addition, it is a substrate for both cytochrome P450 (CYP) enzymes 3A4/5, which increases the possibility of drug-drug interactions. Finally, the inhibition of ITK that is seen with ibrutinib has the potential to abrogate NK cell ADCC, which makes combination with monoclonal antibodies less effective. Kohrt, et al., Ibrutinib antagonizes rituximab-dependent NK cell-mediated cytotoxicity. *Blood* 2014, 123, 1957-60. These liabilities support the development of alternative BTK inhibitors for use in the therapy of lymphoid cancers.

In this Phase 1B study, two cohorts (relapsed/refractory and treatment-naïve) will be evaluated with slightly staggered enrollment. First, 6 subjects with R/R CLL will be enrolled into Cohort 1. Once the safety has been evaluated, the R/R cohort will be expanded to 26 subjects and enrollment of 6 treatment-naïve subjects can begin in Cohort 2. Once safety is established for Cohort 2, then the cohort will be expanded to 19 subjects.

Formula (XVIII) will be administered starting cycle 1 day 1 and will be administered twice daily (100 mg BID) until disease progression. Obinutuzumab will be given in the standard dosing fashion starting on cycle 2 day 1. On cycle 2 day 1, patients will receive 100 mg IV. On cycle 2 day 2, patients will receive 900 mg. On cycle 2 days 8 and 15, patients will receive 1000 mg IV. On cycles 3-7, patients will receive 1000 mg on day 1 of each cycle. For patients treated at dose level −1, 100 mg will be given on Day 1 and 650 mg on Day 2 of Cycle 2. On cycle 2 day 8 and 15, patients will receive 750 mg IV and during cycles 3-7, patients will receive 750 mg on Day 1 of each cycle. It is acceptable for cycles to begin <a 24-hour (1 business day) window before and after the protocol-defined date for Day 1 of a new cycle.

The inclusion criteria for patient eligibility are as follows: (1) Patients with a diagnosis of intermediate or high risk CLL (or variant immunophenotype), SLL, or B-PLL by IWCLL 2008 criteria" who have: (a) COHORT 1: Previously received at least one therapy for their disease; (b) COHORT 2: Previously untreated disease and >65 years old OR under 65 years old and refuse or are ineligible for chemoimmunotherapy; (2) Patients on Cohort 1 may have received previous ibrutinib (or another BTK inhibitor) as long as discontinuation was for a reason other than "on-treatment" disease progression; (3) All patients must satisfy one of the following criteria for active disease requiring therapy: (a) Evidence of marrow failure as manifested by the development or worsening of anemia or thrombocytopenia (not attributable to autoimmune hemolytic anemia or thrombocytopenia); (b) Massive (>6 cm below the costal margin), progressive or symptomatic splenomegaly; (c) Massive nodes (>10 cm) or progressive or symptomatic lymphadenopathy; (d) Constitutional symptoms, which include any of the following: Unintentional weight loss of 10% or more within 6 months, Significant fatigue limiting activity, Fevers >100.5 degrees F. for 2 weeks or more without evidence of infection, Night sweats >1 month without evidence of infection; (4) Measurable nodal disease by computed tomography (CT). Measurable nodal disease is defined as >1 lymph node >1.5 cm in the longest diameter in a site; (5) Patients with a history of Richter's syndrome are eligible if they now have evidence of CLL only, with <10% large cells in the bone marrow; (6) Subjects must have adequate organ function, defined as creatinine <2.5 times the upper limit of normal (ULN), ALT and AST <3.0×ULN, and bilirubin <2.5×ULN; (7) Platelets >50×10$^9$/L. In subjects with CLL involvement of the marrow, >30×10$^9$/L; (8) ANC >750/mm$^3$ In subjects with CLL involvement of the marrow, ANC >500/mm$^3$; (9) Subject must have an ECOG performance status <2; (10) Subject must not have secondary cancers that result in a life expectancy of <2 years or that would confound assessment of toxicity in this study; (11) Subjects must be >18 years of age; (12) Subject must provide written informed consent. A signed copy of the consent form will be retained in the patient's chart; (13) Subject must be able to receive outpatient treatment and follow-up at the treating institution; (14) Subject must have completed all CLL therapies >4 weeks prior to first study dose. Palliative steroids are allowed, but must be at a dose equivalent of <20 mg prednisone daily for at least 1 week prior to treatment initiation; (15) Subjects capable of reproduction and male subjects who have partners capable of reproduction must agree to use an effective contraceptive method during the course of the study and for 2 months following the completion of their last treatment. Females of childbearing potential must have a negative β-hCG pregnancy test result within 3 days of first study dose. Female patients who are surgically sterilized or who are >45 years old and have not experienced menses for >2 years may have ther3-hCG pregnancy test waived; (16) Subjects must be able to swallow whole capsules.

The exclusion criteria for patient eligibility are as follows: (1) For cohort 1, previous therapy for CLL. Treatment of autoimmune complications of CLL with steroids or rituximab is allowed, however, CD20 must have returned on 10% of the CLL cells if rituximab was recently administered. Palliative steroids are acceptable at doses <20 mg prednisone equivalent daily; (2) Any life-threatening illness, medical condition, or organ dysfunction which, in the investigator's opinion, could compromise the patients' safety, interfere with the absorption or metabolism of Formula (XVIII), or put the study outcomes at undue risk; (3) Female subjects who are pregnant or breastfeeding; (4) Subjects with active cardiovascular disease not medically controlled or those who have had myocardial infarction in the past 6 months, or QTc >480 ms; (5) Malabsorption syndrome, disease significantly affecting gastrointestinal function, or resection of the stomach or small bowel or gastric bypass, ulcerative colitis, symptomatic inflammatory bowel disease, or partial or complete bowel obstruction; (6) Grade 2 toxicity (other than alopecia) continuing from prior anticancer therapy including radiation; (7) Major surgery within 4 weeks before first dose of study drug; (8) History of a bleeding diathesis (e.g., hemophilia, von Willebrand disease); (9) Uncontrolled autoimmune hemolytic anemia or idiopathic thrombocytopenia purpura; (10) History of stroke or intracranial hemorrhage within 6 months before the first dose of study drug; (11) Requires or receiving anticoagulation with warfarin or equivalent vitamin K antagonists (eg, phenprocoumon) within 28 days of first dose of study drug; (12) Requires treatment with long-acting proton pump inhibitors (e.g., omeprazole, esomeprazole, lansoprazole, dexlansoprazole, rabeprazole, or pantoprazole); (13) Subjects with active infections requiring IV antibiotic/antiviral therapy are not eligible for entry onto the study until resolution of the infection. Patients on prophylactic antibiotics or antivirals are acceptable; (14) Subjects with history of or ongoing drug-induced pneumonitis; (15) Subjects with human immunodeficiency virus (HIV) or active infection with hepatitis C virus (HCV) or hepatitis B virus (HBV) or any uncontrolled active systemic infection; (16) Subjects who are known to have Hepatitis B infection or who are hepatitis B core antibody or surface antigen positive. Patients receiving prophylactic WIG may have false positive hepatitis serologies. Patients who are on WIG who have positive hepatitis serologies must have a negative hepatitis B DNA to be eligible; (17) Subjects with substance abuse or other medical or psychiatric conditions that, in the opinion of the investigator, would confound study interpretation or affect the patient's ability to tolerate or complete the study;

(18) Subjects cannot concurrently participate in another therapeutic clinical trial; (19) Subjects who have received a live virus vaccination within 1 month of starting study drug.

In this study, Formula (XVIII) is administered 100 mg BID, with the second dose 11-13 hours after the first. Obinutuzumab is administered by IV infusion as an absolute (flat) dose. Obinutuzumab is administered in a single day, with the exception of the first administration when patients receive their first dose of obinutuzumab over two consecutive days (split dose) in Cycle 2: 100 mg on Day 1 and 900 mg on Day 2. For patients treated at dose level −1 (750 mg obinutuzumab), −100 mg will be given on Day 1 and 650 mg on Day 2. On days when both Formula (XVIII) and obinutuzumab are given, the order of study treatment administration will be Formula (XVIII) followed at least 1 hour later by obinutuzumab. The full dosing schedule is given in Table 13.

TABLE 13

Dosing of obinutuzumab during 6 treatment cycles each of 28 days duration.

| Day of Treatment Cycle | | Dose of Obinutuzumab | Rate of Infusion (In the absence of infusion reactions/hypersensitivity during previous infusions) |
|---|---|---|---|
| Cycle 2 (loading doses) | Day 1 | 100 mg | Administer at 25 mg/hr over 4 hours. Do not increase the infusion rate. |
| | Day 2 | 900 mg | Administer at 50 mg/hr. The rate of the infusion can be escalated in increments of 50 mg/hr every 30 minutes to a maximum rate of 400 mg/hr. |
| | Day 8 | 1000 mg | Infusions can be started at a rate of 100 mg/hr and increased by 100 mg/hr increments every 30 minutes to a maximum of 400 mg/hr. |
| | Day 15 | 1000 mg | |
| Cycles 3-7 | Day 1 | 1000 mg | |

Anti-CD20 antibodies have a known safety profile, which include infusion related reactions (IRR). Anti-CD20 antibodies, and in particular obinutuzumab, can cause severe and life threatening infusion reactions. Sequelae of the infusion reactions include patient discontinuations from antibody treatment leading to suboptimal efficacy or increased medical resource utilization, such as hospitalization for hypotension or prolonged antibody infusion time. In the initial study of obinutuzumab in relapsed/refractory CLL patients (Cartron, et al., *Blood* 2014, 124, 2196), all patients (n=13) in the Phase 1 portion experienced IRRs (15% Grade 3, no Grade 4, and 100% patients experienced all grade AE), with hypotension and pyrexia the most common symptoms. In the Phase 2 portion of the study, 95% of patients developed IRR, with 60% of cases developing symptoms of hypotension; of those, 25% were Grade 3 reactions. In the pivotal trial of obinutuzumab and chlorambucil in previously untreated patients, 69% developed infusion related reactions, of which 21% were grade 3-4.

The results of the Phase 1b study described in this example for Formula (XVIII) in combination with obinutuzumab for patients with relapsed/refractory or untreated CLL/SLL/PLL are as follows. 6 patients have been treated in the study to date with the combination of Formula (XVIII) and obinutuzumab. Patients are first treated with a month run-in of Formula (XVIII) alone, then on cycle 2, day 1, patients are given obinutuzumab. To date, 41 doses of obinutuzumab have been administered to 6 patients. Lymphocyte counts immediately prior to treatment with obinutuzumab have ranged from 8 to $213 \times 10^9$/L. No cases of serious or Grade 3-4 IRR's have been reported. Only 2 patients have had obinutuzumab temporarily held for chills and arthralgias/sluured, respectively, and were able to complete the planned infusion. An additional 3 patients had adverse events within 24 hours of the infusion, all grade 1 (terms: flushing, palpitations in one patient, rash, and restlessness and headache). Consequently, there has been a substantial decrease in serious or Grade 3-4 IRR"s with the one month lead-in of Formula (XVIII), which could potentially lead to higher efficacy for the combination as well as better tolerability, leading to a decrease in medical resource utilization.

Example 12—BTK Inhibitory Effects on MDSCs in the Solid Tumor Microenvironment

A molecular probe assay was used to calculate the percent irreversible occupancy of total BTK. MDSCs were purified from tumor bearing PDA mice (as described previously) dosed at 15 mg/kg BID of Formula (XVIII). Complete BTK occupancy is observed for both the granulocytic and monocytic MDSC compartment on Day 8 at 4 hours post dose (N=5). The results are shown in FIG. 124.

We claim:

1. A method of treating a hyperproliferative disease, comprising co-administering, to a mammal in need thereof, therapeutically effective amounts of (1) a Janus kinase-2 (JAK-2) inhibitor, and (2) a Bruton's tyrosine kinase (BTK) inhibitor.

2. The method of claim 1, wherein the BTK inhibitor is selected from the group consisting of:

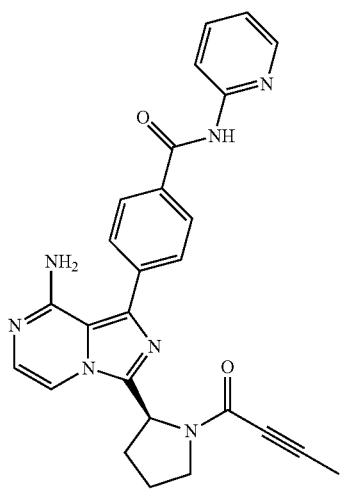

,

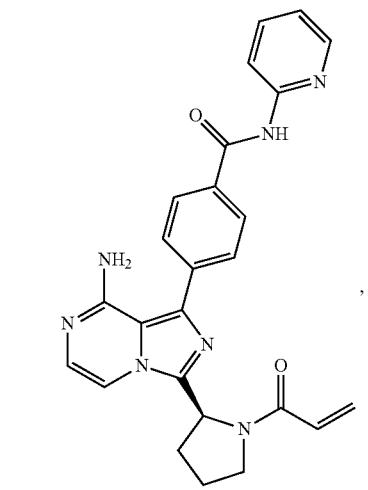

,

327
-continued
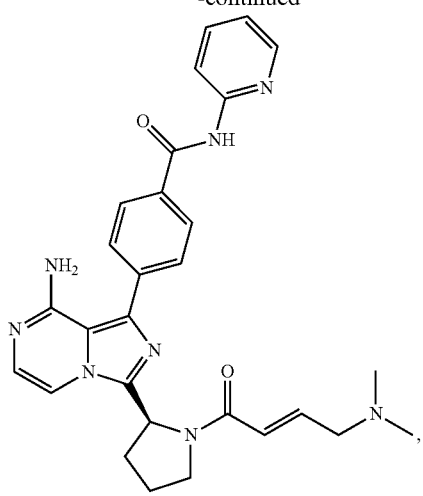
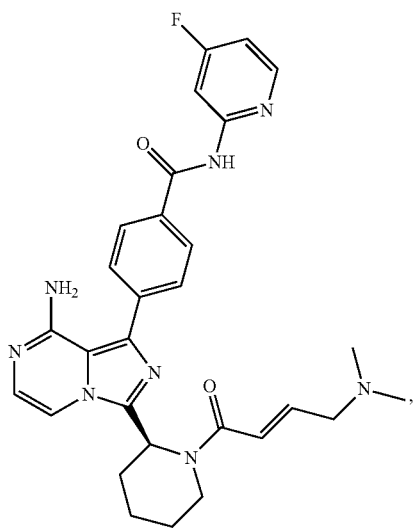
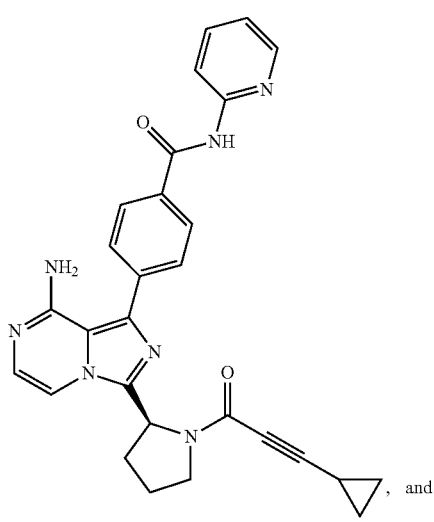
, and
328
-continued
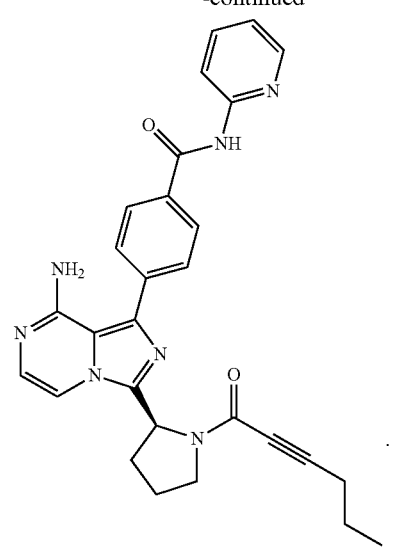
.
3. The method of claim 1, wherein the BTK inhibitor is selected from the group consisting of:
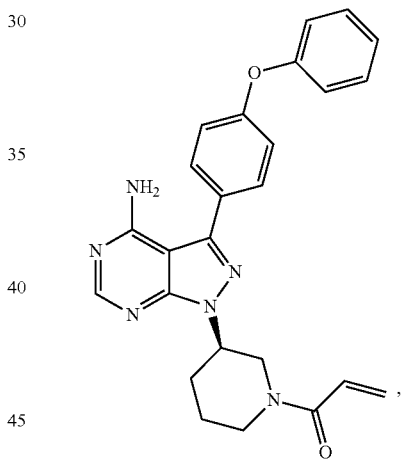
,
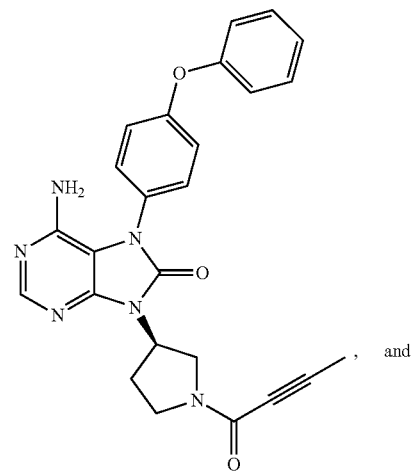
, and -continued

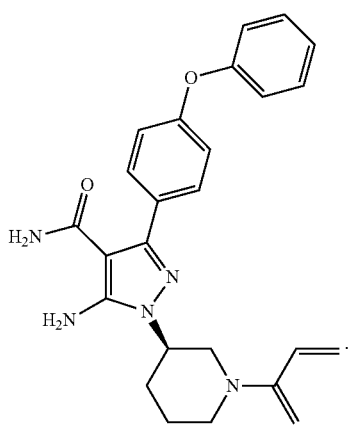

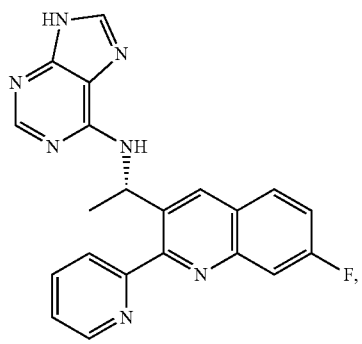

4. The method of claim 1, wherein the JAK-2 inhibitor is selected from the group consisting of:

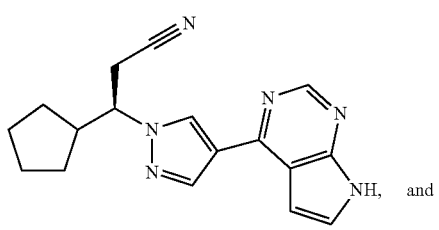

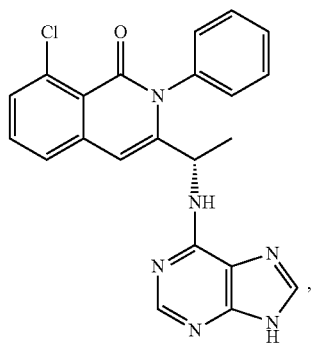

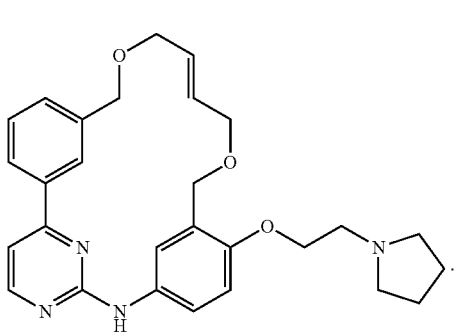

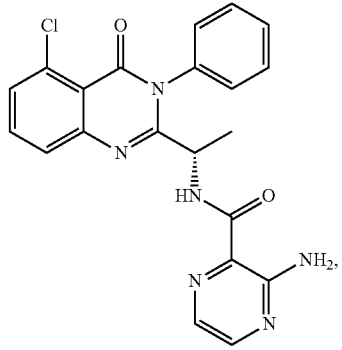

5. The method of claim 1, further comprising the step of administering a therapeutically effective amount of an anti-CD20 antibody selected from the group consisting of rituximab, obinutuzumab, ofatumumab, veltuzumab, tositumomab, and ibritumomab.

6. The method of claim 1, further comprising the step of administering a phosphoinositide 3-kinase (PI3K) inhibitor.

7. The method of claim 6, wherein the PI3K inhibitor is a PI3K-δ inhibitor.

8. The method of claim 6, wherein the PI3K inhibitor is selected from the group consisting of:

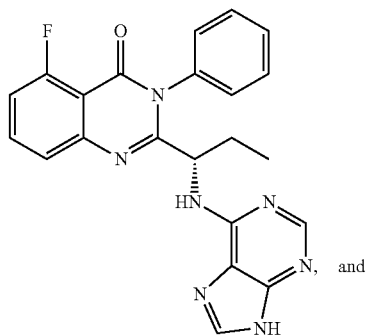

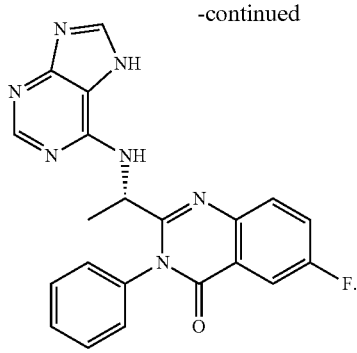

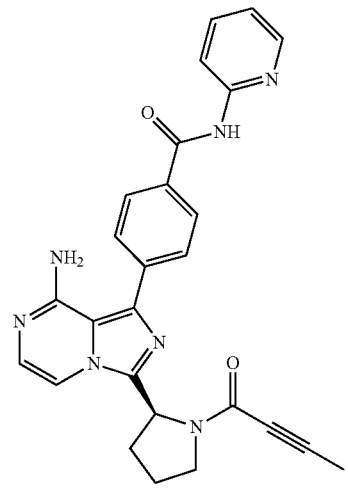

9. The method of claim 1, wherein the hyperproliferative disease is a cancer, and the cancer is a B cell hematological malignancy, and wherein the B cell hematological malignancy is selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, and myelofibrosis.

10. The method of claim 1, wherein the hyperproliferative disease is a cancer, and wherein the cancer is a solid tumor cancer, and wherein the solid tumor cancer is selected from the group consisting of bladder cancer, non-small cell lung cancer, cervical cancer, anal cancer, pancreatic cancer, squamous cell carcinoma including head and neck cancer, renal cell carcinoma, melanoma, ovarian cancer, small cell lung cancer, glioblastoma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, and brain cancer.

11. A method of treating a cancer in a human comprising the step of co-administering (1) a therapeutically effective amount of a Janus kinase-2 (JAK-2) inhibitor, and (2) a therapeutically effective amount of a Bruton's tyrosine kinase (BTK) inhibitor, wherein the therapeutically effective amount is effective to inhibit signaling between a tumor cell of the cancer and at least one tumor microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts.

12. The method of claim 11, wherein the cancer is a solid tumor cancer selected from the group consisting of bladder cancer, non-small cell lung cancer, cervical cancer, anal cancer, pancreatic cancer, squamous cell carcinoma including head and neck cancer, renal cell carcinoma, melanoma, ovarian cancer, small cell lung cancer, glioblastoma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, and brain cancer.

13. The method of claim 11, wherein the BTK inhibitor is selected from the group consisting of:

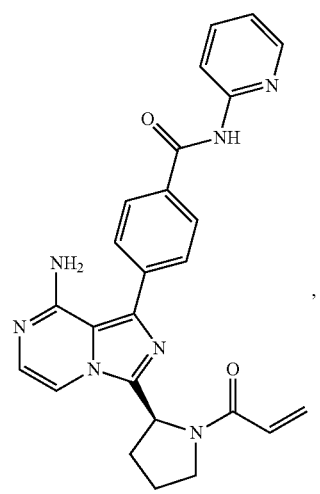

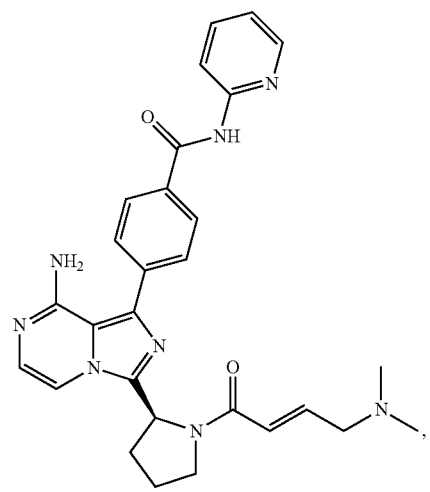

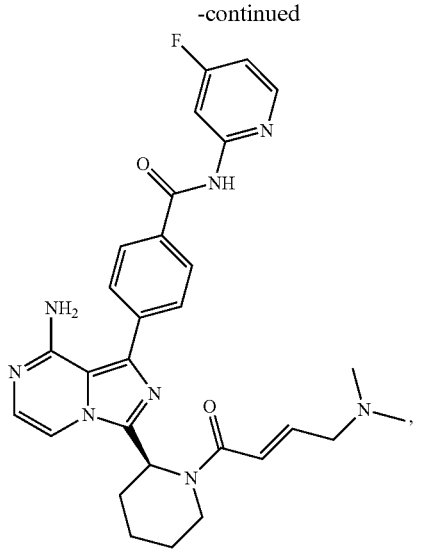
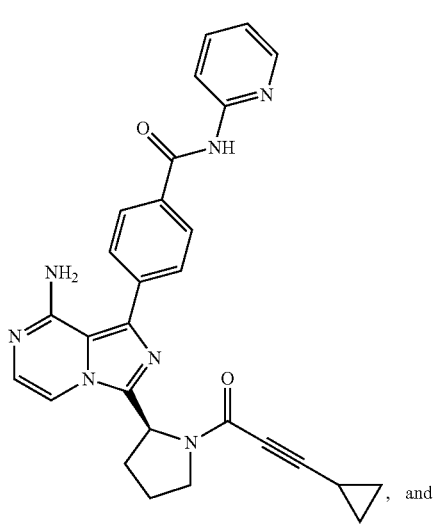
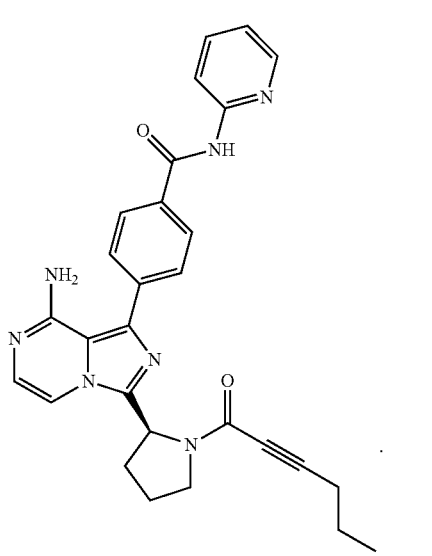
14. The method of claim 11, wherein the JAK-2 inhibitor is selected from the group consisting of:
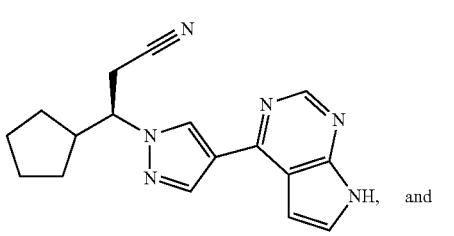
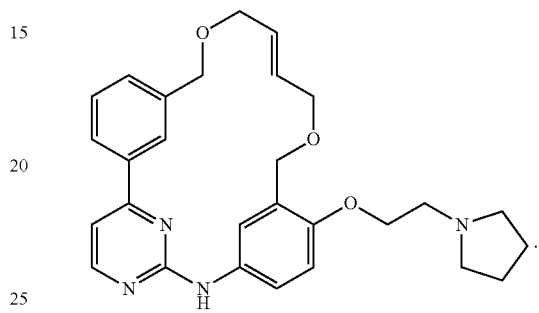
15. The method of claim 11, further comprising the step of administering a therapeutically effective amount of a phosphoinositide 3-kinase (PI3K) inhibitor.
16. The method of claim 15, wherein the PI3K inhibitor is selected from the group consisting of:
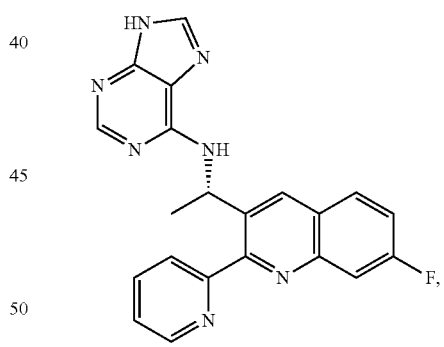
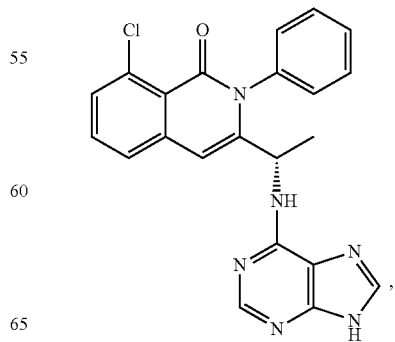

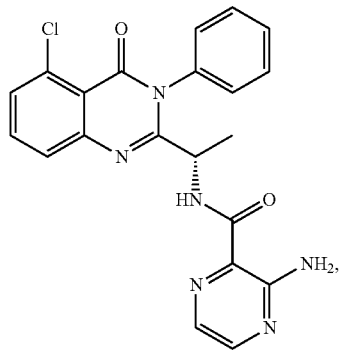
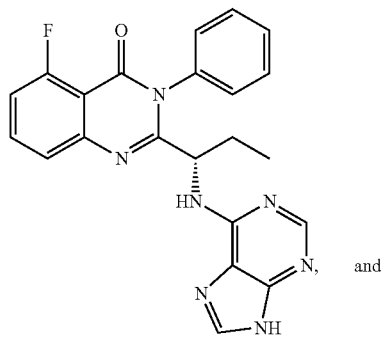
and
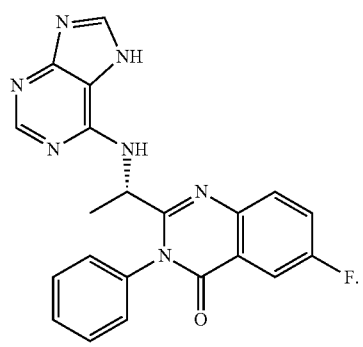 [SMILES: C[C@H](Nc1ncnc2nc[nH]c12)c1nc2ccc(F)cc2c(=O)n1-c1ccccc1]
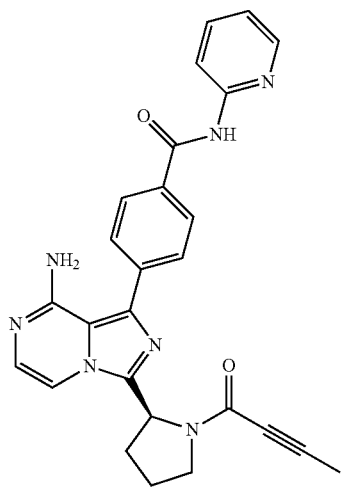
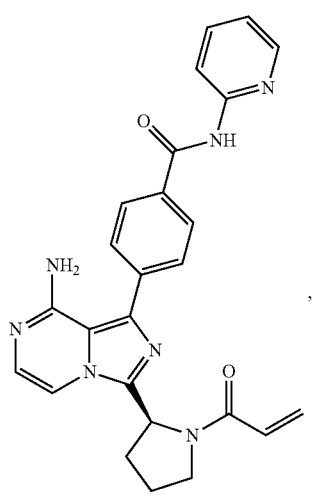
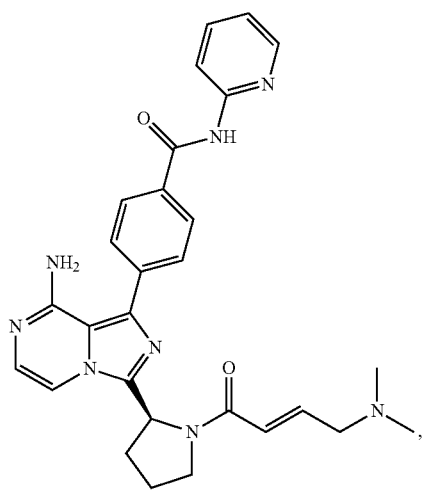
17. A pharmaceutical composition comprising (1) a Janus kinase-2 (JAK-2) inhibitor; and (2) a Bruton's tyrosine kinase (BTK) inhibitor present in an amount therapeutically effective to treat a hyperproliferative disease.
18. The composition of claim 17, wherein the BTK inhibitor is selected from the group consisting of:

19. The composition of claim 17, wherein the BTK inhibitor is selected from the group consisting of:
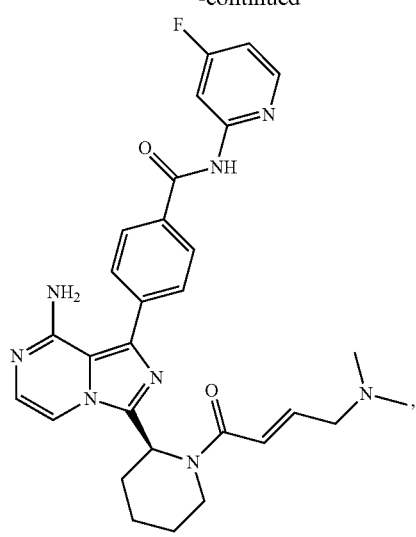
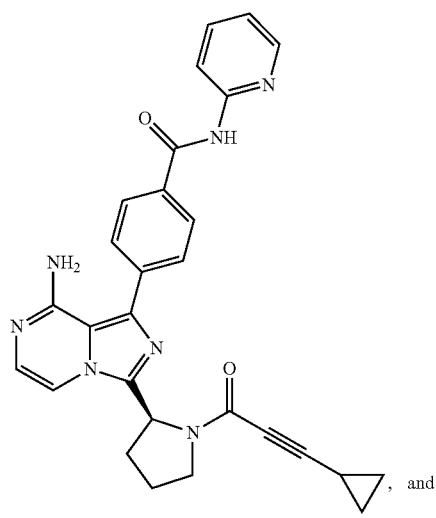
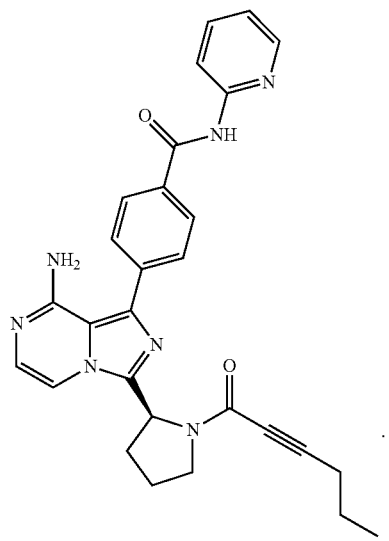
, and
20. The composition of claim 17, wherein the JAK-2 inhibitor is selected from the group consisting of:
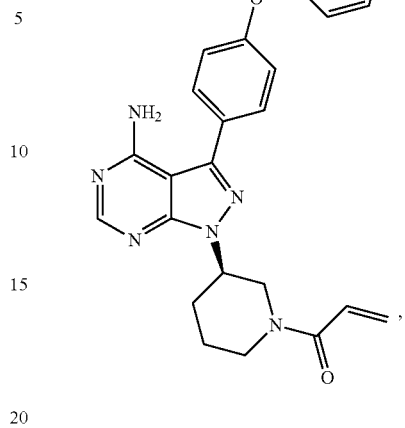
, and
.

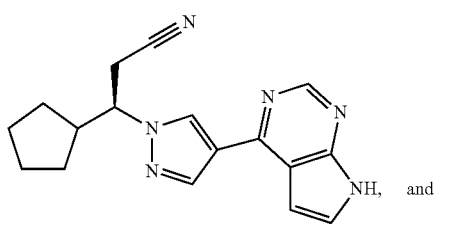

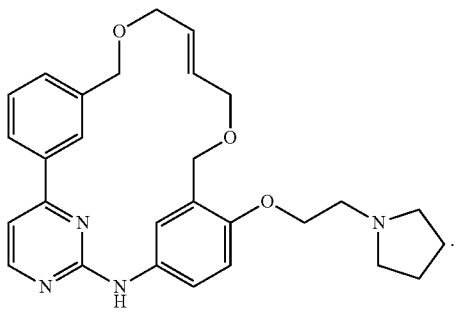

21. The composition of claim 17, further comprising a therapeutically effective amount of an anti-CD20 antibody selected from the group consisting of rituximab, obinutuzumab, ofatumumab, veltuzumab, tositumomab, and ibritumomab.

22. The composition of claim 17, further comprising a phosphoinositide 3-kinase (PI3K) inhibitor.

23. The composition of claim 22, wherein the PI3K inhibitor is a PI3K-δ inhibitor.

24. The composition of claim 23, wherein the PI3K-δ inhibitor is selected from the group consisting of:

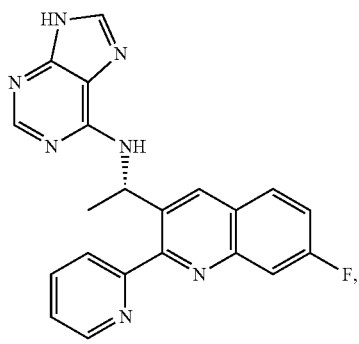

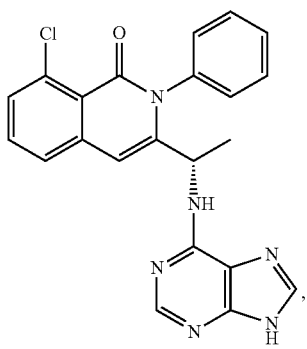

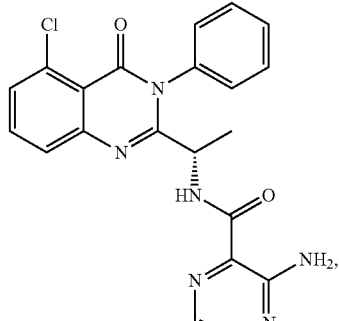

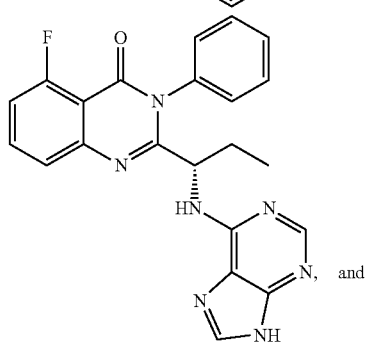

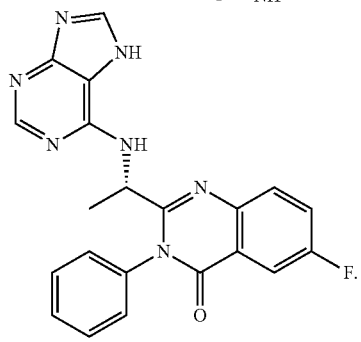

25. The composition of claim 17, wherein the hyperproliferative disease is a cancer, and the cancer is a B cell hematological malignancy, and wherein the B cell hematological malignancy is selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, and myelofibrosis.

26. The composition of claim 17, wherein the hyperproliferative disease is a cancer, and wherein the cancer is a solid tumor cancer, and wherein the solid tumor cancer is selected from the group consisting of bladder cancer, non-small cell lung cancer, cervical cancer, anal cancer, pancreatic cancer, squamous cell carcinoma including head and neck cancer, renal cell carcinoma, melanoma, ovarian cancer, small cell lung cancer, glioblastoma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, and brain cancer.

* * * * *

SEQUENCE LISTING

```
<160> NUMBER OF SEQ ID NOS: 14

<210> SEQ ID NO 1
<211> LENGTH: 451
<212> TYPE: PRT
<213> ORGANISM: Artificial Sequence
<220> FEATURE:
<223> OTHER INFORMATION: Heavy chain amino acid sequence of the
      anti-CD20 monoclonal antibody rituximab.

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45
```

```
Gly Ala Ile Tyr Pro Gly Asn Gly Asp Thr Ser Tyr Asn Gln Lys Phe
 50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
                100                 105                 110
Ala Gly Thr Thr Val Thr Val Ser Ala Ala Ser Thr Lys Gly Pro Ser
                115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
    450
```

```
<210> SEQ ID NO 2
<211> LENGTH: 213
<212> TYPE: PRT
<213> ORGANISM: Artificial sequence
<220> FEATURE:
<223> OTHER INFORMATION: Light chain amino acid sequence of the
      anti-CD20 monoclonal antibody rituximab.

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 449
<212> TYPE: PRT
<213> ORGANISM: Artificial sequence
<220> FEATURE:
<223> OTHER INFORMATION: Heavy chain amino acid sequence of the
      anti-CD20 monoclonal antibody obinutuzumab.

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45
```

```
Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 4
<211> LENGTH: 219
```

```
<212> TYPE: PRT
<213> ORGANISM: Artificial sequence
<220> FEATURE:
<223> OTHER INFORMATION: Light chain amino acid sequence of the
      anti-CD20 monoclonal antibody obinutuzumab.

<400> SEQUENCE: 4

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 122
<212> TYPE: PRT
<213> ORGANISM: Artificial sequence
<220> FEATURE:
<223> OTHER INFORMATION: Variable heavy chain amino acid sequence of
      the anti-CD20 monoclonal antibody ofatumumab.

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95
```

Ala Lys Asp Ile Gln Tyr Gly Asn Tyr Tyr Tyr Gly Met Asp Val Trp
                100                 105                 110

Gly Gln Gly Thr Thr Val Thr Val Ser Ser
        115                 120

<210> SEQ ID NO 6
<211> LENGTH: 107
<212> TYPE: PRT
<213> ORGANISM: Artificial sequence
<220> FEATURE:
<223> OTHER INFORMATION: Variable light chain amino acid sequence of
      the anti-CD20 monoclonal antibody ofatumumab.

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
                100                 105

<210> SEQ ID NO 7
<211> LENGTH: 222
<212> TYPE: PRT
<213> ORGANISM: Artificial Sequence
<220> FEATURE:
<223> OTHER INFORMATION: Fab fragment of heavy chain amino acid sequence
      of the anti-CD20 monoclonal antibody ofatumumab.

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Gly Ser Ser Lys Ser Thr Ser Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro
210                 215                 220

<210> SEQ ID NO 8
<211> LENGTH: 211
<212> TYPE: PRT
<213> ORGANISM: Artificial Sequence
<220> FEATURE:
<223> OTHER INFORMATION: Fab fragment of light chain amino acid sequence
      of the anti-CD20 monoclonal antibody ofatumumab.

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 9
<211> LENGTH: 451
<212> TYPE: PRT
<213> ORGANISM: Artificial Sequence
<220> FEATURE:
<223> OTHER INFORMATION: Heavy chain amino acid sequence of the
      anti-CD20 monoclonal antibody veltuzumab.

<400> SEQUENCE: 9

Gln Val Gln Leu Gln Gln Ser Gly Ala Glu Val Lys Lys Pro Gly Ser
1               5                   10                  15

```
Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
        35                  40                  45

Gly Ala Ile Tyr Pro Gly Met Gly Asp Thr Ser Tyr Asn Gln Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
```

```
                            435                 440                 445

Pro Gly Lys
    450

<210> SEQ ID NO 10
<211> LENGTH: 213
<212> TYPE: PRT
<213> ORGANISM: Artificial Sequence
<220> FEATURE:
<223> OTHER INFORMATION: Light chain amino acid sequence of the
      anti-CD20 monoclonal antibody veltuzumab.

<400> SEQUENCE: 10

Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Val Ser Tyr Ile
            20                  25                  30

His Trp Phe Gln Gln Lys Pro Gly Lys Ala Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 447
<212> TYPE: PRT
<213> ORGANISM: Artificial Sequence
<220> FEATURE:
<223> OTHER INFORMATION: Heavy chain amino acid sequence of the
      anti-CD20 monoclonal antibody tositumomab.

<400> SEQUENCE: 11

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
```

```
            50                  55                  60
Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
                100                 105                 110

Gly Thr Gly Thr Thr Val Thr Val Ser Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 12
<211> LENGTH: 210
<212> TYPE: PRT
<213> ORGANISM: Artificial Sequence
```

<220> FEATURE:
<223> OTHER INFORMATION: Light chain amino acid sequence of the
      anti-CD20 monoclonal antibody tositumomab.

<400> SEQUENCE: 12

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210
```

<210> SEQ ID NO 13
<211> LENGTH: 443
<212> TYPE: PRT
<213> ORGANISM: Artificial Sequence
<220> FEATURE:
<223> OTHER INFORMATION: Heavy chain amino acid sequence of the
      anti-CD20 monoclonal antibody ibritumomab.

<400> SEQUENCE: 13

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95
```

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
                435                 440

<210> SEQ ID NO 14
<211> LENGTH: 209
<212> TYPE: PRT
<213> ORGANISM: Artificial Sequence
<220> FEATURE:
<223> OTHER INFORMATION: Light chain amino acid sequence of the
    anti-CD20 monoclonal antibody ibritumomab.

```
<400> SEQUENCE: 14

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn
```